US012655134B2

(12) United States Patent
Li et al.

(10) Patent No.: US 12,655,134 B2
(45) Date of Patent: Jun. 16, 2026

(54) ORGANIC COMPOUND, AND ELECTRONIC ELEMENT AND ELECTRONIC DEVICE THEREOF

(71) Applicant: Shaanxi Lighte Optoelectronics Material Co., Ltd., Xi'an (CN)

(72) Inventors: Lingang Li, Xi'an (CN); Peng Nan, Xi'an (CN)

(73) Assignee: SHAANXI LIGHTE OPTOELECTRONICS MATERIAL CO., LTD., Xi'an (CN)

(*) Notice: Subject to any disclaimer, the term of this patent is extended or adjusted under 35 U.S.C. 154(b) by 883 days.

(21) Appl. No.: 17/925,787

(22) PCT Filed: May 28, 2021

(86) PCT No.: PCT/CN2021/096926
§ 371 (c)(1),
(2) Date: Nov. 16, 2022

(87) PCT Pub. No.: WO2021/244442
PCT Pub. Date: Dec. 9, 2021

(65) Prior Publication Data

US 2023/0192668 A1 Jun. 22, 2023

(30) Foreign Application Priority Data

Jun. 5, 2020 (CN) ......................... 202010507151.1
Sep. 29, 2020 (CN) ......................... 202011056769.7

(51) Int. Cl.
*H10K 85/60* (2023.01)
*C07D 405/04* (2006.01)
(Continued)

(52) U.S. Cl.
CPC ......... *C07D 405/04* (2013.01); *C07D 405/10* (2013.01); *C07D 405/14* (2013.01);
(Continued)

(58) Field of Classification Search
CPC .. C07D 405/04; C07D 405/10; C07D 405/14; C07D 409/14; C07D 411/14;
(Continued)

(56) References Cited

U.S. PATENT DOCUMENTS 11,283,027 B1 * 3/2022 Suzuki ............... H10K 85/6572
2017/0298077 A1 10/2017 Parham
2018/0040829 A1 * 2/2018 Lee ...................... C07D 413/14

FOREIGN PATENT DOCUMENTS

CN 104411694 A 3/2015
CN 108350351 A 7/2018
(Continued)

OTHER PUBLICATIONS

Office Action from corresponding Chinese Application No. 202011056769.7 dated Dec. 12, 2022, 7 pages.
(Continued)

*Primary Examiner* — James D Sells
(74) *Attorney, Agent, or Firm* — Tucker Ellis LLP

(57) ABSTRACT

The present disclosure relates to an organic compound. The organic compound has a structure as shown in the following formula (1), where $R_1$ and $R_2$ are the same as or different from each other, and are each independently substituted or unsubstituted alkyl with 1 to 4 carbon atoms, or substituted or unsubstituted phenyl; each Y is the same or different, and independently has a structure as shown in a formula (2); $X_1$, $X_2$, $X_3$, $X_4$, and $X_5$ are the same or different, and are each independently $C(R_4)$ or N, and at least one of $X_1$, $X_2$, $X_3$, $X_4$, and $X_5$ is N; m is selected from 1 or 2; and n is selected from 1 or 2. The organic compound of the present disclosure may be used as a hole blocking layer and/or an electron transport layer of an organic electroluminescent device.
(Continued)

Formula (1)

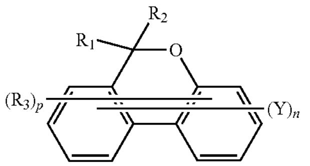

Formula (2)

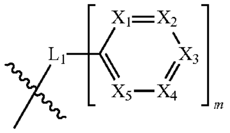

20 Claims, 2 Drawing Sheets

(51) Int. Cl.

| | |
|---|---|
| ***C07D 405/10*** | (2006.01) |
| ***C07D 405/14*** | (2006.01) |
| ***C07D 409/14*** | (2006.01) |
| ***C07D 411/14*** | (2006.01) |
| ***C07D 413/14*** | (2006.01) |
| ***C07D 417/14*** | (2006.01) |
| ***C07D 491/048*** | (2006.01) |
| ***C07F 7/08*** | (2006.01) |
| ***H10K 39/10*** | (2023.01) |
| ***H10K 50/16*** | (2023.01) |
| ***H10K 85/00*** | (2023.01) |
| ***H10K 85/40*** | (2023.01) |
| *H10K 50/10* | (2023.01) |
| *H10K 50/18* | (2023.01) |
| *H10K 102/00* | (2023.01) |

(52) U.S. Cl.

CPC .......... *C07D 409/14* (2013.01); *C07D 411/14* (2013.01); *C07D 413/14* (2013.01); *C07D 417/14* (2013.01); *C07D 491/048* (2013.01); *C07F 7/0812* (2013.01); *H10K 39/10* (2023.02); *H10K 50/16* (2023.02); *H10K 85/00* (2023.02); *H10K 85/40* (2023.02); *H10K 85/652* (2023.02); *H10K 85/654* (2023.02); *H10K 85/657* (2023.02); *H10K 85/6572* (2023.02); *H10K 85/6574* (2023.02); *H10K 85/6576* (2023.02); *C07B 2200/05* (2013.01); *H10K 50/10* (2023.02); *H10K 50/18* (2023.02); *H10K 2102/3026* (2023.02)

(58) Field of Classification Search

CPC ........................... C07D 413/14; C07D 417/14; C07D 491/048; H10K 39/10; H10K 50/15; H10K 85/654; H10K 85/652; H10K 85/6574; H10K 85/657; H10K 85/6572; H10K 85/6576

USPC .......................................................... 428/690

See application file for complete search history.

(56) References Cited

FOREIGN PATENT DOCUMENTS

| | | | |
|---|---|---|---|
| CN | 111051292 | A | 4/2020 |
| KR | 20170120233 | A | 10/2017 |
| KR | 20180021339 | A | 3/2018 |
| KR | 20190066895 | A | 6/2019 |
| WO | 2014007186 | A1 | 1/2014 |
| WO | 2019182360 | A1 | 9/2019 |
| WO | 2020102901 | A1 | 5/2020 |

OTHER PUBLICATIONS

International Search Report from corresponding International Application No. PCT/CN2021/096926, mailed Aug. 3, 2021, 4 pages with translation.

* cited by examiner

ORGANIC COMPOUND, AND ELECTRONIC ELEMENT AND ELECTRONIC DEVICE THEREOF

CROSS REFERENCE TO RELATED APPLICATIONS

The present application claims the priority of Chinese Patent Application No. CN202010507151.1, filed on Jun. 5, 2020, and Chinese Patent Application No. CN202011056769.7, filed on Sep. 29, 2020, the contents of which are incorporated herein by reference in their entirety as a part of the present disclosure.

TECHNICAL FIELD

The present disclosure belongs to the technical field of organic materials, and in particular provides an organic compound, and an electronic element and electronic device using the same.

BACKGROUND

Organic electroluminescent device (OLED) materials as a new-generation display technology, have the advantages of ultra-thinness, self-luminescence, wide viewing angle, fast response, high luminous efficiency, good temperature adaptability, simple production process, low driving voltage, low energy consumption, and the like, and have been widely used in industries such as flat panel display, flexible display, solid state lighting, and automotive display.

An organic luminescence device generally includes an anode, a cathode and an organic material layer arranged between the anode and the cathode. The organic material layer is typically formed in a multilayer structure composed of different materials to improve the brightness, efficiency, and service life of the organic luminescence device, and the organic material layer could be composed of a hole injection layer, a hole transport layer, a luminescence layer, an electron transport layer, an electron injection layer, and the like. In a structure of the organic luminescence device, when a voltage is applied between the anode and the cathode, holes from the anode and electrons from the cathode are injected into the organic material layer, respectively, and excitons are formed when the injected holes and electrons meet, and light is emitted when these excitons return to a ground state.

In the existing organic luminescence device, the most major problem is the service life and efficiency, as the area of the display increases, the driving voltage is also increased, and the luminous efficiency and power efficiency are also required to be increased, and thus, it is necessary to continue to develop a new material to further improve the performance of the organic luminescence device.

SUMMARY

The present disclosure aims to provide an organic compound, and an electronic element and electronic device using the same. The organic compound can be used as a hole blocking layer and/or an electron transport layer of an organic electroluminescent device.

In order to achieve the above purpose, in a first aspect, the present disclosure provides an organic compound, having a structural formula as shown in a formula (1):

Formula (1)

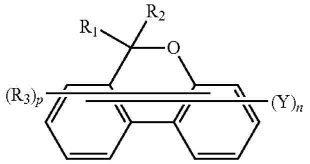

Formula (2)

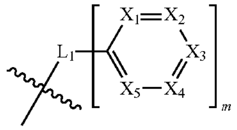

;

in the formula (1), $R_1$ and $R_2$ are the same as or different from each other, and are each independently selected from substituted or unsubstituted alkyl with 1 to 4 carbon atoms, or substituted or unsubstituted phenyl; and when $R_1$ or $R_2$ is substituted alkyl, substituents in the substituted alkyl are the same or different, and are each independently selected from the group consisting of deuterium, fluorine, chlorine, and cyano; and when $R_1$ or $R_2$ is substituted phenyl, substituents in the substituted phenyl are the same or different, and are each independently selected from the group consisting of alkyl with 1 to 6 carbon atoms, cyano, a halogen group, deuterium, and trimethylsilyl;

each $R_3$ is the same as or different from each other, and is independently selected from the group consisting of deuterium; a halogen group; cyano; haloalkyl with 1 to 12 carbon atoms; alkyl with 1 to 12 carbon atoms; alkoxy with 1 to 12 carbon atoms; cycloalkyl with 3 to 12 carbon atoms; alkylthio with 1 to 12 carbon atoms; trialkylsilyl with 3 to 12 carbon atoms; aryl with 6 to 20 carbon atoms which can be optionally substituted by 0, 1, 2, 3, 4, or 5 substituents independently selected from deuterium, fluorine, chlorine, or cyano; heteroaryl with 3 to 20 carbon atoms which can be optionally substituted by 0, 1, 2, 3, 4, or 5 substituents independently selected from deuterium, fluorine, chlorine, or cyano; aryloxy with 6 to 20 carbon atoms; arylthio with 6 to 20 carbon atoms; arylsilyl with 6 to 18 carbon atoms and alkylphosphinyloxy with 1 to 12 carbon atoms;

p is selected from 0, 1, 2, 3, 4, 5, 6 or 7;

each Y is the same as or different from each other, and independently has a structure as shown in a formula (2), $X_1$, $X_2$, $X_3$, $X_4$, and $X_5$ are the same as or different from each other, and are each independently $C(R_4)$ or N, and at least one of $X_1$, $X_2$, $X_3$, $X_4$, and $X_5$ is N; m is selected from 1 or 2; and n is selected from 1 or 2;

in the formula (2), each $R_4$ is the same or different, and is independently hydrogen or

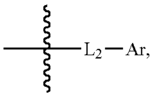

or two adjacent $R_4$ are connected to each other to form a substituted or unsubstituted 5- to 10-membered aromatic ring or a substituted or unsubstituted 5- to 10-membered heteroaromatic ring; substituents in the substituted 5- to 10-membered aromatic ring or the substituted 5- to 10-membered heteroaromatic ring are the same as or different from each other, and are each independently selected from the group consisting of deuterium, a halogen group, cyano, alkyl with 1 to 12 carbon atoms, haloalkyl with 1 to 12 carbon atoms, alkoxy with 1 to 12 carbon atoms, alkylthio with 1 to 12 carbon atoms, aryl with 6 to 25 carbon atoms, heteroaryl with 3 to 20 carbon atoms, trialkylsilyl with 3 to 12 carbon atoms, arylsilyl with 8 to 18 carbon atoms, and cycloalkyl with 3 to 12 carbon atoms;

each Ar is independently selected from the group consisting of substituted or unsubstituted aryl with 6 to 40 carbon atoms, substituted or unsubstituted heteroaryl with 3 to 40 carbon atoms, substituted or unsubstituted alkyl with 1 to 12 carbon atoms, substituted or unsubstituted cycloalkyl with 3 to 12 carbon atoms, substituted or unsubstituted aralkyl with 7 to 30 carbon atoms, and substituted or unsubstituted heteroaralkyl with 4 to 30 carbon atoms;

each $L_1$ and each $L_2$ are the same as or different from each other, and are each independently selected from the group consisting of a single bond, substituted or unsubstituted arylene with 6 to 30 carbon atoms, and substituted or unsubstituted heteroarylene with 3 to 30 carbon atoms; and substituents in each $L_1$, each $L_2$ and each Ar are the same as or different from each other, and are each independently selected from the group consisting of deuterium; a halogen group; cyano, alkyl with 1 to 12 carbon atoms; haloalkyl with 1 to 12 carbon atoms; alkoxy with 1 to 12 carbon atoms; alkylthio with 1 to 12 carbon atoms; aryl with 6 to 25 carbon atoms which can be optionally substituted by substituents selected from deuterium, fluorine, cyano, or alkyl; heteroaryl with 3 to 20 carbon atoms; aryloxy with 6 to 20 carbon atoms; arylthio with 6 to 20 carbon atoms; trialkylsilyl with 3 to 12 carbon atoms; arylsilyl with 8 to 18 carbon atoms; and cycloalkyl with 3 to 12 carbon atoms; and in each $L_1$, each $L_2$ and each Ar, when there are two substituents on a same atom, the two substituents are optionally connected to each other to form a 5- to 18-membered aliphatic ring or a 5- to 18-membered aromatic ring together with the atom to which they are jointly connected.

In a second aspect, the present disclosure provides an electronic element, including an anode and a cathode which are oppositely disposed, and a functional layer disposed between the anode and the cathode; and the functional layer includes the organic compound provided by the first aspect of the present disclosure;

optionally, the functional layer includes an electron transport layer, and the electron transport layer includes the organic compound according to the first aspect of the present disclosure; and optionally, the functional layer includes a hole blocking layer, and the hole blocking layer includes the organic compound according to the first aspect of the present disclosure.

In a third aspect, the present disclosure provides an electronic device, including the electronic element provided by the second aspect of the present disclosure.

Through the above technical solution, in an oxaphenanthrene group of the organic compound provided by the present disclosure, 9-position methyl, 9-position phenyl and an ortho-position oxygen atom can all provide electrons to a benzene ring through a conjugation/hyperconjugation effect, the group thus has a high conjugated electron cloud density; and introduction of substituted electron-deficient heteroaryl as an electron injection and transport group into the core structure, enhances the polarity of the whole molecule, which is more conducive to the directional arrangement of material molecules, thus enhancing the injection and transport of electrons and improving the efficiency of the device. The asymmetry and steric hindrance of the oxaphenanthrene group are greater than those of a general planar conjugated group, which makes it have lower crystallinity and good film-forming properties, and the service life of the device can be effectively improved when the oxaphenanthrene group is applied to an organic electroluminescent device. The substituted nitrogen-containing heteroaryl moiety connected with the oxaphenanthrene core structure belongs to an electron-deficient group and is suitable for accepting electrons to form a negative ion center and thus has excellent effects of electron-transporting and hole-blocking. When a cyano substituent is included in the substituted nitrogen-containing heteroaryl structure, the molecular polarity and dipole moment are further improved, the electron mobility is improved, and the electron transport performance is relatively better, which is more suitable for an electron transport layer in optoelectronic devices; and when the substituted nitrogen-containing heteroaryl structure is without cyano substituent, the hole blocking properties are better and the effect as a hole blocking layer is better. When the 9-position substituent on the oxaphenanthrene core structure is bulky and too rigid, the thermal stability will be reduced, and the service life of the device will be affected.

Other features and advantages of the present disclosure will be described in detail in the following detailed description.

BRIEF DESCRIPTION OF THE DRAWINGS

The accompanying drawings are intended to provide a further understanding of the present disclosure, and constitute a part of the description, and are used to explain the present disclosure together with the following specific examples, but do not constitute a limitation on the present disclosure.

DESCRIPTION OF REFERENCE SIGNS

Figure 1:
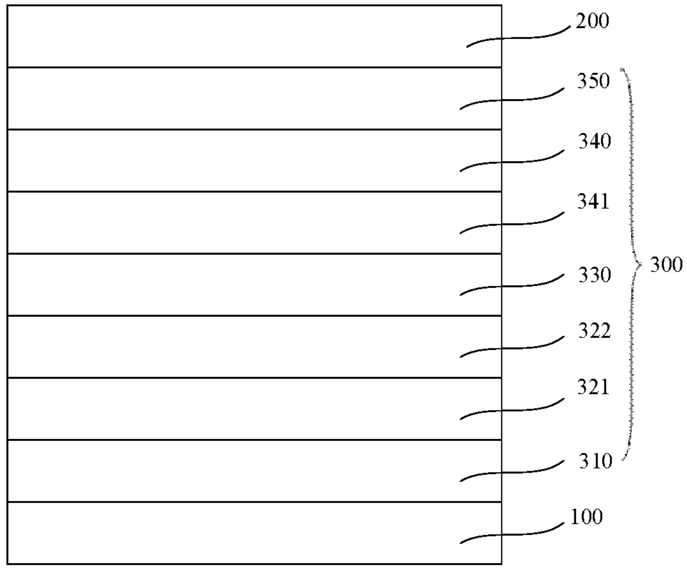
FIG. 1 is a structural schematic diagram of an organic electroluminescent device according to one embodiment of the present disclosure.

100, anode; 200, cathode; 300, functional layer; 310, hole injection layer; 320, first hole transport layer; 321, hole transport layer; 322, electron blocking layer; 330, organic luminescent layer; 341, hole blocking layer, 340, electron transport layer; 350, electron injection layer; 360, photoelectric conversion layer; 400, first electronic device; and 500, second electronic device.

DETAILED DESCRIPTION

Specific embodiments of the present disclosure will be described in detail below with reference to the accompanying drawings. It should be understood that the specific embodiments described herein are only used to illustrate and explain the present disclosure and are not intended to limit the present disclosure.

In a first aspect, the present disclosure provides an organic compound, having a structure as shown in the following formula (1):

Formula (1)

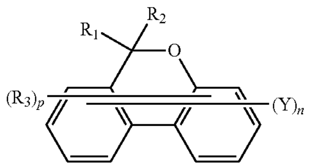

Formula (2)

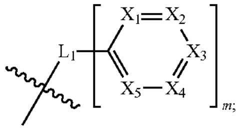

in the formula (1), $R_1$ and $R_2$ are the same as or different from each other, and are each independently selected from substituted or unsubstituted alkyl with 1 to 4 carbon atoms, or substituted or unsubstituted phenyl; and when $R_1$ or $R_2$ is substituted alkyl, substituents in the substituted alkyl are the same or different, and are each independently selected from the group consisting of deuterium, fluorine, chlorine, and cyano; and when $R_1$ or $R_2$ is substituted phenyl, substituents in the substituted phenyl are the same or different, and are each independently selected from the group consisting of alkyl with 1 to 6 carbon atoms, cyano, a halogen group, deuterium, and trimethylsilyl;

each $R_3$ is the same as or different from each other, and is independently selected from the group consisting of deuterium; a halogen group; cyano; haloalkyl with 1 to 12 carbon atoms; alkyl with 1 to 12 carbon atoms; alkoxy with 1 to 12 carbon atoms; cycloalkyl with 3 to 12 carbon atoms; alkylthio with 1 to 12 carbon atoms; trialkylsilyl with 3 to 12 carbon atoms; aryl with 6 to 20 carbon atoms which can be optionally substituted by 0, 1, 2, 3, 4, or 5 substituents independently selected from deuterium, fluorine, chlorine, or cyano; heteroaryl with 3 to 20 carbon atoms which can be optionally substituted by 0, 1, 2, 3, 4, or 5 substituents independently selected from deuterium, fluorine, chlorine, or cyano; aryloxy with 6 to 20 carbon atoms; arylthio with 6 to 20 carbon atoms; arylsilyl with 6 to 18 carbon atoms; and alkylphosphinyloxy with 1 to 12 carbon atoms;

p is selected from 0, 1, 2, 3, 4, 5, 6 or 7;

each Y is the same as or different from each other, and independently has a structure as shown in a formula (2), $X_1$, $X_2$, $X_3$, $X_4$, and $X_5$ are the same as or different from each other, and are each independently $C(R_4)$ or N, and at least one of $X_1$, $X_2$, $X_3$, $X_4$, and $X_5$ is N;

m is selected from 1 or 2; and n is selected from 1 or 2;

in the formula (2), each $R_4$ is the same as or different from each other, and is

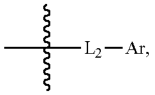

independently hydrogen or $L_2Ar$, or two adjacent $R_4$ are connected to each other to form a substituted or unsubstituted 5- to 10-membered aromatic ring or a substituted or unsubstituted 5- to 10-membered heteroaromatic ring; substituents in the substituted 5- to 10-membered aromatic ring or the substituted 5- to 10-membered heteroaromatic ring are the same as or different from each other, and are each independently selected from the group consisting of deuterium, a halogen group, cyano, alkyl with 1 to 12 carbon atoms, haloalkyl with 1 to 12 carbon atoms, alkoxy with 1 to 12 carbon atoms, alkylthio with 1 to 12 carbon atoms, aryl with 6 to 25 carbon atoms, heteroaryl with 3 to 20 carbon atoms, trialkylsilyl with 3 to 12 carbon atoms, arylsilyl with 8 to 18 carbon atoms, and cycloalkyl with 3 to 12 carbon atoms;

each Ar is independently selected from the group consisting of substituted or unsubstituted aryl with 6 to 40 carbon atoms, substituted or unsubstituted heteroaryl with 3 to 40 carbon atoms, substituted or unsubstituted alkyl with 1 to 12 carbon atoms, substituted or unsubstituted cycloalkyl with 3 to 12 carbon atoms, substituted or unsubstituted aralkyl with 7 to 30 carbon atoms, and substituted or unsubstituted heteroaralkyl with 4 to 30 carbon atoms; and

represents a chemical bond;

each $L_1$ and each $L_2$ are the same as or different from each other, and are each independently selected from the group consisting of a single bond, substituted or unsubstituted arylene with 6 to 30 carbon atoms, and substituted or unsubstituted heteroarylene with 3 to 30 carbon atoms;

when more than one $L_1$ is contained in the compound of the formula (1), each $L_1$ is the same or different;

when more than one $L_2$ is contained in the compound of the formula (1), each $L_2$ is the same or different;

when more than one Ar is contained in the compound of the formula (1), each Ar is the same or different; and substituents in each $L_1$, each $L_2$ and each Ar are the same as or different from each other, and are each independently selected from the group consisting of deuterium; a halogen group; cyano; alkyl with 1 to 12 carbon atoms; haloalkyl with 1 to 12 carbon atoms; alkoxy with 1 to 12 carbon atoms; alkylthio with 1 to 12 carbon atoms; aryl with 6 to 25 carbon atoms which can be optionally substituted by substituents selected from deuterium, fluorine, cyano, or alkyl; heteroaryl with 3 to 20 carbon atoms; aryloxy with 6 to 20 carbon atoms; arylthio with 6 to 20 carbon atoms; trialkylsilyl with 3 to 12 carbon atoms; arylsilyl with 8 to 18 carbon atoms; and cycloalkyl with 3 to 12 carbon atoms; and in each $L_1$, each $L_2$ and each Ar, when there are two substituents on a same atom, the two substituents are optionally connected to each other to form a 5- to 18-membered aliphatic ring or a 5- to 18-membered aromatic ring together with the atom to which they are jointly connected.

In the present disclosure,

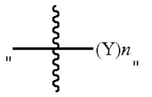

in the formula refers to a total of eight linking positions on an oxadihydrophenanthrene core structure in the formula (1), where n positions are linked to Y, and $R_3$ is linked at a position on the oxadihydrophenanthrene core structure where Y is not linked. And when n is 2 or more, each Y may be the same or different.

In the present disclosure,

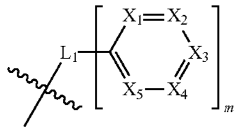

in the formula (2) means that m positions on $L_1$ are connected to heteroaryl

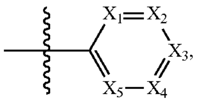

and when m is 2, $X_1$, $X_2$, $X_3$, $X_4$, and $X_5$ in each heteroaryl

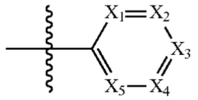

are the same as or different from each other. In the present disclosure, a substituent in $L_1$ refers to other substituents in $L_1$ except

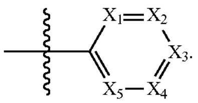

In some embodiments of the present disclosure, m×n≤2, i.e., the number of a group

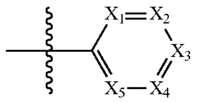

in the compound is 1 or 2.

In the present disclosure, in the formula (2), each $R_4$ is the same as or different from each other, and each $R_4$ is independently hydrogen or

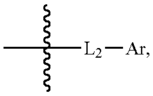

or two adjacent $R_4$ are connected to each other to form a ring, and two situations can coexist; when two adjacent $R_4$ are connected to each other, the formed ring is a substituted or unsubstituted 5- to 10-membered aromatic ring or a substituted or unsubstituted 5- to 10-membered heteroaromatic ring, e.g. when in the formula (2), m=1, $L_1$ is a single bond, $X_1$ and $X_3$ are N, $X_2$ is —CH—, $X_4$ and $X_5$ are $C(R_4)$, and two $R_4$ are connected to each other to form a 6-membered pyridine ring, the structure of the formula (2) is:

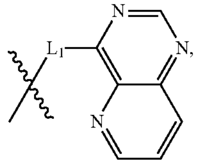

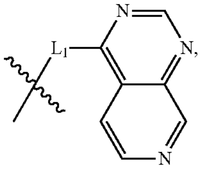

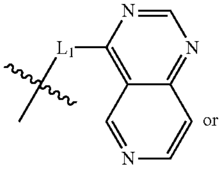

or

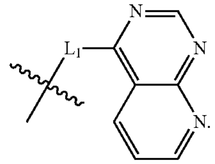

In the oxaphenanthrene group of the organic compound provided by the present disclosure, 9-position methyl, 9-position phenyl and oxygen can all provide electrons to a benzene ring through a conjugation/hyperconjugation effect, the group thus has a very high conjugated electron cloud density, and introduction of substituted electron-deficient heteroaryl as an electron injection and transport group into the core structure enhances the polarity of the whole molecule, which is more conducive to the directional arrangement of material molecules, thus enhancing the injection and transport of electrons and improving the efficiency of the device. The asymmetry and steric hindrance of the oxaphenanthrene group are greater than those of a general planar conjugated group, which makes it have lower crystallinity and good film-forming properties, and the service life of the device can be effectively improved when the oxaphenanthrene group is applied to an organic electroluminescent device.

In the present disclosure, "optional" or "optionally" means that the subsequently described event or circumstance may occur but not have to occur, and that the description includes circumstances where the event or situation occurs or does not occur. For example, "a heterocyclic group which can be optionally substituted by alkyl" means that alkyl may be present, but not have to be present, and the description includes a scenario in which the heterocyclic group is substituted by alkyl and a scenario in which the heterocyclic group is not substituted by alkyl. For example, "when there are two substituents on a same atom, the two substituents are optionally connected to each other to form a 5- to 18-membered aliphatic ring or a 5- to 18-membered aromatic ring together with the atoms to which they are jointly connected", which means that when there are two substituents on a same atom, a scenario in which the two substituents exist independently of each other is included, and a scenario in which the two substituents are connected to each other to form a 5- to 18-membered aliphatic ring or a 5- to 18-membered aromatic ring together with the atom to which they are jointly connected is also included. For another example, "aryl with 6 to 20 carbon atoms which can be optionally substituted by 0, 1, 2, 3, 4, or 5 substituents independently selected from deuterium, fluorine, chlorine, or cyano" means that the aryl with 6 to 20 carbon atoms can have 0, 1, 2, 3, 4, or 5 substituents, and these substituents are each independently selected from deuterium, fluorine, chlorine, or cyano. When the number of the substituents is 0, the aryl is unsubstituted aryl.

In the present disclosure, the used descriptions modes "each . . . is independently", " . . . are respectively and independently"and" . . . is independently selected from" can be interchanged, which should be understood in a broad sense. They indicate that the specific options expressed by a same symbol in different groups do not influence each other, or that specific options expressed by a same symbol in a same group do not influence each other.

For example, in the description of

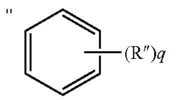

Q-1

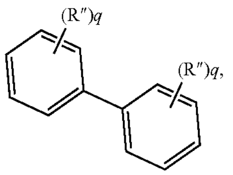

Q-2 wherein each q is independently 0, 1, 2 or 3 and each R" is independently selected from hydrogen, deuterium, fluorine, or chlorine", a formula Q-1 represents that q substituents R" exist on a benzene ring, each R" can be the same or different, and options of each R" do not influence each other; and a formula Q-2 represents that each benzene ring of biphenyl has q substituents R", the number q of the substituents R" on the two benzene rings can be the same or different, each R" can be the same or different, and options of each R" do not influence each other.

In the present disclosure, the term such as "substituted or unsubstituted" means that a functional group described behind the term may or may not have a substituent (the substituent is collectively referred to as Rc hereinafter for ease of description). For example, "substituted or unsubstituted aryl" refers to aryl with a substituent Rc or unsubstituted aryl. The above substituent, i.e. Rc may, for example, be selected from the group consisting of deuterium, a halogen group, cyano, alkyl with 1 to 12 carbon atoms, haloalkyl with 1 to 12 carbon atoms, alkoxy with 1 to 12 carbon atoms, alkylthio with 1 to 12 carbon atoms, aryl with 6 to 25 carbon atoms, heteroaryl with 3 to 20 carbon atoms, aryloxy with 6 to 20 carbon atoms, arylthio with 6 to 20 carbon atoms, trialkylsilyl with 3 to 12 carbon atoms, arylsilyl with 8 to 18 carbon atoms, and cycloalkyl with 3 to 12 carbon atoms. In the present disclosure, a "substituted" functional group can be substituted by one or two or more substituents according to the above Rc; when two substituents Rc are connected to a same atom, the two substituents Rc may independently exist or may be connected to each other to form a ring with the atom; and when two adjacent substituents Rc are present on a functional group, the two adjacent substituents Rc may independently be present or may be fused to a ring with the functional group to which they are connected.

In the present disclosure, the number of carbon atoms of a substituted or unsubstituted functional group refers to the number of all carbon atoms in the functional group and substituents on the functional group. For example, if $R_1$ is selected from substituted aryl with 30 carbon atoms, the number of all carbon atoms of the aryl and substituents on the aryl is 30; and for another example, if $L_1$ is selected from arylene substituted by alkyl with 25 carbon atoms, the number of all carbon atoms of the arylene and the alkyl on the aryl is 25.

In the present disclosure, the number of carbon atoms refers to the number of all carbon atoms. For example: if $L_1$ is substituted arylene with 12 carbon atoms, then the number of all carbon atoms of the arylene and substituents on the arylene is 12. For example: if Ar is

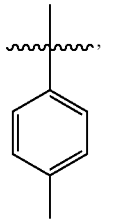

then the number of carbon atoms is 7; and if $L_1$ is

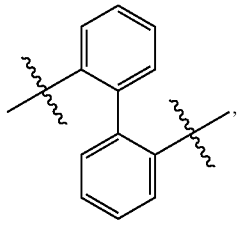 [SMILES: *c1ccccc1-c1ccccc1*]

the number of carbon atoms is 12.

In the present disclosure, aryl refers to an optional functional group or substituent derived from an aromatic carbocyclic ring. The aryl can be monocyclic aryl (e.g., phenyl) or polycyclic aryl, in other words, the aryl can be monocyclic aryl, fused aryl, two or more monocyclic aryls conjugatedly linked by carbon-carbon bonds, monocyclic aryl and fused aryl which are conjugatedly linked by a carbon-carbon bond, and two or more fused aryl conjugatedly linked by carbon-carbon bonds. That is, unless specified otherwise, two or more aromatic groups conjugatedly linked by carbon-carbon bonds can also be regarded as aryl of the present disclosure. The fused aryl may, for example, include bicyclic fused aryl (e.g., naphthyl), tricyclic fused aryl (e.g., phenanthryl, fluorenyl, and anthryl), and the like. The aryl does not contain heteroatoms such as B, N, O, S, P, Se, and Si. For example, in the present disclosure, phenyl, etc., are aryl. Examples of the aryl can include, but are not limited to, phenyl, naphthyl, fluorenyl, 9,9-dimethylfluorenyl, spirobifluorenyl, indenyl, anthryl, phenanthryl, biphenyl, terphenyl, tetraphenyl, pentaphenyl, benzo[9,10]phenanthryl, pyrenyl, fluoranthenyl, benzofluoranthenyl, chrysenyl, perylenyl, and the like. The "aryl" in the present disclosure can have one or more connecting bonds connected to the remaining part of the molecule. In the present disclosure, substituted aryl can be that one or two or more hydrogen atoms in the aryl are substituted by groups such as a deuterium atom, a halogen group, cyano (—CN), aryl, heteroaryl, trialkylsilyl, alkyl, cycloalkyl, alkoxy, alkylthio, and the like. Specific examples of aryl substituted by heteroaryl include, but are not limited to, phenyl substituted by dibenzofuranyl, phenyl substituted by dibenzothioenyl, phenyl substituted by pyridyl, and the like. It should be understood that the number of carbon atoms of the substituted aryl refers to the total number of carbon atoms of the aryl and substituents on the aryl, for example, substituted aryl with 18 carbon atoms means that the total number of carbon atoms of the aryl and the substituents is 18.

The number of carbon atoms of the "substituted or unsubstituted aryl" in the present disclosure is 6-40, and the number of carbon atoms can, for example, be 6, 10, 12, 13, 14, 15, 16, 17, 18, 19, 20, 25, 29, 30, 31, 32, 33, 34, 35, 36, 40, and the like. Specific examples of aryl include, but are not limited to, phenyl, naphthyl, biphenyl, terphenyl, anthryl, phenanthryl, fluorenyl, dimethylfluorenyl, spirobifluorenyl, and the like.

In the present disclosure, the number of carbon atoms of aryl as a substituent is 6-25, and the number of carbon atoms can, for example, be 6, 10, 12, 14, 18, 20, 25, and the like. Specific examples of the aryl as the substituent include, but are not limited to, phenyl, naphthyl, biphenyl, terphenyl, anthryl, phenanthryl, fluorenyl, dimethylfluorenyl, and the like.

In the present disclosure, the number of carbon atoms of substituted or unsubstituted aryl with 6 to 20 carbon atoms is, for example, 6 (phenyl), 10 (naphthyl), 12 (e.g., biphenyl), 14, 15 (dimethylfluorenyl), 16, and the like. The number of carbon atoms of heteroaryl with 3 to 20 carbon atoms is, for example, 5, 8, 12, 15, 18, and the like.

In the present disclosure, the number of carbon atoms of aryl with 6 to 12 carbon atoms is, for example, 6 (phenyl), 10 (naphthyl) or 12 (e.g. biphenyl).

In the present disclosure, involved arylene refers to a group formed by further loss of a hydrogen atom of the aryl. In some embodiments of the present disclosure, the arylene includes groups formed by further loss of one or two or more hydrogen atoms of the aryl, such as arylene. The definition of aryl may apply to arylene and arylidyne. In the formula (2), when m is 2, there are three chemical bonds connected to $L_1$, where one bond is connected to the core structure

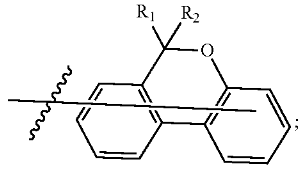

and the other two single bonds are each connected to one group

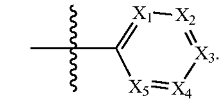

For example, when $L_1$ is phenylene and m is 2, $L_1$ has a structure shown as

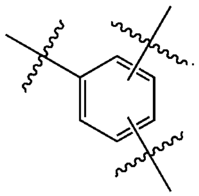

In some embodiments, n is 1 and m is selected from 1 or 2, or n is 2 and m is 1.

In the present disclosure, heteroaryl refers to a monovalent aromatic ring containing 1, 2, 3, 4, 5, 6, or 7 heteroatoms in the ring, or its derivative, where the heteroatoms may be at least one of B, O, N, P, Si, Se, and S. The heteroaryl can be monocyclic heteroaryl or polycyclic heteroaryl, in other words, the heteroaryl can be a single aromatic ring system or a plurality of aromatic ring systems conjugatedly linked via carbon-carbon bonds, and any one aromatic ring system is one aromatic monocyclic ring or one aromatic fused ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenothiazinyl, phenoxazinyl, phthalazinyl, pyridopyrimidinyl, pyridopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, silafluorenyl, dibenzofuranyl, N-phenylcarbazolyl, N-pyridylcarbazolyl, N-methylcarbazolyl and the like, but is not limited to these. Thienyl, furyl, phenanthrolinyl, etc. are heteroaryl of the single aromatic ring system, and N-arylcarbazolyl, and N-heteroarylcarbazolyl are heteroaryl of the plurality of ring systems conjugatedly linked via carbon-carbon bonds.

The number of carbon atoms of "substituted or unsubstituted heteroaryl" in the present disclosure is 3-40, and the number of carbon atoms can, for example, be 3, 4, 5, 6, 7, 8, 9, 10, 11, 12, 13, 14, 15, 16, 17, 18, 19, 20, 25, 29, 30, 31, 32, 33, 34, 35, 36, 40, and the like. Specific examples of the heteroaryl include, but are not limited to, pyridyl, pyrimidinyl, triazinyl, quinolyl, isoquinolyl, benzoxazinyl, carbazolyl, indolyl, dibenzofuranyl, dibenzothienyl, carbazolyl, N-phenylcarbazolyl, benzimidazolyl, benzoxazolyl, dibenzothianthryl, acridinyl, dibenzodioxinyl, phenoxytheophyllinyl, thianthryl, phenothiazinyl, benzoxazinyl and the like.

It can be understood that "heteroaryl" can have one, two, or a plurality of bonds connected to other parts of the molecule.

In the present disclosure, involved heteroarylene refers to a group formed by further loss of hydrogen atoms of the heteroaryl. In some embodiments of the present disclosure, the heteroarylene includes groups formed by further loss of one or two or more hydrogen atoms of the heteroaryl, such as heteroarylidyne. The definition of heteroaryl may apply to heteroarylene and heteroarylidyne. In the present disclosure, substituted heteroaryl may be that one or two or more hydrogen atoms in the heteroaryl are substituted by groups such as a deuterium atom, a halogen group, —CN, aryl, heteroaryl, trialkylsilyl, alkyl, cycloalkyl, alkoxy, alkylthio, and the like. Specific examples of heteroaryl substituted by aryl include, but are not limited to, dibenzofuranyl substituted by phenyl, dibenzothienyl substituted by phenyl, pyridyl substituted by phenyl, and the like. It should be understood that the number of carbon atoms of the substituted heteroaryl refers to the total number of carbon atoms of the heteroaryl and substituents on the heteroaryl.

In the present disclosure, a 5- to 10-membered heteroaromatic ring refers to a heteroaromatic ring having a total number of atoms on one heteroaromatic ring being 5, 6, 7, 8, 9, or 10; for example, a quinoline ring is a 10-membered heteroaromatic ring, a pyrimidine ring is a 6-membered heteroaromatic ring, a pyridine ring is a 6-membered heteroaromatic ring, a pyrrole ring is a 5-membered heteroaromatic ring, and a furan ring is a 5-membered heteroaromatic ring. In other embodiments, the heteroaromatic ring may also be a 5- to 10-membered heteroaromatic ring.

In the present disclosure, the number of carbon atoms of heteroaryl as a substituent is 3 to 20, and the number of carbon atoms can, for example, be 3, 4, 5, 7, 8, 9, 12, 18, 20, and the like. Specific examples of the heteroaryl as the substituent include, but are not limited to, pyridyl, quinolyl, dibenzofuranyl, dibenzothienyl, carbazolyl, N-phenylcarbazolyl, and the like.

In the present disclosure, a 5- to 10-membered aromatic ring refers to an aromatic ring having a total number of atoms on one aromatic ring being 5, 6, 7, 8, 9, or 10; for example, a naphthalene ring is a 10-membered aromatic ring, a benzene ring is a 6-membered aromatic ring, and an indene ring is a 9-membered aromatic ring. In other embodiments, the aromatic ring may also be a 6- to 10-membered aromatic ring.

In the present disclosure, specific examples of trialkylsilyl with 3 to 12 carbon atoms include, but are not limited to, trimethylsilyl, triethylsilyl, tert-butyldimethylsilyl, and the like.

In the present disclosure, specific examples of cycloalkyl with 3 to 12 carbon atoms include, but are not limited to, cyclopentyl, cyclohexyl, adamantyl, and the like. In some embodiments, the cycloalkyl is cycloalkyl with 5 to 7 carbon atoms including cyclopentyl, cyclohexyl, and cycloheptyl.

In the present disclosure, specific examples of arylsilyl with 8 to 18 carbon atoms include, but are not limited to, triphenylsilyl.

In the present disclosure, "alkyl" refers to a saturated linear or branched monovalent hydrocarbyl group, and the alkyl may be optionally substituted by one or more substituents described in the present disclosure. Specifically, the alkyl with 1 to 20 carbon atoms may be linear alkyl with 1 to 20 carbon atoms, or branched alkyl with 3 to 20 carbon atoms. The number of carbon atoms may, for example, be 1, 2, 3, 4, 5, 6, 7, 8, 9, 10, 11, 12, 13, 14, 15, 16, 17, 18, 19 or 20. In some embodiments, the alkyl in the present disclosure contains 1 to 10 carbon atoms; in other embodiments, the alkyl in the present disclosure contains 1 to 6 carbon atoms; in yet other embodiments, the alkyl in the present disclosure contains 1 to 4 carbon atoms; and in other embodiments, the alkyl in the present disclosure contains 1 to 3 carbon atoms. Specific examples of the alkyl include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 2-methylpentyl, 2-ethylbutyl, heptyl, n-heptyl, octyl, n-octyl, tert-octyl, n-nonyl, decyl, and the like, but are not limited to these. Examples of alkyl with 1 to 4 carbon atoms in the present disclosure include, but are not limited to, methyl (Me, $—CH_3$), ethyl (Et, $—CH_2CH_3$), n-propyl (n-Pr, $—CH_2CH_2CH_3$), isopropyl (i-Pr, $—CH(CH_3)_2$), n-butyl (n-Bu, $—CH_2CH_2CH_2CH_3$), t-butyl (t-Bu, $—C(CH_3)_3$), and the like.

In the present disclosure, the halogen group may be fluorine, chlorine, bromine or iodine.

In the present disclosure, a connecting bond is represented by

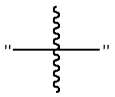 or 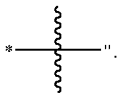

In the present disclosure, an unpositioned connecting bond refers to a single bond

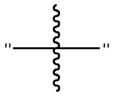

extending from a ring system, which indicates that one end of the connecting bond can be connected to any position in the ring system through which the bond penetrates, and the other end of the connecting bond is connected to the remaining part of a compound molecule.

For example, as shown in the following formula (f), naphthyl represented by the formula (f) is connected to other positions of a molecule through two unpositioned connecting bonds penetrating a dicyclic ring, and its meaning includes any one possible connecting mode represented by formulae (f-1) to (f-10).

(f)

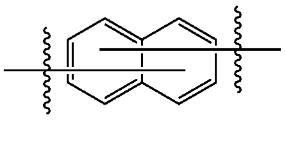

(f-1)

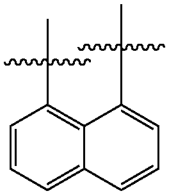

-continued (f-2)

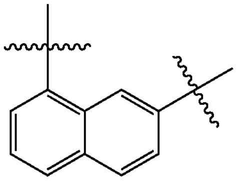

(f-3)

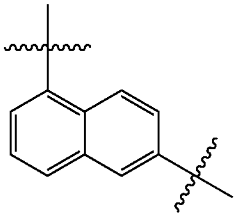

(f-4)

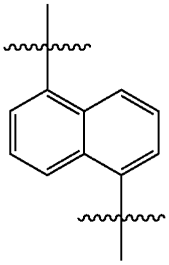

(f-5)

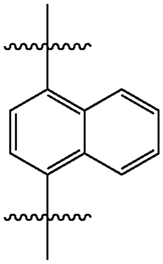

(f-6)

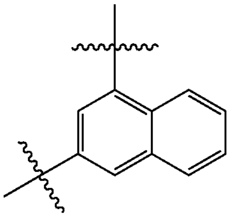

(f-7)

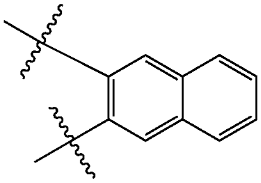

(f-8)

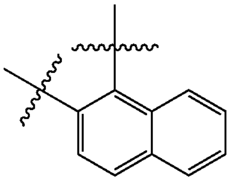

-continued (f-9)

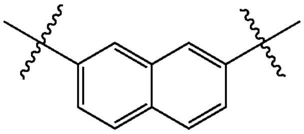

(f-10)

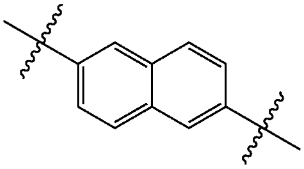

For another example, as shown in the following formula (X'), fluorenyl represented by the formula (X') is connected with other positions of a molecule through one unpositioned connecting bond extending from the center of a benzene ring on one side, and its meaning includes any possible connecting mode represented by formulae (X'-1) to (X'-5).

(X')

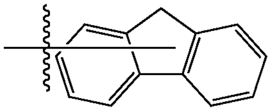

(X'-1)

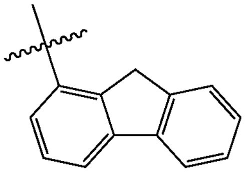

(X'-2)

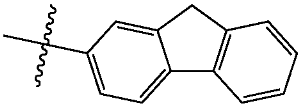

(X'-3)

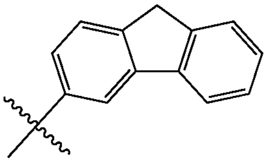

(X'-4)

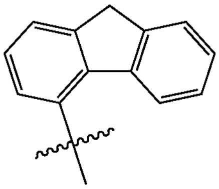

(X'-5)

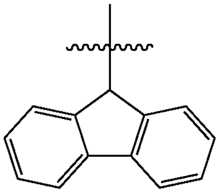

An unpositioned substituent in the present disclosure refers to a substituent connected through a single bond extending from the center of a ring system, which means that the substituent can be connected to any possible position in the ring system. For example, as shown in the following formula (Y), a substituent R represented by the formula (Y) is connected with a quinoline ring through one unpositioned connecting bond, and its meaning includes any possible connecting mode represented by formulae (Y-1) to (Y-7).

(Y)

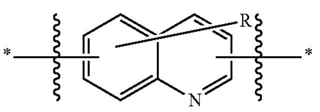

(Y-1)

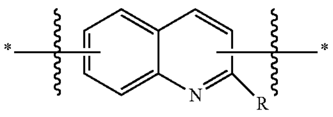

(Y-2)

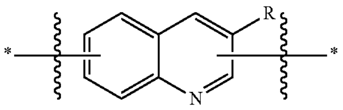

(Y-3)

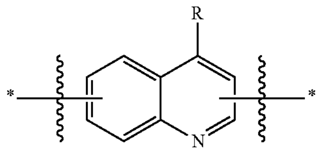

(Y-4)

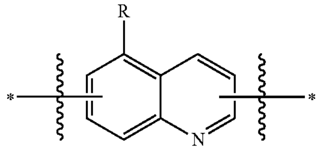

(Y-5)

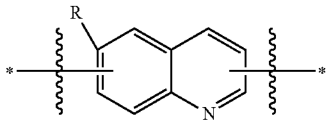

(Y-6)

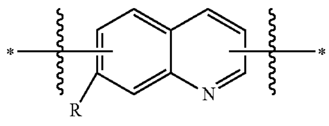

(Y-7)

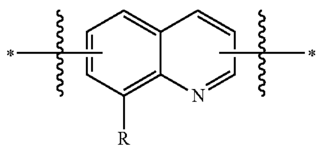

In one specific embodiment of the present disclosure, the organic compound has a structure represented by the following formula (1-1), formula (1-2), formula (1-3), or formula (1-4):

Formula (1-1)

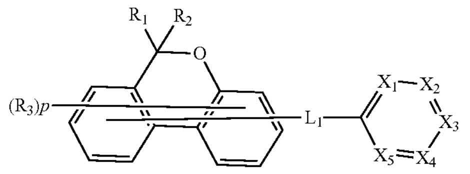

Formula (1-2)

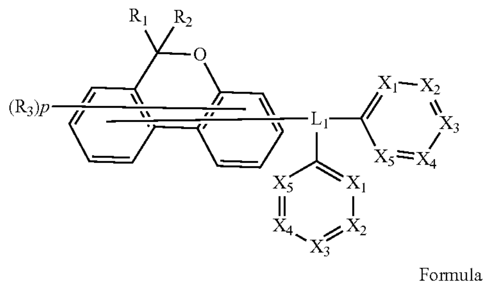

Formula (1-3)

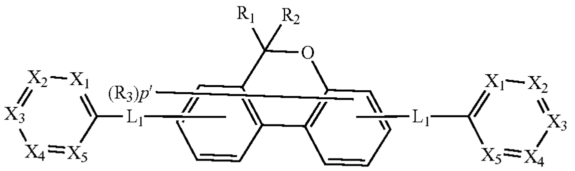

Formula (1-4)

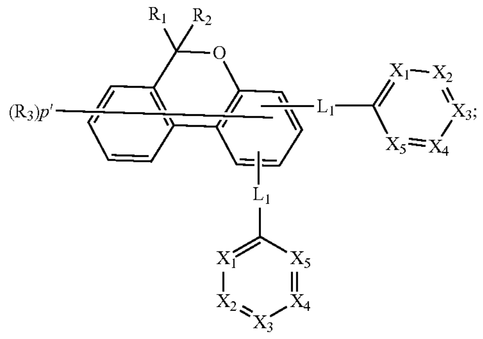

in the formula (1-3) and the formula (1-4), p' is selected from 0, 1, 2, 3, 4, 5 or 6. In the formula (1-2), the formula (1-3) and the formula (1-4), each $X_1$ is the same as or different from each other, each $X_2$ is the same as or different from each other, each $X_3$ is the same as or different from each other, each $X_4$ is the same as or different from each other, and each $X_5$ is the same as or different from each other; and in the formula (1-3) and the formula (1-4), each $L_1$ is the same as or different from each other.

In one specific embodiment of the present disclosure, $X_1$, $X_3$ and $X_5$ are N, and $X_2$ and $X_4$ are $C(R_4)$; each $R_4$ is the same as or different from each other, and is independently

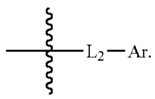

In one specific embodiment of the present disclosure, $R_1$ and $R_2$ are the same as or different from each other, and are each independently selected from substituted or unsubstituted methyl, and substituted or unsubstituted phenyl; substituents on the substituted methyl are each independently selected from the group consisting of cyano, fluorine, chlorine and deuterium, and substituents in the substituted phenyl are each independently selected from the group consisting of cyano, fluorine, chlorine, deuterium, methyl, ethyl, isopropyl, tert-butyl, and trimethylsilyl.

In one specific embodiment of the present disclosure, $R_1$ and $R_2$ are the same as or different from each other, and are each independently selected from methyl, and substituted or unsubstituted phenyl, and the substituents in the substituted phenyl are each independently selected from the group consisting of cyano, fluorine, chlorine, deuterium, methyl, ethyl, isopropyl, tert-butyl, and trimethylsilyl.

In one embodiment of the present disclosure, the Y has a structure represented by the following formula (2-1):

Formula (2-1)

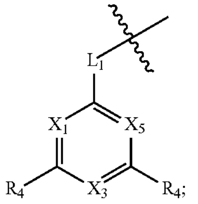

where $X_1$, $X_3$, and $X_5$ are the same or different, and are each independently $C(R_4)$ or N, and any one, any two, or all of $X_1$, $X_3$, and $X_5$ are N; and each $R_4$ is the same or different, and is independently hydrogen or

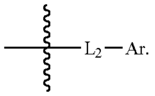

In another embodiment of the present disclosure, the Y has a structure represented by the following formula (2-2):

Formula (2-2)

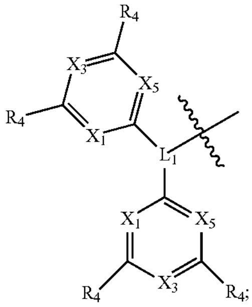

where $X_1$, $X_3$, and $X_5$ are the same or different, and are each independently $C(R_4)$ or N, and any one, any two, or all of $X_1$, $X_3$, and $X_5$ are N; and each $R_4$ is the same or different, and is independently hydrogen or

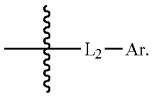

In one specific embodiment of the present disclosure, the Y has a structure represented by the following formulas (2-1-1) to (2-1-5):

Formula (2-1-1)

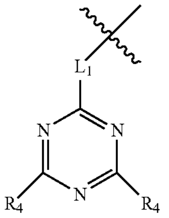

Formula (2-1-2)

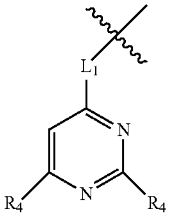

Formula (2-1-3)

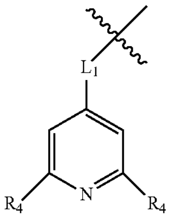

Formula (2-1-4)

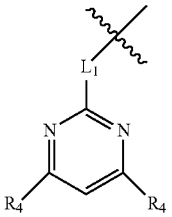

Formula (2-1-51)

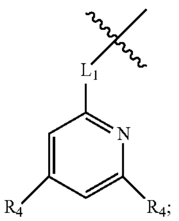

each $R_4$ is the same or different, and is independently hydrogen or $+L_2$-Ar.

In another specific embodiment of the present disclosure, the Y has a structure represented by the following formula (2-1-6):

Formula (2-1-6)

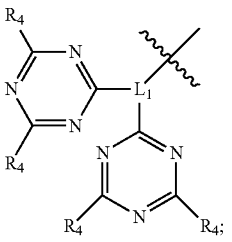

each $R_4$ is the same or different, and is independently hydrogen or

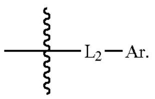

In one embodiment of the present disclosure, each Ar is independently selected from substituted or unsubstituted alkyl with 1 to 6 carbon atoms, substituted or unsubstituted cycloalkyl with 5 to 10 carbon atoms, or the group consisting of groups represented by the following formulae (i-1) to (i-18):

(i-1)

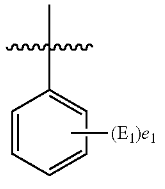

(i-2)

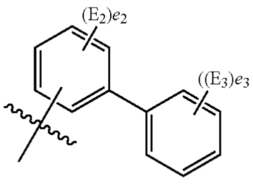

(i-3)

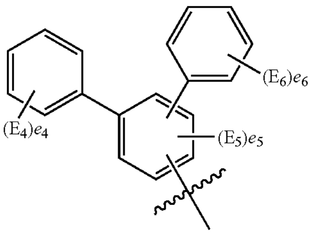

(i-4)

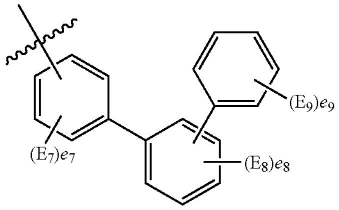

-continued (i-5)

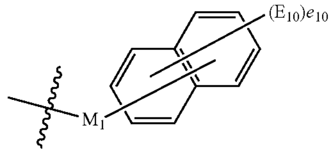

(i-6)

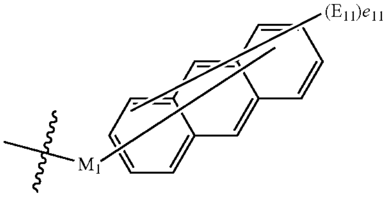

(i-7)

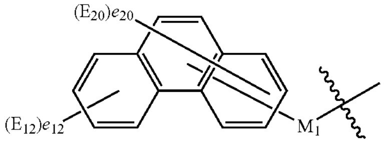

(i-8)

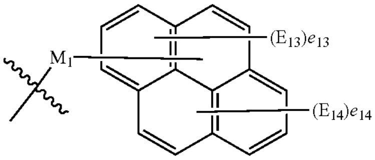

(i-9)

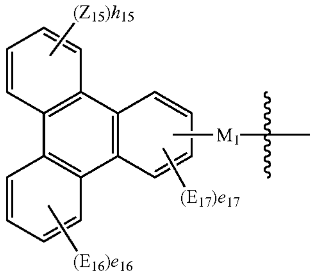

(i-10)

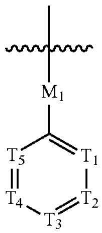

(i-11)

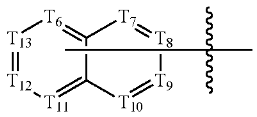

(i-12)

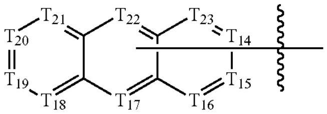

-continued (i-13)

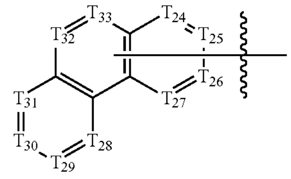

(i-14)

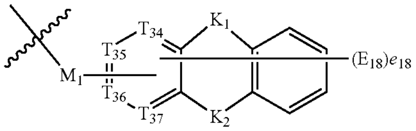

(i-15)

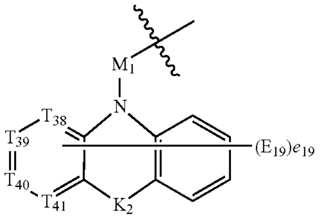

(i-16)

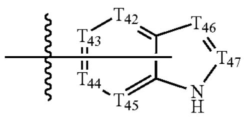

(i-17)

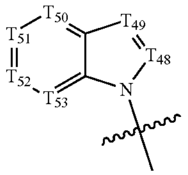

(i-18)

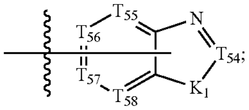

where $M_1$ is selected from a single bond or

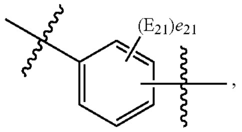

$T_1$ to $T_5$ are each independently selected from N or $C(Q_1)$, and at least one of $T_1$ to $T_5$ is selected from N; and when two or more of $T_1$ to $T_5$ are selected from $C(Q_1)$, any two $Q_1$ are the same or different;

$T_6$ to $T_{13}$ are each independently selected from N or $C(Q_2)$, and at least one of $T_6$ to $T_{13}$ is selected from N; and when two or more of $T_6$ to $T_{13}$ are selected from $C(Q_2)$, any two $Q_2$ are the same or different;

$T_{14}$ to $T_{23}$ are each independently selected from N or $C(Q_3)$, and at least one of $T_{14}$ to $T_{23}$ is selected from N; and when two or more of $T_{14}$ to $T_{23}$ are selected from $C(Q_3)$, any two $Q_3$ are the same or different;

$T_{24}$ to $T_{33}$ are each independently selected from N or $C(Q_4)$, and at least one of $T_{24}$ to $T_{33}$ is selected from N; and when two or more of $T_{24}$ to $T_{33}$ are selected from $C(Q_4)$, any two $Q_4$ are the same or different;

$T_{34}$ to $T_{37}$ are each independently selected from N or $C(Q_5)$, and at least one of $T_{34}$ to $T_{37}$ is selected from N; when two or more of $T_{34}$ to $T_{37}$ are selected from $C(Q_5)$, any two $Q_5$ are the same or different; and optionally, two adjacent $Q_5$ form a 6- to 10-membered aromatic ring or a 5- to 10-membered heteroaromatic ring;

$T_{38}$ to $T_{41}$ are each independently selected from N or $C(Q_6)$, and at least one of $T_{38}$ to $T_{41}$ is selected from N; when two or more of $T_{38}$ to $T_{41}$ are selected from $C(Q_6)$, any two $Q_6$ are the same or different; and optionally, two adjacent $Q_6$ form a 6- to 10-membered aromatic ring or a 5- to 10-membered heteroaromatic ring;

$T_{42}$ to $T_{58}$ are each independently selected from N or $C(Q_7)$, and at least one of $T_{42}$ to $T_{58}$ is selected from N; when two or more of $T_{42}$ to $T_{58}$ are selected from $C(Q_7)$, any two $Q_7$ are the same or different; and optionally, two adjacent $Q_7$ form a 6- to 10-membered aromatic ring or a 5- to 10-membered heteroaromatic ring;

$E_1$ is selected from hydrogen, deuterium, fluorine, chlorine, bromine, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, and alkylthio with 1 to 10 carbon atoms;

$E_2$ to $E_6$, and $E_{21}$ are each independently selected from hydrogen, deuterium, fluorine, chlorine, bromine, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, or heteroaryl with 3 to 18 carbon atoms;

$E_7$ to $E_2M$, and $Q_1$ to $Q_7$ are each independently selected from hydrogen, deuterium, fluorine, chlorine, bromine, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, aryl with 6 to 18 carbon atoms, and heteroaryl with 3 to 18 carbon atoms;

$e_1$ to $e_{21}$ are represented by $e_k$, $E_1$ to $E_{21}$ are represented by $E_k$, k is a variable, and represents any integer from 1 to 21, and $e_k$ represents the number of a substituent $E_k$;

when k is selected from 5 or 17, $e_k$ is selected from 1, 2 or 3;

when k is selected from 2, 7, 8, 12, 15, 16, 18 or 21, $e_k$ is selected from 1, 2, 3 or 4;

when k is selected from 1, 3, 4, 6, 9, 14 or 20, $e_k$ is selected from 1, 2, 3, 4 or 5;

when k is 13, $e_k$ is selected from 1, 2, 3, 4, 5, or 6;

when k is selected from 10 or 19, $e_k$ is selected from 1, 2, 3, 4, 5, 6 or 7;

when k is 11, $e_k$ is selected from 1, 2, 3, 4, 5, 6, 7, 8 or 9; and when $e_k$ is greater than 1, any two $E_k$ are the same or different;

$K_1$ is selected from O, S, $N(E_{22})$, $C(E_{23}E_{24})$, and $Si(E_{23}E_{24})$; where $E_{22}$, $E_{23}$, and $E_{24}$ are each independently selected from hydrogen, aryl with 6 to 18 carbon atoms, heteroaryl with 3 to 18 carbon atoms, alkyl with 1 to 10 carbon atoms, or cycloalkyl with 3 to 10 carbon atoms, or the $E_{23}$ and the $E_{24}$ are connected to each other to form a saturated or unsaturated ring with 3 to 15 carbon atoms together with the atoms to which they are jointly connected; and $K_2$ is selected from a single bond, O, S, $N(E_{25})$, $C(E_{26}E_{27})$, and $Si(E_{26}E_{27})$; where $E_{25}$, $E_{26}$, and $E_{27}$ are each independently selected from hydrogen, aryl with 6 to 18 carbon atoms, heteroaryl with 3 to 18 carbon atoms, alkyl with 1 to 10 carbon atoms, or cycloalkyl with 3 to 10 carbon atoms, or the $E_{26}$ and the $E_{27}$ are connected to each other to form a saturated or unsaturated ring with 3 to 15 carbon atoms together with the atoms to which they are jointly connected.

In the present disclosure, in both groups of the $E_{23}$ and the $E_{24}$, and the $E_{26}$ and the $E_{27}$, the two groups in each group may be present independently of each other and may be connected to each other to form a ring, and the ring formed by connecting the two groups with each other may be a saturated or unsaturated ring with 3 to 15 carbon atoms. For example, in the formula (i-14), when $K_2$ and $M_1$ are both a single bond, each $E_{18}$ is hydrogen, $T_{34}$ to $T_{37}$ are all C(H), and $K_1$ is $C(E_{23}E_{24})$, and $E_{23}$ and $E_{24}$ are connected to each other to form a 5-membered ring together with the atoms to which they are jointly connected, the formula (i-14) is

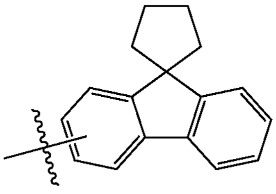
;

likewise, the formula (i-14) may also represent

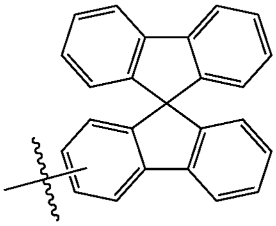
, that is, $E_{23}$ and $E_{24}$ are connected to each other to form a partially unsaturated 13-membered ring together with the atoms to which they are jointly connected. Of course, the number of atoms of the formed ring can also be other numbers, which will not be repeated here.

In the present disclosure, "optionally, two adjacent $Q_5$ form a 6- to 10-membered aromatic ring or a 5- to 10-membered heteroaromatic ring", which means that in the formula (i-14), any two adjacent $Q_5$ may be present independently of each other and may also be connected to each other to form a fused aromatic or heteroaromatic ring, and the fused ring formed may be a 5- to 10-membered aromatic ring or a 5- to 10-membered heteroaromatic ring. For example, in the formula (i-14), when $K_2$ and $M_1$ are both a single bond, each $E_{18}$ is hydrogen, and $K_1$ is —NH—, $T_{34}$ and $T_{37}$ are —CH—, $T_{35}$ and $T_{36}$ are $C(Q_5)$, and the two are connected to each other to form a 6-membered aromatic ring, the formula (i-14) is

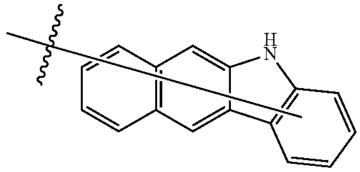
;

of course, the number of atoms of the formed ring can also be other numbers, which will not be repeated here. "Optionally, two adjacent $Q_6$ form a 6- to 10-membered aromatic ring or a 5- to 10-membered heteroaromatic ring" and "optionally, two adjacent $Q_7$ form a 6- to 10-membered aromatic ring or a 5- to 10-membered heteroaromatic ring", which have a same meaning, which will not be repeated.

In some embodiments, each Ar is independently selected from the group consisting of substituted or unsubstituted aryl with 6 to 19 carbon atoms, substituted or unsubstituted heteroaryl with 5 to 18 carbon atoms, substituted or unsubstituted alkyl with 1 to 4 carbon atoms, and substituted or unsubstituted cycloalkyl with 5 to 7 carbon atoms. Further, each Ar is independently selected from substituted or unsubstituted aryl with 6, 10, 12, 13, 14, 15, 16, 17, 18, 19, or 20 carbon atoms, or substituted or unsubstituted heteroaryl with 3, 5, 8, 9, 12, 16, or 18 carbon atoms.

In some embodiments, substituents in each Ar are independently selected from the group consisting of alkyl with 1 to 4 carbon atoms, alkoxy with 1 to 4 carbon atoms, trifluoromethyl, trimethylsilyl, triphenylsilyl, cycloalkyl with 5 to 7 carbon atoms, phenyl, naphthyl, dibenzofuranyl, dibenzothienyl, carbazolyl, pyridyl, pyrimidinyl, indolyl, and benzimidazolyl.

Further, the substituents in each Ar are independently selected from the group consisting of deuterium, fluorine, chlorine, cyano, methyl, ethyl, isopropyl, tert-butyl, methoxy, ethoxy, isopropoxy, propoxy, cyclopentyl, cyclohexyl, trifluoromethyl, phenyl, biphenyl, naphthyl, trimethylsilyl, and triphenylsilyl.

In some specific embodiments of the present disclosure, each Ar is independently selected from a substituted or unsubstituted group $W_3$, and the unsubstituted group $W_3$ is selected from the group consisting of:

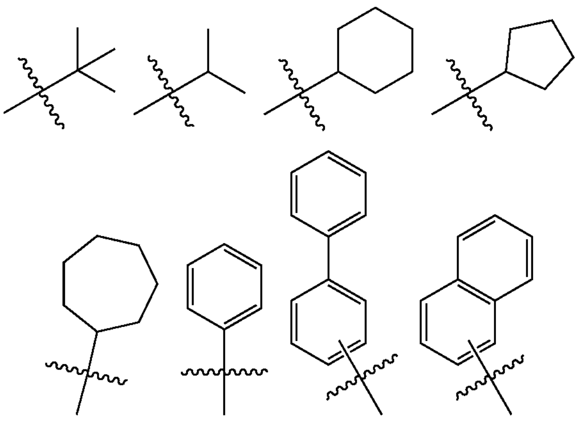

-continued
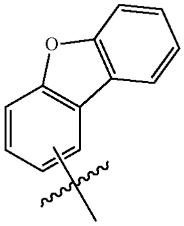
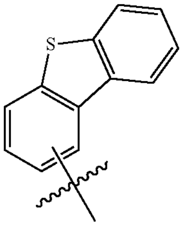
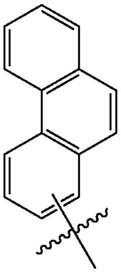
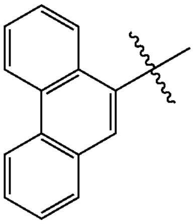
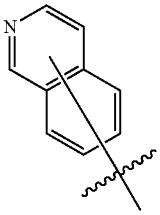
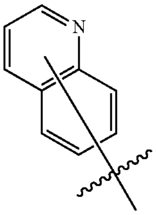
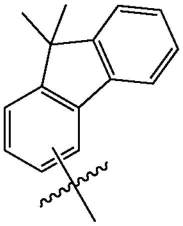
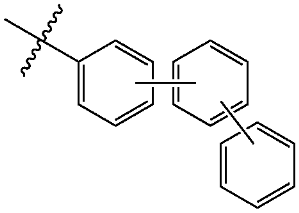
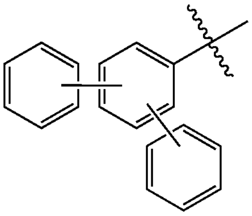
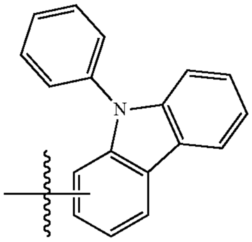
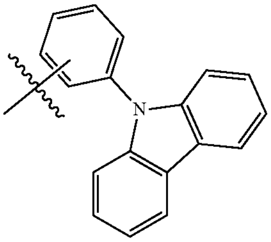
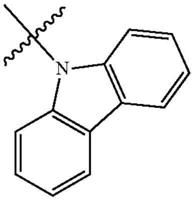
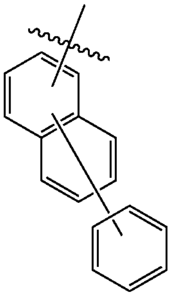
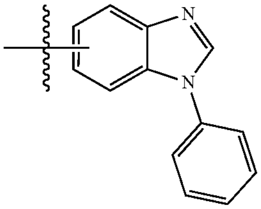
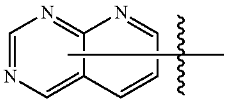
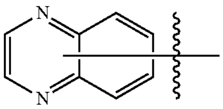
-continued
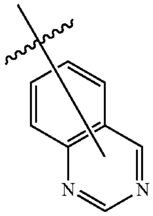
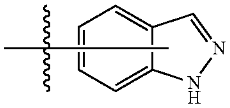
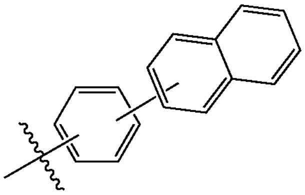
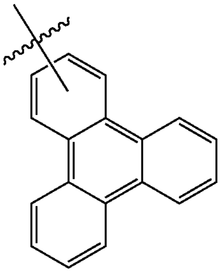
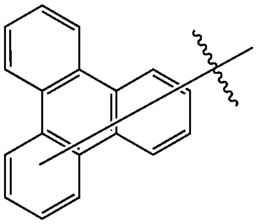
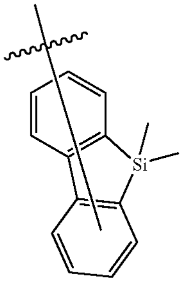
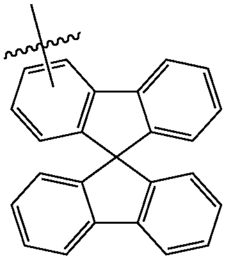
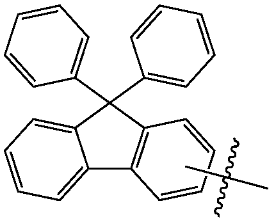
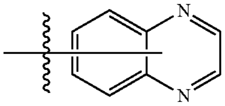
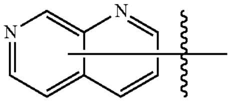
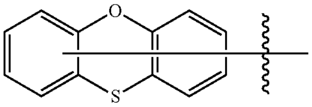
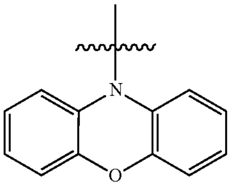
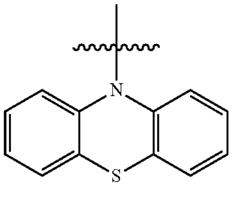
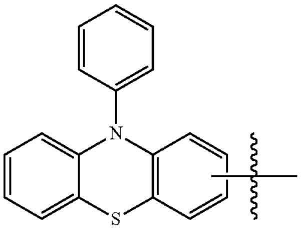
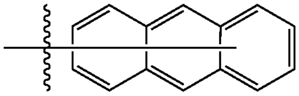

-continued

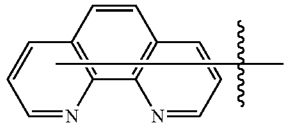

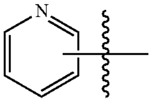

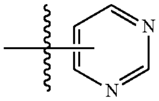

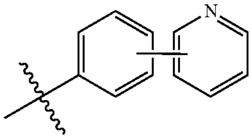

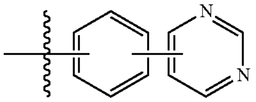

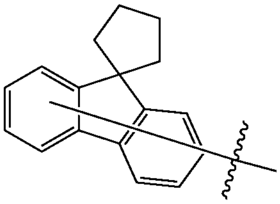

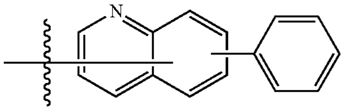

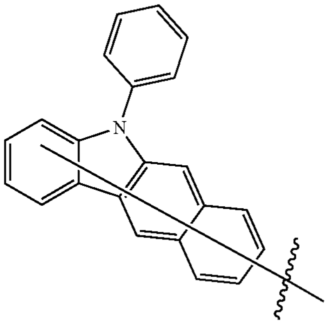

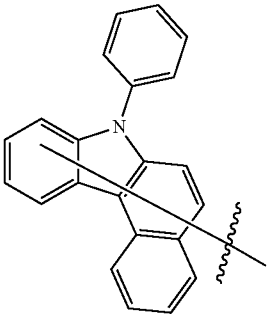

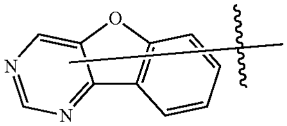

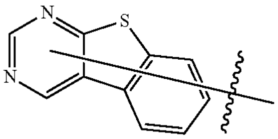

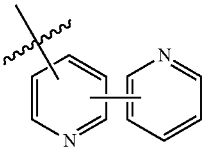

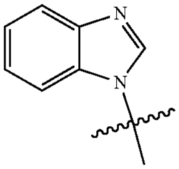

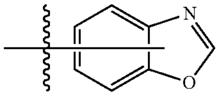

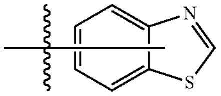

-continued

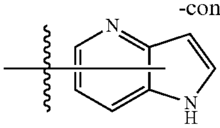

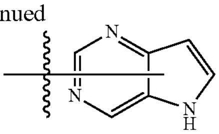

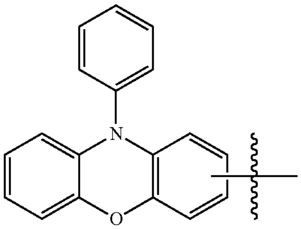

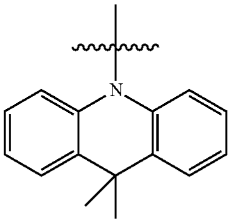

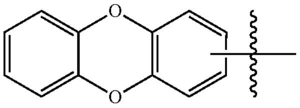

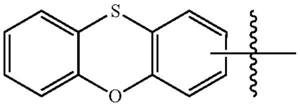

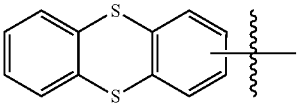

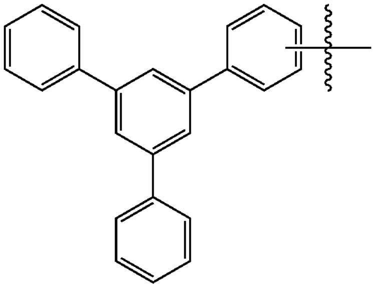

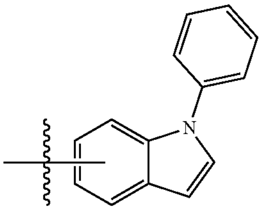

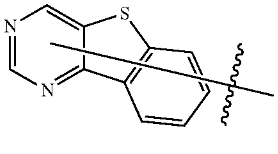

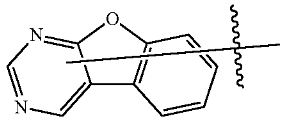

;

and when the group $W_3$ is substituted, the substituents in the group $W_3$ are selected from the group consisting of deuterium, fluorine, chlorine, cyano, alkyl with 1 to 4 carbon atoms, alkoxy with 1 to 4 carbon atoms, trifluoromethyl, trimethylsilyl, triphenylsilyl, cycloalkyl with 5 to 7 carbon atoms, phenyl, naphthyl, dibenzofuranyl, dibenzothienyl, carbazolyl, pyridyl, pyrimidinyl, indolyl, and benzimidazolyl; and when the group $W_3$ has a plurality of substituents, the substituents are the same as or different from each other.

In some more specific embodiments, each Ar is independently selected from: substituted or unsubstituted phenyl, substituted or unsubstituted biphenyl, substituted or unsubstituted terphenyl, substituted or unsubstituted naphthyl, substituted or unsubstituted dibenzofuranyl, substituted or unsubstituted dibenzothienyl, substituted or unsubstituted quinolyl, substituted or unsubstituted carbazolyl, substituted or unsubstituted naphthyl, substituted or unsubstituted fluorenyl, substituted or unsubstituted anthryl, substituted or unsubstituted phenanthryl, substituted or unsubstituted pyrimidinyl, substituted or unsubstituted pyridyl, substituted or unsubstituted pyrazinyl, substituted or unsubstituted quinolyl, substituted or unsubstituted isoquinolyl, substituted or unsubstituted quinazolinyl, substituted or unsubstituted benzoxazinyl, substituted or unsubstituted indolyl, substituted or unsubstituted benzimidazolyl, substituted or unsubstituted benzoxazolyl, substituted or unsubstituted dibenzothianthryl, substituted or unsubstituted acridinyl, substituted or unsubstituted dibenzodioxinyl, substituted or unsubstituted phenoxytheophyllinyl, substituted or unsubstituted thianthryl, substituted or unsubstituted phenothiazinyl, substituted or unsubstituted benzoxazinyl, or a group formed by linking two or three of the above groups via a single bond; and substitution in each Ar means that each Ar is optionally substituted by 1, 2, 3, 4, 5, 6, 7, or 8 substituents selected from deuterium, fluorine, chlorine, cyano, methyl, ethyl, isopropyl, tert-butyl, methoxy, ethoxy, isopropoxy, propoxy, cyclopentyl, cyclohexyl, trifluoromethyl, phenyl, biphenyl, naphthyl, trimethylsilyl, or triphenylsilyl.

In one more specific embodiment, each Ar is independently selected from any one of the following groups:

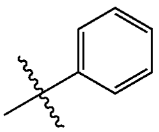
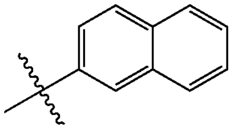
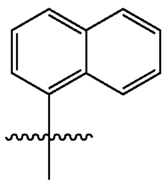
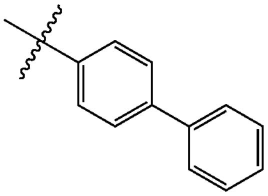
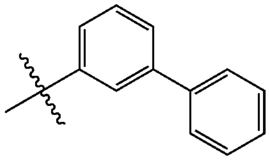
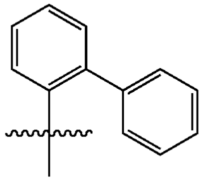
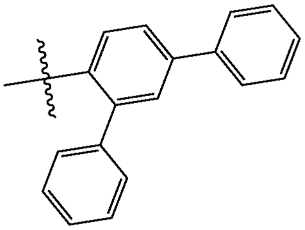
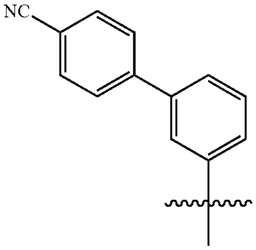

-continued

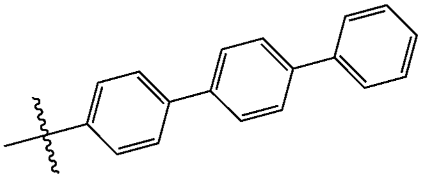
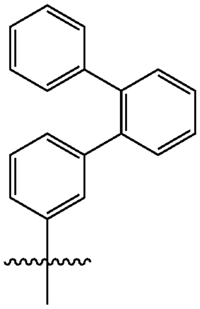
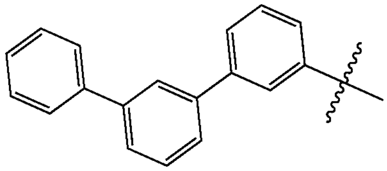
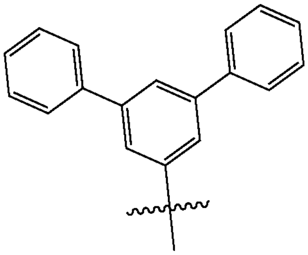
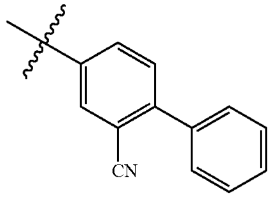
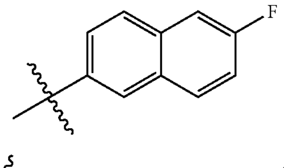
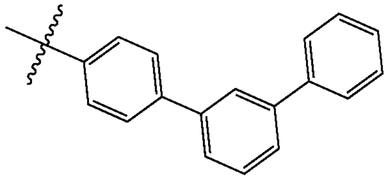
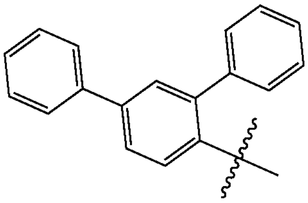

-continued
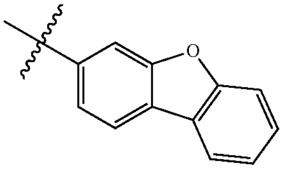
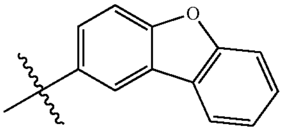
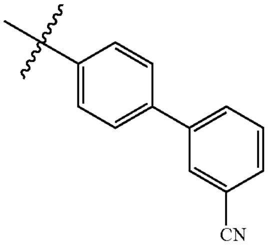
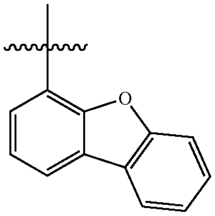
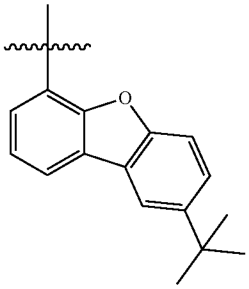
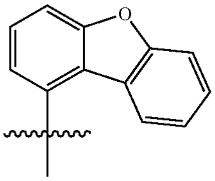
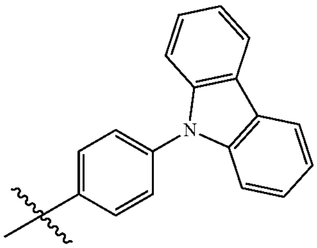
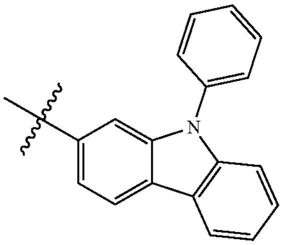
-continued
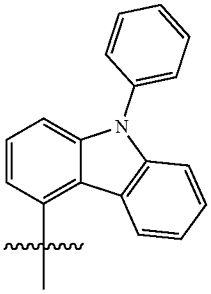
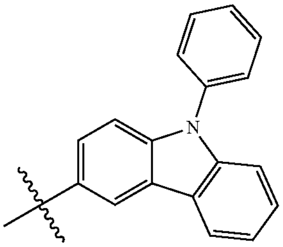
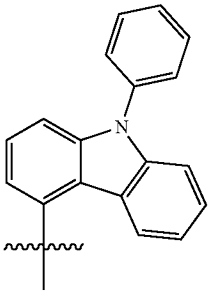
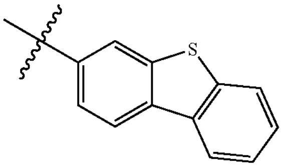
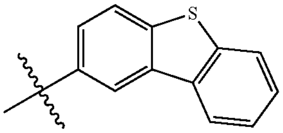
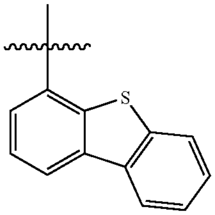
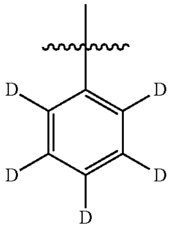
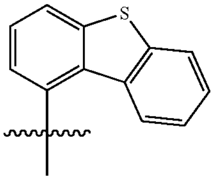
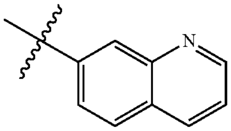
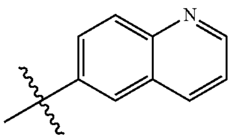

-continued
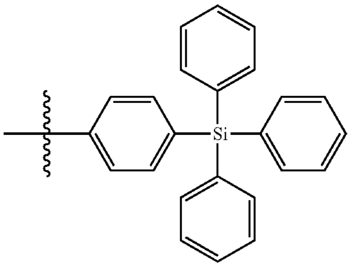
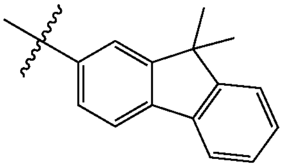
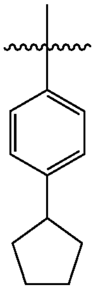
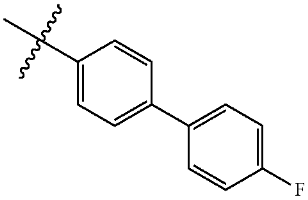
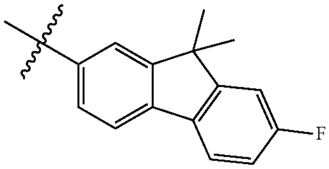
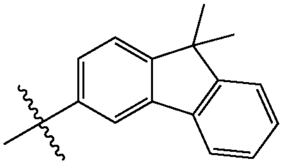
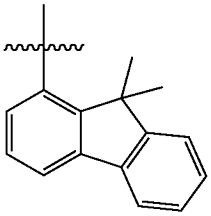
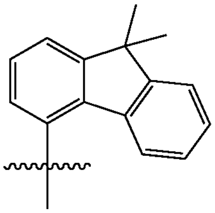
-continued
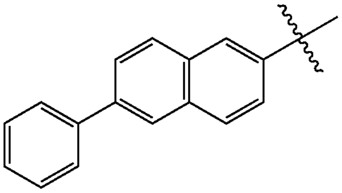
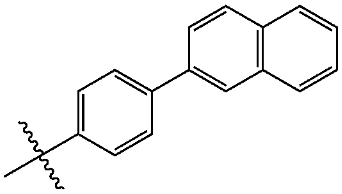
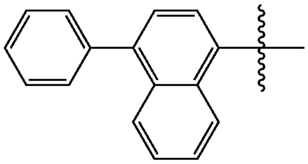
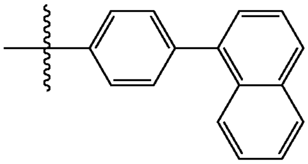
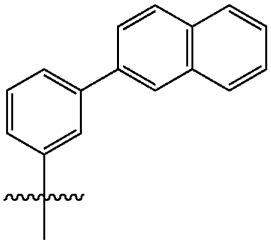
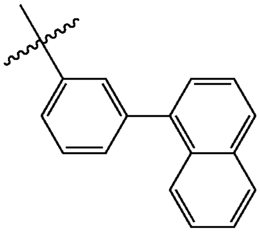
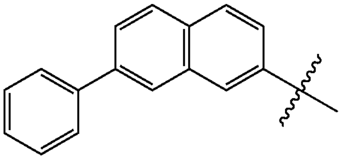
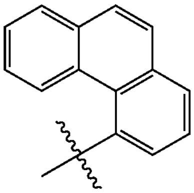
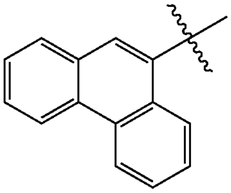

-continued
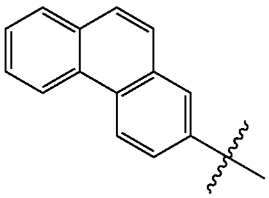
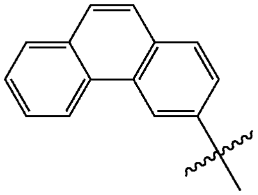
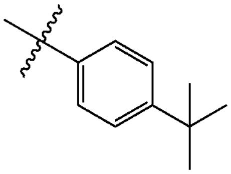
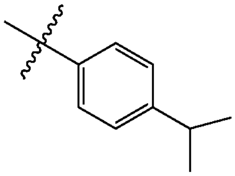
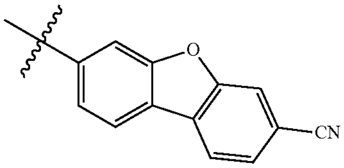
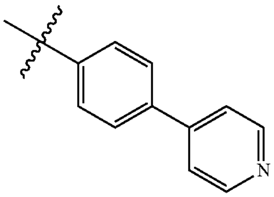
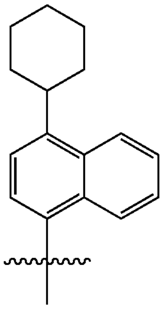
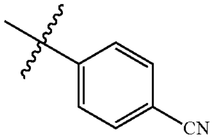
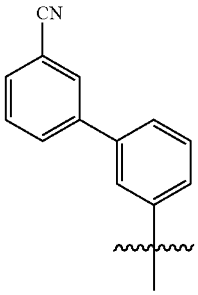
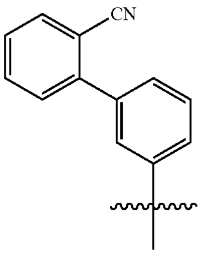
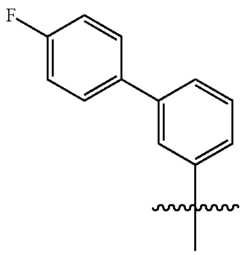
-continued
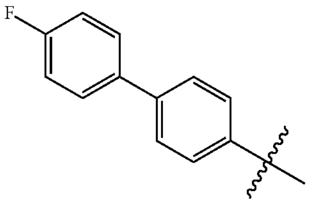
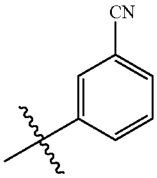
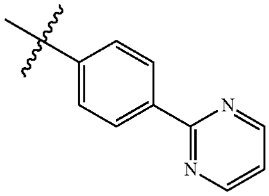
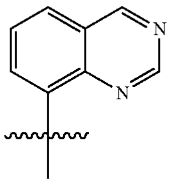
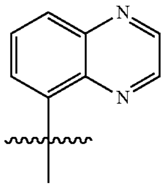
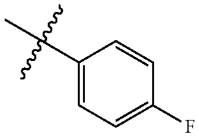
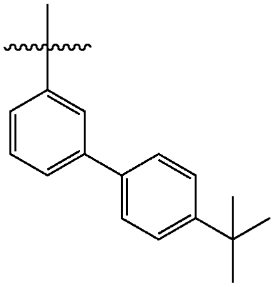
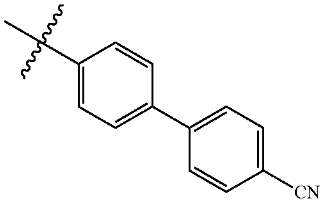
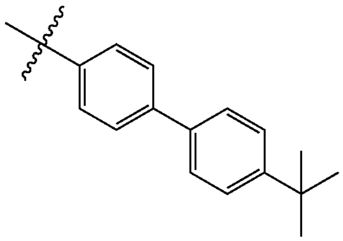
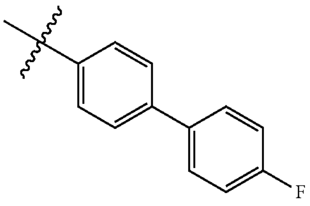

-continued
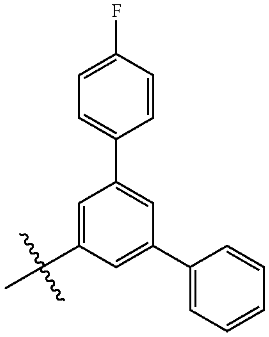
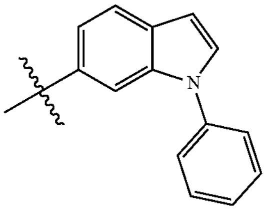
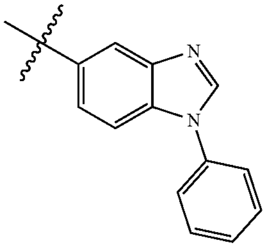
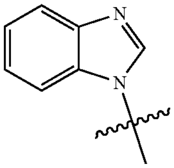
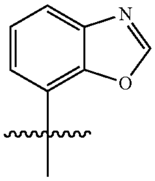
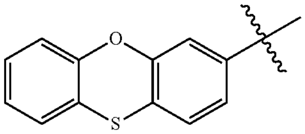
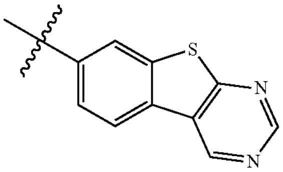
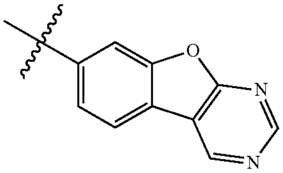
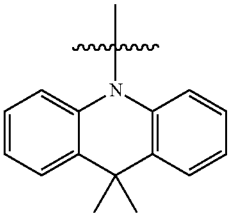
-continued
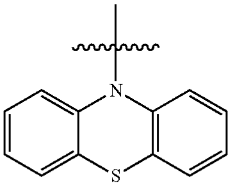
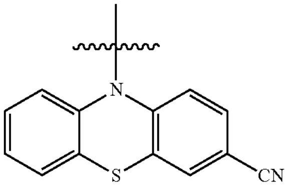
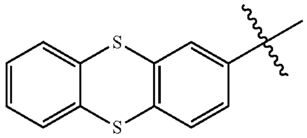
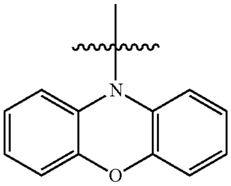
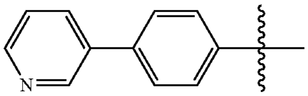
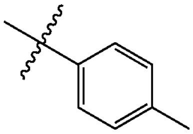
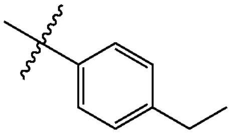
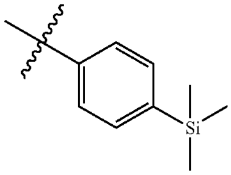
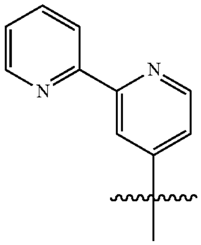
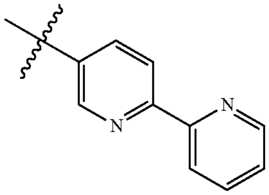
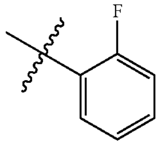
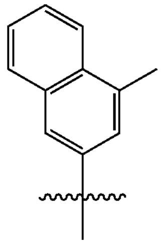

-continued
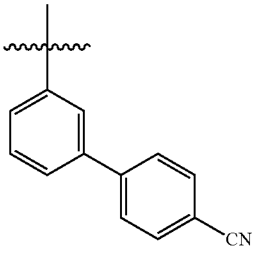
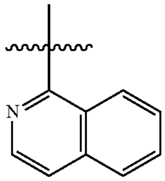
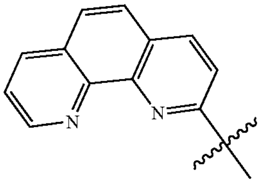
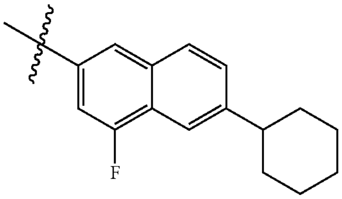
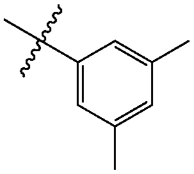
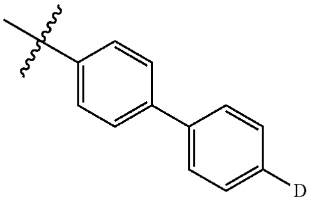
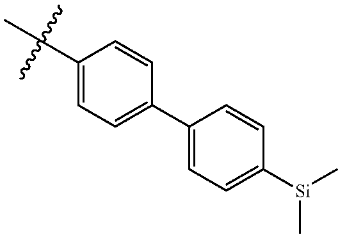
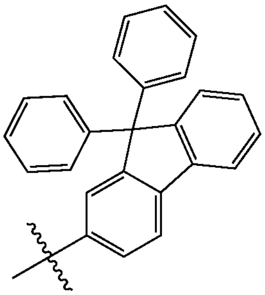
-continued
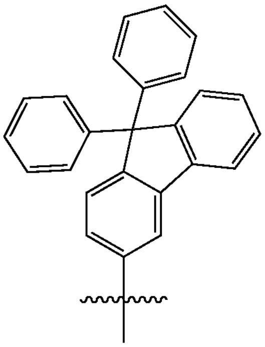
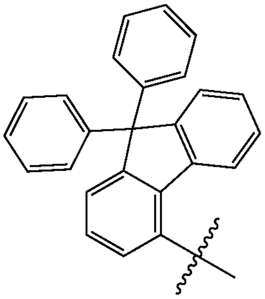
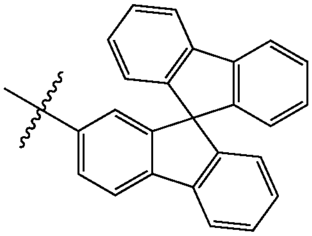
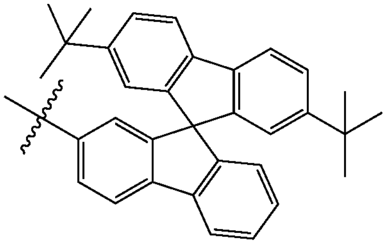
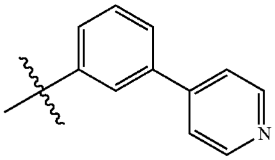
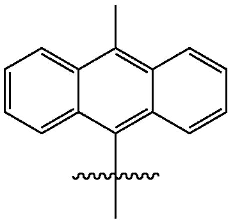

-continued
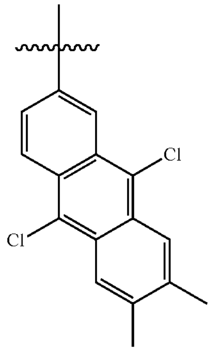
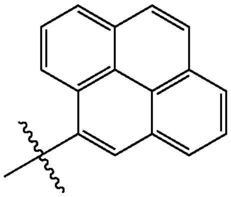
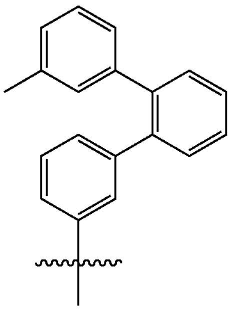
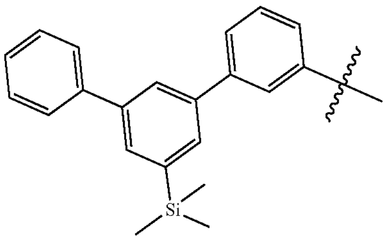
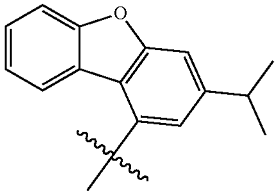
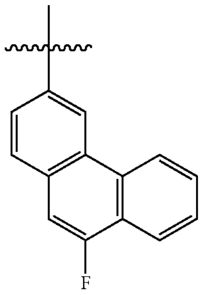
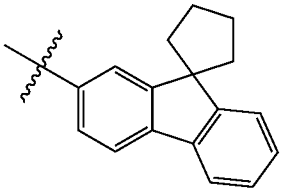
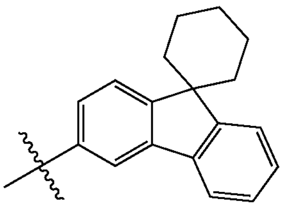
-continued
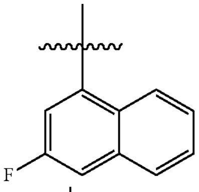
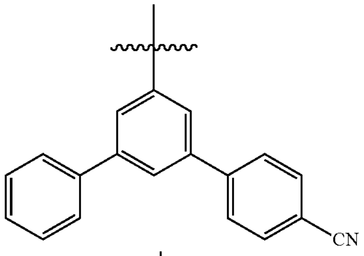
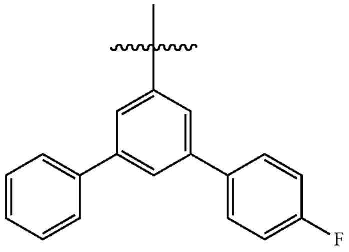
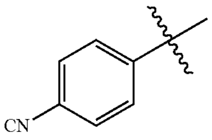
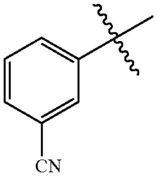
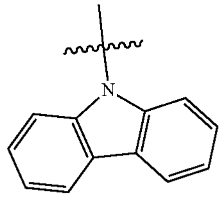
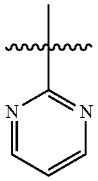
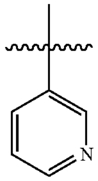
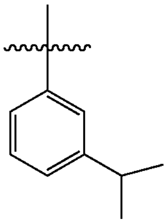
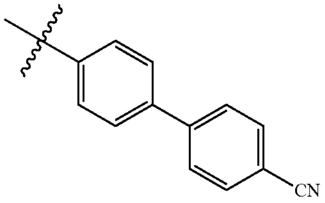
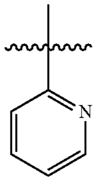
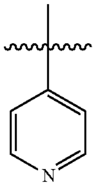
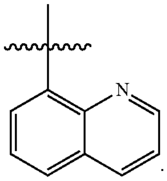
.
In one specific embodiment, $L_1$ and $L_2$ are the same or different, and are each independently selected from a single bond or the group consisting of groups represented by the following formulae (j-1) to (j-20):
(j-1)
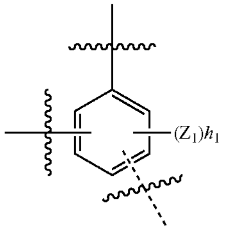
(j-2)
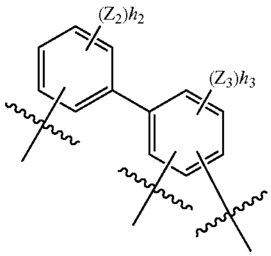
(j-3)
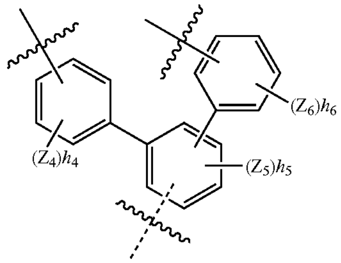
(j-4)
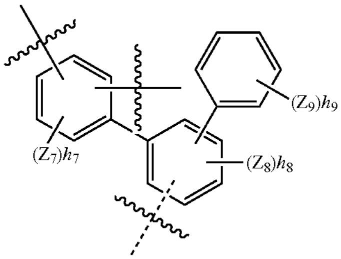
(j-5)
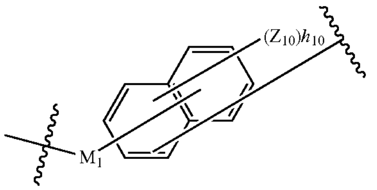
(j-6)
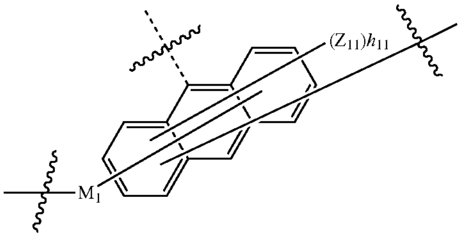
-continued
(j-7)
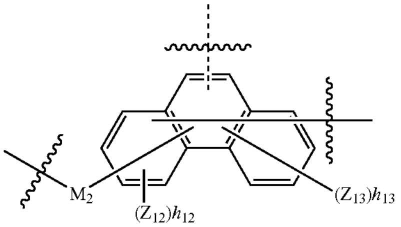
(j-8)
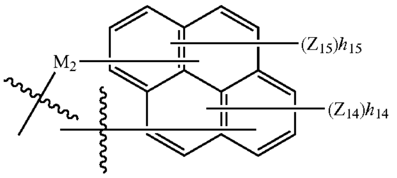
(j-9)
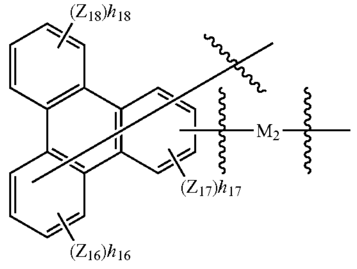
(j-10)
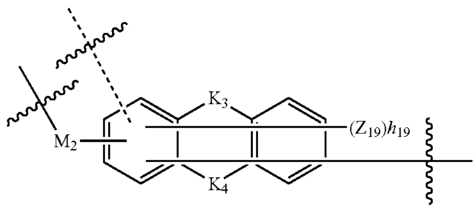
(j-11)
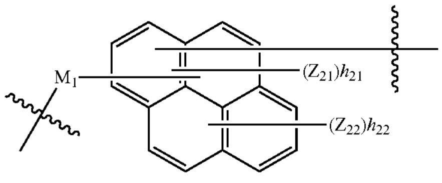
(j-12)
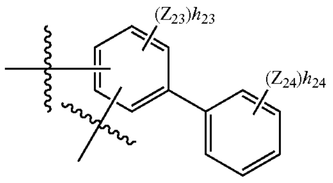
(j-13)
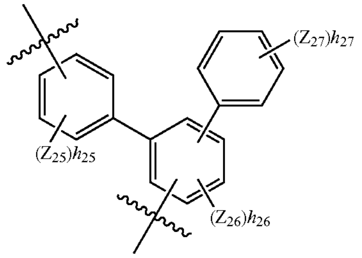

-continued (j-14)

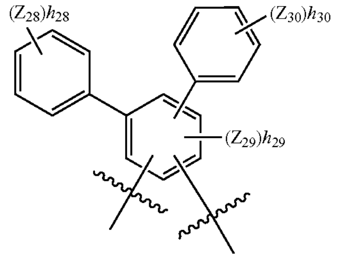

(j-15)

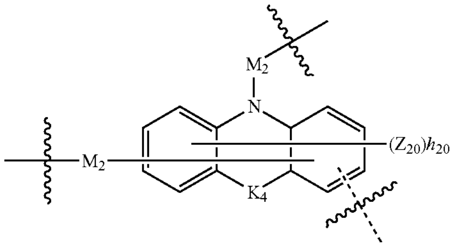

(j-16)

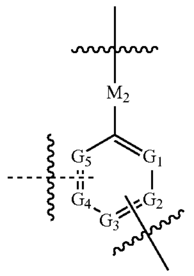

(j-17)

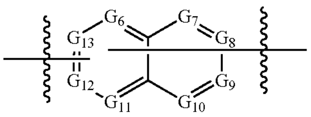

(j-18)

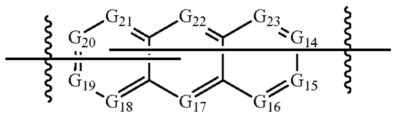

(j-19)

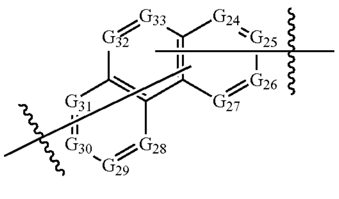

(j-20)

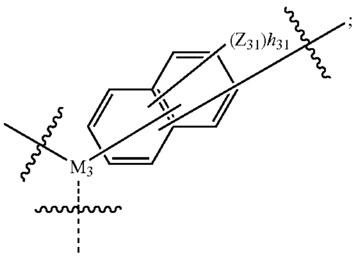

where $M_2$ is selected from a single bond or

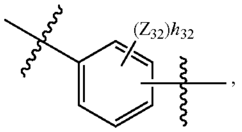

and $M_3$ is selected from

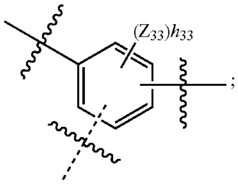

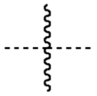

represents a single bond or is absent, when m in the formula (1) is equal to 2,

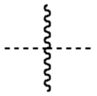

in $L_1$ is a single bond, and when m is equal to 1,

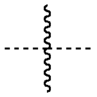

is absent;

$G_1$ to $G_5$ are each independently selected from N or $C(F_1)$, and at least one of $G_1$ to $G_5$ is selected from N; and when two or more of $G_1$ to $G_5$ are selected from $C(F_1)$, any two $F_1$ are the same or different;

$G_6$ to $G_{13}$ are each independently selected from N or $C(F_2)$, and at least one of $G_6$ to $G_{13}$ is selected from N; and when two or more of $G_6$ to $G_{13}$ are selected from $C(F_2)$, any two $F_2$ are the same or different;

$G_{14}$ to $G_{23}$ are each independently selected from N or $C(F_3)$, and at least one of $G_{14}$ to $G_{23}$ is selected from N; and when two or more of $G_{14}$ to $G_{23}$ are selected from $C(F_3)$, any two $F_3$ are the same or different;

$G_{24}$ to $G_{33}$ are each independently selected from N or $C(F_4)$, and at least one of $G_{24}$ to $G_{33}$ is selected from N; and when two or more of $G_{24}$ to $G_{33}$ are selected from $C(F_4)$, any two $F_4$ are the same or different;

$Z_1$ to $Z_2$ are selected from hydrogen, deuterium, fluorine, chlorine, bromine, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, and alkylthio with 1 to 10 carbon atoms;

$Z_3$ to $Z_{33}$, and $F_1$ to $F_4$ are each independently selected from hydrogen, deuterium, fluorine, chlorine, bromine, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, aryl with 6 to 18 carbon atoms, and heteroaryl with 3 to 18 carbon atoms;

$h_1$ to $h_{33}$ are represented by $h_k$, $Z_1$ to $Z_{33}$ are represented by $Z_k$, k is a variable, and represents any integer from 1 to 33, and $h_k$ represents the number of a substituent $Z_k$;

when k is selected from 1, 2, 3, 4, 5, 6, 8, 12, 14, 15, 16, 18, 25, or 32, $h_k$ is selected from 1, 2, 3 or 4;

when k is selected from 3, 9, 22, 24, 27, 28, or 30, $h_k$ is selected from 1, 2, 3, 4 or 5;

when k is selected from 7, 17, 21, 23, or 26, $h_k$ is selected from 1, 2 or 3;

when k is 29, $h_k$ is selected from 1 or 2;

when k is selected from 10, 13, 19, or 31, $h_k$ is selected from 1, 2, 3, 4, 5 or 6;

when k is 11, $h_k$ is selected from 1, 2, 3, 4, 5, 6, 7 or 8;

when k is selected from 20, $h_k$ is selected from 1, 2, 3, 4, 5, 6 or 7; and when $h_k$ is greater than 1, any two $Z_k$ are the same or different;

$K_3$ is selected from O, S, $N(Z_{24})$, $C(Z_{25}Z_{26})$, or $Si(Z_{25}Z_{26})$; where $Z_{24}$, $Z_{25}$, and $Z_{26}$ are each independently selected from hydrogen, aryl with 6 to 18 carbon atoms, heteroaryl with 3 to 18 carbon atoms, alkyl with 1 to 10 carbon atoms, or cycloalkyl with 3 to 10 carbon atoms, or the $Z_{25}$ and the $Z_{26}$ are connected to each other to form a ring together with the atoms to which they are jointly connected; and $K_4$ is selected from a single bond, O, S, $N(Z_{27})$, $C(Z_{28}Z_{29})$, or $Si(Z_{28}Z_{29})$; where $Z_{27}$, $Z_{28}$, and $Z_{29}$ are each independently selected from hydrogen, aryl with 6 to 18 carbon atoms, heteroaryl with 3 to 18 carbon atoms, alkyl with 1 to 10 carbon atoms, or cycloalkyl with 3 to 10 carbon atoms, or the aforesaid $Z_{28}$ and the $Z_{29}$ are connected to each other to form a ring together with the atoms to which they are jointly connected.

In some embodiments, $L_1$ and $L_2$ are each independently selected from substituted or unsubstituted arylene with 6 to 18 carbon atoms, substituted or unsubstituted heteroarylene with 4 to 18 carbon atoms, or a subunit group formed by linking two of the above groups via a single bond; and preferably, substituents in $L_1$ and $L_2$ are independently selected from the group consisting of deuterium, fluorine, chlorine, cyano, methyl, ethyl, isopropyl, tert-butyl, methoxy, ethoxy, isopropoxy, propoxy, trifluoromethyl, trimethylsilyl, phenyl, naphthyl, dibenzofuranyl, dibenzothienyl, carbazolyl, pyridyl, pyrimidinyl, and triphenylsilyl.

In some embodiments, $L_1$ and $L_2$ are each independently selected from substituted or unsubstituted arylene with 6 to 18 carbon atoms, substituted or unsubstituted heteroarylene with 4 to 18 carbon atoms, or a group formed by linking the two of the above groups via a single bond. Further, the $L_1$ and the $L_2$ are each independently selected from substituted or unsubstituted arylene with 6, 10, 12, 13, 14, 15, 16, 17, or 18 carbon atoms, or substituted or unsubstituted heteroarylene with 4, 5, 8, 9, 10, 12, 16, or 18 carbon atoms.

In some embodiments, the substituents in $L_1$ and $L_2$ are independently selected from the group consisting of deuterium, fluorine, cyano, methyl, ethyl, isopropyl, tert-butyl, methoxy, ethoxy, isopropoxy, trifluoromethyl, trimethylsilyl, phenyl, naphthyl, dibenzofuranyl, dibenzothienyl, carbazolyl, pyridyl, and pyrimidinyl.

In some more specific embodiments, each $L_1$ and each $L_2$ are each independently selected from substituted or unsubstituted phenylene, substituted or unsubstituted biphenylene, substituted or unsubstituted terphenylene, substituted or unsubstituted naphthylene, substituted or unsubstituted dibenzofurylene, substituted or unsubstituted dibenzothienylene, substituted or unsubstituted quinolylene, substituted or unsubstituted carbazolylene, substituted or unsubstituted fluorenylene, substituted or unsubstituted anthrylene, substituted or unsubstituted phenanthrylene, substituted or unsubstituted pyrimidylene, substituted or unsubstituted pyridylene, substituted or unsubstituted pyrazinylene, substituted or unsubstituted quinolylene, substituted or unsubstituted isoquinolylene, substituted or unsubstituted quinazolinylene, or a subunit group formed by linking two or three of the above groups via a single bond; and substitution in each $L_1$ and each $L_2$ means that each $L_1$ and each $L_2$ are each independently substituted by 1, 2, 3 or 4 substituents selected from deuterium, fluorine, chlorine, cyano, methyl, ethyl, isopropyl, tert-butyl, methoxy, ethoxy, isopropoxy, propoxy, trifluoromethyl, phenyl, carbazolyl, naphthyl, trimethylsilyl, or triphenylsilyl.

In one more specific embodiment, when m in the formula (1) is equal to 1, each $L_1$ is independently selected from a single bond or a substituted or unsubstituted group $W_1$, and the unsubstituted group $W_1$ is selected from the group consisting of:

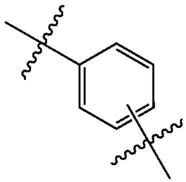

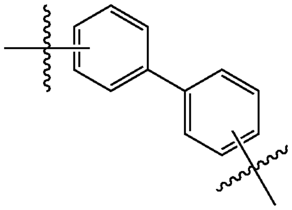

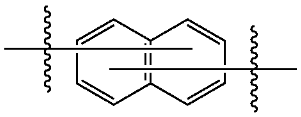

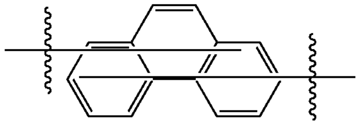

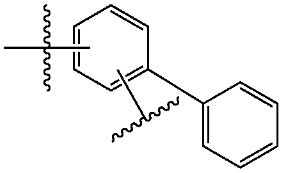

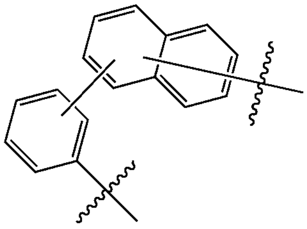

-continued
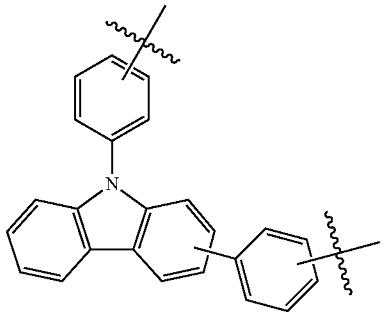
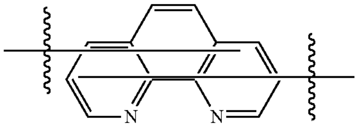
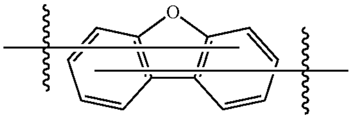
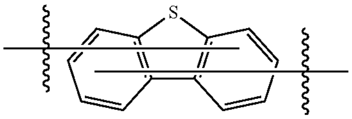
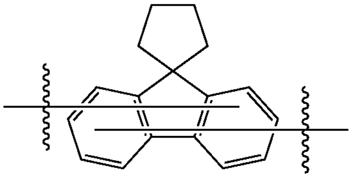
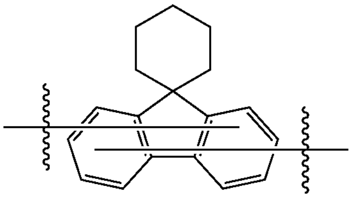
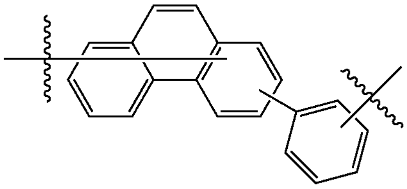
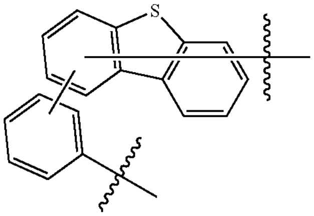
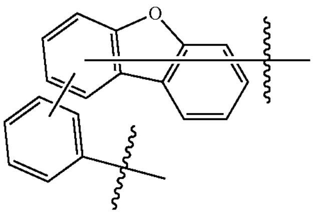
-continued
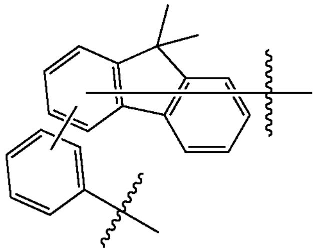
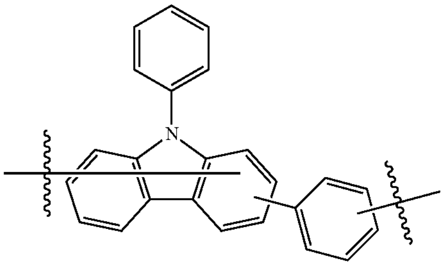
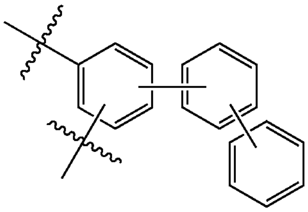
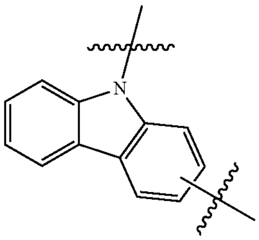
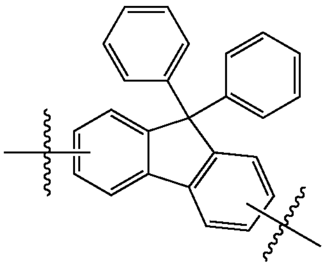
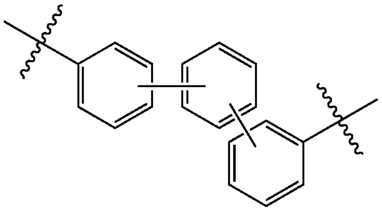

-continued

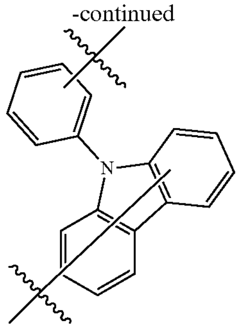

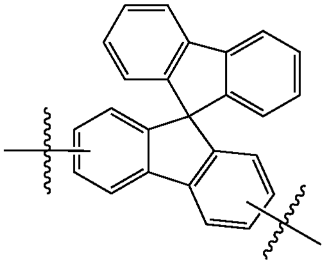

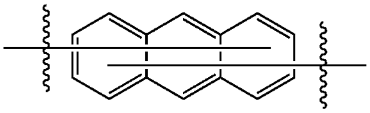

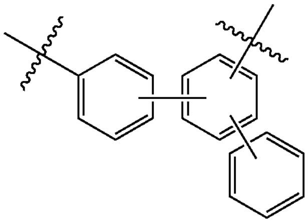

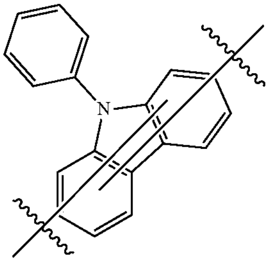

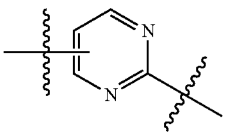

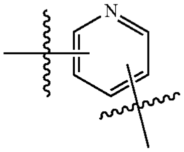

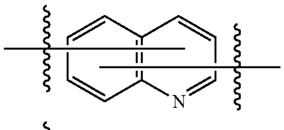

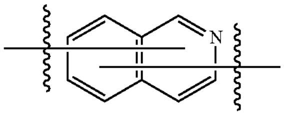

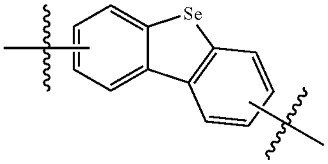

-continued

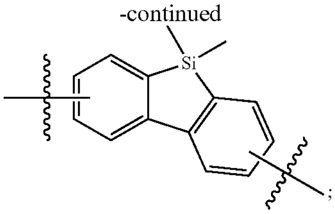

;

and when the group $W_1$ is substituted by one or more substituents, the substituents in the group $W_1$ are each independently selected from the group consisting of deuterium; fluorine; chlorine; cyano; alkyl with 1 to 4 carbon atoms; alkoxy with 1 to 4 carbon atoms; trifluoromethyl; trimethylsilyl; cyclopentyl; cyclohexyl; aryl with 6 to 12 carbon atoms which can be optionally substituted by 0, 1, 2, 3, 4, or 5 substituents selected from deuterium, fluorine, cyano, methyl, isopropyl, or tert-butyl; and heteroaryl with 5 to 12 carbon atoms; and when the number of the substituents in the group $W_1$ is more than 1, the substituents are the same or different;

when m in the formula (1) is equal to 2, each $L_1$ is independently selected from a single bond or a substituted or unsubstituted group $W_2$, and the unsubstituted group $W_2$ is selected from the group consisting of:

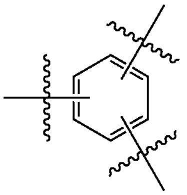

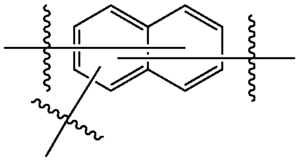

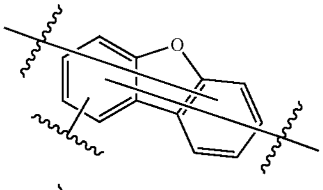

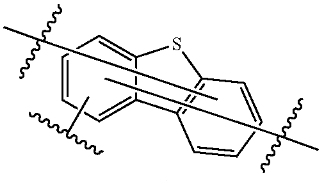

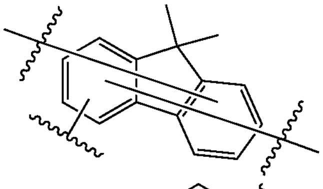

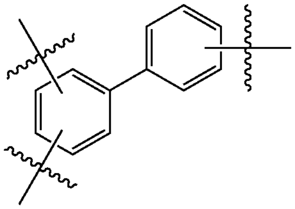

-continued
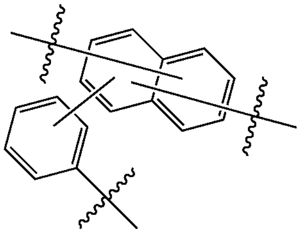
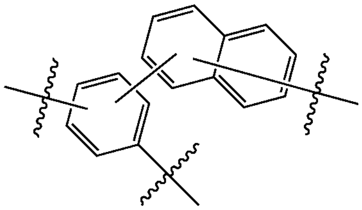
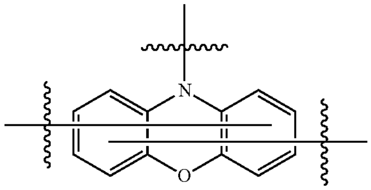
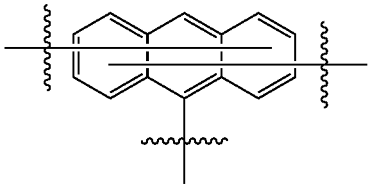
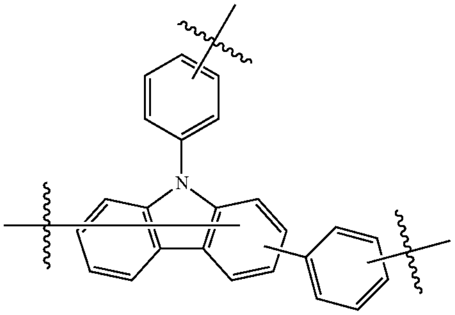
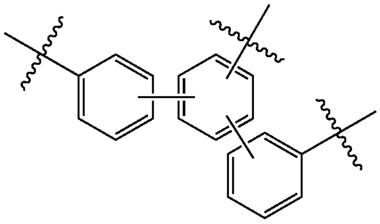
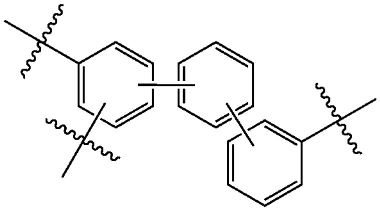
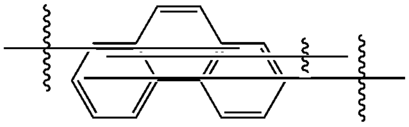
-continued
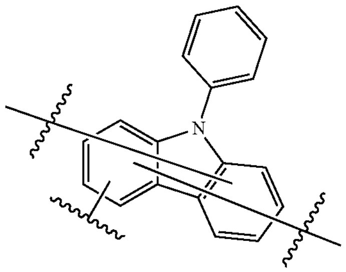
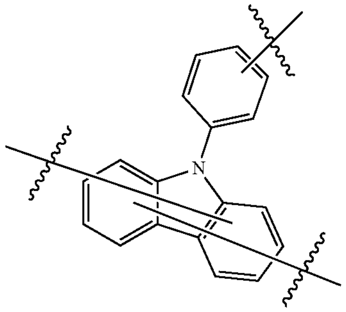
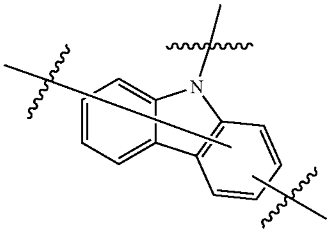
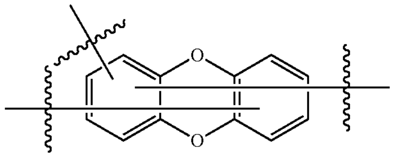
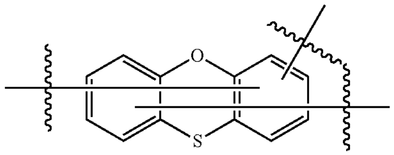
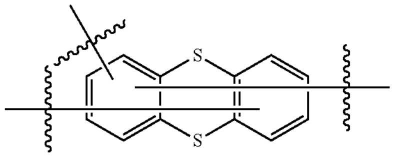
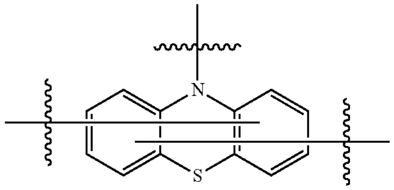
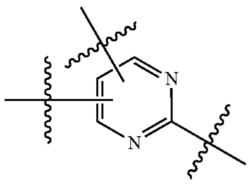
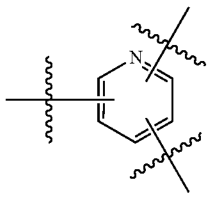

-continued

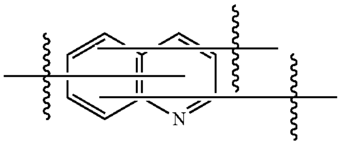

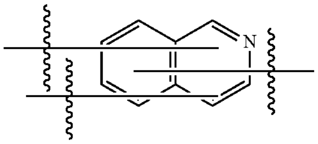

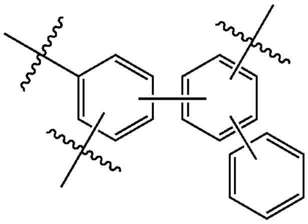

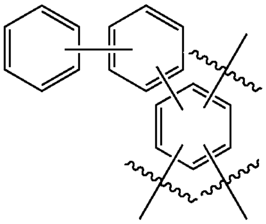

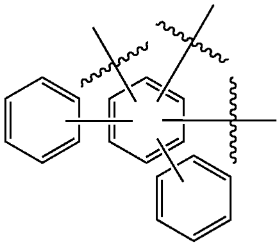

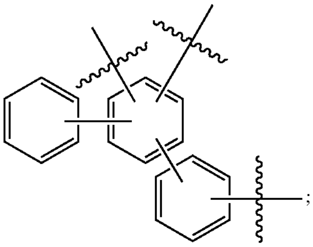
;

and when the group $W_2$ is substituted by one or more substituents, the substituents in the group $W_2$ are each independently selected from the group consisting of deuterium; fluorine; chlorine; cyano; alkyl with 1 to 4 carbon atoms; alkoxy with 1 to 4 carbon atoms; trifluoromethyl; trimethylsilyl; cyclopentyl; cyclohexyl; aryl with 6 to 12 carbon atoms which can be optionally substituted by 0, 1, 2, 3, 4, or 5 substituents selected from deuterium, fluorine, cyano, methyl, isopropyl, or tert-butyl; and heteroaryl with 5 to 12 carbon atoms; and when the number of the substituents in the group $W_2$ is more than 1, the substituents are the same or different.

In some more specific embodiments, $L_1$ is a single bond or any one of the following groups:

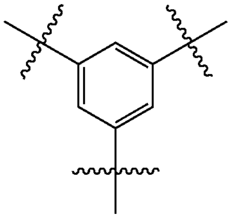

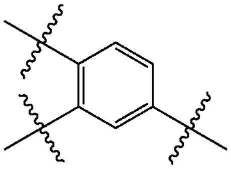

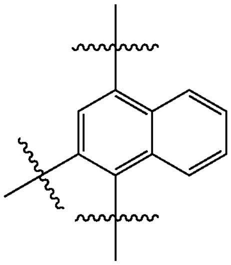

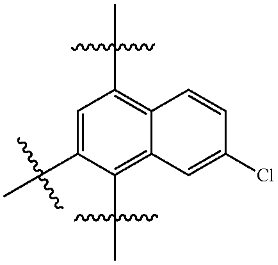

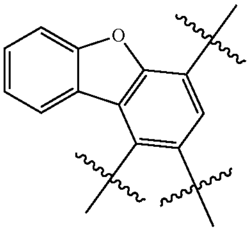

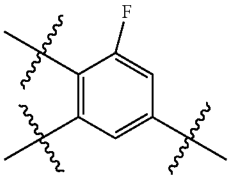

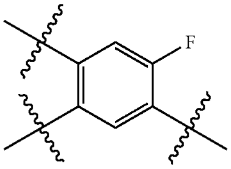

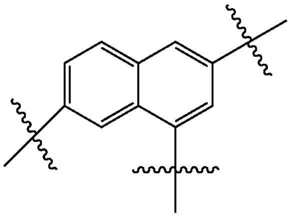

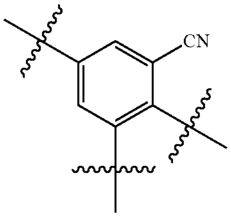

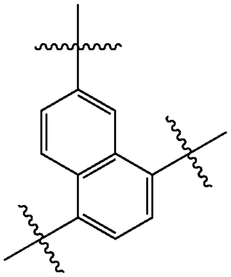

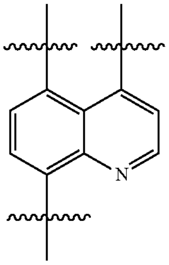

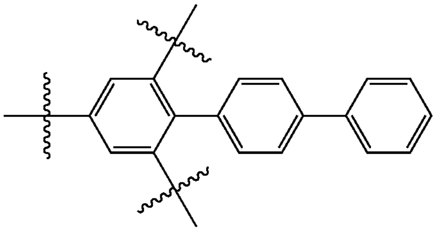

-continued
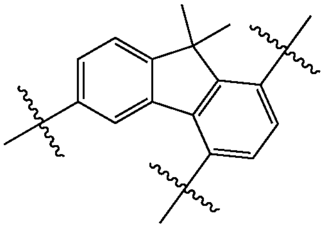
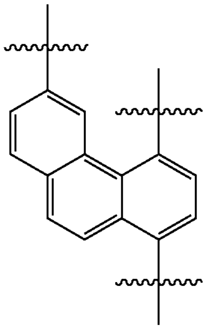
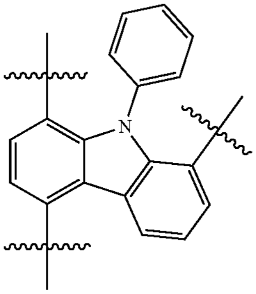
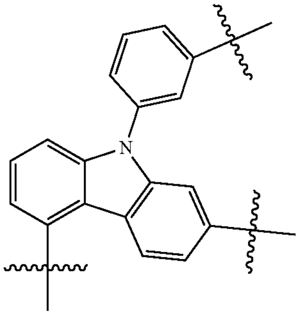
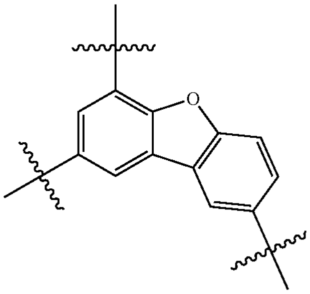
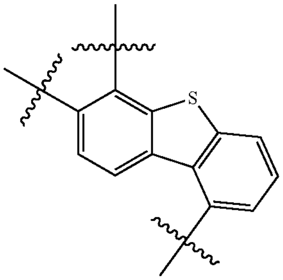
-continued
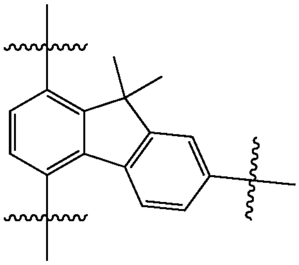
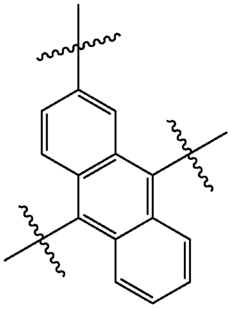
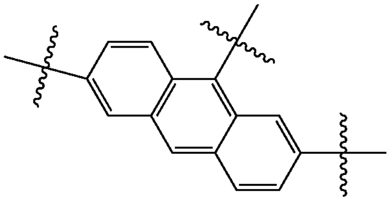
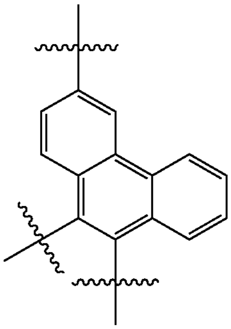
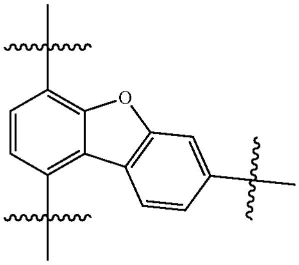
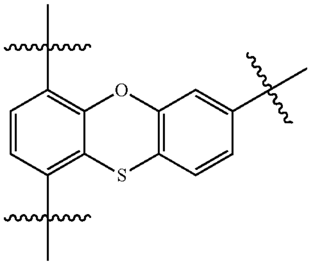
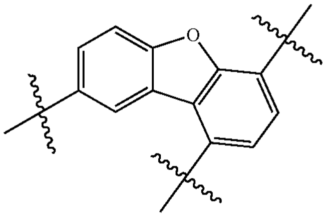
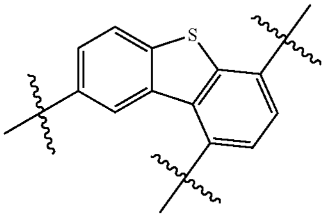
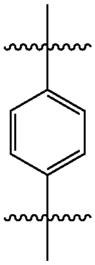
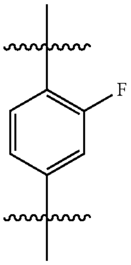

-continued
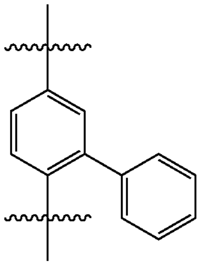
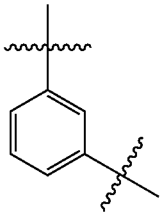
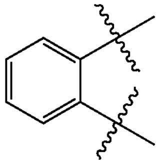
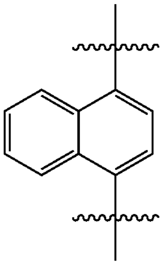
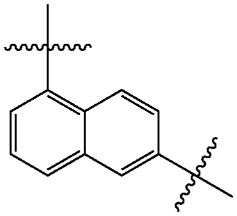
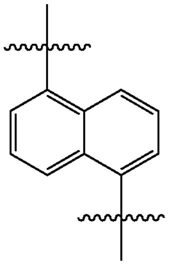
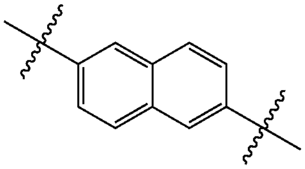
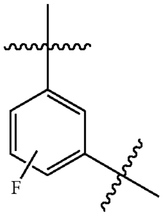
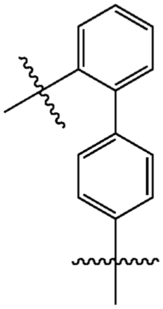
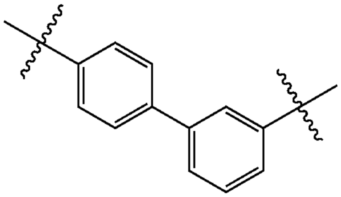
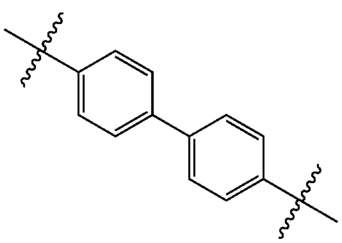
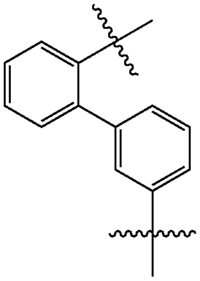
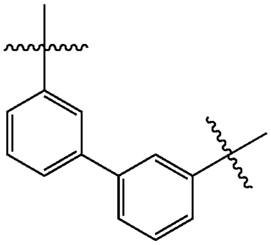
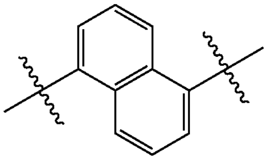
-continued
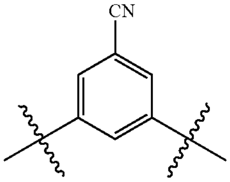
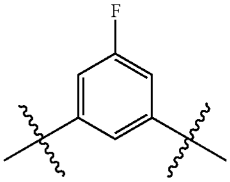
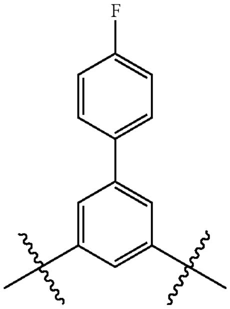
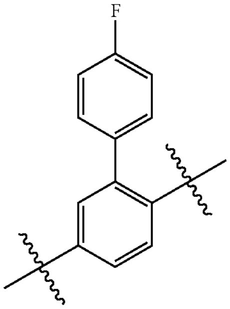
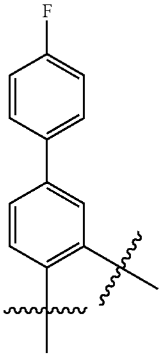
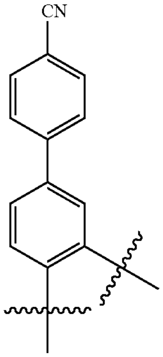
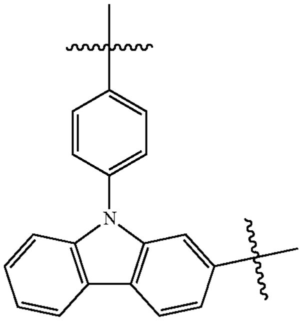
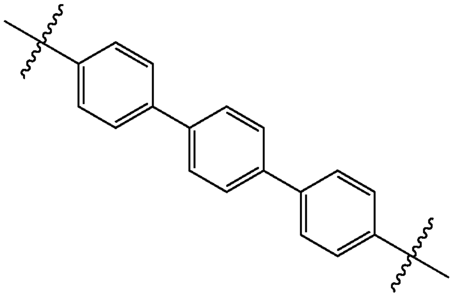
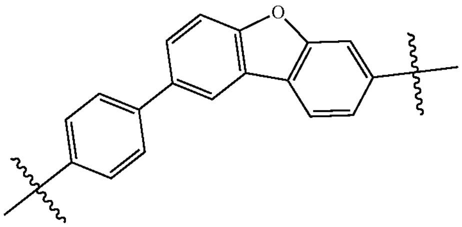

-continued
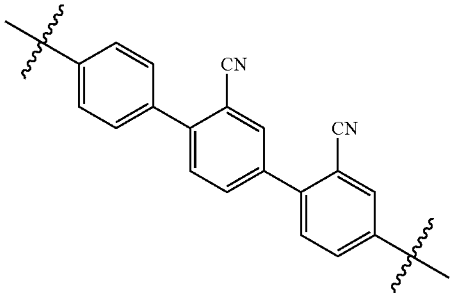
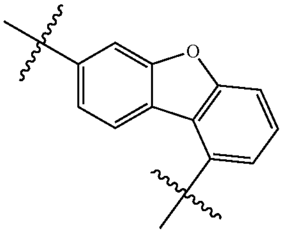
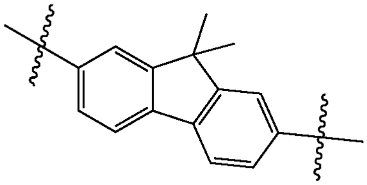
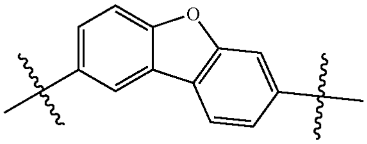
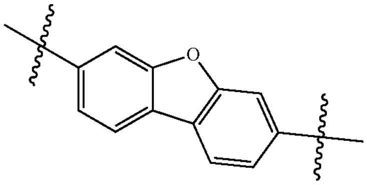
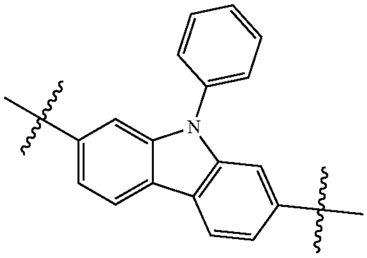
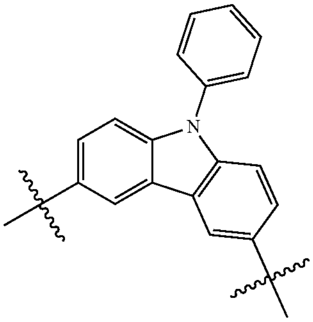
-continued
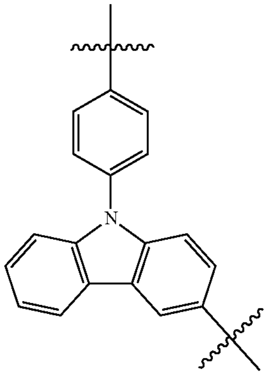
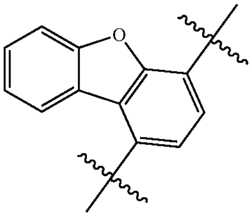
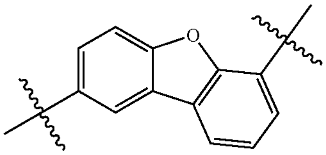
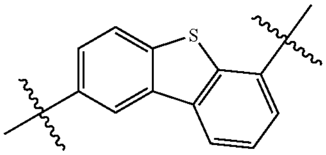
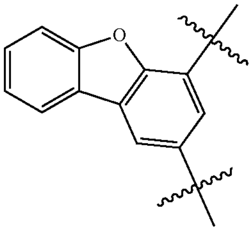
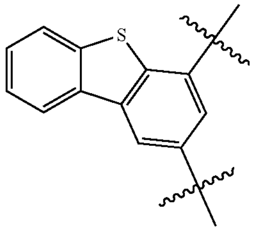
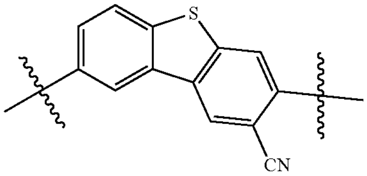
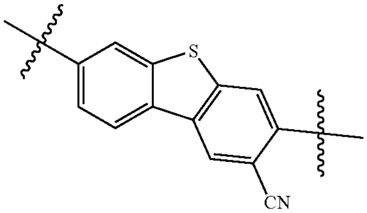
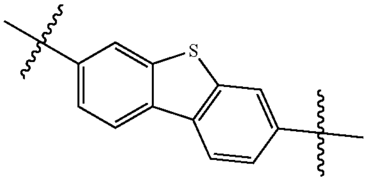
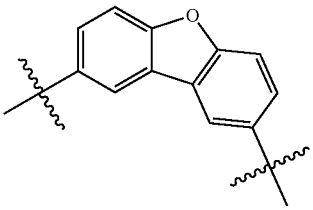

-continued
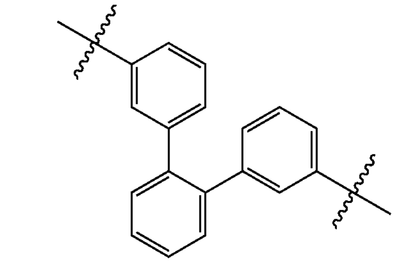
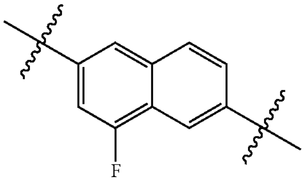
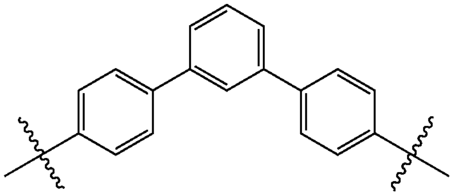
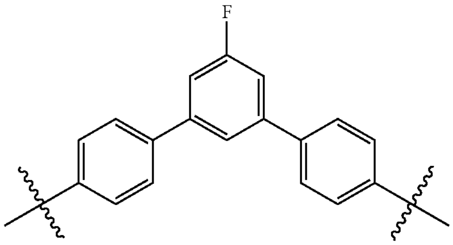
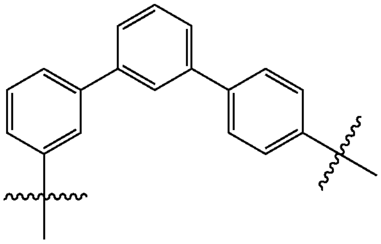
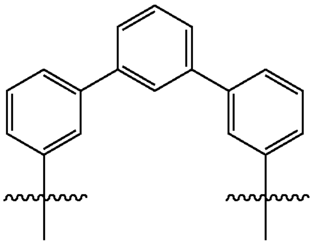
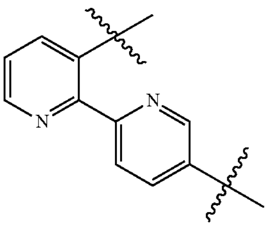
-continued
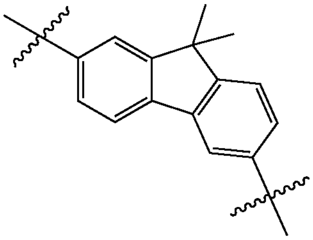
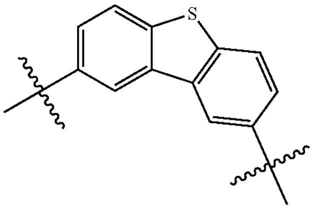
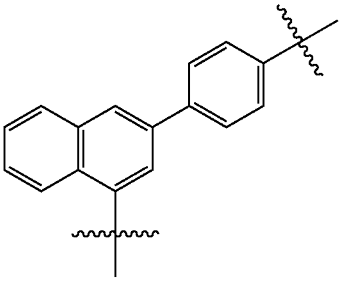
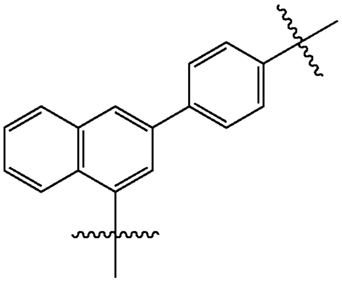
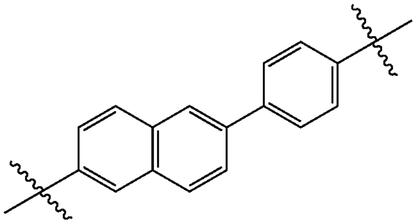
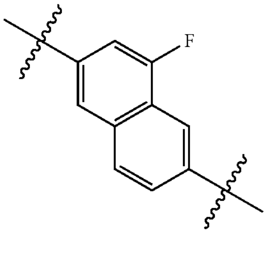

-continued
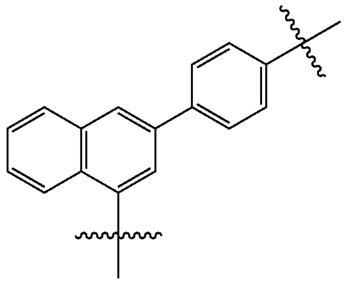
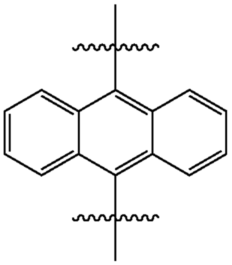
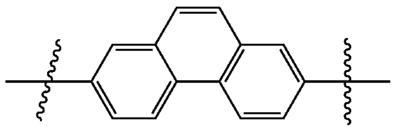
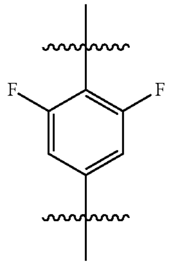
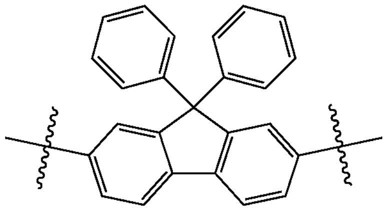
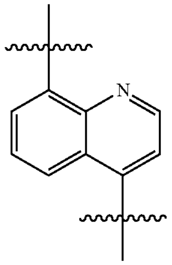
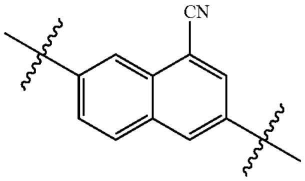
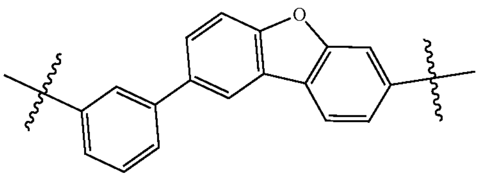
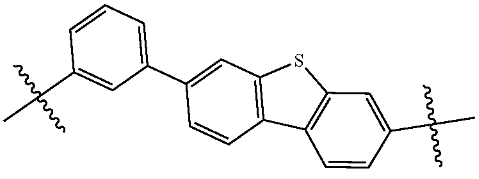
-continued
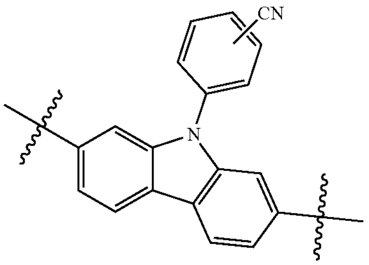
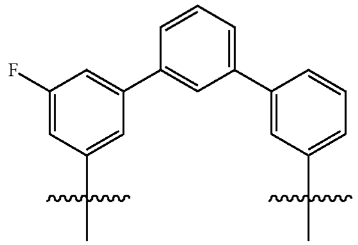
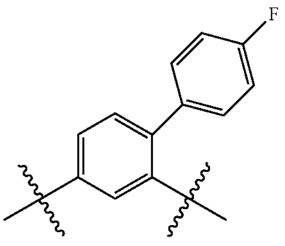
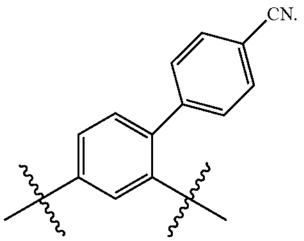
In one specific embodiment, each 2 is independently selected from a single bond, and a substituted or unsubstituted group $W_4$, and the unsubstituted group $W_4$ is selected from the group consisting of:
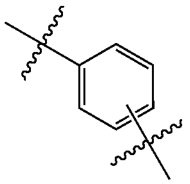
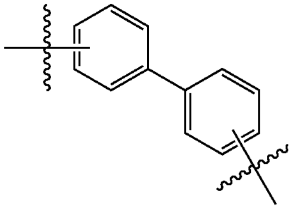
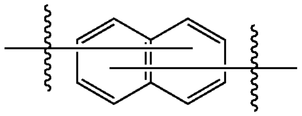
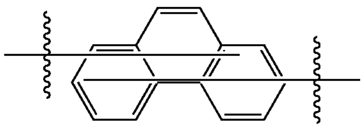

-continued
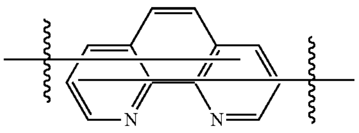
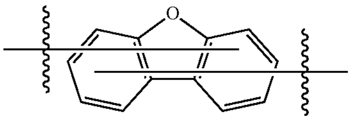
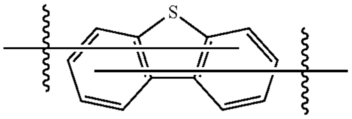
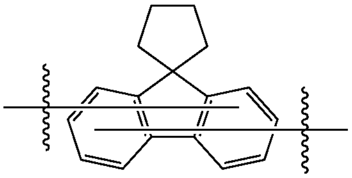
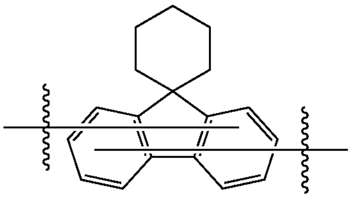
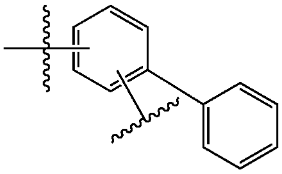
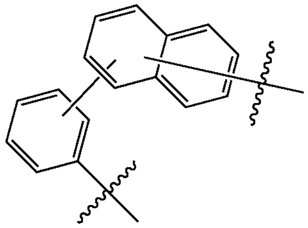
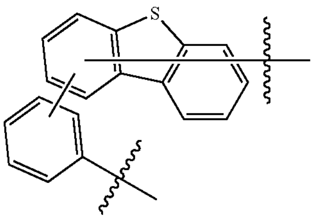
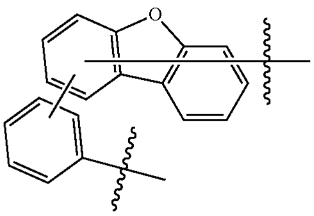
-continued
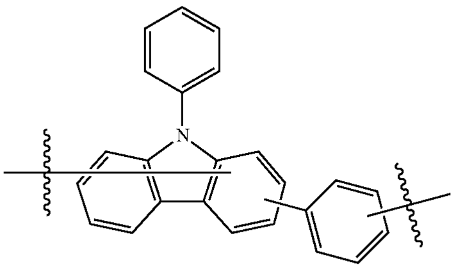
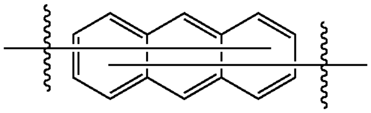
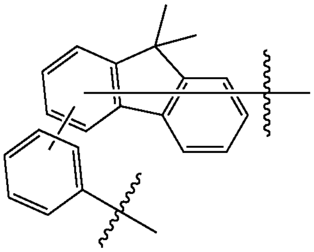
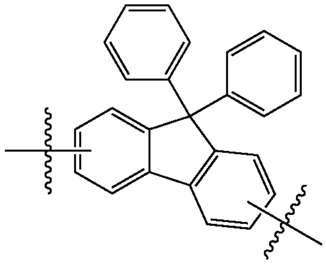
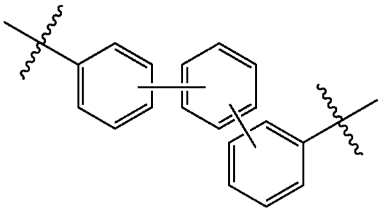
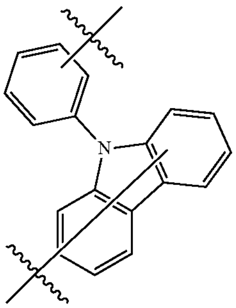
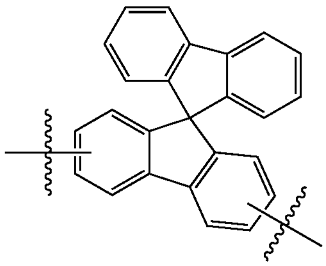

-continued

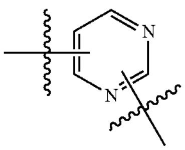
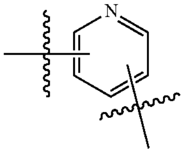
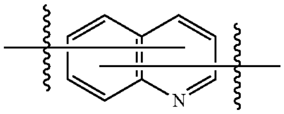
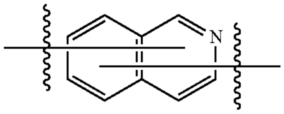
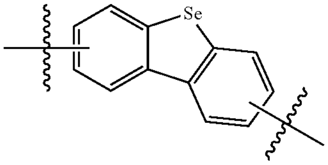
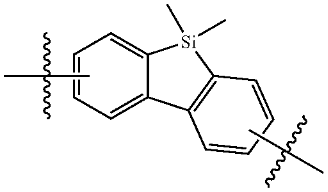
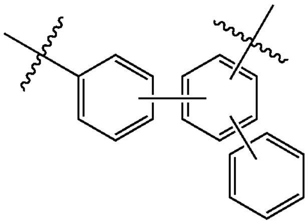
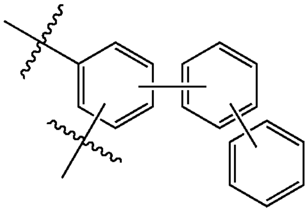
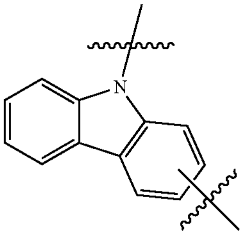
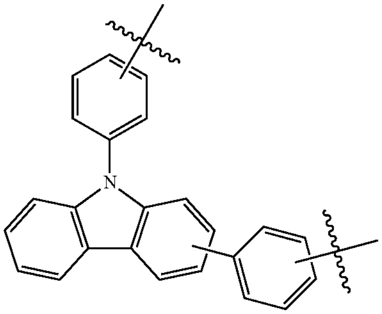

-continued

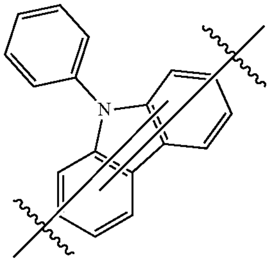
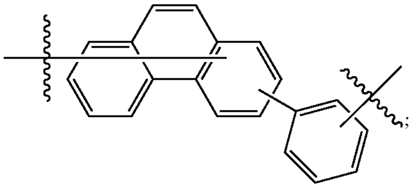

and when the group $W_4$ is substituted by one or more substituents, the substituents in the group $W_4$ are each independently selected from the group consisting of deuterium, fluorine, chlorine, cyano, methyl, ethyl, isopropyl, n-propyl, tert-butyl, alkoxy with 1 to 4 carbon atoms, trifluoromethyl, trimethylsilyl, cyclopentyl, cyclohexyl, phenyl, naphthyl and heteroaryl with 5 to 12 carbon atoms; and when the number of the substituents in the group $W_4$ is more than 1, the substituents are the same or different.

In one more specific embodiment, $L_2$ is selected from a single bond or any one of the following groups:

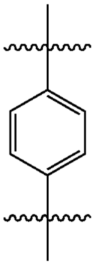
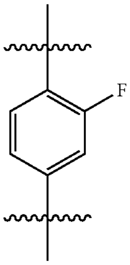
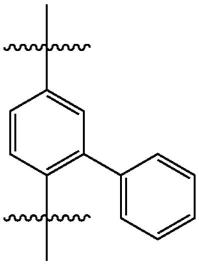
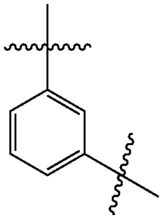
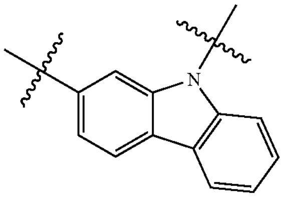
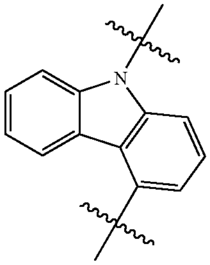

-continued
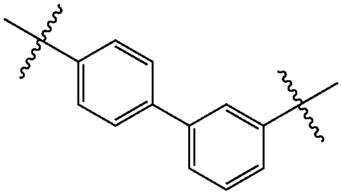
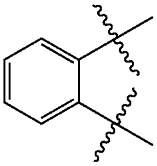
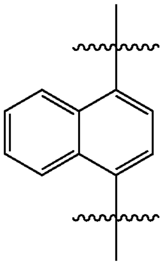
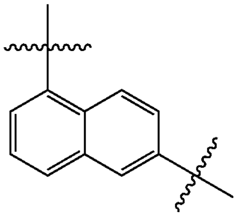
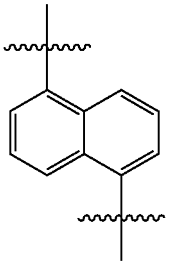
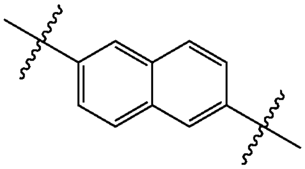
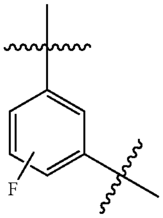
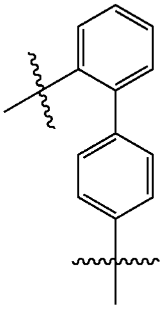
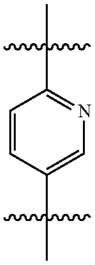
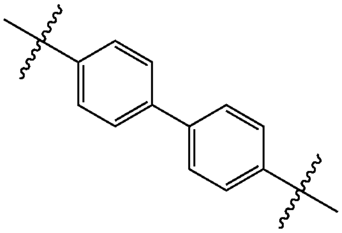
-continued
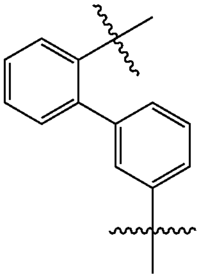
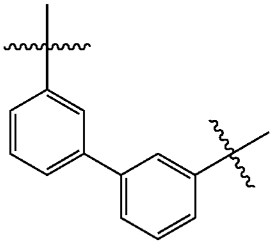
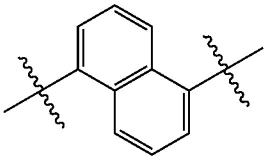
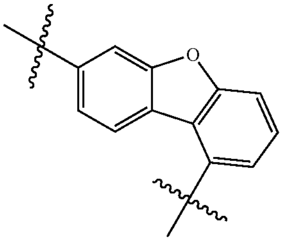
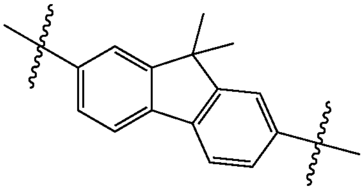
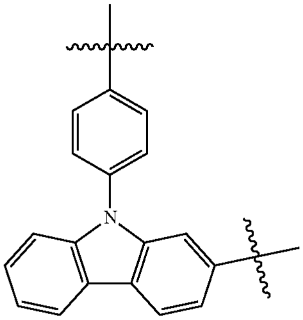
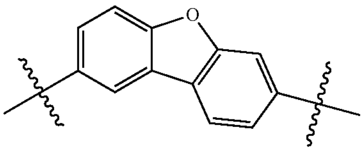
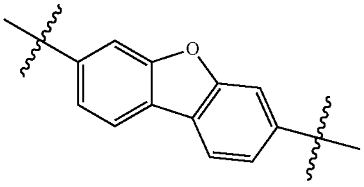 [SMILES: *c1ccc2c(c1)oc1cc(*)ccc12]

-continued
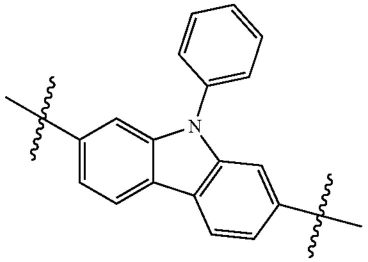
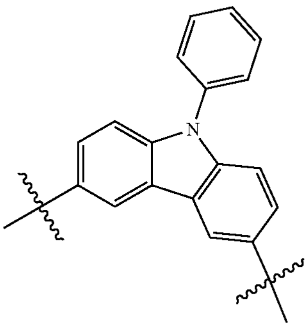
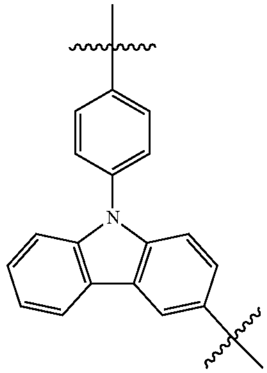
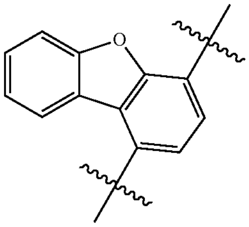
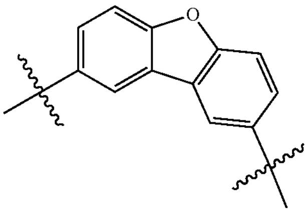
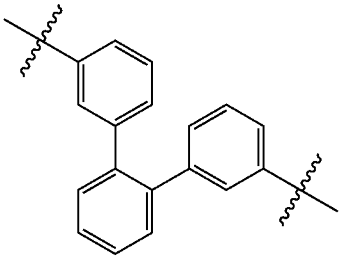
-continued
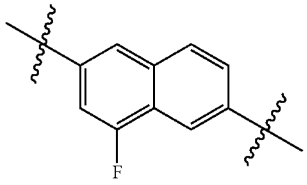
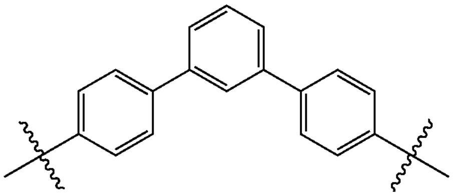
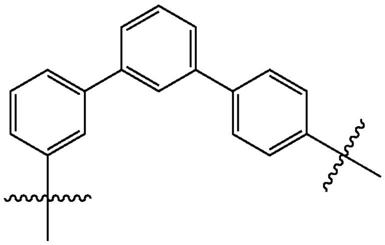
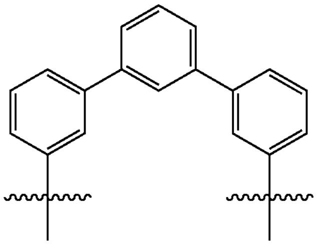
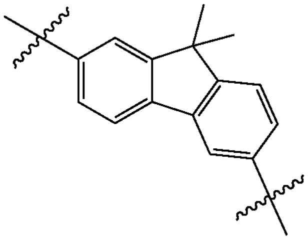
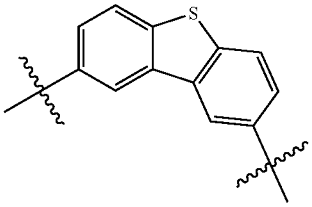
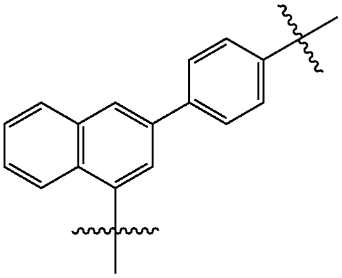

-continued
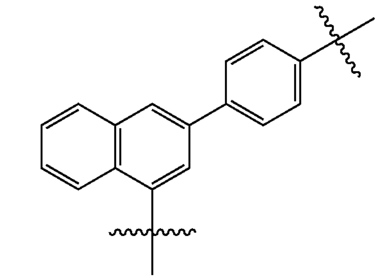
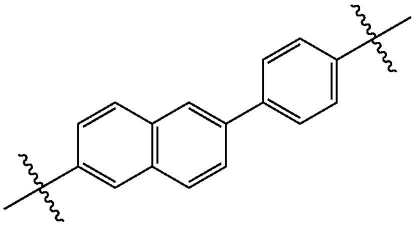
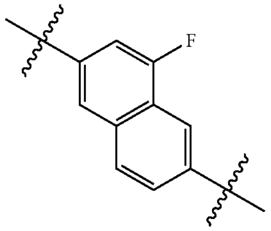
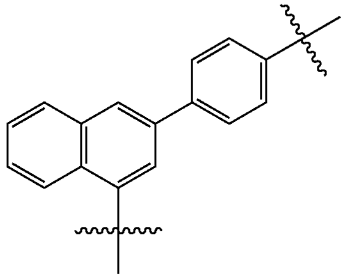
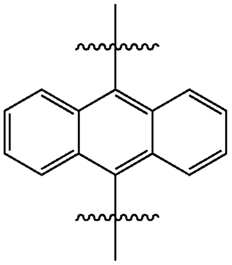
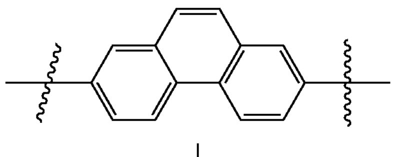
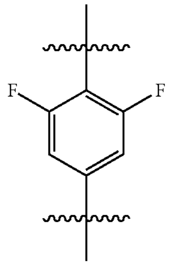
-continued
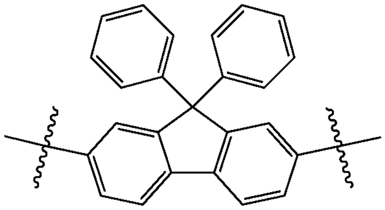
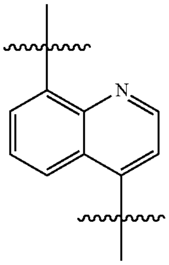
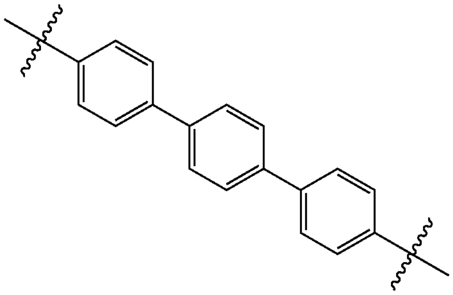
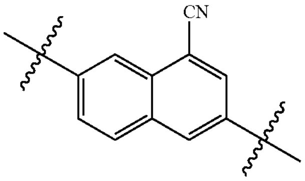
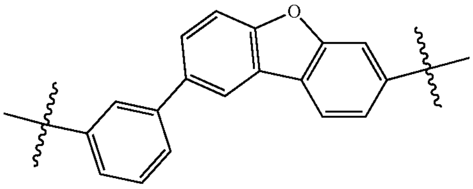
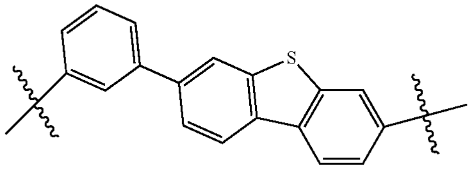
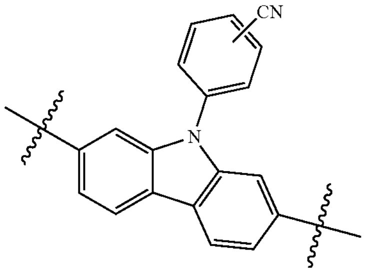

-continued

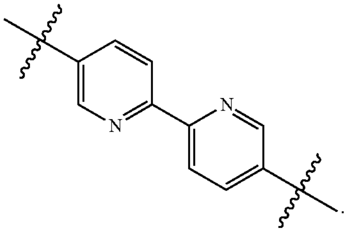 [SMILES: *c1ccc(-c2ccc(*)cn2)nc1]

In some specific embodiments, each $R_3$ is independently selected from deuterium; fluorine; chlorine; cyano; alkyl with 1 to 4 carbon atoms; alkoxy with 1 to 4 carbon atoms; haloalkyl with 1 to 4 carbon atoms; trimethylsilyl; cycloalkyl with 5 to 7 carbon atoms; aryl with 6 to 15 carbon atoms which can be optionally substituted by 0, 1, 2, 3, 4, or 5 substituents independently selected from deuterium, fluorine, chlorine, or cyano; or heteroaryl with 3 to 18 carbon atoms which can be optionally substituted by 0, 1, 2, 3, 4, or 5 substituents independently selected from deuterium, fluorine, chlorine, or cyano; and when the number of the $R_3$ is more than 1, each $R_3$ is the same or different.

In some specific embodiments, each $R_3$ is independently selected from deuterium, fluorine, chlorine, cyano, methyl, ethyl, isopropyl, n-propyl, tert-butyl, alkoxy with 1 to 4 carbon atoms, trifluoromethyl, trimethylsilyl, cyclopentyl, cyclohexyl, phenyl, biphenyl, naphthyl, 9,9-dimethylfluorenyl, dibenzothienyl, dibenzofuranyl, or N-phenylcarbazolyl; and when the number of $R_3$ is more than 1, each $R_3$ is the same or different.

In one specific embodiment, $R_1$ and $R_2$ are the same, and are selected from methyl or phenyl.

In one specific embodiment, the organic compound is selected from the group consisting of the following organic compounds:

1

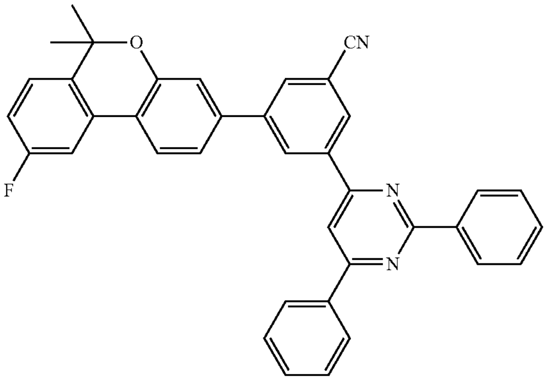

2

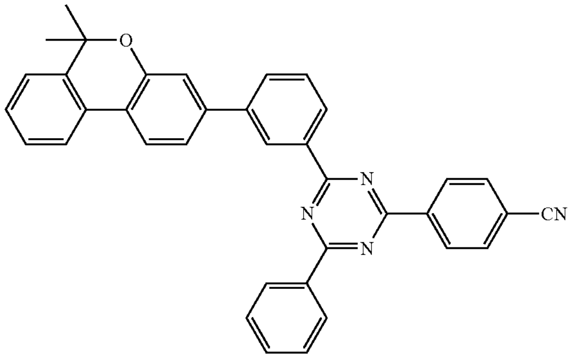

3

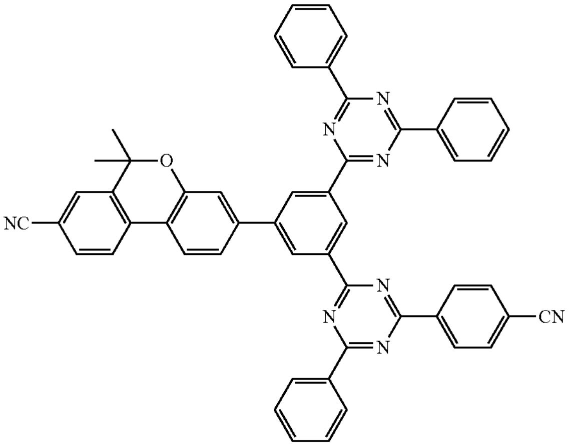

4

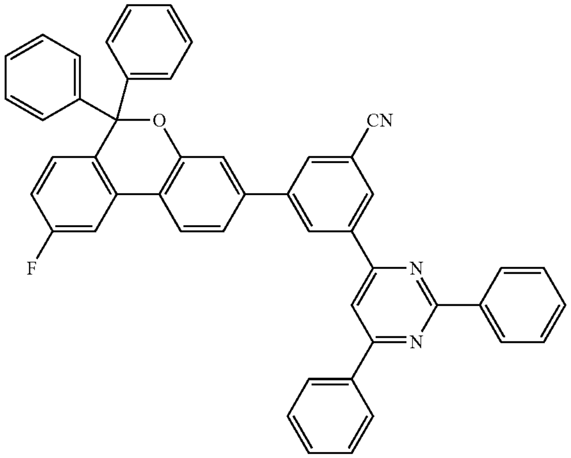

-continued
5
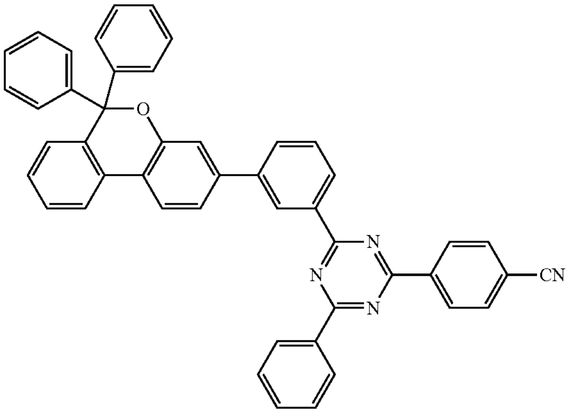
6
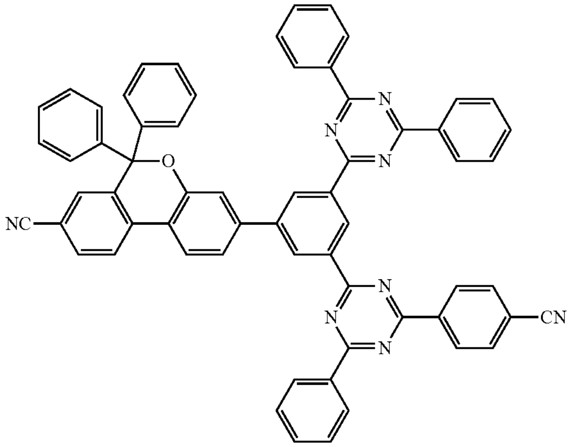
7
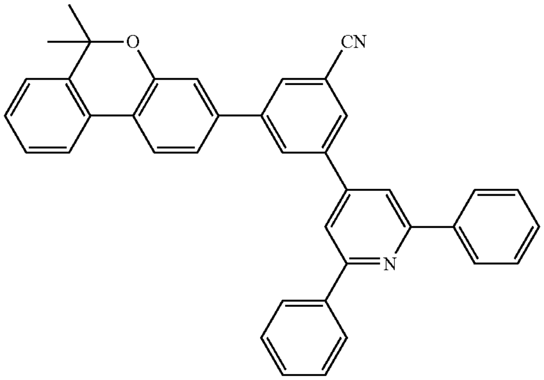
8
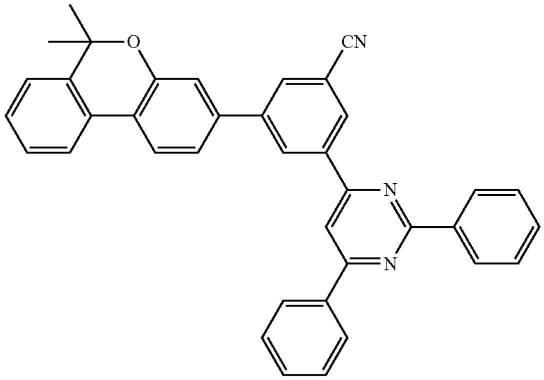
9
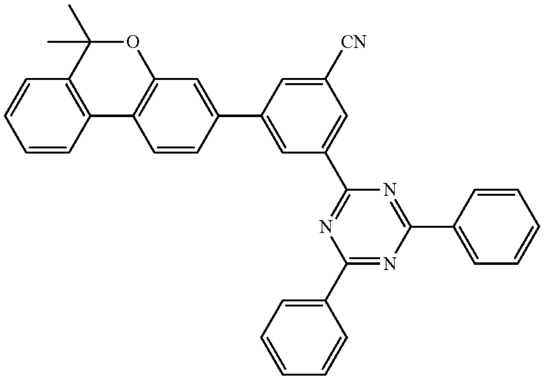
10
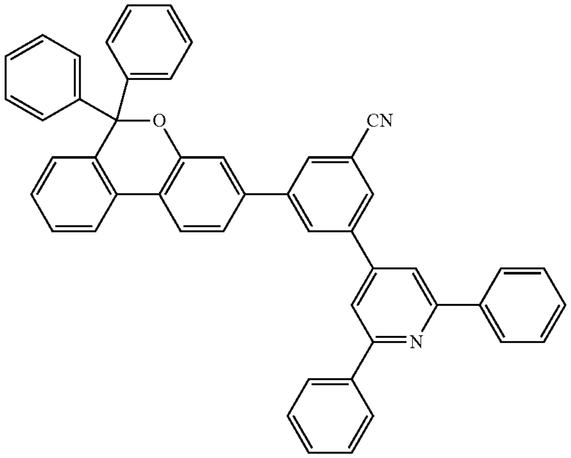

-continued
11
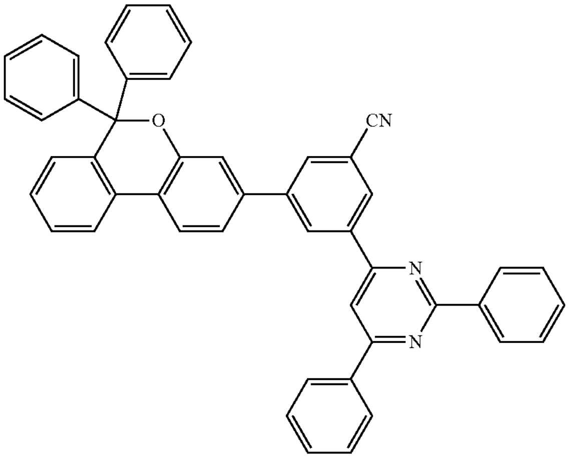
12
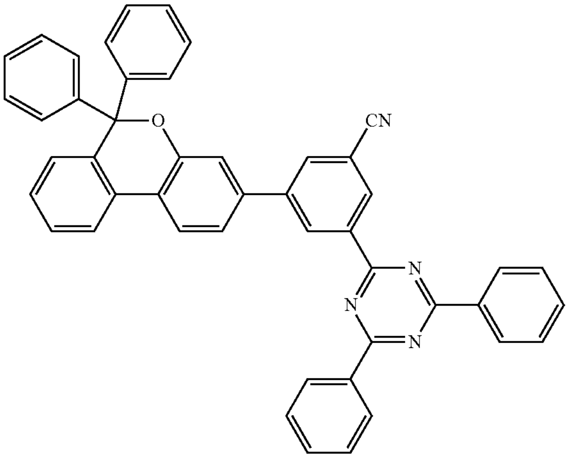
13
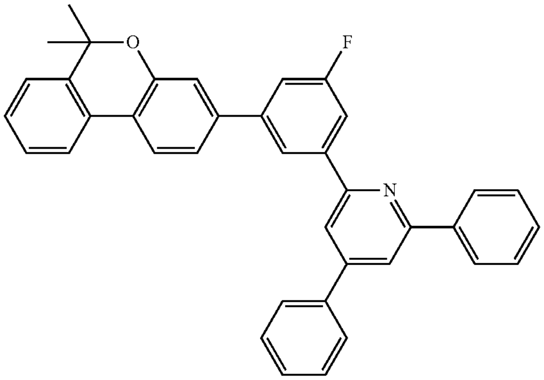
14
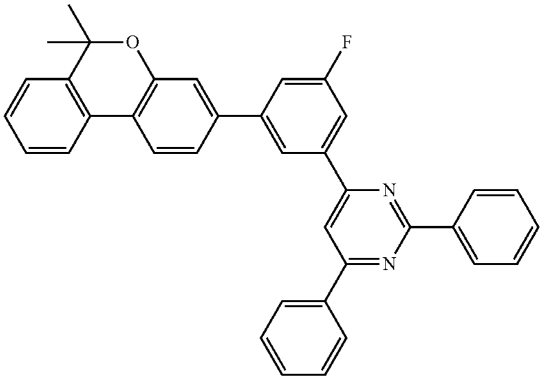
15
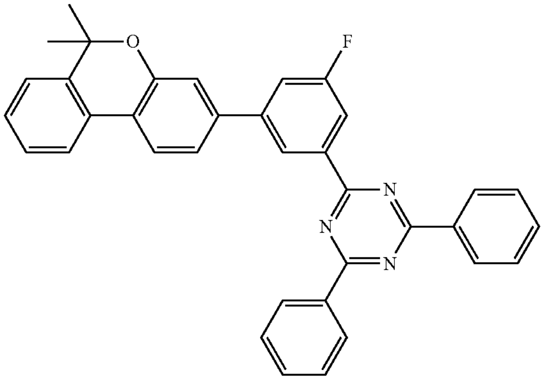
16
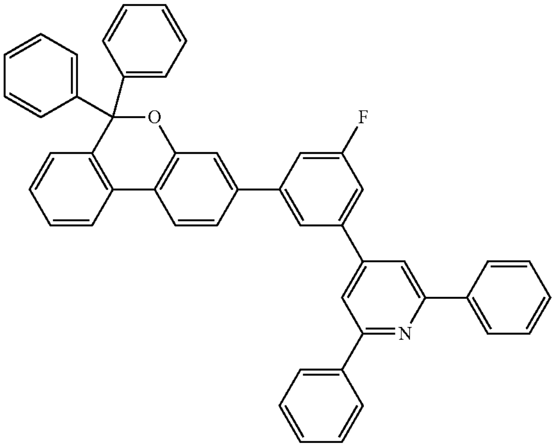

-continued
17
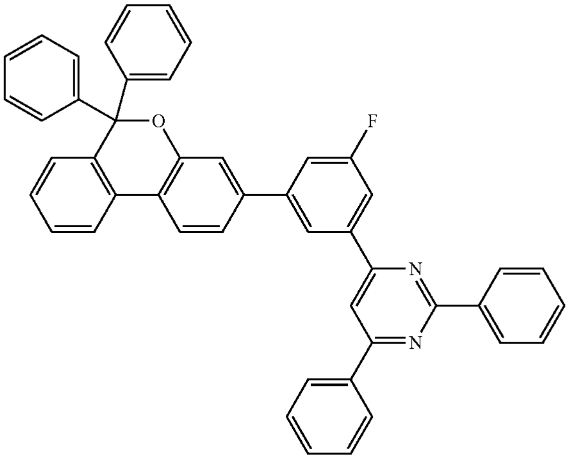
18
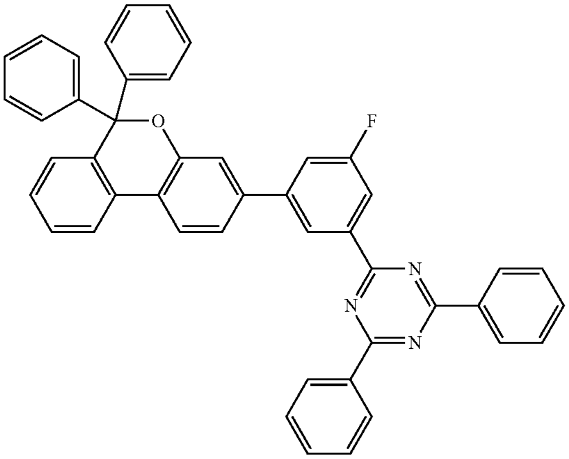
19
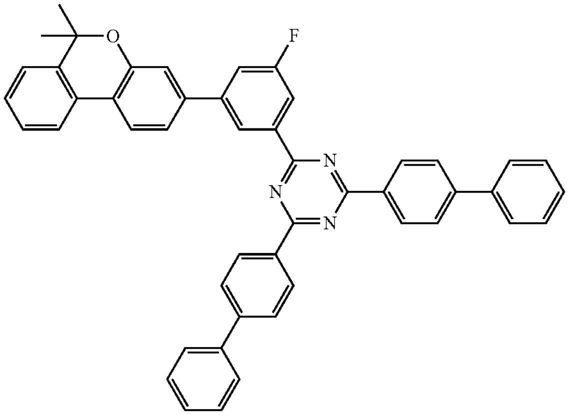
20
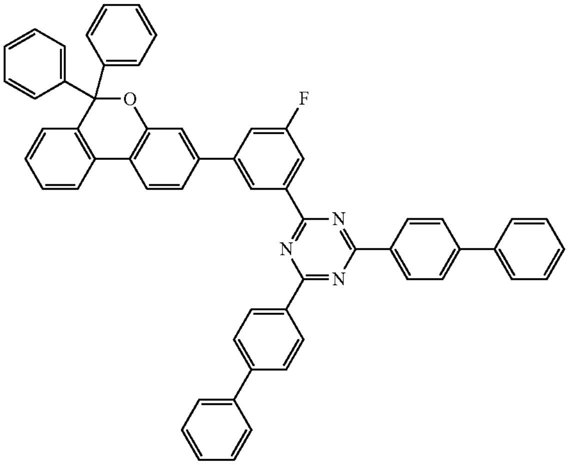
21
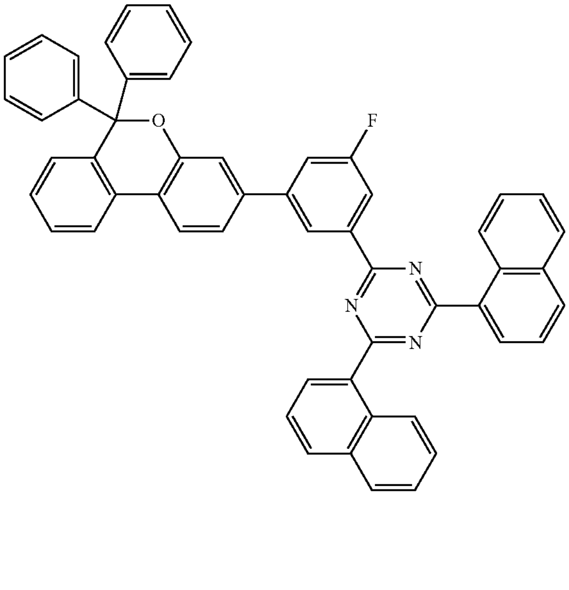
22
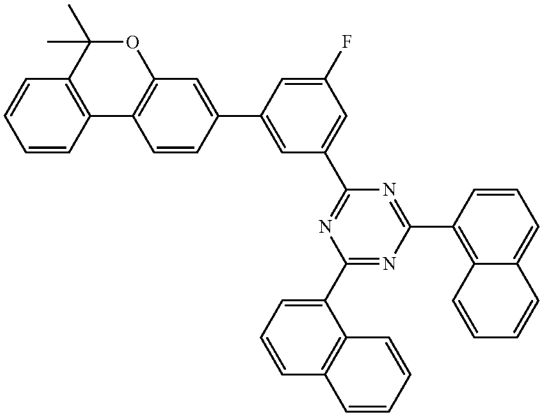

-continued
23
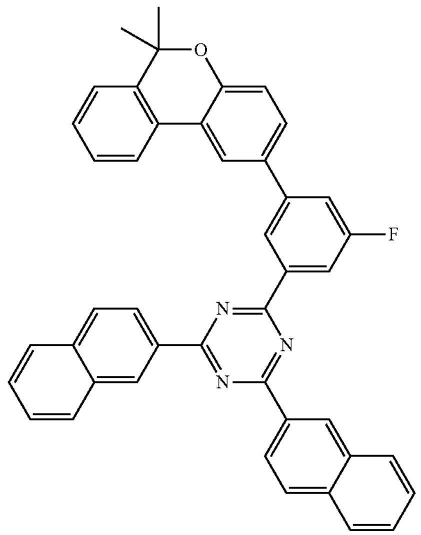
24
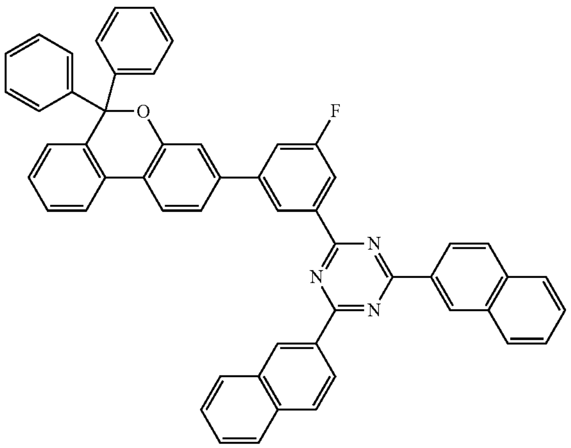
25
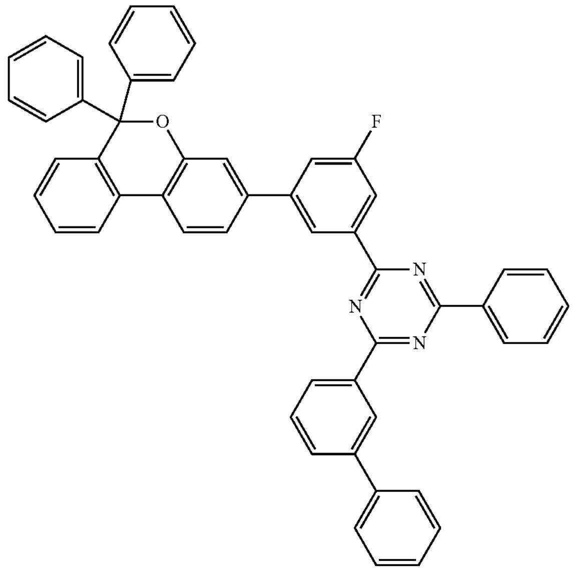
26
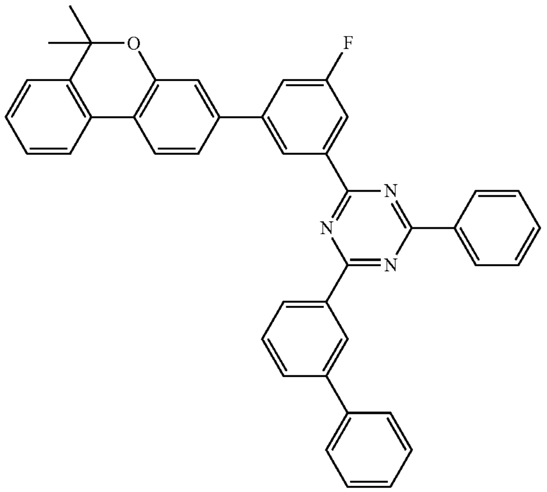
27
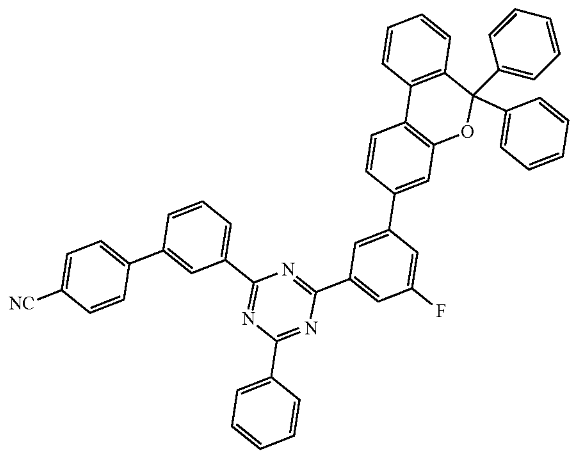
28
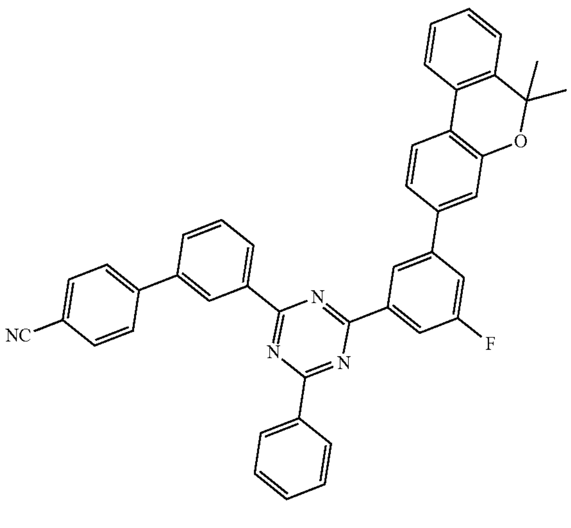

-continued
29
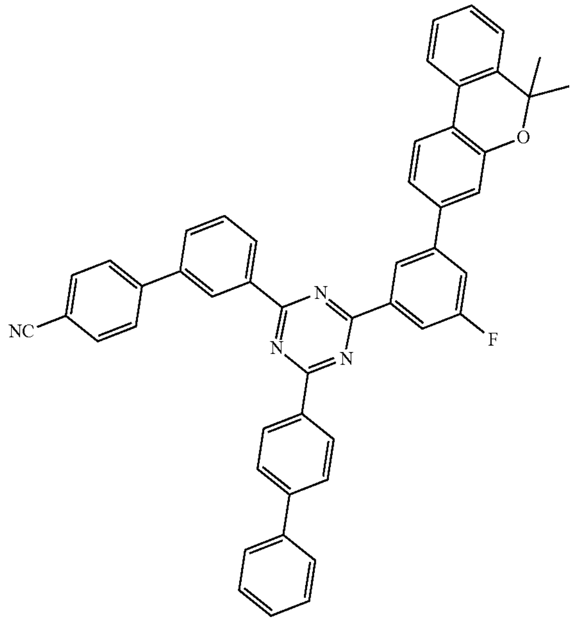
30
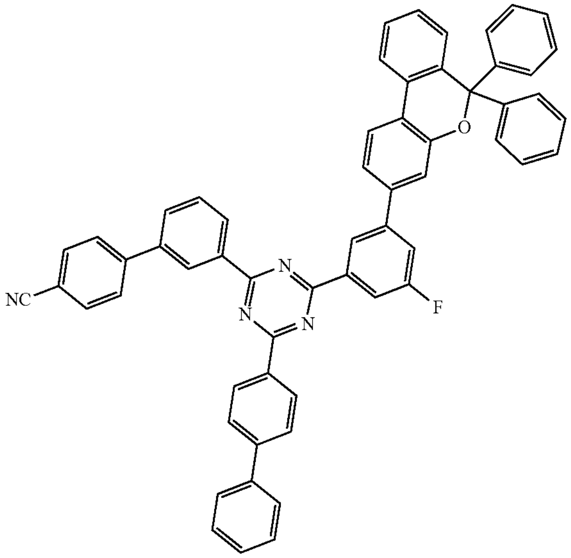
31
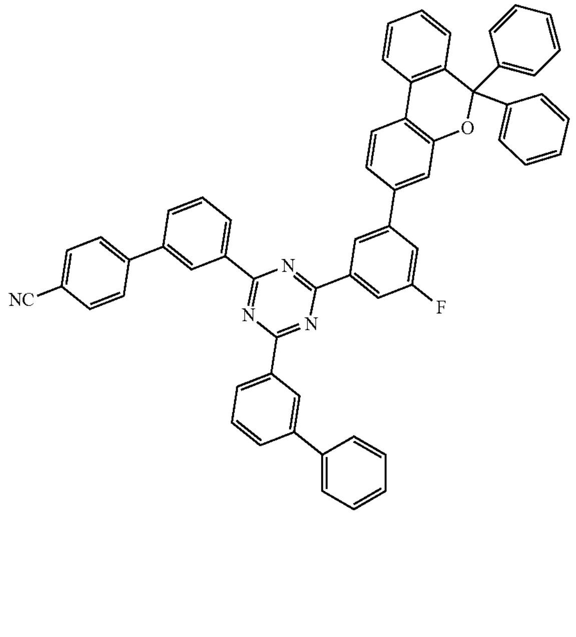
32
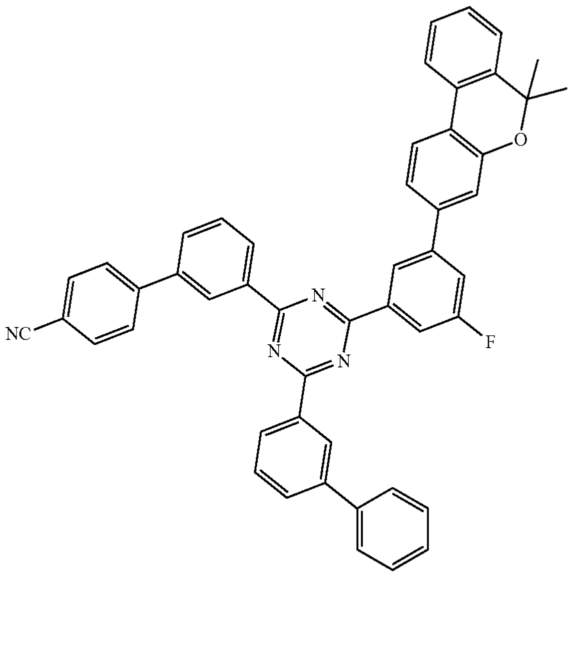

-continued
33
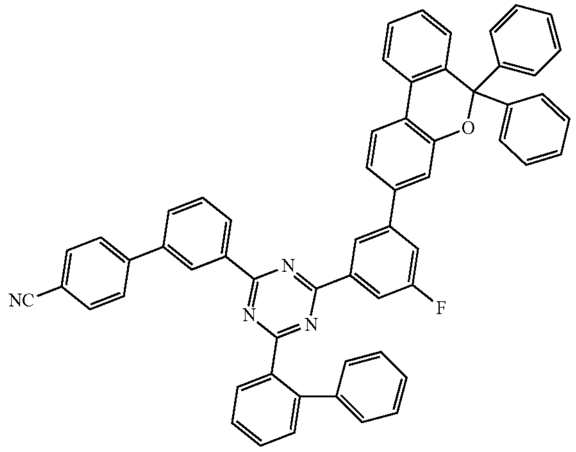
34
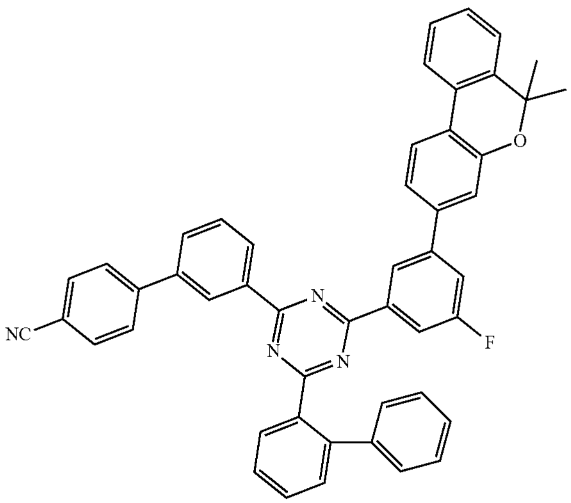
35
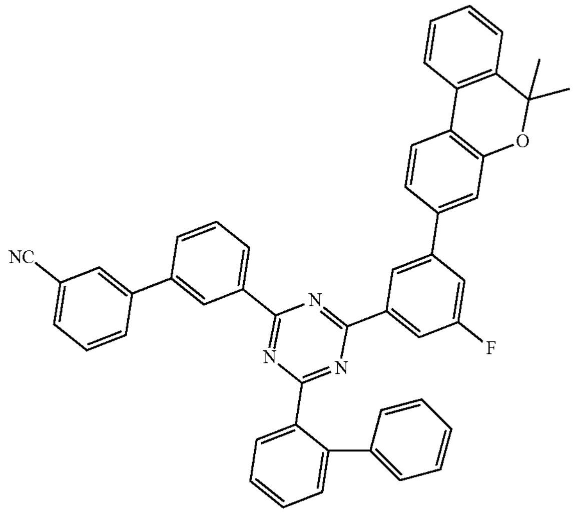
36
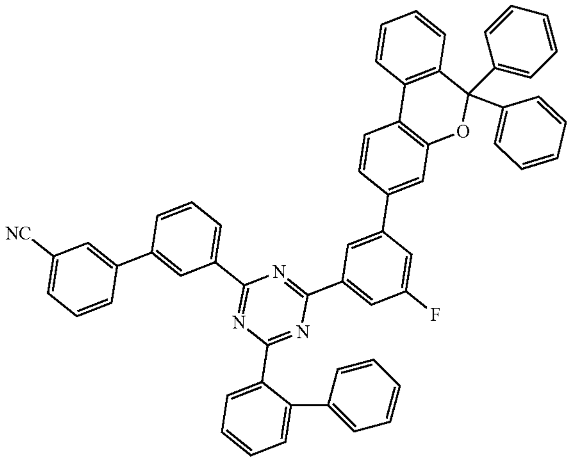
37
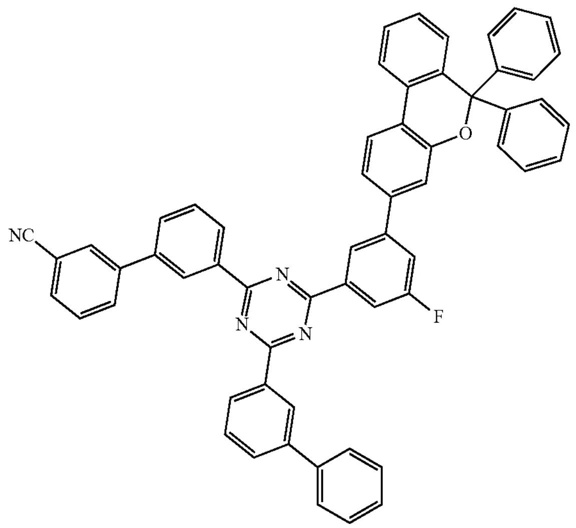
38
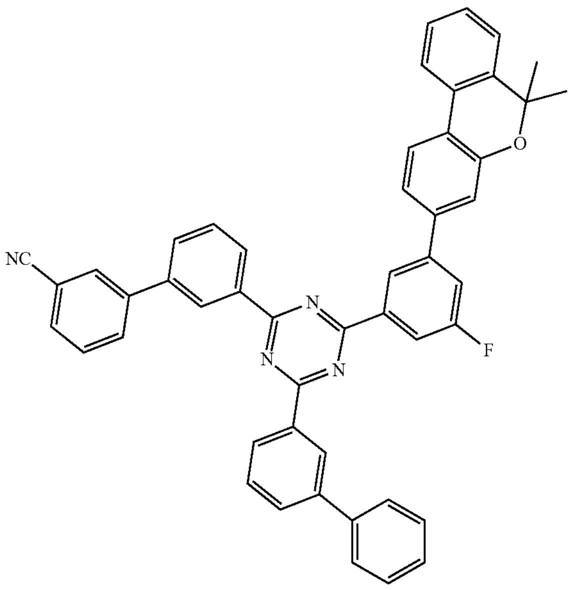

-continued
39
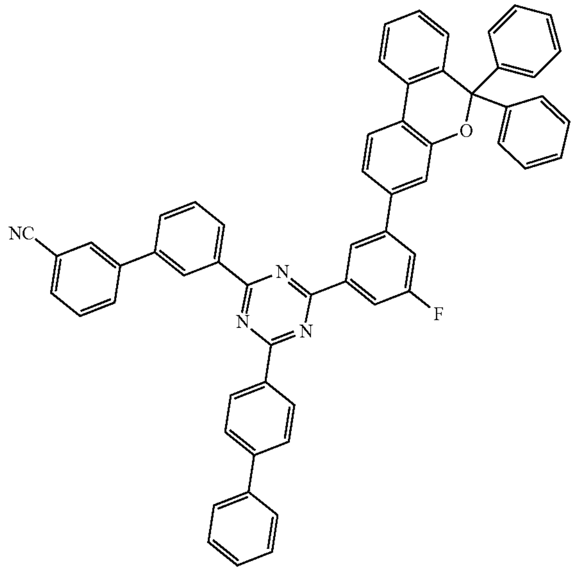
40
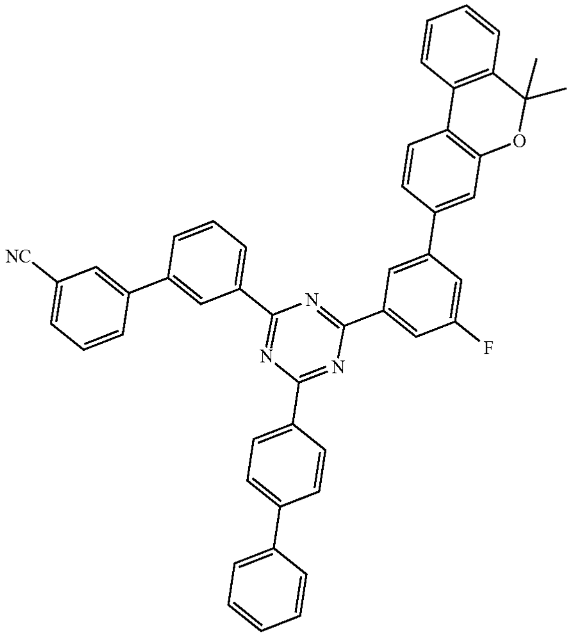
41
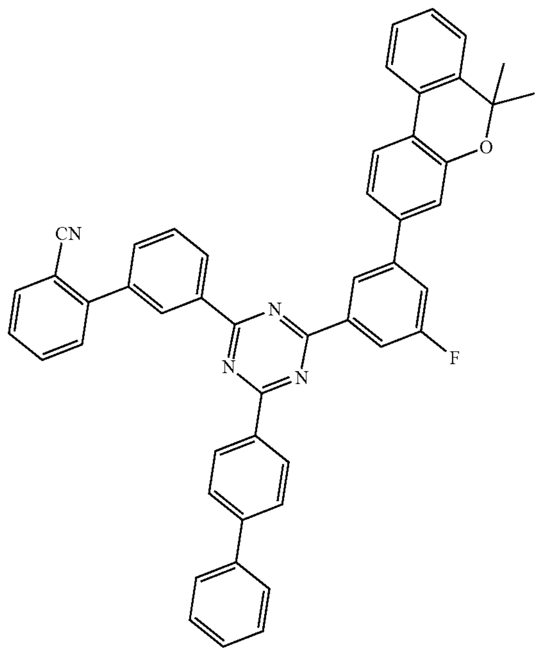
42
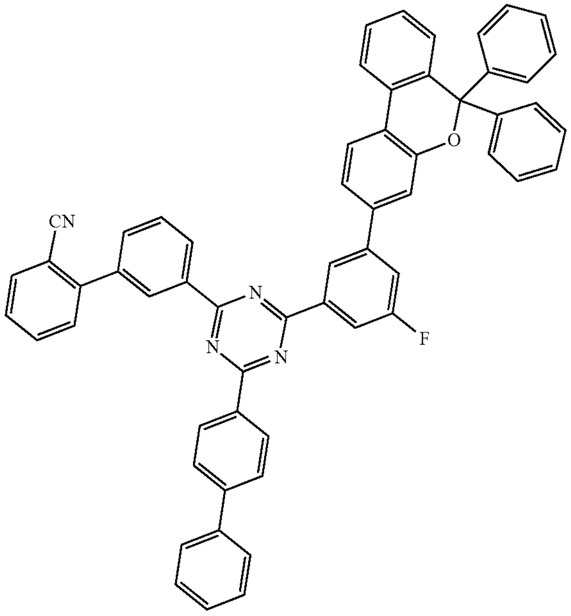

-continued
43
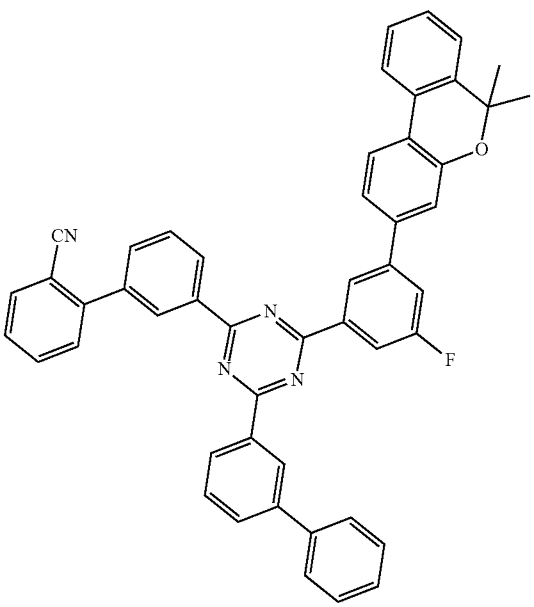
44
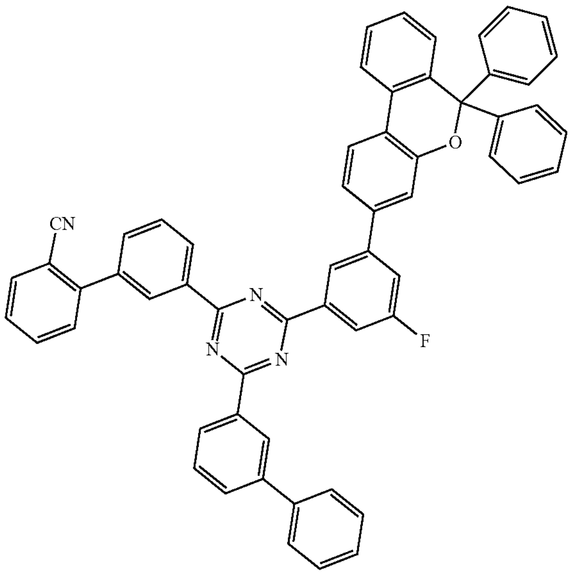
45
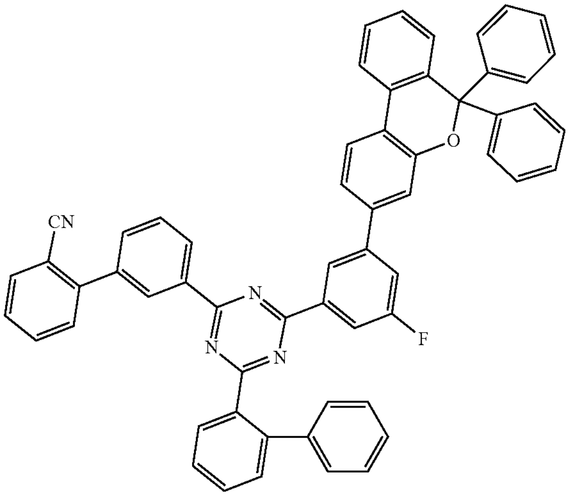
46
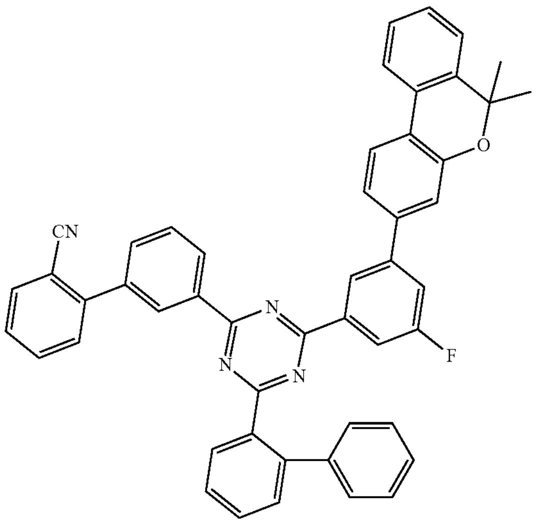
47
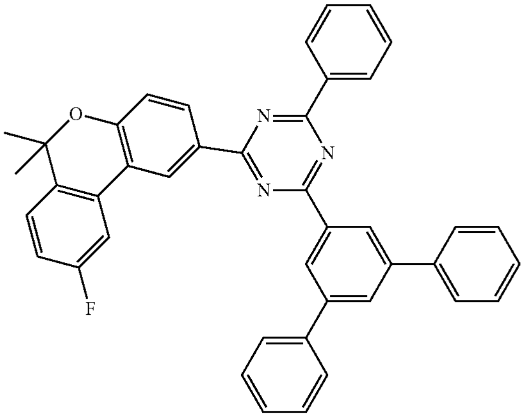
48
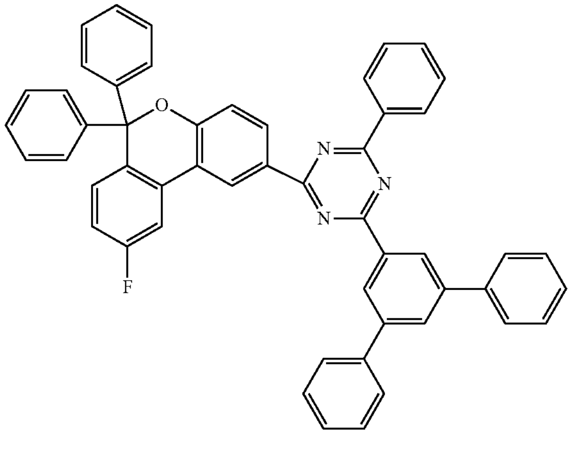

-continued
49
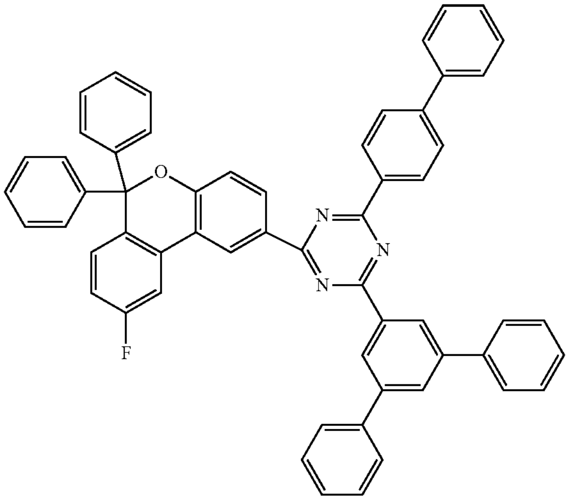
50
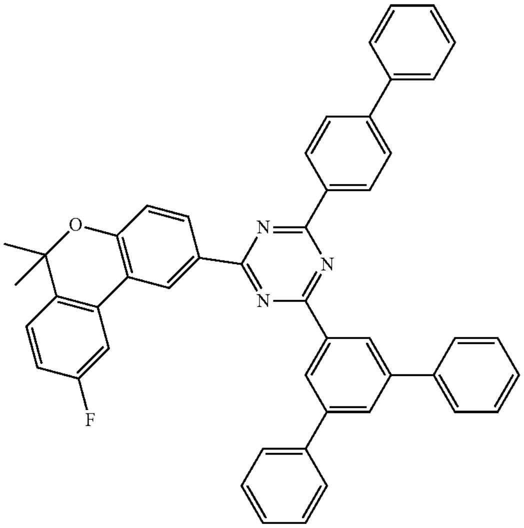
51
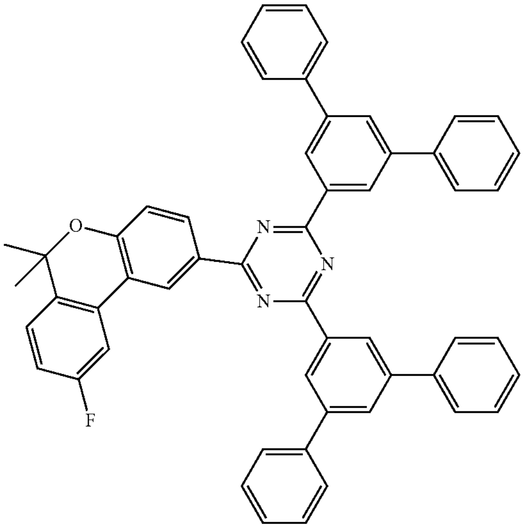
52
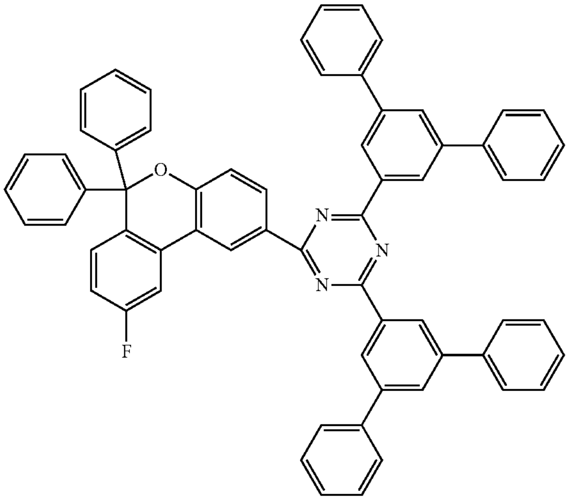
53
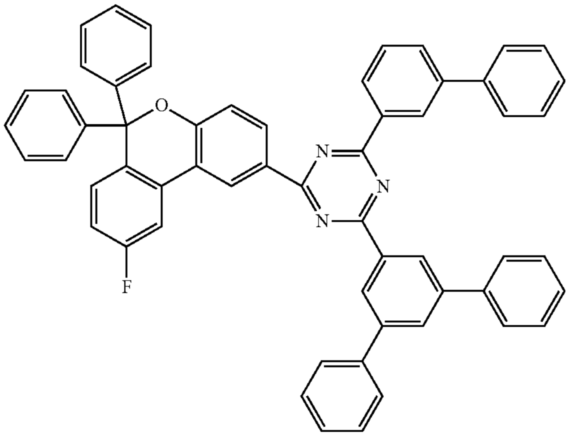
54
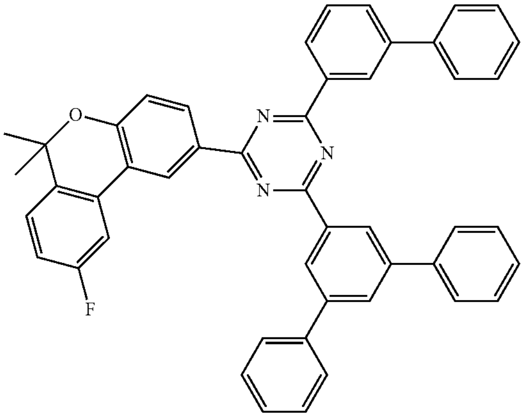

-continued
55
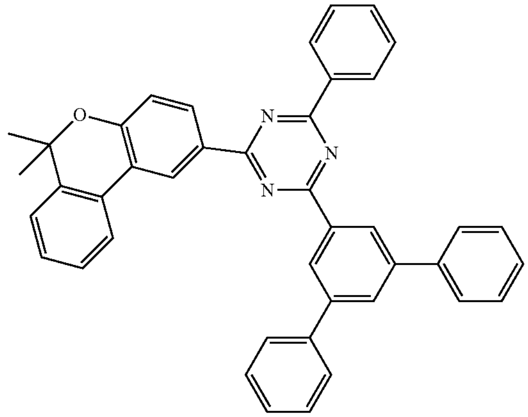
56
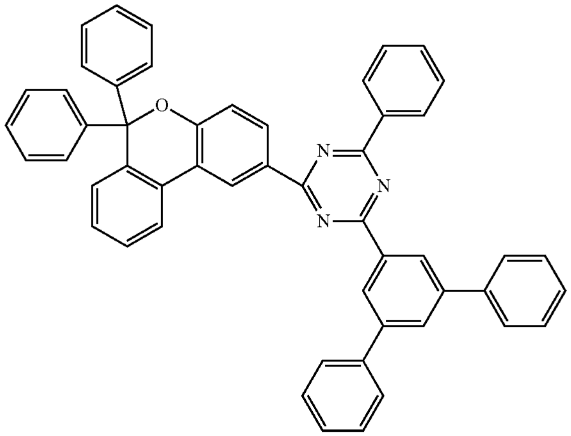
57
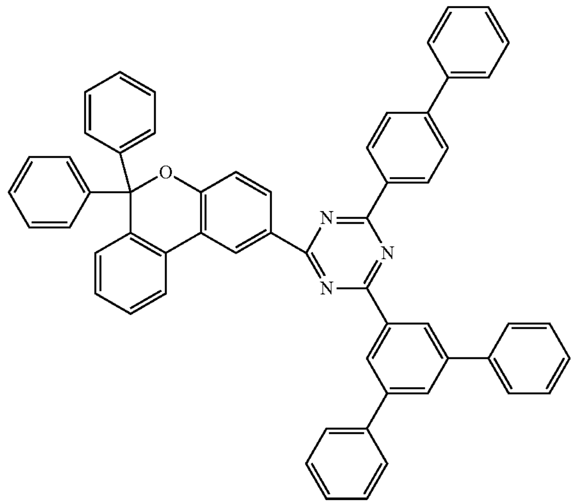
58
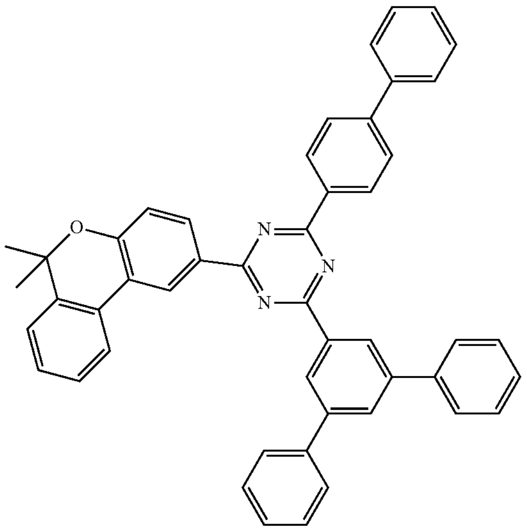
59
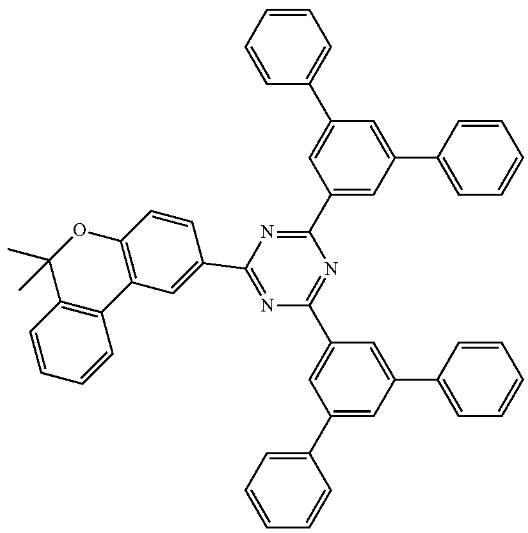
60
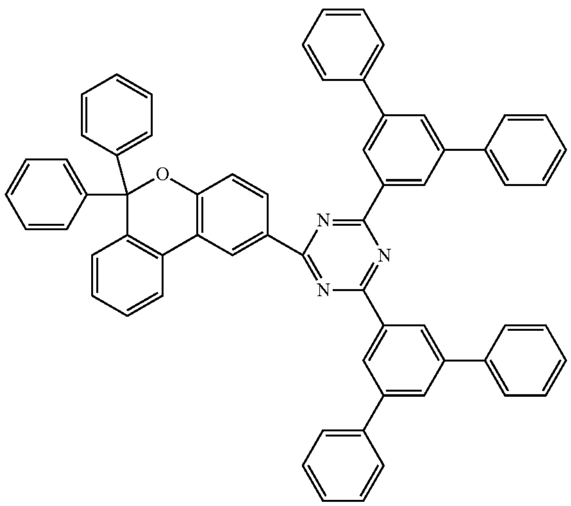

-continued
61
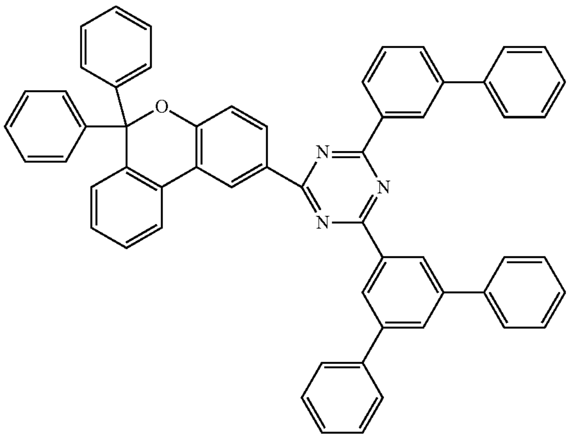
62
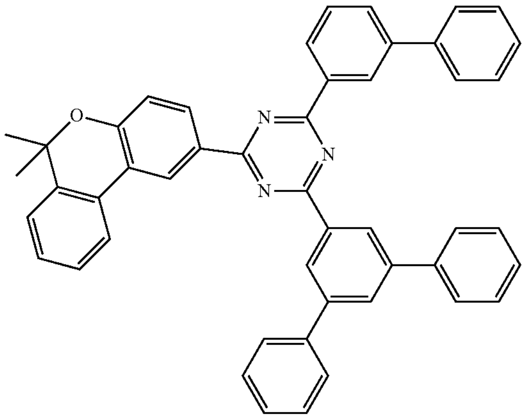
63
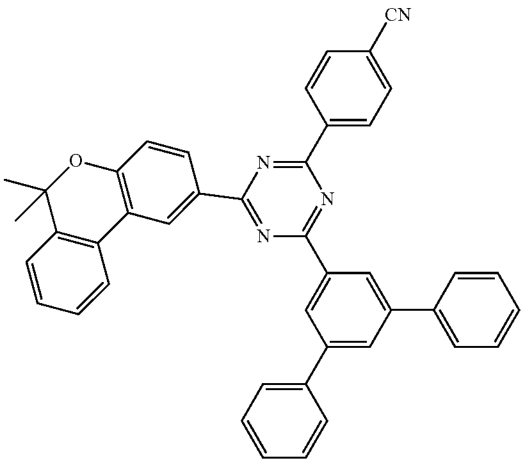
64
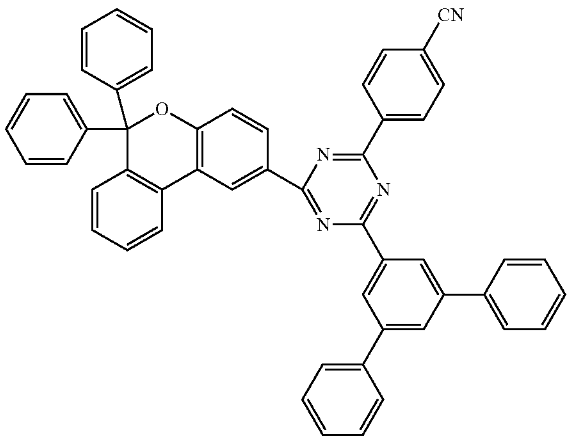
65
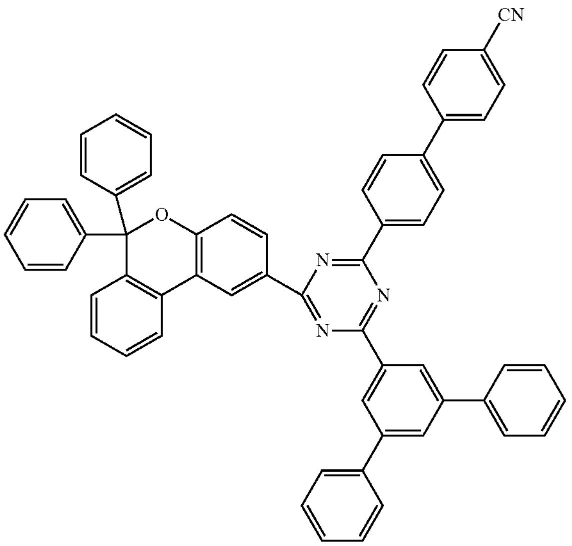
66
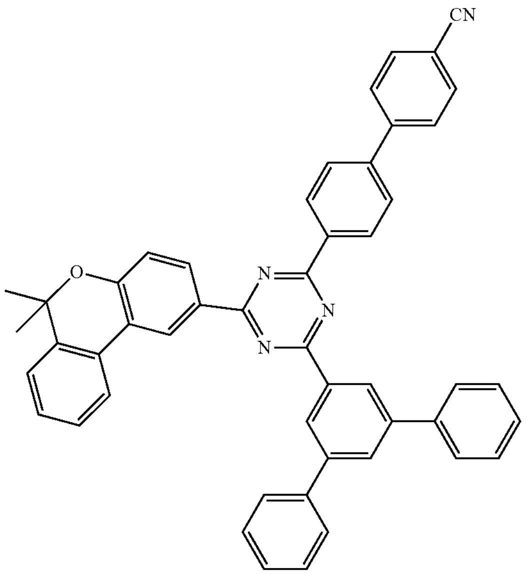

-continued
67
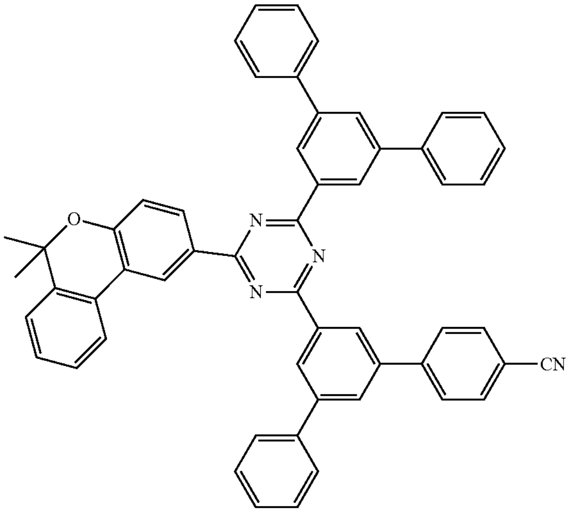
68
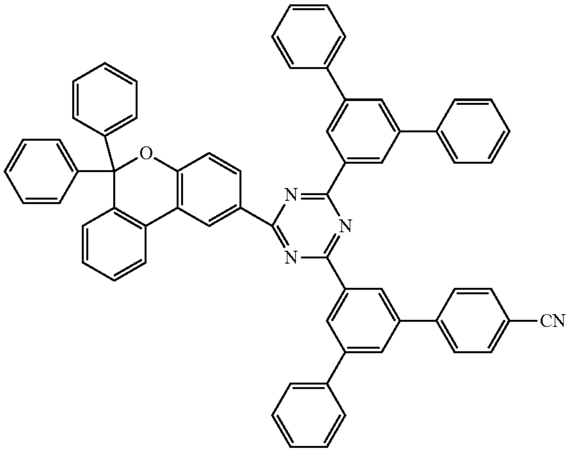
69
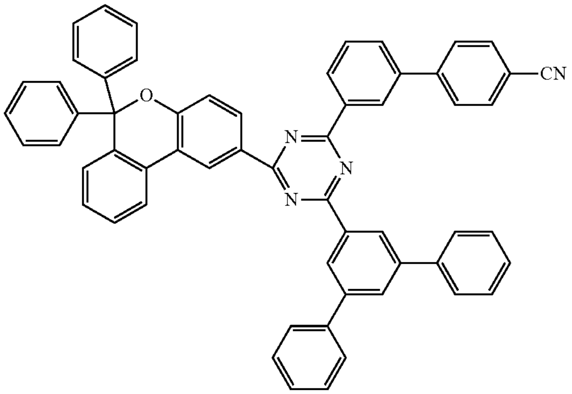
70
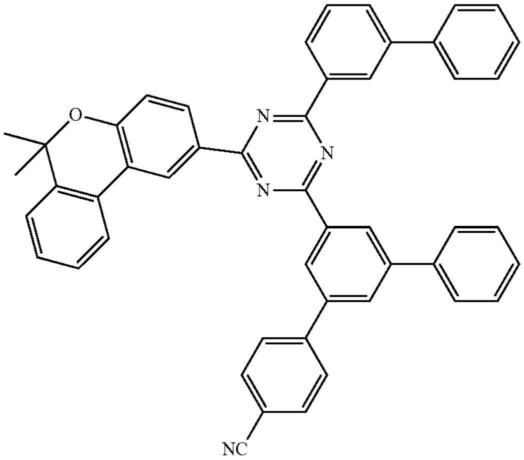
71
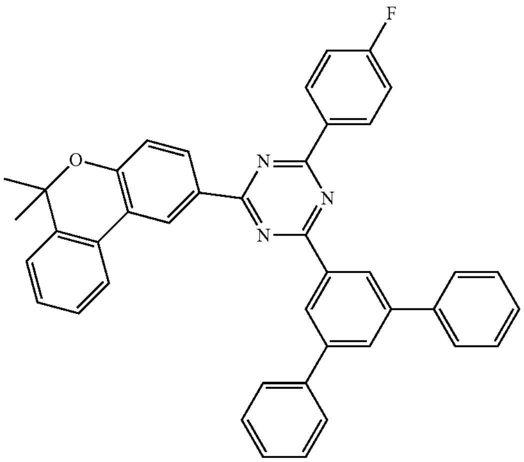
72
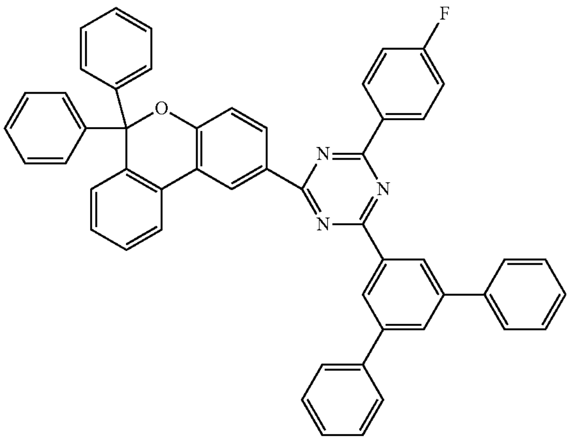

-continued
73
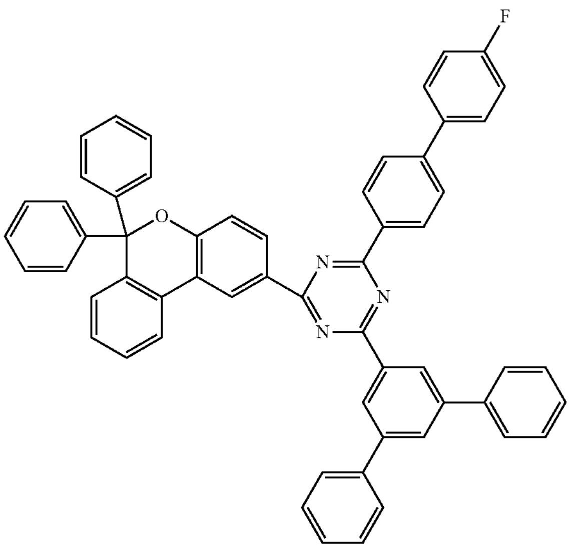
74
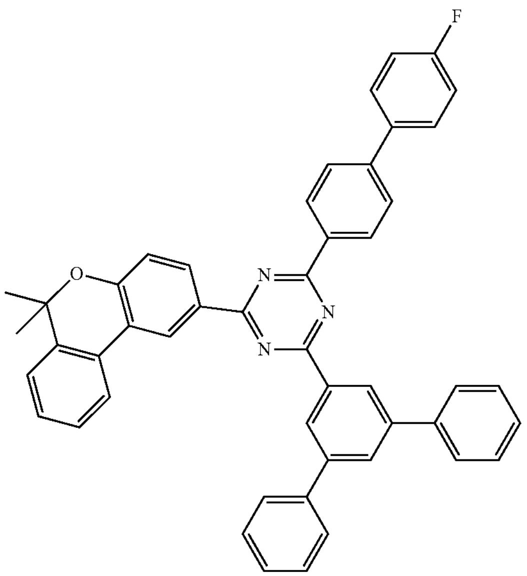
75
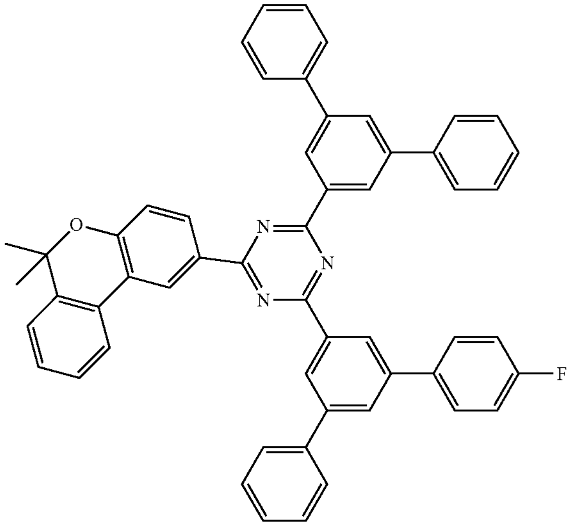
76
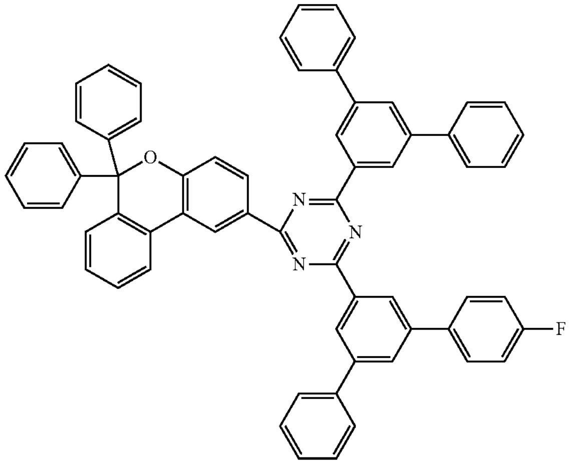
77
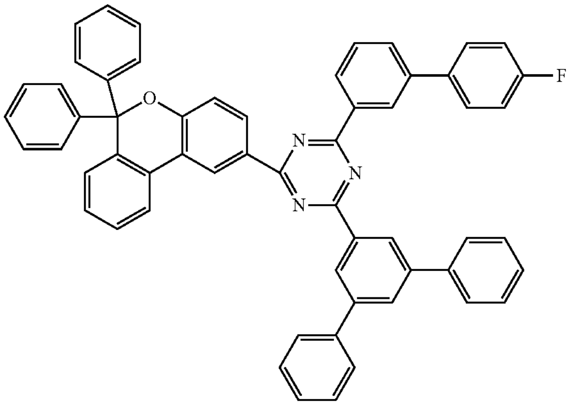
78
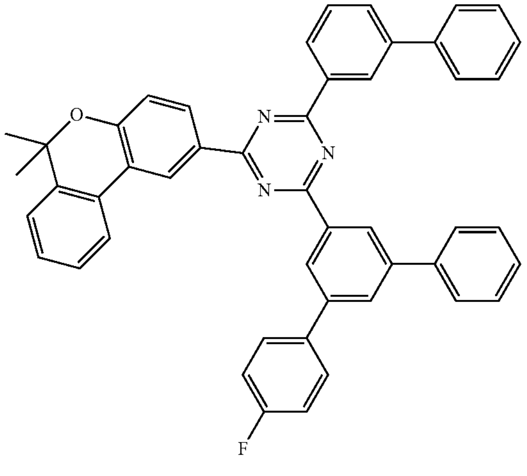

-continued
79
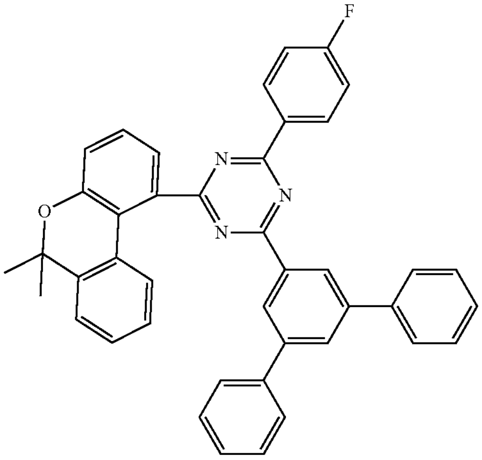
80
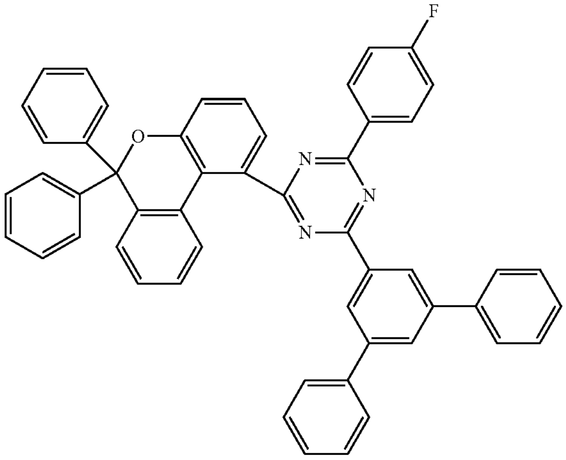
81
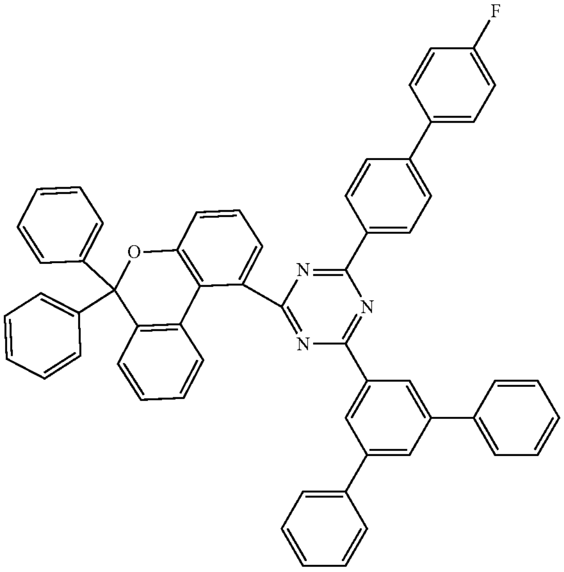
82
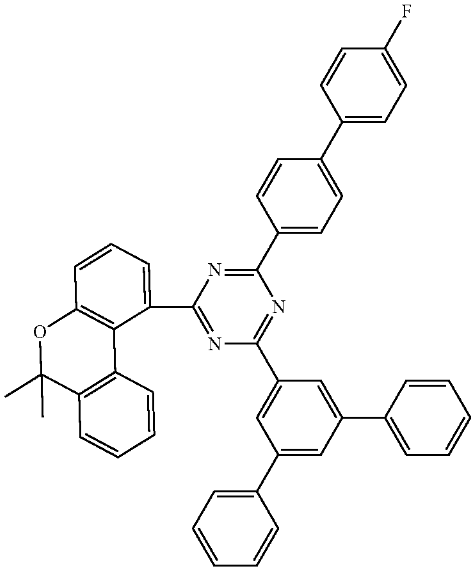
83
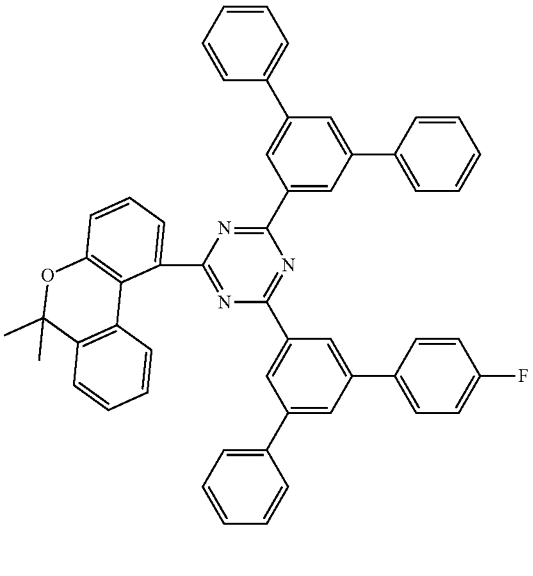
84
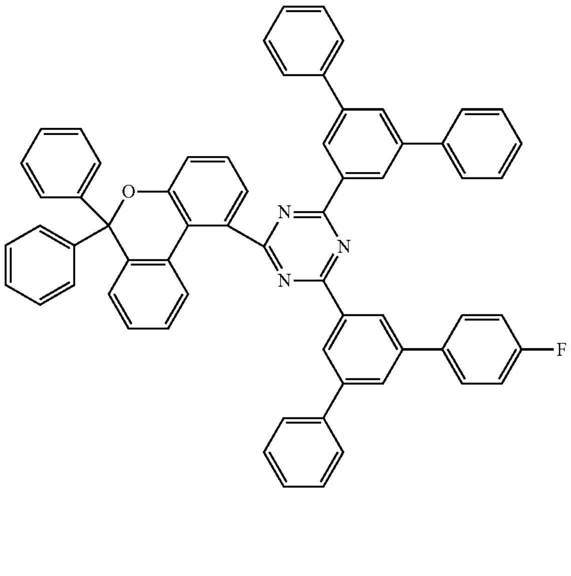

-continued
85
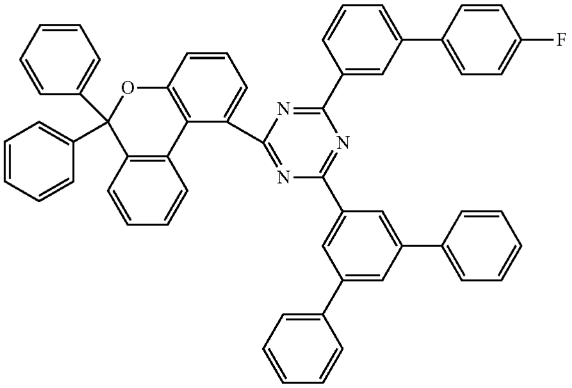
86
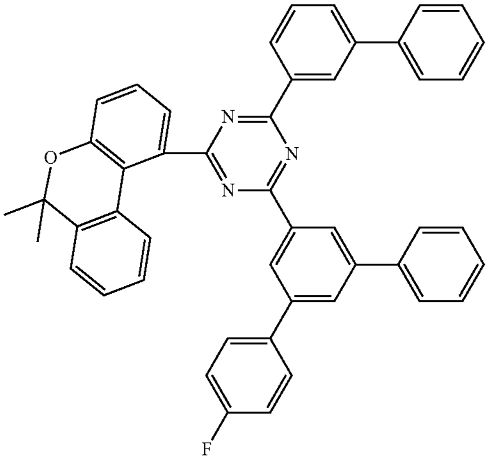
87
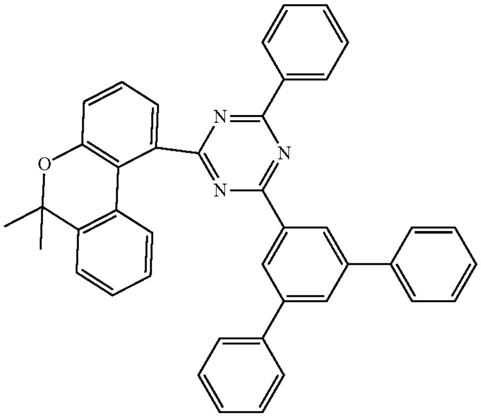
88
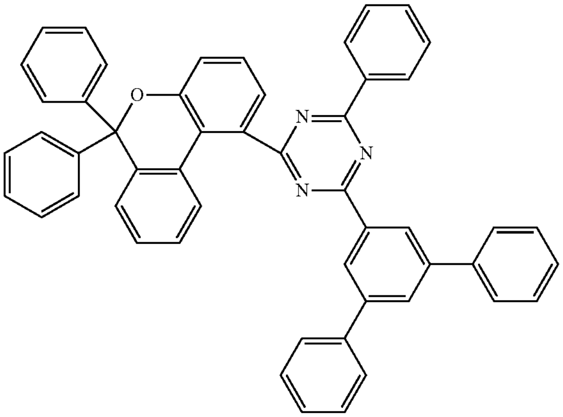
89
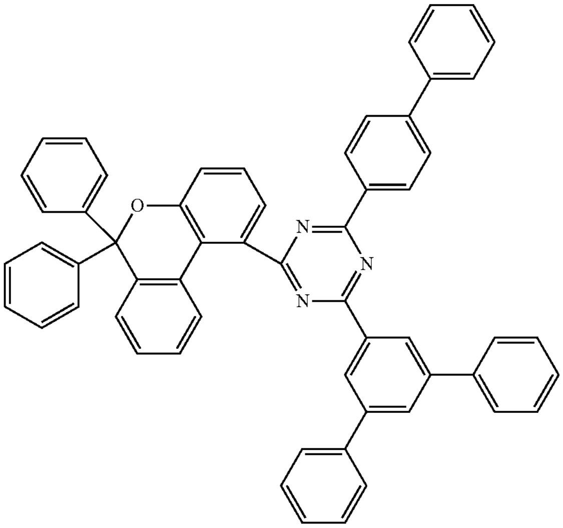
90
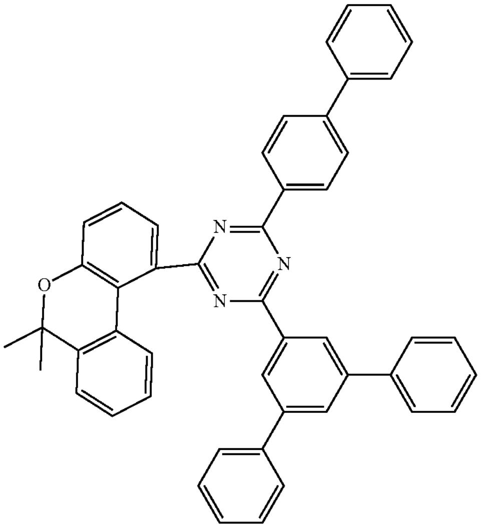

-continued
91
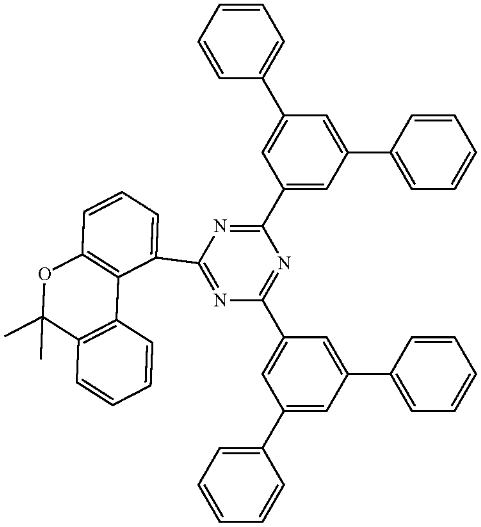
92
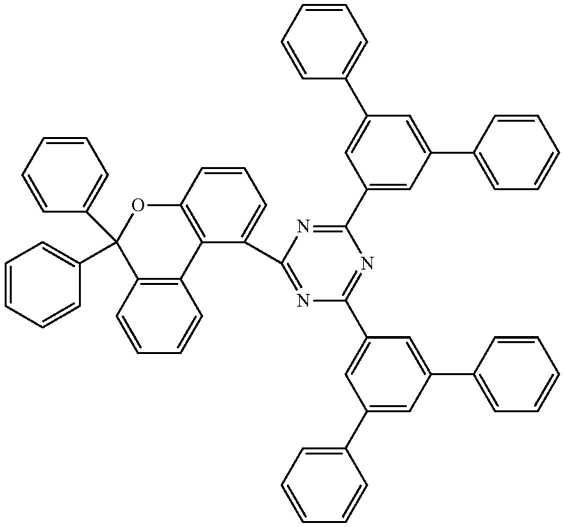
93
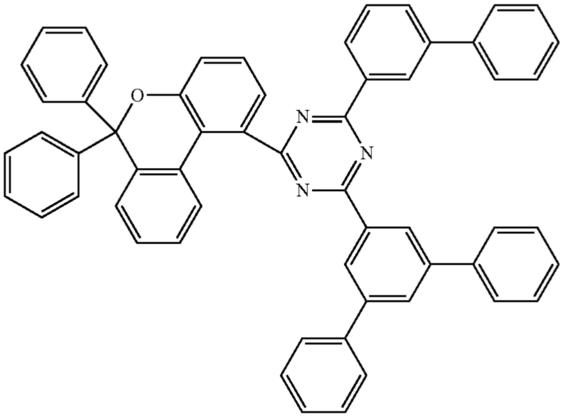
94
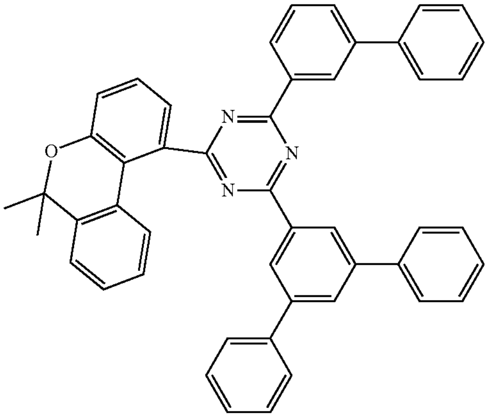
95
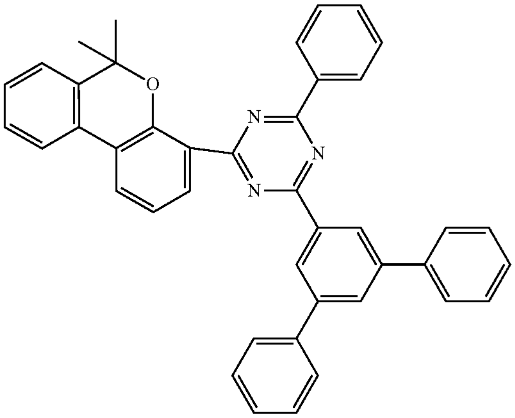
96
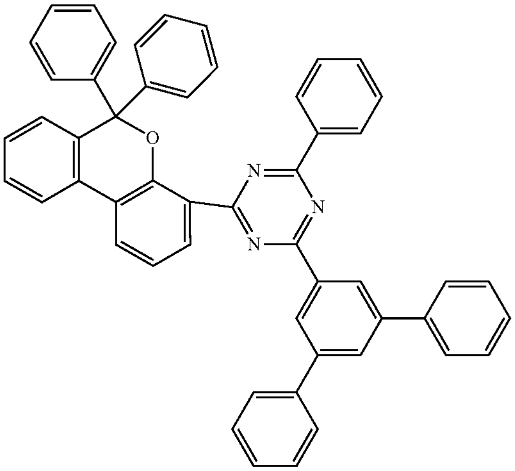

-continued
97
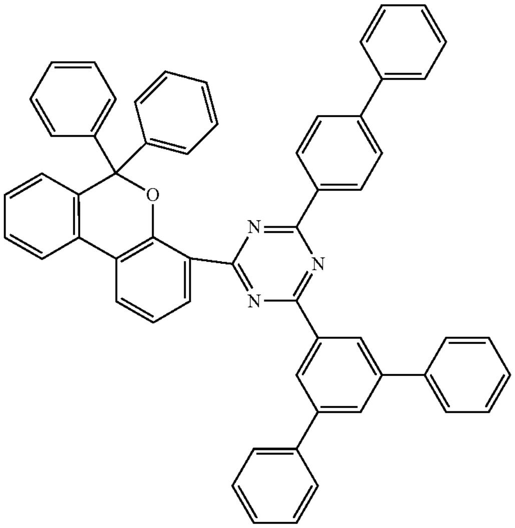
98
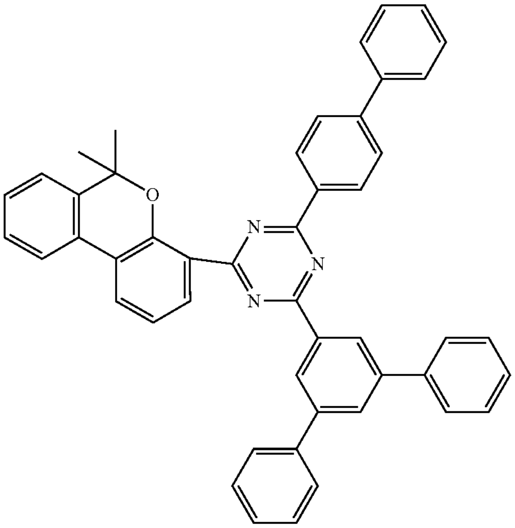
99
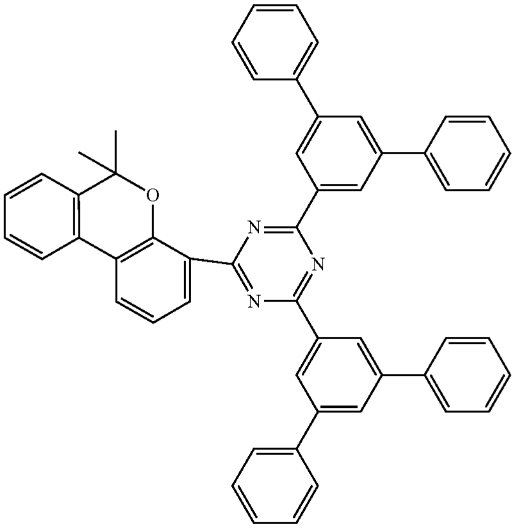
100
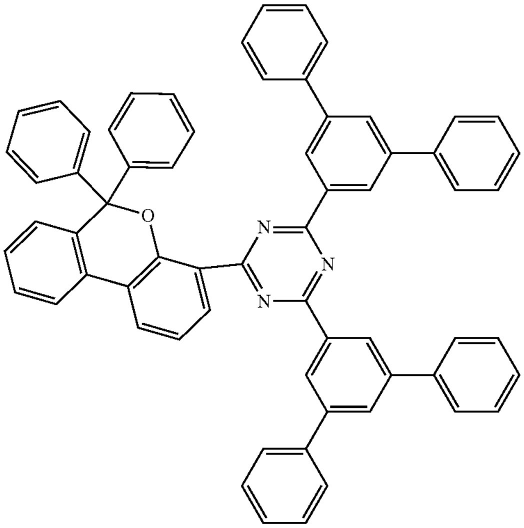
101
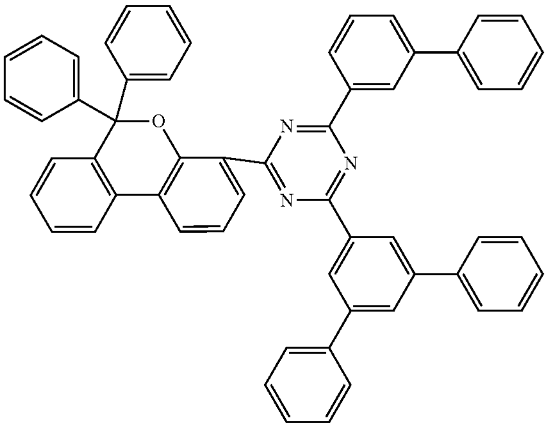
102
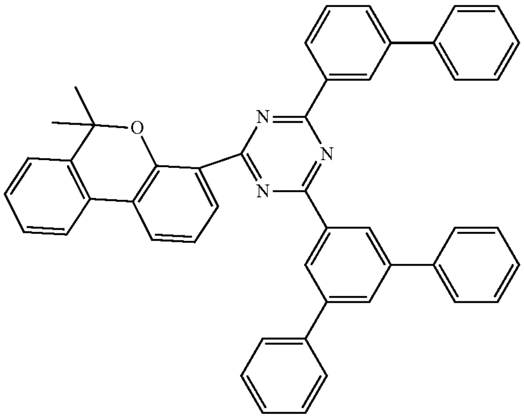

-continued
103
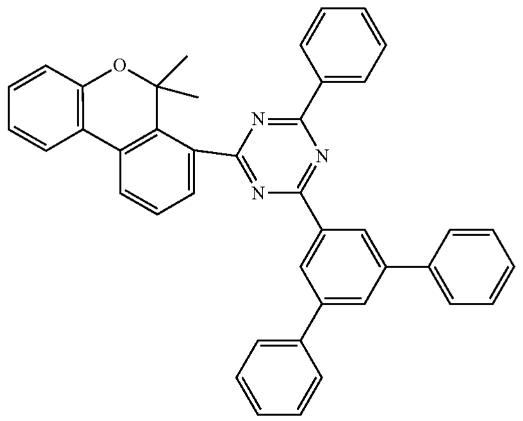
104
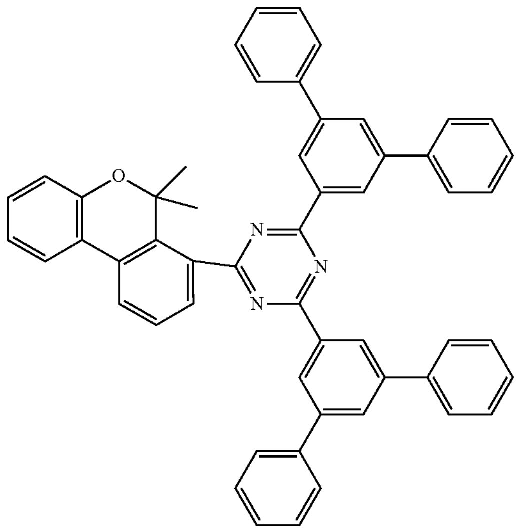
105
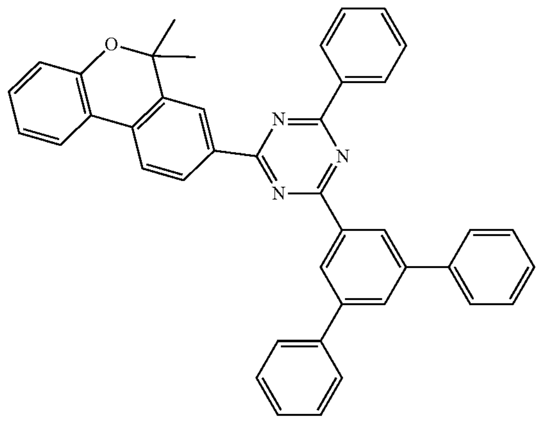
106
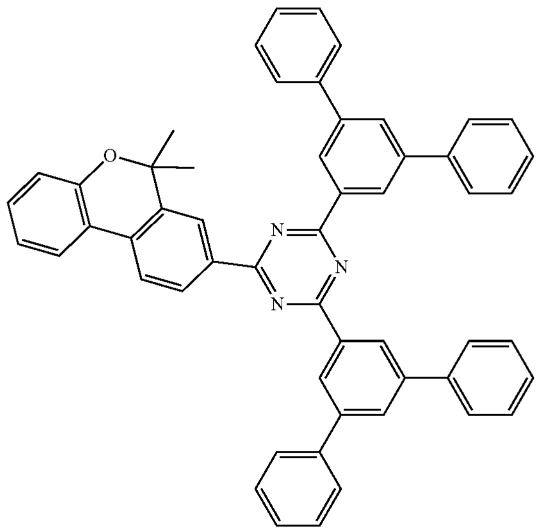
107
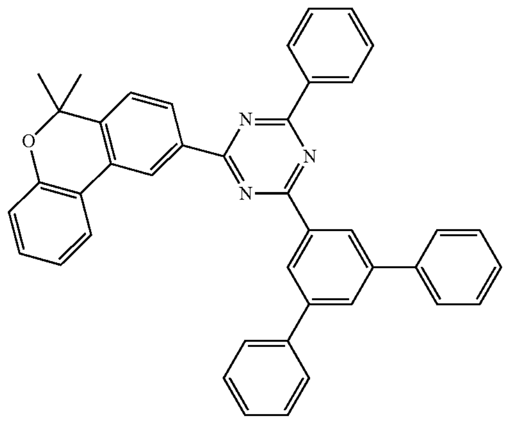
108
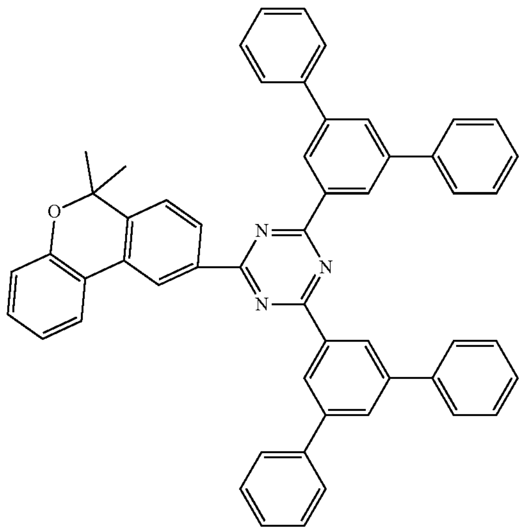

-continued
109
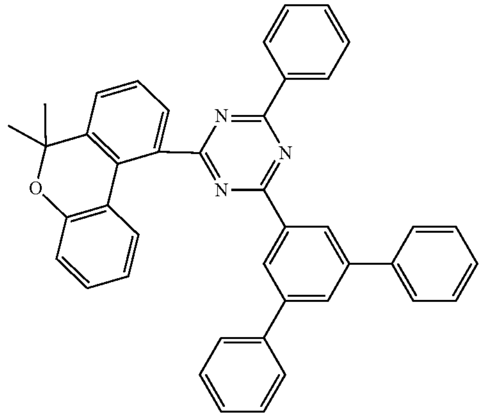
110
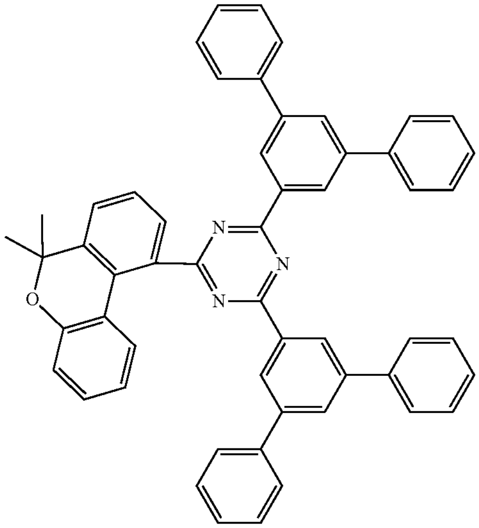
111
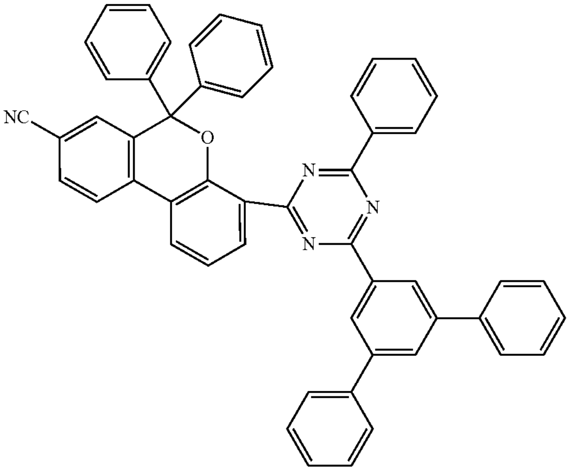
112
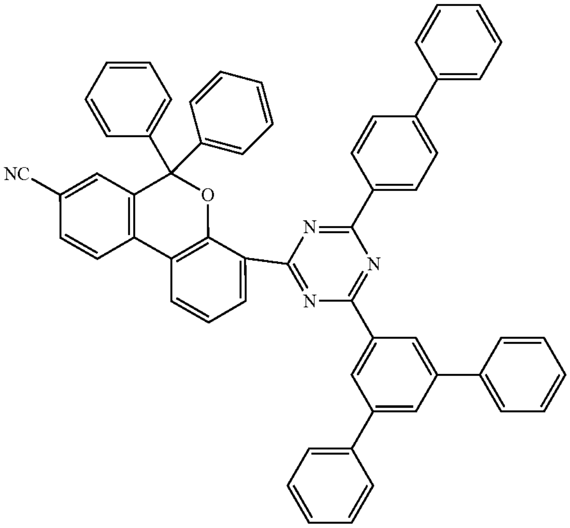
113
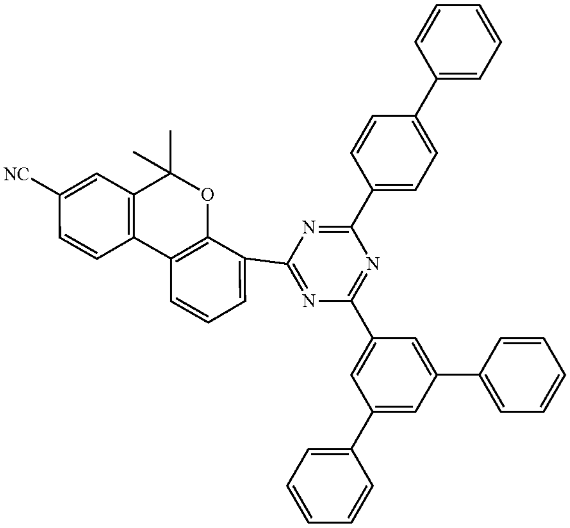
114
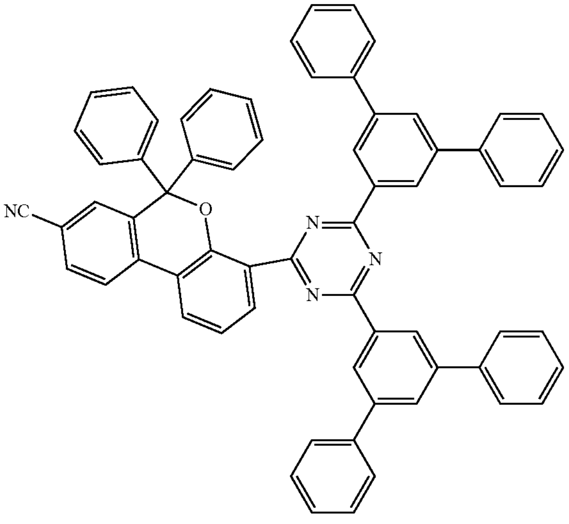

-continued
115
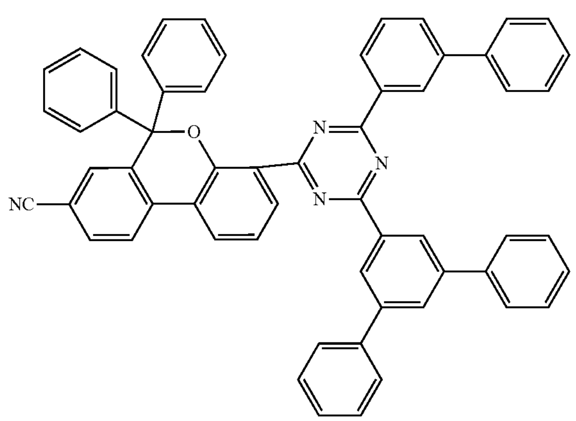
116
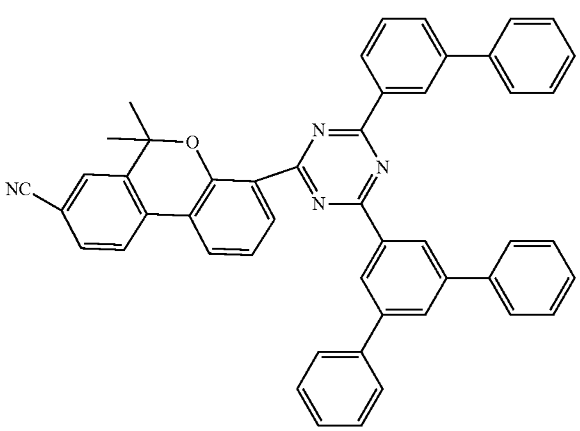
117
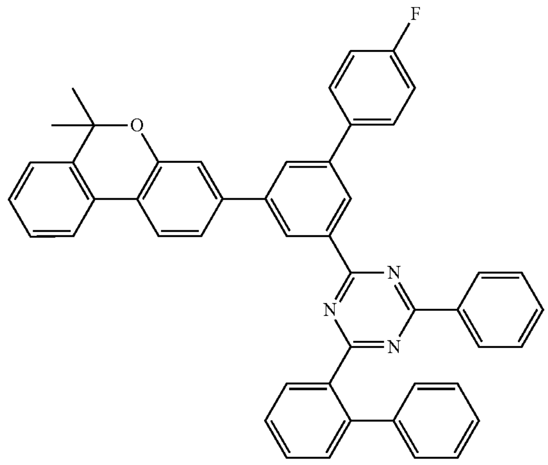
118
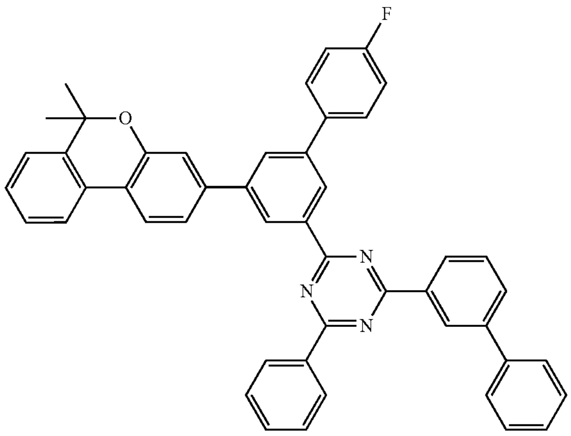
119
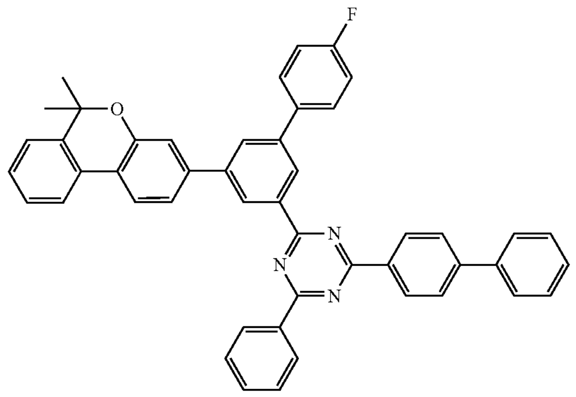
120
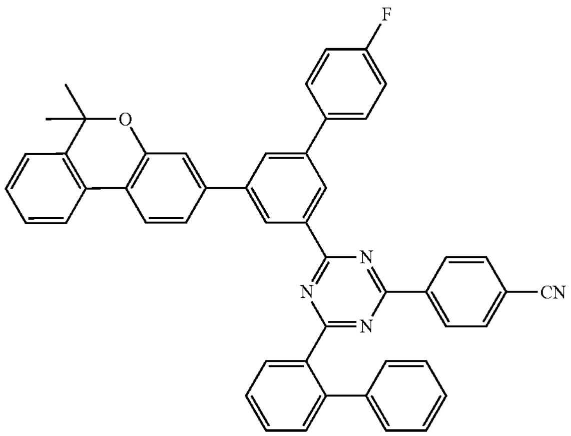

-continued
121
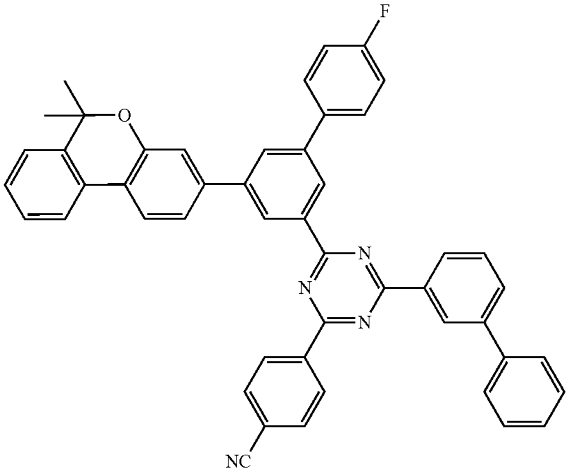
122
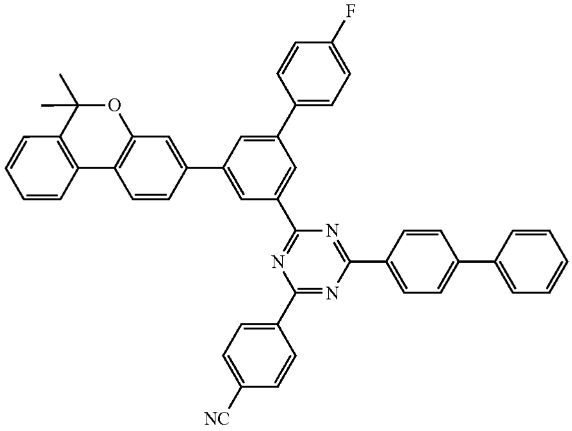
123
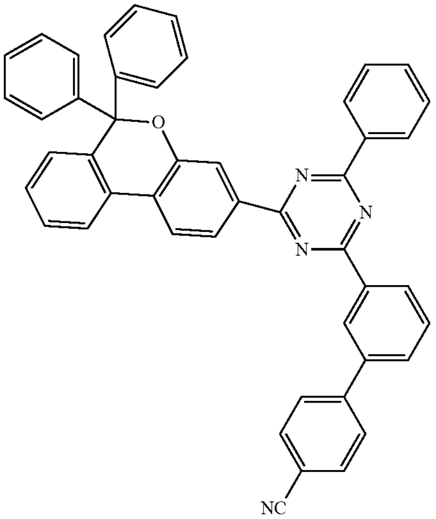
124
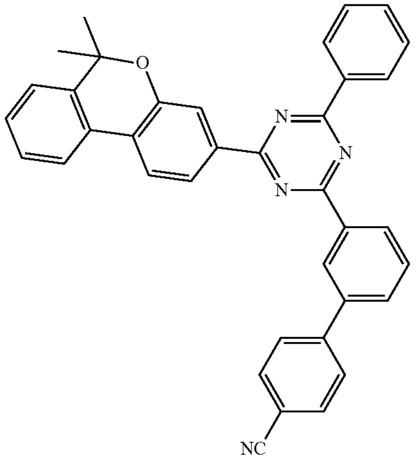
125
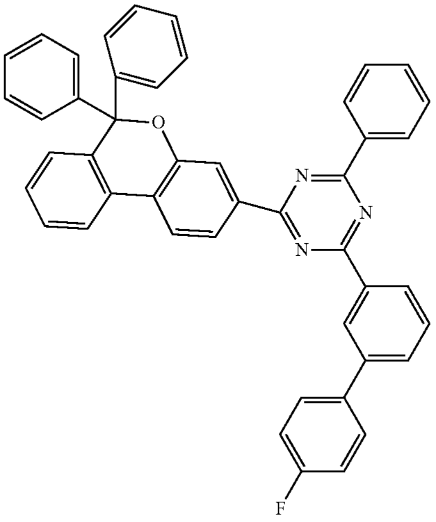
126
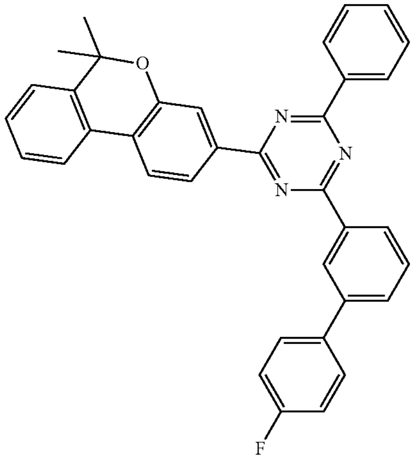

-continued
127
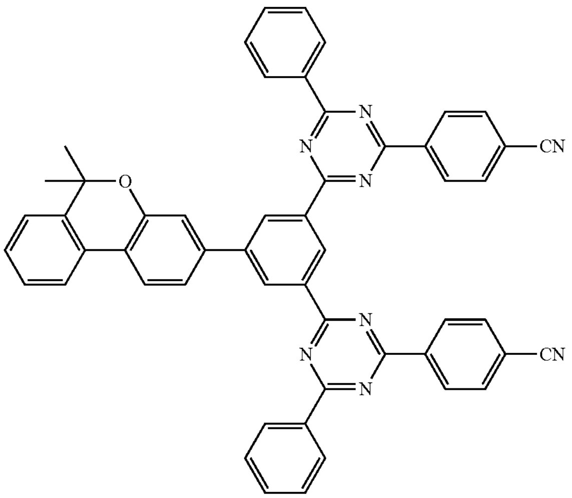
128
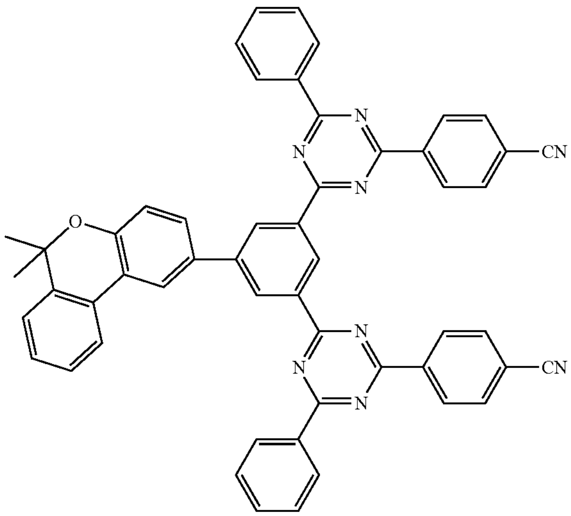
129
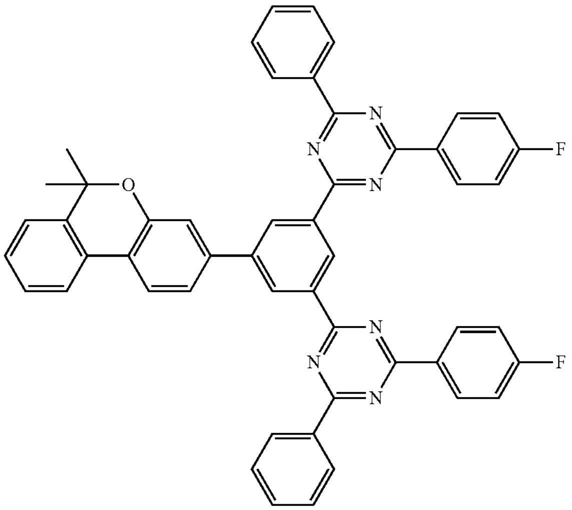
130
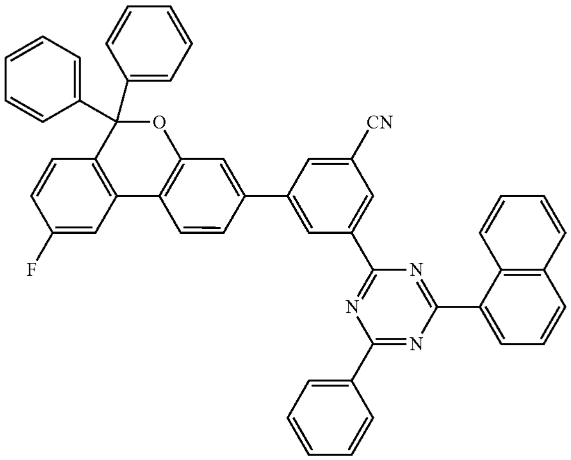
131
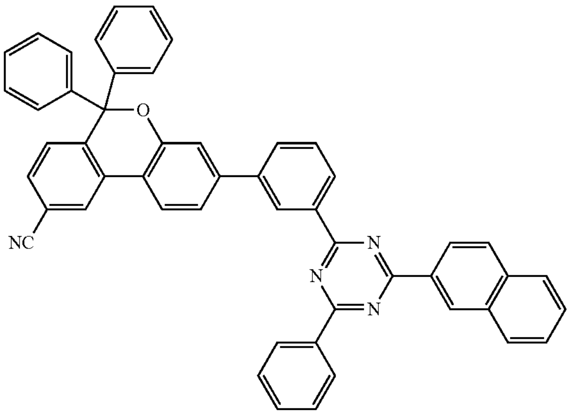
132
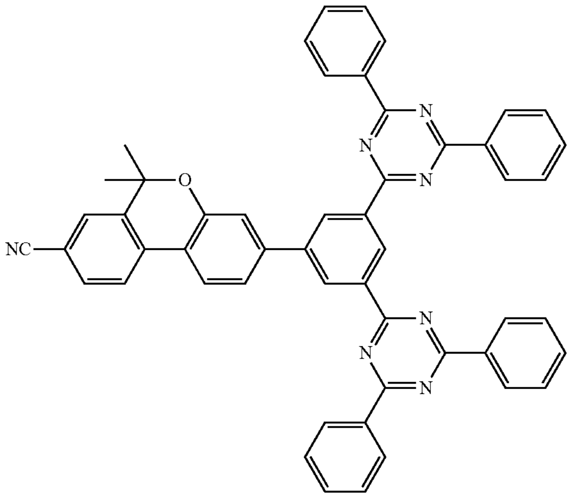

-continued
133
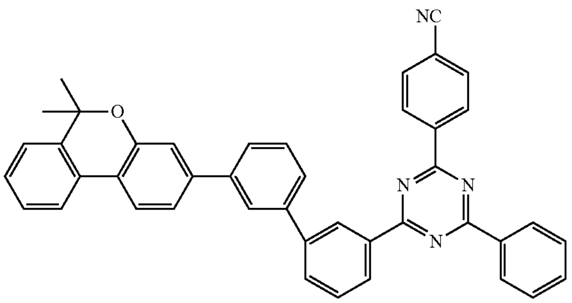
134
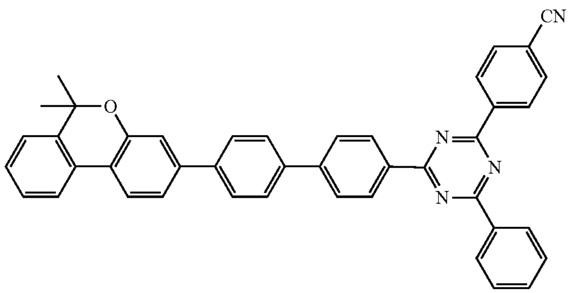
135
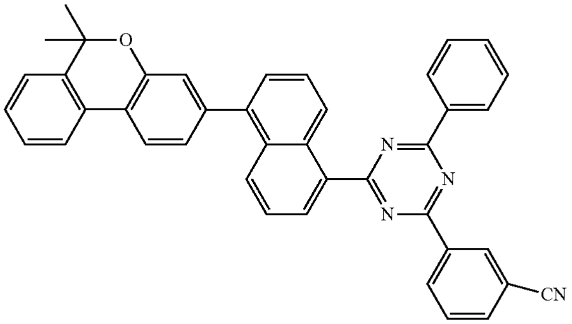
136
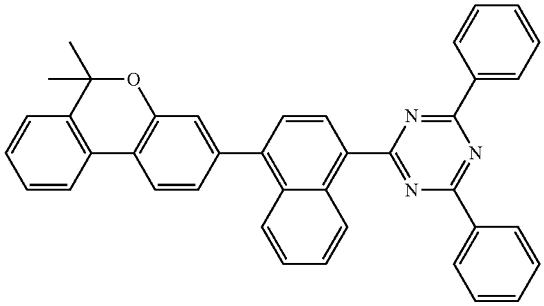
137
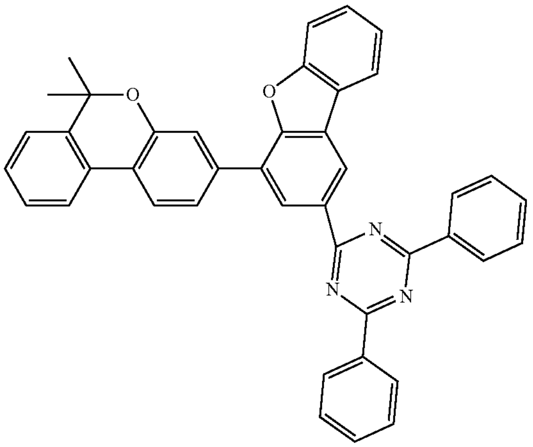
138
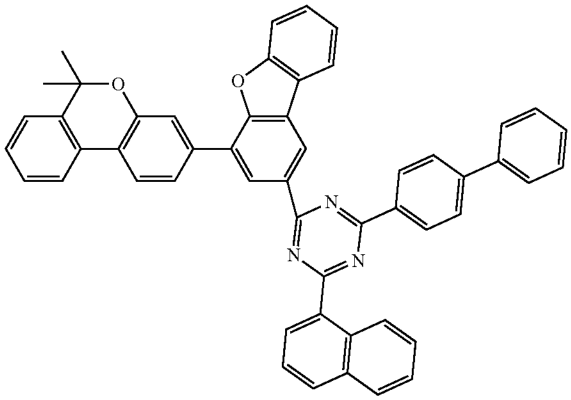
139
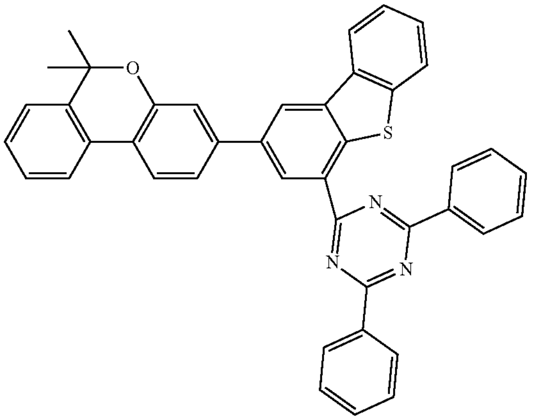
140
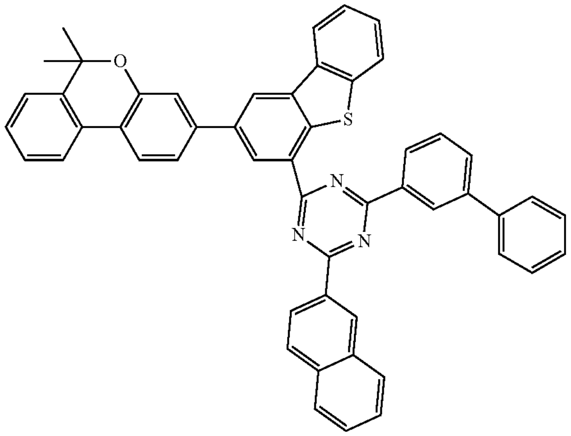

-continued
141
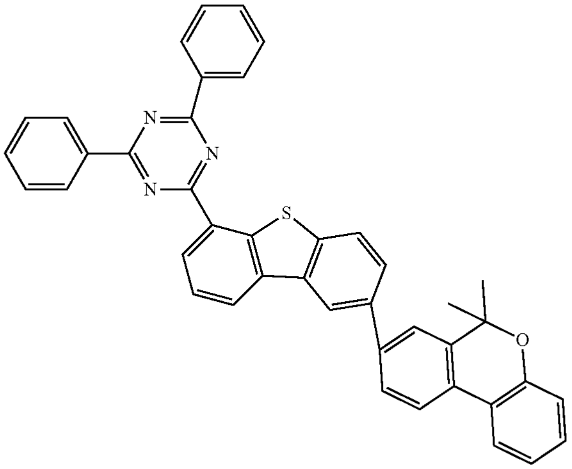
142
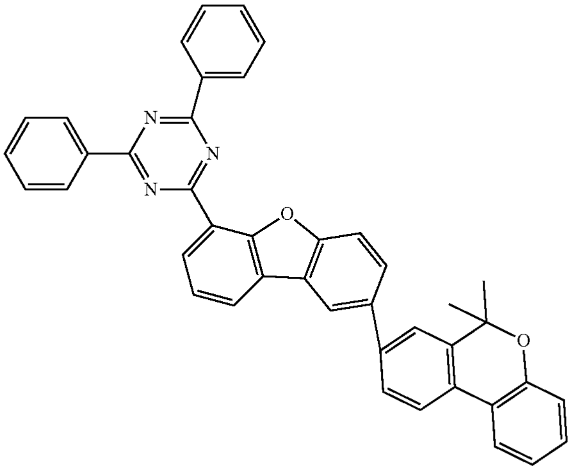
143
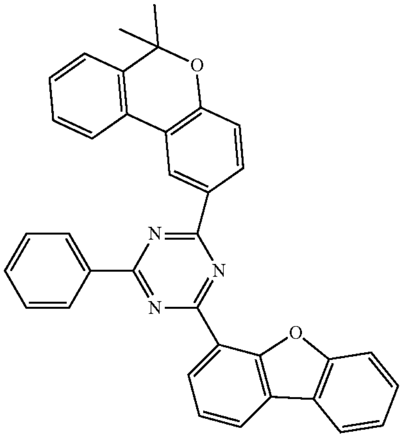
144
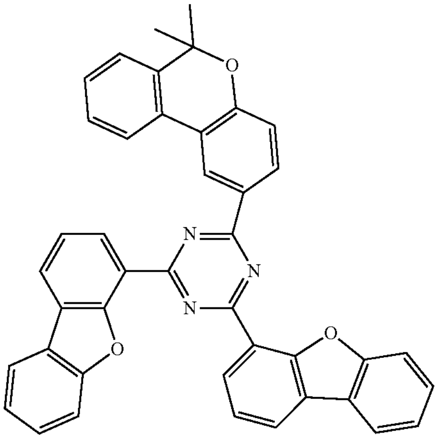
145
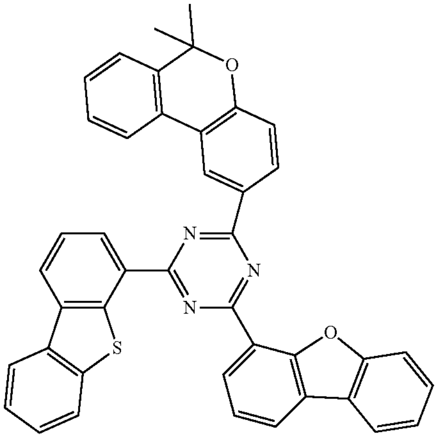
146
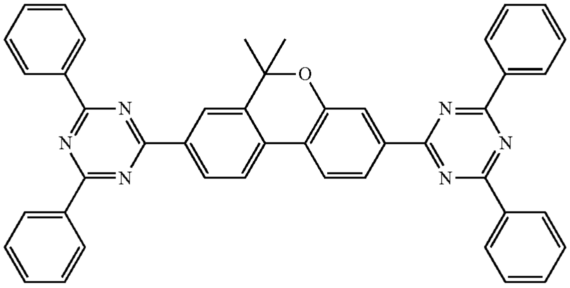

-continued
147
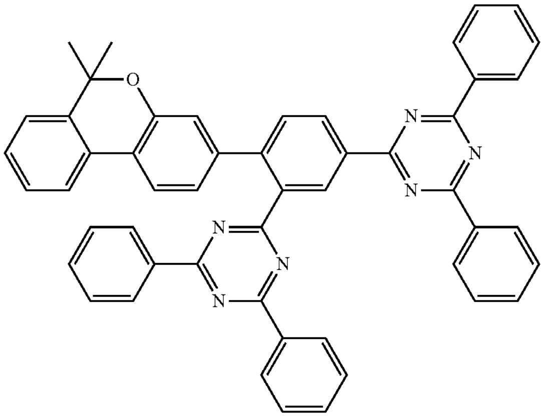
148
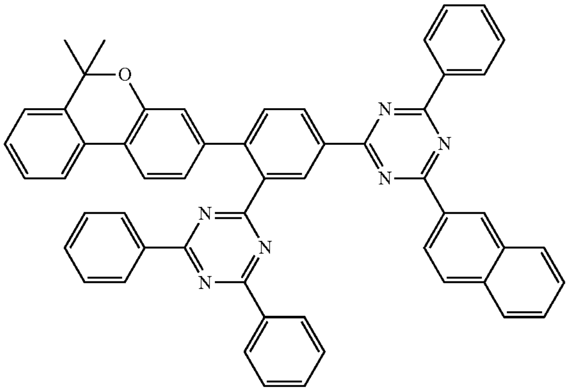
149
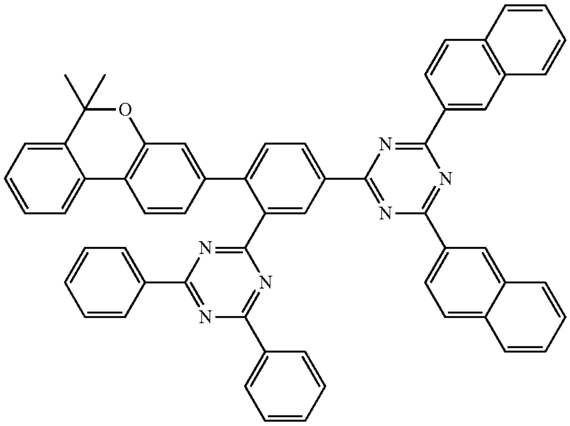
150
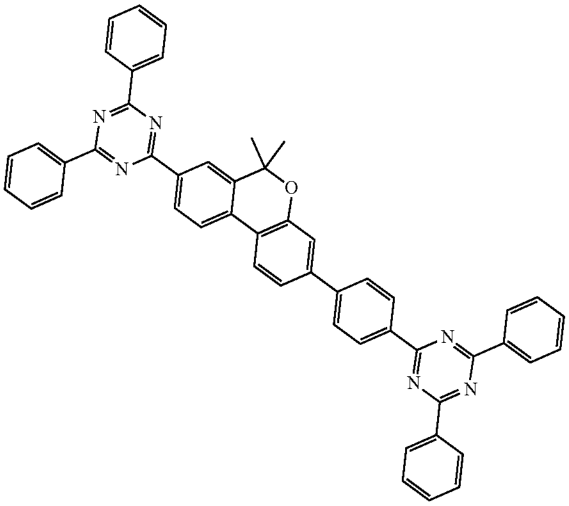
151
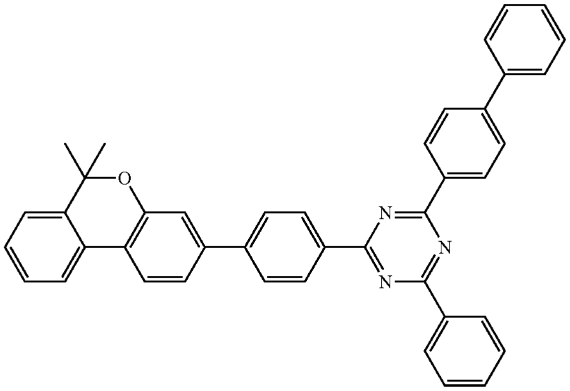
152
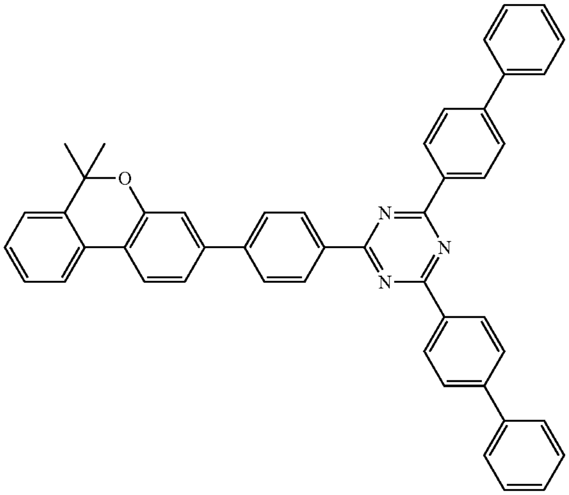

-continued
153
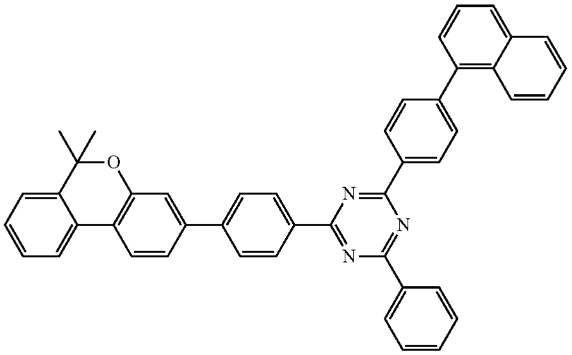
154
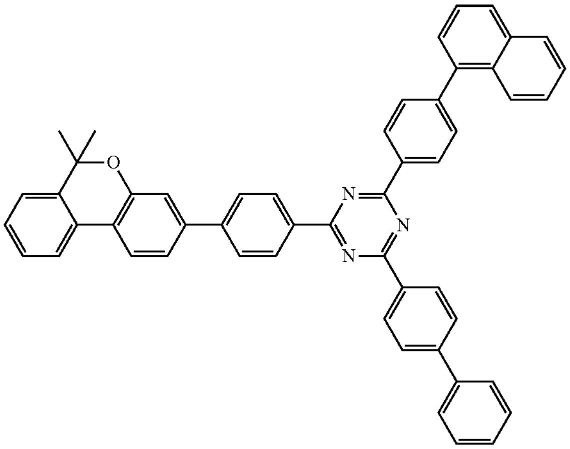
155
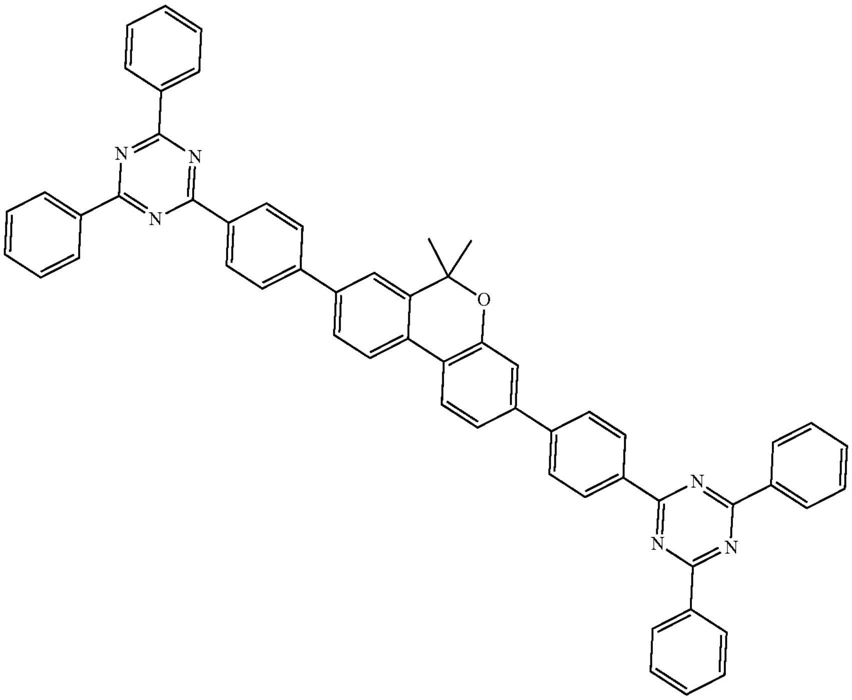
156
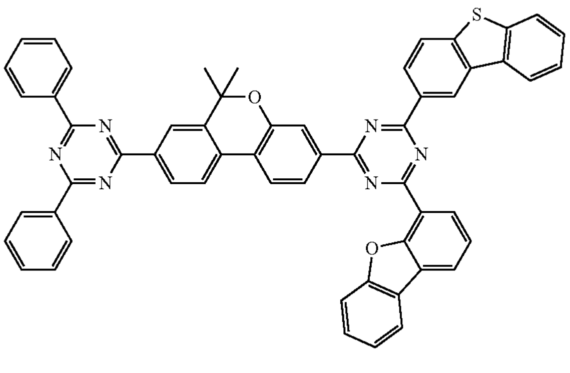
157
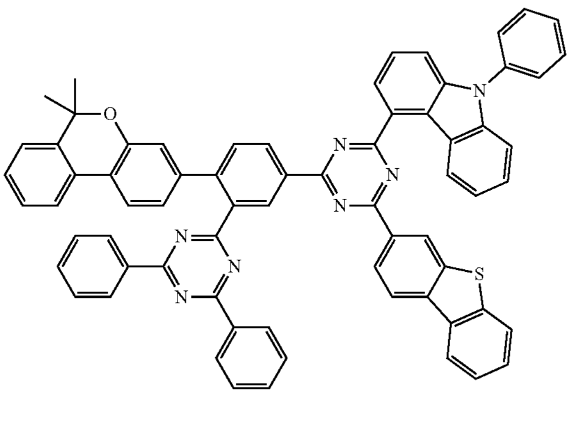

-continued
158
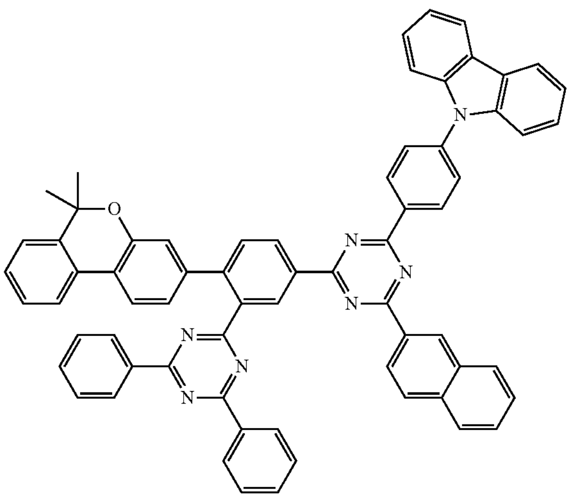
159
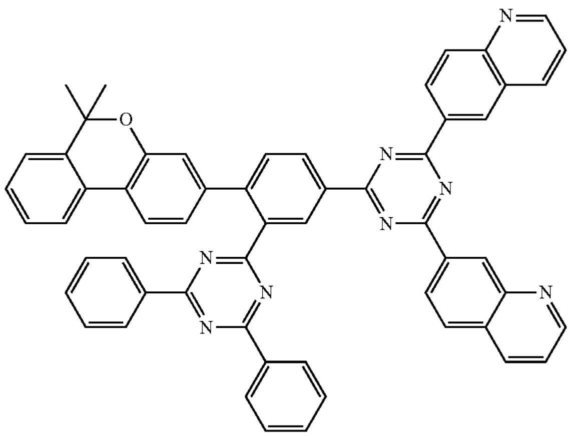
160
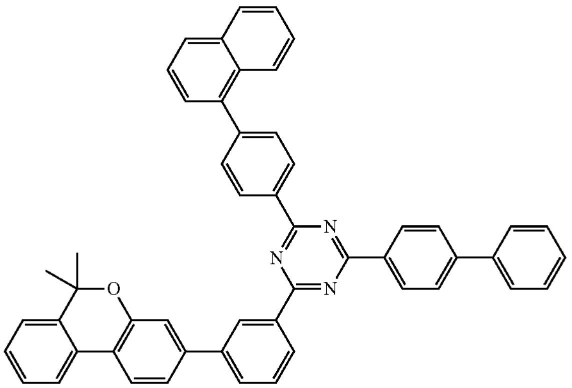
161
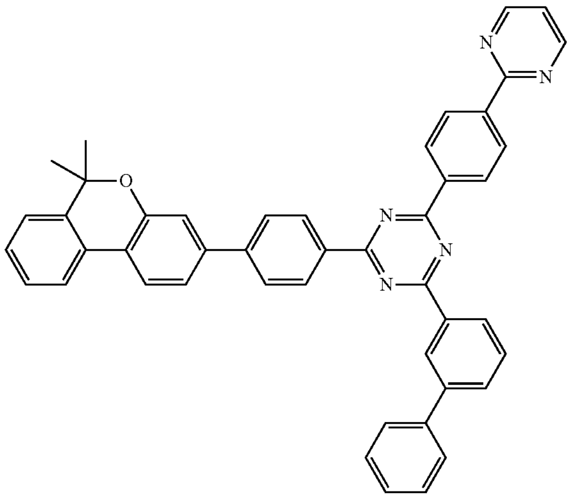
162
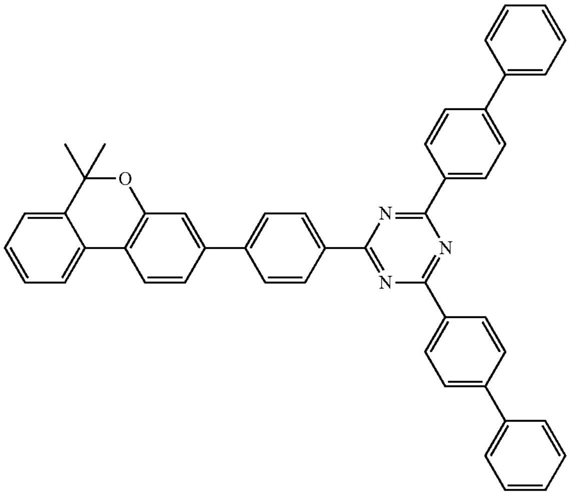
163
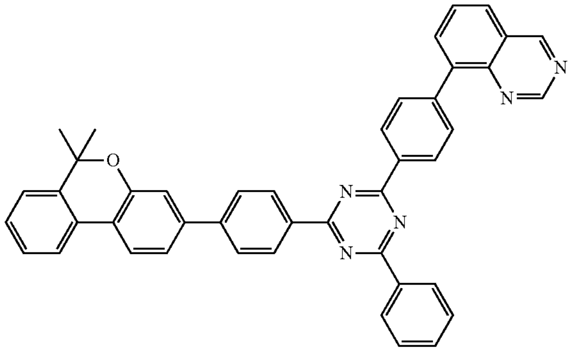

-continued
164
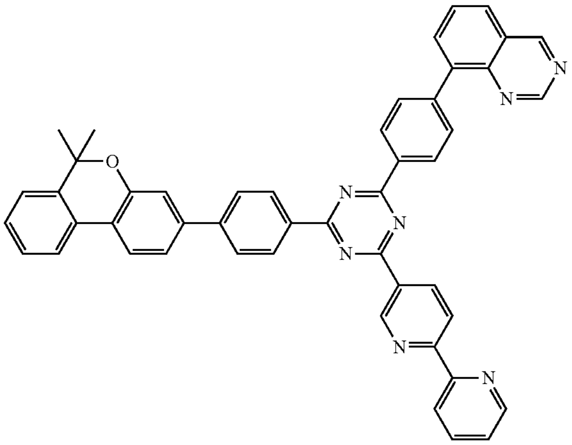
165
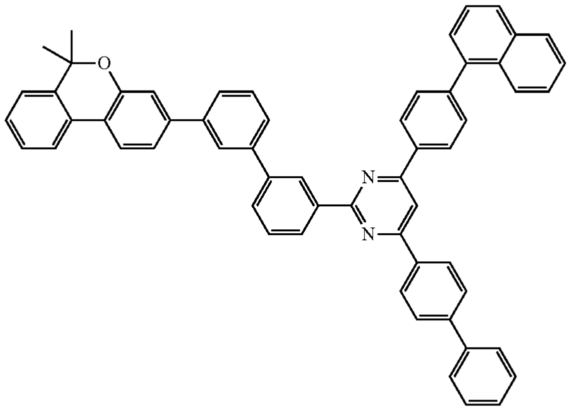
166
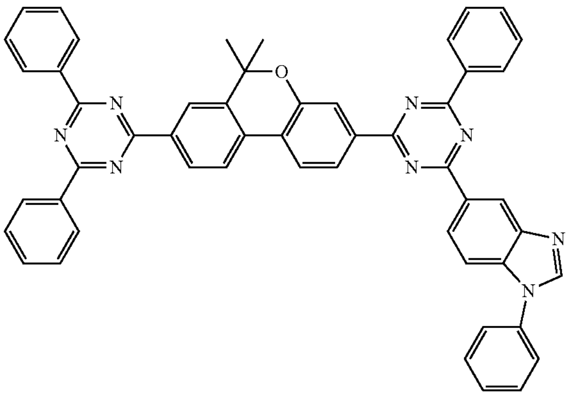
167
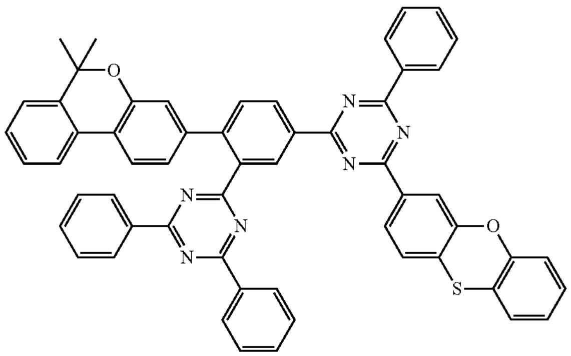
168
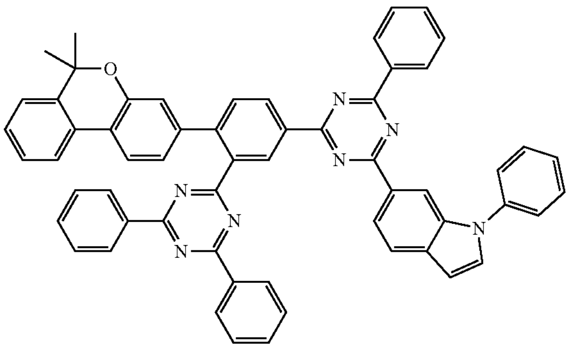
169
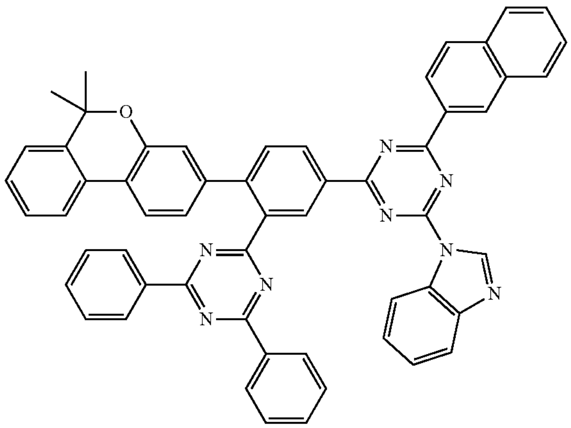

-continued
170
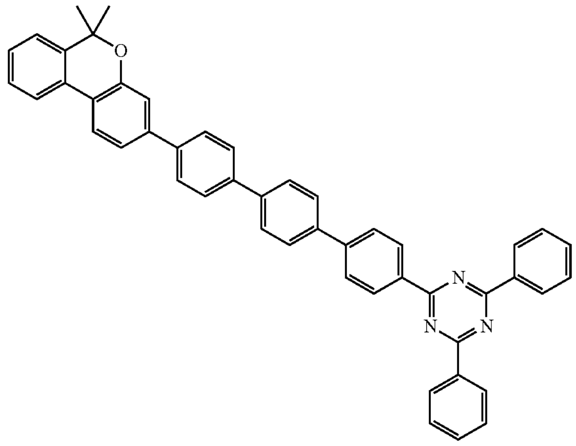
171
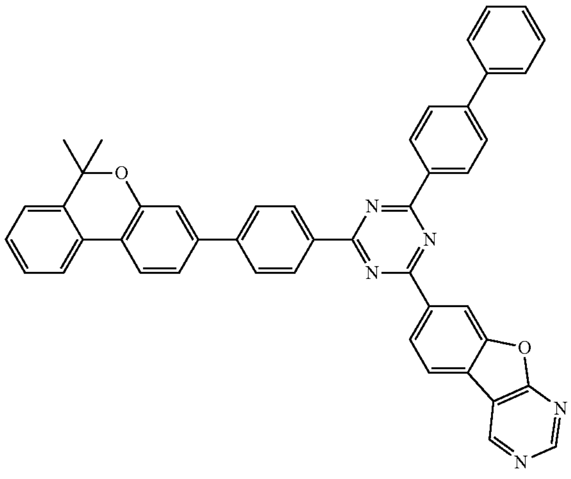
172
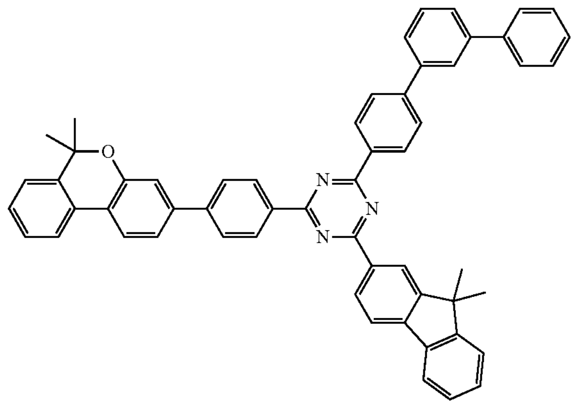
173
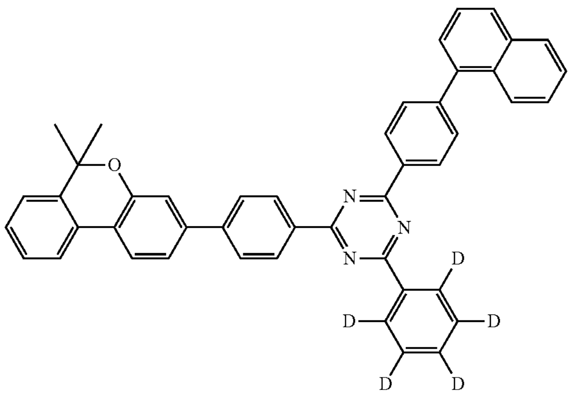
174
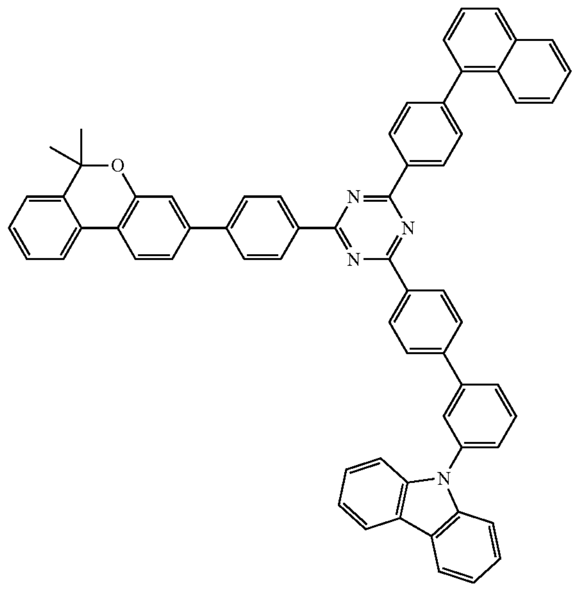
175
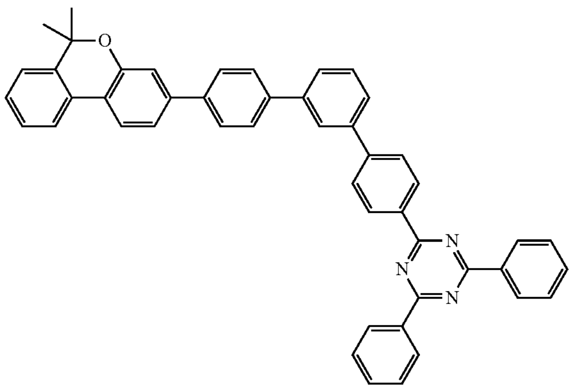

-continued
176
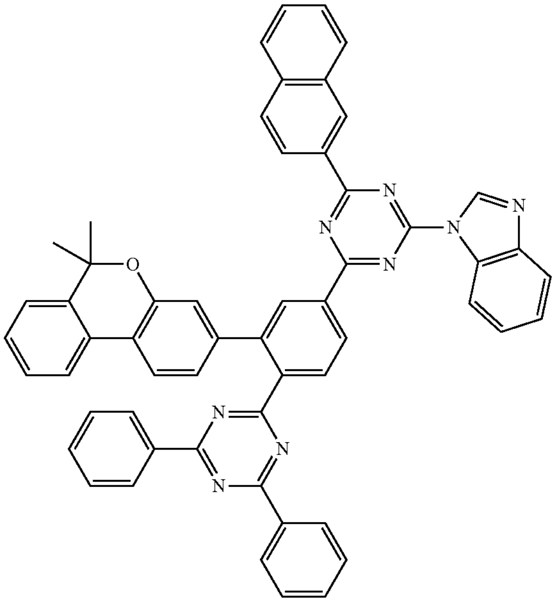
177
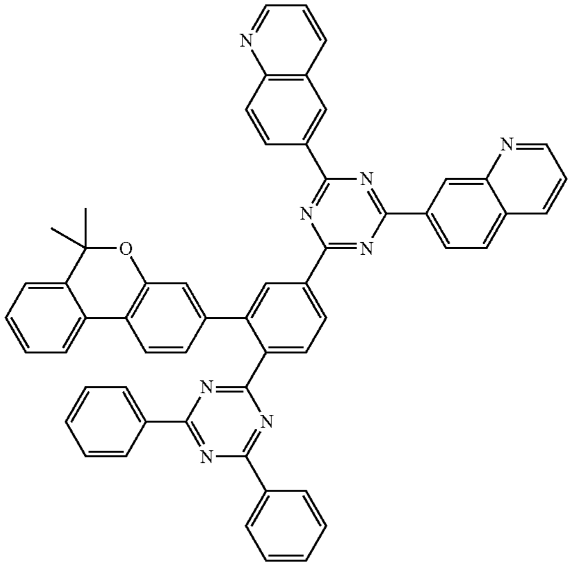
178
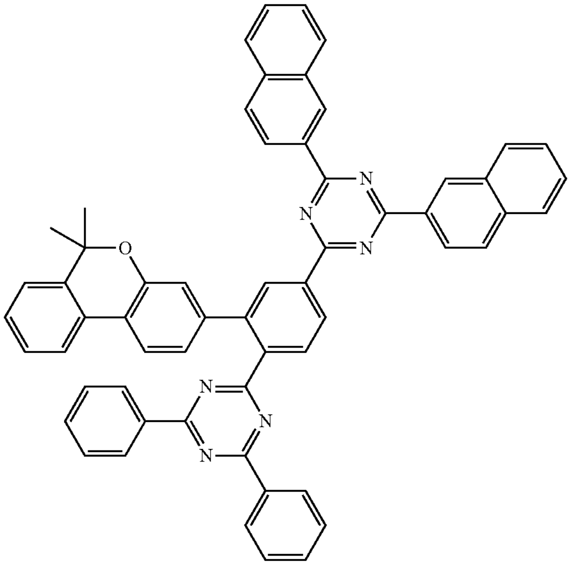
179
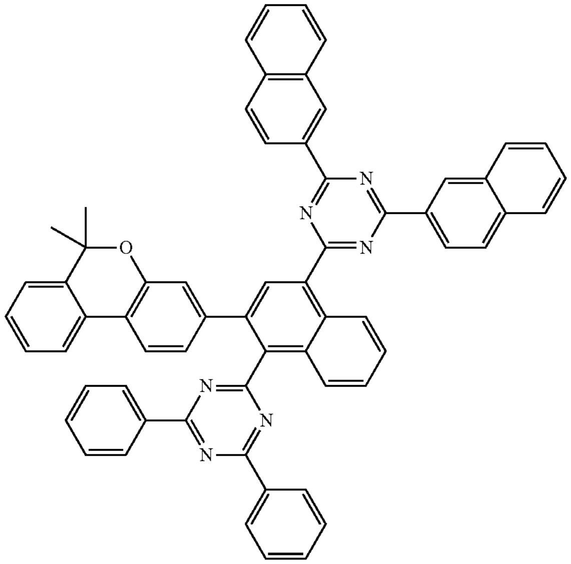

-continued
180
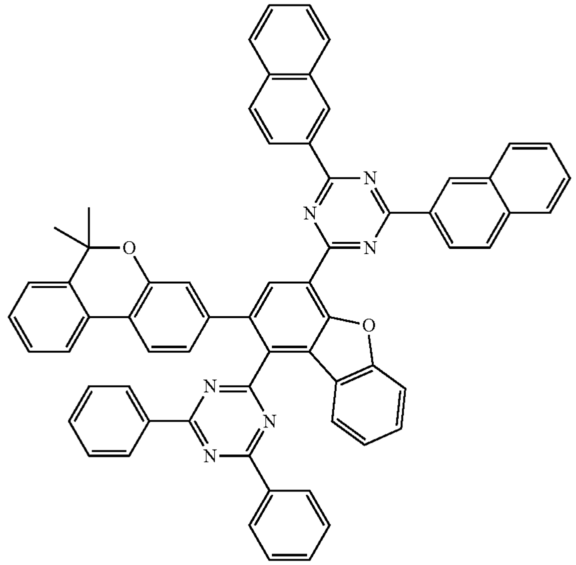
181
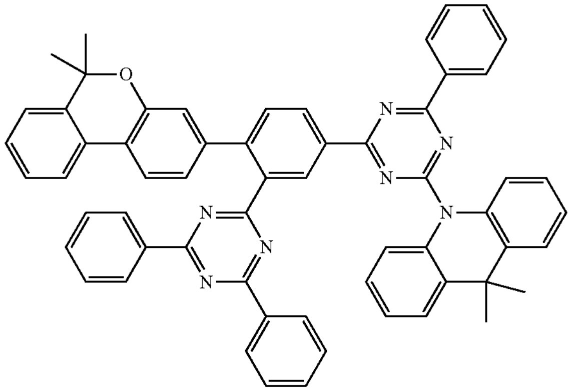
182
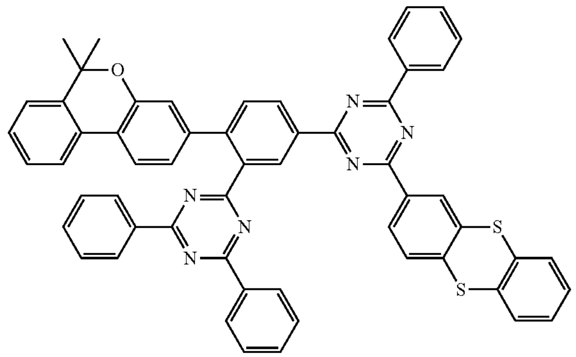
183
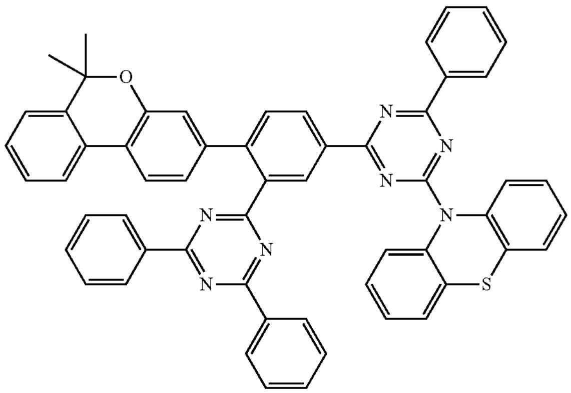
184
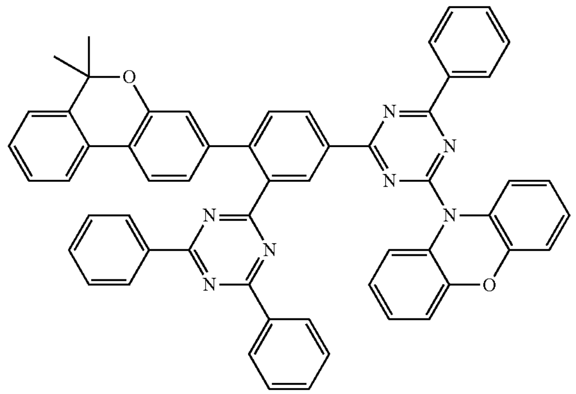
185
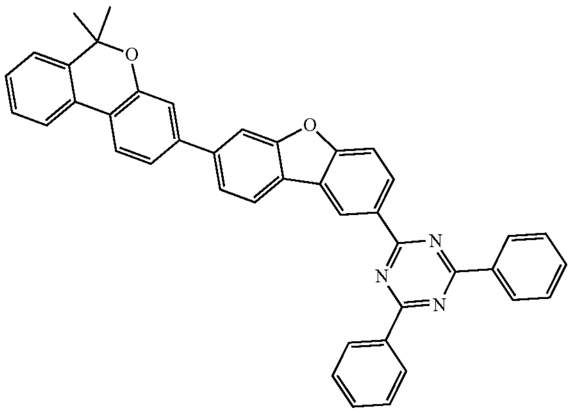

-continued
186
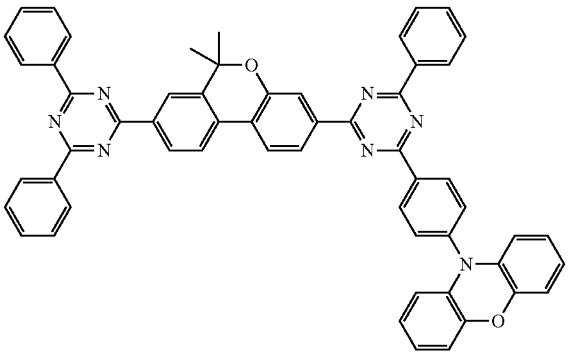
187
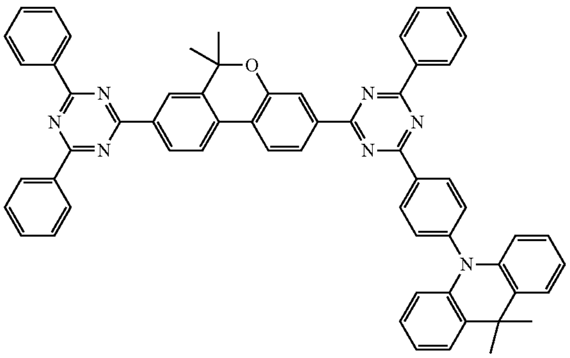
188
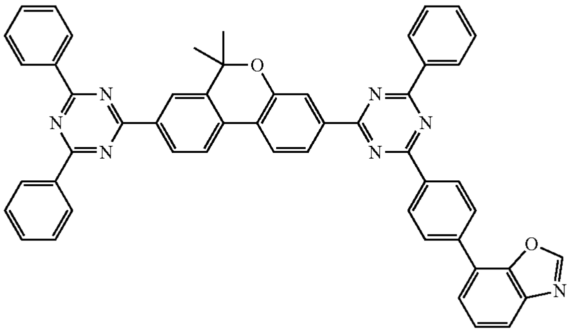
189
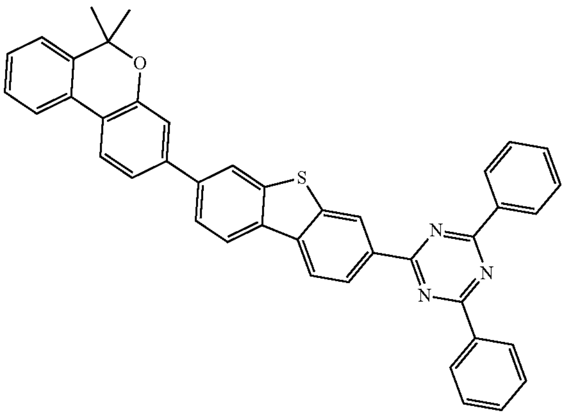
190
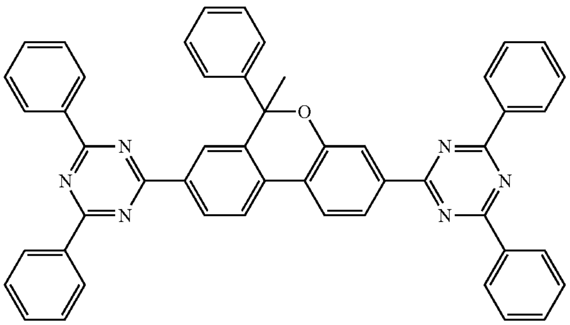
191
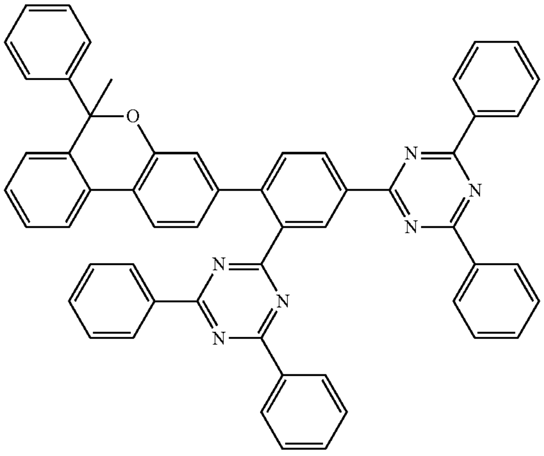
192
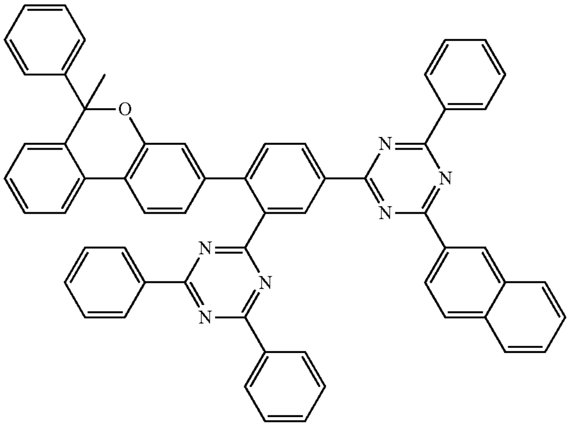

-continued
193
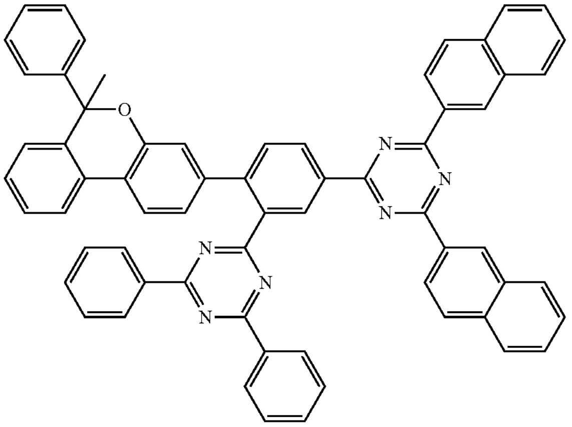
194
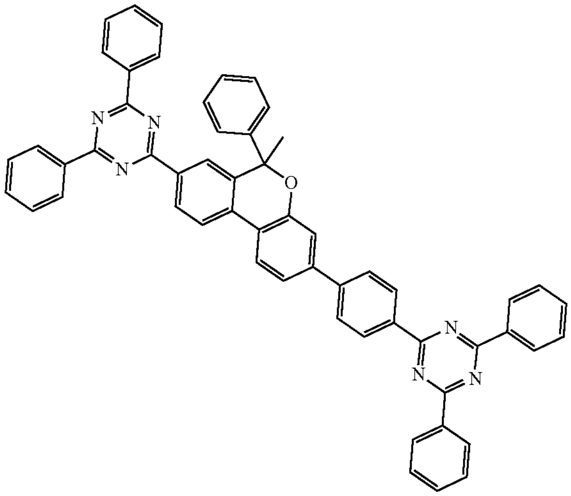
195
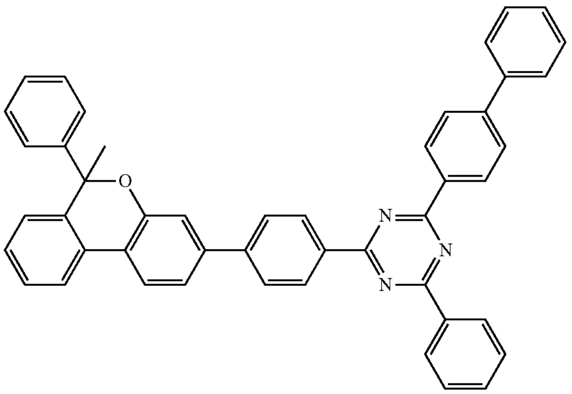
196
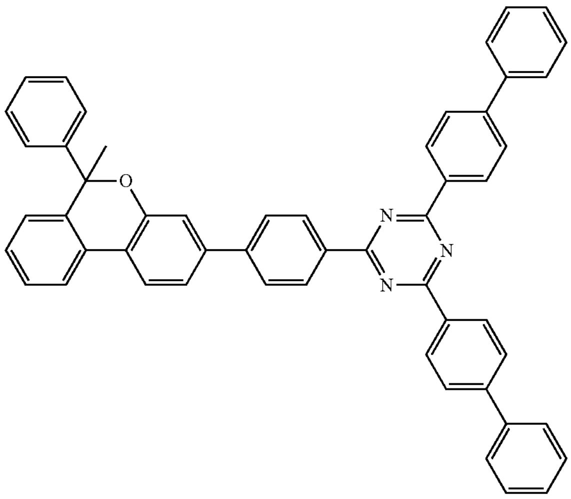
197
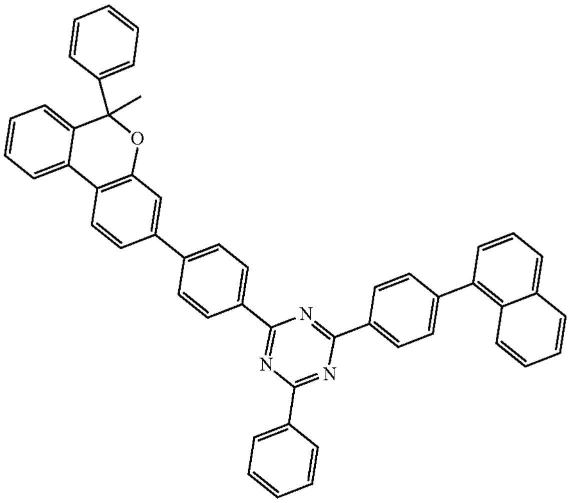
198
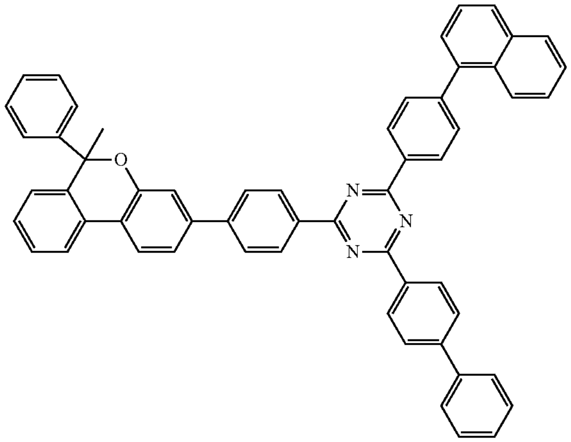

-continued
199
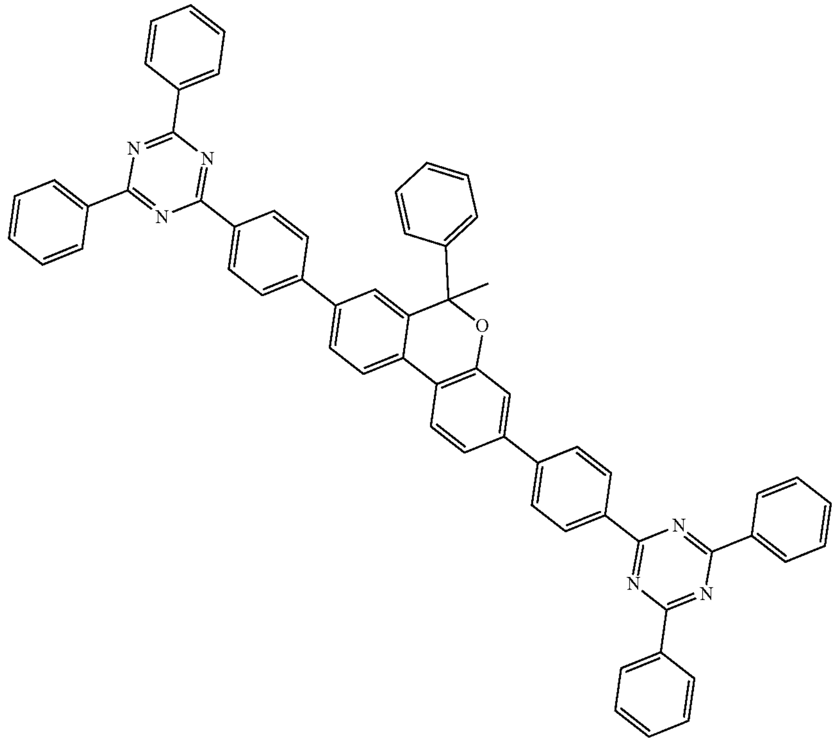
200
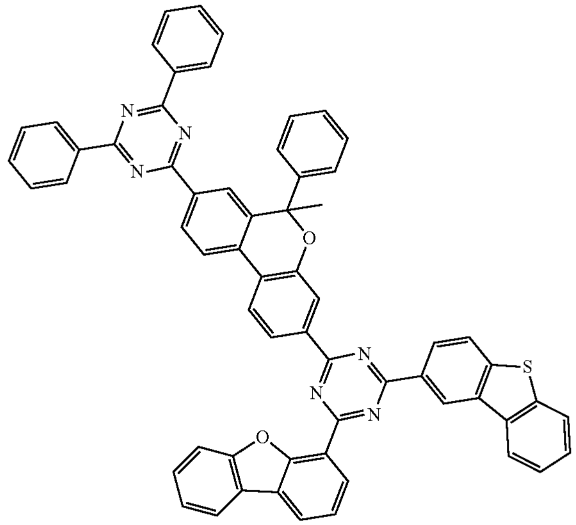
201
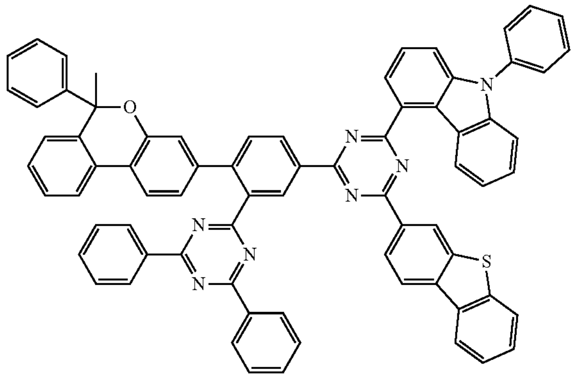

-continued
202
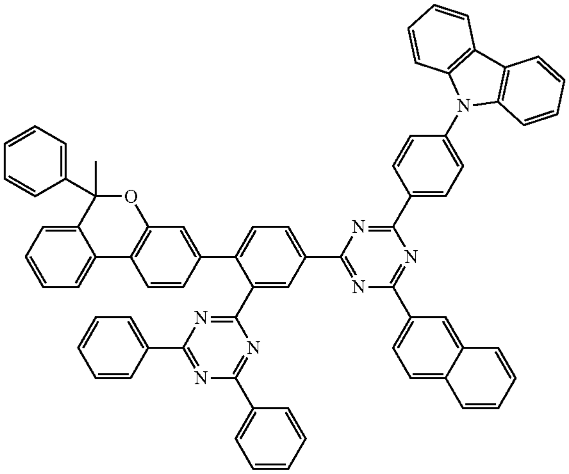
203
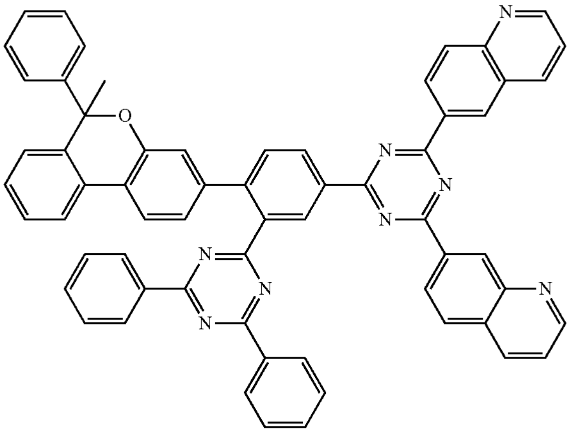
204
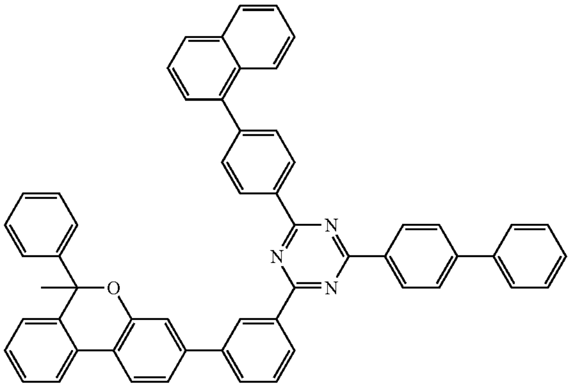
205
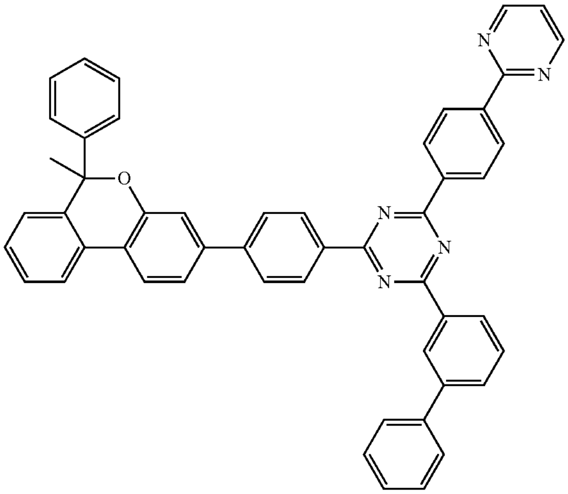
206
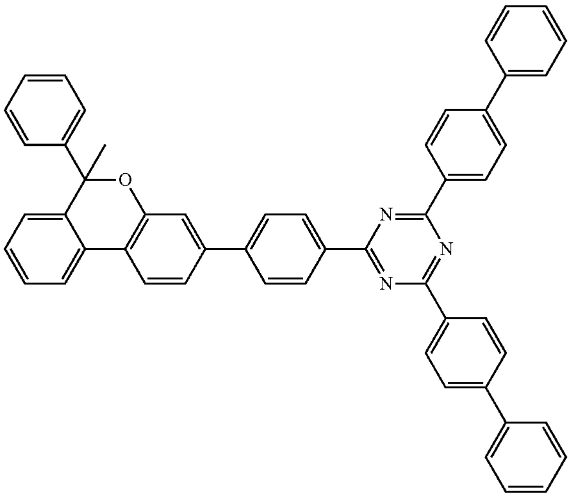
207
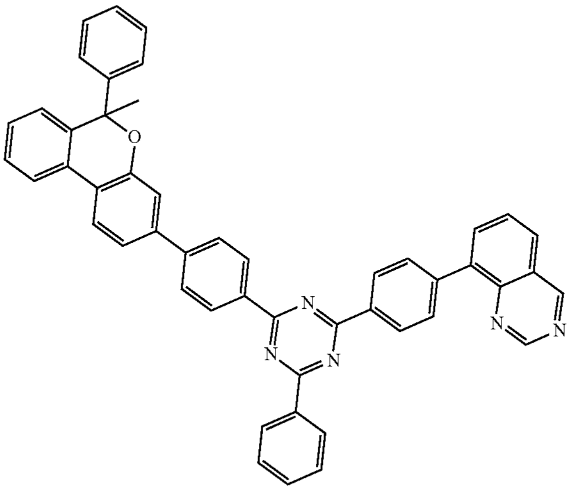

-continued
208
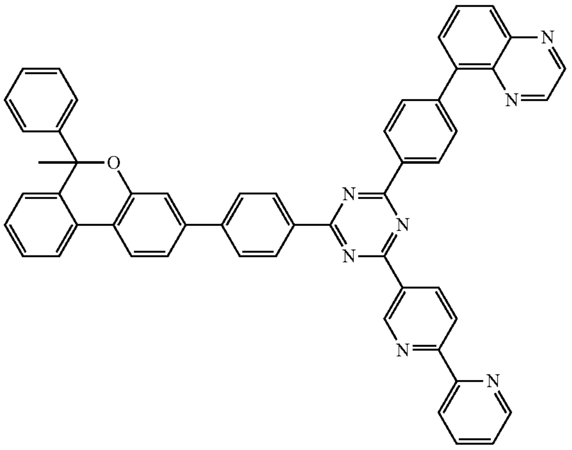
209
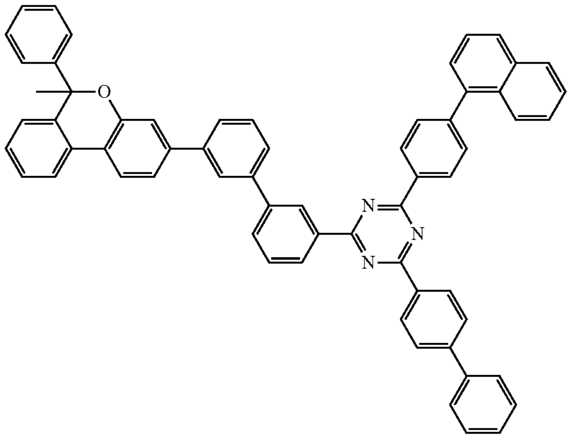
210
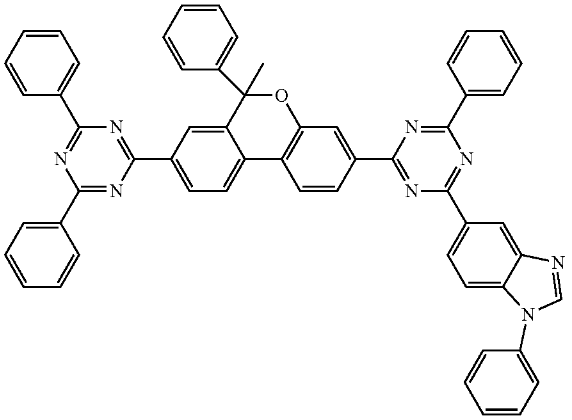
211
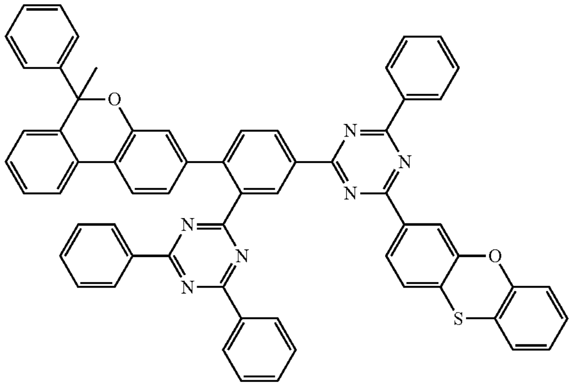
212
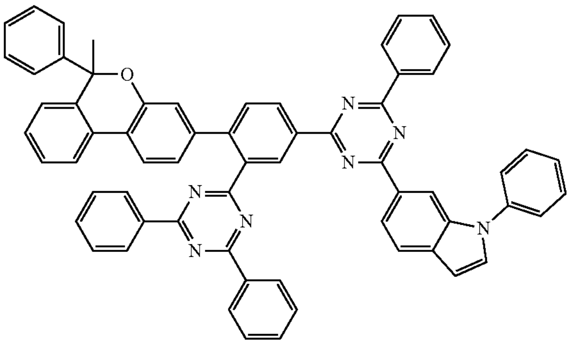
213
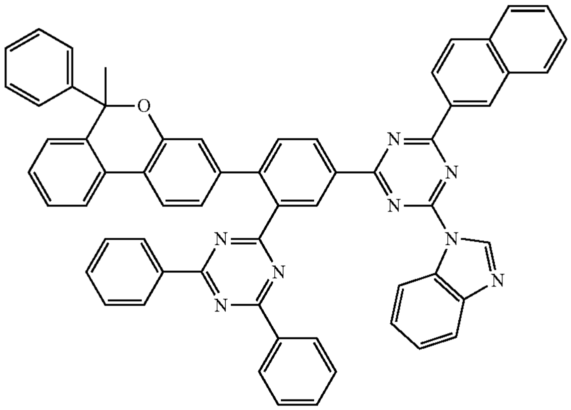

-continued
214
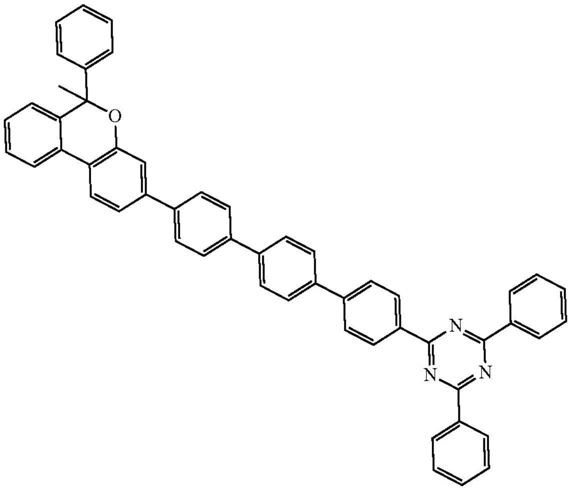
215
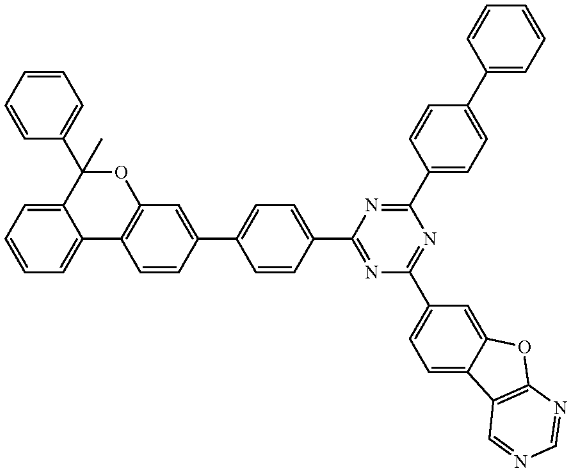
216
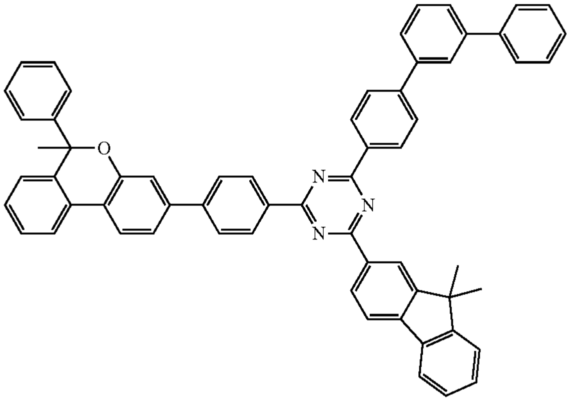
217
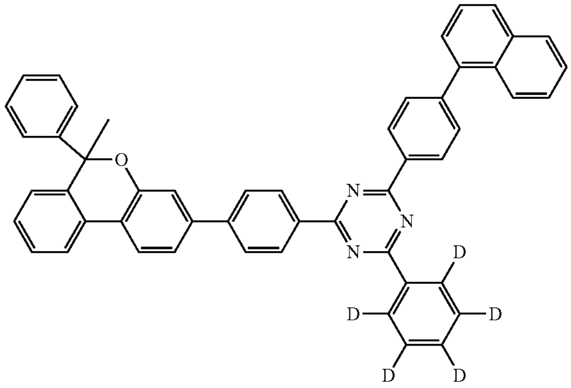
218
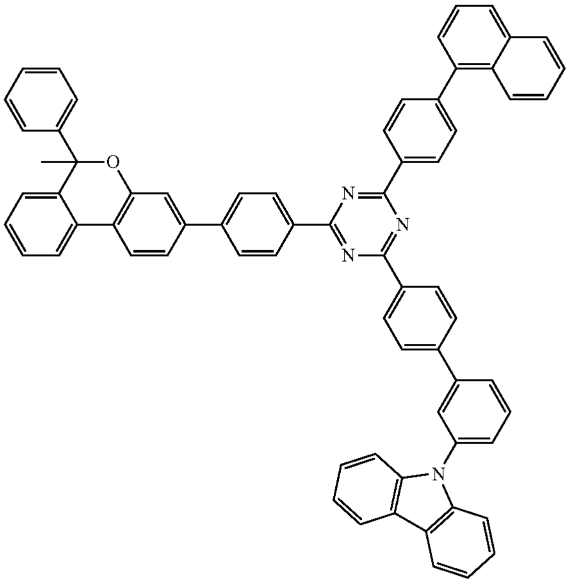
219
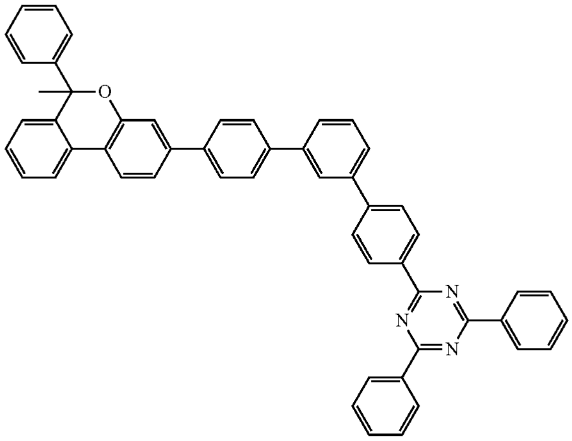

-continued
220
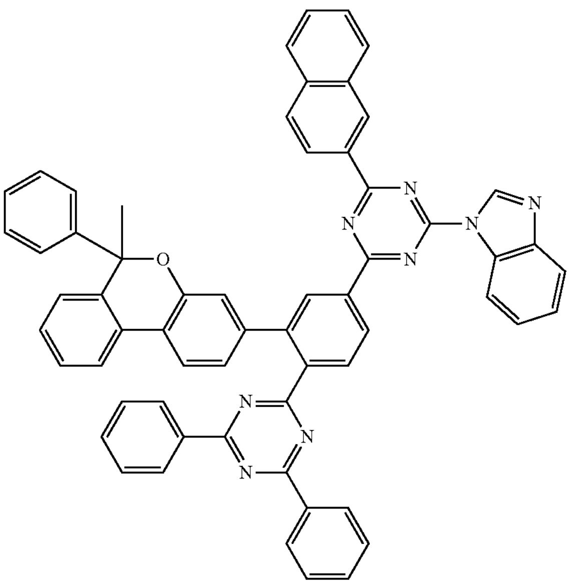
221
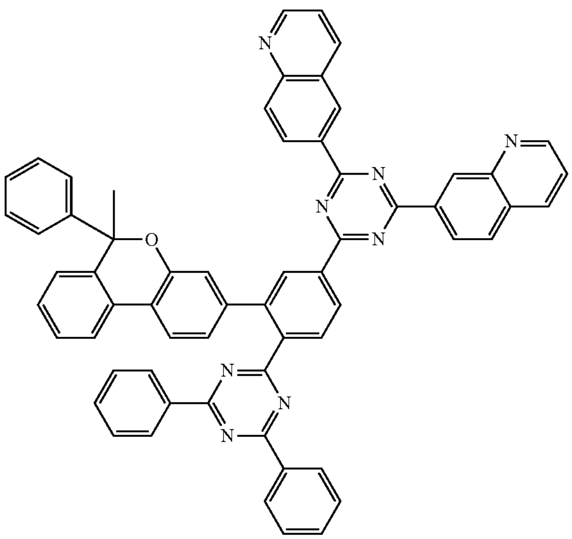
222
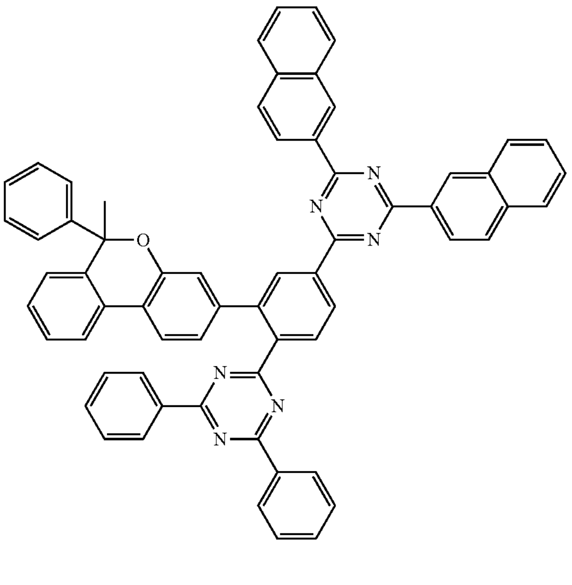
223
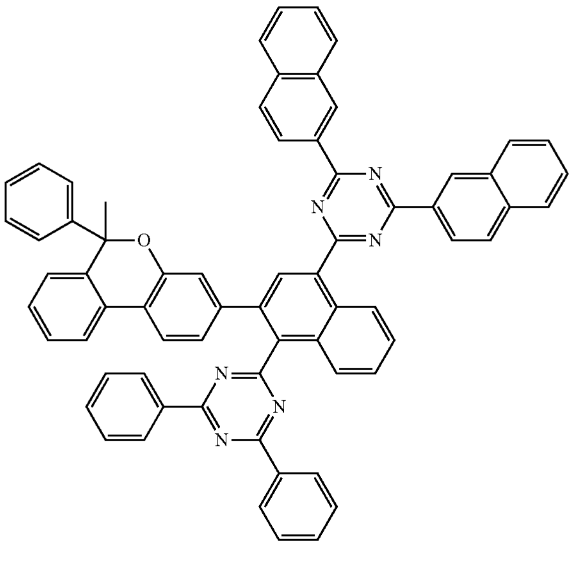

-continued
224
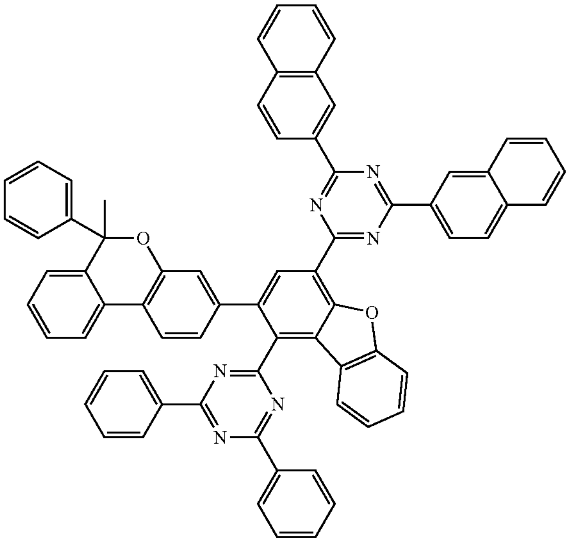
225
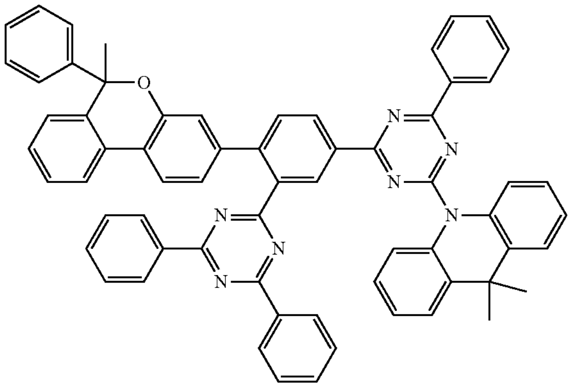
226
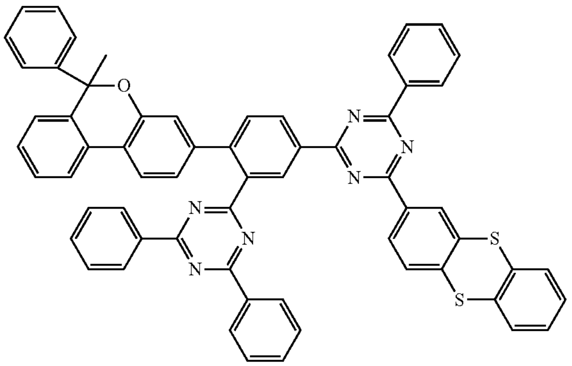
227
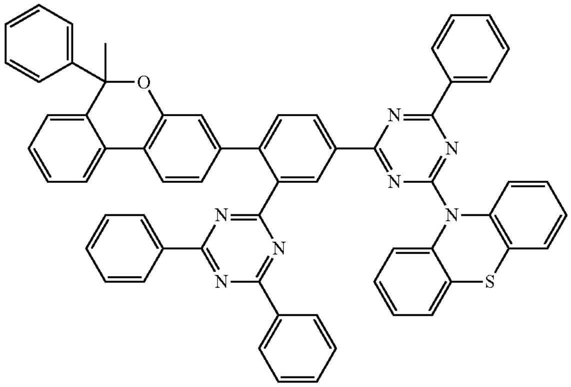
228
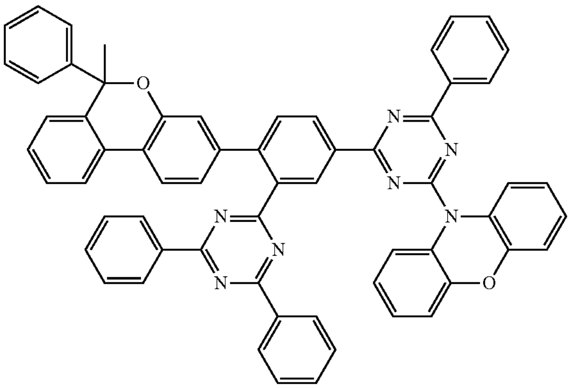
229
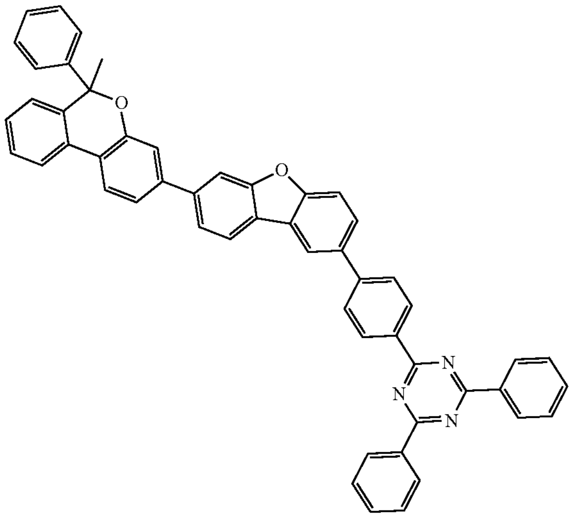

-continued
230
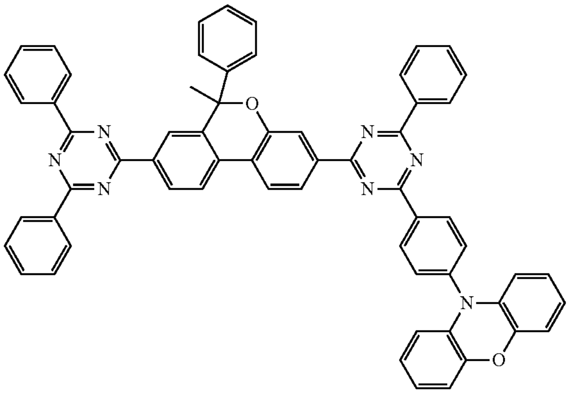
231
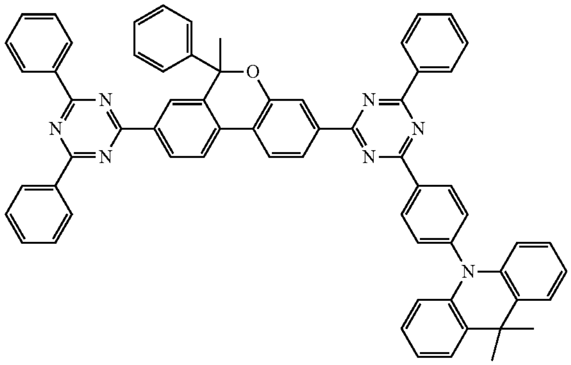
232
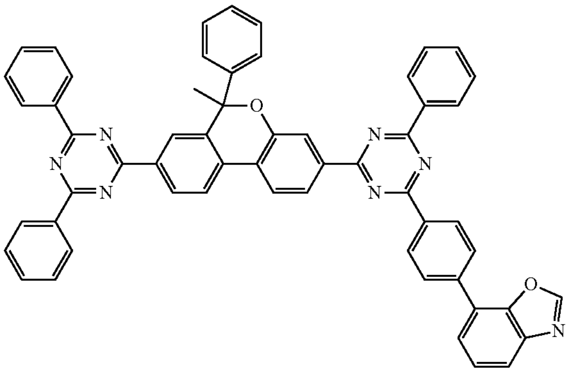
233
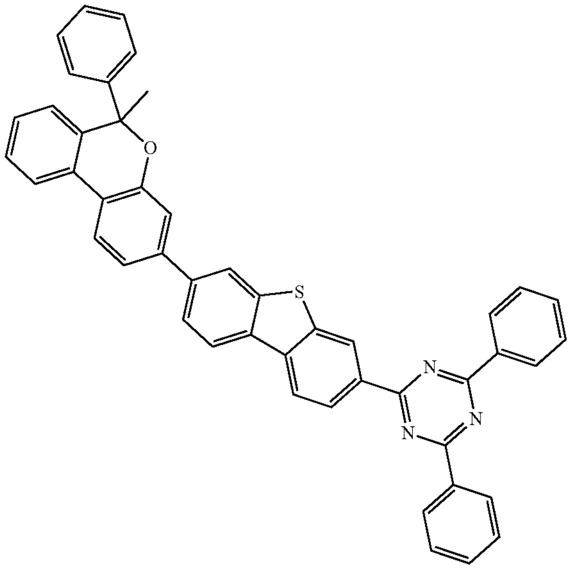
234
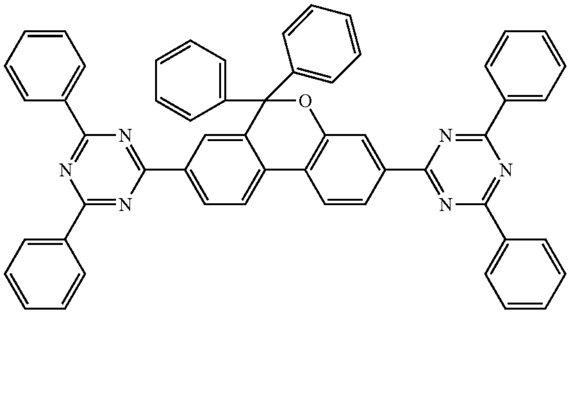
235
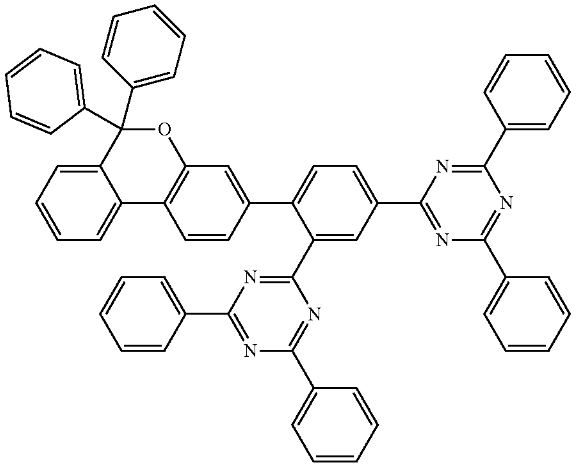

-continued
236
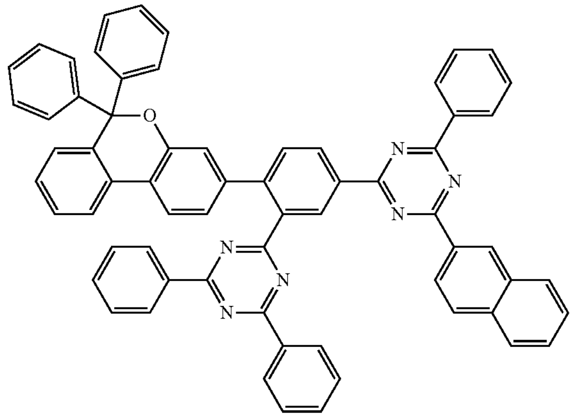
237
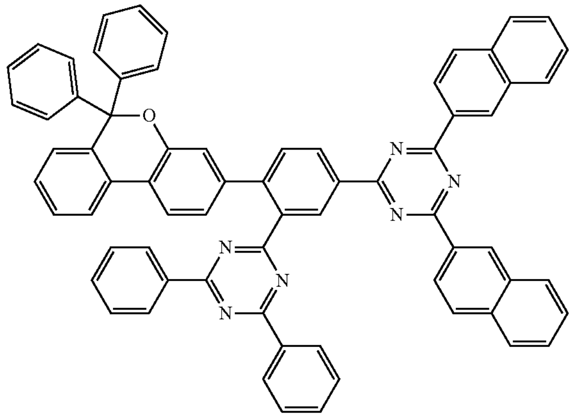
238
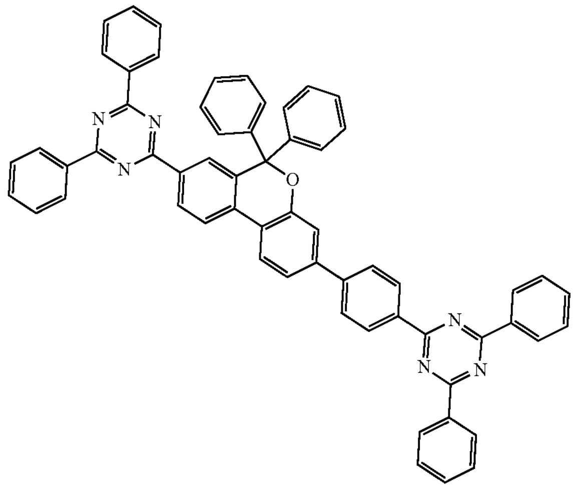
239
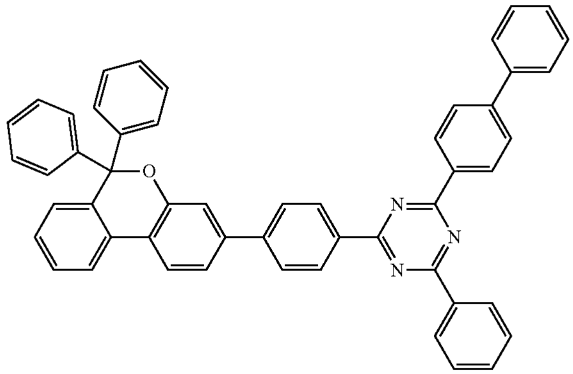
240
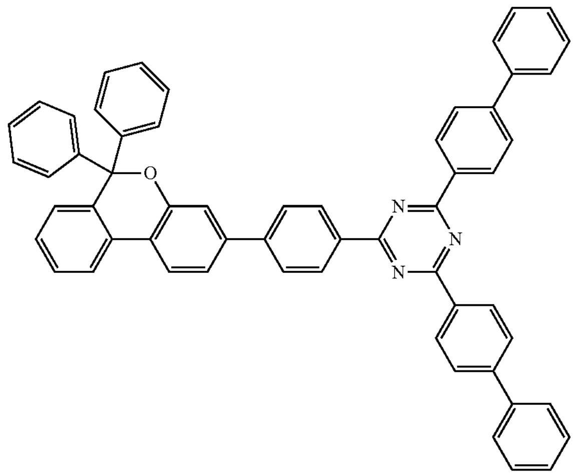
241
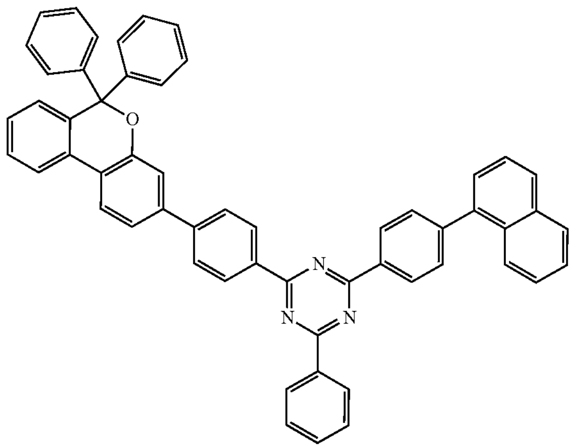

-continued
242
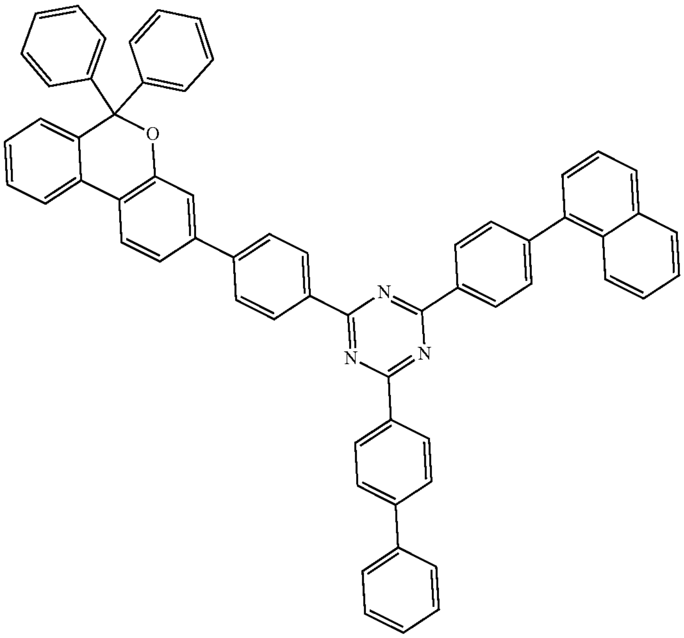
243
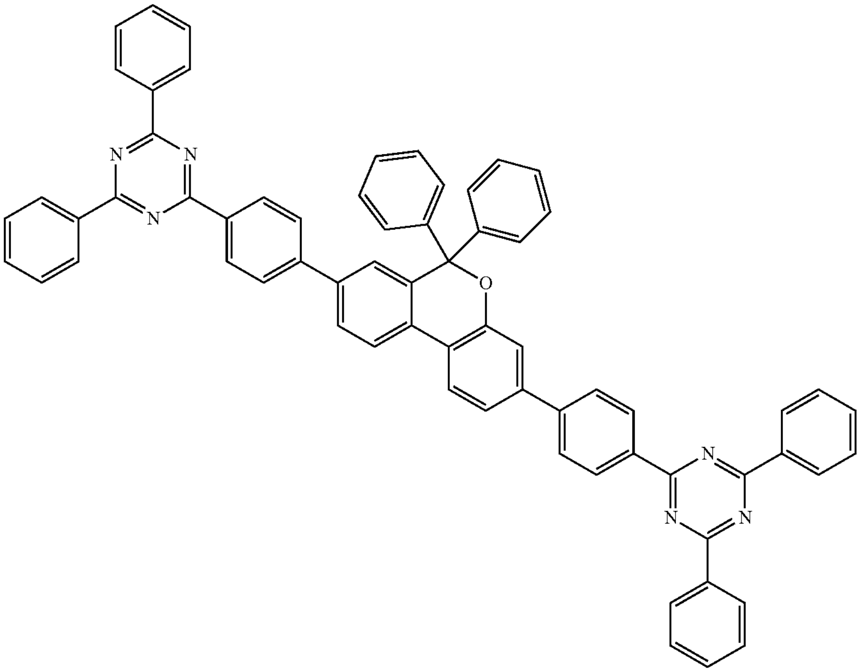

-continued
244
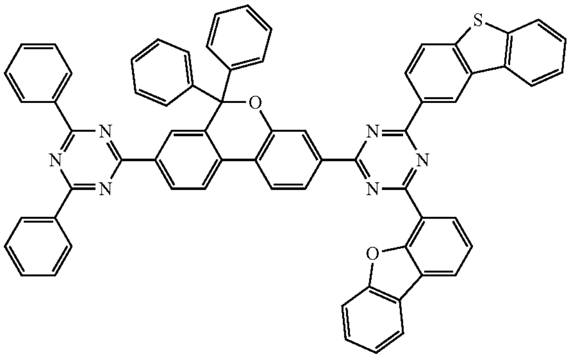
245
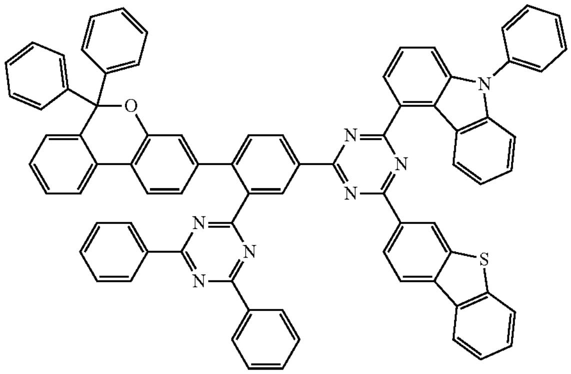
246
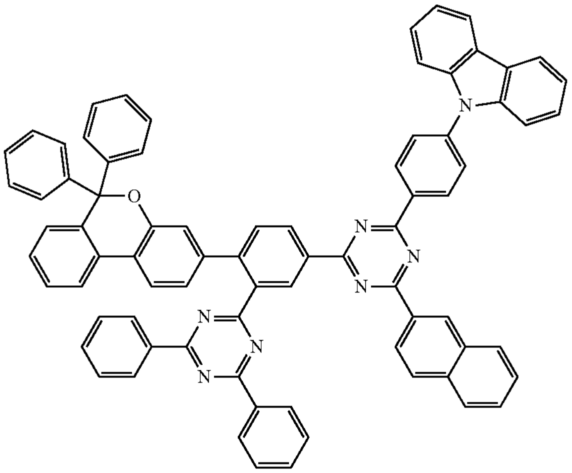
247
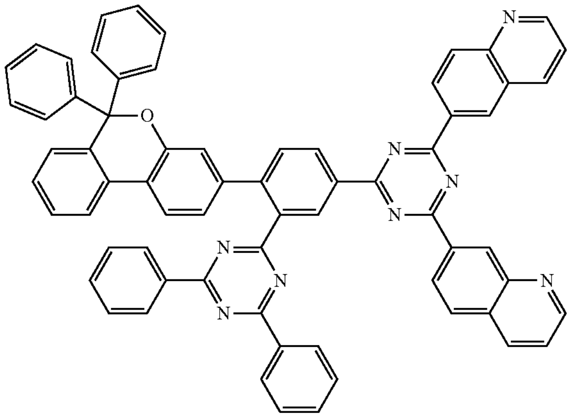
248
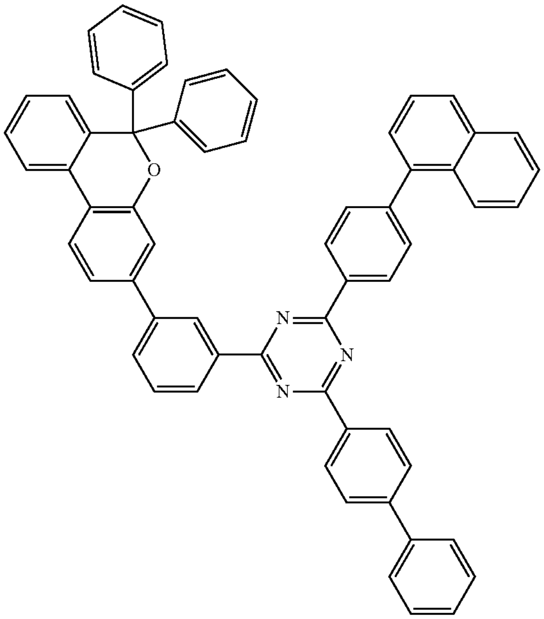
249
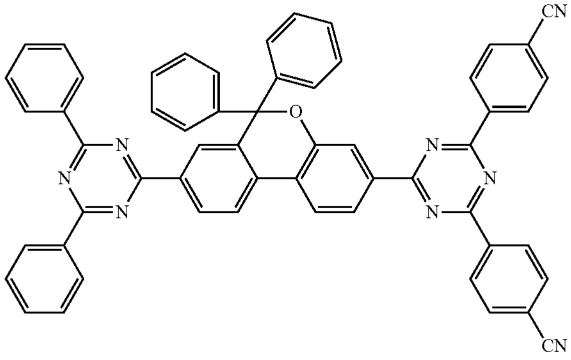

-continued
250
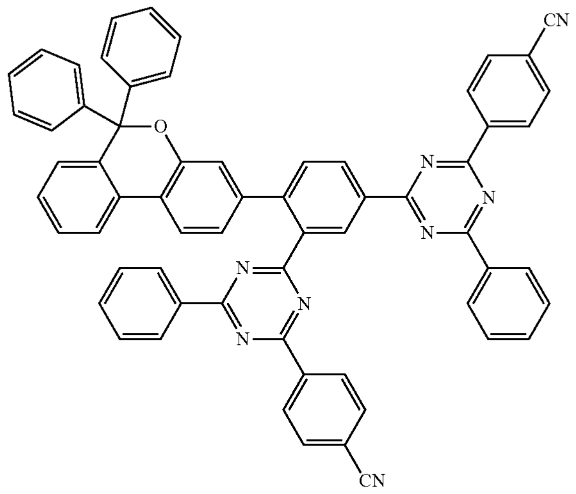
251
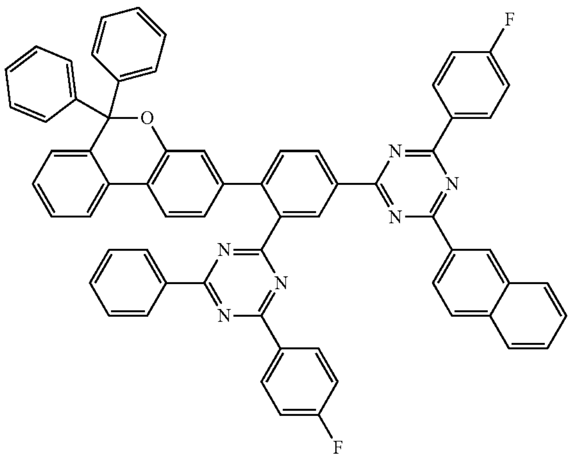
252
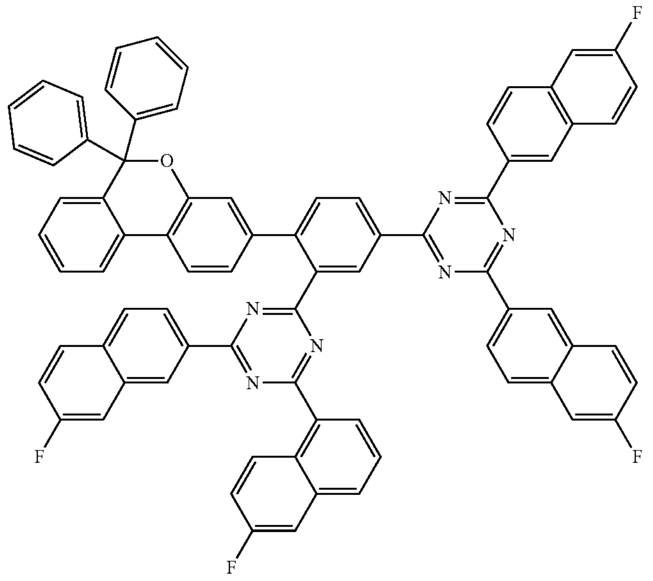

-continued
253
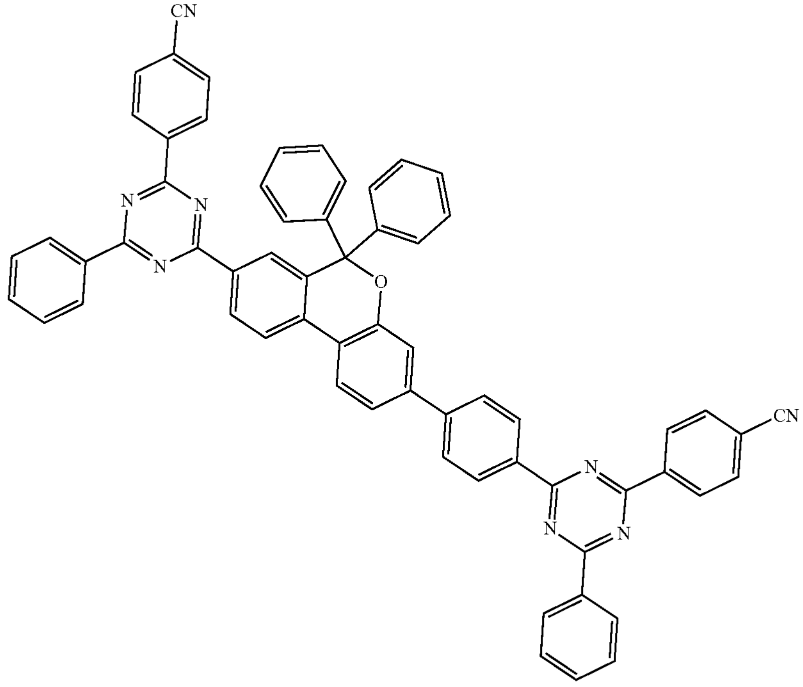
254
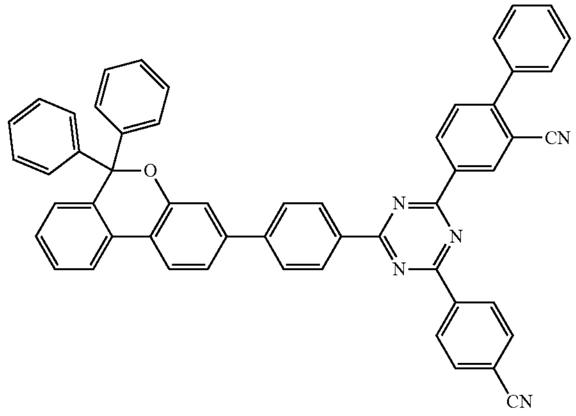
255
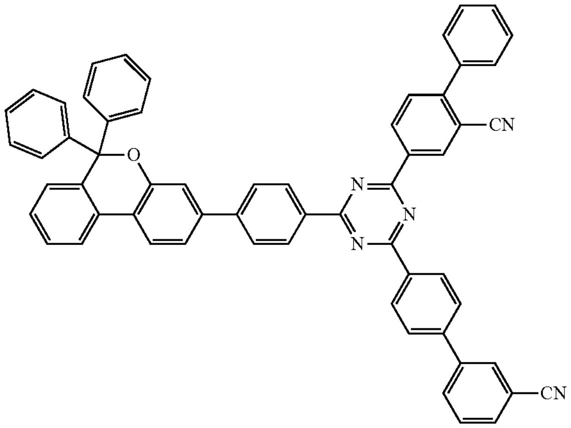
256
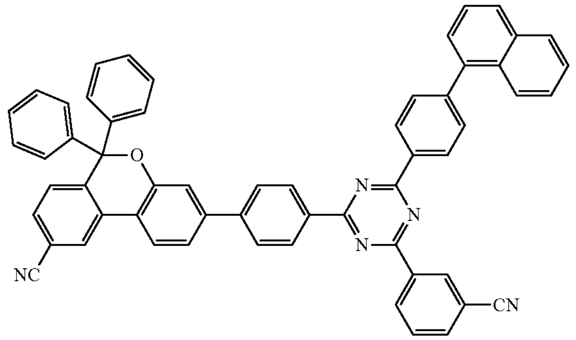
257
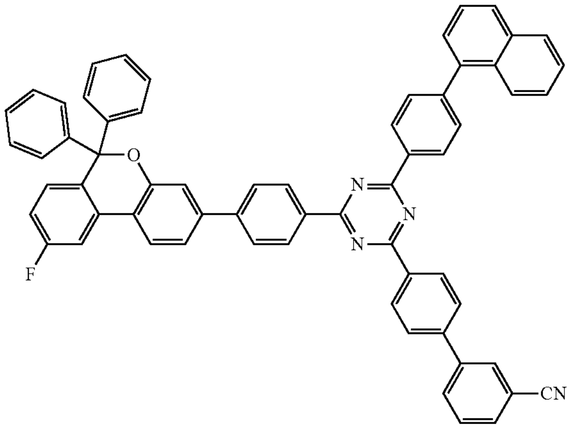

-continued
258
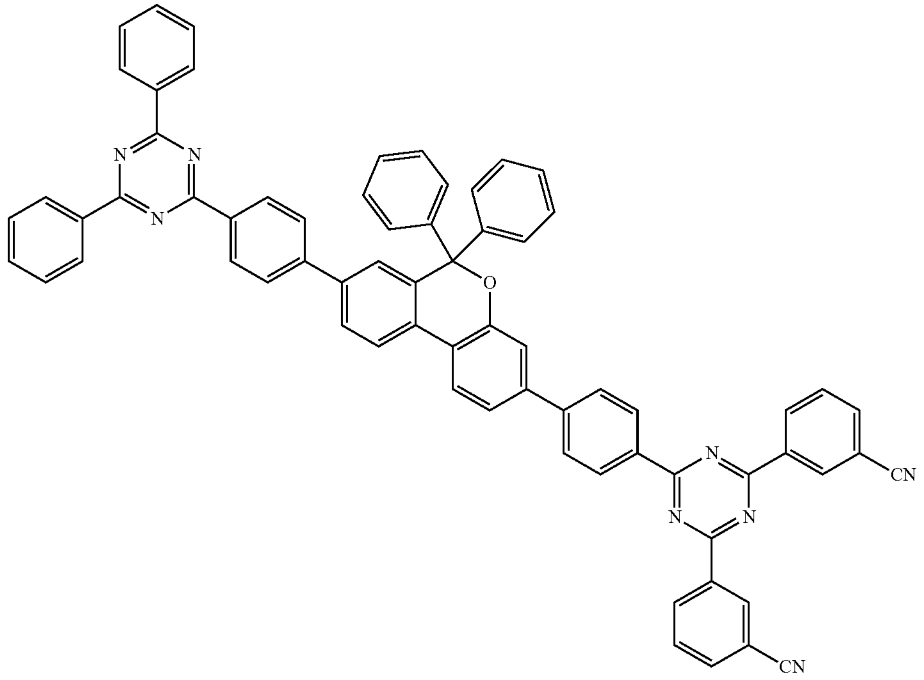
259
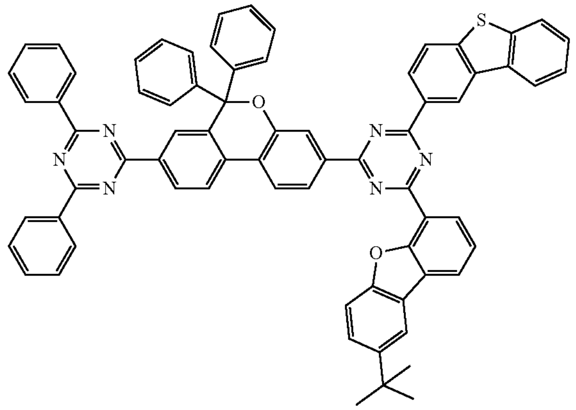
260
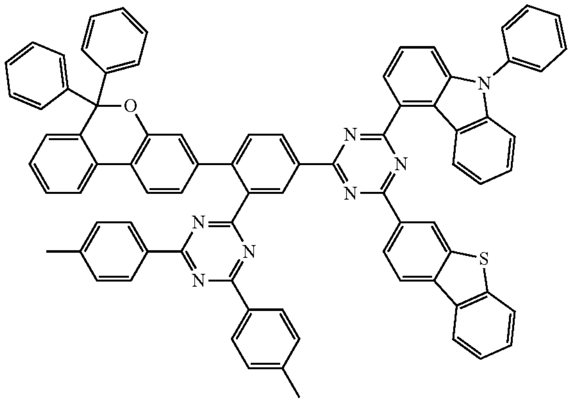
261
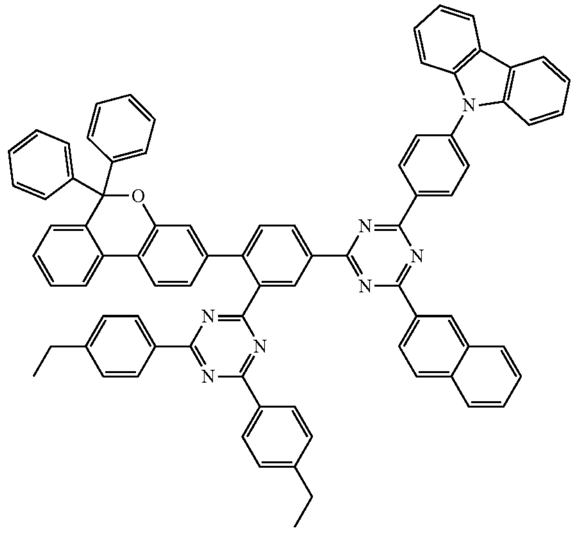
262
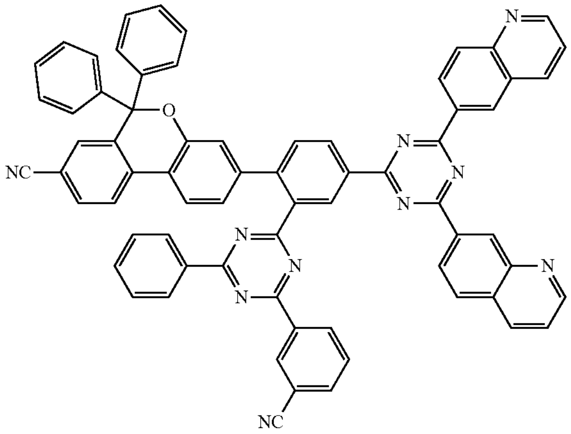

-continued
263
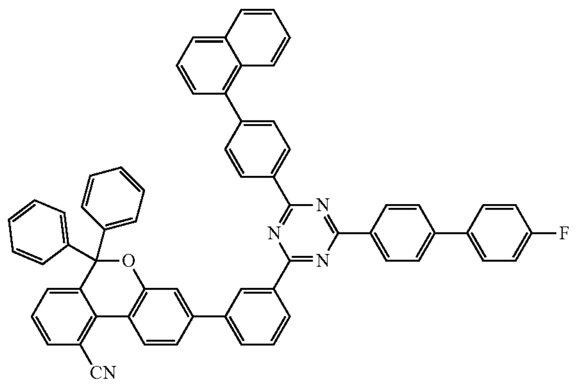
264
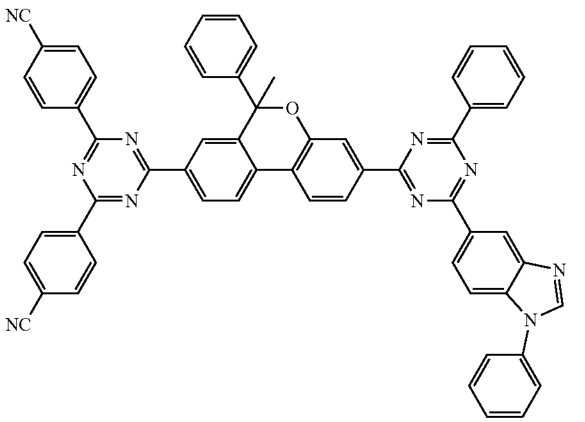
265
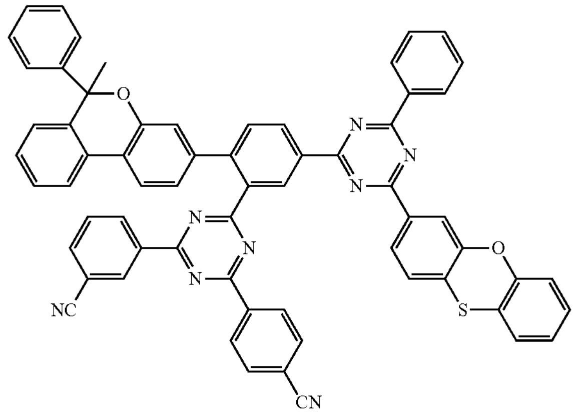
266
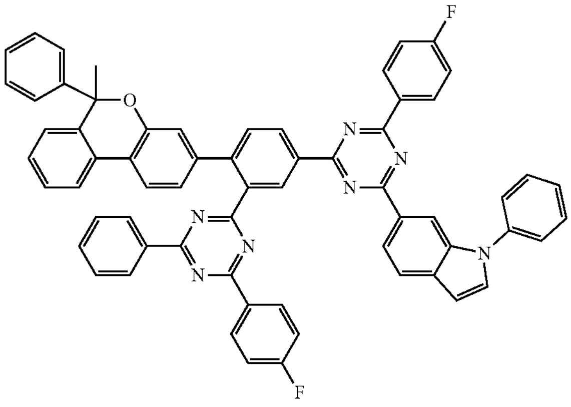
267
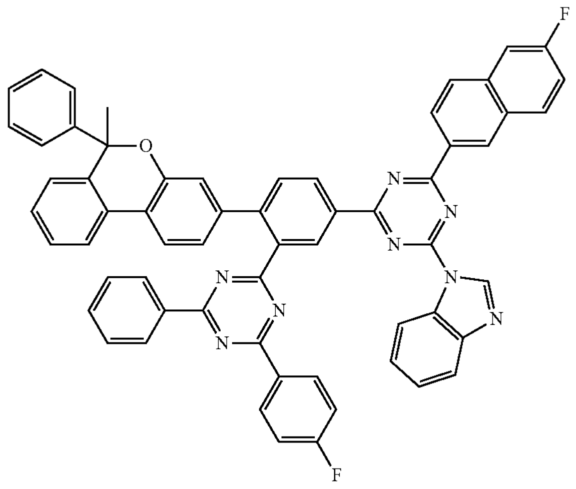
268
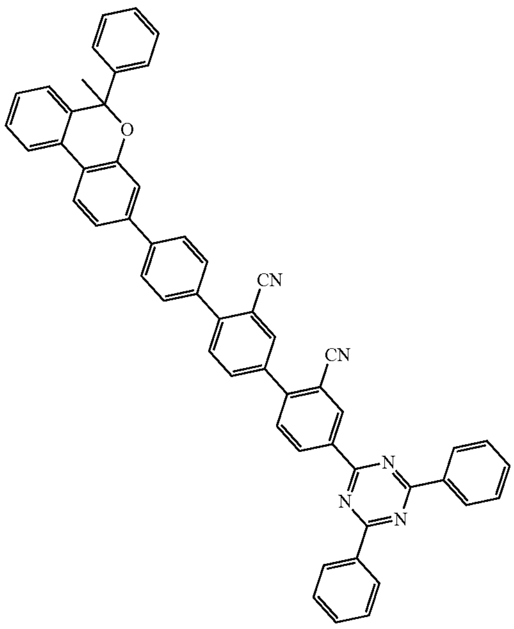

-continued
269
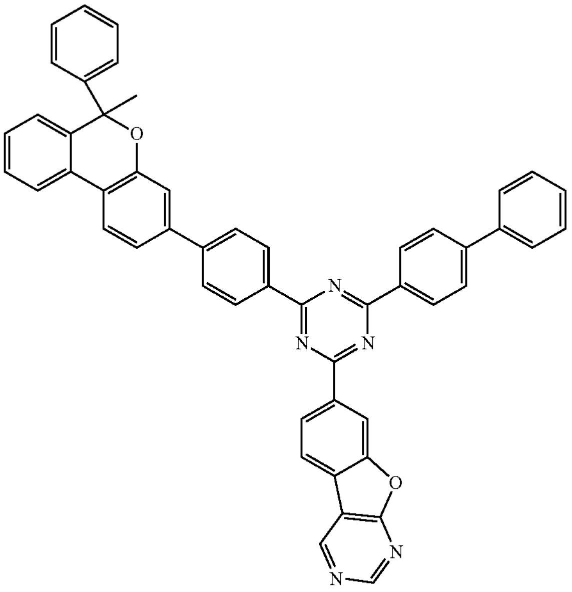
270
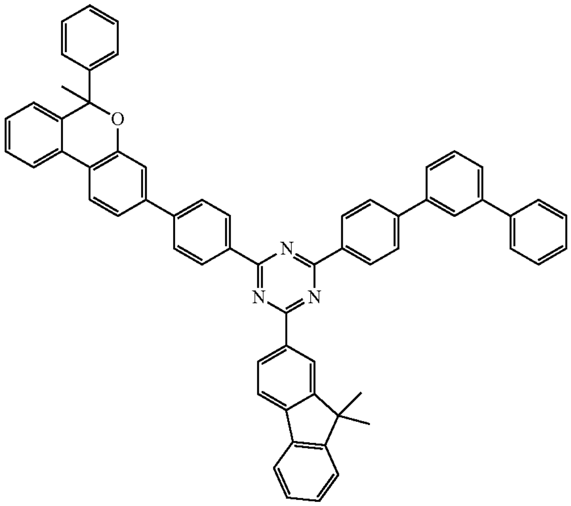
271
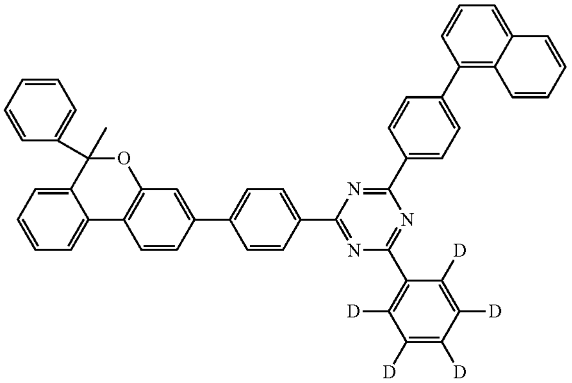
272
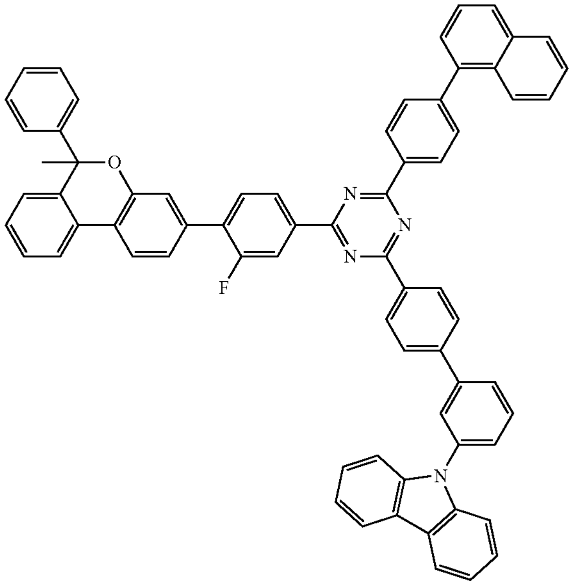

-continued
273
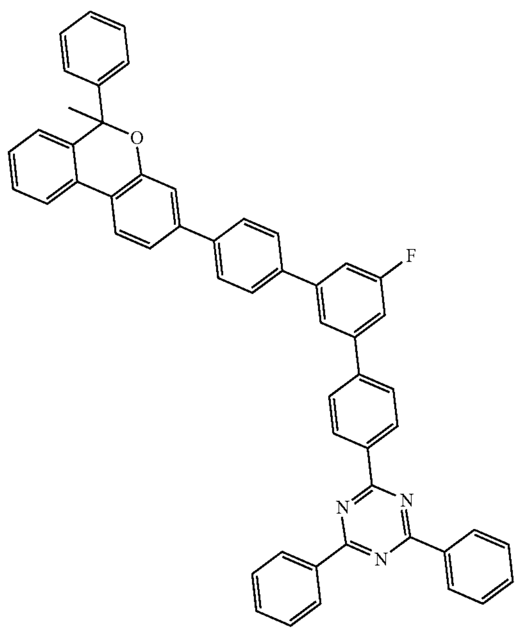
274
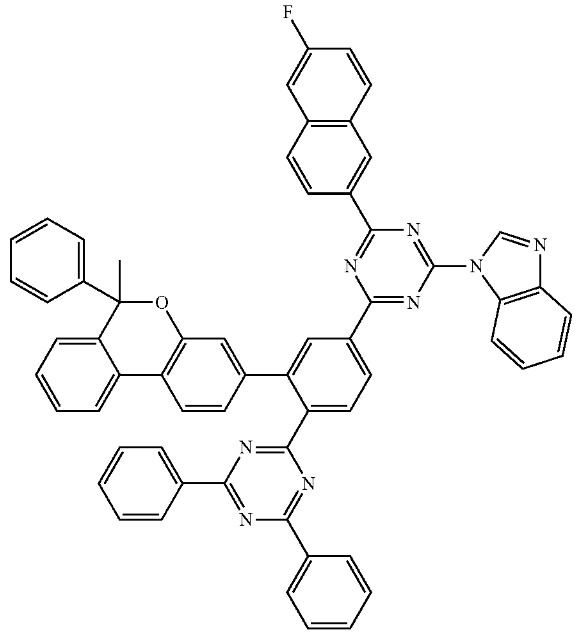
275
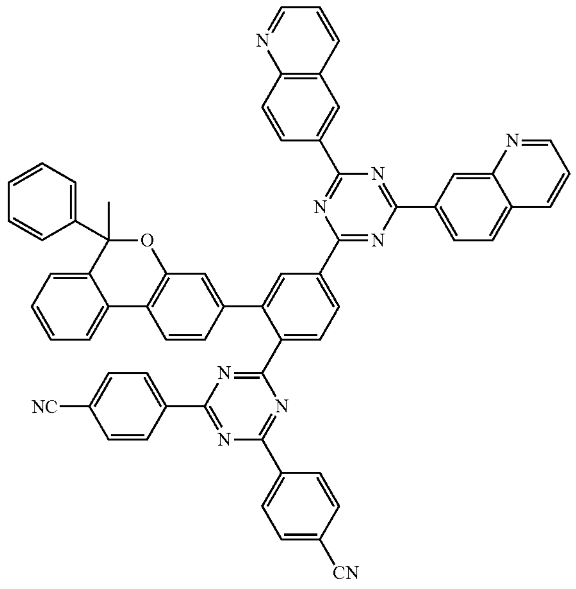
276
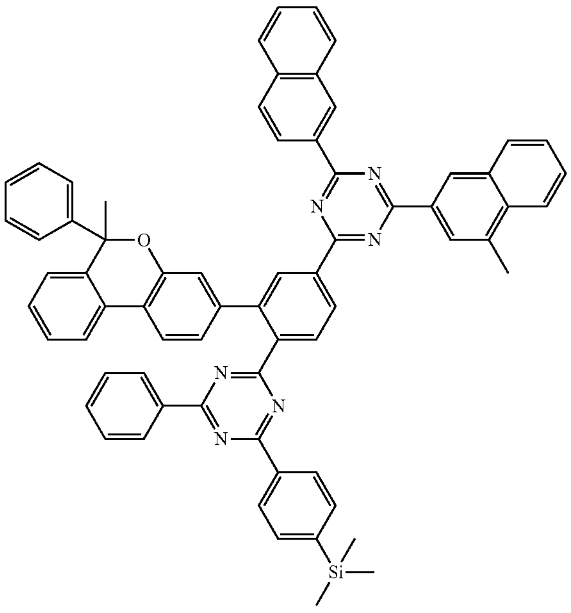

-continued
277
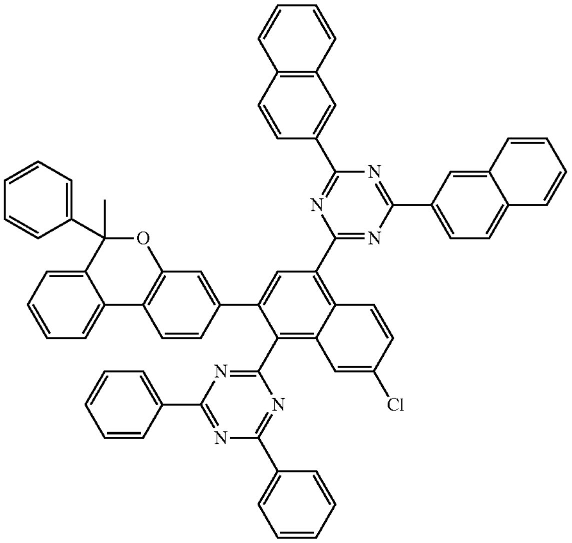
278
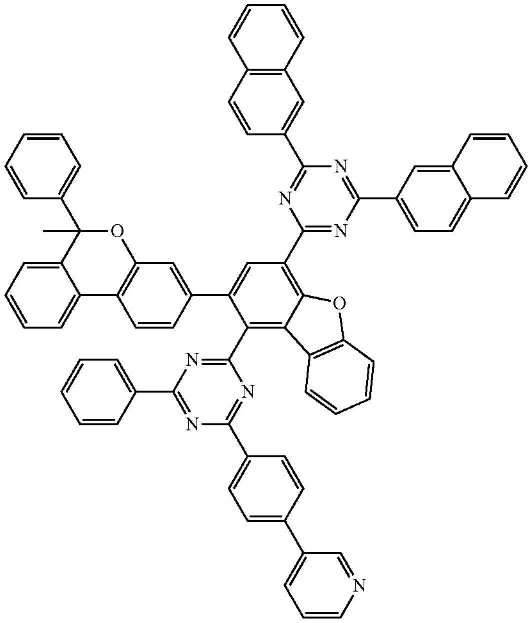
279
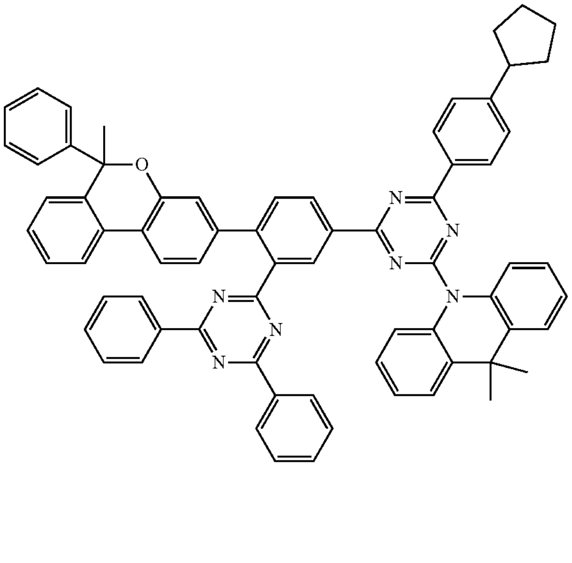
280
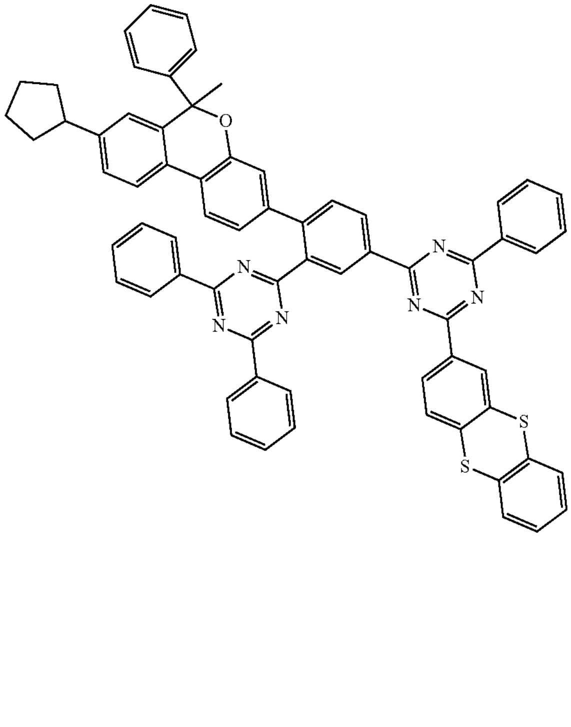

-continued
281
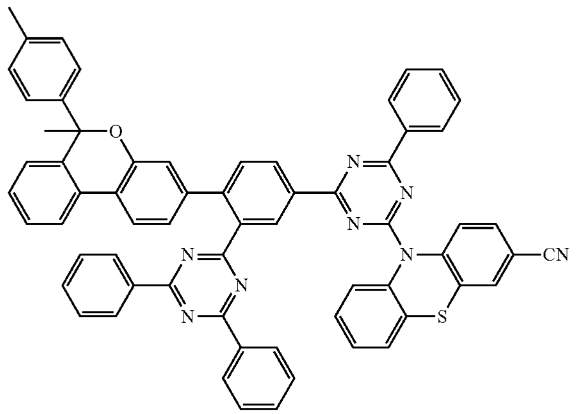
282
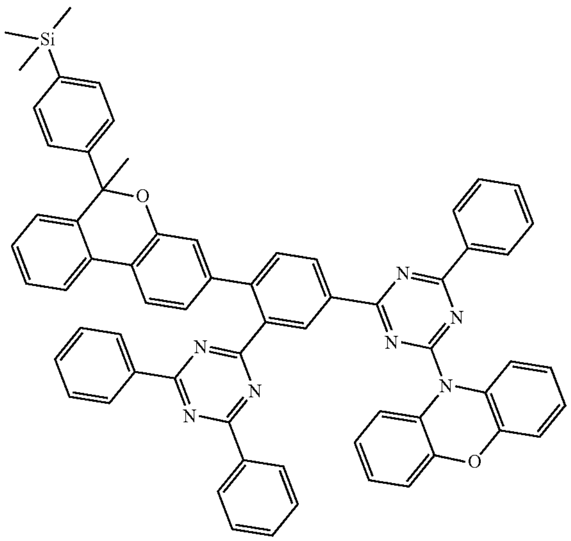
283
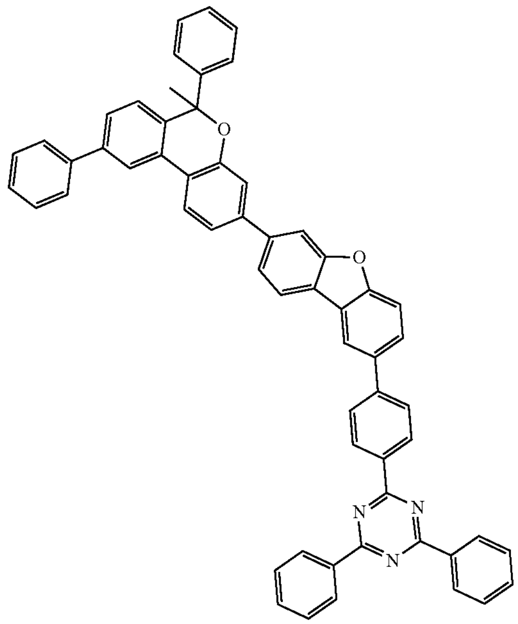
284
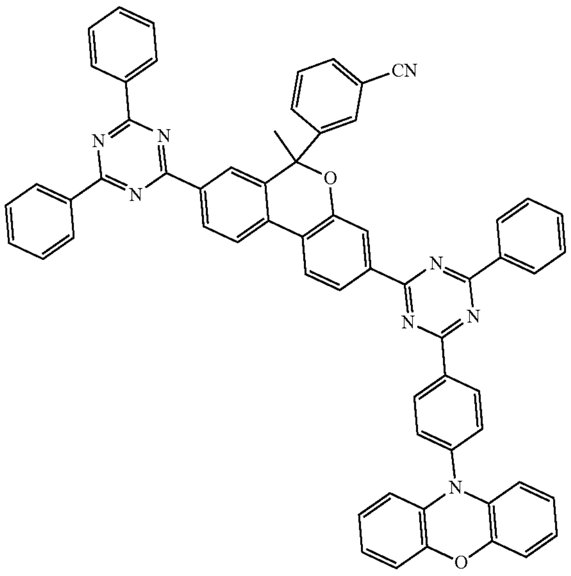

-continued
285
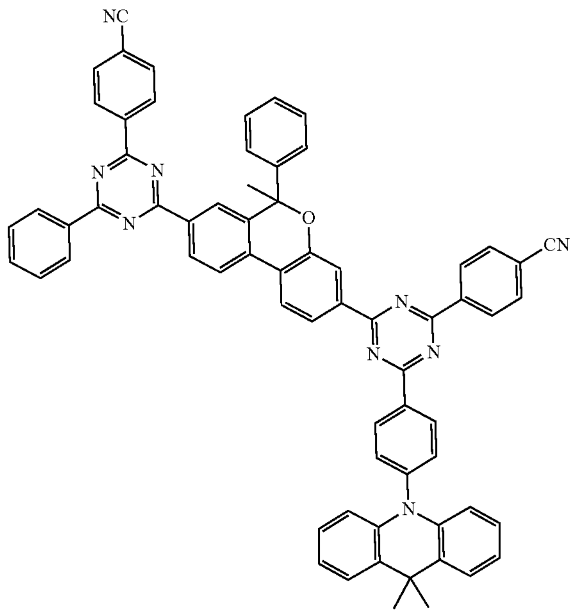
286
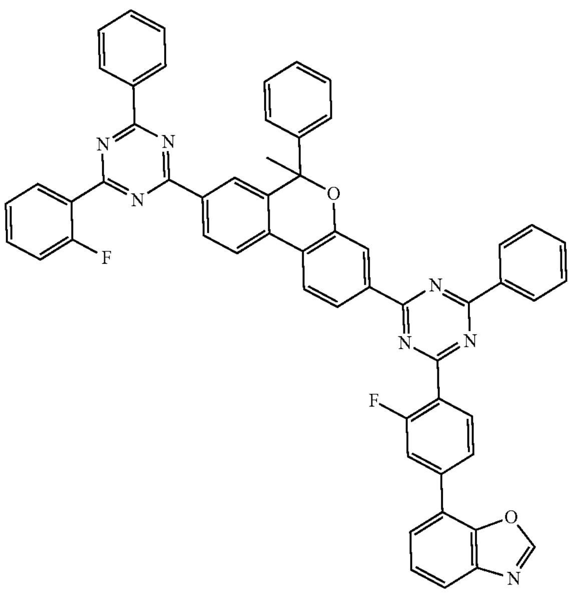
287
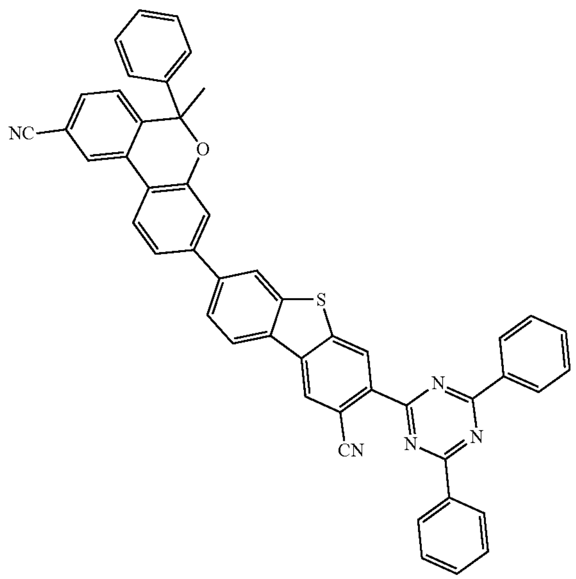
288
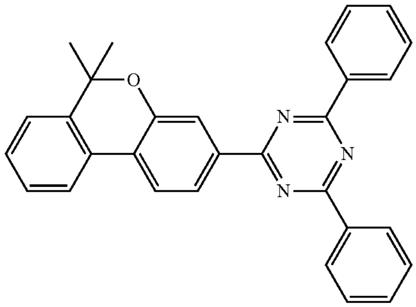

-continued
289
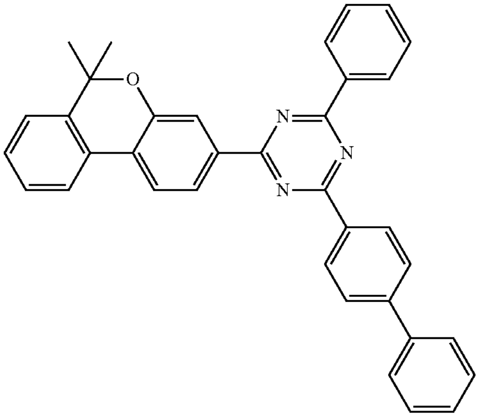
290
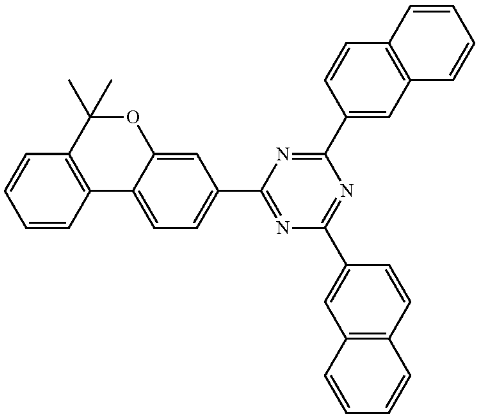
291
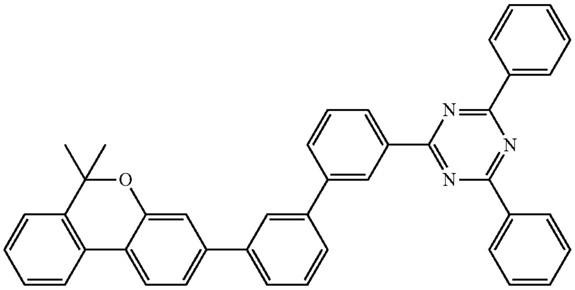
292
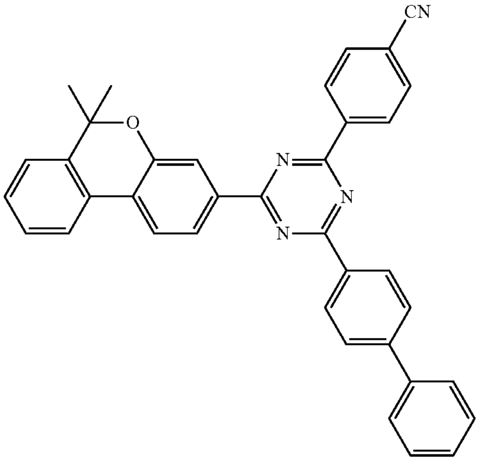
293
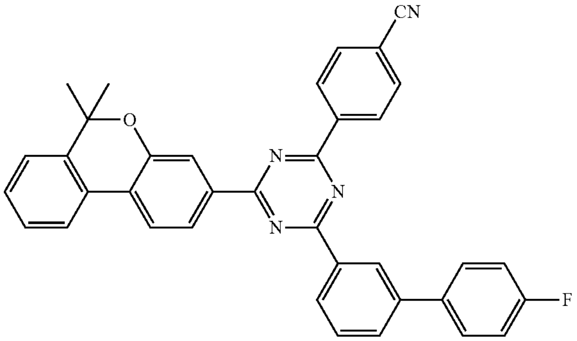
294
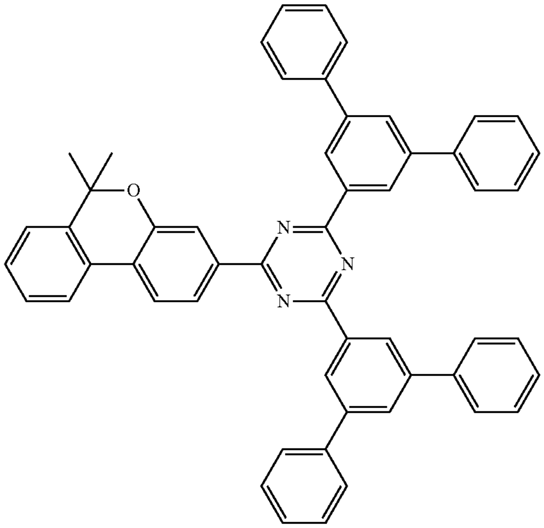
295
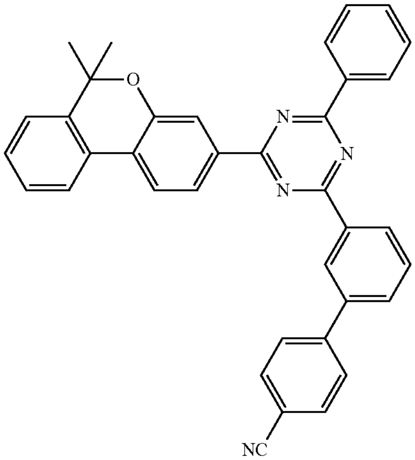

-continued
296
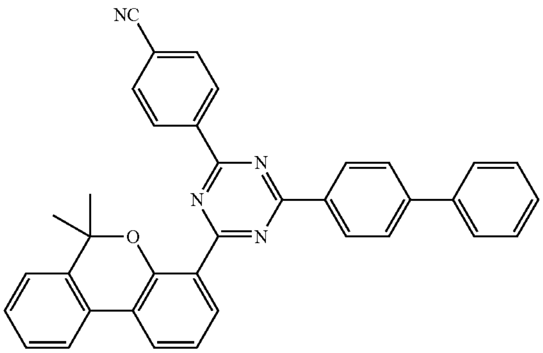
297
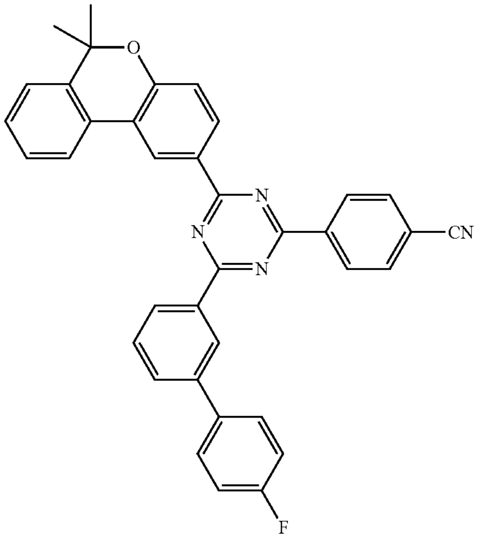
298
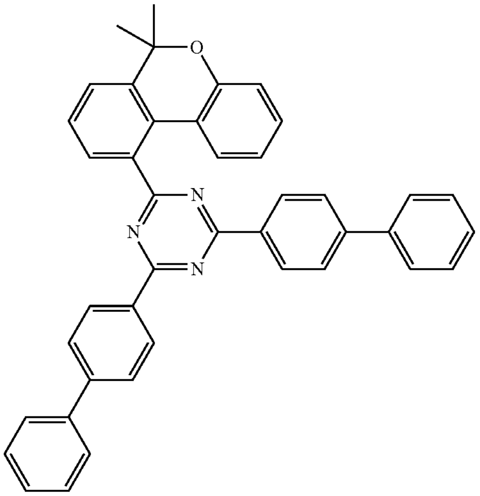
-continued
299
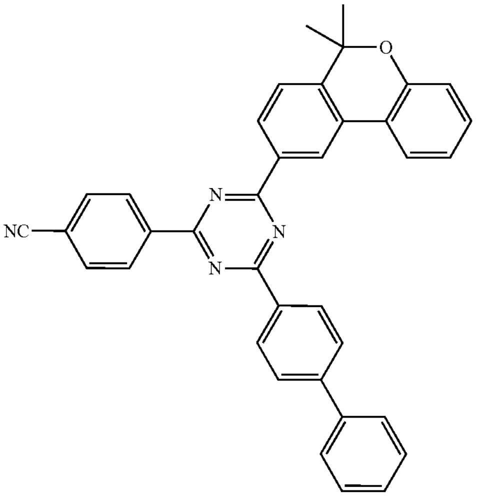
300
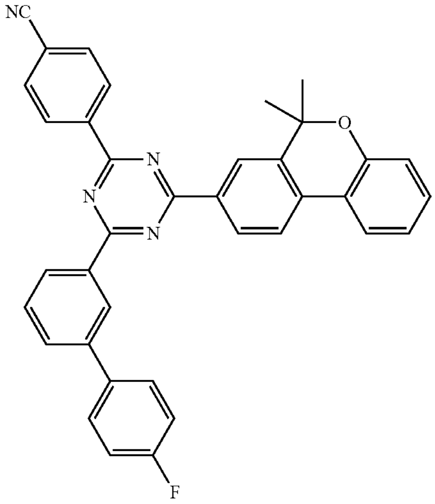
301
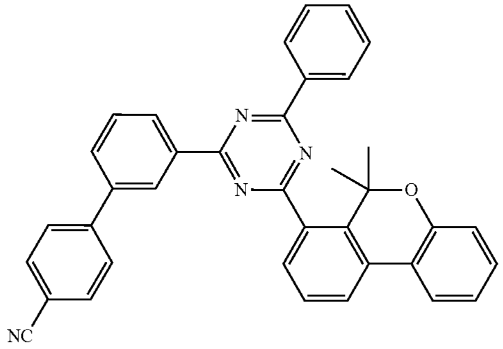

-continued
302
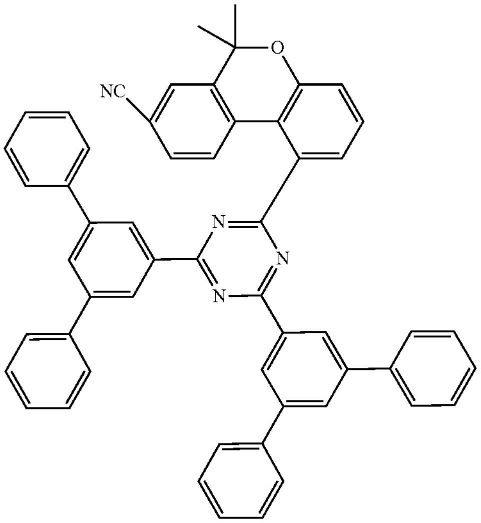
303
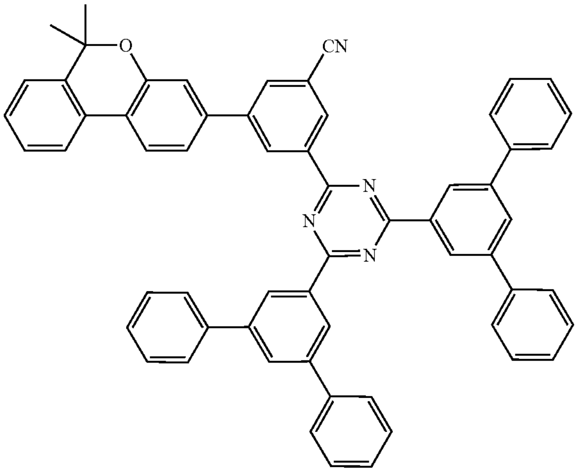
304
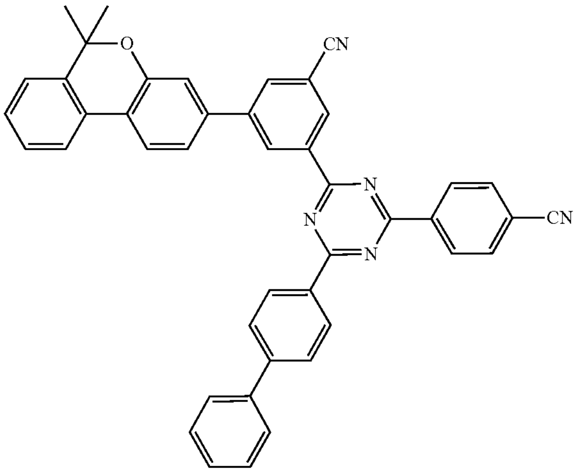
-continued
305
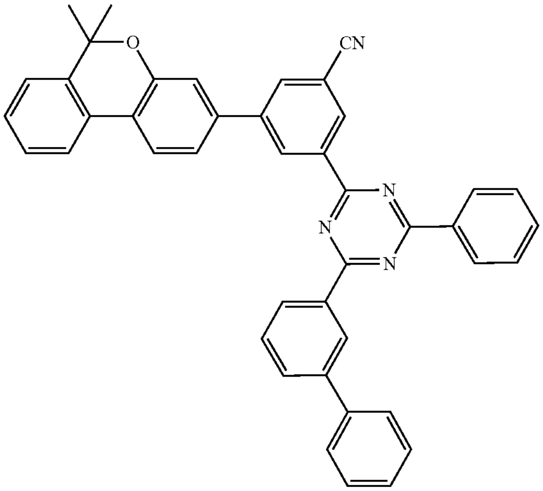
306
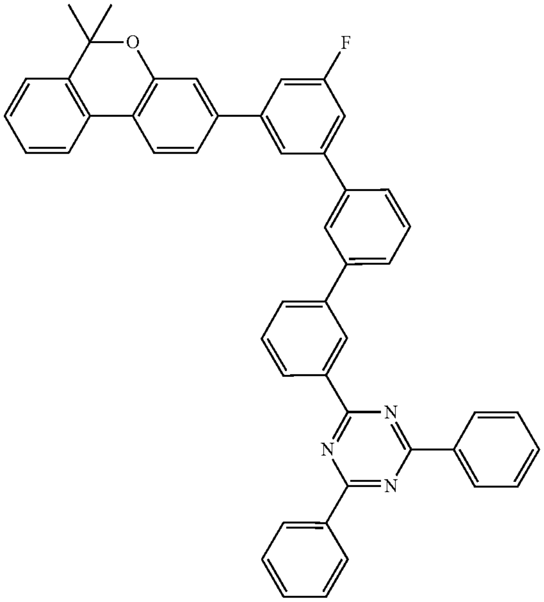
307
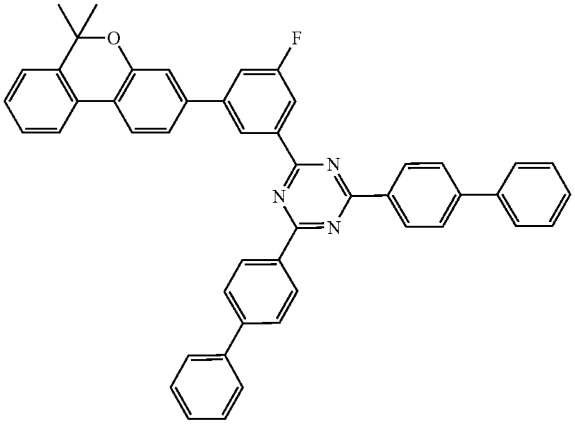

308
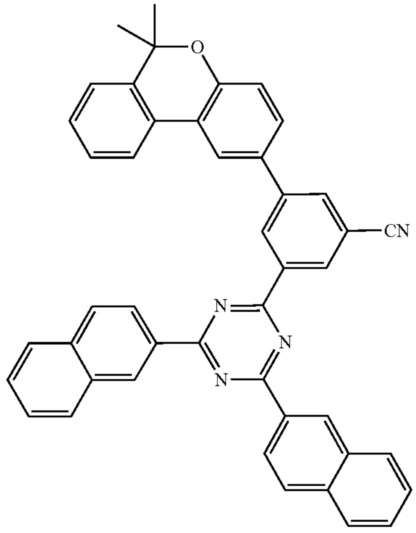
309
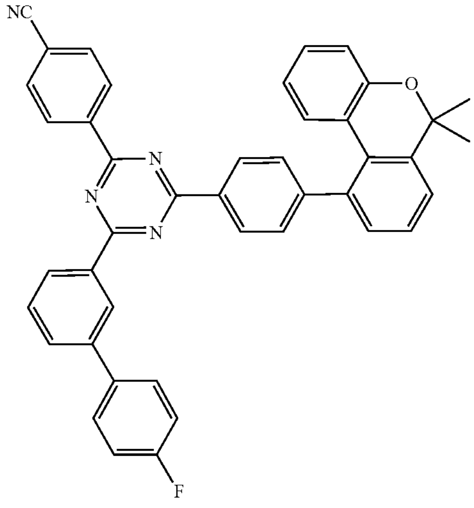
310
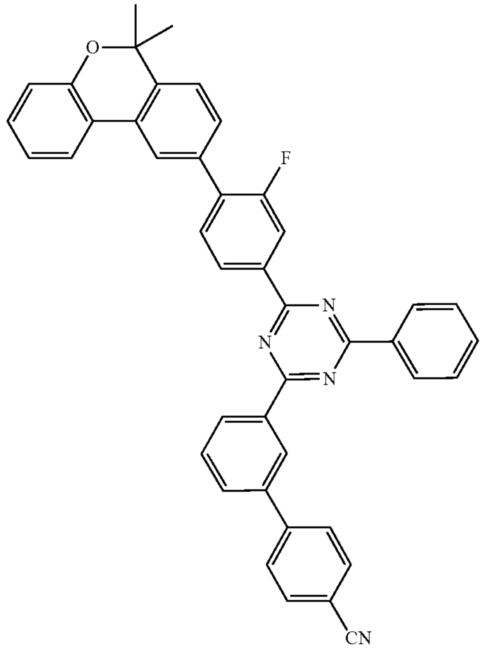
311
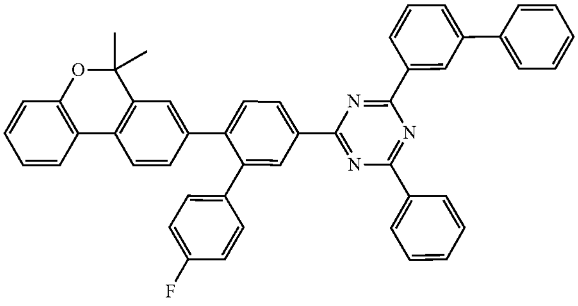
312
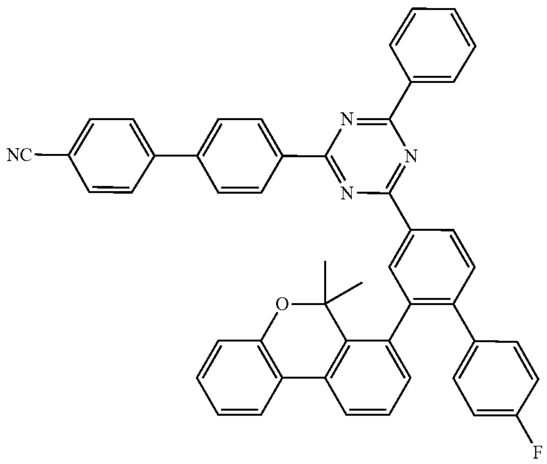

-continued
313
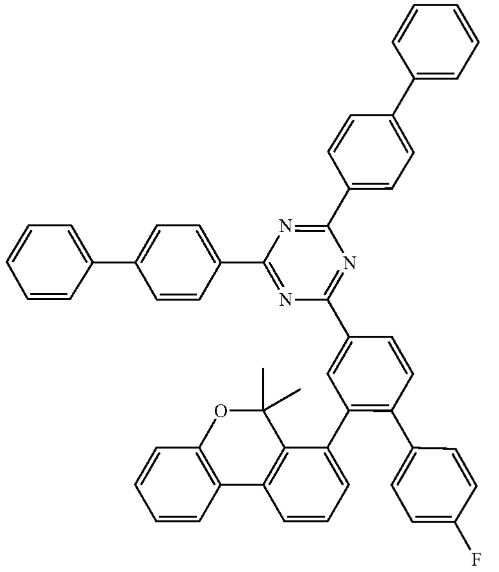
314
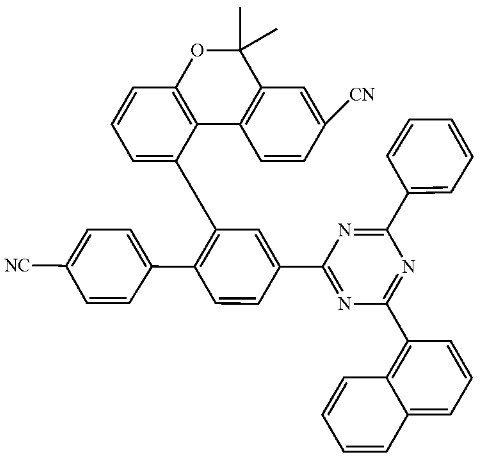
315
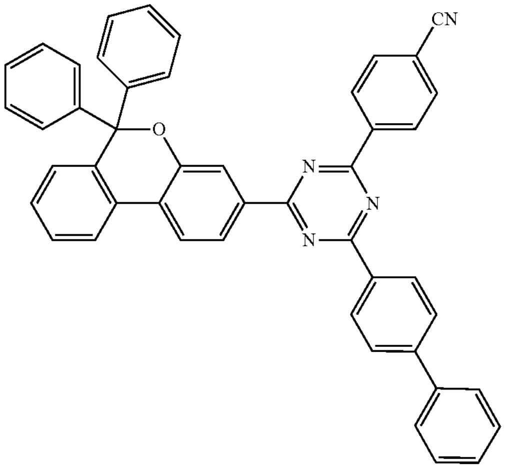
-continued
316
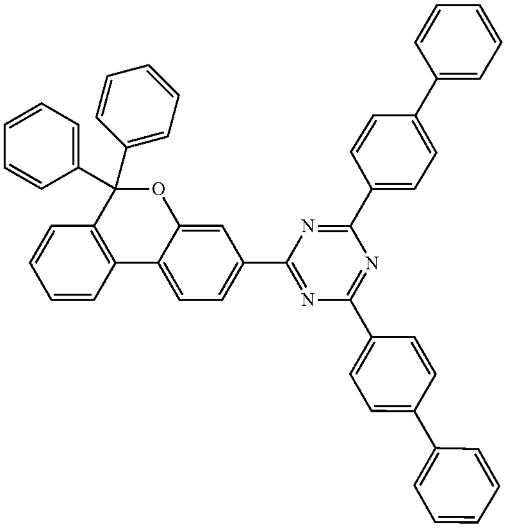
317
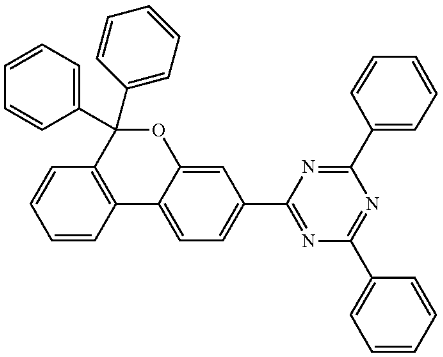
318
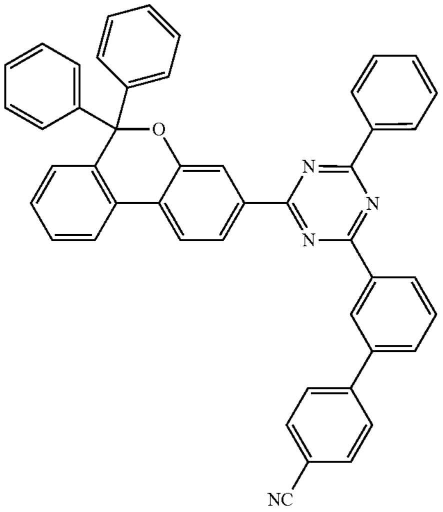

-continued
319
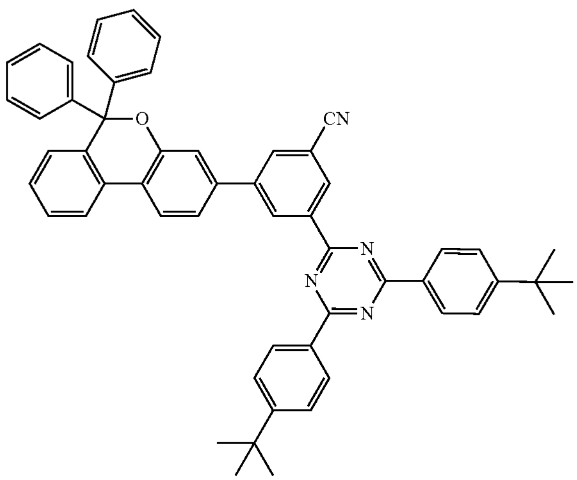
320
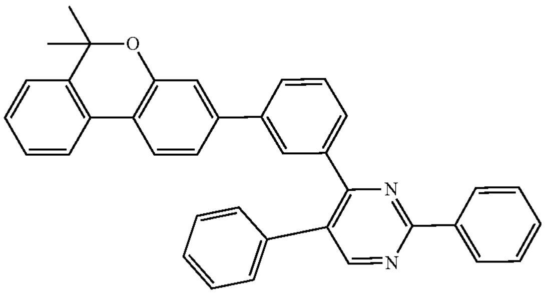
321
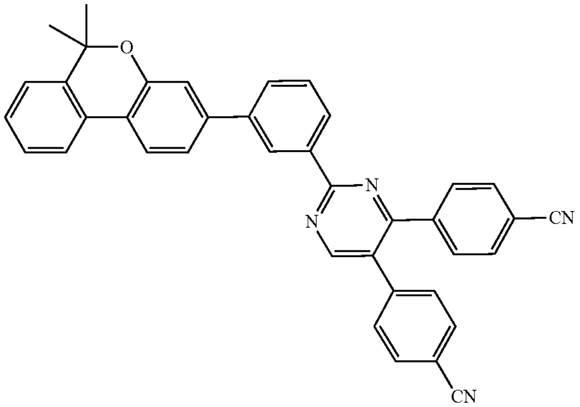
322
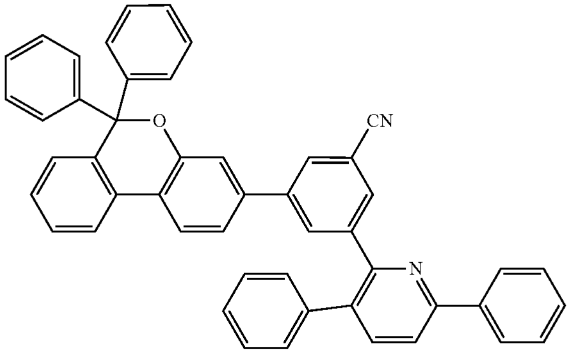
-continued
323
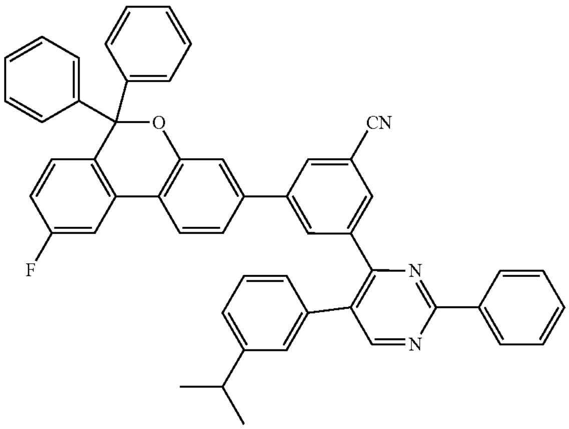
324
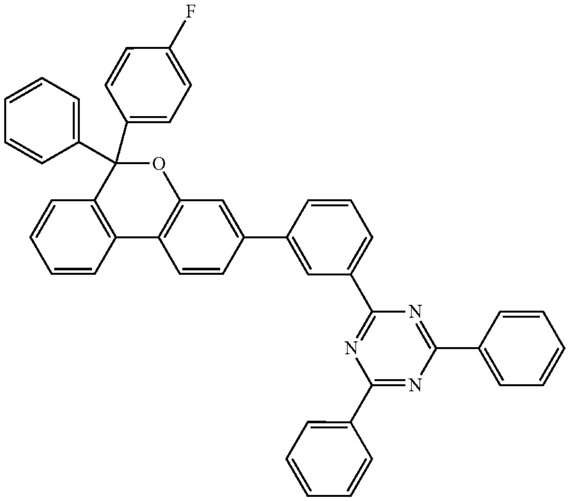
325
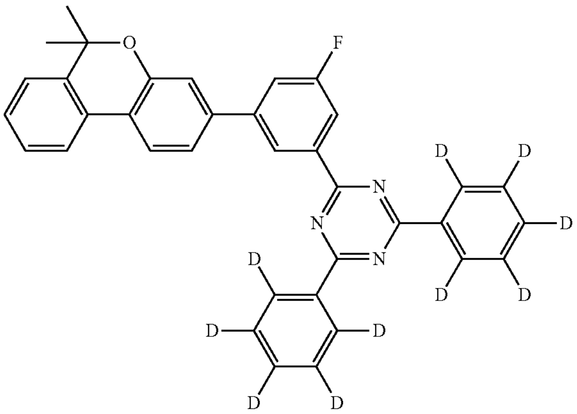

-continued
326
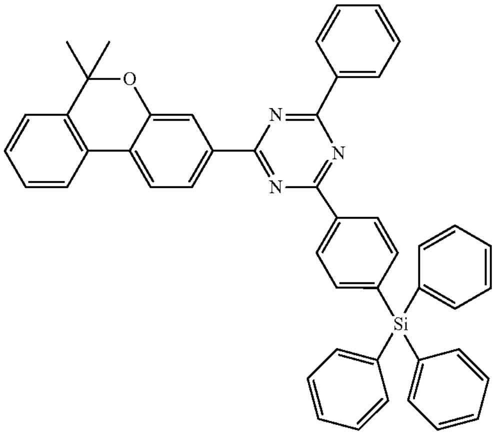
327
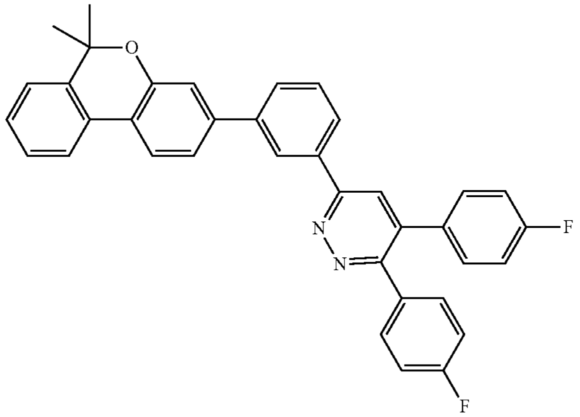
328
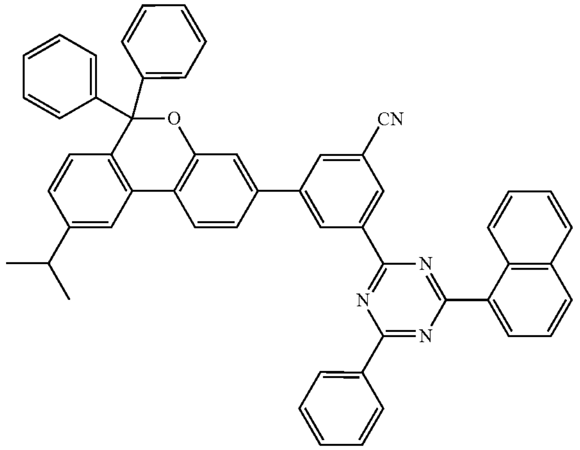
329
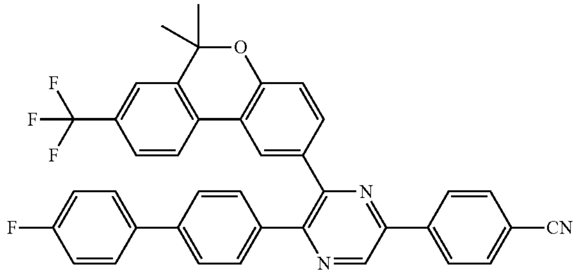
-continued
330
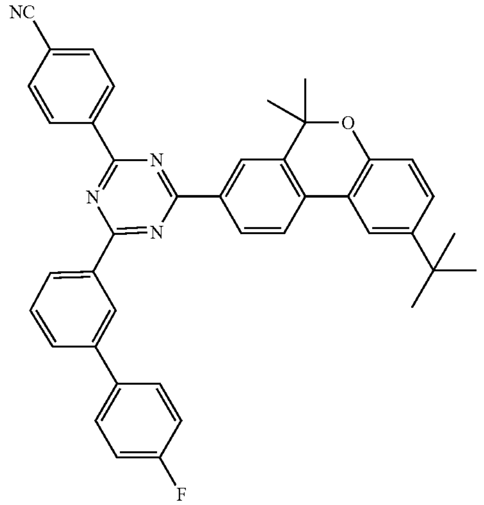
331
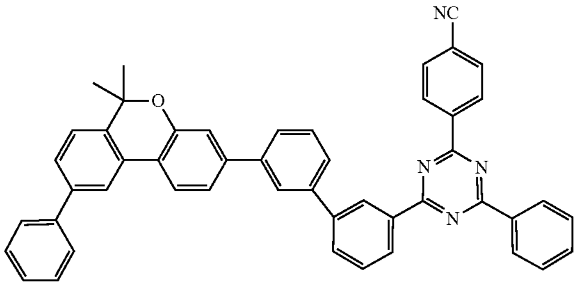
332
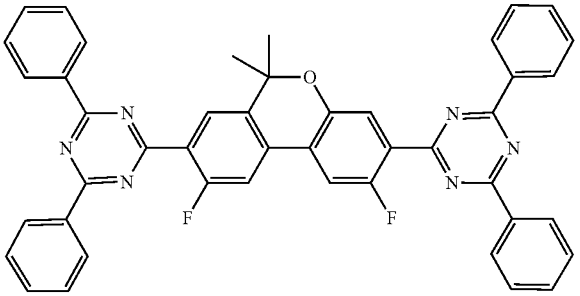
333
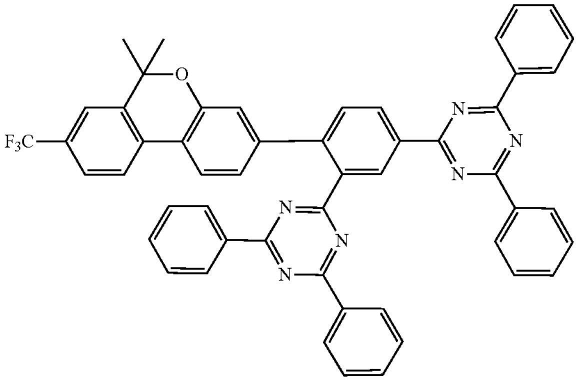

-continued

334

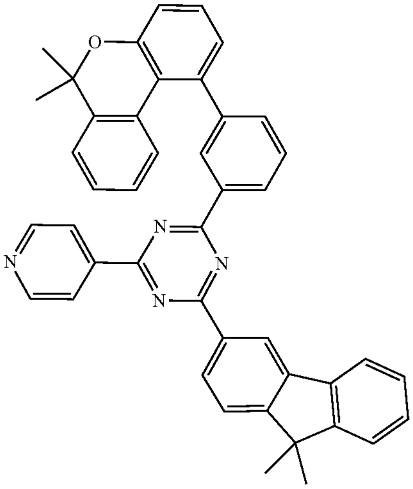

335

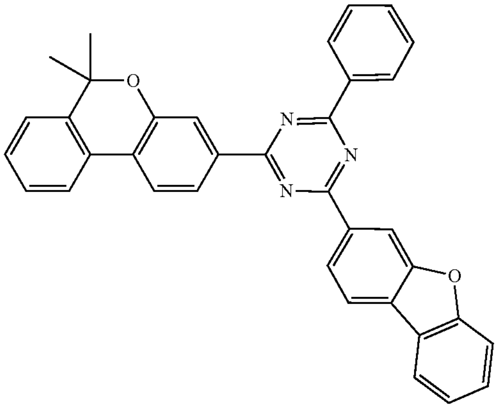

336

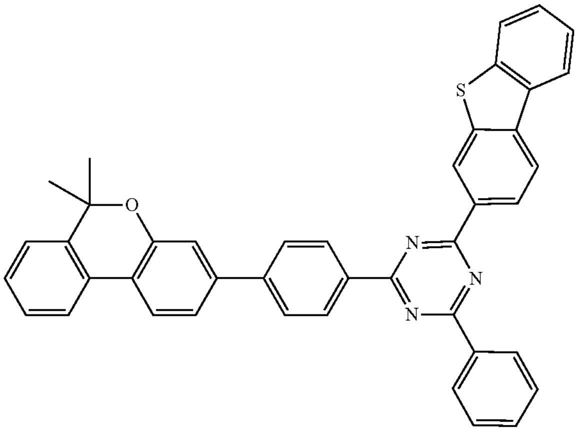

-continued

337

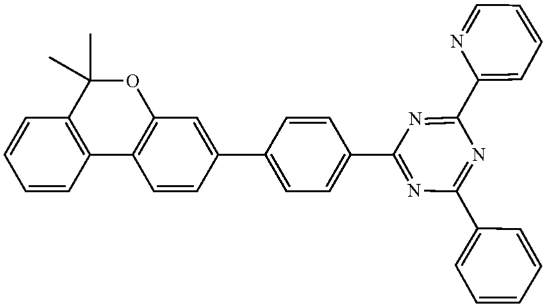

338

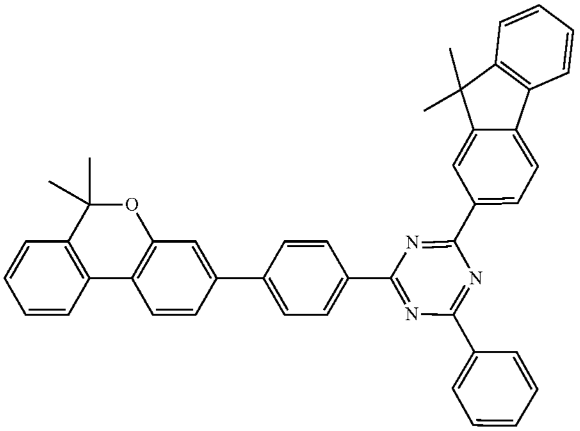

339

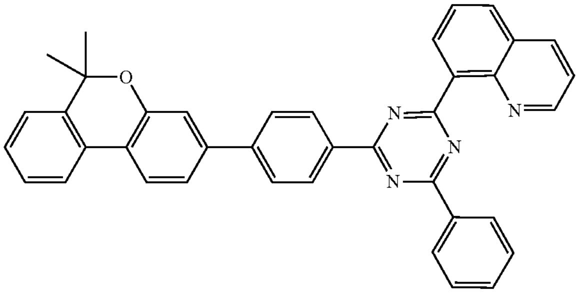

340

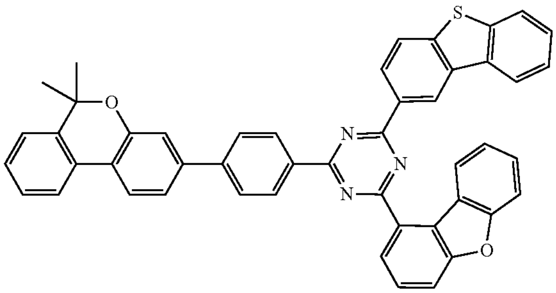

.

A synthesis method of the organic compound provided is not specially limited in the present disclosure, and those skilled in the art can determine a suitable synthesis method according to the organic compound of the present disclosure in combination with preparation methods provided in synthesis examples. In other words, the synthesis examples in the present disclosure exemplarily provides preparation methods for the organic compounds, and raw materials used may be commercially obtained or obtained by a method well known in the art. Those skilled in the art can obtain all organic compounds provided by the present disclosure according to these exemplary preparation methods, and all specific preparation methods for the organic compounds are not described in detail herein, and those skilled in the art should not understand as limiting the present disclosure.

In a second aspect, the present disclosure provides an electronic element, including an anode and a cathode which are oppositely disposed, and a functional layer disposed between the anode and the cathode; and the functional layer includes the organic compound according to the first aspect of the present disclosure.

In one specific embodiment, the functional layer includes an electron transport layer including the organic compound. The electron transport layer may be composed of the organic compound provided by the present disclosure or may be composed of the organic compound provided by the present disclosure together with other materials. The electron transport layer may be one layer or two or more layers.

In one specific embodiment, the functional layer includes a hole blocking layer including the organic compound.

In one specific embodiment, the electronic element is an organic electroluminescent device or a photoelectric conversion device.

In one specific embodiment, the electronic element is the organic electroluminescent device, for example a red electroluminescent device, a green electroluminescent device or a blue electroluminescent device.

In one more specific embodiment, the electronic element may be the organic electroluminescent device. As shown in FIG. 1, the organic electroluminescent device may include an anode 100, a hole transport layer 321, an electron blocking layer 322, an organic luminescent layer 330 as an energy conversion layer, a hole blocking layer 341, an electron transport layer 340, and a cathode 200 which are stacked in sequence.

Optionally, the anode 100 includes an anode material, which is preferably a material with a large work function that facilitates hole injection into the functional layer. Specific examples of the anode material include: metals such as nickel, platinum, vanadium, chromium, copper, zinc, and gold, or their alloy; metal oxides such as zinc oxide, indium oxide, indium tin oxide (ITO) and indium zinc oxide (IZO); combined metals and oxides, such as ZnO:Al or $SnO_2$:Sb; or a conductive polymer such as poly(3-methylthiophene), poly[3,4-(ethylene-1,2-dioxy)thiophene] (PEDT), polypyrrole, and polyaniline, but are not limited to these. A transparent electrode containing indium tin oxide (ITO) as the anode is preferably included.

Optionally, the hole transport layer 321 and the electron blocking layer 322 include one or more hole transport materials respectively, and the hole transport materials may be selected from a carbazole polymer, carbazole-linked triarylamine type compounds, or other types of compounds, which are not specially limited in the present disclosure. For example, the hole transport layer 321 may be composed of a compound NPB or a compound HT-01, and the electron blocking layer 322 may include a compound HT-02.

Optionally, the organic luminescent layer 330 may be composed of a single luminescent material and may also include a host material and a doping material. Optionally, the organic luminescent layer 330 is composed of the host material and the doping material, and holes injected into the organic luminescent layer 330 and electrons injected into the organic luminescent layer 330 can be recombined in the organic luminescent layer 330 to form excitons, the excitons transfer energy to the host material, and the host material transfers energy to the doping material, thus enabling the doping material to emit light.

The host material of the organic luminescent layer 330 may be a metal chelate compound, a bis-styryl derivative, an aromatic amine derivative, a dibenzofuran derivative, or other types of materials, which is not specially limited in the present disclosure. In one embodiment of the present disclosure, the host material of the organic luminescent layer 330 is BH-01.

The doping material of the organic luminescent layer 330 may be a compound having a condensed aryl ring or its derivative, a compound having a heteroaryl ring or its derivative, an aromatic amine derivative, or other materials, which is not specially limited in the present disclosure. In one embodiment of the present disclosure, the doping material of the organic luminescent layer 330 is BD-01.

The hole blocking layer 341 may include one or more hole blocking materials, and the hole blocking materials may be selected from the compounds of the present disclosure or BCP.

The electron transport layer 340 may be of a single-layer structure or a multi-layer structure and may include one or more electron transport materials, and the electron transport materials can be selected from, but are not limited to, a benzimidazole derivative, an oxadiazole derivative, a quinoxaline derivative, or other electron transport materials. In one embodiment of the present disclosure, the electron transport layer material contains the organic compound of the present disclosure. In one embodiment of the present disclosure, the electron transport layer material contains BCP.

In the present disclosure, the cathode 200 includes a cathode material, which is a material having a small work function that facilitates electron injection into the functional layer. Specific examples of the cathode material include, but are not limited to, metals such as magnesium, calcium, natrium, kalium, titanium, indium, yttrium, lithium, gadolinium, aluminum, argentum, tin, and lead or their alloy; or multilayer materials such as LiF/Al, Liq/Al, $LiO_2$/Al, LiF/Ca, LiF/Al, and $BaF_2$/Ca. A metal electrode containing magnesium and argentum as the cathode is preferably included.

Optionally, as shown in FIG. 1, a hole injection layer 310 may also be arranged between the anode 100 and the hole transport layer 321 to enhance the ability to inject holes into the hole transport layer 321. The hole injection layer 310 can be made of a benzidine derivative, a starburst arylamine compound, a phthalocyanine derivative or other materials, which is not specially limited in the present disclosure. For example, the hole injection layer 310 may be composed of F4-TCNQ.

Optionally, as shown in FIG. 1, an electron injection layer 350 may also be arranged between the cathode 200 and the electron transport layer 340 to enhance the ability to inject electrons into the electron transport layer 340. The electron injection layer 350 may include an inorganic material such as an alkali metal sulfide and an alkali metal halide, or may include a complex of an alkali metal and an organic compound. For example, the electron injection layer 350 may include Yb or LiQ.

Figure 3:
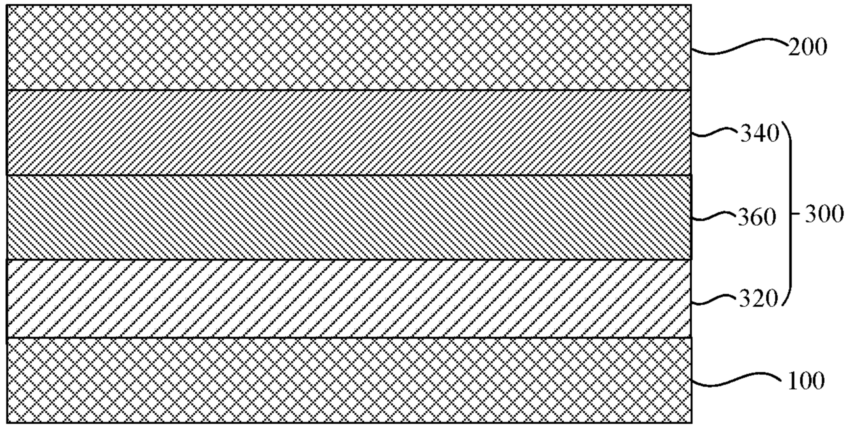
FIG. 3 is a structural schematic diagram of a photoelectric conversion device according to one embodiment of the present disclosure.

According to another embodiment, the electronic element may be a photoelectric conversion device. As shown in FIG. 3, the photoelectric conversion device may include an anode 100 and a cathode 200 which are disposed oppositely, and a functional layer 300 disposed between the anode 100 and the cathode 200; and the functional layer 300 includes the organic compound provided by the present disclosure.

According to one specific embodiment, as shown in FIG. 3, the photoelectric conversion device may include an anode 100, a first hole transport layer 320, a photoelectric conversion layer 360, an electron transport layer 340, and a cathode 200 which are stacked in sequence.

Optionally, the photoelectric conversion device may be a solar cell, and in particular may be an organic thin film solar cell. For example, in one embodiment of the present disclosure, the solar cell may include an anode, a hole transport layer, a photoelectric conversion layer, an electron transport layer and a cathode which are stacked in sequence, and the electron transport layer includes the organic compound of the present disclosure.

In a third aspect, the present disclosure provides an electronic device, including the electronic element according to the second aspect of the present disclosure.

Figure 2:
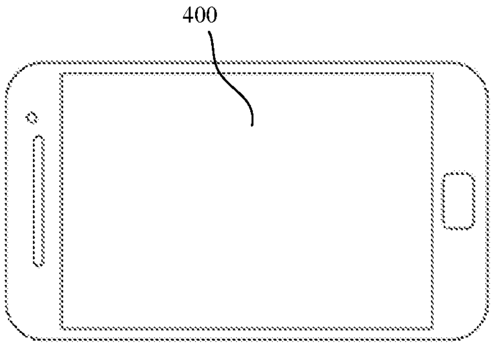
FIG. 2 is a structural schematic diagram of a first electronic device according to one embodiment of the present disclosure.

According to one embodiment, as shown in FIG. 2, the electronic device is a first electronic device 400 including the organic electroluminescent device described above. The first electronic device 400 may, for example, be a display device, a lighting device, an optical communication device, or other types of electronic devices, and may include, for example, but is not limited to, a computer screen, a mobile phone screen, a television, electronic paper, an emergency lighting lamp, an optical module, and the like.

Figure 4:
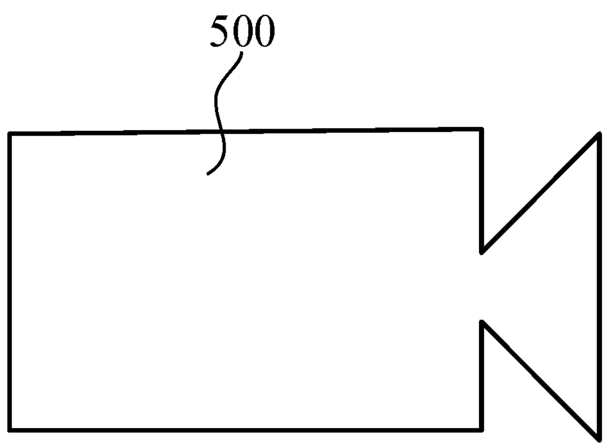
FIG. 4 is a structural schematic diagram of a second electronic device according to one embodiment of the present disclosure.

According to another embodiment, as shown in FIG. 4, the electronic device is a second electronic device 500 including the photoelectric conversion device described above. The second electronic device 500 may, for example, be a solar power plant, a light detector, a fingerprint recognition device, an optical module, a CCD camera, or other types of electronic devices.

The synthesis method of the organic compound of the present disclosure is specifically described below in conjunction with synthesis examples, but the present disclosure is not limited in any way.

SYNTHESIS EXAMPLE

In the synthesis examples described below, unless otherwise stated, all temperatures were in degrees Celsius. Some reagents were purchased from commodity suppliers such as Aldrich Chemical Company, Arco Chemical Company and Alfa Chemical Company and were used without further purification unless otherwise stated. Compounds of which the synthesis methods were not mentioned in the present disclosure were all commercially obtained raw material products.

During purification, a chromatographic column was a silica gel column and silica gel (100 to 200 mesh) was purchased from the Qingdao ocean chemical plant.

In the synthesis examples, low resolution mass spectrum (MS) data were measured by using Agilent 6120 Quadrupole HPLC-M (a column model: Zorbax SB-C18, 2.1×30 mm, 3.5 m, 6 min at a flow rate of 0.6 mL/min. Mobile phase: 5% to 95% (a ratio of acetonitrile containing 0.1% formic acid in water containing 0.1% formic acid), using electrospray ionization (ESI) at 210 nm/254 nm with UV detection.

$^1$H-NMR: Bruker 400 MHz nuclear magnetic resonance spectrometer with $CDCl_3$ as a solvent (in ppm) and TMS (0 ppm) as a reference standard at room temperature. When multiplets appear, the following abbreviations will be used: s (singlet), d (doublet), t (triplet), and m (multiplet).

Target compounds were detected by UV at 210 nm/254 nm by using Agilent 1260 pre-HPLC or Calesep pump 250 pre-HPLC (a column model: NOVASEP 50/80 mm DAC).

Intermediates and compounds in the present disclosure were analyzed and detected by an ICP-7700 mass spectrometer and an M5000 elemental analyzer.

Synthesis of Intermediate I-A1 to Intermediate I-A10

Step (1): Synthesis of intermediate I-1-A

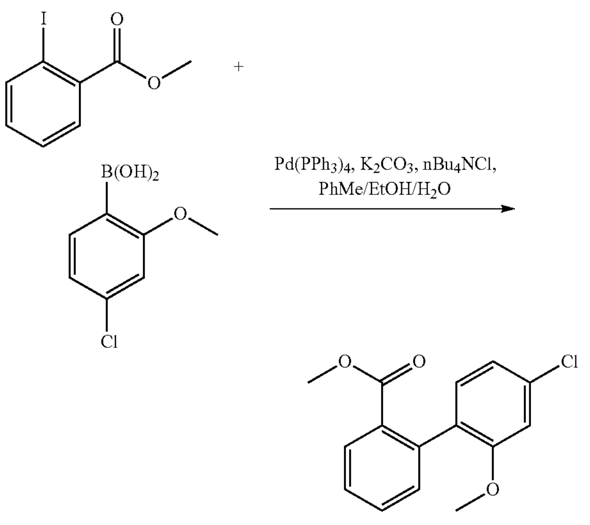

I-1-A

Methyl 2-iodobenzoate (10.0 g, 38.2 mmol), 4-chloro-2-methoxyphenylboronic acid (7.83 g, 42.0 mmol), potassium carbonate (10.54 g, 76.4 mmol), tetrabutylammonium bromide (1.27 g, 3.82 mmol), toluene (50 mL), ethanol (30 mL) and deionized water (20 mL) were added to a three-necked flask and stirred for 15 min under nitrogen protection, tetrakis(triphenylphosphine)palladium (0.44 g, 0.0382 mmol) was added thereto, and the mixture was heated to 75° C. to 80° C. and stirred for 5 h. The reaction solution was cooled to room temperature, toluene (100 mL) was added for extraction. The combined organic phases were dried over anhydrous magnesium sulfate, and then concentrated in a vacuum to obtain a crude product. The crude product was purified by flash silica gel column chromatography, and eluent was concentrated to obtain an intermediate I-1-A (9.50 g, 90%) as a yellow oil.

Step (2): Synthesis of intermediate I-1-B

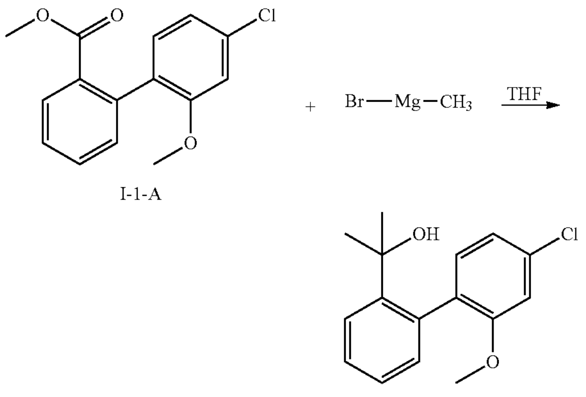

I-1-B

The intermediate I-1-A (5.54 g, 20 mmol) and tetrahydrofuran (55 mL) were added to a three-necked flask, and the reaction mixture was stirred, then a solution of methylmagnesium bromide in THE (3M, 20 mL, 60 mmol) was added slowly dropwise under nitrogen atmosphere. After the dropwise addition, the mixture was stirred at room temperature for 1 h, then was heated to 60° C. to 66° C. and stirred for another 6 h. Then reaction solution was cooled to room temperature, dichloromethane (110 mL) was added thereto, and deionized water (55 mL) was slowly added under stirring, then 1 mol/L diluted hydrochloric acid (55 mL) was slowly added, after stirring, the solution was allowed to stand for liquid separation. The separated organic phase was dried over anhydrous magnesium sulfate, and filtered, and the filtrate was concentrated in a vacuum to obtain an intermediate I-1-B (5 g, 90.25%) as a light yellow oil.

Step (3): Synthesis of intermediate I-A1

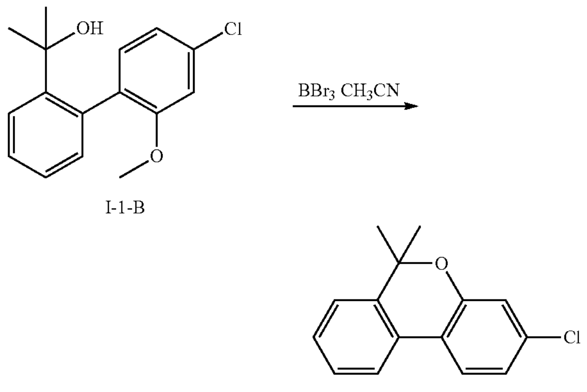

I-1-B

I-A1

The intermediate I-1-B (5 g, 18 mmol) and acetonitrile (50 mL) were added to a three-necked flask, stirring was started and the system was cooled to 0° C. to 10° C., then a 1M solution of boron tribromide in dichloromethane (18 mL, 18 mmol) was added thereto dropwise, the temperature was kept at 0° C. to 10° C., and after 1 h, the system was naturally heated to room temperature, and stirred for about 5 h. Deionized water (50 mL), and dichloromethane (50 mL) were added to the reaction solution, liquid separation was performed, an organic phase was dried over anhydrous magnesium sulfate, then filtered, and concentrated in a vacuum to obtain a crude product; and the obtained yellow oily crude product was purified by silica gel column chromatography and eluted with n-heptane to obtain an intermediate I-A1 (3 g, 68.0%) as a white solid.

GC-MS (pos. Ion) m/z: 244.10 $[M]^+$;

$^1H$ NMR (400 MHz, $CDCl_3$): δ 7.74-7.71 (m, 2H), 7.40-7.37 (m, 2H), 7.30 (d, 1H), 7.05 (dd, 1H), 6.99 (d, 1H), 1.66 (s, 6H) ppm.

Intermediates I-A2 to I-A10 in Table 1 were prepared by using the same method as that for the preparation of the intermediate I-A1, except that a raw material 1 in Table 1 was used instead of the raw material methyl 2-iodobenzoate used for the synthesis of the intermediate I-A1, and a raw material 2 in Table 1 was used instead of the raw material 4-chloro-2-methoxyphenylboronic acid used for the synthesis of the intermediate I-A1.

TABLE 1

| Intermediate I-A No. | Raw material 1 | Raw material 2 | Product structure (Intermediate I-A) | Yield/% (here is the total yield in step (3)) |
|---|---|---|---|---|
| I-A2 | 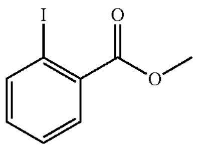 | 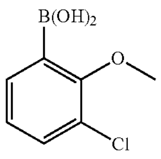 | 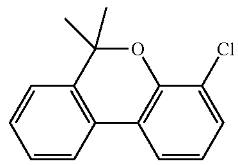 [SMILES: CC1(C)Oc2c(Cl)cccc2-c2ccccc21] | 54 |
| I-A3 | | 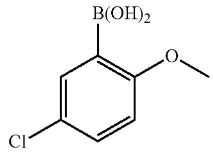 | 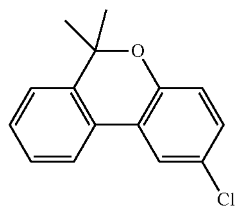 [SMILES: CC1(C)Oc2ccc(Cl)cc2-c2ccccc21] | 55 |
| I-A4 | | 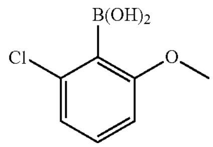 | 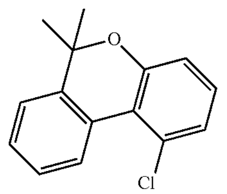 [SMILES: CC1(C)Oc2cccc(Cl)c2-c2ccccc21] | 50 |

TABLE 1-continued
| Intermediate I-A No. | Raw material 1 | Raw material 2 | Product structure (Intermediate I-A) | Yield/% (here is the total yield in step (3)) |
|---|---|---|---|---|
| I-A5 | 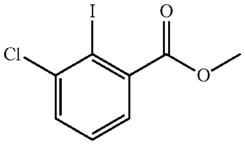 | 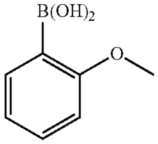 | 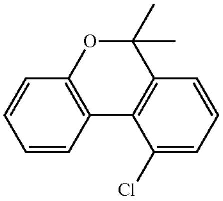 [SMILES: CC1(C)Oc2ccccc2-c2c(Cl)cccc21] | 52 |
| I-A6 | 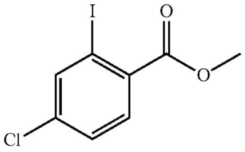 | | 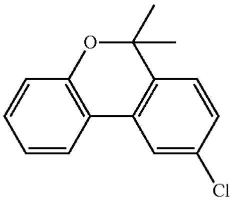 [SMILES: CC1(C)Oc2ccccc2-c2cc(Cl)ccc21] | 54 |
| I-A7 | 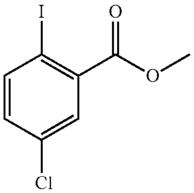 | | 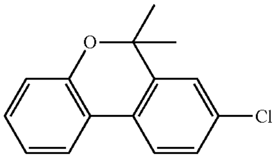 [SMILES: CC1(C)Oc2ccccc2-c2ccc(Cl)cc21] | 55 |
| I-A8 | 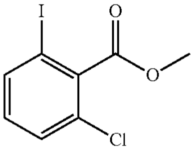 | | 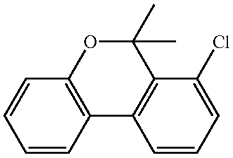 [SMILES: CC1(C)Oc2ccccc2-c2cccc(Cl)c21] | 56 |
| I-A9 | 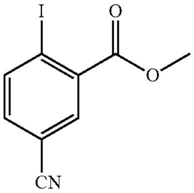 | 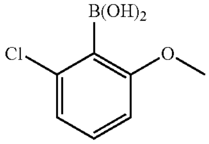 | 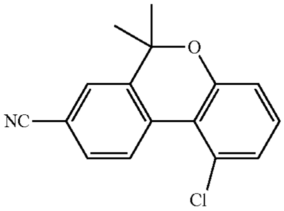 [SMILES: CC1(C)Oc2cccc(Cl)c2-c2ccc(C#N)cc21] | 55 |
| I-A10 | 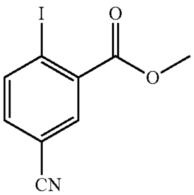 | 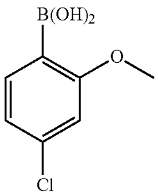 | 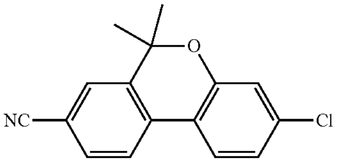 [SMILES: CC1(C)Oc2cc(Cl)ccc2-c2ccc(C#N)cc21] | 60 |
Synthesis of Intermediate I-B1 to Intermediate I-B10:
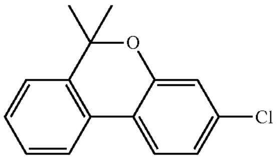
I-A1
+
-continued
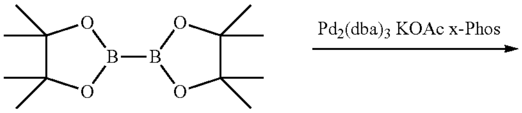

-continued

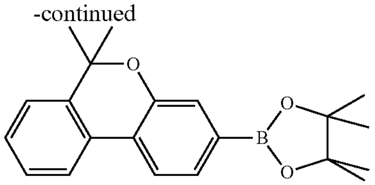

I-B1

The intermediate I-A1 (2.5 g, 10.22 mmol), bis(pinacolato)diboron (3.37 g, 13.28 mmol), tris(dibenzylideneacetone)dipalladium (0.094 g, 0.10 mmol), 2-dicyclohexylphosphino-2',4',6'-triisopropylbiphenyl (0.15 g, 0.31 mmol), potassium acetate (2.51 g, 25.54 mmol) and 1,4-dioxane (25 mL) were added to a three-necked round bottom flask, and heated to 80° C. under nitrogen atmosphere, and stirred for 3 h; cooled to room temperature, then the reaction solution was washed with water. The separated organic phase was dried over magnesium sulfate, and filtered, and then concentrated in a vacuum to obtain a crude product. The crude product was purified by recrystallization using toluene to obtain an intermediate I-B1 (2.8 g, yield: 81.5%) as a solid.

Intermediates I-B2 to I-B10 were prepared by using the same method as that for the preparation of the intermediate I-B1, except that a raw material 3 (the intermediate I-A) in Table 2 was used instead of the raw material, namely the intermediate I-A1, used for the synthesis of the intermediate I-B1.

TABLE 2

| Intermediate I-B No. | Raw material 3 (Intermediate I-A) | Product structure (Intermediate I-B) | Yield/% |
|---|---|---|---|
| I-B2 | 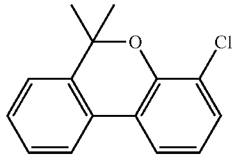 [SMILES: CC1(C)Oc2c(Cl)cccc2-c2ccccc21] | 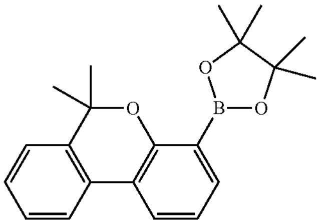 [SMILES: CC1(C)Oc2c(B3OC(C)(C)C(C)(C)O3)cccc2-c2ccccc21] | 84 |
| I-B3 | 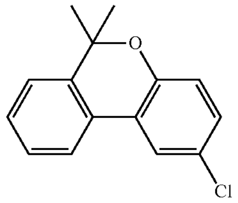 [SMILES: CC1(C)Oc2ccc(Cl)cc2-c2ccccc21] | 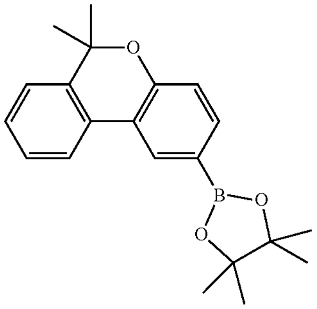 [SMILES: CC1(C)Oc2ccc(B3OC(C)(C)C(C)(C)O3)cc2-c2ccccc21] | 85 |
| I-B4 | 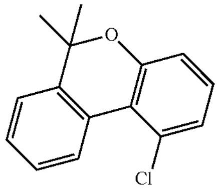 [SMILES: CC1(C)Oc2cccc(Cl)c2-c2ccccc21] | 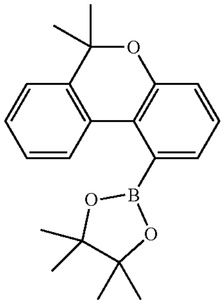 [SMILES: CC1(C)Oc2cccc(B3OC(C)(C)C(C)(C)O3)c2-c2ccccc21] | 80 |
| I-B5 | 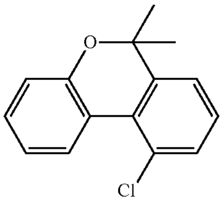 [SMILES: CC1(C)Oc2ccccc2-c2c(Cl)cccc21] | 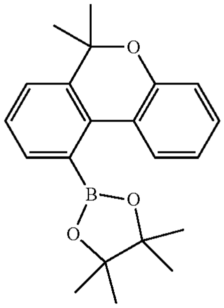 [SMILES: CC1(C)Oc2ccccc2-c2c(B3OC(C)(C)C(C)(C)O3)cccc21] | 82 |

TABLE 2-continued
| Intermediate I-B No. | Raw material 3 (Intermediate I-A) | Product structure (Intermediate I-B) | Yield/% |
| --- | --- | --- | --- |
| I-B6 | 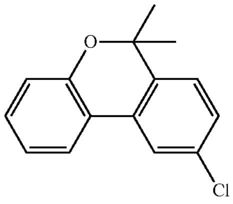 [SMILES: CC1(C)Oc2ccccc2-c2cc(Cl)ccc21] | 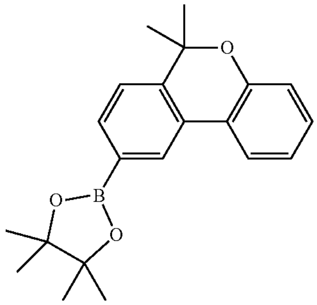 [SMILES: CC1(C)Oc2ccccc2-c2cc(B3OC(C)(C)C(C)(C)O3)ccc21] | 84 |
| I-B7 | 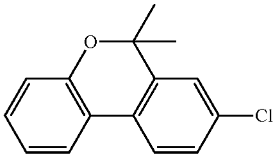 | 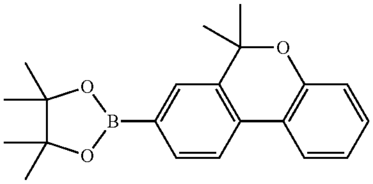 [SMILES: CC1(C)Oc2ccccc2-c2ccc(B3OC(C)(C)C(C)(C)O3)cc21] | 85 |
| I-B8 | 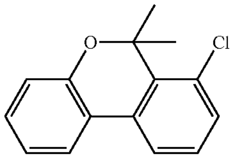 [SMILES: CC1(C)Oc2ccccc2-c2cccc(Cl)c21] | 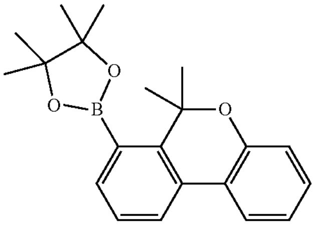 [SMILES: CC1(C)Oc2ccccc2-c2cccc(B3OC(C)(C)C(C)(C)O3)c21] | 86 |
| I-B9 | 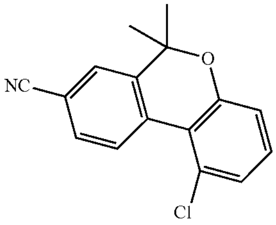 [SMILES: CC1(C)Oc2cccc(Cl)c2-c2ccc(C#N)cc21] | 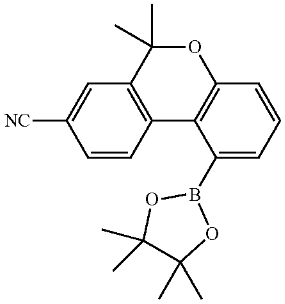 [SMILES: CC1(C)Oc2cccc(B3OC(C)(C)C(C)(C)O3)c2-c2ccc(C#N)cc21] | 55 |
| I-B10 | 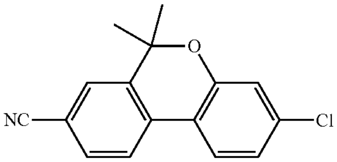 [SMILES: CC1(C)Oc2cc(Cl)ccc2-c2ccc(C#N)cc21] | 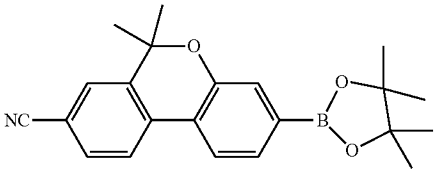 [SMILES: CC1(C)Oc2cc(B3OC(C)(C)C(C)(C)O3)ccc2-c2ccc(C#N)cc21] | 58 |

Synthesis of Intermediate I-D1 to Intermediate I-D15

1. Synthesis of Intermediate I-D1:

(1)

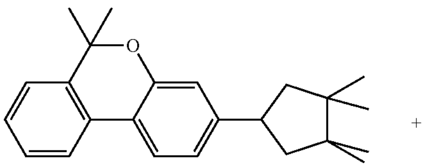

I-B1

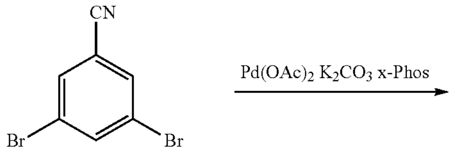

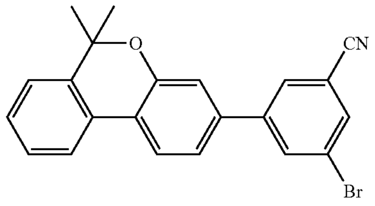

I-C1

The intermediate I-B1 (2.8 g, 8.33 mmol), 3,5-dibromobenzonitrile (2.17 g, 8.33 mmol), palladium acetate (0.0187 g, 0.0833 mmol), 2-dicyclohexylphosphino-2',4',6'-triisopropylbiphenyl (0.08 g, 0.17 mmol), potassium carbonate (2.30 g, 16.65 mmol), toluene (15 mL), absolute ethanol (10 mL) and deionized water (5 mL) were added to a round bottom flask, the mixture was heated to 78° C. under nitrogen atmosphere, and stirred for 4 h; then cooled to room temperature. The reaction solution was washed with water, and the separated organic phase was dried over magnesium sulfate, and filtered, and then concentrated in a vacuum to obtain a crude product; and the crude product was purified by recrystallization using a mixture of dichloromethane and n-heptane to obtain an intermediate I-C1 (2.06 g, yield: 63.6%) as a solid.

(2)

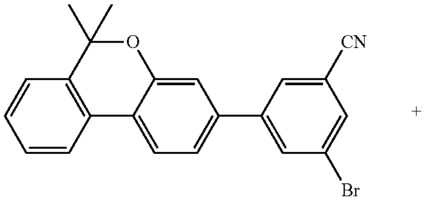

I-C1

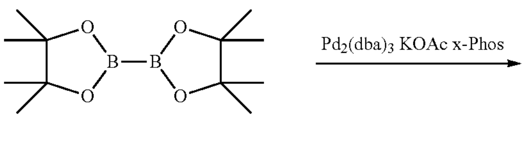

-continued

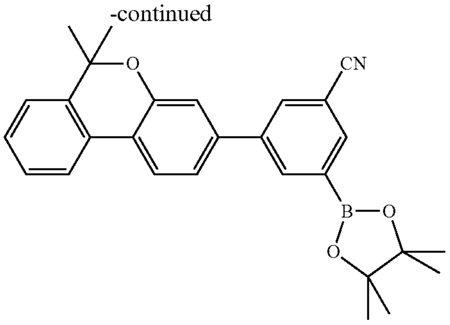

I-D1

The intermediate I-C1 (3.98 g, 10.22 mmol), bis(pinacolato)diboron (3.37 g, 13.28 mmol), tris(dibenzylideneacetone)dipalladium (0.094 g, 0.10 mmol), 2-dicyclohexylphosphino-2',4',6'-triisopropylbiphenyl (0.15 g, 0.31 mmol), potassium acetate (2.51 g, 25.54 mmol) and 1,4-dioxane (25 mL) were added to a three-necked round bottom flask. The mixture was heated to 80° C. under nitrogen atmosphere, and stirred for 3 h; then cooled to room temperature. The reaction solution was washed with water, dried over magnesium sulfate, and filtered, and concentrated in a vacuum to obtain a crude product. The crude product was purified by recrystallization using toluene to obtain an intermediate I-D1 (3.61 g, yield: 81%) as a solid.

2. Synthesis of intermediate I-D2:

(1)

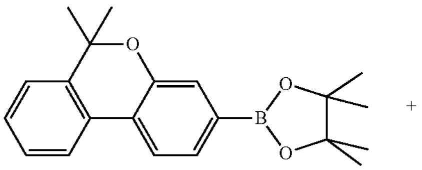

I-B1

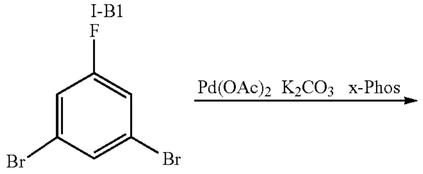

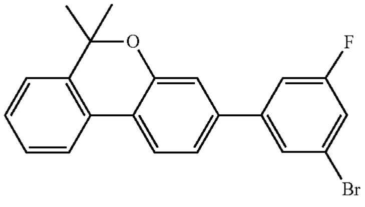

I-C2

The intermediate I-B1 (2.8 g, 8.33 mmol), 3,5-dibromofluorobenzene (2.11 g, 8.33 mmol), palladium acetate (0.0187 g, 0.0833 mmol), 2-dicyclohexylphosphino-2',4',6'-triisopropylbiphenyl (0.08 g, 0.17 mmol), potassium carbonate (2.30 g, 16.65 mmol), toluene (15 mL), absolute ethanol (10 mL) and deionized water (5 mL) were added to a round bottom flask, the reaction mixture was heated to 78° C. under nitrogen atmosphere, and stirred for 4 h; then cooled to room temperature. The reaction solution was washed with water, dried over magnesium sulfate, and filtered, and concentrated in a vacuum to obtain a crude product; and the crude product was purified by recrystallization using a mixture of dichloromethane and n-heptane to obtain an intermediate I-C2 (1.81 g, yield: 56.8%) as a solid.

(2)

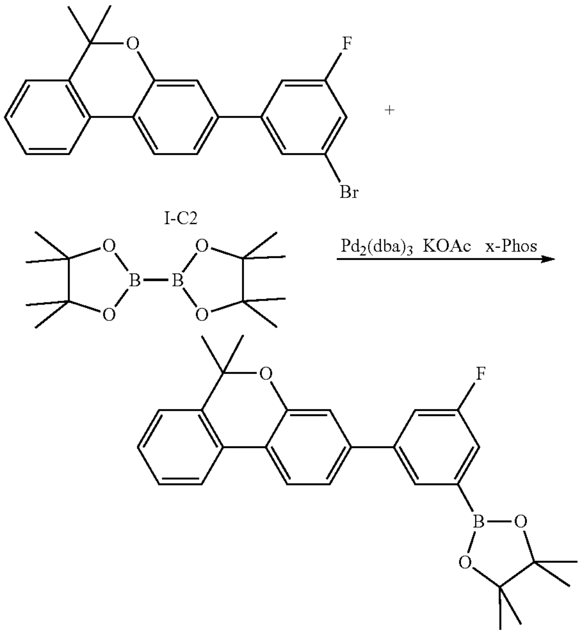

I-C2

I-D2

The intermediate I-C2 (3.91 g, 10.22 mmol), bis(pinacolato)diboron (3.37 g, 13.28 mmol), tris(dibenzylideneacetone)dipalladium (0.094 g, 0.10 mmol), 2-dicyclohexylphosphino-2',4',6'-triisopropylbiphenyl (0.15 g, 0.31 mmol), potassium acetate (2.51 g, 25.54 mmol) and 1,4-dioxane (25 mL) were added to a three-necked round bottom flask, the reaction mixture was heated to 80° C. under nitrogen atmosphere, and stirred for 3 h; then cooled to room temperature. The reaction solution was washed with water, dried over magnesium sulfate, and filtered, and concentrated in a vacuum to obtain a crude product; and the crude product was purified by recrystallization using toluene to obtain an intermediate I-D2 (3.73 g, yield: 85%) as a solid.

3. Synthesis of intermediates I-D3 to 1-D15

1) Synthesis of intermediates I-C3 to I-C18:

Intermediates I-C3 to I-C18 were synthesized by the same method as that for the synthesis of the intermediate I-C2 except that the raw material, namely the intermediate I-B1 used for the synthesis of the intermediate I-C2 was replaced with an intermediate I-B in Table 3, and the raw material 3,5-dibromofluorobenzene used for the synthesis of the intermediate I-C2 was replaced with a raw material 4 in Table 3.

TABLE 3

| Intermediate I-C No. | Intermediate I-B | Raw material 4 | Product structure (Intermediate I-C) | Yield/ % |
|---|---|---|---|---|
| I-C3 | 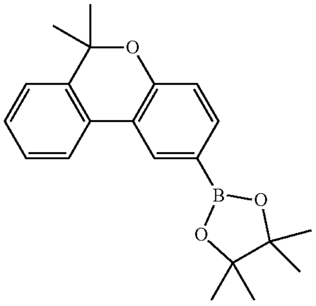 I-B3 | 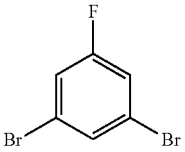 | 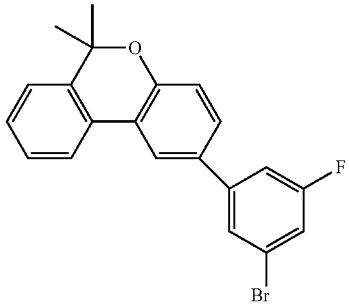 [SMILES: CC1(C)Oc2ccc(-c3cc(F)cc(Br)c3)cc2-c2ccccc21] | 58 |
| I-C4 | 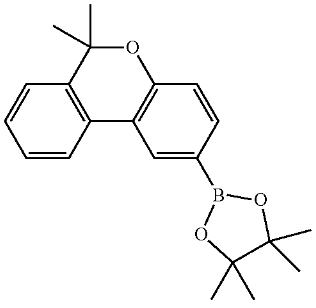 I-B3 | 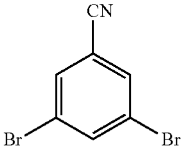 | 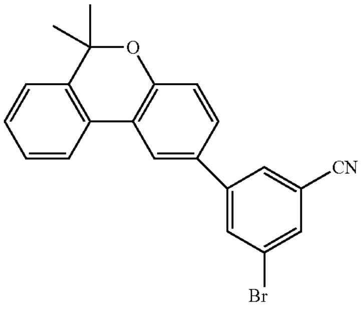 [SMILES: CC1(C)Oc2ccc(-c3cc(Br)cc(C#N)c3)cc2-c2ccccc21] | 75 |

TABLE 3-continued
| Intermediate I-C No. | Intermediate I-B | Raw material 4 | Product structure (Intermediate I-C) | Yield/ % |
|---|---|---|---|---|
| I-C5 | 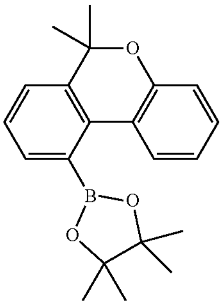 I-B5 | 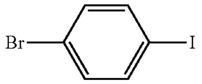 | 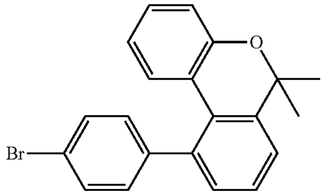 [SMILES: CC1(C)Oc2ccccc2-c2c(-c3ccc(Br)cc3)cccc21] | 65 |
| I-C6 | 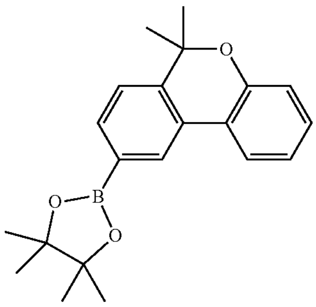 I-B6 | 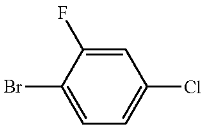 | 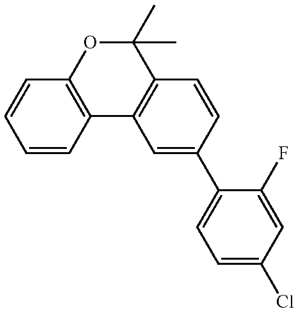 [SMILES: CC1(C)Oc2ccccc2-c2cc(-c3ccc(Cl)cc3F)ccc21] | 56 |
| I-C7 | 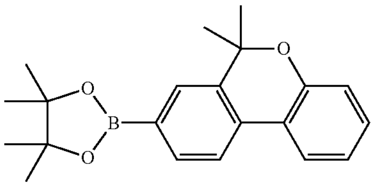 I-B7 | 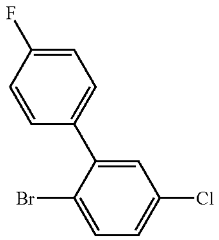 [SMILES: Fc1ccc(-c2cc(Cl)ccc2Br)cc1] | 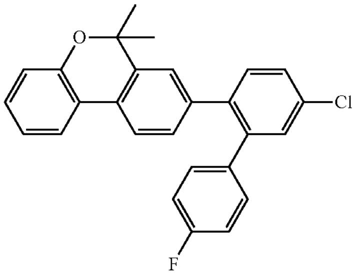 [SMILES: CC1(C)Oc2ccccc2-c2ccc(-c3ccc(Cl)cc3-c3ccc(F)cc3)cc21] | 55 |
| I-C8 | 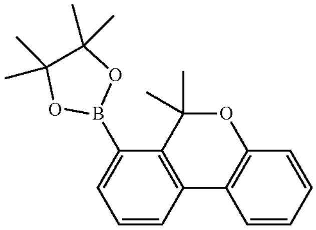 IB-8 | 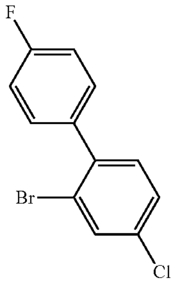 [SMILES: Fc1ccc(-c2ccc(Cl)cc2Br)cc1] | 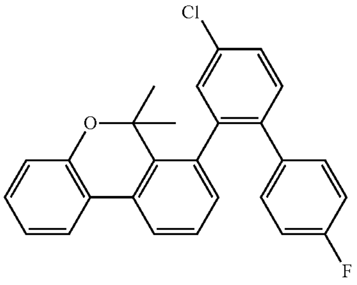 [SMILES: CC1(C)Oc2ccccc2-c2cccc(-c3cc(Cl)ccc3-c3ccc(F)cc3)c21] | 59 |

TABLE 3-continued
| Intermediate I-C No. | Intermediate I-B | Raw material 4 | Product structure (Intermediate I-C) | Yield/% |
|---|---|---|---|---|
| I-C9 | 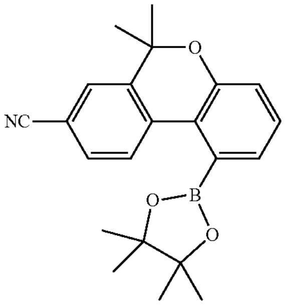 I-B9 | 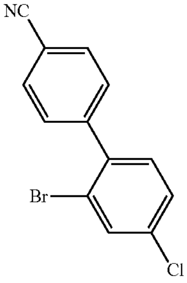 [SMILES: N#Cc1ccc(-c2ccc(Cl)cc2Br)cc1] | 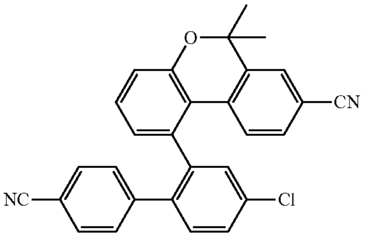 [SMILES: CC1(C)Oc2cccc(-c3cc(Cl)ccc3-c3ccc(C#N)cc3)c2-c2ccc(C#N)cc21] | 81 |
| I-C10 | 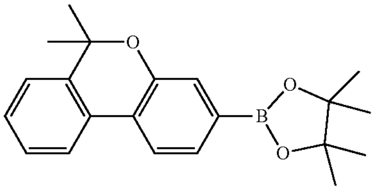 I-B1 | 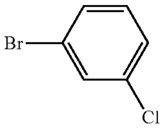 | 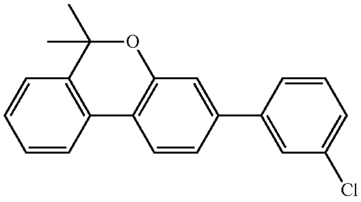 [SMILES: CC1(C)Oc2cc(-c3cccc(Cl)c3)ccc2-c2ccccc21] | 75 |
| I-C11 | 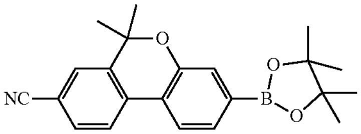 I-B10 | 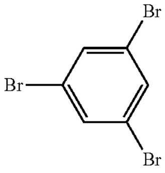 | 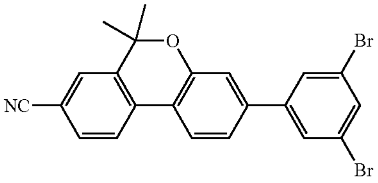 [SMILES: CC1(C)Oc2cc(-c3cc(Br)cc(Br)c3)ccc2-c2ccc(C#N)cc21] | 70 |
| I-C13 | 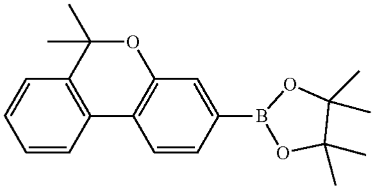 I-B1 | 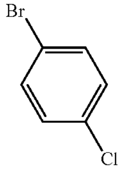 | 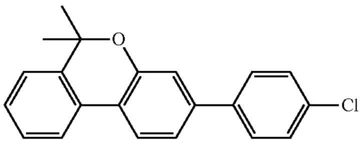 [SMILES: CC1(C)Oc2cc(-c3ccc(Cl)cc3)ccc2-c2ccccc21] | 75 |
| I-C14 | 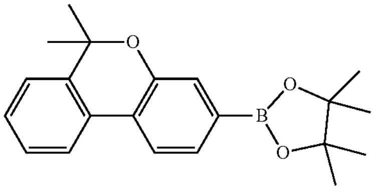 I-B1 | 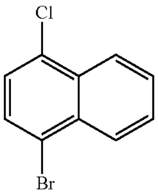 [SMILES: Clc1ccc(Br)c2ccccc12] | 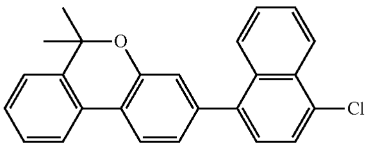 [SMILES: CC1(C)Oc2cc(-c3ccc(Cl)c4ccccc34)ccc2-c2ccccc21] | 72 |
| I-C15 | 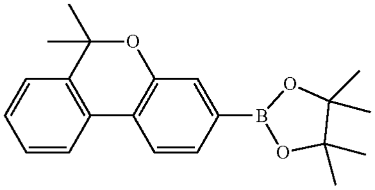 I-B1 | 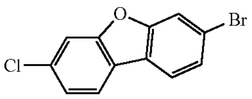 [SMILES: Clc1ccc2c(c1)oc1cc(Br)ccc12] | 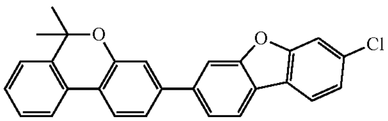 [SMILES: CC1(C)Oc2cc(-c3ccc4c(c3)oc3cc(Cl)ccc34)ccc2-c2ccccc21] | 70 |

TABLE 3-continued

| Intermediate I-C No. | Intermediate I-B | Raw material 4 | Product structure (Intermediate I-C) | Yield/% |
|---|---|---|---|---|
| I-C16 | 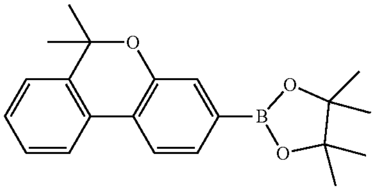 I-B1 | 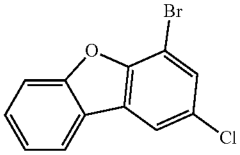 [SMILES: Clc1cc(Br)c2oc3ccccc3c2c1] | 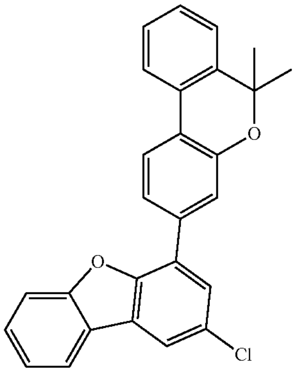 [SMILES: CC1(C)Oc2cc(-c3cc(Cl)cc4c3oc3ccccc34)ccc2-c2ccccc21] | 52 |
| I-C17 | 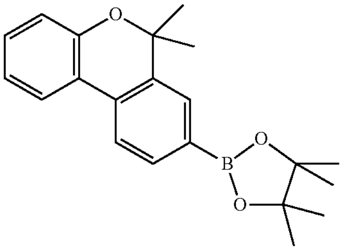 I-B7 | 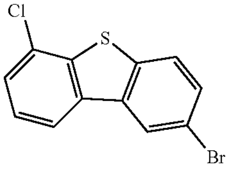 [SMILES: Clc1cccc2c1sc1ccc(Br)cc12] | 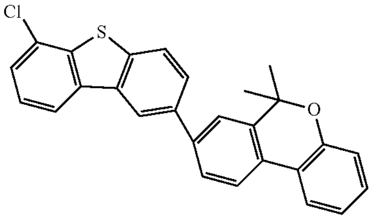 [SMILES: CC1(C)Oc2ccccc2-c2ccc(-c3ccc4sc5c(Cl)cccc5c4c3)cc21] | 68 |
| I-C18 | 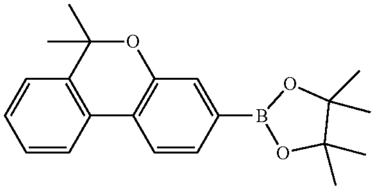 I-B1 | 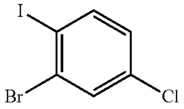 | 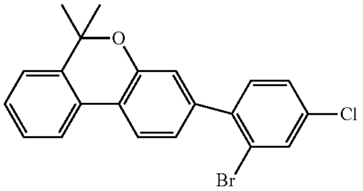 [SMILES: CC1(C)Oc2cc(-c3ccc(Cl)cc3Br)ccc2-c2ccccc21] | 35 |

2) Synthesis of intermediates I-D3 to I-D15:

Intermediates I-D3 to I-D15 were prepared by using the same method as that for the preparation of the intermediate I-D2 except that the raw material, namely the intermediate I-C2 used for the Synthesis of h intermediate I-D2 was replaced with an intermediate I-C in Table 4.

TABLE 4

| Intermediate I-D No. | Intermediate I-C | Product structure (Intermediate I-D) | Yield/% |
|---|---|---|---|
| I-D3 | 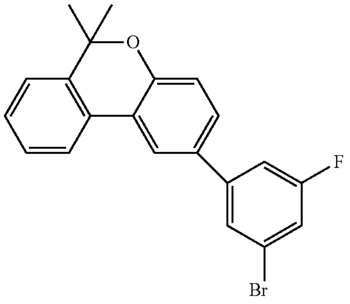 I-C3 | 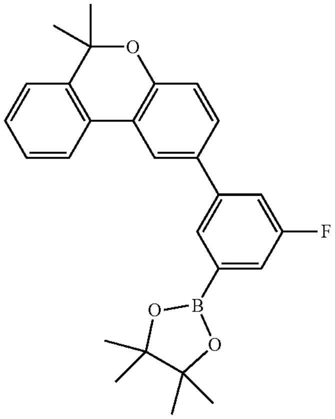 [SMILES: CC1(C)Oc2ccc(-c3cc(F)cc(B4OC(C)(C)C(C)(C)O4)c3)cc2-c2ccccc21] | 80 |

TABLE 4-continued
| Intermediate I-D No. | Intermediate I-C | Product structure (Intermediate I-D) | Yield/% |
|---|---|---|---|
| I-D4 | 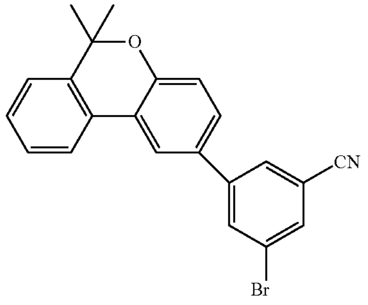 I-C4 | 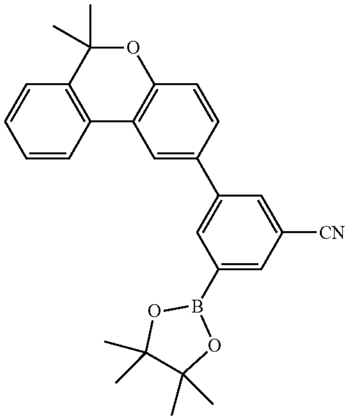 [SMILES: CC1(C)Oc2ccc(-c3cc(C#N)cc(B4OC(C)(C)C(C)(C)O4)c3)cc2-c2ccccc21] | 70 |
| I-D5 | 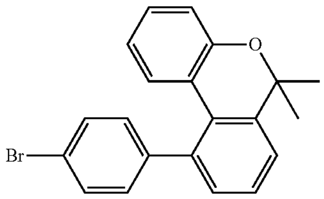 I-C5 | 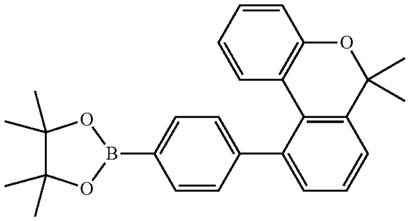 | 89 |
| I-D6 | 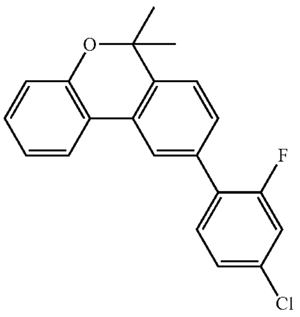 I-C6 | 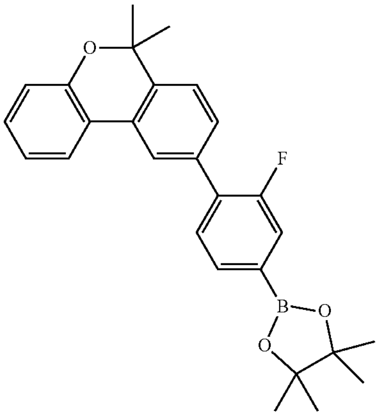 [SMILES: CC1(C)Oc2ccccc2-c2cc(-c3ccc(B4OC(C)(C)C(C)(C)O4)cc3F)ccc21] | 75 |
| I-D7 | 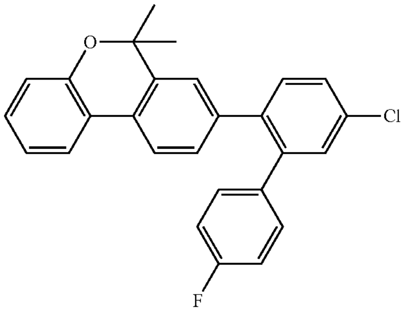 I-C7 | 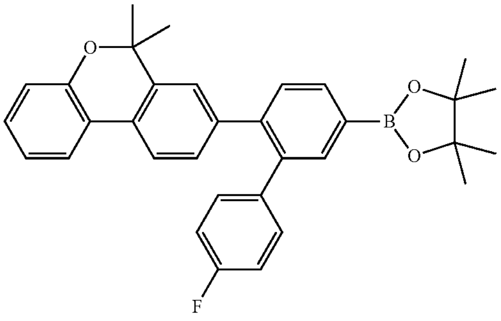 [SMILES: CC1(C)Oc2ccccc2-c2ccc(-c3ccc(B4OC(C)(C)C(C)(C)O4)cc3-c3ccc(F)cc3)cc21] | 78 |

TABLE 4-continued
| Intermediate I-D No. | Intermediate I-C | Product structure (Intermediate I-D) | Yield/% |
|---|---|---|---|
| I-D8 | 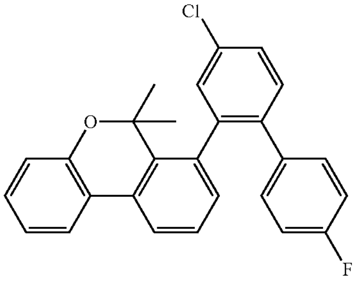 I-C8 | 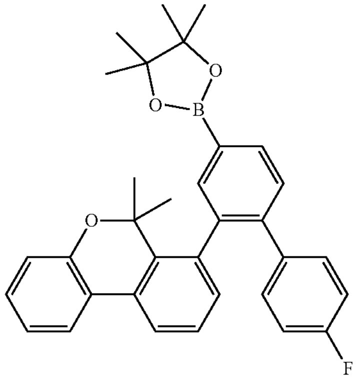 [SMILES: CC1(C)Oc2ccccc2-c2cccc(-c3cc(B4OC(C)(C)C(C)(C)O4)ccc3-c3ccc(F)cc3)c21] | 75 |
| I-D9 | 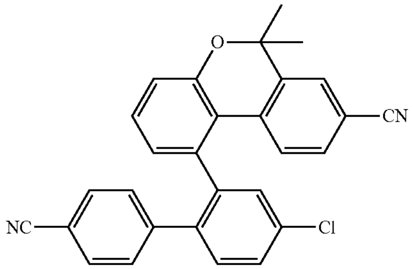 I-C9 | 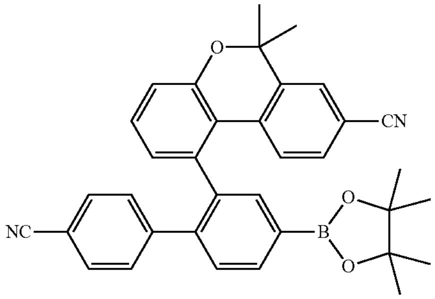 [SMILES: CC1(C)Oc2cccc(-c3cc(B4OC(C)(C)C(C)(C)O4)ccc3-c3ccc(C#N)cc3)c2-c2ccc(C#N)cc21] | 60 |
| I-D10 | 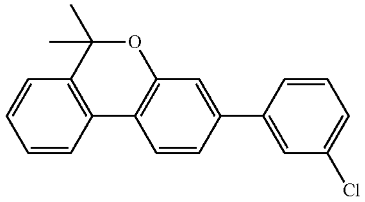 I-C10 | 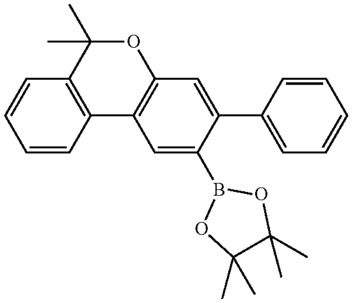 [SMILES: CC1(C)Oc2cc(-c3ccccc3)c(B3OC(C)(C)C(C)(C)O3)cc2-c2ccccc21] | 63 |
| I-D11 | 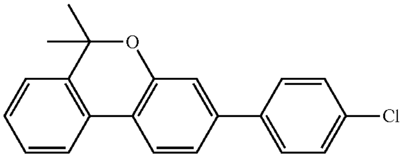 I-C13 | 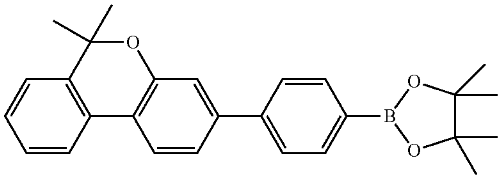 [SMILES: CC1(C)Oc2cc(-c3ccc(B4OC(C)(C)C(C)(C)O4)cc3)ccc2-c2ccccc21] | 65 |
| I-D12 | 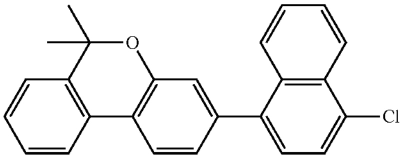 I-C14 | 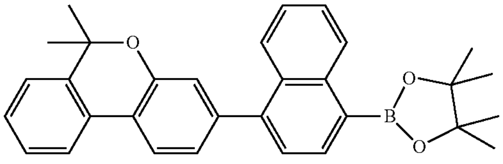 [SMILES: CC1(C)Oc2cc(-c3ccc(B4OC(C)(C)C(C)(C)O4)c4ccccc34)ccc2-c2ccccc21] | 68 |
| I-D13 | 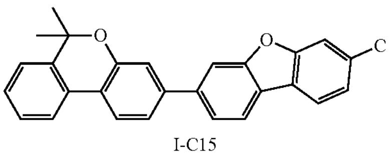 I-C15 | 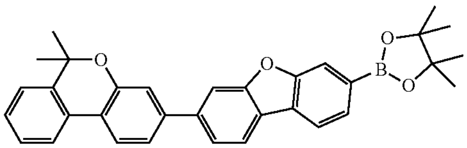 [SMILES: CC1(C)Oc2cc(-c3ccc4c(c3)oc3cc(B5OC(C)(C)C(C)(C)O5)ccc34)ccc2-c2ccccc21] | 70 |

TABLE 4-continued

| Intermediate I-D No. | Intermediate I-C | Product structure (Intermediate I-D) | Yield/% |
|---|---|---|---|
| I-D14 | 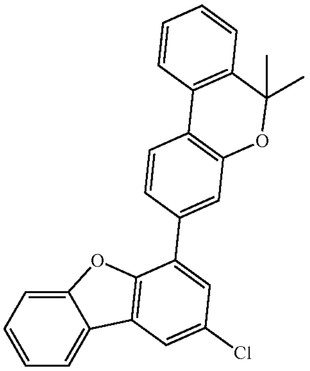 I-C16 | 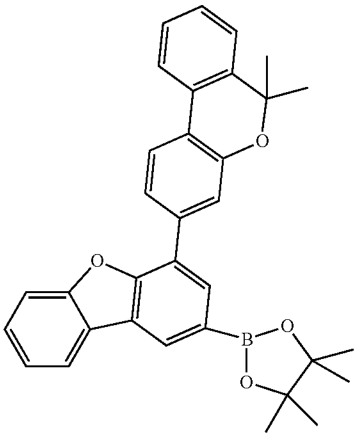 [SMILES: CC1(C)Oc2cc(-c3cc(B4OC(C)(C)C(C)(C)O4)cc4c3oc3ccccc34)ccc2-c2ccccc21] | 63 |
| I-D15 | 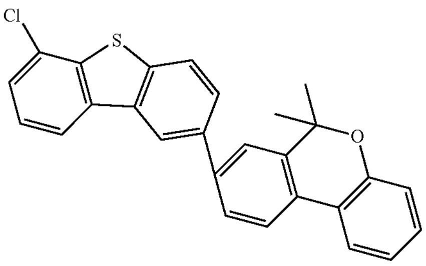 I-C17 | 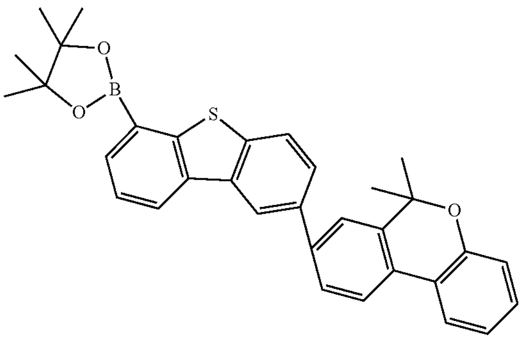 [SMILES: CC1(C)Oc2ccccc2-c2ccc(-c3ccc4sc5c(B6OC(C)(C)C(C)(C)O6)cccc5c4c3)cc21] | 66 |

Synthesis of Intermediate I-E1

Step (1):

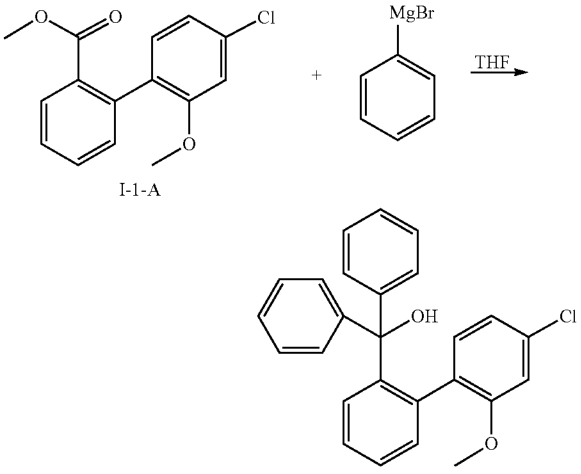

I-1-A

I-E1-A

The intermediate I-1-A (5.54 g, 20 mmol) and tetrahydrofuran (55 mL) were added to a three-necked flask, and stirring was started, a 3M solution of phenylmagnesium bromide in THE (20 mL, 60 mmol) was added thereto slowly dropwise under nitrogen atmosphere, and after the dropwise addition was complete, the mixture was stirred at room temperature for 1 h, then was heated to 60° C. to 66° C., and was subjected to a reaction for 6 h under stirring. The reaction solution was cooled to room temperature, dichloromethane (110 mL) was added thereto, deionized water (55 mL) was slowly added thereto under stirring, 1 mol/L diluted hydrochloric acid (55 mL) was slowly added thereto, after stirring, the solution was allowed to stand for liquid separation. A separated organic phase was dried over anhydrous magnesium sulfate, and filtered, and then concentrated in a vacuum to obtain an intermediate I-E1-A (6.57 g, 820%) as a light yellow oil.

Step (2):

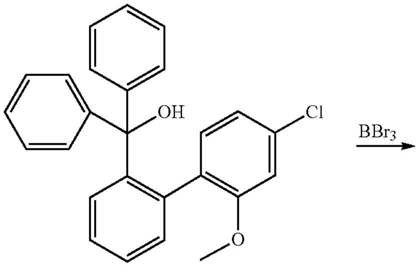

I-E1-A

-continued

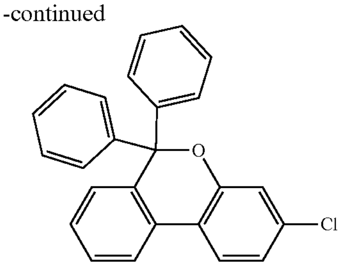

I-E1-B

The intermediate I-E1-A (6 g, 15 mmol) and acetonitrile (50 mL) were added to a three-necked flask, stirring was started and the system was cooled to 0° C. to 10° C., then a 1M solution of boron tribromide in dichloromethane (18 mL, 18 mmol) was added thereto dropwise, the temperature was kept at 0° C. to 10° C., and after 1 h, the system was naturally heated to room temperature, and stirred for about 5 h; deionized water (50 mL), and dichloromethane (50 mL) were added to the reaction solution, liquid separation was performed. A separated organic phase was dried over anhydrous magnesium sulfate, and filtered, and then concentrated in a vacuum to obtain a crude product; and the resulting yellow oily crude product was purified by silica gel column chromatography and eluted with n-heptane to obtain an intermediate I-E1-B (3.3 g, 60.0%) as a white solid.

Step (3):

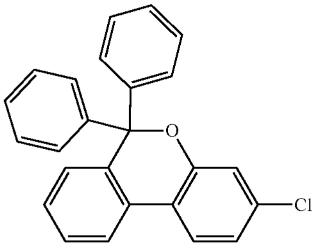

I-E1-B

+

-continued

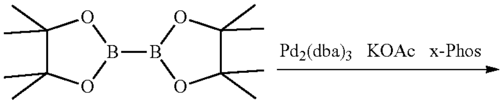

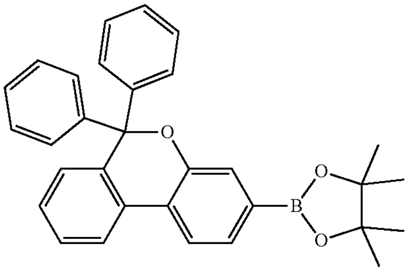

I-E1

The intermediate I-E1-B (3.3 g, 8.62 mmol), bis(pinacolato)diboron (2.84 g, 11.22 mmol), tris(dibenzylideneacetone)dipalladium (0.08 g, 0.09 mmol), 2-dicyclohexylphosphino-2',4',6'-triisopropylbiphenyl (0.135 g, 0.25 mmol), potassium acetate (2.12 g, 21.45 mmol) and 1,4-dioxane (25 mL) were added to a three-necked round bottom flask, and the reaction mixture was heated to 80° C. under nitrogen atmosphere, and stirred for 3 h; then cooled to room temperature. The reaction solution was washed with water, dried over magnesium sulfate, and filtered, and then concentrated in a vacuum to obtain a crude product; and the crude product was purified by recrystallization using toluene to obtain an intermediate I-E1 (3.37 g, yield: 85%) as a solid.

According to the steps for synthesis of the intermediate I-E1, only two raw materials in the preparation of the intermediate I-1-A were replaced: raw materials 11 and 12 in Table 5 were subjected to a reaction to give different intermediates, and subsequent two-step reactions were the same as those for the synthesis of the intermediate I-E1 to give an intermediate I-E2, and intermediates I-E4 to I-E6.

TABLE 5

| Intermediate I-E No. | Raw material 11 | Raw material 12 | Product structure (Intermediate I-E) | Yield for last step/% |
|---|---|---|---|---|
| I-E2 | 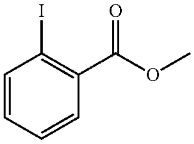 | 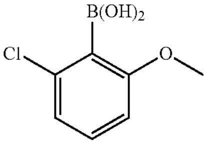 | 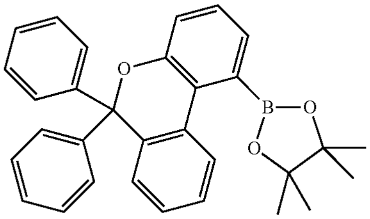 [SMILES: CC1(C)OB(c2cccc3c2-c2ccccc2C(c2ccccc2)(c2ccccc2)O3)OC1(C)C] | 70 |

TABLE 5-continued

| Intermediate I-E No. | Raw material 11 | Raw material 12 | Product structure (Intermediate I-E) | Yield for last step/% |
|---|---|---|---|---|
| I-E4 | 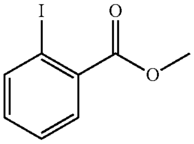 | 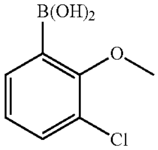 | 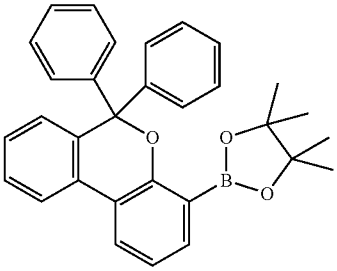 [SMILES: CC1(C)OB(c2cccc3c2OC(c2ccccc2)(c2ccccc2)c2ccccc2-3)OC1(C)C] | 66 |
| I-E5 | 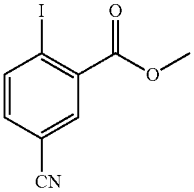 | 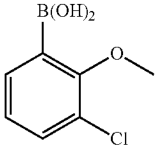 | 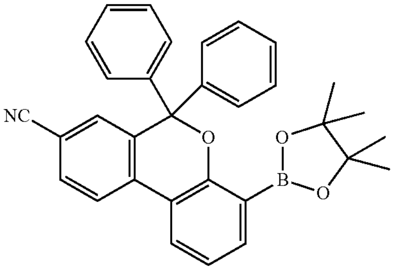 [SMILES: CC1(C)OB(c2cccc3c2OC(c2ccccc2)(c2ccccc2)c2cc(C#N)ccc2-3)OC1(C)C] | 68 |
| I-E6 | 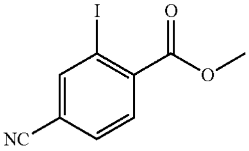 | 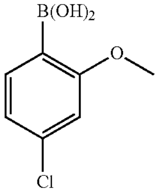 | 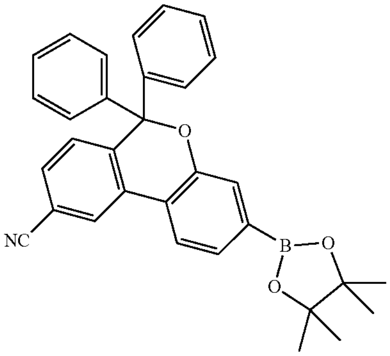 [SMILES: CC1(C)OB(c2ccc3c(c2)OC(c2ccccc2)(c2ccccc2)c2ccc(C#N)cc2-3)OC1(C)C] | 70 |

Synthesis of Intermediate I-F1

An intermediate I-F1 was prepared by using the same method as that for the synthesis of the intermediate I-D2 except that the raw material I-B1 used for the synthesis of the intermediate I-D2 was replaced with an intermediate I-E1.

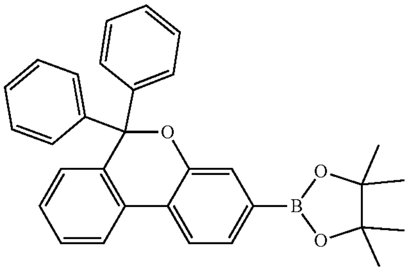

I-E1

+

-continued

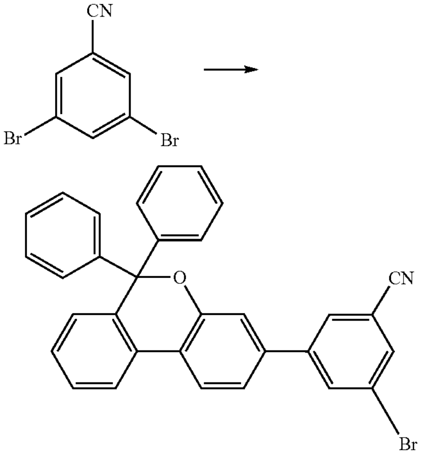

-continued

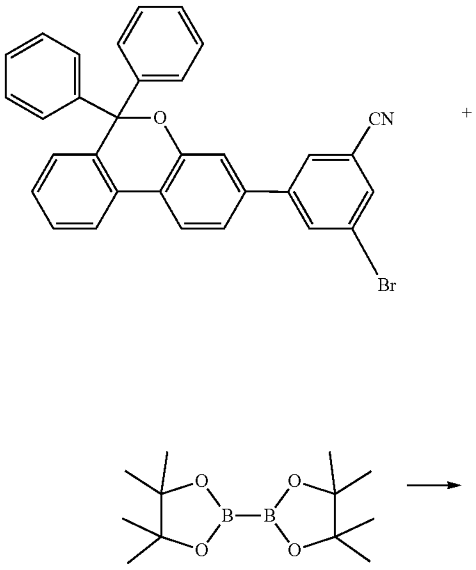

-continued

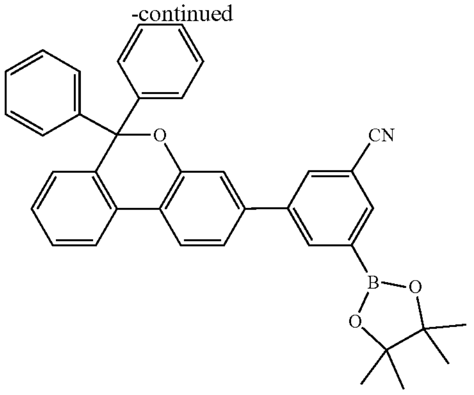

I-F1

Synthesis of Intermediate I-F3 and Intermediate I-F6

According to the steps for synthesis of the intermediate I-F1, only the intermediate I-E1 was replaced with a raw material 13 in Table 6, and 3,5-dibromobenzonitrile was replaced with a raw material 14 in Table 6, and an intermediate I-F3 and an intermediate I-F6 were obtained from the two raw materials in the preparation.

TABLE 6

| Intermediate I-F No. | Raw material 13 | Raw material 14 | Product structure (Intermediate I-F) | Total yield/% |
|---|---|---|---|---|
| I-F3 | 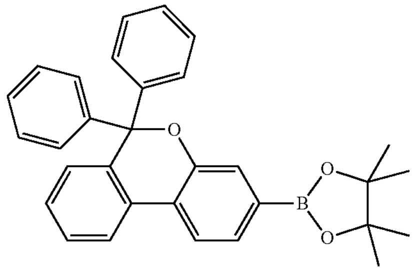 I-E1 | 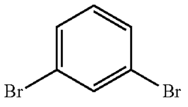 | 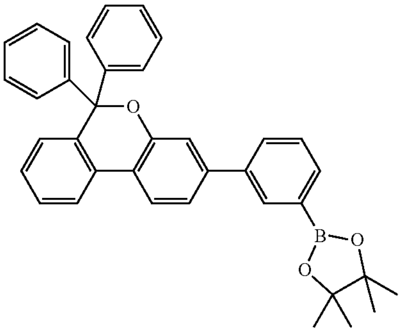 [SMILES: CC1(C)OB(c2cccc(-c3ccc4c(c3)OC(c3ccccc3)(c3ccccc3)c3ccccc3-4)c2)OC1(C)C] | 56 |
| I-F6 | 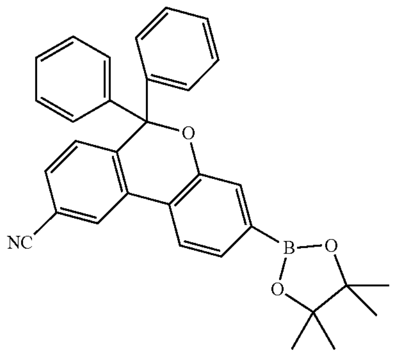 I-E6 | 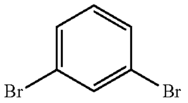 | 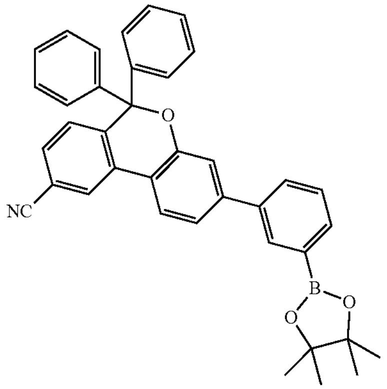 [SMILES: CC1(C)OB(c2cccc(-c3ccc4c(c3)OC(c3ccccc3)(c3ccccc3)c3ccc(C#N)cc3-4)c2)OC1(C)C] | 47 |

Synthesis of Raw Material II:

a. Synthesis of Intermediate II-A1

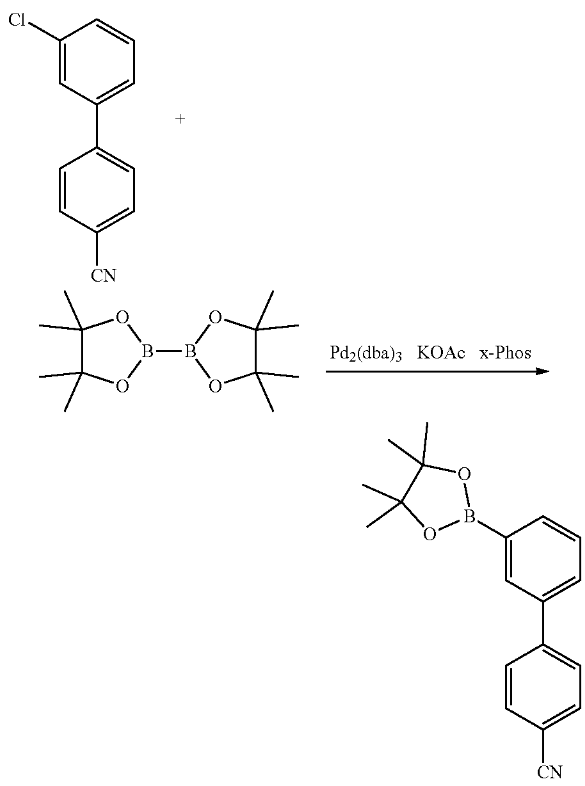

II-A-1

(1) 3'-Chloro-[1,1'-biphenyl]-4-carbonitrile (CAS 5728-39-2, 21.3 g, 100 mmol), bis(pinacolato)diboron (30.4 g, 120 mmol), potassium acetate (19.6 g, 200 mmol), and 1000 mL of 1,4-dioxane were weighed and heated to 40° C. to 45° C., $pd_2(dba)_3$ (0.28 g, 1 mmol), and x-phos (0.14 g, 0.25 mmol) were added thereto, the mixture was continued to heated to 80° C. to 85° C., heat preservation was performed for 2 h, then the reaction was stopped. The reaction solution was poured into 20 L of water, toluene was added thereto under stirring, stirring was performed for 10 min, the solution was allowed to stand for 10 min, liquid separation was performed, an aqueous phase was extracted twice with toluene. The organic phases were mixed, washed with water to pH=7, dried over anhydrous sodium sulfate, and concentrated (T=60° C. to 70° C., P=0.075 to 0.09 MPa), suction filtration was performed to obtain a solid, and the solid was oven-dried to obtain an intermediate II-A-1 (24.4 g, yield: 80%).

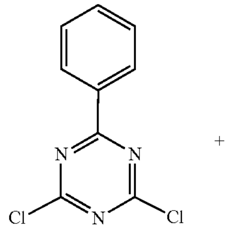

-continued

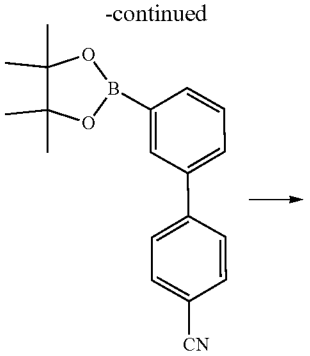

II-A-1

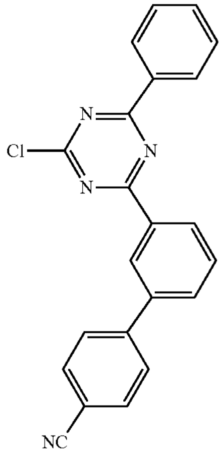

II-A1

(2) 2,4-Dichloro-6-phenyl-1,3,5-triazine (33.9 g, 150 mmol), the intermediate II-A-1 (30.5 g, 100 mmol), 21.2 g of sodium carbonate, 300 mL of tetrahydrofuran, and 150 mL of water were added to a reaction flask, and heated to 40 to 45° C., 0.35 g of tetrakis(triphenylphosphine)palladium was added thereto, the mixture was continued to heated to 60 to 65° C., heat preservation was performed for 2 h, and the reaction was stopped. The reaction solution was poured into water under stirring, and cooled to room temperature while stirring for about 30 min, filtering was performed, and the obtained filter cake was oven-dried. The oven-dried filter cake was dissolved with dichloroethane to be clear, the obtained solution was allowed to pass through a silica gel chromatographic column (80 to 120 mesh, normal temperature and normal pressure), elution was performed with dichloroethane, the temperature was reduced to room temperature, suction filtration was performed to obtain a large amount of white solid, and the solid was oven-dried (a blast oven, 55° C. to 65° C., about 5 h) to obtain an intermediate II-A1 (16.5 g, yield: 45%).

b. Synthesis of Intermediate II-A2

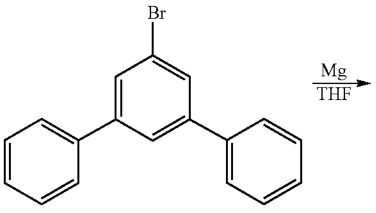

-continued

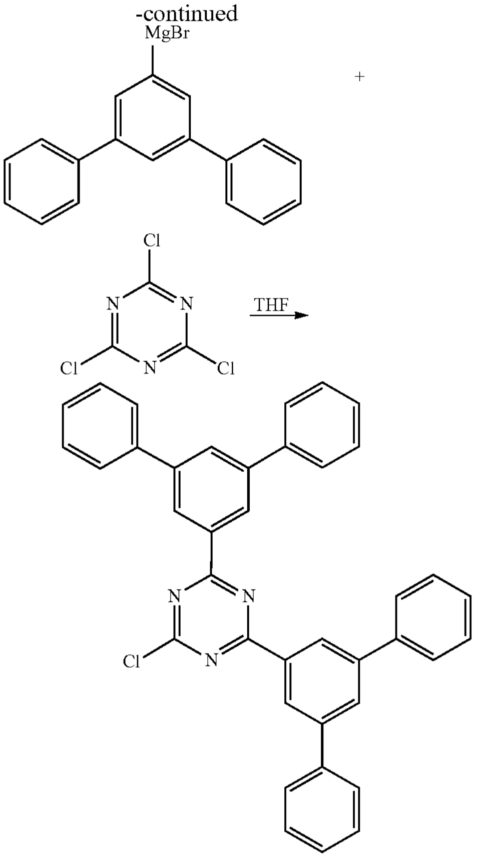

II-A2

3,5-Diphenylbromobenzene (30.9 g, 100 mmol) was added into a reaction flask A under nitrogen atmosphere, stirring was started, the reaction mixture was heated to 50° C. to 55° C., after it was confirmed that 3,5-diphenylbromobenzene was dissolved to obtain a clear solution, magnesium powder (2.88 g) was added thereto quickly, violent reflux was produced for approximately 3 min, and the solution was turned from pale yellow to viscous purple-black, and heat preservation was performed for 1 h to prepare a Grignard reagent. Cyanuric chloride (10.4 g, 56.8 mmol) was added into a reaction flask B under nitrogen atmosphere, stirring was started, after cyanuric chloride was dissolved to obtain a clear solution, the reaction system was cooled with frozen ethanol, when the temperature of the reaction system was reduced to −15° C. to −10° C., the prepared Grignard reagent was slowly added dropwise by using a constant pressure dropping funnel while controlling the reaction temperature to be −10° C.±5° C., after dropwise addition was complete, the reaction mixture was stirred for 2 h, so that a large amount of off-white solid was precipitated, and the solid was filtered, washed with water, and recrystallized with toluene to obtain an intermediate II-A2 (12.87 g, yield: 45%).

c. Synthesis of Intermediates II-A3 to II-A5

Intermediates II-A3 to II-A5 were synthesized by using the same method as for the synthesis of the intermediate II-A1 except that a raw material 5 in Table 7 was used instead of the raw material 2,4-dichloro-6-phenyl-1,3,5-triazine used for the synthesis of the intermediate II-A1, and a raw material 6 in Table 7 was used instead of the raw material, namely the Intermediate II-A-1 used for the synthesis of the intermediate II-A1.

TABLE 7

| Intermediate II-A No. | Raw material 5 | Raw material 6 | Product structure (Intermediate II-A) | Yield | Mass spectrum (m/z) $[M + H]^+$ |
|---|---|---|---|---|---|
| II-A3 | 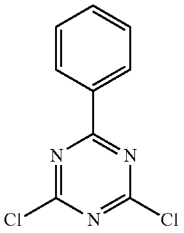 [SMILES: Clc1nc(Cl)nc(-c2ccccc2)n1] | 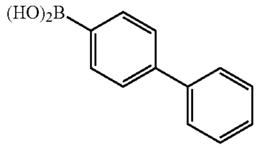 [SMILES: OB(O)c1ccc(-c2ccccc2)cc1] | 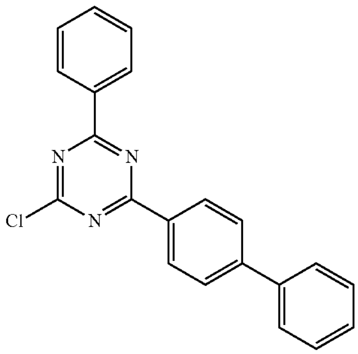 [SMILES: Clc1nc(-c2ccccc2)nc(-c2ccc(-c3ccccc3)cc2)n1] | 65% | 344 |

TABLE 7-continued

| Intermediate II-A No. | Raw material 5 | Raw material 6 | Product structure (Intermediate II-A) | Yield | Mass spectrum (m/z) [M + H]+ |
| --- | --- | --- | --- | --- | --- |
| II-A4 | 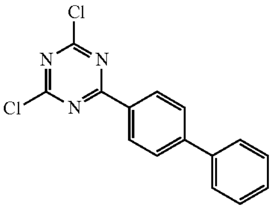 [SMILES: Clc1nc(Cl)nc(-c2ccc(-c3ccccc3)cc2)n1] | 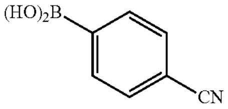 [SMILES: N#Cc1ccc(B(O)O)cc1] | 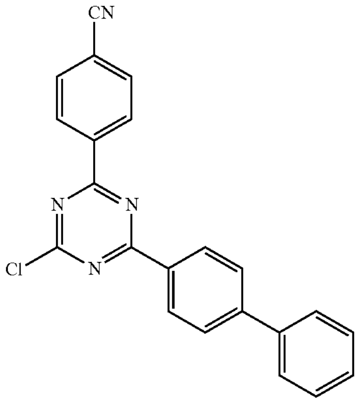 [SMILES: N#Cc1ccc(-c2nc(Cl)nc(-c3ccc(-c4ccccc4)cc3)n2)cc1] | 53% | 369 |
| II-A5 | 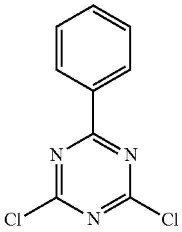 [SMILES: Clc1nc(Cl)nc(-c2ccccc2)n1] | 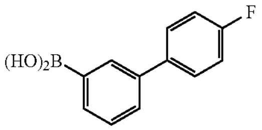 [SMILES: OB(O)c1cccc(-c2ccc(F)cc2)c1] | 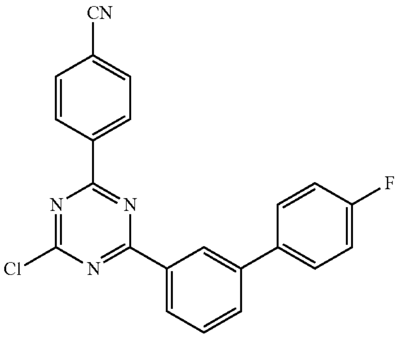 [SMILES: N#Cc1ccc(-c2nc(Cl)nc(-c3cccc(-c4ccc(F)cc4)c3)n2)cc1] | 48% | 389 |

Synthesis of Intermediate II-A6, Intermediate II-A9, Intermediate II-A10, and Intermediate II-A11:

An intermediate II-A6, an intermediate II-A9, an intermediate II-A10, and an intermediate II-A11 were prepared as follows, and reaction procedures referred to the synthesis process of the intermediate II-A1 described above.

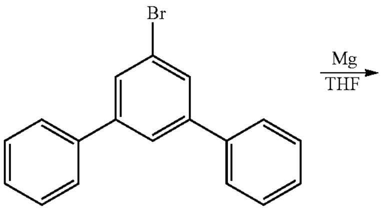

-continued

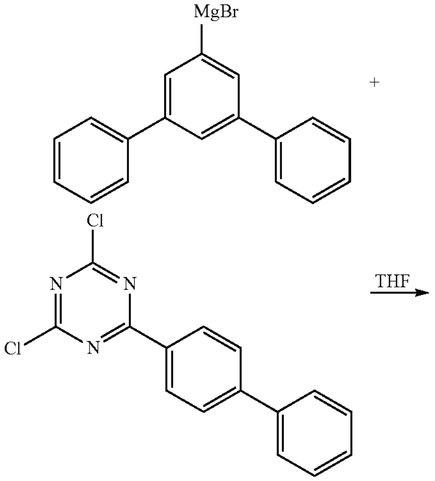

-continued
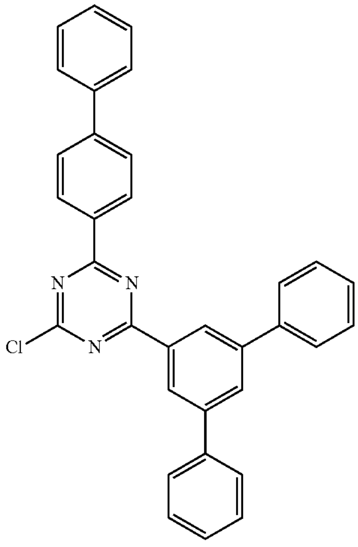
II-A6
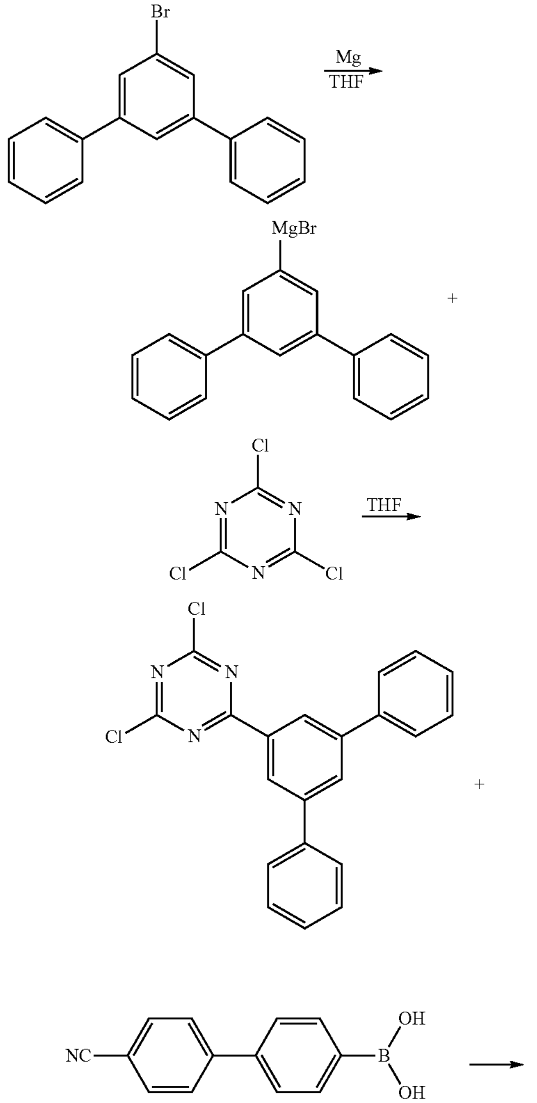
-continued
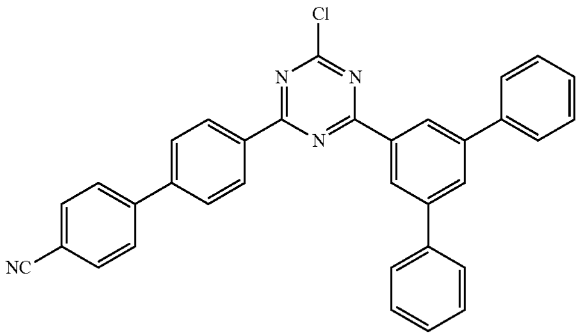
II-A9
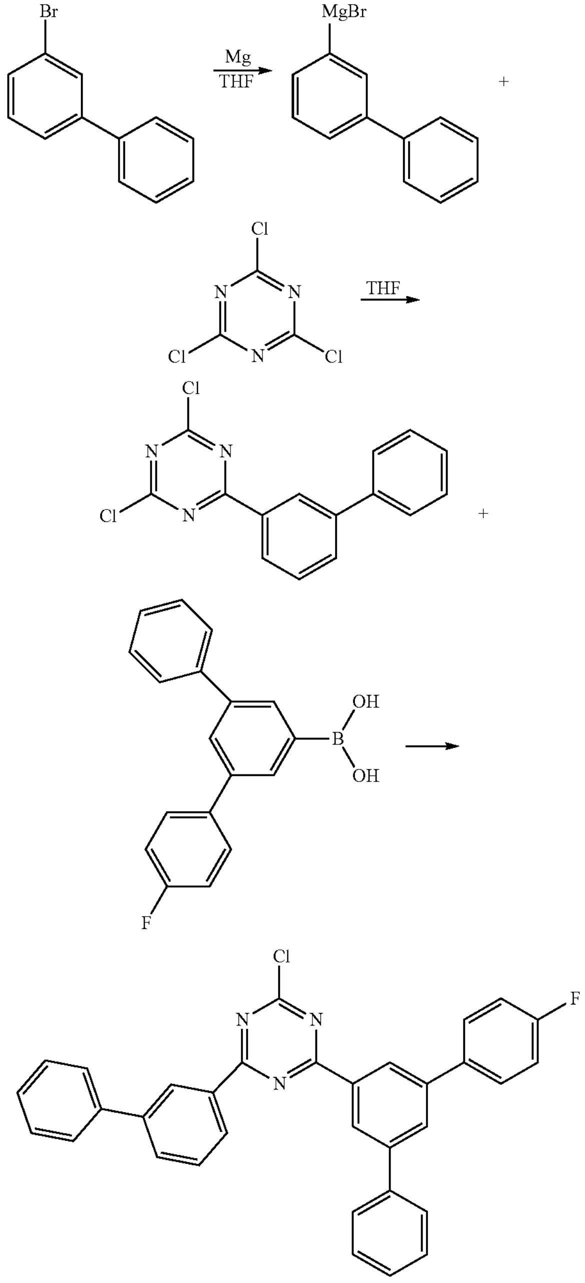
II-A10

-continued

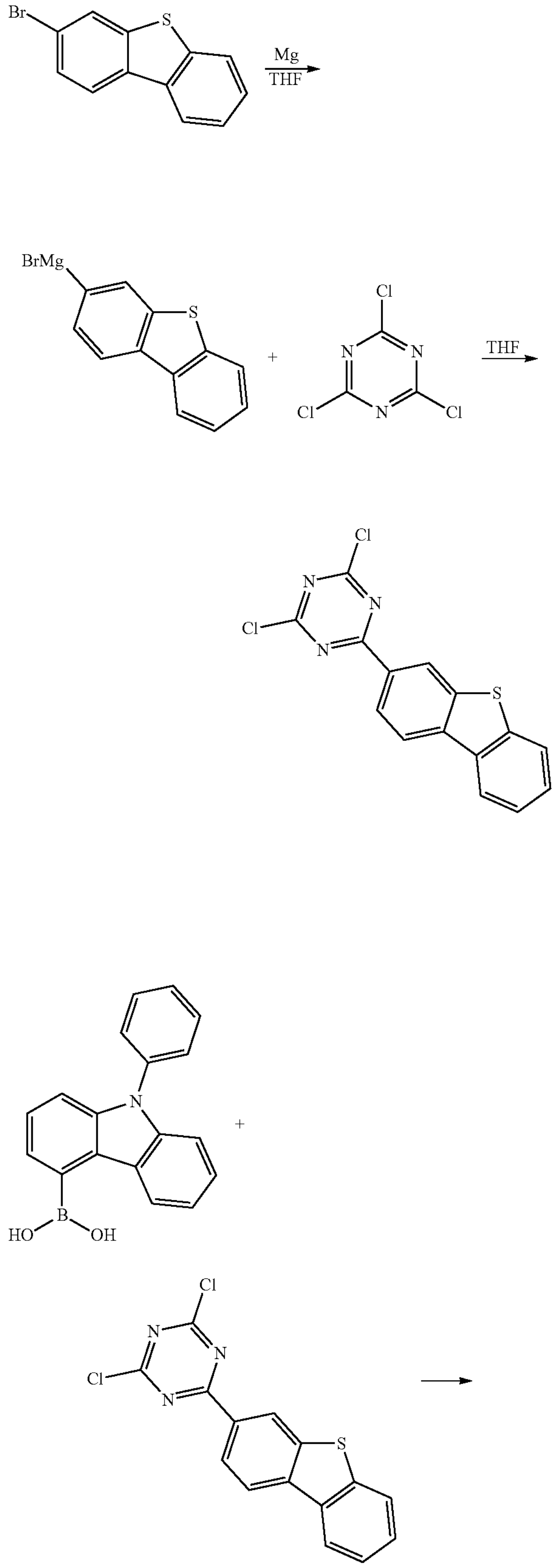

-continued

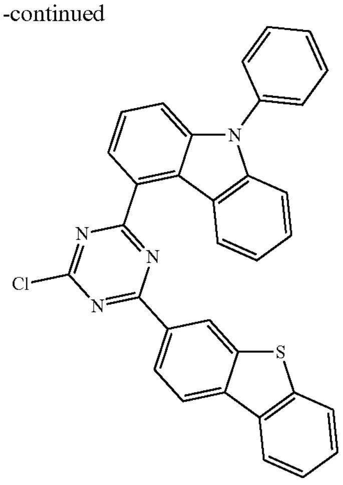

II-A11

Synthesis of Compounds (1) Synthesis of Compound 124

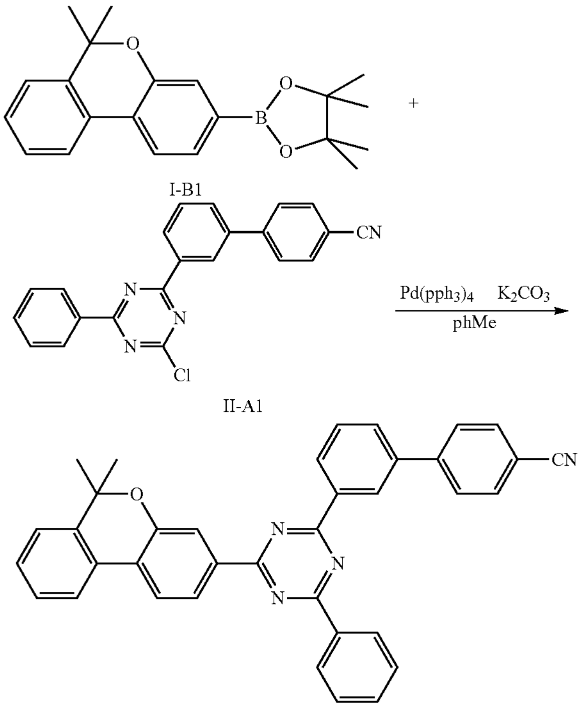

I-B1

II-A1

124

The intermediate I-B1 (13.44 g, 40 mmol), the intermediate II-A1 (16.19 g, 44.0 mmol), potassium carbonate (11.04 g, 80 mmol), tetrabutylammonium bromide (1.32 g, 4 mmol), toluene (100 mL), ethanol (50 mL) and deionized water (50 mL) were added to a three-necked flask, and stirred for 15 min under nitrogen atmosphere, tetrakis(triphenylphosphine)palladium (0.46 g, 0.4 mmol) was added thereto, and the mixture was heated to 75° C. to 80° C., and stirred for 5 h. The reaction solution was cooled to room temperature, toluene (100 mL) was added thereto for extraction, the organic phases were mixed and dried over anhydrous magnesium sulfate, then concentrated in a vacuum to obtain a residue, and the obtained residue was directly purified by flash silica gel column chromatography, and concentrated the eluent to obtain a compound 124 (16.9 g, yield: 78%) as an off-white solid. LC-MS (ESI, pos.ion) m/z: 543.2 $[M+H]^+$.

(2) Synthesis of Compound 76

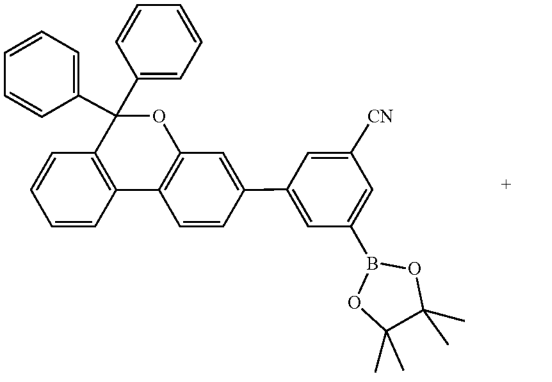

I-F1

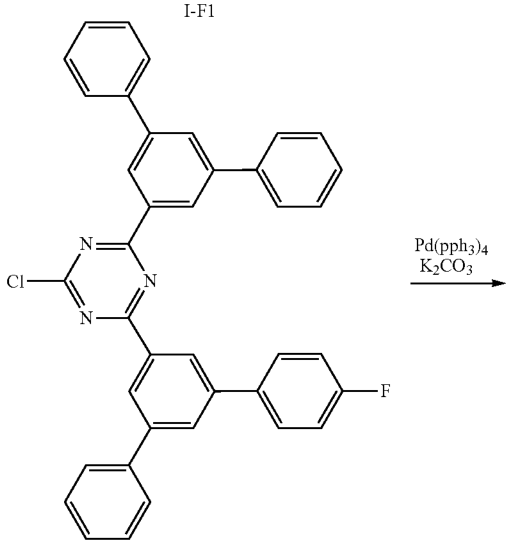

C

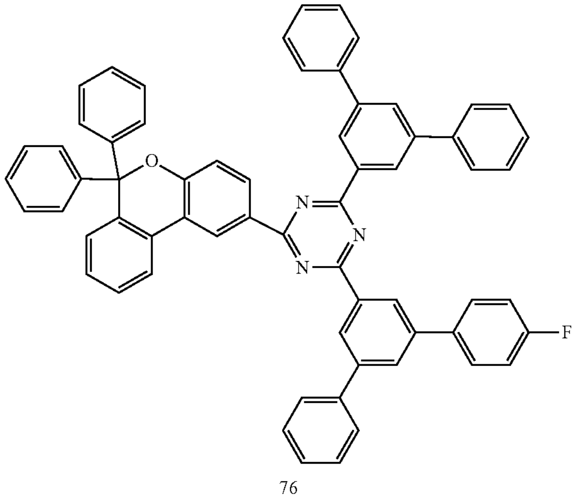

76

The intermediate I-$F_1$ (14.0 g, 25 mmol), a raw material C (16.2 g, 27.5 mmol), potassium carbonate (6.9 g, 50 mmol), tetrabutylammonium bromide (0.83 g, 2.5 mmol), toluene (100 mL), ethanol (50 mL) and deionized water (50 mL) were added to a three-necked flask, and stirred for 15 min under nitrogen atmosphere, tetrakis(triphenylphosphine)palladium (0.29 g, 0.24 mmol) was added thereto, and the mixture was heated to 75° C. to 80° C., and stirred for 5 h. The reaction solution was cooled to room temperature, toluene (100 mL) was added thereto for extraction, the organic phases were mixed, and dried over anhydrous magnesium sulfate, then concentrated in a vacuum to obtain a residue, and the obtained residue was directly purified by flash silica gel column chromatography, and concentrated eluent to obtain a compound 76 (15.98 g, yield: 72%) as an off-white solid. LC-MS (ESI, pos.ion) m/z: 888.3 $[M+H]^+$.

(3) Synthesis of Compound 129

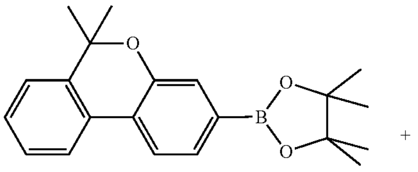

I-B1

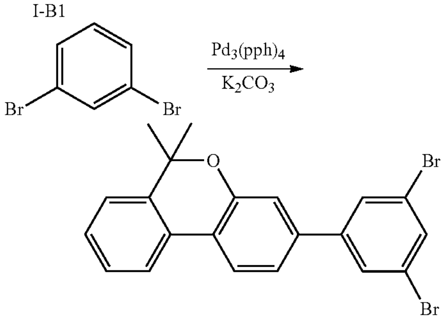

I-C12

The intermediate I-B1 (13.44 g, 40 mmol), 3,5-dibromoiodobenzene (14.47 g, 40 mmol), potassium carbonate (11.04 g, 80 mmol), tetrabutylammonium bromide (1.32 g, 4 mmol), toluene (100 mL), ethanol (50 mL) and deionized water (50 mL) were added to a three-necked flask, and stirred for 15 min under nitrogen atmosphere, tetrakis(triphenylphosphine)palladium (0.92 g, 0.08 mmol) was added thereto, and the mixture was heated to 75° C. to 80° C., and stirred for 8 h; and the reaction solution was cooled to room temperature, toluene (100 mL) was added thereto for extraction. The combined organic phases were dried over anhydrous magnesium sulfate, and then concentrated in a vacuum to obtain a residue, and the obtained residue was directly purified by flash silica gel column chromatography, and concentrated the eluent to obtain an intermediate I-C12 (12.08 g, yield: 68%) as an off-white solid.

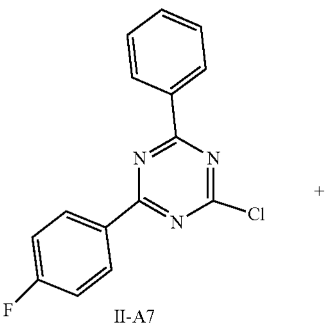

II-A7

-continued

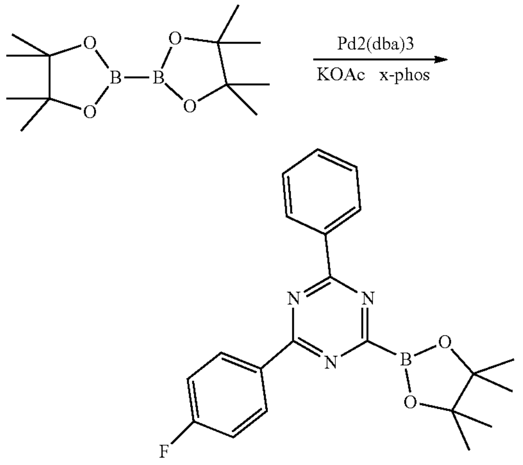

II-A8

An intermediate II-A7 (5.7 g, 20 mmol), bis(pinacolato) diboron (6.09 g, 24 mmol), tris(dibenzylideneacetone)dipalladium (0.18 g, 0.20 mmol), 2-dicyclohexylphosphino-2',4',6'-triisopropylbiphenyl (0.19 g, 0.40 mmol), potassium acetate (3.84 g, 40 mmol) and 1,4-dioxane (50 mL) were added to a three-necked round bottom flask, the reaction mixture was heated to 80° C. under nitrogen atmosphere, and stirred for 5 h; then cooled to room temperature. The reaction solution was washed with water, dried over magnesium sulfate, and filtered, and concentrated in a vacuum to obtain a crude product; and the crude product was purified by recrystallization using toluene to obtain an intermediate II-A8 (3.92 g, yield: 52%) as a solid.

According to the preparation method of the intermediate II-A8, the following intermediate was prepared by using 2-chloro-4,6-diphenyltriazine instead of the intermediate II-A7:

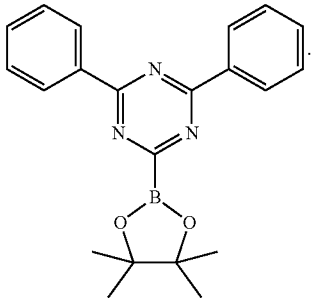 [SMILES: CC1(C)OB(c2nc(-c3ccccc3)nc(-c3ccccc3)n2)OC1(C)C]

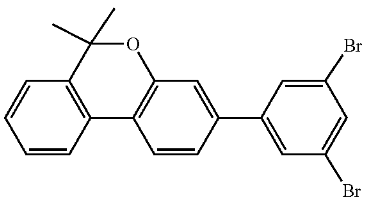

+

I-C12

-continued

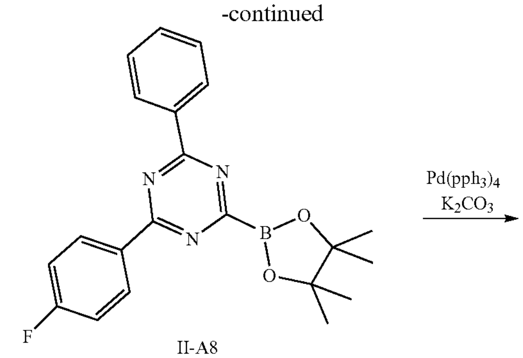

II-A8

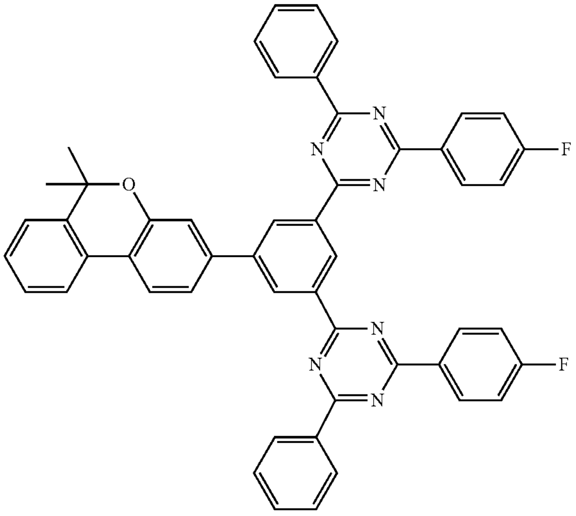

129

The intermediate I-C12 (8.88 g, 20 mmol), the intermediate II-A8 (16.58 g, 44 mmol), potassium carbonate (11.04 g, 80 mmol), tetrabutylammonium bromide (1.32 g, 4 mmol), toluene (100 mL), ethanol (50 mL) and deionized water (50 mL) were added to a three-necked flask, and stirred for 15 min under nitrogen atmosphere, tetrakis(triphenylphosphine)palladium (0.92 g, 0.08 mmol) was added thereto, and the mixture was heated to 75° C. to 80° C., and stirred for 8 h; and the reaction solution was cooled to room temperature, toluene (100 mL) was added thereto for extraction. The organic phases were mixed, and dried over anhydrous magnesium sulfate, concentrated in a vacuum to obtain a residue, and the obtained residue was directly purified by flash silica gel column chromatography, and concentrated the eluent to obtain a compound 129 (8.15 g, yield: 520%) as an off-white solid. LC-MS (ESI, pos.ion) m/z: 785.3 [M+H]+.

(4) Synthesis of Compounds 12, 15, 22, 23, 28 and 288 to 319

Compounds 12, 15, 22, 23, 28 and 288 to 319 were synthesized by using the same method as that for the synthesis of the compound 124 except that a raw material 7 in Table 8 was used instead of the intermediate I-B1 used for the synthesis of the compound 124, and a raw material 8 in Table 8 was used instead of the intermediate I-A1 used for the synthesis of the compound 124.

-continued
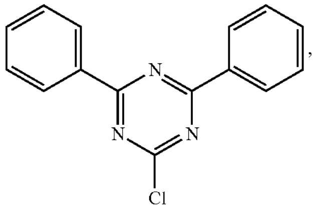
,
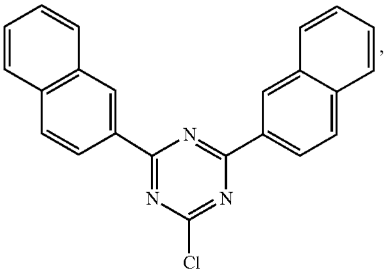
,
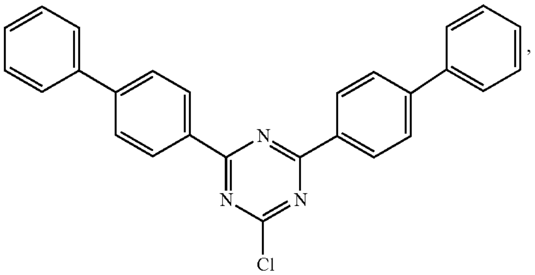
,
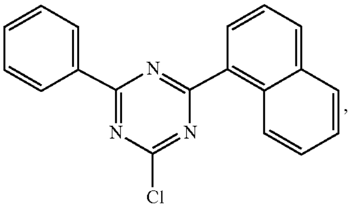
,
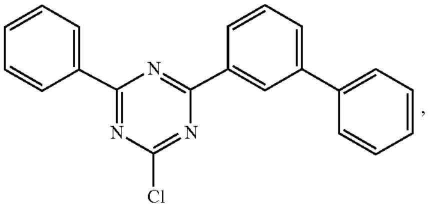
,
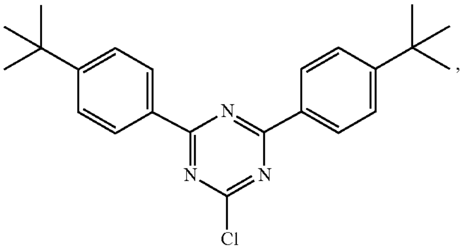
,
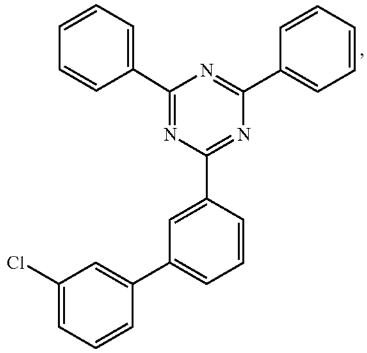
, and
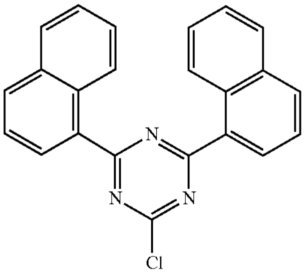
were all commercially obtained.
TABLE 8
| Compound No. | Raw material 7 | Raw material 8 (Intermediate II-A) |
|---|---|---|
| 288 | 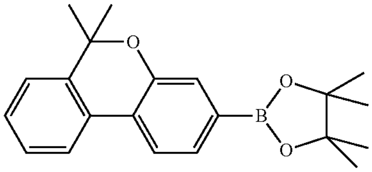 I-B1 | 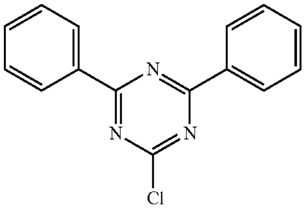 [SMILES: Clc1nc(-c2ccccc2)nc(-c2ccccc2)n1] |

TABLE 8-continued
289 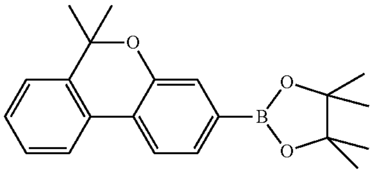
I-B1
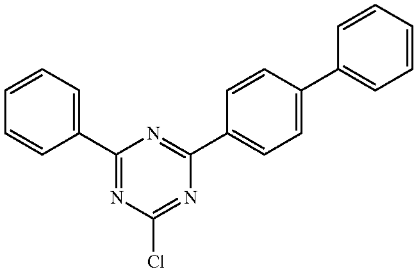
Intermediate II-A3
290 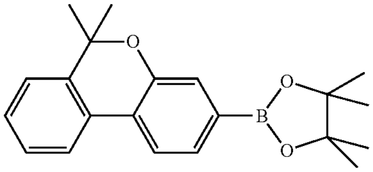
I-B1
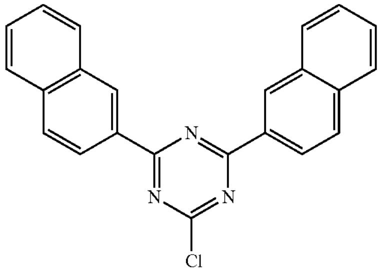 [SMILES: Clc1nc(-c2ccc3ccccc3c2)nc(-c2ccc3ccccc3c2)n1]
291 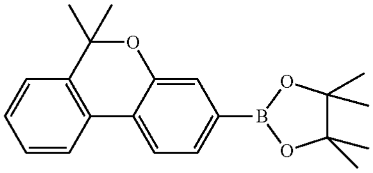
I-B1
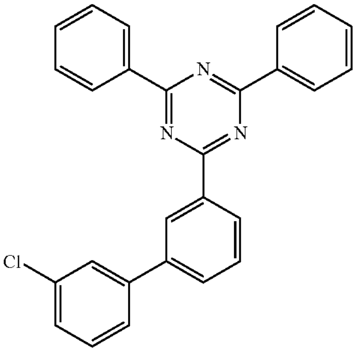 [SMILES: Clc1cccc(-c2cccc(-c3nc(-c4ccccc4)nc(-c4ccccc4)n3)c2)c1]
292 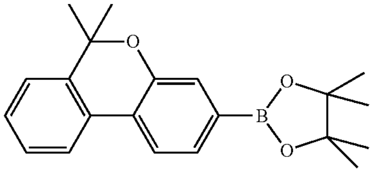
I-B1
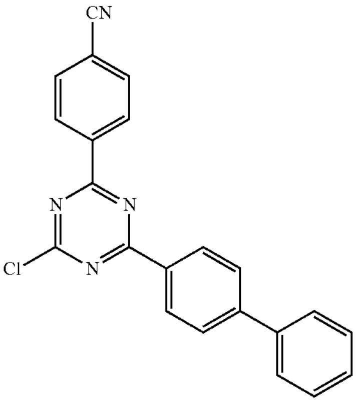
II-A4

TABLE 8-continued
293 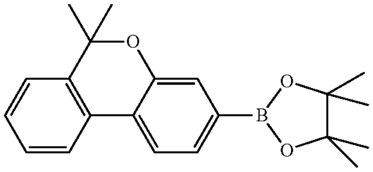
I-B1
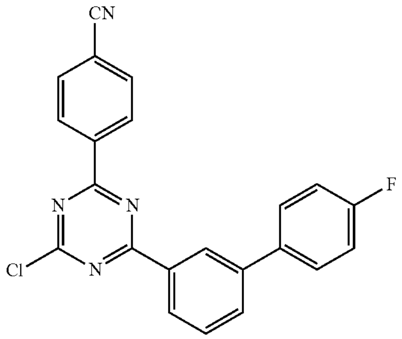
II-A5
294 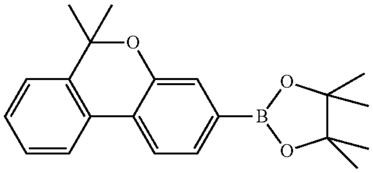
I-B1
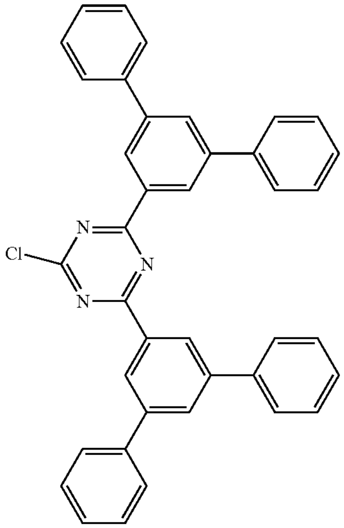
II-A2
295 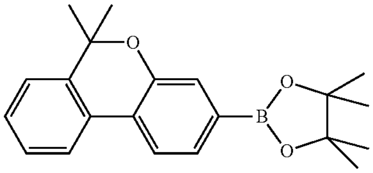
I-B1
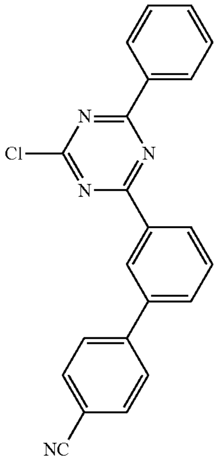
II-A1

TABLE 8-continued
296
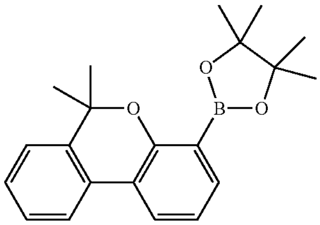
I-B2
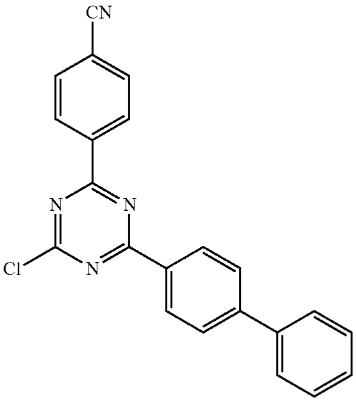
II-A4
297
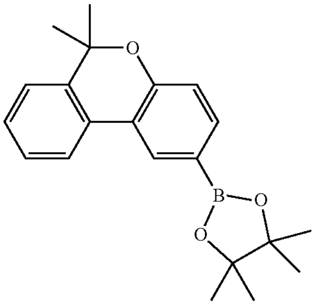
I-B3
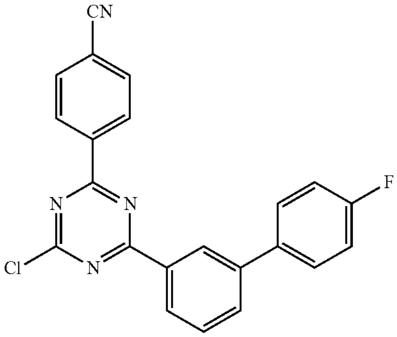
II-A5
91
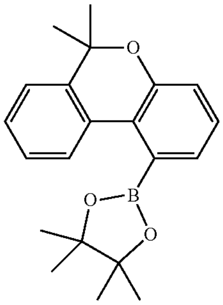
I-B4
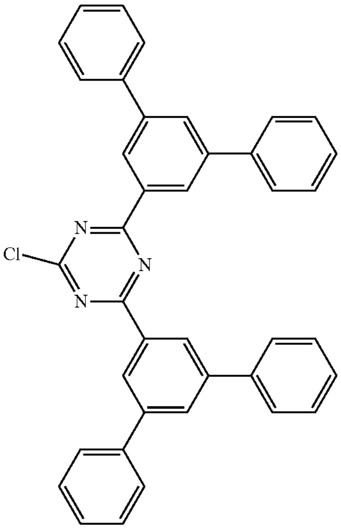
II-A2

TABLE 8-continued
| | | |
|---|---|---|
| 298 | 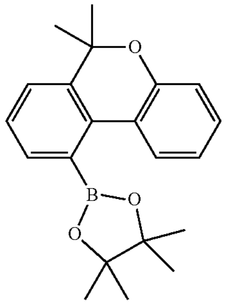 I-B5 | 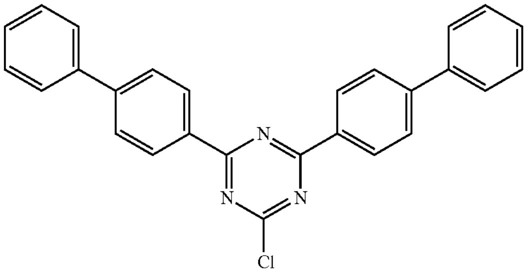 [SMILES: Clc1nc(-c2ccc(-c3ccccc3)cc2)nc(-c2ccc(-c3ccccc3)cc2)n1] |
| 299 | 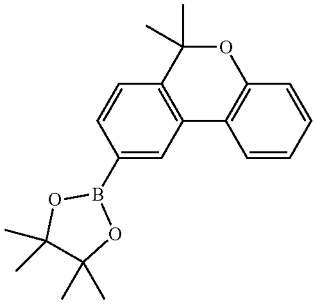 I-B6 | 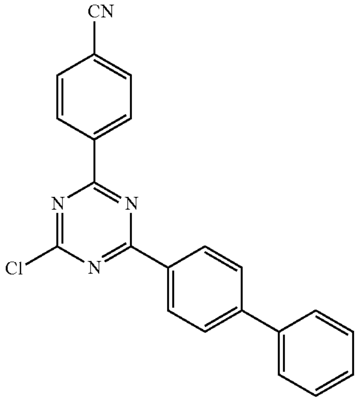 II-A4 |
| 300 | 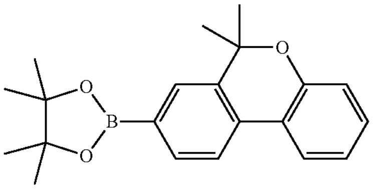 I-B7 | 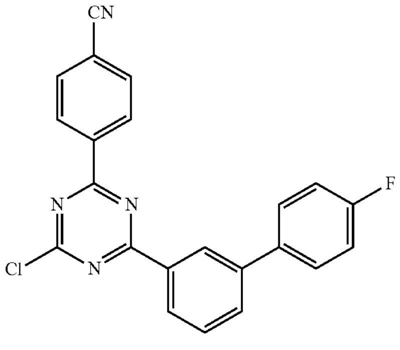 II-A5 |
| 301 | 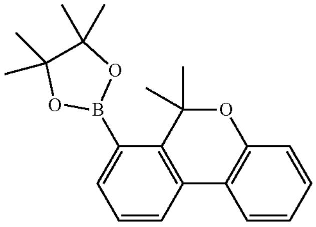 I-B8 | 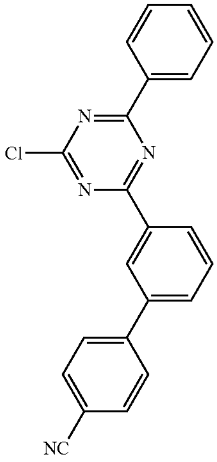 II-A1 |

TABLE 8-continued
302
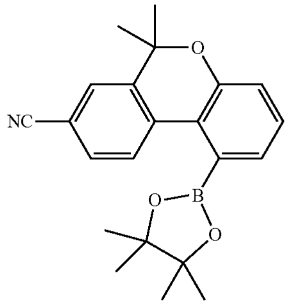
I-B9
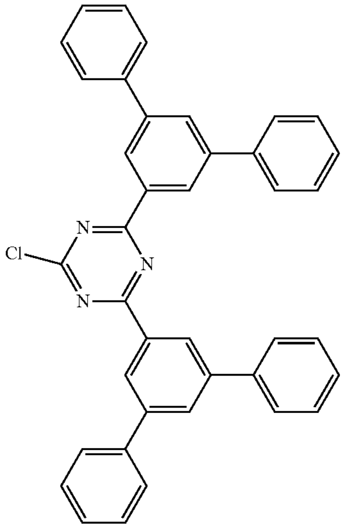
II-A2
303
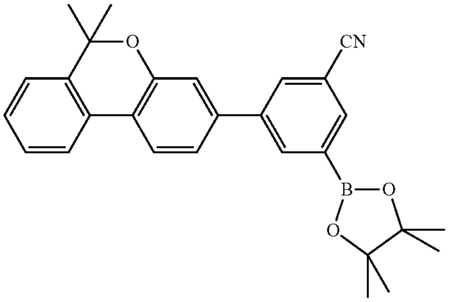
I-D1
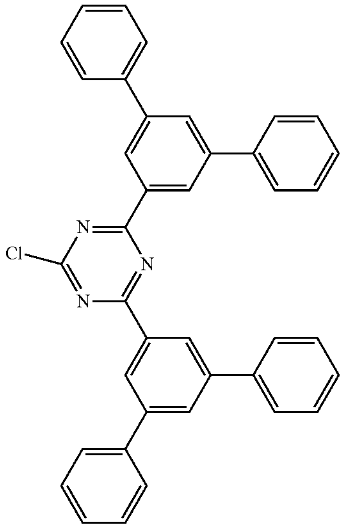
II-A2
304
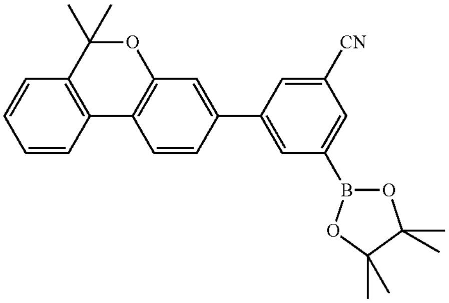
I-D1
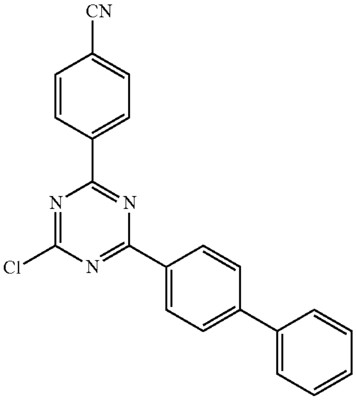
II-A4

TABLE 8-continued
305
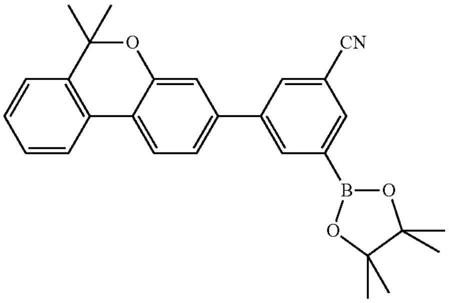
I-D1
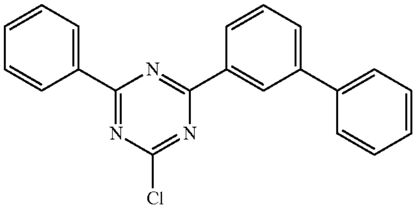 [SMILES: Clc1nc(-c2ccccc2)nc(-c2cccc(-c3ccccc3)c2)n1]
9
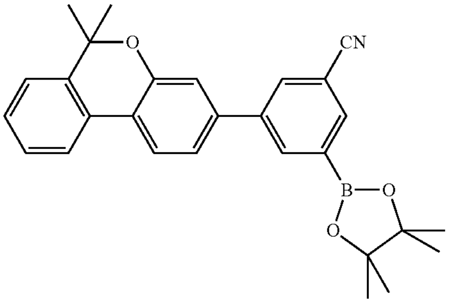
I-D1
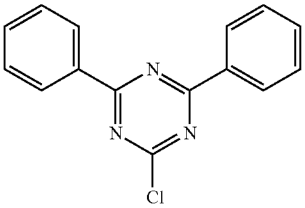 [SMILES: Clc1nc(-c2ccccc2)nc(-c2ccccc2)n1]
306
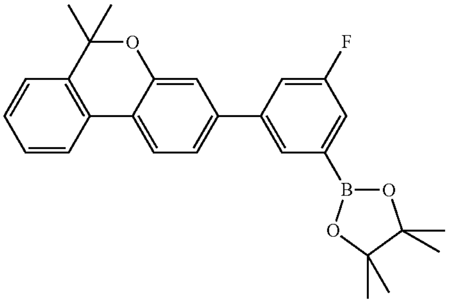
I-D2
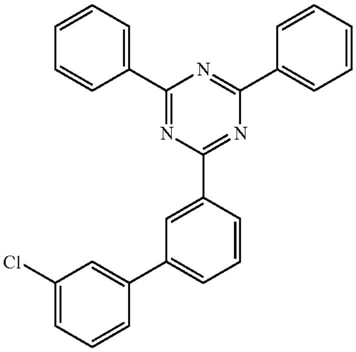 [SMILES: Clc1cccc(-c2cccc(-c3nc(-c4ccccc4)nc(-c4ccccc4)n3)c2)c1]
28
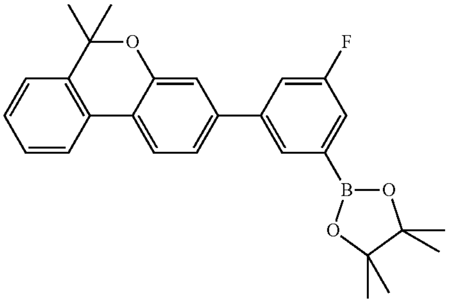
I-D2
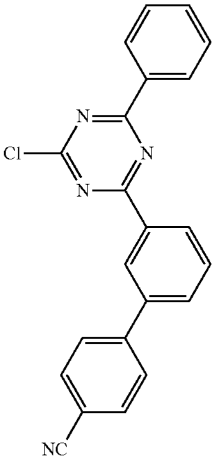
II-A1

TABLE 8-continued
15
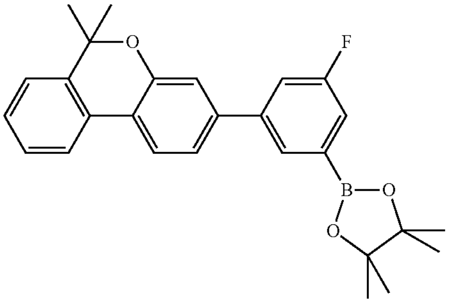
I-D2
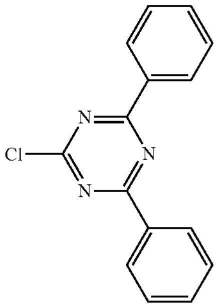 [SMILES: Clc1nc(-c2ccccc2)nc(-c2ccccc2)n1]
22
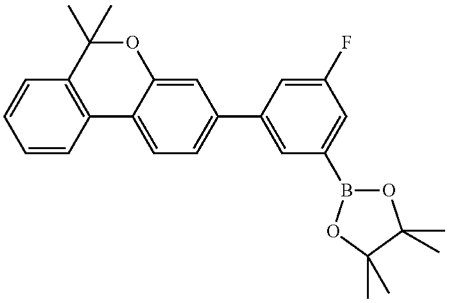
I-D2
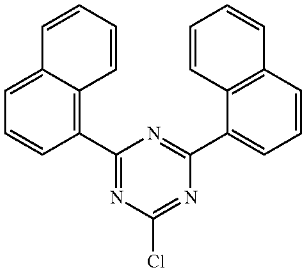 [SMILES: Clc1nc(-c2cccc3ccccc23)nc(-c2cccc3ccccc23)n1]
23
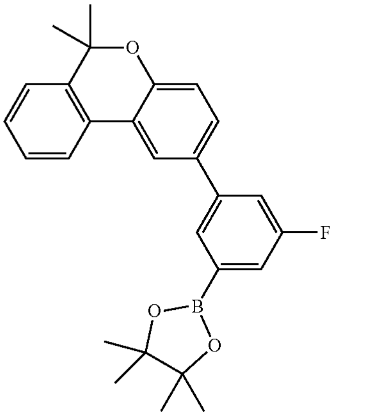
I-D3
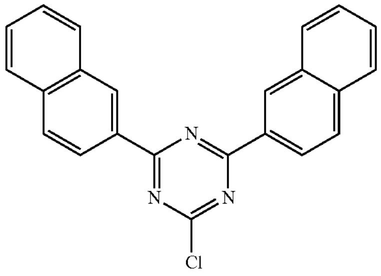 [SMILES: Clc1nc(-c2ccc3ccccc3c2)nc(-c2ccc3ccccc3c2)n1]
307
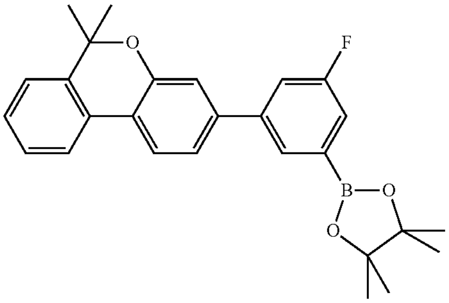
I-D2
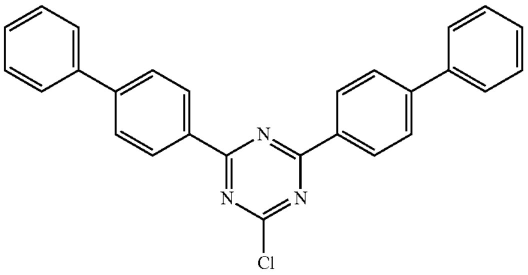 [SMILES: Clc1nc(-c2ccc(-c3ccccc3)cc2)nc(-c2ccc(-c3ccccc3)cc2)n1]

TABLE 8-continued
308
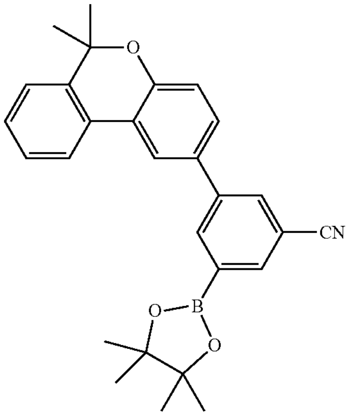
I-D4
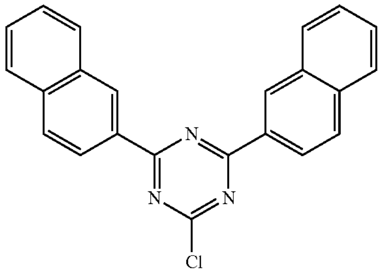 [SMILES: Clc1nc(-c2ccc3ccccc3c2)nc(-c2ccc3ccccc3c2)n1]
309
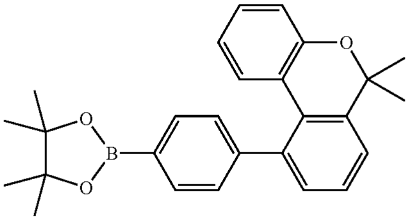
I-D5
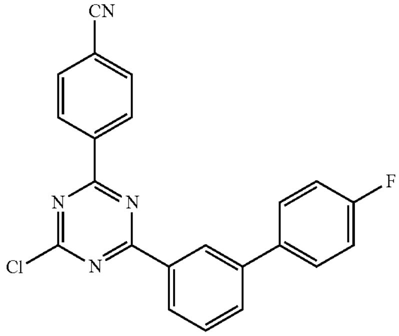
II-A5
310
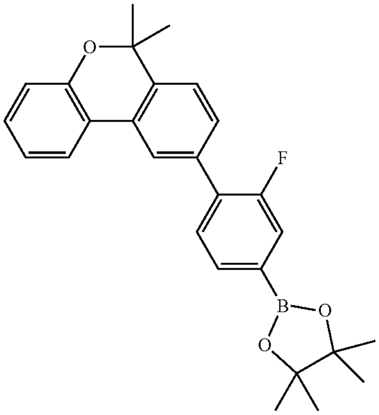
I-D6
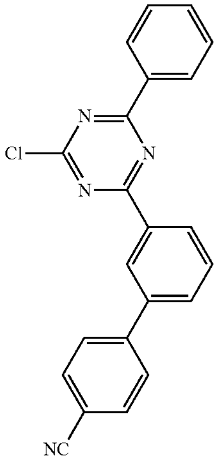
II-A1

TABLE 8-continued
311
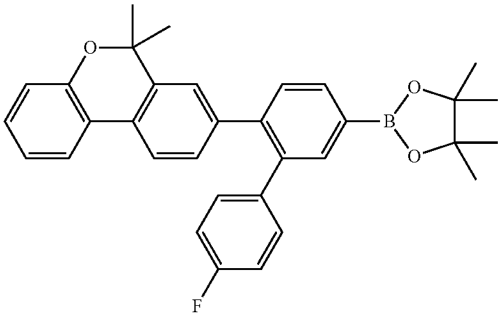
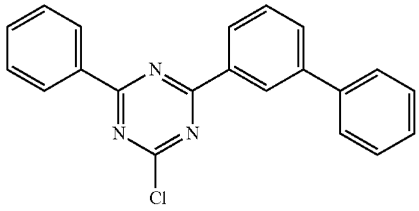 [SMILES: Clc1nc(-c2ccccc2)nc(-c2cccc(-c3ccccc3)c2)n1]
ID-7
312
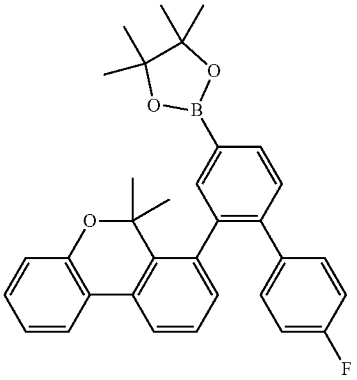
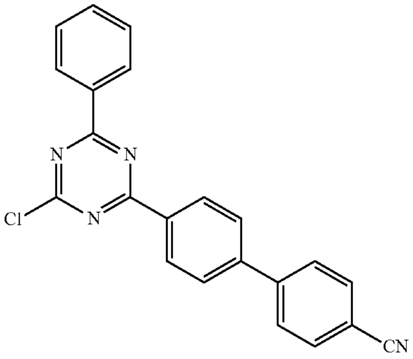 [SMILES: N#Cc1ccc(-c2ccc(-c3nc(Cl)nc(-c4ccccc4)n3)cc2)cc1]
ID-8
313
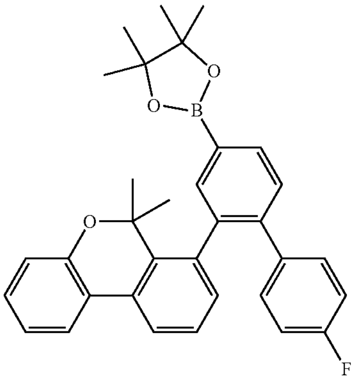
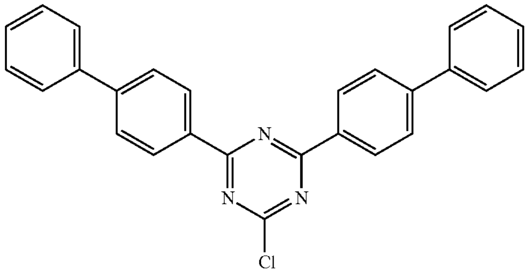 [SMILES: Clc1nc(-c2ccc(-c3ccccc3)cc2)nc(-c2ccc(-c3ccccc3)cc2)n1]
ID-8
314
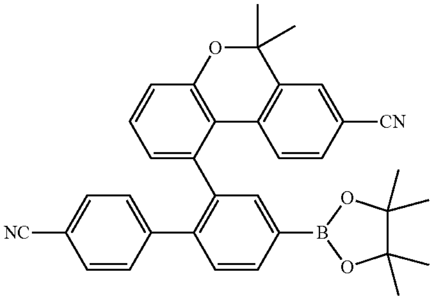
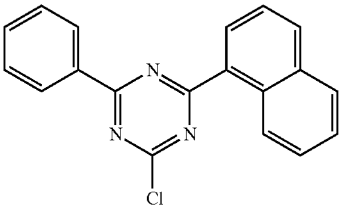 [SMILES: Clc1nc(-c2ccccc2)nc(-c2cccc3ccccc23)n1]
I-D9

TABLE 8-continued
315
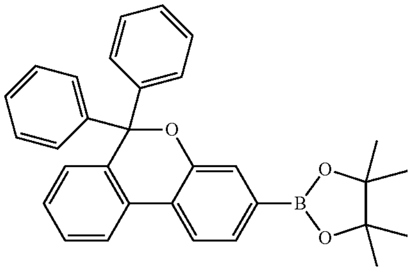
I-E1
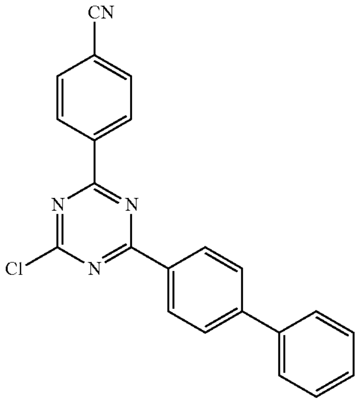 [SMILES: N#Cc1ccc(-c2nc(Cl)nc(-c3ccc(-c4ccccc4)cc3)n2)cc1]
316
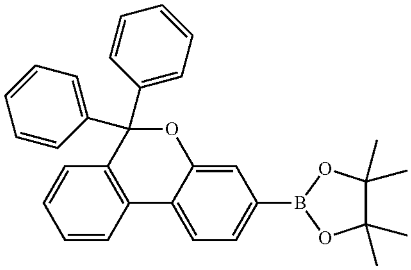
I-E1
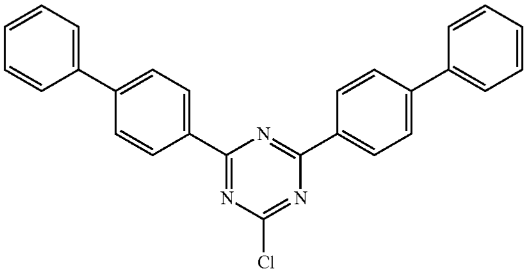 [SMILES: Clc1nc(-c2ccc(-c3ccccc3)cc2)nc(-c2ccc(-c3ccccc3)cc2)n1]
317
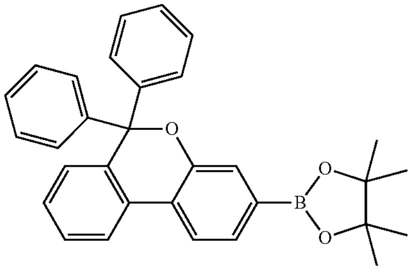
I-E1
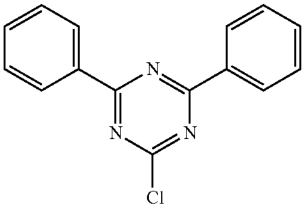 [SMILES: Clc1nc(-c2ccccc2)nc(-c2ccccc2)n1]
318
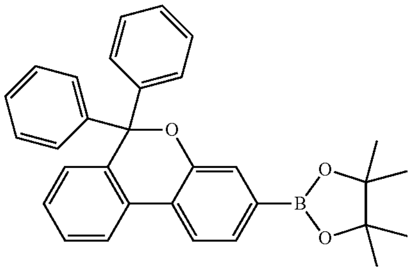
I-E1
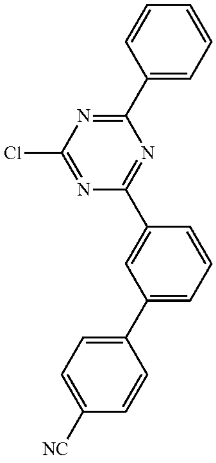
II-A1

TABLE 8-continued
| | | |
|---|---|---|
| 319 | 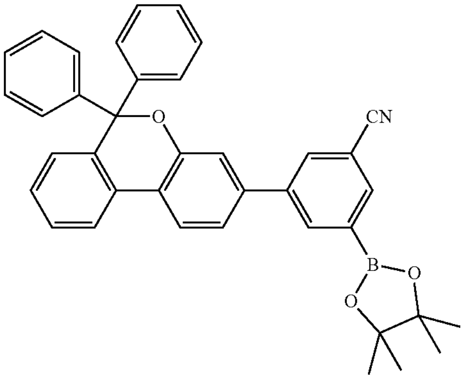 I-F1 | 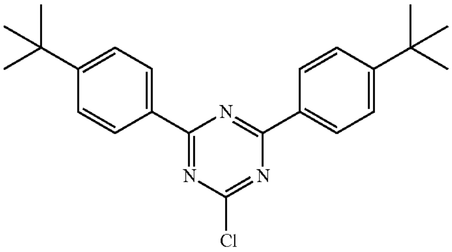 [SMILES: CC(C)(C)c1ccc(-c2nc(Cl)nc(-c3ccc(C(C)(C)C)cc3)n2)cc1] |
| 12 | 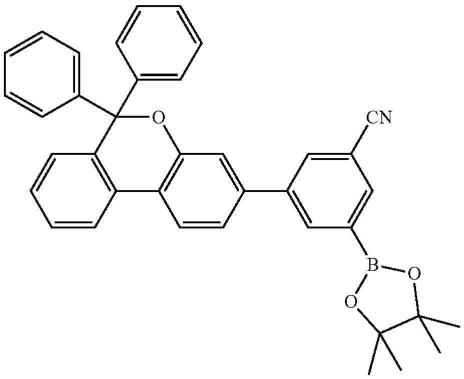 I-F1 | 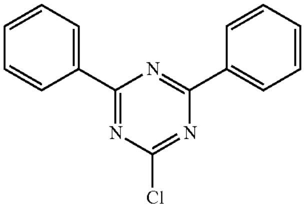 [SMILES: Clc1nc(-c2ccccc2)nc(-c2ccccc2)n1] |
| Compound No. | Product structure | Mass spectrum (m/z) [M + H]+ | Mass (g) | Yield (%) |
|---|---|---|---|---|
| 288 | 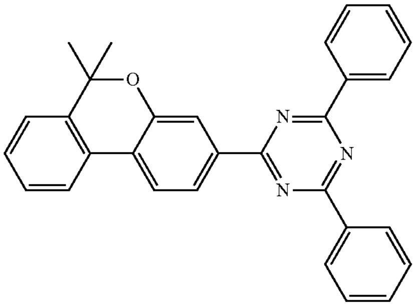 [SMILES: CC1(C)Oc2cc(-c3nc(-c4ccccc4)nc(-c4ccccc4)n3)ccc2-c2ccccc21] | 442.2 | 3.12 | 56 |

TABLE 8-continued
| | | | | |
|---|---|---|---|---|
| 289 | 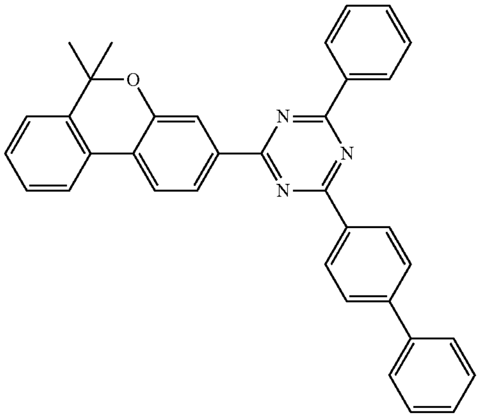 [SMILES: CC1(C)Oc2cc(-c3nc(-c4ccccc4)nc(-c4ccc(-c5ccccc5)cc4)n3)ccc2-c2ccccc21] | 517.3 | 4.30 | 78 |
| 290 | 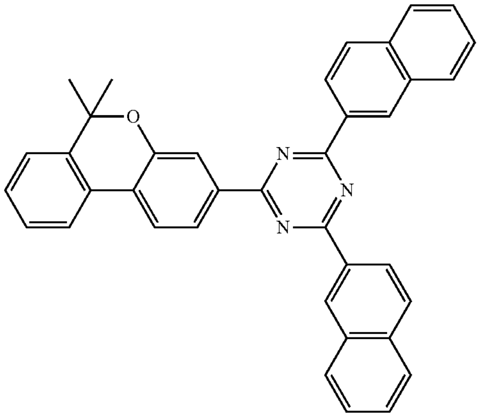 [SMILES: CC1(C)Oc2cc(-c3nc(-c4ccc5ccccc5c4)nc(-c4ccc5ccccc5c4)n3)ccc2-c2ccccc21] | 542.3 | 6.64 | 68 |
| 291 | 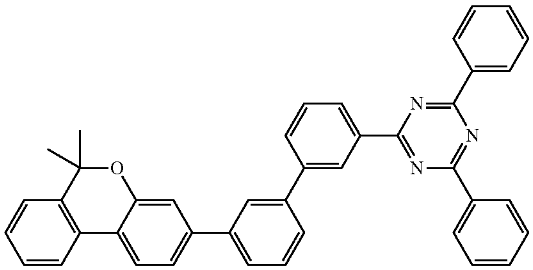 [SMILES: CC1(C)Oc2cc(-c3cccc(-c4cccc(-c5nc(-c6ccccc6)nc(-c6ccccc6)n5)c4)c3)ccc2-c2ccccc21] | 594.3 | 5.14 | 70 |
| 292 | 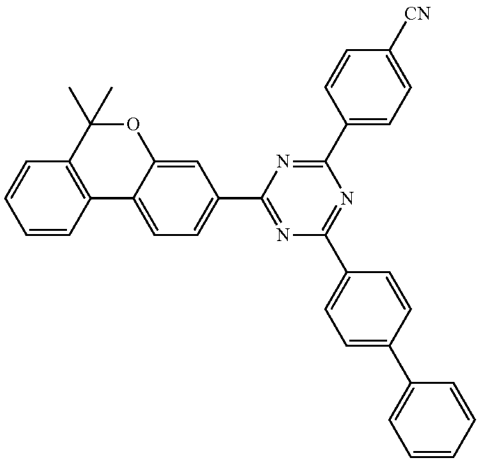 [SMILES: CC1(C)Oc2cc(-c3nc(-c4ccc(C#N)cc4)nc(-c4ccc(-c5ccccc5)cc4)n3)ccc2-c2ccccc21] | 543.2 | 6.26 | 69 |

TABLE 8-continued
| | | | | |
|---|---|---|---|---|
| 293 | 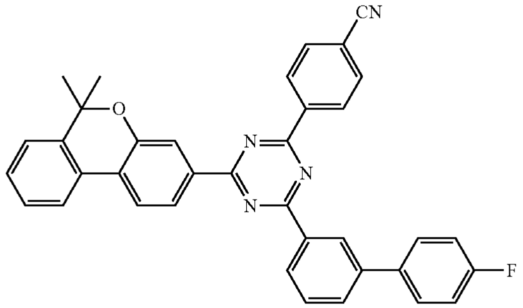 [SMILES: CC1(C)Oc2cc(-c3nc(-c4ccc(C#N)cc4)nc(-c4cccc(-c5ccc(F)cc5)c4)n3)ccc2-c2ccccc21] | 561.2 | 13.10 | 74 |
| 294 | 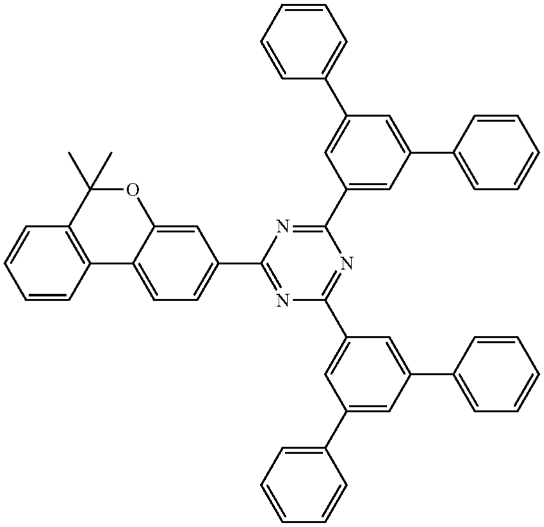 [SMILES: CC1(C)Oc2cc(-c3nc(-c4cc(-c5ccccc5)cc(-c5ccccc5)c4)nc(-c4cc(-c5ccccc5)cc(-c5ccccc5)c4)n3)ccc2-c2ccccc21] | 746.3 | 4.76 | 75 |
| 295 | 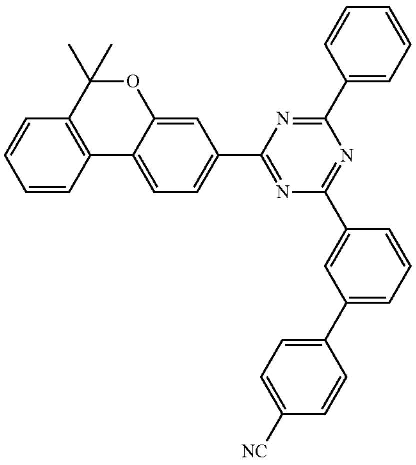 [SMILES: CC1(C)Oc2cc(-c3nc(-c4ccccc4)nc(-c4cccc(-c5ccc(C#N)cc5)c4)n3)ccc2-c2ccccc21] | 543.3 | 7.15 | 68 |
| 296 | 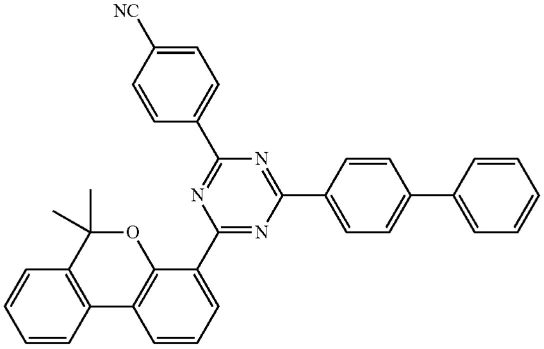 [SMILES: CC1(C)Oc2c(-c3nc(-c4ccc(C#N)cc4)nc(-c4ccc(-c5ccccc5)cc4)n3)cccc2-c2ccccc21] | 543.4 | 11.98 | 65 |

TABLE 8-continued
| | | | | |
|---|---|---|---|---|
| 297 | 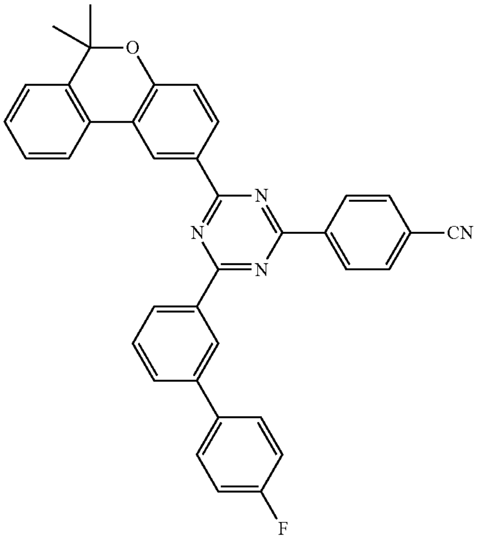 [SMILES: CC1(C)Oc2ccc(-c3nc(-c4ccc(C#N)cc4)nc(-c4cccc(-c5ccc(F)cc5)c4)n3)cc2-c2ccccc21] | 560.3 | 12.76 | 70 |
| 91 | 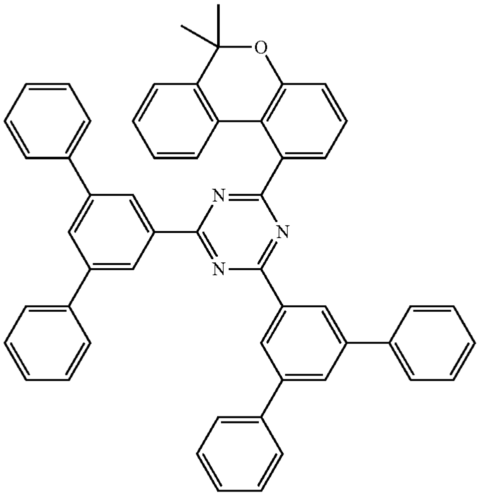 [SMILES: CC1(C)Oc2cccc(-c3nc(-c4cc(-c5ccccc5)cc(-c5ccccc5)c4)nc(-c4cc(-c5ccccc5)cc(-c5ccccc5)c4)n3)c2-c2ccccc21] | 746.4 | 4.80 | 75 |
| 298 | 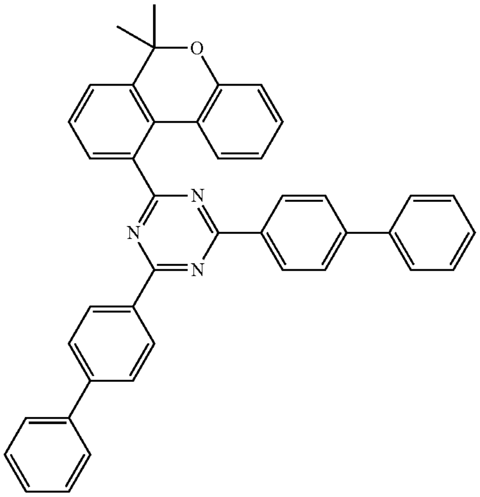 [SMILES: CC1(C)Oc2ccccc2-c2c(-c3nc(-c4ccc(-c5ccccc5)cc4)nc(-c4ccc(-c5ccccc5)cc4)n3)cccc21] | 594.3 | 5.09 | 80 |

TABLE 8-continued
| | | | | |
|---|---|---|---|---|
| 299 | 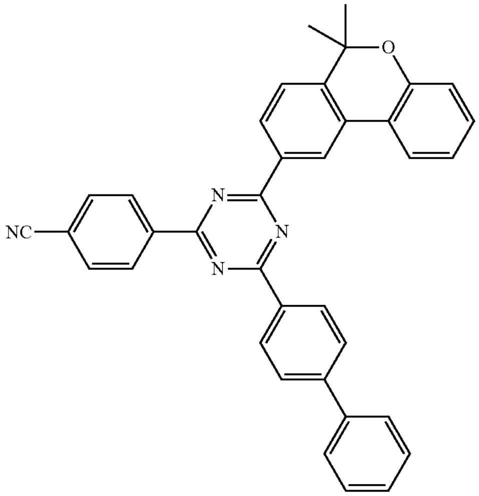 [SMILES: CC1(C)Oc2ccccc2-c2cc(-c3nc(-c4ccc(C#N)cc4)nc(-c4ccc(-c5ccccc5)cc4)n3)ccc21] | 543.3 | 12.80 | 70 |
| 300 | 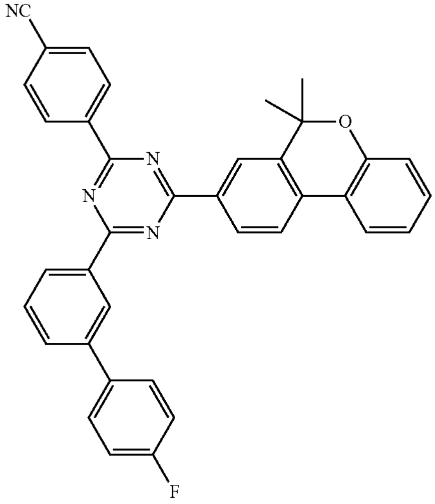 [SMILES: CC1(C)Oc2ccccc2-c2ccc(-c3nc(-c4ccc(C#N)cc4)nc(-c4cccc(-c5ccc(F)cc5)c4)n3)cc21] | 561.2 | 3.29 | 70 |
| 301 | 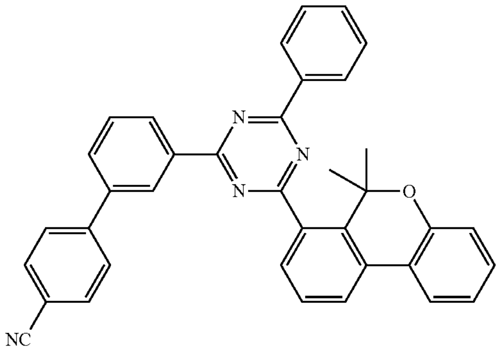 [SMILES: CC1(C)Oc2ccccc2-c2cccc(-c3nc(-c4ccccc4)nc(-c4cccc(-c5ccc(C#N)cc5)c4)n3)c21] | 543.3 | 10.50 | 68 |

TABLE 8-continued
| | | | | |
|---|---|---|---|---|
| 302 | 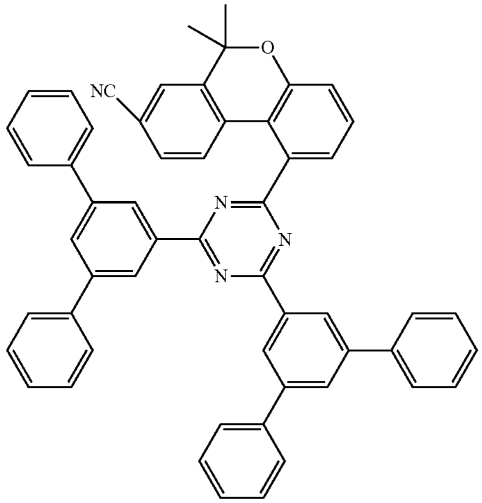 [SMILES: CC1(C)Oc2cccc(-c3nc(-c4cc(-c5ccccc5)cc(-c5ccccc5)c4)nc(-c4cc(-c5ccccc5)cc(-c5ccccc5)c4)n3)c2-c2ccc(C#N)cc21] | 771.4 | 4.78 | 65 |
| 303 | 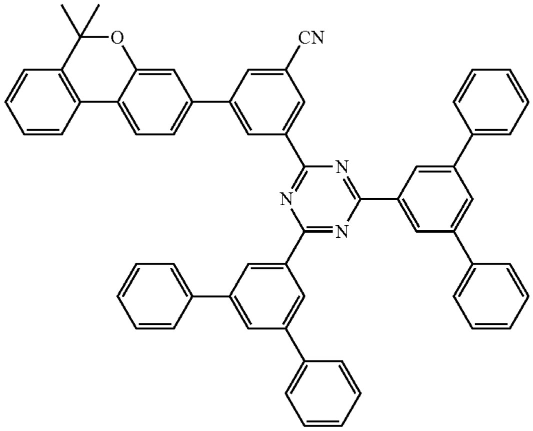 [SMILES: CC1(C)Oc2cc(-c3cc(C#N)cc(-c4nc(-c5cc(-c6ccccc6)cc(-c6ccccc6)c5)nc(-c5cc(-c6ccccc6)cc(-c6ccccc6)c5)n4)c3)ccc2-c2ccccc21] | 867.4 | 2.50 | 50 |
| 304 | 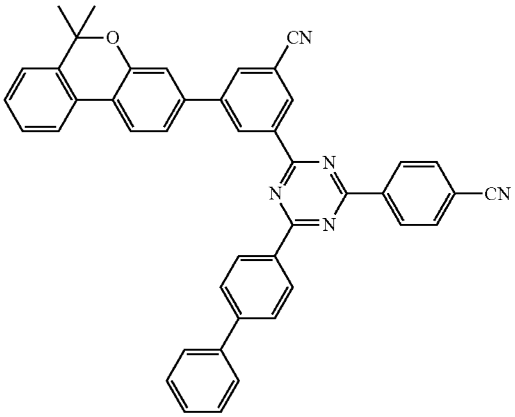 [SMILES: CC1(C)Oc2cc(-c3cc(C#N)cc(-c4nc(-c5ccc(C#N)cc5)nc(-c5ccc(-c6ccccc6)cc5)n4)c3)ccc2-c2ccccc21] | 644.3 | 4.90 | 58 |

TABLE 8-continued
| | | | | |
|---|---|---|---|---|
| 305 | 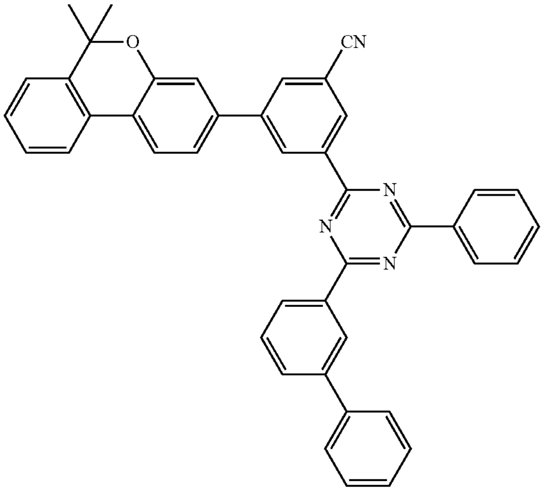 [SMILES: CC1(C)Oc2cc(-c3cc(C#N)cc(-c4nc(-c5ccccc5)nc(-c5cccc(-c6ccccc6)c5)n4)c3)ccc2-c2ccccc21] | 619.3 | 3.80 g | 76 |
| 9 | 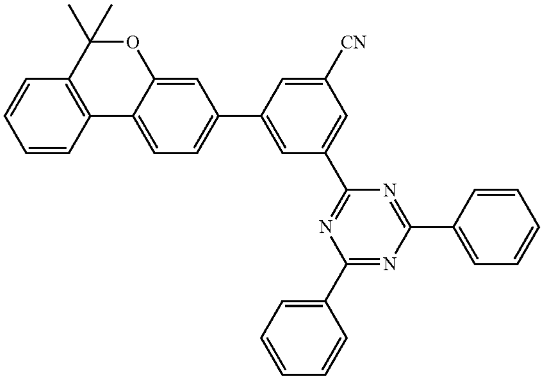 [SMILES: CC1(C)Oc2cc(-c3cc(C#N)cc(-c4nc(-c5ccccc5)nc(-c5ccccc5)n4)c3)ccc2-c2ccccc21] | 543.2 | 6.55 | 79 |
| 306 | 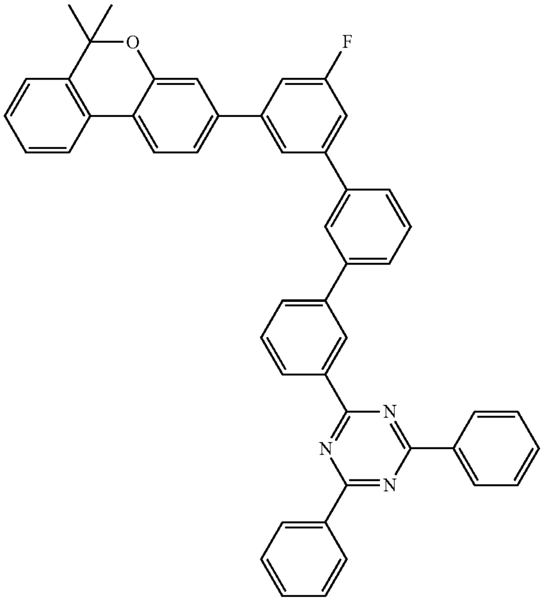 [SMILES: CC1(C)Oc2cc(-c3cc(F)cc(-c4cccc(-c5cccc(-c6nc(-c7ccccc7)nc(-c7ccccc7)n6)c5)c4)c3)ccc2-c2ccccc21] | 688.4 | 6.60 | 70 |

TABLE 8-continued
| | | | | |
|---|---|---|---|---|
| 28 | 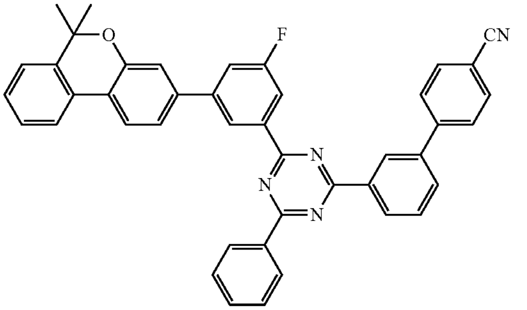 [SMILES: CC1(C)Oc2cc(-c3cc(F)cc(-c4nc(-c5ccccc5)nc(-c5cccc(-c6ccc(C#N)cc6)c5)n4)c3)ccc2-c2ccccc21] | 637.3 | 7.90 | 70 |
| 15 | 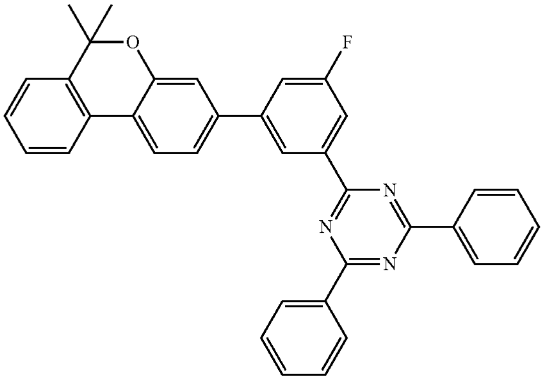 [SMILES: CC1(C)Oc2cc(-c3cc(F)cc(-c4nc(-c5ccccc5)nc(-c5ccccc5)n4)c3)ccc2-c2ccccc21] | 536.3 | 2.45 | 80 |
| 22 | 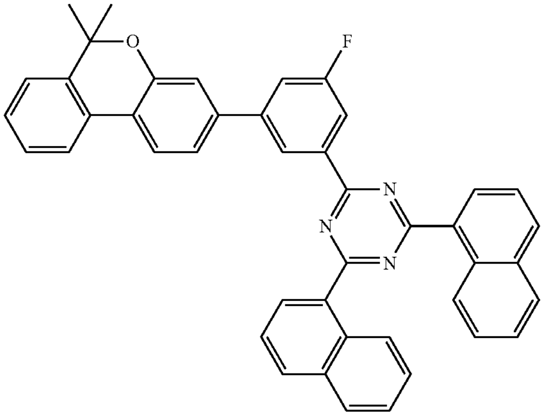 [SMILES: CC1(C)Oc2cc(-c3cc(F)cc(-c4nc(-c5cccc6ccccc56)nc(-c5cccc6ccccc56)n4)c3)ccc2-c2ccccc21] | 636.2 | 5.8 | 80 |
| 23 | 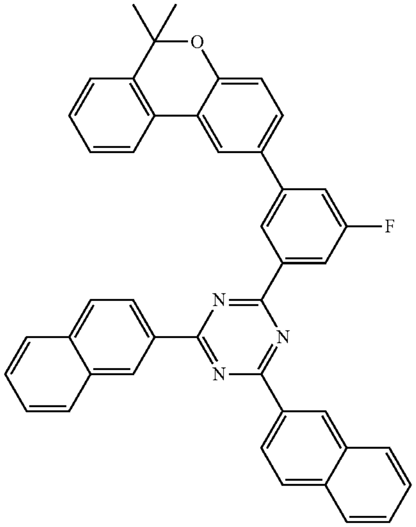 [SMILES: CC1(C)Oc2ccc(-c3cc(F)cc(-c4nc(-c5ccc6ccccc6c5)nc(-c5ccc6ccccc6c5)n4)c3)cc2-c2ccccc21] | 636.2 | 16.9 | 75 |

TABLE 8-continued
| | | | | |
|---|---|---|---|---|
| 307 | 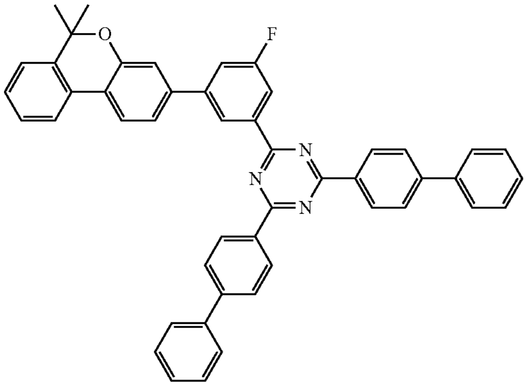 [SMILES: CC1(C)Oc2cc(-c3cc(F)cc(-c4nc(-c5ccc(-c6ccccc6)cc5)nc(-c5ccc(-c6ccccc6)cc5)n4)c3)ccc2-c2ccccc21] | 688.3 | 11.97 | 80 |
| 308 | 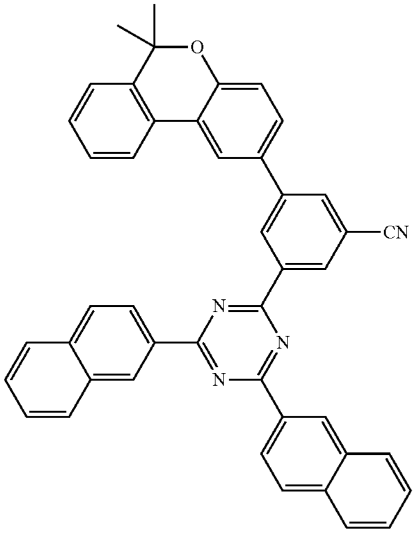 [SMILES: CC1(C)Oc2ccc(-c3cc(C#N)cc(-c4nc(-c5ccc6ccccc6c5)nc(-c5ccc6ccccc6c5)n4)c3)cc2-c2ccccc21] | 643.3 | 9.50 | 80 |
| 309 | 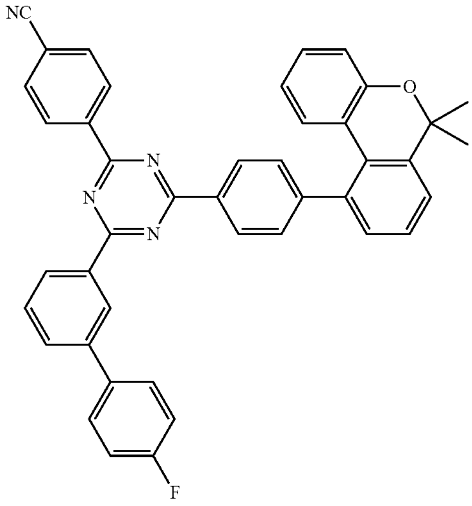 [SMILES: CC1(C)Oc2ccccc2-c2c(-c3ccc(-c4nc(-c5ccc(C#N)cc5)nc(-c5cccc(-c6ccc(F)cc6)c5)n4)cc3)cccc21] | 637.2 | 5.89 | 68 |

TABLE 8-continued
| | | | | |
|---|---|---|---|---|
| 310 | 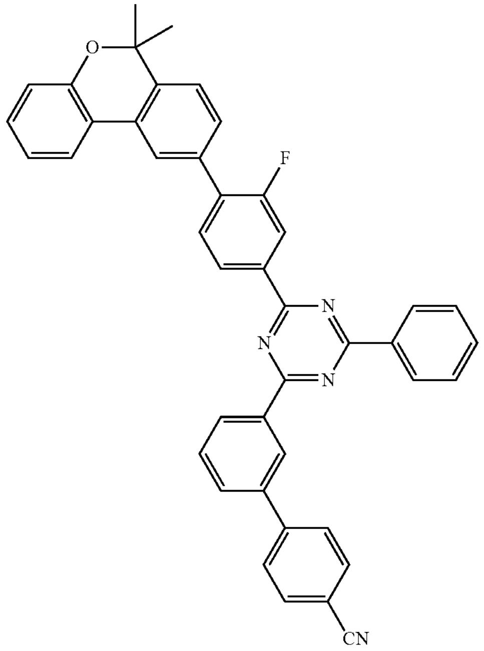 [SMILES: CC1(C)Oc2ccccc2-c2cc(-c3ccc(-c4nc(-c5ccccc5)nc(-c5cccc(-c6ccc(C#N)cc6)c5)n4)cc3F)ccc21] | 637.5 | 9.60 | 79 |
| 311 | 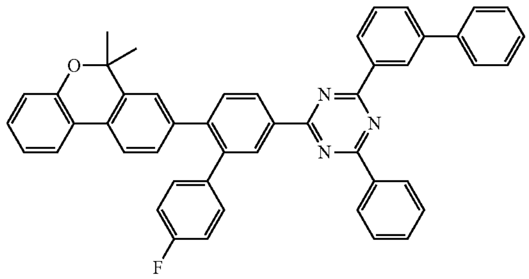 [SMILES: CC1(C)Oc2ccccc2-c2ccc(-c3ccc(-c4nc(-c5ccccc5)nc(-c5cccc(-c6ccccc6)c5)n4)cc3-c3ccc(F)cc3)cc21] | 688.1 | 12.35 | 75 |
| 312 | 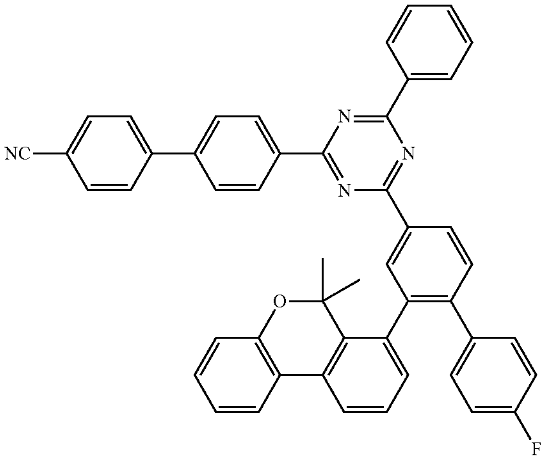 [SMILES: CC1(C)Oc2ccccc2-c2cccc(-c3cc(-c4nc(-c5ccccc5)nc(-c5ccc(-c6ccc(C#N)cc6)cc5)n4)ccc3-c3ccc(F)cc3)c21] | 713.2 | 10.35 | 74 |

TABLE 8-continued
| | | | | |
|---|---|---|---|---|
| 313 | 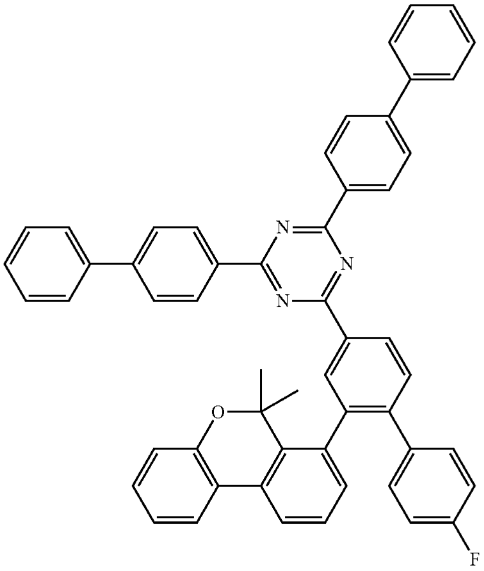 [SMILES: CC1(C)Oc2ccccc2-c2cccc(-c3cc(-c4nc(-c5ccc(-c6ccccc6)cc5)nc(-c5ccc(-c6ccccc6)cc5)n4)ccc3-c3ccc(F)cc3)c21] | 761.2 | 5.76 | 76 |
| 314 | 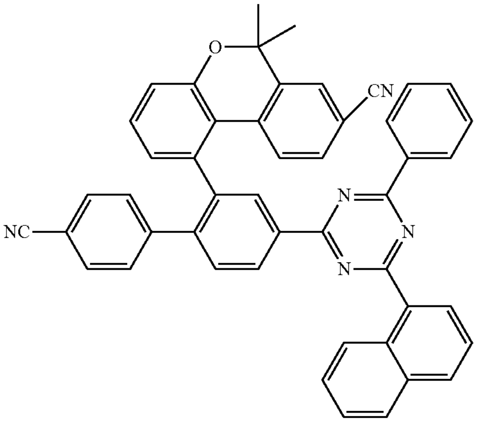 [SMILES: CC1(C)Oc2cccc(-c3cc(-c4nc(-c5ccccc5)nc(-c5cccc6ccccc56)n4)ccc3-c3ccc(C#N)cc3)c2-c2ccc(C#N)cc21] | 694.1 | 5.87 | 81 |
| 315 | 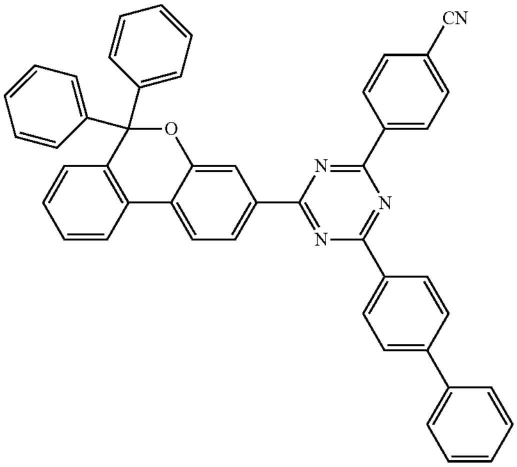 [SMILES: N#Cc1ccc(-c2nc(-c3ccc(-c4ccccc4)cc3)nc(-c3ccc4c(c3)OC(c3ccccc3)(c3ccccc3)c3ccccc3-4)n2)cc1] | 667.2 | 8.90 | 69 |

TABLE 8-continued
| | | | | |
|---|---|---|---|---|
| 316 | 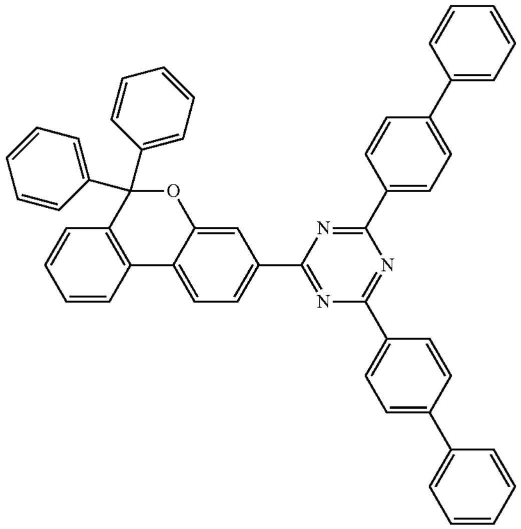 [SMILES: c1ccc(-c2ccc(-c3nc(-c4ccc(-c5ccccc5)cc4)nc(-c4ccc5c(c4)OC(c4ccccc4)(c4ccccc4)c4ccccc4-5)n3)cc2)cc1] | 718.2 | 6.74 | 65 |
| 317 | 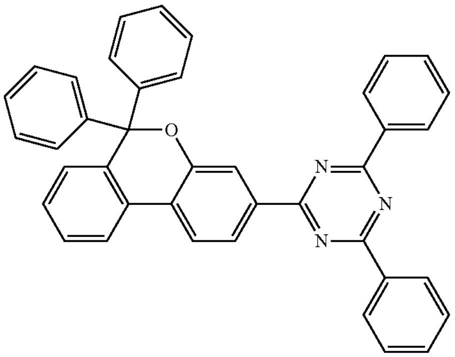 [SMILES: c1ccc(-c2nc(-c3ccccc3)nc(-c3ccc4c(c3)OC(c3ccccc3)(c3ccccc3)c3ccccc3-4)n2)cc1] | 566.2 | 6.80 | 89 |
| 318 | 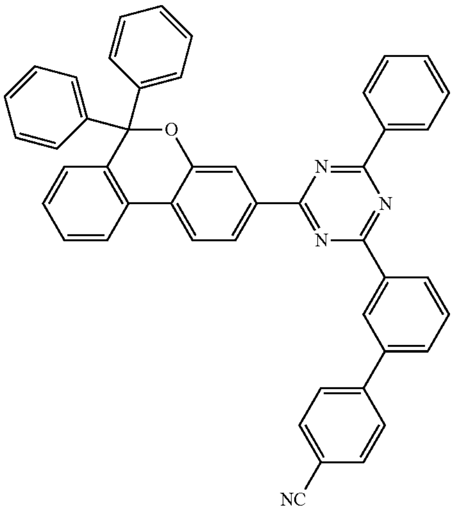 [SMILES: N#Cc1ccc(-c2cccc(-c3nc(-c4ccccc4)nc(-c4ccc5c(c4)OC(c4ccccc4)(c4ccccc4)c4ccccc4-5)n3)c2)cc1] | 667.2 | 6.89 | 84 |

TABLE 8-continued

| | | | | |
|---|---|---|---|---|
| 319 | 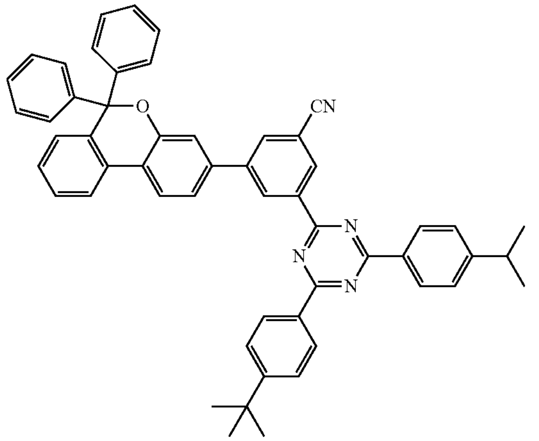 [SMILES: CC(C)c1ccc(-c2nc(-c3ccc(C(C)(C)C)cc3)nc(-c3cc(C#N)cc(-c4ccc5c(c4)OC(c4ccccc4)(c4ccccc4)c4ccccc4-5)c3)n2)cc1] | 779.3 | 7.00 | 80 |
| 12 | 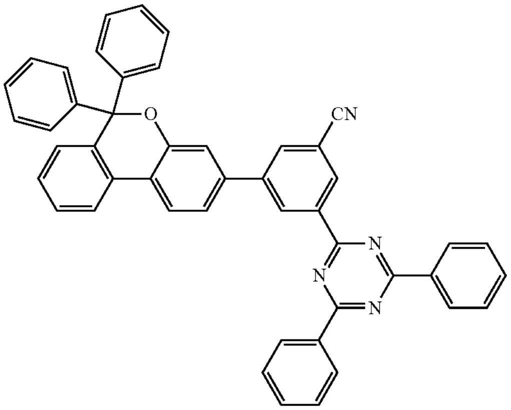 [SMILES: N#Cc1cc(-c2ccc3c(c2)OC(c2ccccc2)(c2ccccc2)c2ccccc2-3)cc(-c2nc(-c3ccccc3)nc(-c3ccccc3)n2)c1] | 667.2 | 5.90 | 82 |

(5) Compounds 2, 5, 63, 66, 86, 89, 97, 99, 103 to 111, 123, 131, 132, 136, 137, 141, 157, etc., were synthesized by using the same method as that for the synthesis of the compound 124 except that the intermediate I-B1 used for the synthesis of the compound 124 was replaced with a raw material 9 in Table 9, and the intermediate II-A1 used for the synthesis of the compound 124 was replaced with a raw material 10 in Table 9. The raw materials in Table 9 below were all commercially available.

An intermediate I-D16 was prepared by using the prepared intermediate I-C18 according to the following synthetic method.

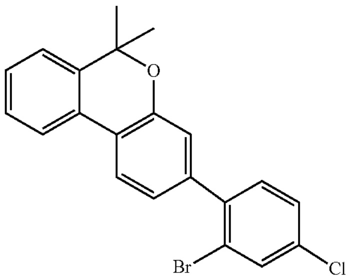

I-C18

+

-continued

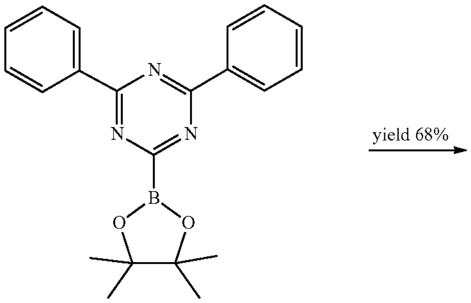

-continued
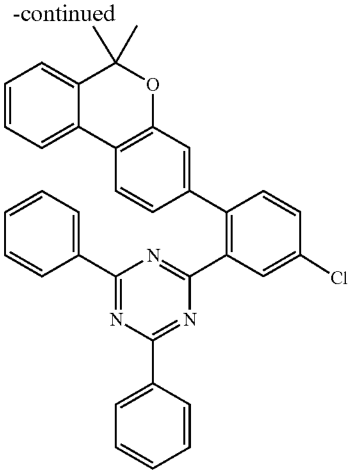
I-C19
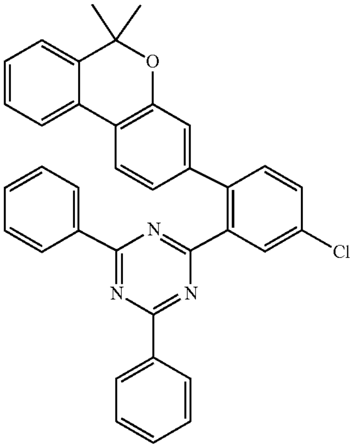
I-C19
+
-continued
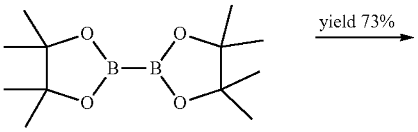
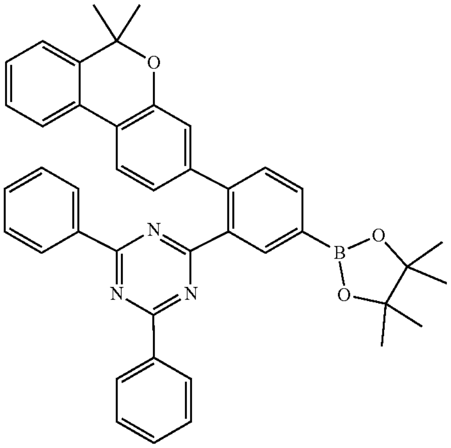
I-D16
TABLE 9
| Com pound No. | Raw material 9 | Raw material 10 |
|---|---|---|
| 10 2 | 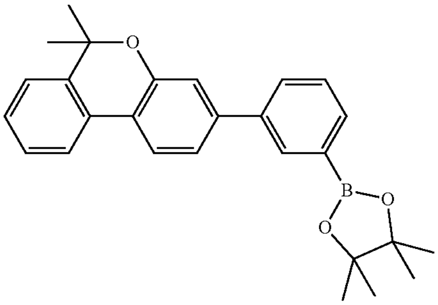 I-D10 | 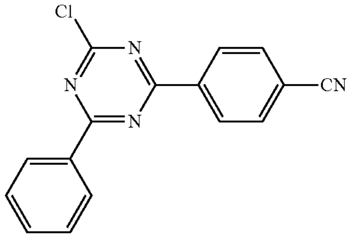 [SMILES: N#Cc1ccc(-c2nc(Cl)nc(-c3ccccc3)n2)cc1] |

TABLE 9-continued
| | | |
|---|---|---|
| 151 | 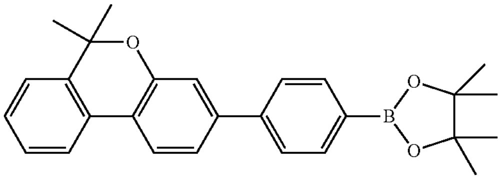 | 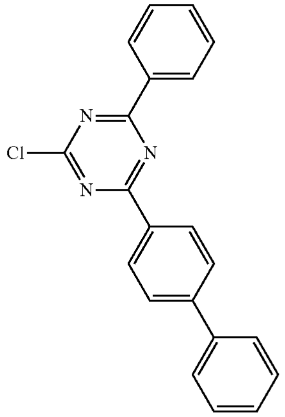 [SMILES: Clc1nc(-c2ccccc2)nc(-c2ccc(-c3ccccc3)cc2)n1] |
| 5 | 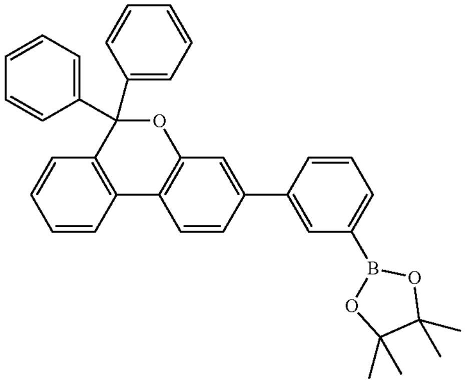<br>I-F3 | 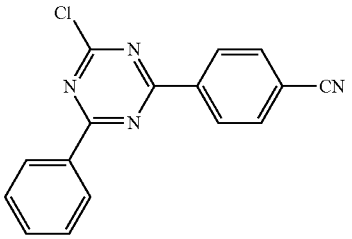 [SMILES: N#Cc1ccc(-c2nc(Cl)nc(-c3ccccc3)n2)cc1] |
| 63 | 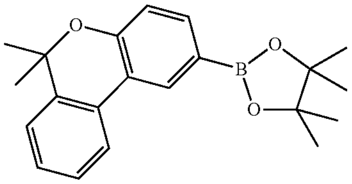<br>I-B3 | 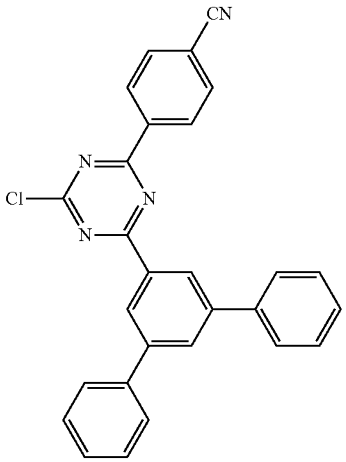 [SMILES: N#Cc1ccc(-c2nc(Cl)nc(-c3cc(-c4ccccc4)cc(-c4ccccc4)c3)n2)cc1] |

TABLE 9-continued
66
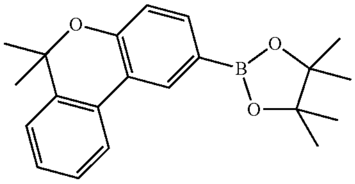
I-B3
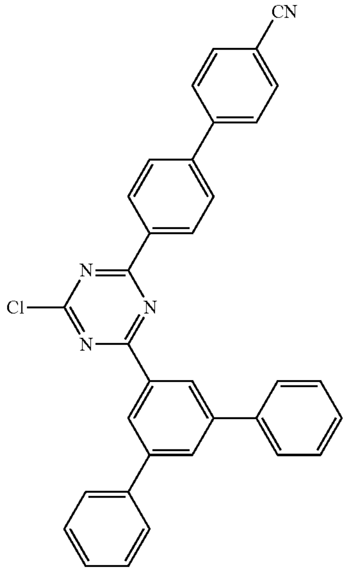 [SMILES: N#Cc1ccc(-c2ccc(-c3nc(Cl)nc(-c4cc(-c5ccccc5)cc(-c5ccccc5)c4)n3)cc2)cc1]
86
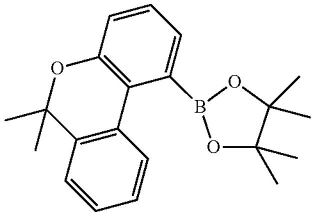
I-B4
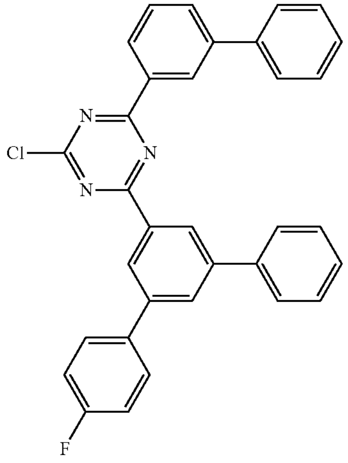 [SMILES: Fc1ccc(-c2cc(-c3ccccc3)cc(-c3nc(Cl)nc(-c4cccc(-c5ccccc5)c4)n3)c2)cc1]
89
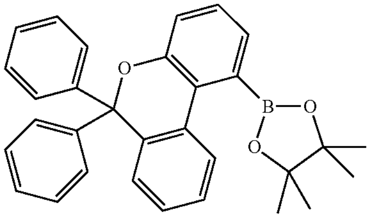
I-E2
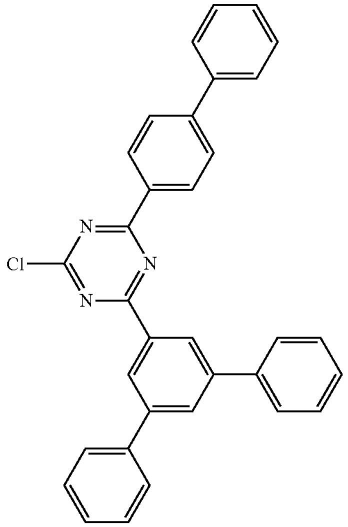 [SMILES: Clc1nc(-c2ccc(-c3ccccc3)cc2)nc(-c2cc(-c3ccccc3)cc(-c3ccccc3)c2)n1]

TABLE 9-continued
97
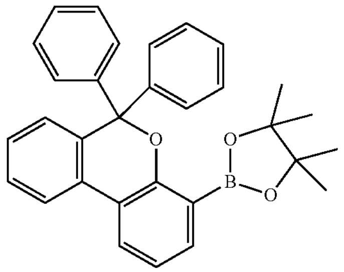
I-E4
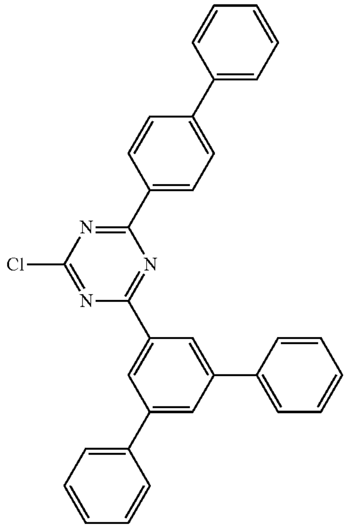
II-A6
99
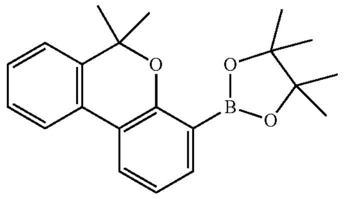
I-B2
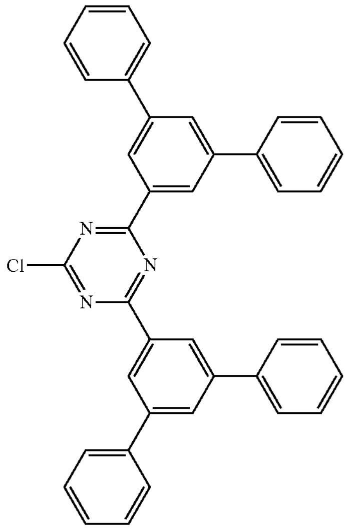
II-A2
103
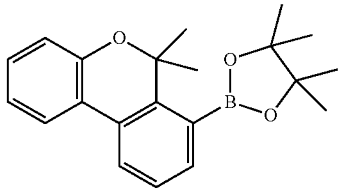
I-B8
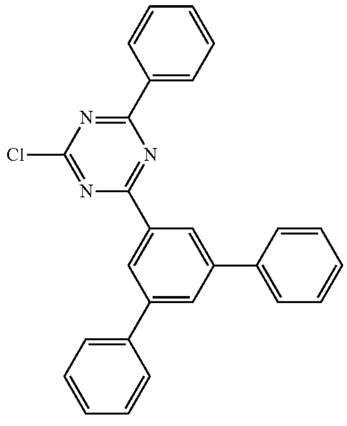 [SMILES: Clc1nc(-c2ccccc2)nc(-c2cc(-c3ccccc3)cc(-c3ccccc3)c2)n1]

TABLE 9-continued
| | | |
|---|---|---|
| 104 | 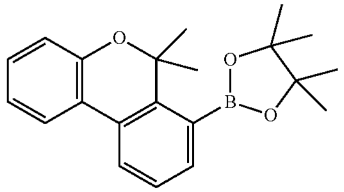 I-B8 | 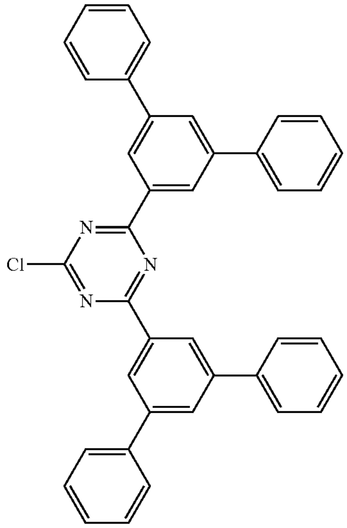 II-A2 |
| 105 | 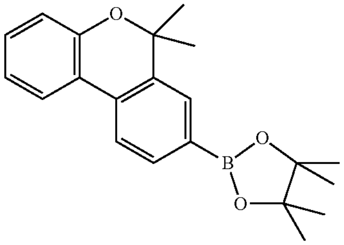 I-B7 | 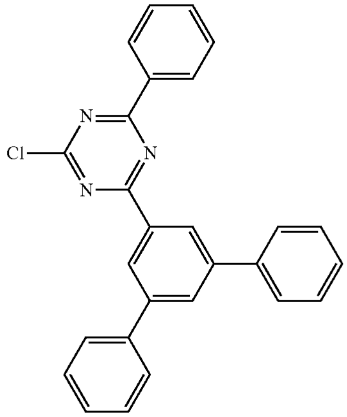 |
| 106 | 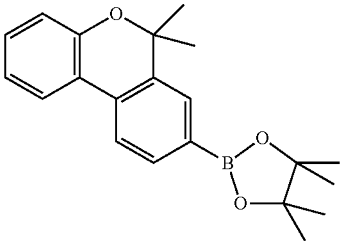 I-B7 | 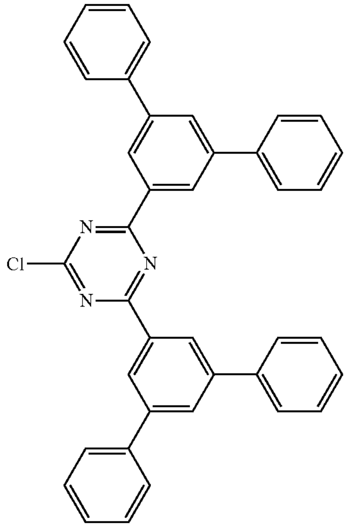 II-A2 |

TABLE 9-continued
107
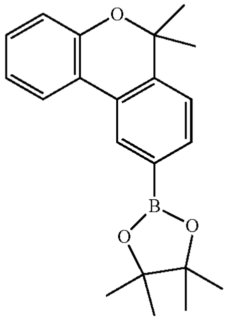
I-B6
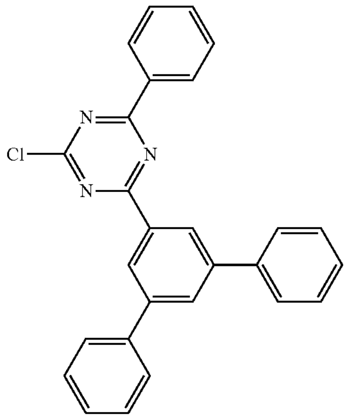 [SMILES: Clc1nc(-c2ccccc2)nc(-c2cc(-c3ccccc3)cc(-c3ccccc3)c2)n1]
108
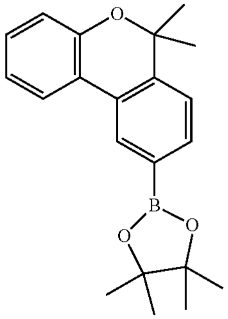
I-B6
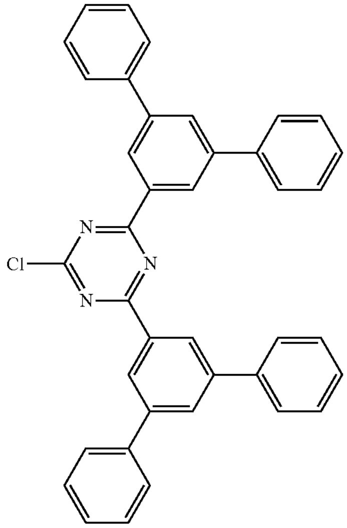
II-A2
109
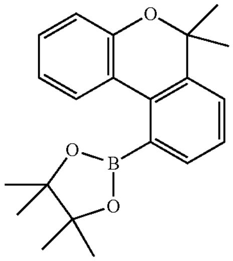
I-B5
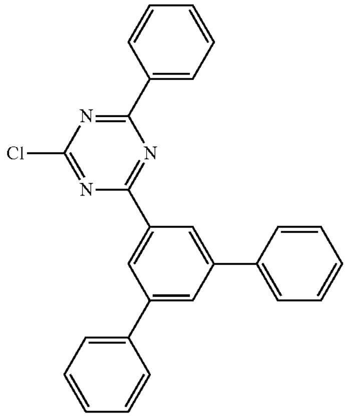 [SMILES: Clc1nc(-c2ccccc2)nc(-c2cc(-c3ccccc3)cc(-c3ccccc3)c2)n1]

TABLE 9-continued
| | | |
|---|---|---|
| 110 | 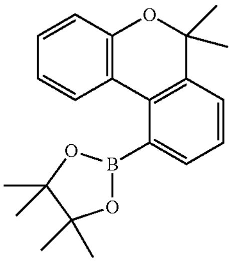<br>I-B5 | 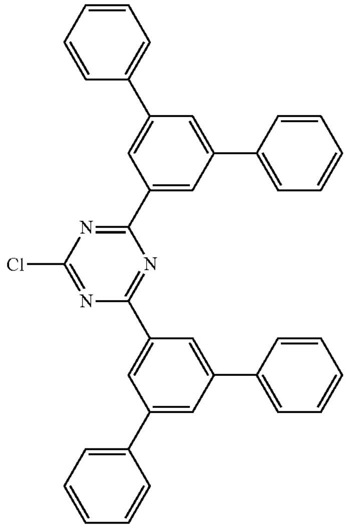<br>II-A2 |
| 111 | 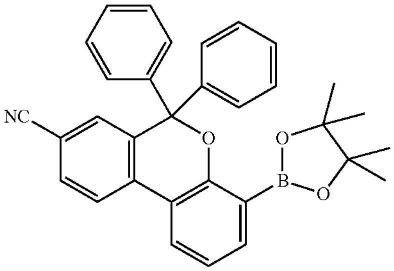<br>I-E5 | 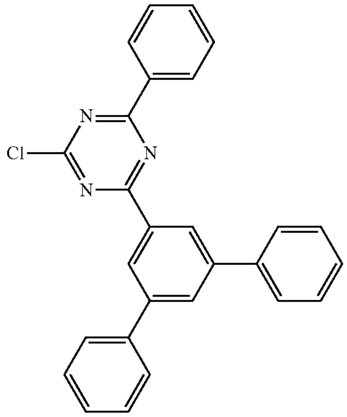<br>II-A2 |
| 123 | 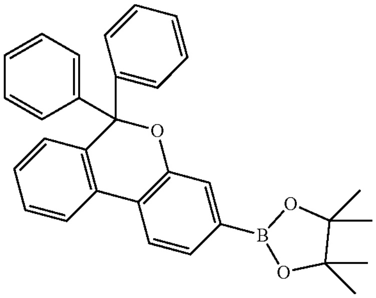<br>I-E1 | 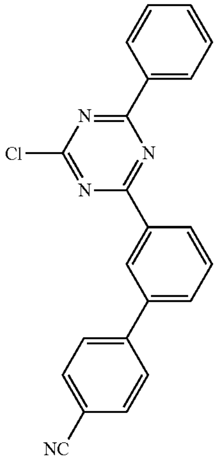<br>II-A1 |

TABLE 9-continued
| | | |
|---|---|---|
| 131 | 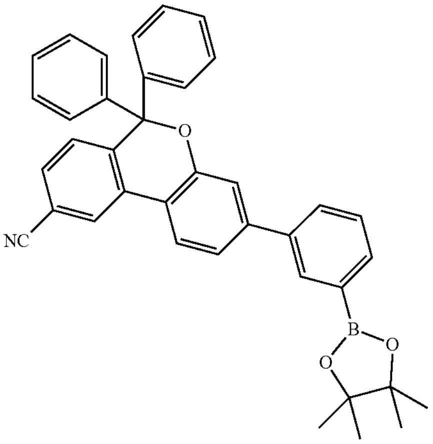 I-F6 | 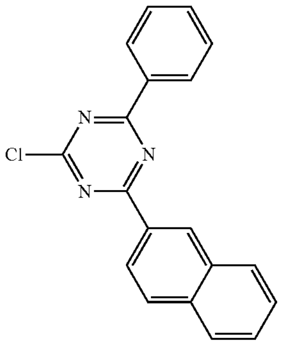 |
| 132 | 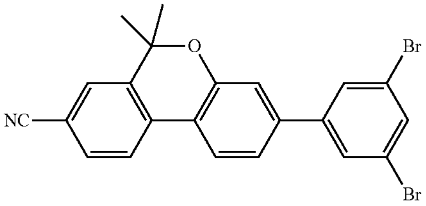 I-C11 | 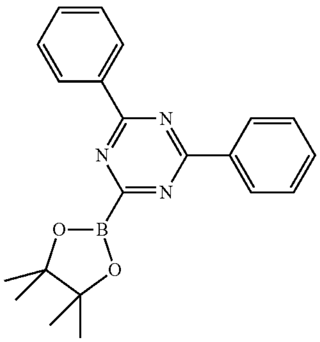 |
| 136 | 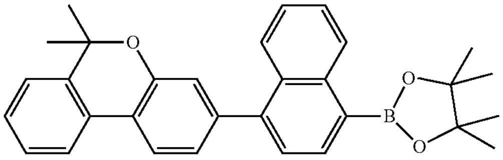 I-D12 | 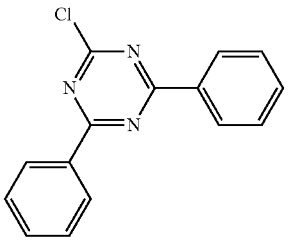 |
| 137 | 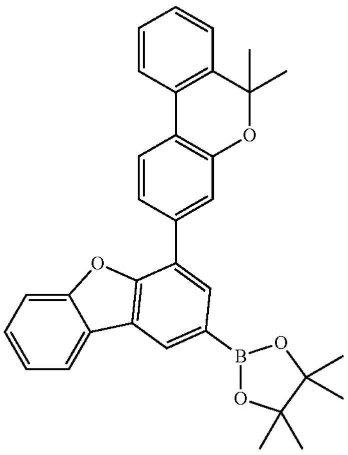 I-D14 | 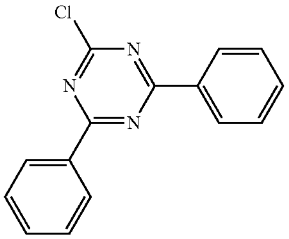 |

TABLE 9-continued
141
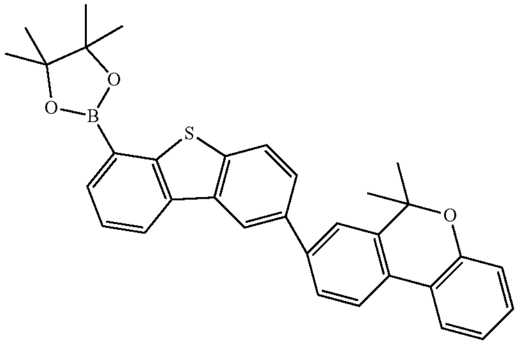
I-D15
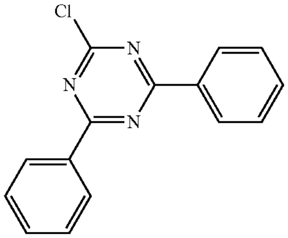 [SMILES: Clc1nc(-c2ccccc2)nc(-c2ccccc2)n1]
157
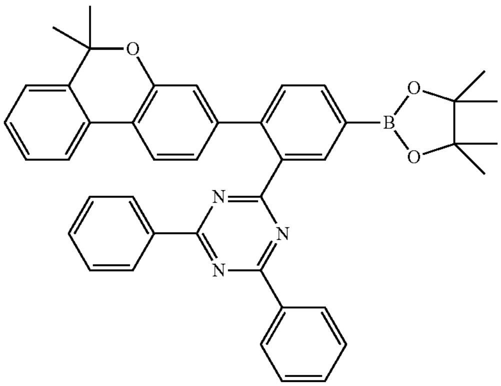
I-D16
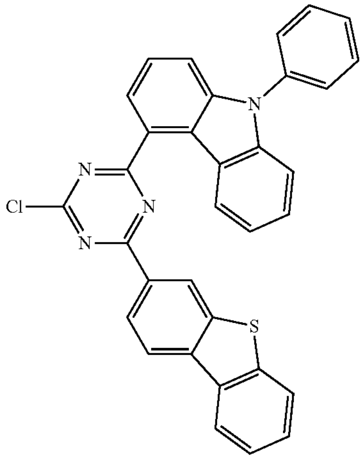
II-A11
335
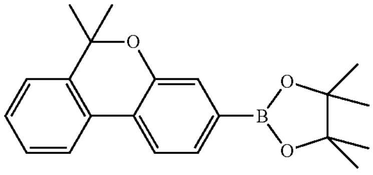
I-B1
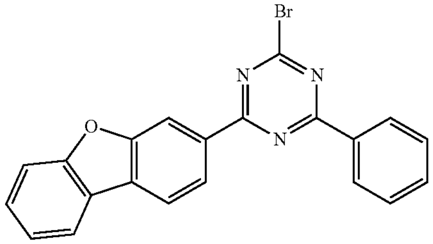 [SMILES: Brc1nc(-c2ccccc2)nc(-c2ccc3c(c2)oc2ccccc23)n1]
336
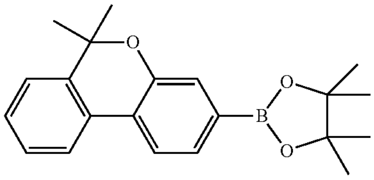
I-D11
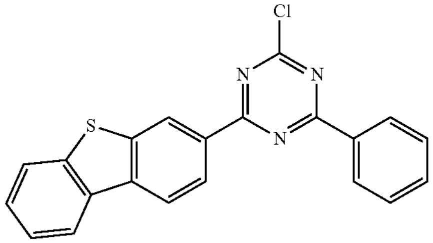 [SMILES: Clc1nc(-c2ccccc2)nc(-c2ccc3c(c2)sc2ccccc23)n1]
337
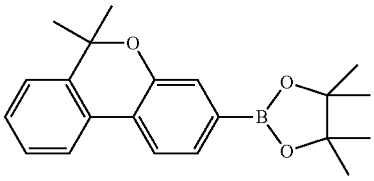
I-D11
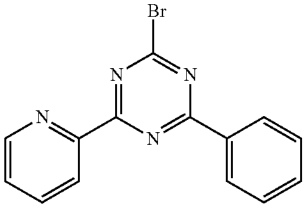 [SMILES: Brc1nc(-c2ccccc2)nc(-c2ccccn2)n1]

TABLE 9-continued
| | | |
|---|---|---|
| 338 | 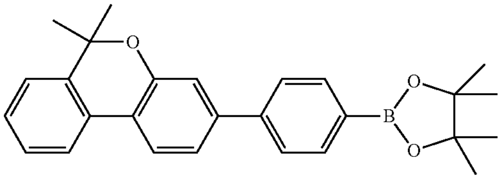<br>I-D11 | 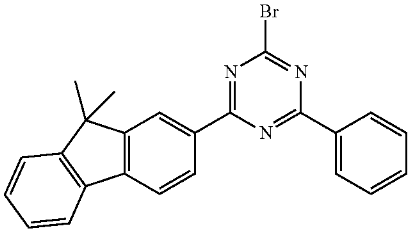 |
| Compound No. | Product structure | Yield % | Mass spectrum (m/z) [M + H]$^+$ |
|---|---|---|---|
| 2 | 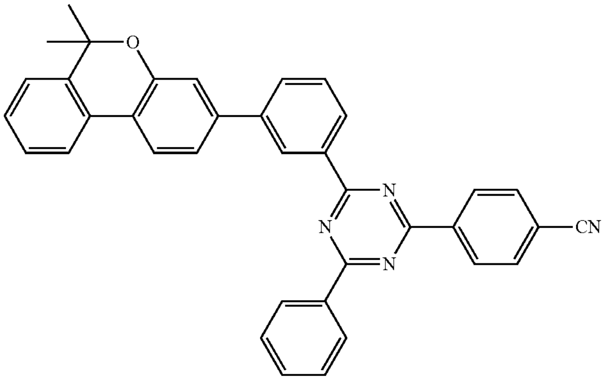 [SMILES: CC1(C)Oc2cc(-c3cccc(-c4nc(-c5ccccc5)nc(-c5ccc(C#N)cc5)n4)c3)ccc2-c2ccccc21] | 63 | 543.2 |
| 151 | 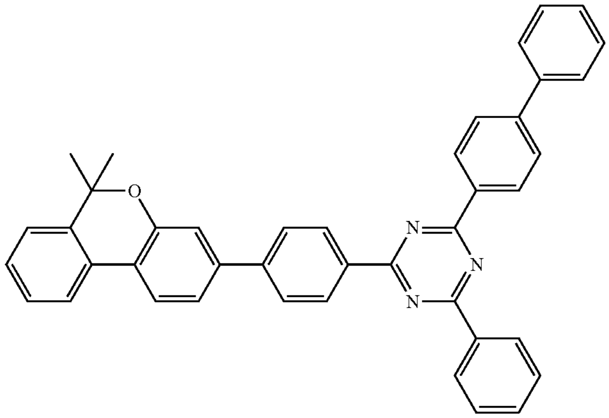 [SMILES: CC1(C)Oc2cc(-c3ccc(-c4nc(-c5ccccc5)nc(-c5ccc(-c6ccccc6)cc5)n4)cc3)ccc2-c2ccccc21] | 76 | 594.3 |
| 5 | 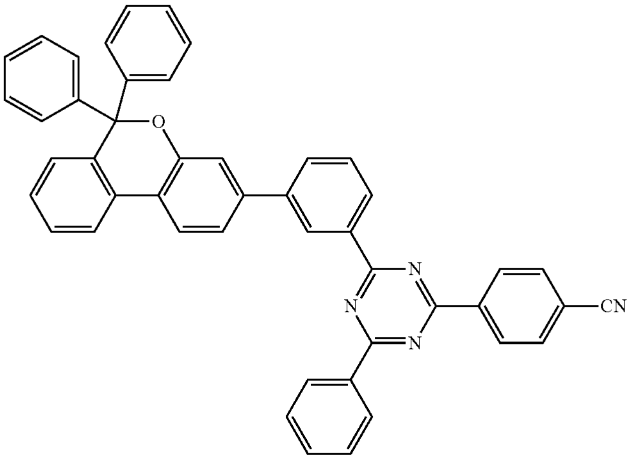 [SMILES: N#Cc1ccc(-c2nc(-c3ccccc3)nc(-c3cccc(-c4ccc5c(c4)OC(c4ccccc4)(c4ccccc4)c4ccccc4-5)c3)n2)cc1] | 65 | 667.2 |

TABLE 9-continued
| | | | |
|---|---|---|---|
| 63 | 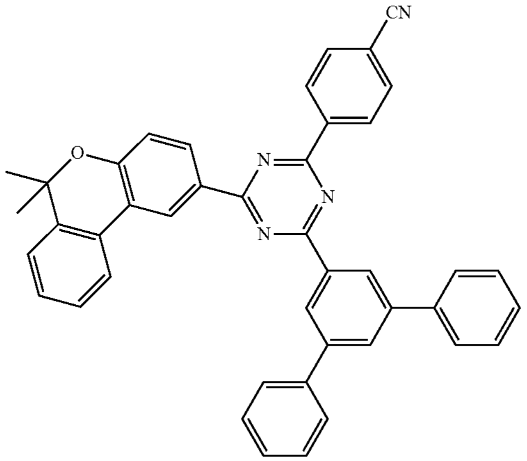 [SMILES: CC1(C)Oc2ccc(-c3nc(-c4ccc(C#N)cc4)nc(-c4cc(-c5ccccc5)cc(-c5ccccc5)c4)n3)cc2-c2ccccc21] | 68 | 619.2 |
| 66 | 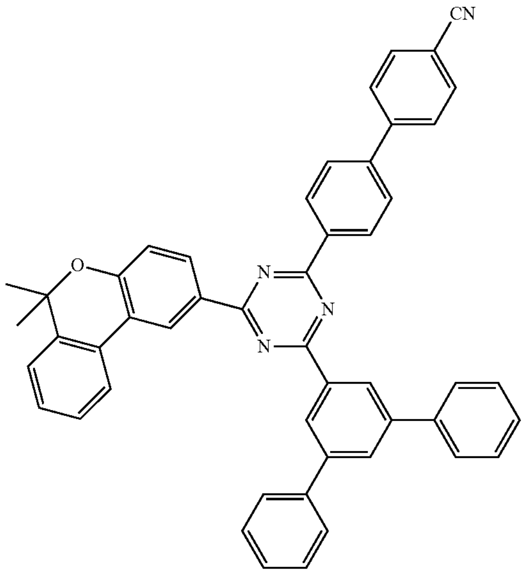 [SMILES: CC1(C)Oc2ccc(-c3nc(-c4ccc(-c5ccc(C#N)cc5)cc4)nc(-c4cc(-c5ccccc5)cc(-c5ccccc5)c4)n3)cc2-c2ccccc21] | 68 | 695.3 |
| 86 | 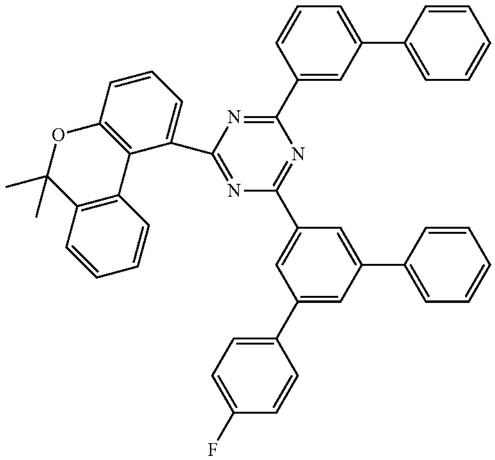 [SMILES: CC1(C)Oc2cccc(-c3nc(-c4cccc(-c5ccccc5)c4)nc(-c4cc(-c5ccccc5)cc(-c5ccc(F)cc5)c4)n3)c2-c2ccccc21] | 56 | 688.3 |

TABLE 9-continued
| | | | |
|---|---|---|---|
| 89 | 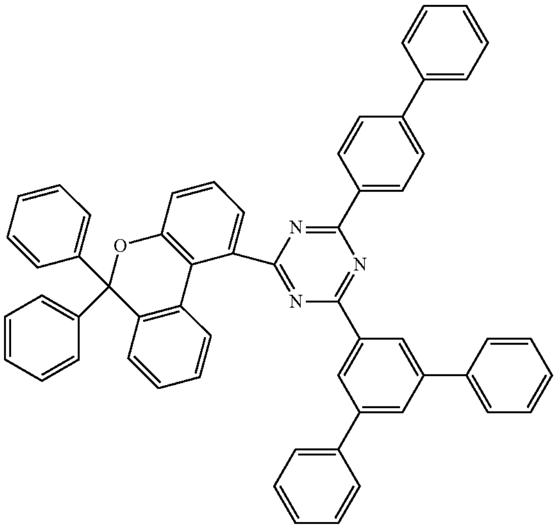 [SMILES: c1ccc(-c2ccc(-c3nc(-c4cc(-c5ccccc5)cc(-c5ccccc5)c4)nc(-c4cccc5c4-c4ccccc4C(c4ccccc4)(c4ccccc4)O5)n3)cc2)cc1] | 58 | 794.3 |
| 97 | 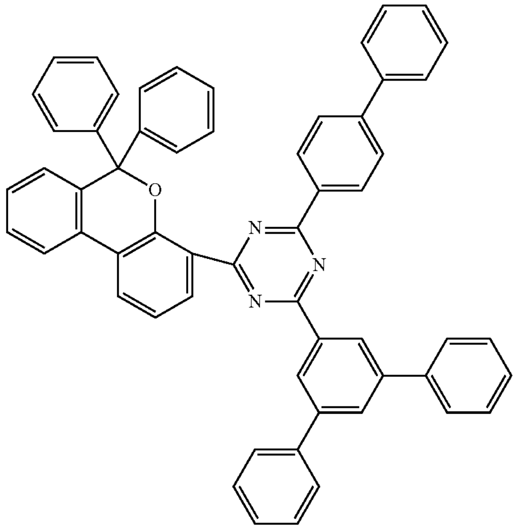 [SMILES: c1ccc(-c2ccc(-c3nc(-c4cc(-c5ccccc5)cc(-c5ccccc5)c4)nc(-c4cccc5c4OC(c4ccccc4)(c4ccccc4)c4ccccc4-5)n3)cc2)cc1] | 61 | 794.3 |
| 99 | 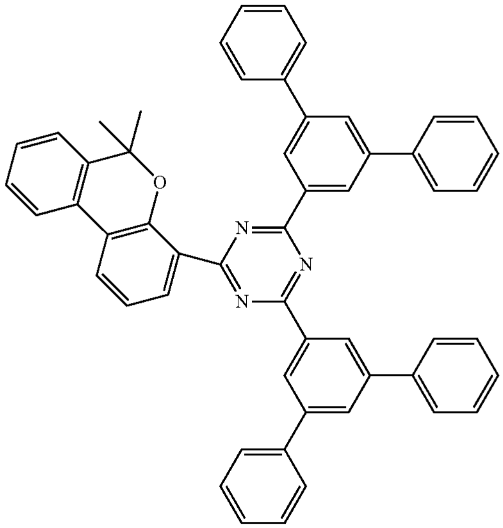 [SMILES: CC1(C)Oc2c(-c3nc(-c4cc(-c5ccccc5)cc(-c5ccccc5)c4)nc(-c4cc(-c5ccccc5)cc(-c5ccccc5)c4)n3)cccc2-c2ccccc21] | 62 | 746.3 |

TABLE 9-continued
| | | | |
|---|---|---|---|
| 103 | 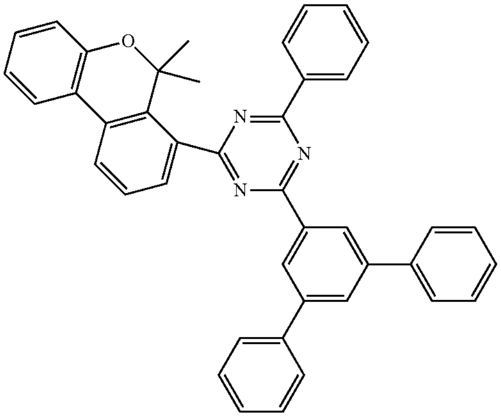 [SMILES: CC1(C)Oc2ccccc2-c2cccc(-c3nc(-c4ccccc4)nc(-c4cc(-c5ccccc5)cc(-c5ccccc5)c4)n3)c21] | 52 | 594.2 |
| 104 | 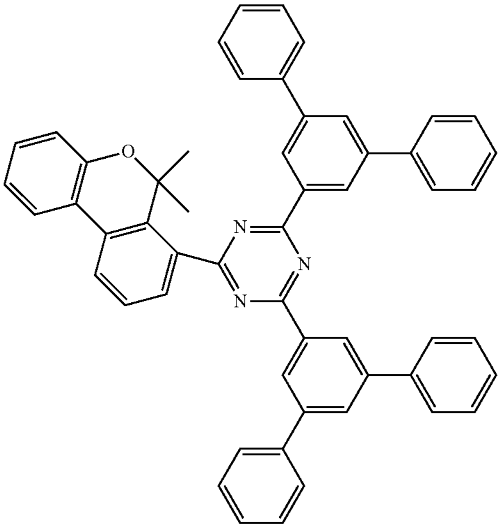 [SMILES: CC1(C)Oc2ccccc2-c2cccc(-c3nc(-c4cc(-c5ccccc5)cc(-c5ccccc5)c4)nc(-c4cc(-c5ccccc5)cc(-c5ccccc5)c4)n3)c21] | 59 | 746.3 |
| 105 | 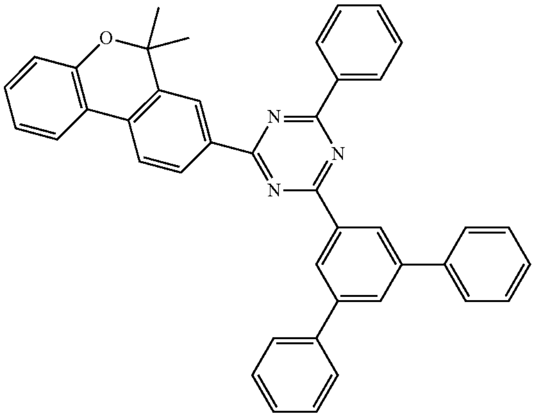 [SMILES: CC1(C)Oc2ccccc2-c2ccc(-c3nc(-c4ccccc4)nc(-c4cc(-c5ccccc5)cc(-c5ccccc5)c4)n3)cc21] | 72 | 594.2 |

TABLE 9-continued
| | | | |
|---|---|---|---|
| 106 | 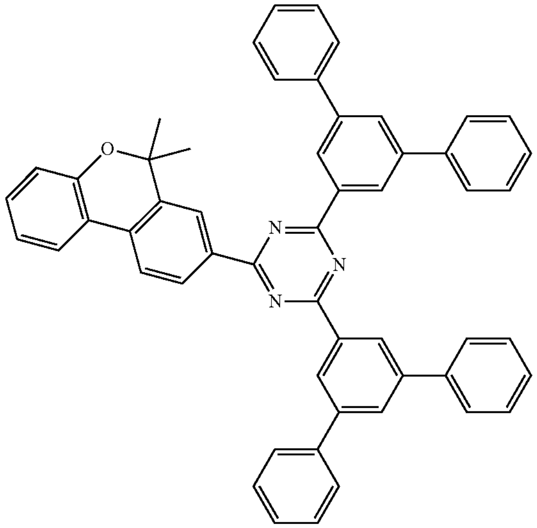 [SMILES: CC1(C)Oc2ccccc2-c2ccc(-c3nc(-c4cc(-c5ccccc5)cc(-c5ccccc5)c4)nc(-c4cc(-c5ccccc5)cc(-c5ccccc5)c4)n3)cc21] | 75 | 746.3 |
| 107 | 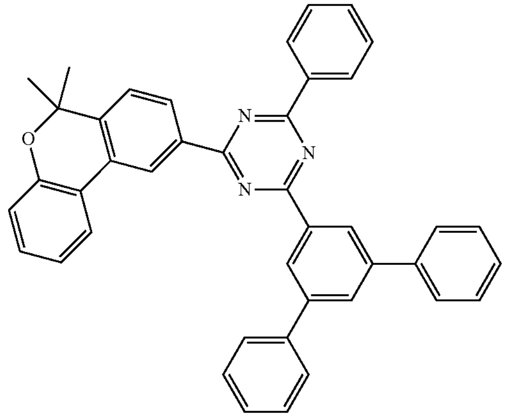 [SMILES: CC1(C)Oc2ccccc2-c2cc(-c3nc(-c4ccccc4)nc(-c4cc(-c5ccccc5)cc(-c5ccccc5)c4)n3)ccc21] | 70 | 594.2 |
| 108 | 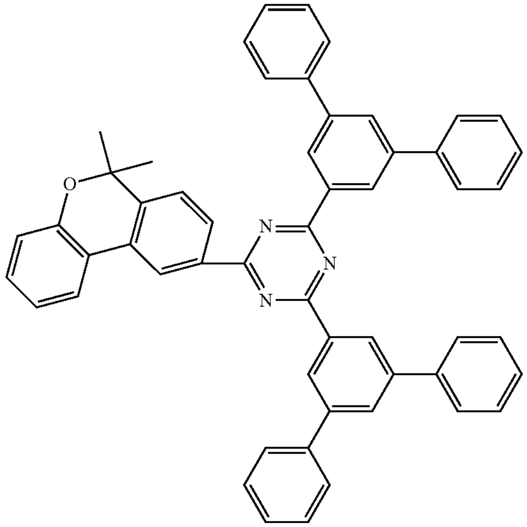 [SMILES: CC1(C)Oc2ccccc2-c2cc(-c3nc(-c4cc(-c5ccccc5)cc(-c5ccccc5)c4)nc(-c4cc(-c5ccccc5)cc(-c5ccccc5)c4)n3)ccc21] | 76 | 746.3 |

TABLE 9-continued
| | | | |
|---|---|---|---|
| 109 | 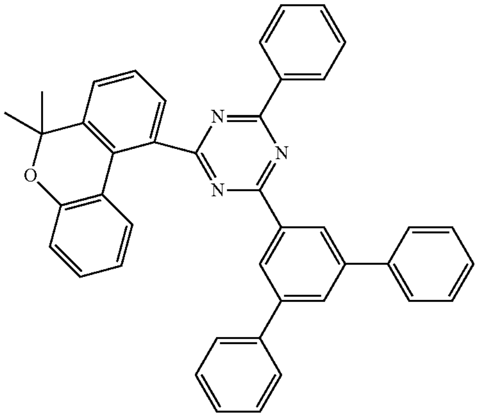 [SMILES: CC1(C)Oc2ccccc2-c2c(-c3nc(-c4ccccc4)nc(-c4cc(-c5ccccc5)cc(-c5ccccc5)c4)n3)cccc21] | 52 | 594.2 |
| 110 | 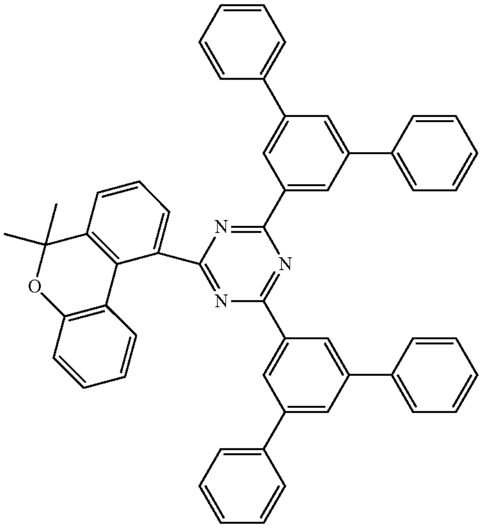 [SMILES: CC1(C)Oc2ccccc2-c2c(-c3nc(-c4cc(-c5ccccc5)cc(-c5ccccc5)c4)nc(-c4cc(-c5ccccc5)cc(-c5ccccc5)c4)n3)cccc21] | 50 | 746.3 |
| 111 | 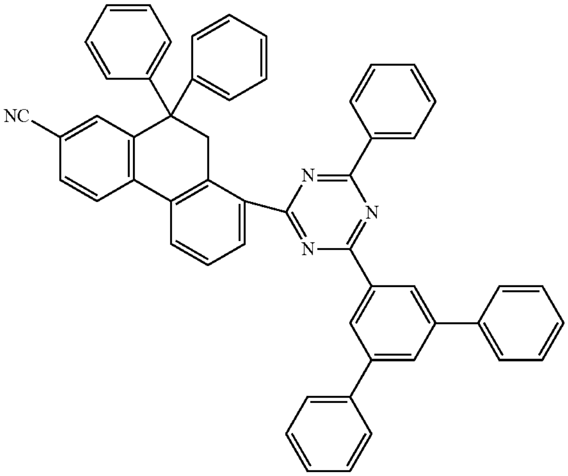 [SMILES: N#Cc1ccc2c(c1)C(c1ccccc1)(c1ccccc1)Cc1c(-c3nc(-c4ccccc4)nc(-c4cc(-c5ccccc5)cc(-c5ccccc5)c4)n3)cccc1-2] | 49 | 743.3 |

TABLE 9-continued
| | | | |
|---|---|---|---|
| 123 | 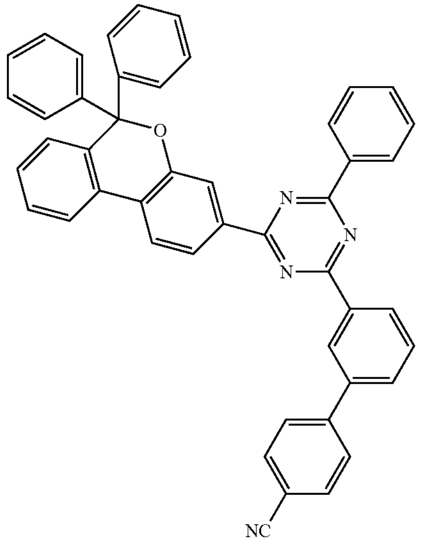 [SMILES: N#Cc1ccc(-c2cccc(-c3nc(-c4ccccc4)nc(-c4ccc5c(c4)OC(c4ccccc4)(c4ccccc4)c4ccccc4-5)n3)c2)cc1] | 76 | 667.2 |
| 131 | 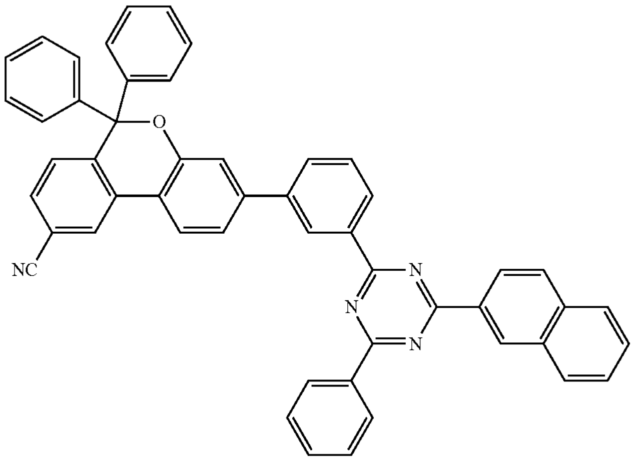 [SMILES: N#Cc1ccc2c(c1)-c1ccc(-c3cccc(-c4nc(-c5ccccc5)nc(-c5ccc6ccccc6c5)n4)c3)cc1OC2(c1ccccc1)c1ccccc1] | 75 | 717.2 |
| 132 | 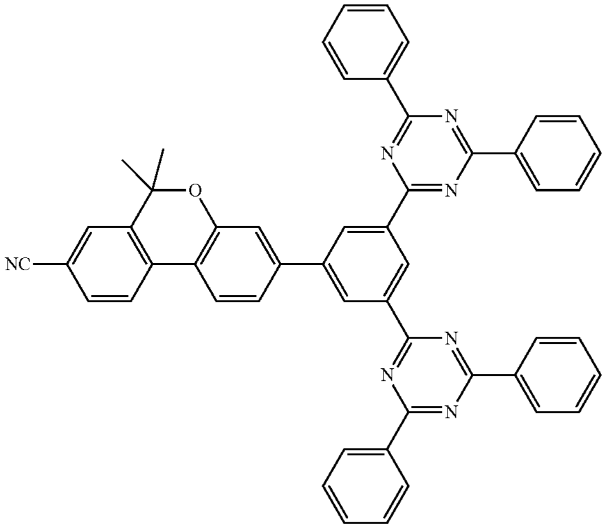 [SMILES: CC1(C)Oc2cc(-c3cc(-c4nc(-c5ccccc5)nc(-c5ccccc5)n4)cc(-c4nc(-c5ccccc5)nc(-c5ccccc5)n4)c3)ccc2-c2ccc(C#N)cc21] | 42 | 774.3 |

TABLE 9-continued
| | | | |
|---|---|---|---|
| 136 | 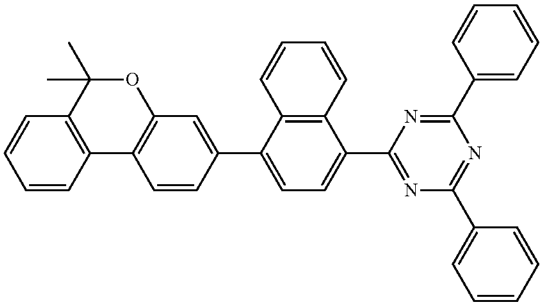 [SMILES: CC1(C)Oc2cc(-c3ccc(-c4nc(-c5ccccc5)nc(-c5ccccc5)n4)c4ccccc34)ccc2-c2ccccc21] | 72 | 552.2 |
| 137 | 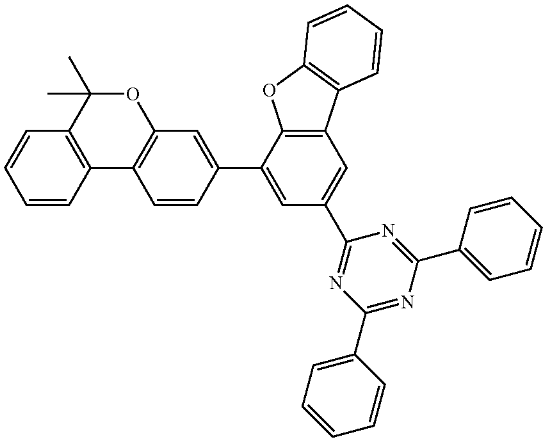 [SMILES: CC1(C)Oc2cc(-c3cc(-c4nc(-c5ccccc5)nc(-c5ccccc5)n4)cc4c3oc3ccccc34)ccc2-c2ccccc21] | 65 | 607.2 |
| 141 | 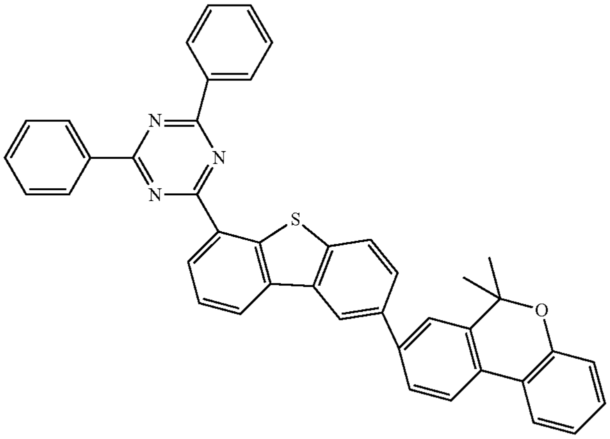 [SMILES: CC1(C)Oc2ccccc2-c2ccc(-c3ccc4sc5c(-c6nc(-c7ccccc7)nc(-c7ccccc7)n6)cccc5c4c3)cc21] | 66 | 624.3 |
| 157 | 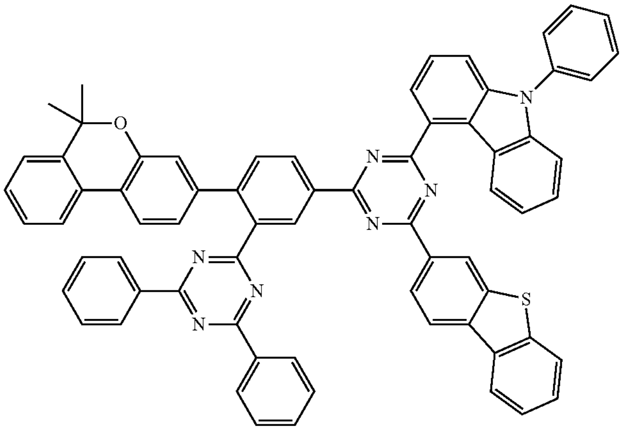 [SMILES: CC1(C)Oc2cc(-c3ccc(-c4nc(-c5ccc6c(c5)sc5ccccc56)nc(-c5cccc6c5c5ccccc5n6-c5ccccc5)n4)cc3-c3nc(-c4ccccc4)nc(-c4ccccc4)n3)ccc2-c2ccccc21] | 42 | 1020.2 |

TABLE 9-continued
| | | | |
|---|---|---|---|
| 335 | 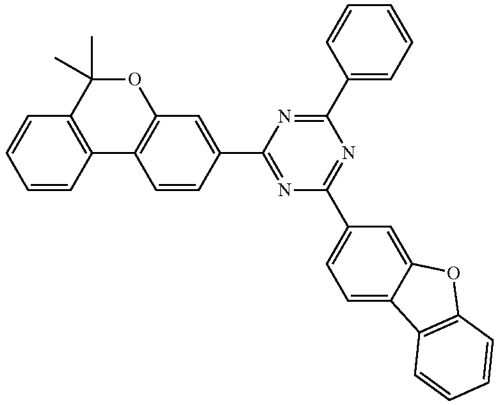 [SMILES: CC1(C)Oc2cc(-c3nc(-c4ccccc4)nc(-c4ccc5c(c4)oc4ccccc45)n3)ccc2-c2ccccc21] | 68 | 532.2 |
| 336 | 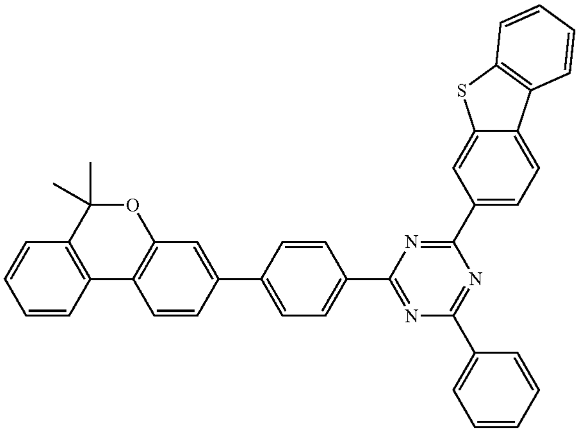 [SMILES: CC1(C)Oc2cc(-c3ccc(-c4nc(-c5ccccc5)nc(-c5ccc6c(c5)sc5ccccc56)n4)cc3)ccc2-c2ccccc21] | 72 | 624.2 |
| 337 | 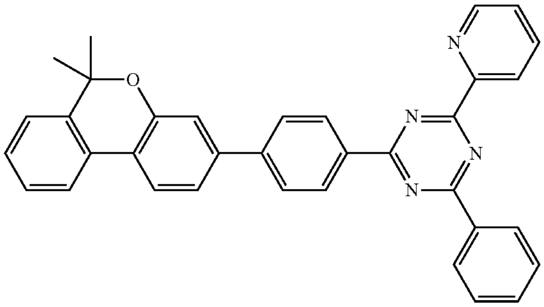 [SMILES: CC1(C)Oc2cc(-c3ccc(-c4nc(-c5ccccc5)nc(-c5ccccn5)n4)cc3)ccc2-c2ccccc21] | 69 | 519.2 |
| 338 | 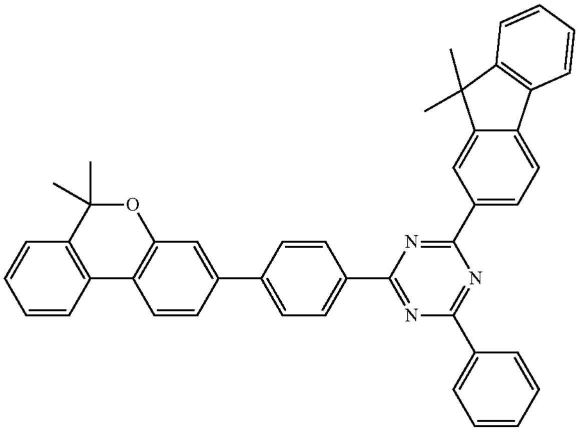 [SMILES: CC1(C)Oc2cc(-c3ccc(-c4nc(-c5ccccc5)nc(-c5ccc6c(c5)C(C)(C)c5ccccc5-6)n4)cc3)ccc2-c2ccccc21] | 72 | 634.3 |

NMR Data of Some Compounds in the Above Table are as Follows:

NMR data of compound 2: $^1H$-NMR (400 MHz, $CDCl_3$): δ 8.92-8.88 (m, 3H), 8.68-8.62 (m, 3H), 8.26 (d, 1H), 8.24 (d, 1H), 7.85-7.50 (m, 8H), 7.38-7.29 (m, 3H), 7.17 (t, 1H) 1.66 (s, 6H) ppm.

NMR data of compound 151: $^1H$-NMR (400 MHz, $CDCl_3$): δ 8.90-8.88 (d, 2H), 8.30-8.25 (m, 4H), 7.98-7.88 (m, 5H), 7.72-7.51 (m, 8H), 7.42-7.29 (m, 4H), 7.19 (t, 1H) 7.16 (s, 1H), 1.66 (s, 6H) ppm.

Other compounds of the present disclosure can be synthesized according to the synthesis methods in the synthesis examples.

DEVICE PREPARATION EXAMPLES

Example 1 Blue Organic Electroluminescent Device

An anode was prepared by the following process: an ITO substrate (manufactured by Corning) having a thickness of 1500 Å was cut into a dimension of 40 mm×40 mm×0.7 mm to be prepared into an experimental substrate with a cathode pattern, an anode pattern and an insulating layer pattern by adopting a photoetching process, and surface treatment was performed by utilizing ultraviolet ozone and $O_2$:$N_2$ plasma so as to increase the work function of the anode (the experimental substrate) and remove scum.

F4-TCNQ was vacuum-evaporated on the experimental substrate (the anode) to form a hole injection layer (HIL) having a thickness of 100 Å, and HT-01 was evaporated on the hole injection layer to form a hole transport layer having a thickness of 1000 Å.

HT-02 was vacuum-evaporated on the hole transport layer to form an electron blocking layer having a thickness of 100 Å.

BH-01 and BD-01 were co-evaporated on the electron blocking layer in a ratio of 98%:2% (an evaporation rate) to form an organic luminescent layer (EML) having a thickness of 220 Å.

A compound BCP was evaporated on the organic luminescent layer to form a hole blocking layer (a-ETL) having a thickness of 50 Å.

A compound 2 and LiQ were mixed at a weight ratio of 1:1 and evaporated on the hole blocking layer to form an electron transport layer (ETL) having a thickness of 300 Å, LiQ was evaporated on the electron transport layer to form an electron injection layer (EIL) having a thickness of 10 Å, and then magnesium (Mg) and argentum (Ag) were mixed at an evaporation rate of 1:9 and vacuum-evaporated on the electron injection layer to form a cathode having a thickness of 115 Å.

In addition, CP-1 having a thickness of 630 Å was evaporated on the cathode to form an organic capping layer (CPL), thus completing the manufacturing of the organic light-emitting device.

Examples 2 to 32

Organic electroluminescent devices were manufactured by the same method as that in Example 1 except that compounds shown in the following Table 11 were used instead of the compound 2 when the electron transport layer was formed.

Example 33

An organic electroluminescent device was manufactured by the same method as that in Example 1 except that when the hole blocking layer was formed, a compound 129 was used instead of BCP to be evaporated on the organic luminescent layer to form the hole blocking layer (a-ETL) having the thickness of 50 Å, and the compound BCP was used instead of the compound 2 to be mixed with LiQ at a weight ratio of 1:1 and evaporated to form the electron transport layer (ETL) having the thickness of 300 Å.

Examples 34 to 71

Organic electroluminescent devices were manufactured by the same method as that in Example 33 except that compounds shown in the following Table 11 were used instead of the compound 129 when the hole blocking layer was formed.

Comparative Example 1

An organic electroluminescent device was manufactured by the same method as that in Example 1 except that a compound A shown in the following Table 10 was used instead of the compound 2 when the electron transport layer was formed.

Comparative Example 2

An organic electroluminescent device was manufactured by the same method as that in Example 1 except that a compound B shown in the following Table 10 was used instead of the compound 2 when the electron transport layer was formed.

Comparative Example 3

An organic electroluminescent device was manufactured by the same method as that in Example 1 except that a compound C shown in the following Table 10 was used instead of the compound 2 when the electron transport layer was formed.

Comparative Example 4

An organic electroluminescent device was manufactured by the same method as that in Example 33 except that the compound A shown in the following Table 10 was used instead of the compound 129 when the hole blocking layer was formed.

Comparative Example 5

An organic electroluminescent device was manufactured by the same method as that in Example 33 except that the compound B shown in the following Table 10 was used instead of the compound 129 when the hole blocking layer was formed.

Comparative Example 6

An organic electroluminescent device was manufactured by the same method as that in Example 33 except that the compound C shown in the following Table 10 was used instead of the compound 129 when the hole blocking layer was formed.

The structures of main materials used in the above examples and comparative examples are shown in Table 10.

TABLE 10
F4-TCNQ
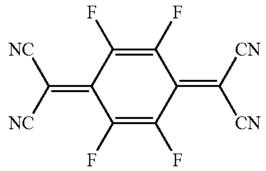 [SMILES: N#CC(C#N)=c1c(F)c(F)c(=C(C#N)C#N)c(F)c1F]
HT-01
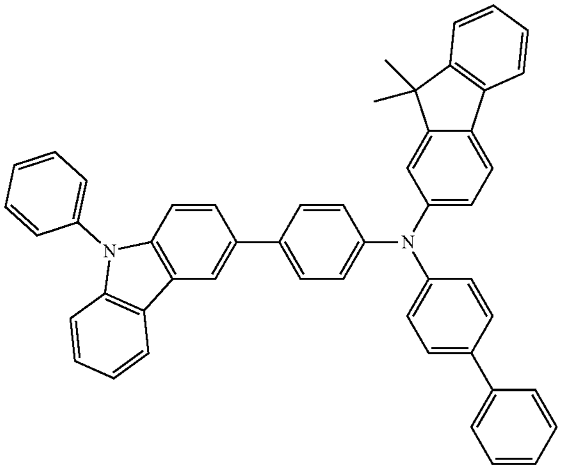 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
HT-02
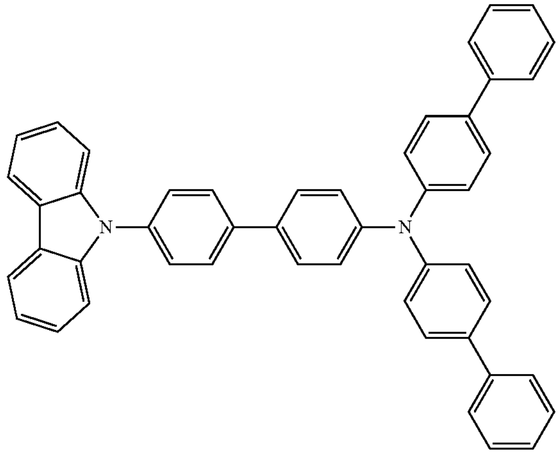 [SMILES: c1ccc(-c2ccc(N(c3ccc(-c4ccccc4)cc3)c3ccc(-c4ccc(-n5c6ccccc6c6ccccc65)cc4)cc3)cc2)cc1]
BH-01
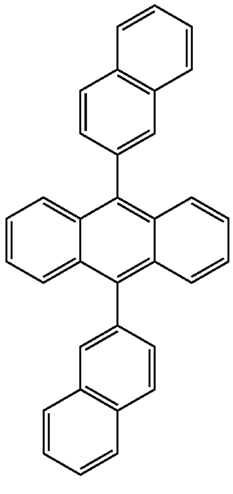 [SMILES: c1ccc2cc(-c3c4ccccc4c(-c4ccc5ccccc5c4)c4ccccc34)ccc2c1]

TABLE 10-continued
BD-01
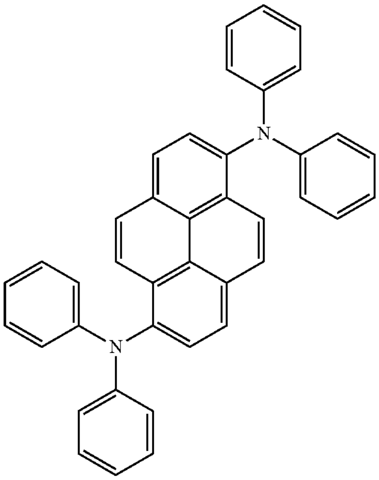 [SMILES: c1ccc(N(c2ccccc2)c2ccc3ccc4c(N(c5ccccc5)c5ccccc5)ccc5ccc2c3c54)cc1]
BCP
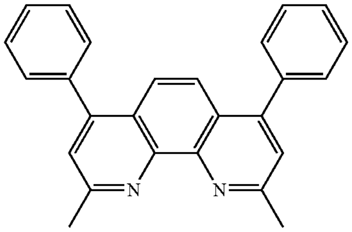 [SMILES: Cc1cc(-c2ccccc2)c2ccc3c(-c4ccccc4)cc(C)nc3c2n1]
LiQ
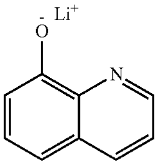 [SMILES: [Li+] ; Oc1cccc2cccnc12]
CP-101
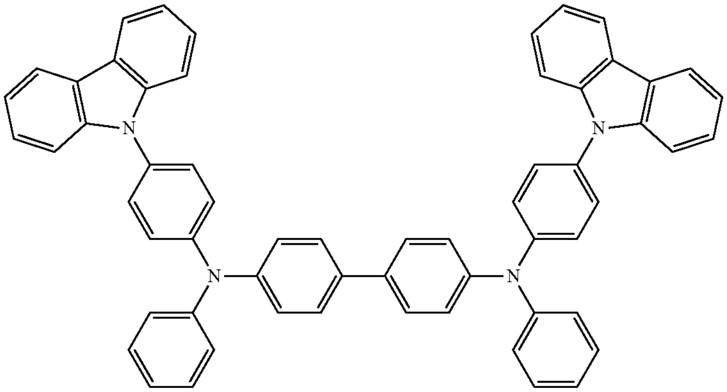 [SMILES: c1ccc(N(c2ccc(-c3ccc(N(c4ccccc4)c4ccc(-n5c6ccccc6c6ccccc65)cc4)cc3)cc2)c2ccc(-n3c4ccccc4c4ccccc43)cc2)cc1]
Compound A
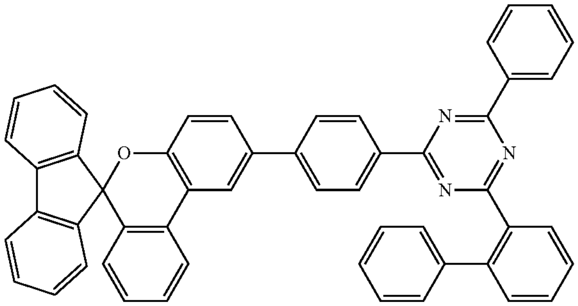 [SMILES: c1ccc(-c2nc(-c3ccc(-c4ccc5c(c4)-c4ccccc4C4(O5)c5ccccc5-c5ccccc54)cc3)nc(-c3ccccc3-c3ccccc3)n2)cc1]

TABLE 10-continued

Compound B

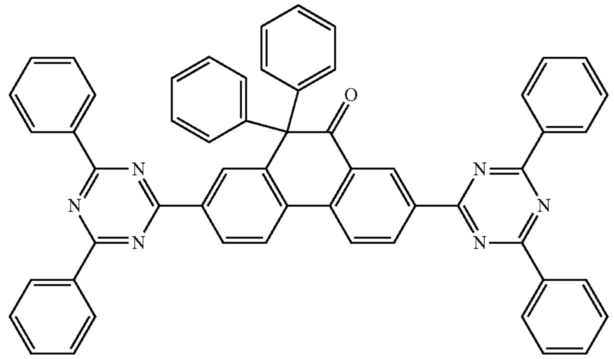 [SMILES: O=C1c2cc(-c3nc(-c4ccccc4)nc(-c4ccccc4)n3)ccc2-c2ccc(-c3nc(-c4ccccc4)nc(-c4ccccc4)n3)cc2C1(c1ccccc1)c1ccccc1]

Compound C

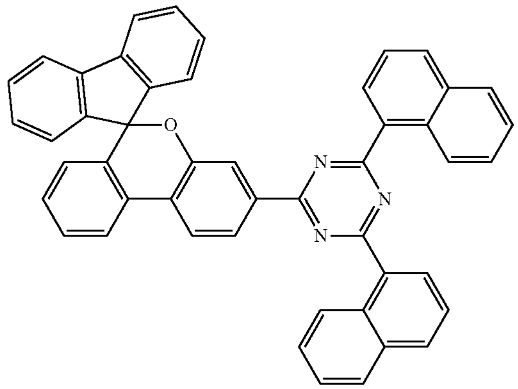 [SMILES: c1ccc2c(c1)-c1ccc(-c3nc(-c4cccc5ccccc45)nc(-c4cccc5ccccc45)n3)cc1OC21c2ccccc2-c2ccccc21]

For the organic electroluminescent devices manufactured in the above examples and comparative examples, the photoelectric performance of the devices under a condition of 10 mA/$cm^2$, and the $T_{95}$ service life of the devices under a condition of 20 mA/$cm^2$ were analyzed, and the results are shown in the following Table 11:

TABLE 11

| No. | a-ETL | ETL | Volt (V) | Cd/A | lm/W | CIE-x | CIE-y | EQE % | T95 (hrs)@20 mA/$cm^2$ |
|---|---|---|---|---|---|---|---|---|---|
| Example 1 | BCP | Compound 2 | 3.75 | 6.52 | 5.46 | 0.14 | 0.05 | 13.41 | 222 |
| Example 2 | BCP | Compound 5 | 3.83 | 6.58 | 5.40 | 0.14 | 0.05 | 13.54 | 181 |
| Example 3 | BCP | Compound 9 | 3.91 | 6.68 | 5.37 | 0.14 | 0.05 | 13.74 | 217 |
| Example 4 | BCP | Compound 12 | 3.74 | 6.52 | 5.48 | 0.14 | 0.05 | 13.41 | 183 |
| Example 5 | BCP | Compound 28 | 3.75 | 6.69 | 5.62 | 0.14 | 0.05 | 13.76 | 220 |
| Example 6 | BCP | Compound 63 | 3.86 | 6.66 | 5.42 | 0.14 | 0.05 | 13.72 | 217 |
| Example 7 | BCP | Compound 66 | 3.89 | 6.77 | 5.47 | 0.14 | 0.05 | 13.93 | 219 |
| Example 8 | BCP | Compound 111 | 3.76 | 6.75 | 5.64 | 0.14 | 0.05 | 13.88 | 179 |
| Example 9 | BCP | Compound 123 | 3.92 | 6.52 | 5.23 | 0.14 | 0.05 | 13.41 | 182 |
| Example 10 | BCP | Compound 124 | 3.77 | 6.69 | 5.57 | 0.14 | 0.05 | 13.76 | 221 |
| Example 11 | BCP | Compound 131 | 3.94 | 6.78 | 5.41 | 0.14 | 0.05 | 13.95 | 185 |
| Example 12 | BCP | Compound 132 | 3.74 | 6.63 | 5.57 | 0.14 | 0.05 | 13.64 | 214 |
| Example 13 | BCP | Compound 292 | 3.79 | 6.79 | 5.63 | 0.14 | 0.05 | 13.97 | 215 |
| Example 14 | BCP | Compound 293 | 3.76 | 6.47 | 5.41 | 0.14 | 0.05 | 13.31 | 219 |
| Example 15 | BCP | Compound 295 | 3.84 | 6.54 | 5.35 | 0.14 | 0.05 | 13.45 | 220 |
| Example 16 | BCP | Compound 296 | 3.77 | 6.62 | 5.52 | 0.14 | 0.05 | 13.62 | 208 |
| Example 17 | BCP | Compound 297 | 3.91 | 6.51 | 5.22 | 0.14 | 0.05 | 13.37 | 216 |
| Example 18 | BCP | Compound 299 | 3.79 | 6.73 | 5.58 | 0.14 | 0.05 | 13.84 | 209 |
| Example 19 | BCP | Compound 300 | 3.88 | 6.76 | 5.47 | 0.14 | 0.05 | 13.91 | 218 |
| Example 20 | BCP | Compound 301 | 3.85 | 6.59 | 5.38 | 0.14 | 0.05 | 13.56 | 210 |
| Example 21 | BCP | Compound 302 | 3.87 | 6.48 | 5.26 | 0.14 | 0.05 | 13.33 | 219 |
| Example 22 | BCP | Compound 303 | 3.76 | 6.78 | 5.66 | 0.14 | 0.05 | 13.95 | 208 |
| Example 23 | BCP | Compound 304 | 3.91 | 6.58 | 5.30 | 0.14 | 0.05 | 13.54 | 203 |
| Example 24 | BCP | Compound 305 | 3.74 | 6.55 | 5.50 | 0.14 | 0.05 | 13.47 | 211 |
| Example 25 | BCP | Compound 308 | 3.86 | 6.57 | 5.35 | 0.14 | 0.05 | 13.51 | 217 |
| Example 26 | BCP | Compound 309 | 3.78 | 6.59 | 5.48 | 0.14 | 0.05 | 13.56 | 212 |
| Example 27 | BCP | Compound 310 | 3.88 | 6.74 | 5.46 | 0.14 | 0.05 | 13.86 | 213 |
| Example 28 | BCP | Compound 312 | 3.95 | 6.72 | 5.34 | 0.14 | 0.05 | 13.82 | 214 |
| Example 29 | BCP | Compound 314 | 3.91 | 6.73 | 5.42 | 0.14 | 0.05 | 13.84 | 211 |
| Example 30 | BCP | Compound 315 | 3.91 | 6.62 | 5.33 | 0.14 | 0.05 | 13.62 | 184 |

TABLE 11-continued

| No. | a-ETL | ETL | Volt (V) | Cd/A | lm/W | CIE-x | CIE-y | EQE % | T95 (hrs)@20 mA/cm$^2$ |
|---|---|---|---|---|---|---|---|---|---|
| Example 31 | BCP | Compound 318 | 3.92 | 6.6 | 5.29 | 0.14 | 0.05 | 13.58 | 180 |
| Example 32 | BCP | Compound 319 | 3.83 | 6.63 | 5.44 | 0.14 | 0.05 | 13.64 | 183 |
| Example 33 | Compound 129 | BCP | 3.82 | 6.45 | 5.30 | 0.14 | 0.05 | 13.27 | 219 |
| Example 34 | Compound 15 | BCP | 3.93 | 6.66 | 5.32 | 0.14 | 0.05 | 13.74 | 211 |
| Example 35 | Compound 22 | BCP | 3.76 | 6.59 | 5.51 | 0.14 | 0.05 | 13.56 | 211 |
| Example 36 | Compound 23 | BCP | 3.79 | 6.47 | 5.36 | 0.14 | 0.05 | 13.31 | 226 |
| Example 37 | Compound 76 | BCP | 3.79 | 6.73 | 5.55 | 0.14 | 0.05 | 13.78 | 178 |
| Example 38 | Compound 86 | BCP | 3.75 | 6.78 | 5.68 | 0.14 | 0.05 | 13.95 | 209 |
| Example 39 | Compound 89 | BCP | 3.76 | 6.78 | 5.66 | 0.14 | 0.05 | 13.95 | 182 |
| Example 40 | Compound 97 | BCP | 3.76 | 6.75 | 5.64 | 0.14 | 0.05 | 13.88 | 185 |
| Example 41 | Compound 99 | BCP | 3.87 | 6.67 | 5.41 | 0.14 | 0.05 | 13.72 | 214 |
| Example 42 | Compound 103 | BCP | 3.85 | 6.46 | 5.27 | 0.14 | 0.05 | 13.29 | 215 |
| Example 43 | Compound 104 | BCP | 3.77 | 6.79 | 5.66 | 0.14 | 0.05 | 13.97 | 224 |
| Example 44 | Compound 105 | BCP | 3.91 | 6.78 | 5.45 | 0.14 | 0.05 | 13.95 | 218 |
| Example 45 | Compound 106 | BCP | 3.81 | 6.52 | 5.38 | 0.14 | 0.05 | 13.41 | 214 |
| Example 47 | Compound 108 | BCP | 3.83 | 6.58 | 5.42 | 0.14 | 0.05 | 13.54 | 218 |
| Example 48 | Compound 109 | BCP | 3.83 | 6.53 | 5.36 | 0.14 | 0.05 | 13.43 | 221 |
| Example 49 | Compound 110 | BCP | 3.79 | 6.53 | 5.41 | 0.14 | 0.05 | 13.43 | 219 |
| Example 50 | Compound 151 | BCP | 3.77 | 6.71 | 5.59 | 0.14 | 0.05 | 13.80 | 208 |
| Example 51 | Compound 288 | BCP | 3.86 | 6.77 | 5.51 | 0.14 | 0.05 | 13.93 | 214 |
| Example 52 | Compound 289 | BCP | 3.92 | 6.61 | 5.30 | 0.14 | 0.05 | 13.62 | 211 |
| Example 53 | Compound 290 | BCP | 3.82 | 6.51 | 5.38 | 0.14 | 0.05 | 13.39 | 227 |
| Example 54 | Compound 291 | BCP | 3.82 | 6.59 | 5.45 | 0.14 | 0.05 | 13.56 | 230 |
| Example 55 | Compound 294 | BCP | 3.88 | 6.51 | 5.27 | 0.14 | 0.05 | 13.39 | 224 |
| Example 56 | Compound 91 | BCP | 3.78 | 6.59 | 5.48 | 0.14 | 0.05 | 13.56 | 215 |
| Example 57 | Compound 298 | BCP | 3.75 | 6.47 | 5.42 | 0.14 | 0.05 | 13.31 | 212 |
| Example 58 | Compound 306 | BCP | 3.81 | 6.53 | 5.36 | 0.14 | 0.05 | 13.37 | 209 |
| Example 59 | Compound 307 | BCP | 3.85 | 6.57 | 5.36 | 0.14 | 0.05 | 13.51 | 221 |
| Example 61 | Compound 313 | BCP | 3.85 | 6.50 | 5.32 | 0.14 | 0.05 | 13.37 | 204 |
| Example 62 | Compound 316 | BCP | 3.93 | 6.58 | 5.26 | 0.14 | 0.05 | 13.54 | 185 |
| Example 63 | Compound 317 | BCP | 3.91 | 6.77 | 5.44 | 0.14 | 0.05 | 13.93 | 183 |
| Example 64 | Compound 136 | BCP | 3.74 | 6.67 | 5.64 | 0.14 | 0.05 | 14.23 | 213 |
| Example 65 | Compound 137 | BCP | 3.84 | 6.76 | 5.67 | 0.14 | 0.05 | 14.33 | 230 |
| Example 66 | Compound 141 | BCP | 3.81 | 6.79 | 5.57 | 0.14 | 0.49 | 13.98 | 241 |
| Example 67 | Compound 157 | BCP | 3.91 | 6.50 | 5.34 | 0.14 | 0.05 | 13.81 | 183 |
| Example 68 | Compound 335 | BCP | 3.70 | 6.75 | 5.66 | 0.14 | 0.05 | 13.95 | 239 |
| Example 69 | Compound 336 | BCP | 3.69 | 6.73 | 5.60 | 0.14 | 0.05 | 13.80 | 232 |
| Example 70 | Compound 337 | BCP | 3.93 | 6.60 | 5.30 | 0.14 | 0.05 | 13.55 | 220 |
| Example 71 | Compound 338 | BCP | 3.72 | 6.73 | 5.65 | 0.14 | 0.05 | 13.91 | 229 |
| Comparative example 1 | BCP | Compound A | 4.02 | 5.27 | 4.15 | 0.14 | 0.05 | 11.65 | 138 |
| Comparative example 2 | BCP | Compound B | 4.02 | 5.15 | 4.42 | 0.14 | 0.05 | 11.62 | 123 |
| Comparative example 3 | BCP | Compound C | 4.19 | 5.32 | 4.29 | 0.14 | 0.05 | 11.77 | 142 |
| Comparative example 4 | Compound A | BCP | 4.01 | 5.83 | 4.32 | 0.14 | 0.05 | 11.93 | 143 |
| Comparative example 5 | Compound B | BCP | 4.12 | 5.47 | 4.07 | 0.14 | 0.05 | 11.25 | 121 |
| Comparative example 6 | Compound C | BCP | 4.07 | 5.86 | 4.27 | 0.14 | 0.05 | 11.93 | 145 |

With reference to the above table, it can be seen that the driving voltage and service life of the devices were significantly improved when the compounds according to the present disclosure were used as electron transport layer materials in examples 1 to 32 compared with comparative examples 1 to 3, where the luminous efficiency was increased by at least 21.8%, the external quantum efficiency was increased by at least 13.1%, and the service life was increased by at least 26.1%.

The luminous efficiency and service life of the devices were significantly improved when the compounds according to the present disclosure were used as hole blocking layer materials in examples 33 to 71 compared with comparative examples 4 to 6, where the luminous efficiency was increased by at least 10.1%, the external quantum efficiency was increased by at least 11.2% and the service life was increased by at least 22.8%.

The reason may be that ortho positions of oxygen atoms in the compounds A and C are spiro rings, a spatial conformation is essentially fixed, and transport efficiency of carriers is not sufficient, leading to lower device efficiency than the compounds according to the present disclosure, and the compounds A and C generate more Joule heat between the organic layers of the luminescent device, or between the organic layers and the metal electrodes, reducing the service life of the device to a certain extent. A core structure of a comparative compound B contains carbonyl, and a C—C bond in the core structure of the compound becomes weakened, reducing the service life of the device to a certain extent.

Thus, when the novel compounds of the present disclosure are used for manufacturing an organic electroluminescent device, the driving voltage of the device can be effectively reduced while also having an improvement on the service life of the device.

Thermal Stability Test of Compounds

The thermal stability data of some materials are shown in Table 12 below, where Tg was measured by using a thermogravimetric analyzer (TGA) and Te was an evaporation temperature of the compounds in an evaporation machine at an evaporation rate of 1 Å/S.

When the compounds were used in mass production of devices, the compounds needed to be heated under evaporation conditions for a long period of time. If the thermal stability of the molecular structures of the compounds is poor under heated conditions, the purity of the compounds will decreases under heated conditions over a long period of time, resulting large differences of performance of devices which are manufactured in the early, middle and late stage of mass production.

In the present disclosure, the stability of the molecular structures of the organic compounds of the present disclosure under heated conditions over a long period of time during mass production evaporation was evaluated by the following method:

the heat resistance test (thermal preservation treatment) was carried out on the compounds of the present disclosure and comparative compounds for 24 hours in a high vacuum environment (<$10^{-6}$ Pa) at a temperature corresponding to an evaporation rate of 5 Å/s. The stability of the organic compound of the present disclosure under mass production conditions was determined by purity decrease values before and after the heat resistance test.

Comparative Compounds:

Compound D

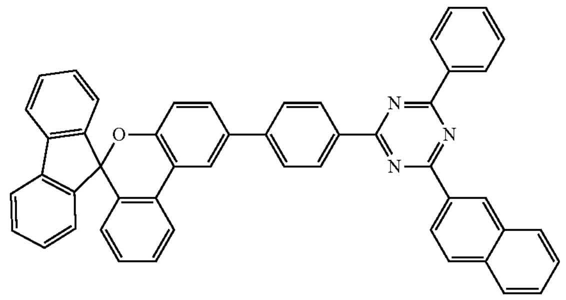

Compound E

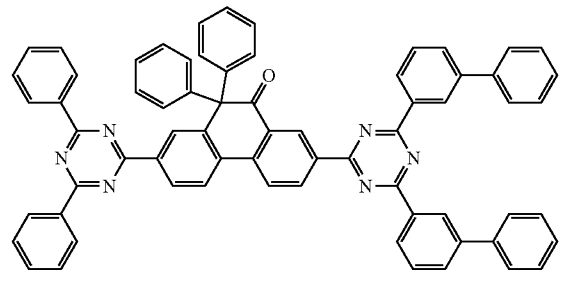

TABLE 12

Test temperature and purity drop value for compounds

| Example | Compound No. | Tg (° C.) | Te (° C.) | Heat resistance test temper-ature (° C.) | Purity drop value (HPLC, %) |
|---|---|---|---|---|---|
| Example R-1 | Compound 124 | 121.3 | 238.3 | 308 | 0.04 |
| Example R-2 | Compound 76 | 187.4 | 276.5 | 346 | 0.07 |

TABLE 12-continued

Test temperature and purity drop value for compounds

| Example | Compound No. | Tg (° C.) | Te (° C.) | Heat resistance test temper-ature (° C.) | Purity drop value (HPLC, %) |
|---|---|---|---|---|---|
| Example R-3 | Compound 129 | 175.5 | 265.3 | 335 | 0.06 |
| Example R-4 | Compound 288 | 110.9 | 220.5 | 290 | 0.01 |
| Example R-5 | Compound 289 | 118.6 | 235.6 | 305 | 0.02 |
| Example R-6 | Compound 290 | 120.6 | 239.3 | 309 | 0.03 |
| Example R-7 | Compound 291 | 134.6 | 231.4 | 301 | 0.03 |
| Example R-8 | Compound 292 | 123.9 | 239.0 | 309 | 0.02 |
| Example R-9 | Compound 293 | 126.1 | 233.7 | 303 | 0.03 |
| Example R-10 | Compound 294 | 164.3 | 259.7 | 329 | 0.06 |
| Example R-11 | Compound 295 | 122.9 | 241.3 | 311 | 0.05 |
| Example R-12 | Compound 296 | 121.4 | 243.5 | 313 | 0.04 |
| Example R-13 | Compound 297 | 125.2 | 252.7 | 322 | 0.04 |
| Example R-14 | Compound 91 | 167.5 | 258.7 | 328 | 0.07 |
| Example R-15 | Compound 298 | 144.2 | 253.4 | 323 | 0.05 |
| Example R-16 | Compound 299 | 127.5 | 245.8 | 315 | 0.03 |
| Example R-17 | Compound 300 | 127.4 | 265.6 | 335 | 0.03 |
| Example R-18 | Compound 301 | 126.3 | 238.5 | 308 | 0.02 |
| Example R-19 | Compound 302 | 174.7 | 276.6 | 346 | 0.06 |
| Example R-20 | Compound 303 | 180.4 | 273.5 | 343 | 0.08 |
| Example R-21 | Compound 304 | 136.3 | 249.6 | 319 | 0.03 |
| Example R-22 | Compound 305 | 132.1 | 248.6 | 318 | 0.03 |
| Example R-23 | Compound 9 | 124.5 | 237.5 | 307 | 0.02 |
| Example R-24 | Compound 306 | 157.3 | 247.5 | 317 | 0.06 |
| Example R-25 | Compound 28 | 152.5 | 239.6 | 309 | 0.04 |
| Example R-26 | Compound 15 | 125.8 | 235.4 | 305 | 0.03 |
| Example R-27 | Compound 22 | 156.3 | 241.4 | 311 | 0.05 |
| Example R-28 | Compound 23 | 155.5 | 242.3 | 312 | 0.04 |
| Example R-29 | Compound 307 | 167.6 | 247.8 | 317 | 0.06 |
| Example R-30 | Compound 308 | 166.5 | 240.9 | 310 | 0.06 |
| Example R-31 | Compound 309 | 164.5 | 246.7 | 316 | 0.04 |
| Example R-32 | Compound 310 | 165.3 | 239.4 | 309 | 0.05 |
| Example R-33 | Compound 311 | 168.7 | 264.5 | 334 | 0.06 |
| Example R-34 | Compound 312 | 170.4 | 265.5 | 335 | 0.06 |
| Example R-35 | Compound 313 | 172.3 | 275.2 | 345 | 0.07 |
| Example R-36 | Compound 314 | 168.4 | 268.5 | 338 | 0.06 |
| Example R-37 | Compound 315 | 170.0 | 268.4 | 338 | 0.05 |
| Example R-38 | Compound 316 | 167.5 | 264.9 | 334 | 0.05 |
| Example R-39 | Compound 317 | 127.3 | 231.5 | 301 | 0.03 |
| Example R-40 | Compound 318 | 163.3 | 246.9 | 316 | 0.04 |
| Example R-41 | Compound 319 | 175.8 | 273.5 | 343 | 0.06 |
| Example R-42 | Compound 12 | 173.3 | 245.8 | 315 | 0.05 |
| Example R-43 | Compound 2 | 126.4 | 241.2 | 311 | 0.04 |
| Example R-44 | Compound 5 | 166.9 | 244.3 | 314 | 0.05 |
| Example R-45 | Compound 63 | 163.5 | 230.0 | 300 | 0.05 |
| Example R-46 | Compound 66 | 168.3 | 267.2 | 337 | 0.06 |
| Example R-47 | Compound 86 | 169.1 | 265.3 | 335 | 0.05 |
| Example R-48 | Compound 89 | 168.4 | 268.5 | 338 | 0.08 |
| Example R-49 | Compound 97 | 169.4 | 271.5 | 341 | 0.08 |
| Example R-50 | Compound 99 | 154.3 | 264.3 | 334 | 0.06 |
| Example R-51 | Compound 103 | 127.2 | 228.5 | 278 | 0.03 |
| Example R-52 | Compound 104 | 165.5 | 265.9 | 335 | 0.04 |
| Example R-53 | Compound 105 | 129.4 | 232.7 | 302 | 0.02 |
| Example R-54 | Compound 106 | 166.4 | 267.2 | 337 | 0.04 |
| Example R-55 | Compound 107 | 164.6 | 232.9 | 302 | 0.02 |
| Example R-56 | Compound 108 | 167.7 | 265.1 | 335 | 0.03 |
| Example R-57 | Compound 109 | 131.8 | 236.8 | 306 | 0.02 |
| Example R-58 | Compound 110 | 162.5 | 268.0 | 338 | 0.03 |
| Example R-59 | Compound 111 | 165.6 | 264.8 | 334 | 0.03 |
| Example R-60 | Compound 123 | 169.3 | 254.4 | 324 | 0.03 |
| Example R-61 | Compound 131 | 158.5 | 261.2 | 331 | 0.05 |
| Example R-62 | Compound 132 | 175.6 | 270.5 | 340 | 0.05 |
| Example R-63 | Compound 136 | 126.7 | 247.4 | 317 | 0.05 |
| Example R-64 | Compound 137 | 139.5 | 239.4 | 309 | 0.04 |
| Example R-65 | Compound 141 | 135.7 | 235.2 | 305 | 0.03 |
| Example R-66 | Compound 157 | 194.8 | 278.1 | 358 | 0.08 |
| Example R-67 | Compound 151 | 163.5 | 258.0 | 328 | 0.02 |
| Example R-68 | Compound 335 | 119.4 | 237.5 | 307 | 0.02 |
| Example R-69 | Compound 336 | 133.6 | 248.2 | 318 | 0.03 |
| Example R-70 | Compound 337 | 118.9 | 232.4 | 302 | 0.06 |

TABLE 12-continued

Test temperature and purity drop value for compounds

| Example | Compound No. | Tg (° C.) | Te (° C.) | Heat resistance test temperature (° C.) | Purity drop value (HPLC, %) |
|---|---|---|---|---|---|
| Example R-71 | Compound 338 | 135.6 | 250.2 | 320 | 0.04 |
| Comparative example R-1 | Compound D | 169.2 | 284.3 | 335 | 1.4 |
| Comparative example R-2 | Compound E | 188.6 | 298.1 | 338 | 2.2 |

It can be seen from Table 12 above that the compounds of the present disclosure have lower decomposition possibility in the film-forming process of devices through evaporation at a high temperature, and have higher crystallization resistance in the electric Joule thermal environment during device operation.

The evaporation temperature (Te) of the compounds of the present disclosure is lower under the condition that the molecular weight is not much different compared with the compounds of the comparative examples. According to Table 12, it can be seen that the purity decrease values of the organic compounds of the present disclosure are all less than 0.1% after heated. Whereas in the comparative examples, the purity decrease values are more than 1%, and thus the compounds of the present disclosure have better thermal stability.

When the purity decrease values of the compounds are more than 1%, the efficiency and service life of the device will be significantly reduced; and thermally unstable compounds will lead to large differences in the performance of devices manufactured in the early, middle and late stage of actual mass production use. The heat resistance test of the compounds in the present disclosure demonstrates that the purity decrease values are all less than 0.1%, and the purity decrease values of the compounds in comparative examples are more than 1% at a test temperature (Te+70° C.), and thus the compounds of the present disclosure have better thermal stability in mass production than the compounds in comparative examples.

Preferred embodiments of the present disclosure have been described above in detail with reference to the accompanying drawings, but the present disclosure is not limited to specific details in the above-described embodiments, and many simple modifications may be made to the technical solutions of the present disclosure within the technical idea of the present disclosure, and these simple modifications are all within the scope of protection of the present disclosure.

What is claimed is:

1. An organic compound, having a structure as shown in the following formula (1):

Formula (1)

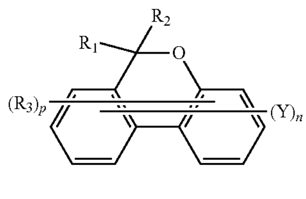

-continued

Formula (2)

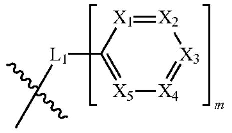

wherein in the formula (1), $R_1$ and $R_2$ are the same as or different from each other, and are each independently selected from substituted or unsubstituted alkyl with 1 to 4 carbon atoms, or substituted or unsubstituted phenyl; and when $R_1$ or $R_2$ is substituted alkyl, substituents in the substituted alkyl are the same or different, and are each independently selected from the group consisting of deuterium, fluorine, chlorine, and cyano; and when $R_1$ or $R_2$ is substituted phenyl, substituents in the substituted phenyl are the same or different, and are each independently selected from the group consisting of alkyl with 1 to 6 carbon atoms, cyano, a halogen group, deuterium, and trimethylsilyl;

each $R_3$ is the same as or different from each other, and is independently selected from the group consisting of deuterium; a halogen group; cyano; haloalkyl with 1 to 12 carbon atoms; alkyl with 1 to 12 carbon atoms; alkoxy with 1 to 12 carbon atoms; cycloalkyl with 3 to 12 carbon atoms; alkylthio with 1 to 12 carbon atoms; trialkylsilyl with 3 to 12 carbon atoms; aryl with 6 to 20 carbon atoms which can be unsubstituted or substituted by 1, 2, 3, 4, or 5 substituents independently selected from deuterium, fluorine, chlorine, or cyano; heteroaryl with 3 to 20 carbon atoms which can be unsubstituted or substituted by 1, 2, 3, 4, or 5 substituents independently selected from deuterium, fluorine, chlorine, or cyano; aryloxy with 6 to 20 carbon atoms; arylthio with 6 to 20 carbon atoms; arylsilyl with 6 to 18 carbon atoms; and alkylphosphinyloxy with 1 to 12 carbon atoms;

p is selected from 0, 1, 2, 3, 4, 5, 6 or 7;

each Y is the same as or different from each other, and independently has a structure as shown in a formula (2), $X_1$, $X_2$, $X_3$, $X_4$, and $X_5$ are the same as or different from each other, and are each independently $C(R_4)$ or N, and at least one of $X_1$, $X_2$, $X_3$, $X_4$, and $X_5$ is N;

m is selected from 1 or 2; and n is selected from 1 or 2;

in the formula (2), each $R_4$ is the same as or different from each other, and is independently hydrogen or

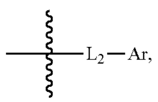

or two adjacent $R_4$ are connected to each other to form a substituted or unsubstituted 5- to 10-membered aromatic ring or a substituted or unsubstituted 5- to 10-membered heteroaromatic ring; substituents in the substituted 5- to 10-membered aromatic ring or the substituted 5- to 10-membered heteroaromatic ring are the same as or different from each other, and are each independently selected from the group consisting of deuterium, a halogen group, cyano, alkyl with 1 to 12 carbon atoms, haloalkyl with 1 to 12 carbon atoms, alkoxy with 1 to 12 carbon atoms, alkylthio with 1 to 12 carbon atoms, aryl with 6 to 25 carbon atoms, heteroaryl with 3 to 20 carbon atoms, trialkylsilyl with 3 to 12 carbon atoms, arylsilyl with 8 to 18 carbon atoms, and cycloalkyl with 3 to 12 carbon atoms;

each Ar is independently selected from the group consisting of substituted or unsubstituted aryl with 6 to 40 carbon atoms, substituted or unsubstituted heteroaryl with 3 to 40 carbon atoms, substituted or unsubstituted alkyl with 1 to 12 carbon atoms, substituted or unsubstituted cycloalkyl with 3 to 12 carbon atoms, substituted or unsubstituted aralkyl with 7 to 30 carbon atoms, and substituted or unsubstituted heteroaralkyl with 4 to 30 carbon atoms;

each $L_1$ and each $L_2$ are the same as or different from each other, and are each independently selected from the group consisting of a single bond, substituted or unsubstituted arylene with 6 to 30 carbon atoms, and substituted or unsubstituted heteroarylene with 3 to 30 carbon atoms; and substituents in each $L_1$, each $L_2$ and each Ar are the same as or different from each other, and are each independently selected from the group consisting of deuterium; a halogen group; cyano; alkyl with 1 to 12 carbon atoms; haloalkyl with 1 to 12 carbon atoms; alkoxy with 1 to 12 carbon atoms; alkylthio with 1 to 12 carbon atoms; aryl with 6 to 25 carbon atoms which can be substituted or substituted by substituents selected from deuterium, fluorine, cyano, or alkyl; heteroaryl with 3 to 20 carbon atoms; aryloxy with 6 to 20 carbon atoms; arylthio with 6 to 20 carbon atoms; trialkylsilyl with 3 to 12 carbon atoms; arylsilyl with 8 to 18 carbon atoms; and cycloalkyl with 3 to 12 carbon atoms; and in each $L_1$, each $L_2$ and each Ar, when there are two substituents on a same atom, the two substituents are connected to each other to form a 5- to 18-membered aliphatic ring or a 5- to 18-membered aromatic ring together with the atoms to which they are jointly connected, or the two substituents exist independently of each other.

2. The organic compound according to claim 1, wherein the organic compound has a structure represented by the following formula (1-1), formula (1-2), formula (1-3), or formula (1-4):

Formula (1-1)

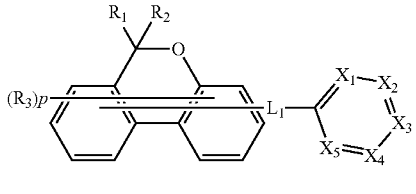

Formula (1-2)

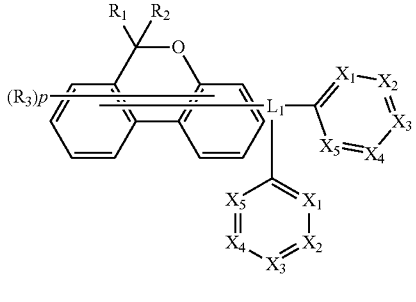

-continued

Formula (1-3)

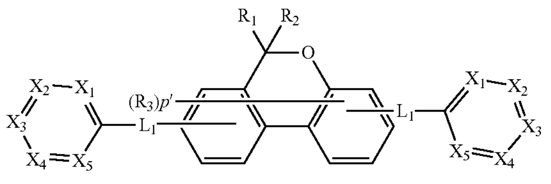

Formula (1-4)

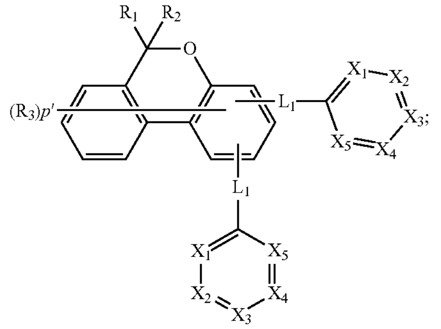

wherein in the formula (1-3) and the formula (1-4), p' is selected from 0, 1, 2, 3, 4, 5, or 6.

3. The organic compound according to claim 1, wherein $R_1$ and $R_2$ are the same as or different from each other, and are each independently selected from methyl, or substituted or unsubstituted phenyl, and the substituents in the substituted phenyl are each independently selected from the group consisting of cyano, fluorine, chlorine, deuterium, methyl, ethyl, isopropyl, tert-butyl, and trimethylsilyl.

4. The organic compound according to claim 1, wherein the Y has a structure represented by the following formula (2-1):

Formula (2-1)

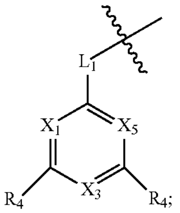

wherein $X_1$, $X_3$, and $X_5$ are the same or different, and are each independently $C(R_4)$ or N, and any one, any two, or all of $X_1$, $X_3$, and $X_5$ are N; and each $R_4$ is the same or different, and is independently hydrogen or

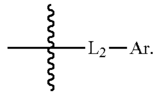

5. The organic compound according to claim 1, wherein the Y has a structure represented by the following formula (2-2):

Formula (2-2)

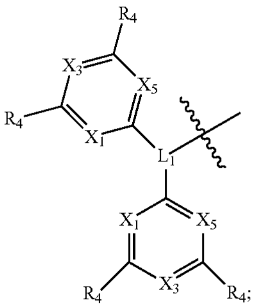

wherein $X_1$, $X_3$, and $X_5$ are the same or different, and are each independently $C(R_4)$ or N, and any one, any two, or all of $X_1$, $X_3$, and $X_5$ are N; and each $R_4$ is the same or different, and is independently hydrogen or

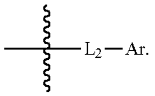

6. The organic compound according to claim 1, wherein each Ar is independently selected from substituted or unsubstituted aryl with 6 to 19 carbon atoms, substituted or unsubstituted heteroaryl with 5 to 18 carbon atoms, substituted or unsubstituted alkyl with 1 to 4 carbon atoms, or substituted or unsubstituted cycloalkyl with 5 to 7 carbon atoms;

substituents in each Ar are independently selected from the group consisting of alkyl with 1 to 4 carbon atoms, alkoxy with 1 to 4 carbon atoms, trifluoromethyl, trimethylsilyl, triphenylsilyl, cycloalkyl with 5 to 7 carbon atoms, phenyl, naphthyl, dibenzofuranyl, dibenzothienyl, carbazolyl, pyridyl, pyrimidinyl, indolyl, and benzimidazolyl.

7. The organic compound according to claim 1, wherein each Ar is independently selected from a substituted or unsubstituted group $W_3$; and the unsubstituted group $W_3$ is selected from the group consisting of:

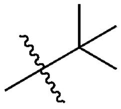
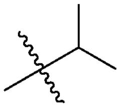
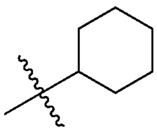
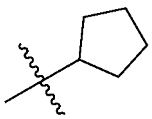
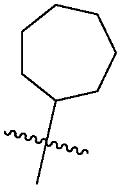
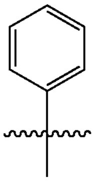

-continued

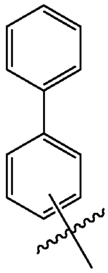
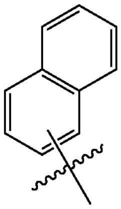
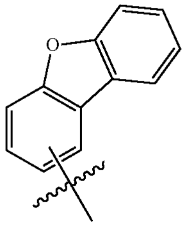
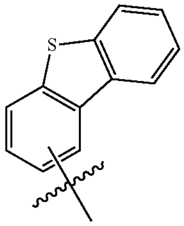
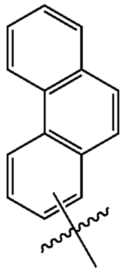
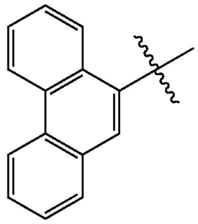
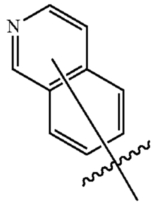
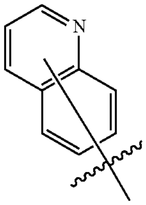
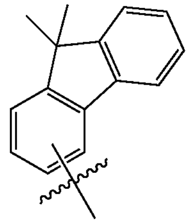
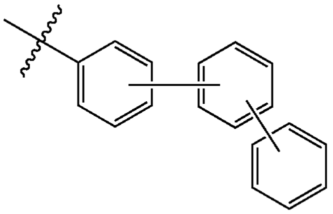
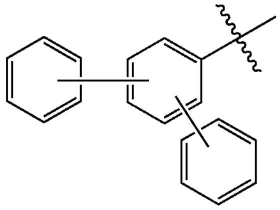

-continued
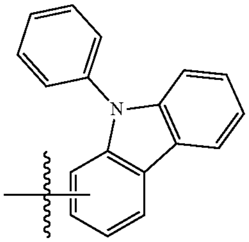
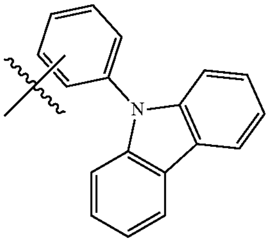
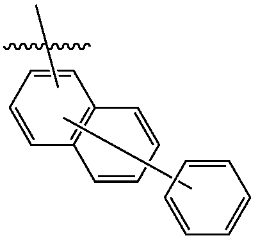
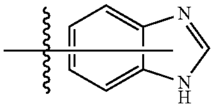
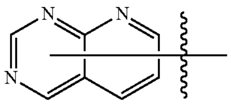
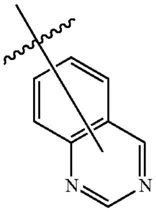
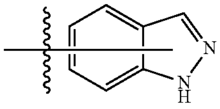
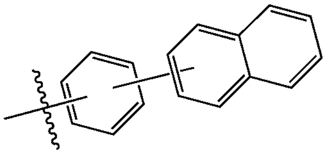
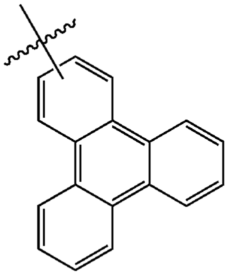
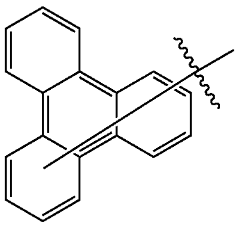
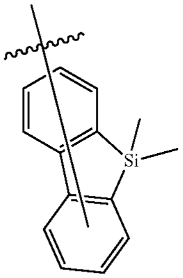
-continued
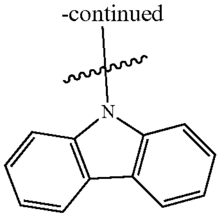
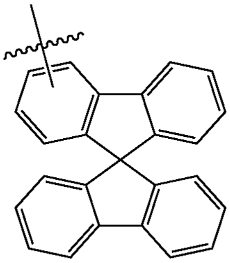
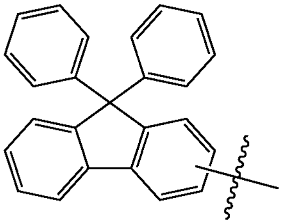
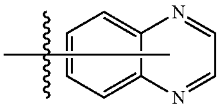
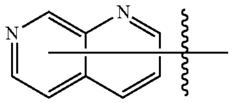
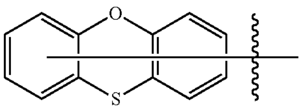
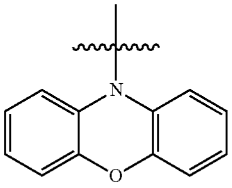
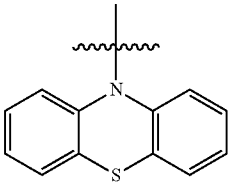
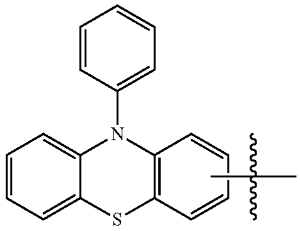
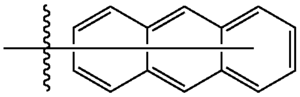
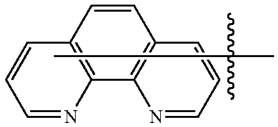

-continued
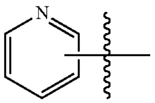
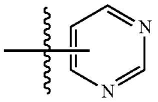
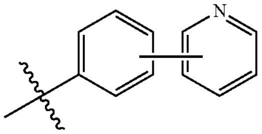
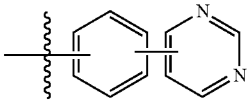
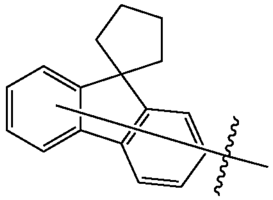
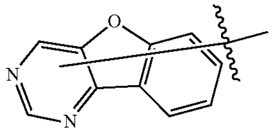
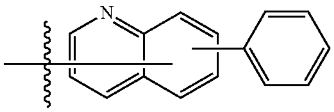
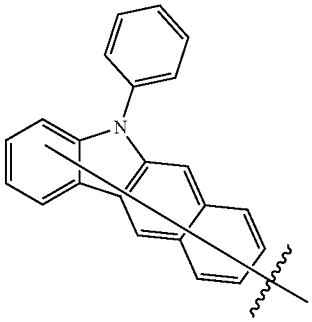
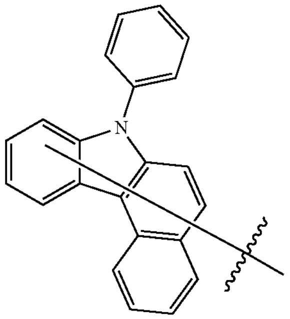
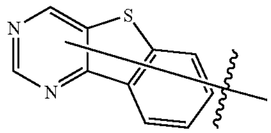
-continued
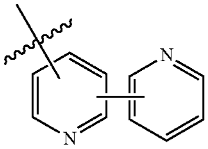
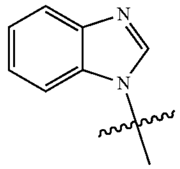
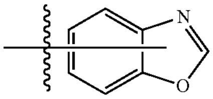
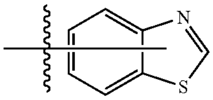
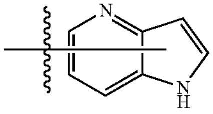
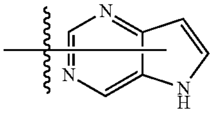
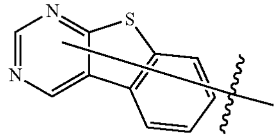
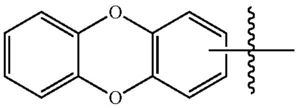
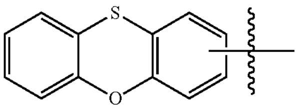
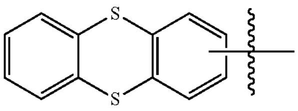
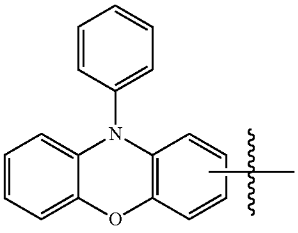
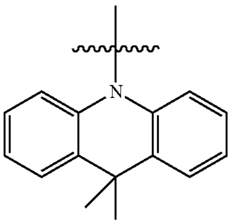

-continued

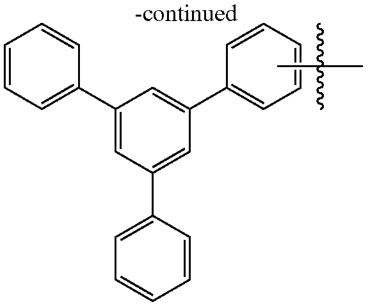

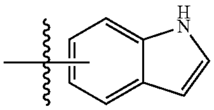

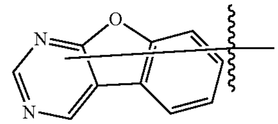

;

when the group $W_3$ is substituted, substituents in the group $W_3$ are selected from the group consisting of deuterium, fluorine, chlorine, cyano, alkyl with 1 to 4 carbon atoms, alkoxy with 1 to 4 carbon atoms, trifluoromethyl, trimethylsilyl, triphenylsilyl, cycloalkyl with 5 to 7 carbon atoms, phenyl, naphthyl, dibenzofuranyl, dibenzothienyl, carbazolyl, pyridyl, pyrimidinyl, indolyl, and benzimidazolyl; and when the group $W_3$ has a plurality of substituents, the substituents are the same as or different from each other.

8. The organic compound according to claim 1, wherein each Ar is independently selected from: substituted or unsubstituted phenyl, substituted or unsubstituted biphenyl, substituted or unsubstituted terphenyl, substituted or unsubstituted naphthyl, substituted or unsubstituted dibenzofuranyl, substituted or unsubstituted dibenzothienyl, substituted or unsubstituted quinolyl, substituted or unsubstituted carbazolyl, substituted or unsubstituted naphthyl, substituted or unsubstituted fluorenyl, substituted or unsubstituted anthryl, substituted or unsubstituted phenanthryl, substituted or unsubstituted pyrimidinyl, substituted or unsubstituted pyridyl, substituted or unsubstituted pyrazinyl, substituted or unsubstituted quinolyl, substituted or unsubstituted isoquinolyl, substituted or unsubstituted quinazolinyl, substituted or unsubstituted benzoxazinyl, substituted or unsubstituted indolyl, substituted or unsubstituted benzimidazolyl, substituted or unsubstituted benzoxazolyl, substituted or unsubstituted dibenzothianthryl, substituted or unsubstituted acridinyl, substituted or unsubstituted dibenzodioxinyl, substituted or unsubstituted phenoxytheophyllinyl, substituted or unsubstituted thianthryl, substituted or unsubstituted phenothiazinyl, substituted or unsubstituted benzoxazinyl, or a group formed by linking two or three of the above groups via a single bond; and substitution in each Ar means that each Ar is substituted by 1, 2, 3, 4, 5, 6, 7, or 8 substituents selected from deuterium, fluorine, chlorine, cyano, methyl, ethyl, isopropyl, tert-butyl, methoxy, ethoxy, isopropoxy, propoxy, cyclopentyl, cyclohexyl, trifluoromethyl, phenyl, biphenyl, naphthyl, trimethylsilyl, or triphenylsilyl.

9. The organic compound according to claim 1, wherein $L_1$ and $L_2$ are each independently selected from substituted or unsubstituted arylene with 6 to 18 carbon atoms, substituted or unsubstituted heteroarylene with 4 to 18 carbon atoms, or a subunit group formed by linking two of the above groups via a single bond; and substituents in $L_1$ and $L_2$ are independently selected from the group consisting of deuterium, fluorine, chlorine, cyano, methyl, ethyl, isopropyl, tert-butyl, methoxy, ethoxy, isopropoxy, propoxy, trifluoromethyl, trimethylsilyl, phenyl, naphthyl, dibenzofuranyl, dibenzothienyl, carbazolyl, pyridyl, pyrimidinyl, and triphenylsilyl.

10. The organic compound according to claim 1, wherein each $L_2$ is independently selected from a single bond, and a substituted or unsubstituted group $W_4$, and the unsubstituted group $W_4$ is selected from the group consisting of:

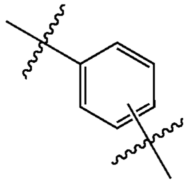

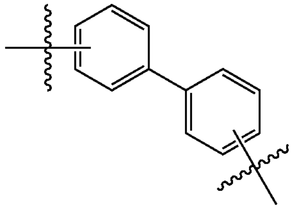

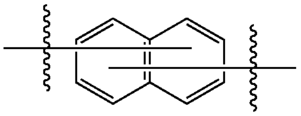

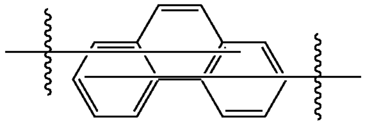

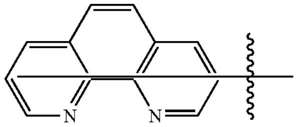

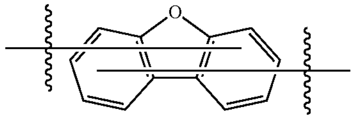

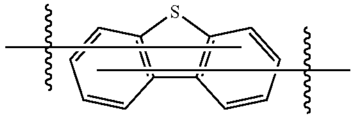

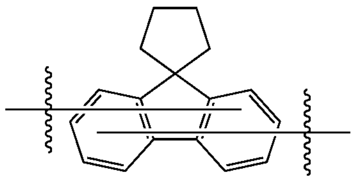

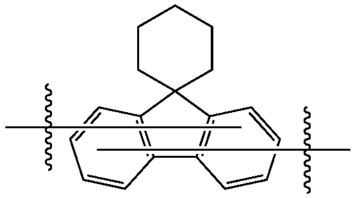

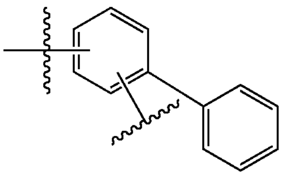

-continued
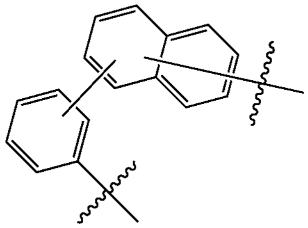
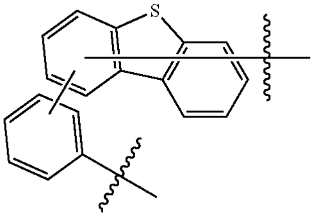
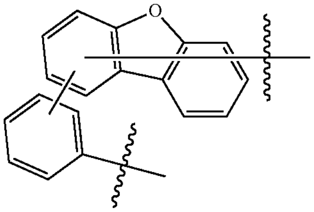
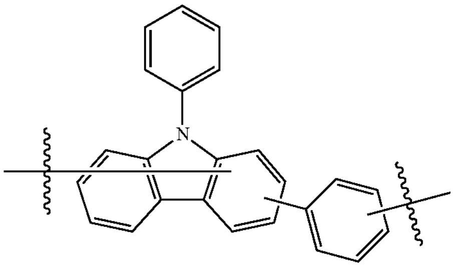
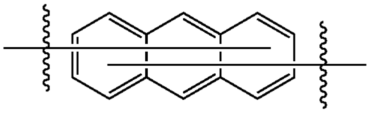
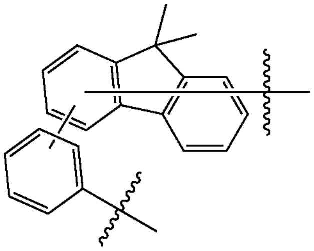
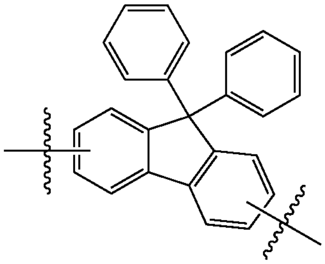
-continued
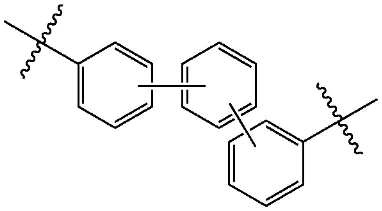
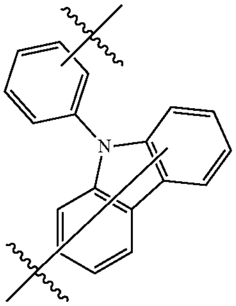
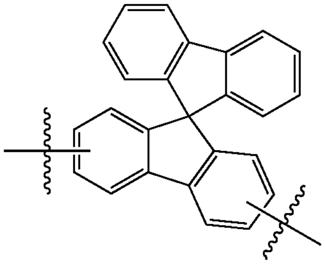
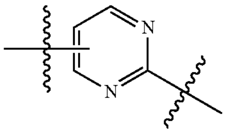
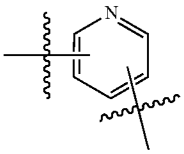
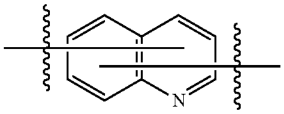
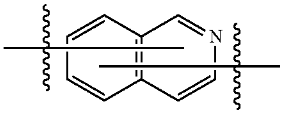
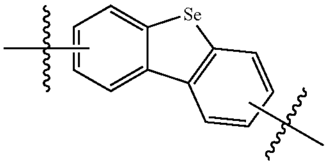
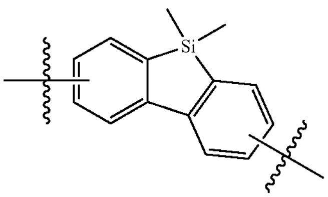

-continued

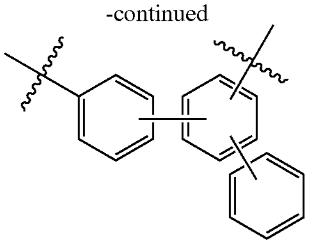

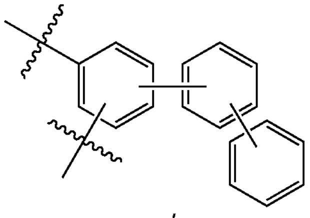

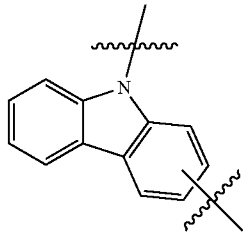

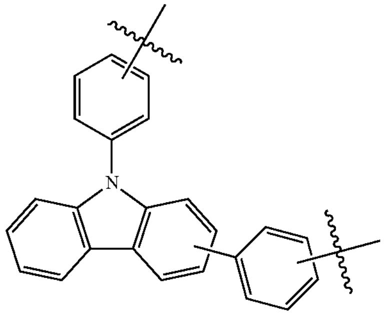

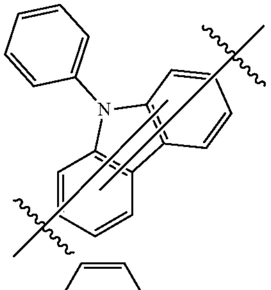

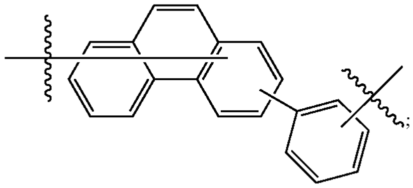;

and when the group $W_4$ is substituted by one or more substituents, the substituents in the group $W_4$ are each independently selected from the group consisting of deuterium, fluorine, chlorine, cyano, methyl, ethyl, isopropyl, n-propyl, tert-butyl, alkoxy with 1 to 4 carbon atoms, trifluoromethyl, trimethylsilyl, cyclopentyl, cyclohexyl, phenyl, naphthyl and heteroaryl with 5 to 12 carbon atoms; and when the number of the substituents in the group $W_4$ is more than 1, the substituents are the same or different.

11. The organic compound according to claim 1, wherein when m in the formula (1) is equal to 1, each $L_1$ is independently selected from a single bond or a substituted or unsubstituted group $W_1$, and the unsubstituted group $W_1$ is selected from the group consisting of:

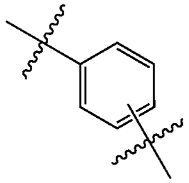

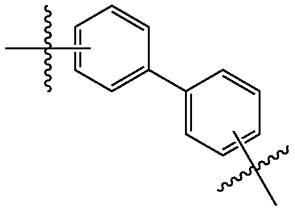

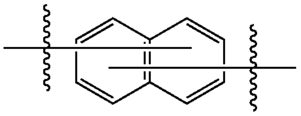

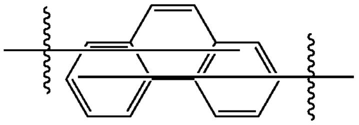

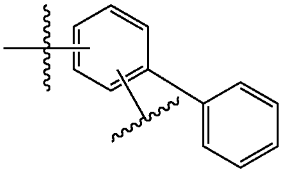

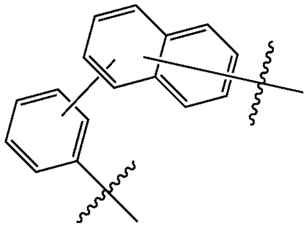

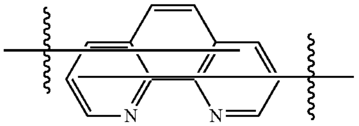

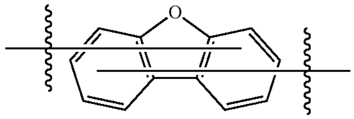

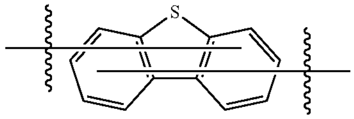

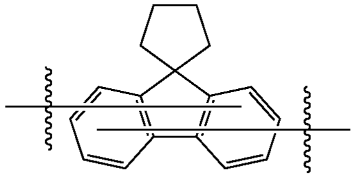

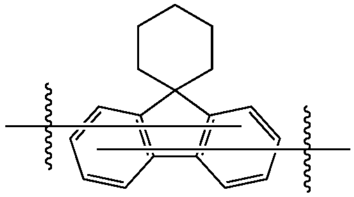

-continued
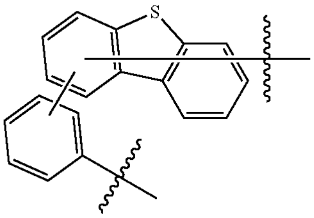
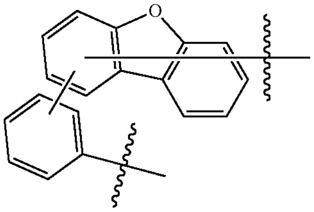
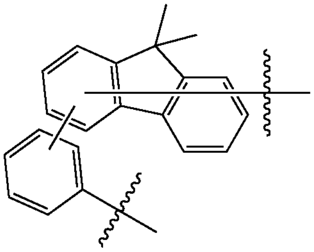
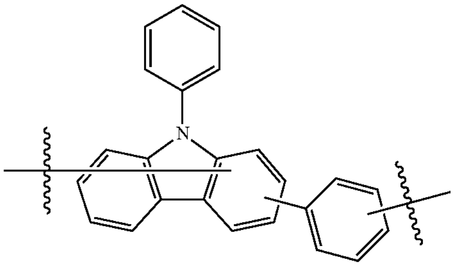
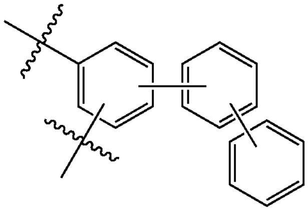
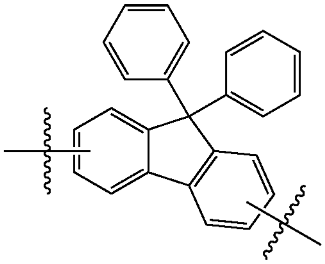
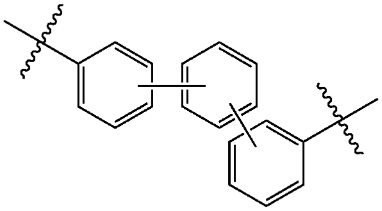
-continued
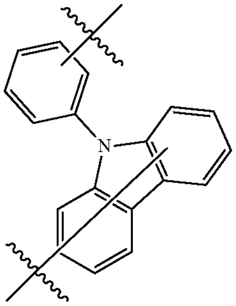
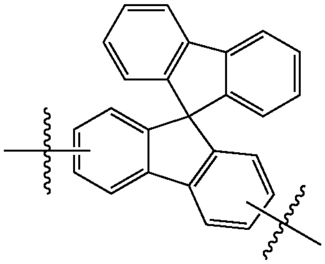
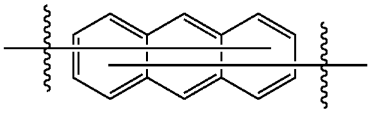
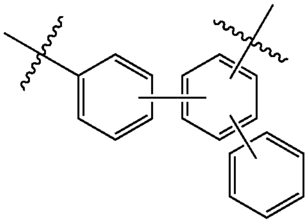
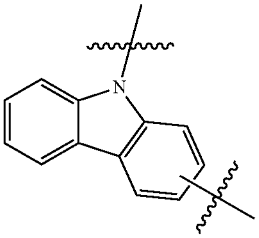
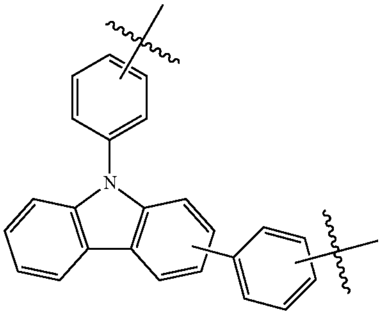
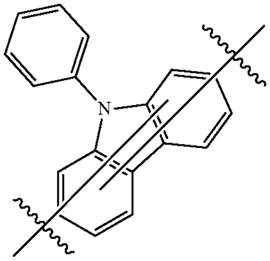

-continued

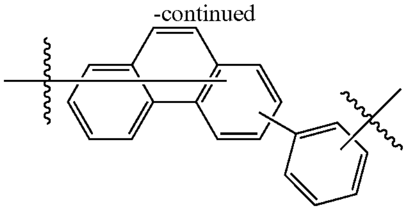

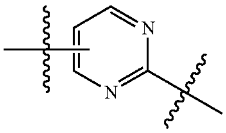

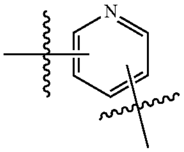

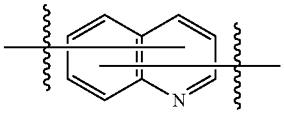

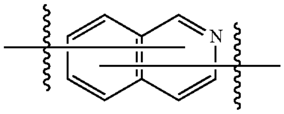

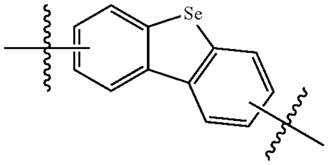

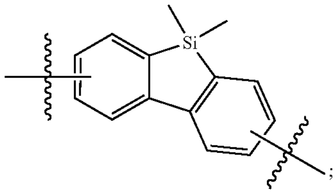

;

when the group $W_1$ is substituted by one or more substituents, the substituents in the group $W_1$ are each independently selected from the group consisting of deuterium; fluorine; chlorine; cyano; alkyl with 1 to 4 carbon atoms; alkoxy with 1 to 4 carbon atoms; trifluoromethyl; trimethylsilyl; cyclopentyl; cyclohexyl; aryl with 6 to 12 carbon atoms which can be unsubstituted or substituted by 1, 2, 3, 4, or 5 substituents selected from deuterium, fluorine, cyano, methyl, isopropyl, or tert-butyl; and heteroaryl with 5 to 12 carbon atoms; and when the number of the substituents in the group $W_1$ is more than 1, the substituents are the same or different;

when m in the formula (1) is equal to 2, each $L_1$ is independently selected from a single bond or a substituted or unsubstituted group $W_2$, and the unsubstituted group $W_2$ is selected from the group consisting of:

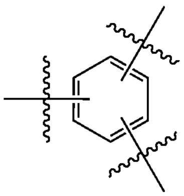

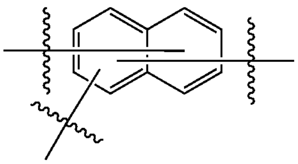

-continued

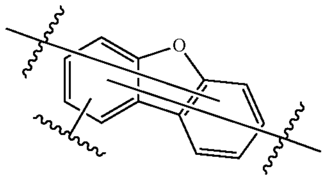

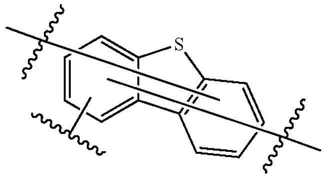

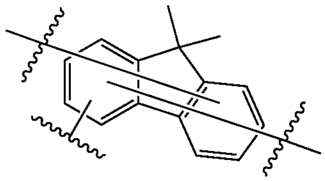

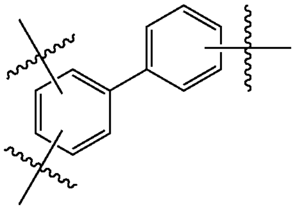

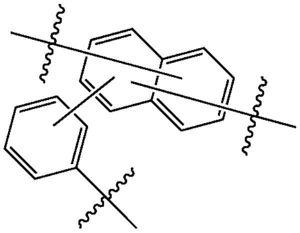

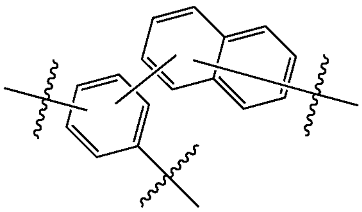

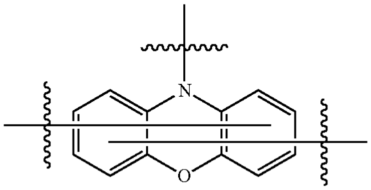

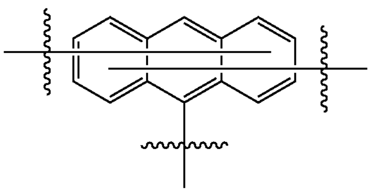

-continued
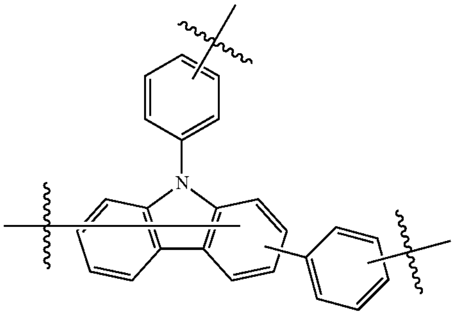
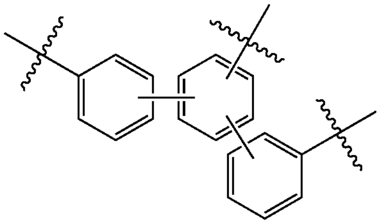
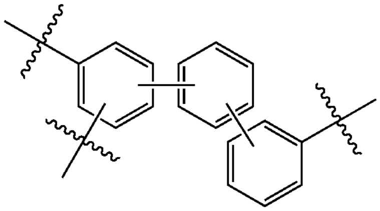
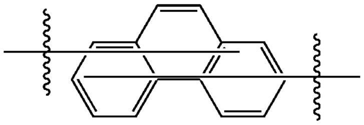
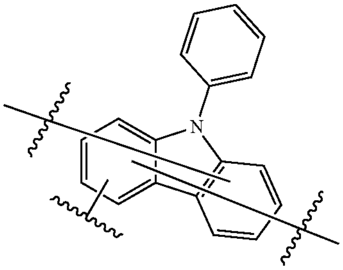
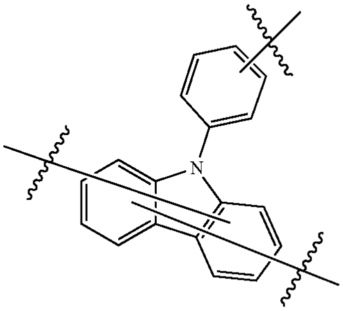
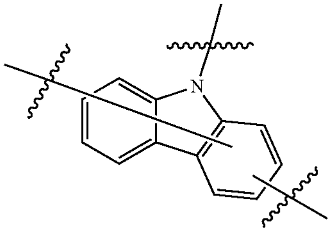
-continued
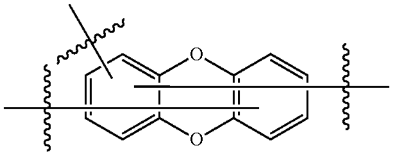
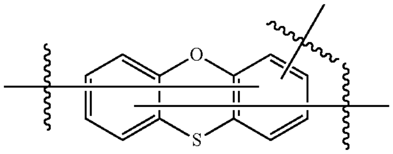
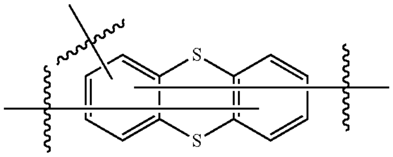
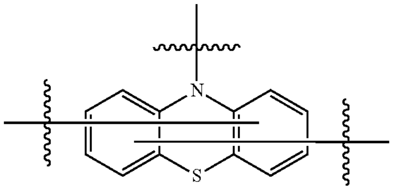
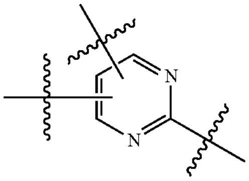
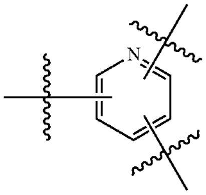
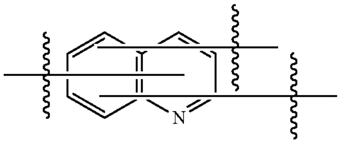
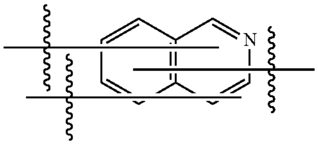
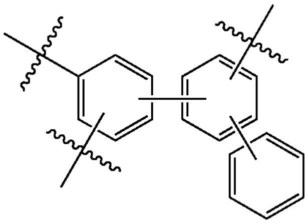
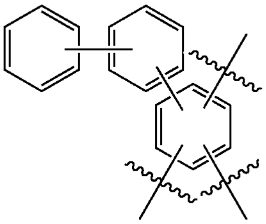

-continued

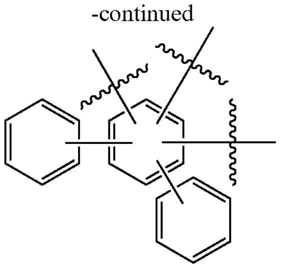

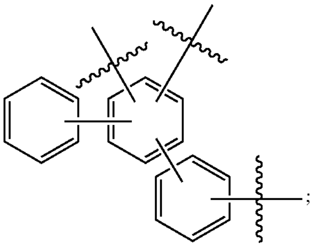

;

and when the group $W_2$ is substituted by one or more substituents, the substituents in the group $W_2$ are each independently selected from the group consisting of deuterium; fluorine; chlorine; cyano; alkyl with 1 to 4 carbon atoms; alkoxy with 1 to 4 carbon atoms; trifluoromethyl; trimethylsilyl; cyclopentyl; cyclohexyl; aryl with 6 to 12 carbon atoms which can be unsubstituted or substituted by 1, 2, 3, 4, or 5 substituents selected from deuterium, fluorine, cyano, methyl, isopropyl, or tert-butyl; and heteroaryl with 5 to 12 carbon atoms; and when the number of the substituents in the group $W_2$ is more than 1, the substituents are the same or different.

12. The organic compound according to claim 1, wherein each $L_1$ and each $L_2$ are each independently selected from: substituted or unsubstituted phenylene, substituted or unsubstituted biphenylene, substituted or unsubstituted terphenylene, substituted or unsubstituted naphthylene, substituted or unsubstituted dibenzofurylene, substituted or unsubstituted dibenzothienylene, substituted or unsubstituted quinolylene, substituted or unsubstituted carbazolylene, substituted or unsubstituted naphthylene, substituted or unsubstituted fluorenylene, substituted or unsubstituted anthrylene, substituted or unsubstituted phenanthrylene, substituted or unsubstituted pyrimidylene, substituted or unsubstituted pyridylene, substituted or unsubstituted pyrazinylene, substituted or unsubstituted quinolylene, substituted or unsubstituted isoquinolylene, substituted or unsubstituted quinazolinylene, or a subunit group formed by linking two or three of the above groups via a single bond; and substitution in each $L_1$ and each $L_2$ means that each $L_1$ and each $L_2$ are each independently substituted by 1, 2, 3 or 4 substituents selected from deuterium, fluorine, chlorine, cyano, methyl, ethyl, isopropyl, tert-butyl, methoxy, ethoxy, isopropoxy, propoxy, trifluoromethyl, phenyl, carbazolyl, naphthyl, trimethylsilyl, or triphenylsilyl.

13. The organic compound according to claim 1, wherein each $R_3$ is independently selected from deuterium; fluorine; chlorine; cyano; alkyl with 1 to 4 carbon atoms; alkoxy with 1 to 4 carbon atoms; haloalkyl with 1 to 4 carbon atoms; trimethylsilyl; cycloalkyl with 5 to 7 carbon atoms; aryl with 6 to 15 carbon atoms which can be unsubstituted or substituted by 1, 2, 3, 4, or 5 substituents independently selected from deuterium, fluorine, chlorine, or cyano; or heteroaryl with 3 to 18 carbon atoms which can be unsubstituted or substituted by 1, 2, 3, 4, or 5 substituents independently selected from deuterium, fluorine, chlorine, or cyano; and when the number of the $R_3$ is more than 1, each $R_3$ is the same or different.

14. The organic compound according to claim 1, wherein $R_1$ and $R_2$ are the same, and are selected from methyl or phenyl.

15. The organic compound according to claim 1, wherein the organic compound is selected from the group consisting of the following organic compounds:

1

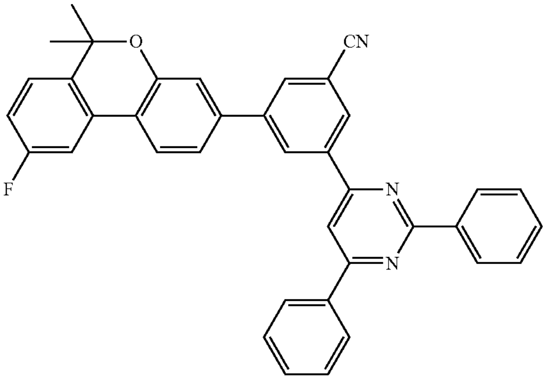

2

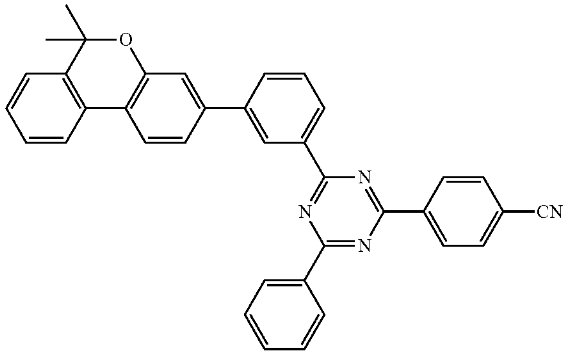

3

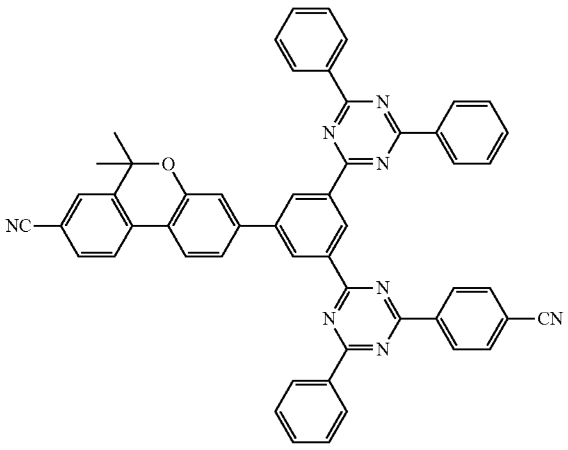

-continued
4
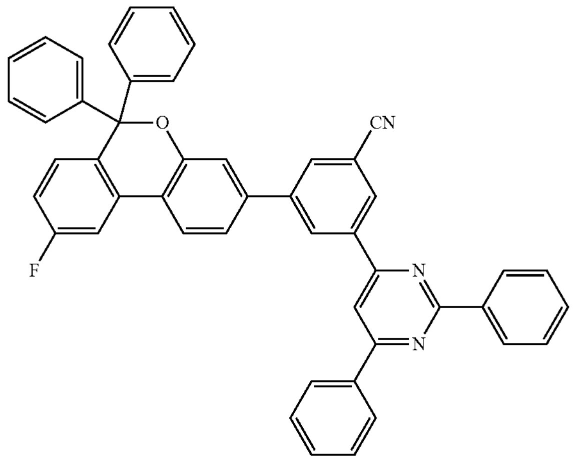
5
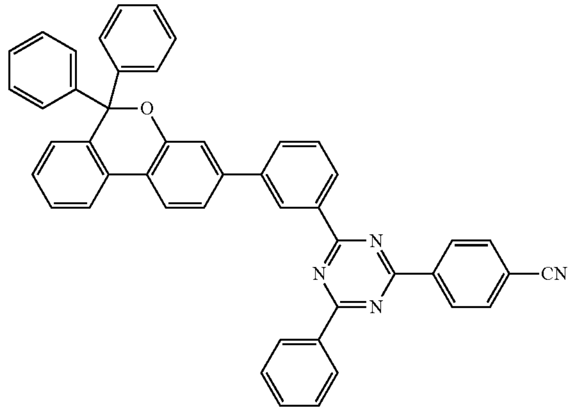
6
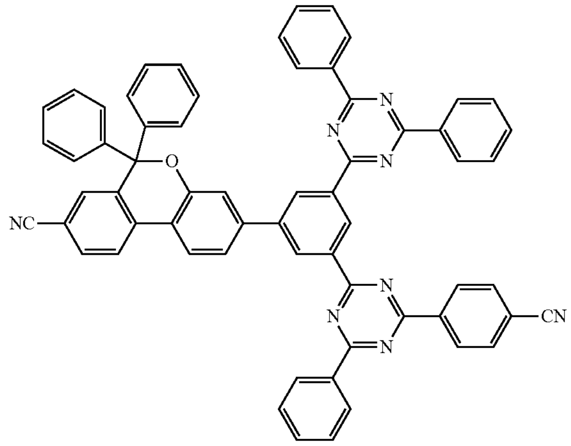
-continued
7
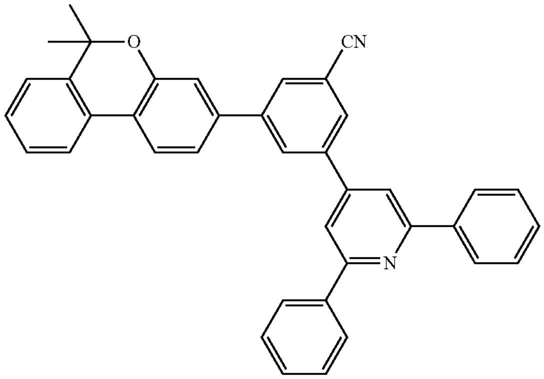
8
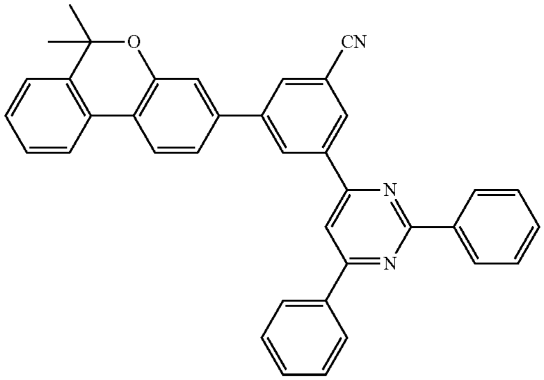
9
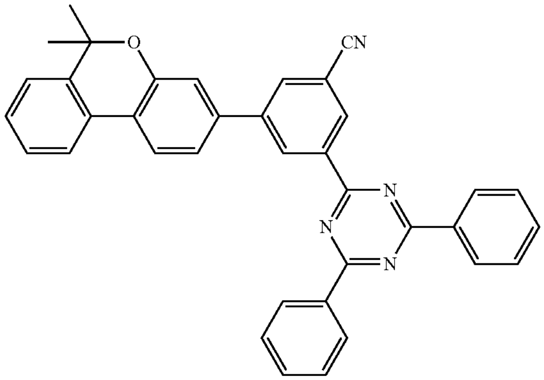
10
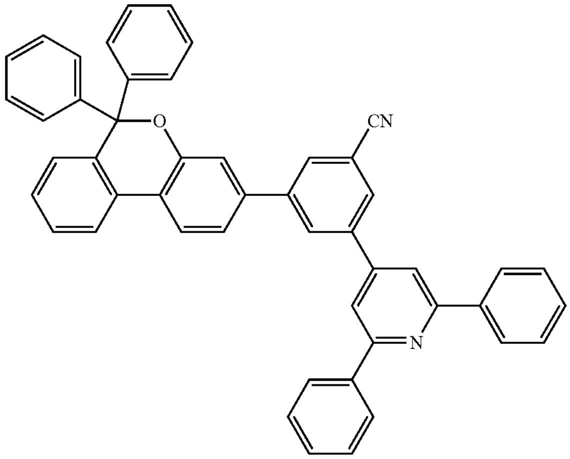

-continued
11
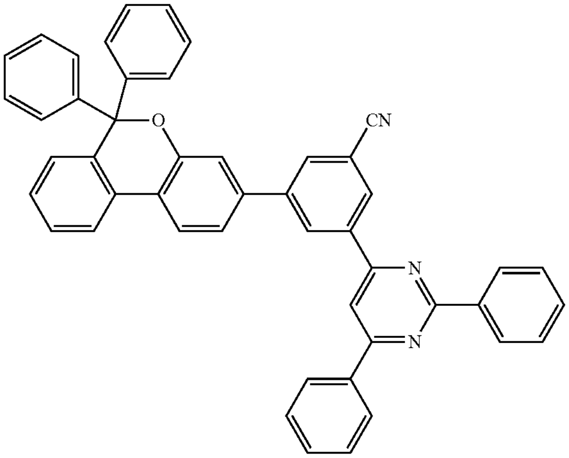
12
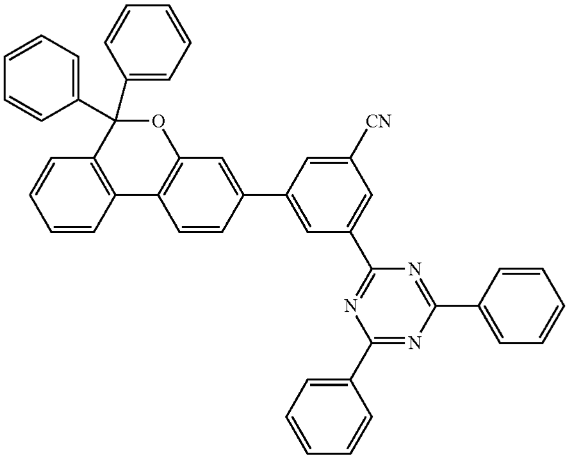
13
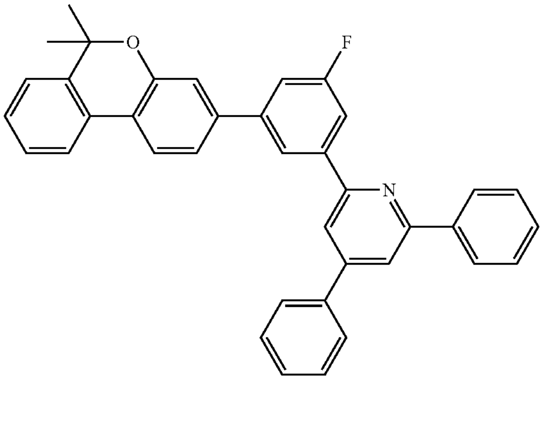
-continued
14
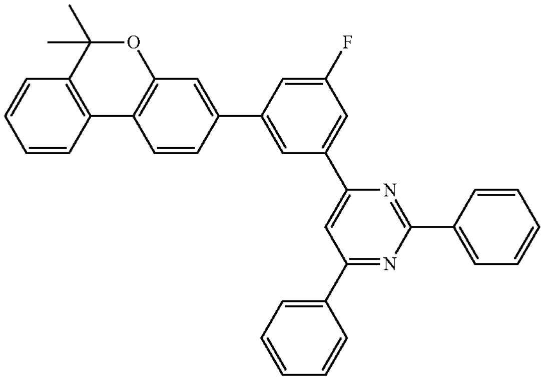
15
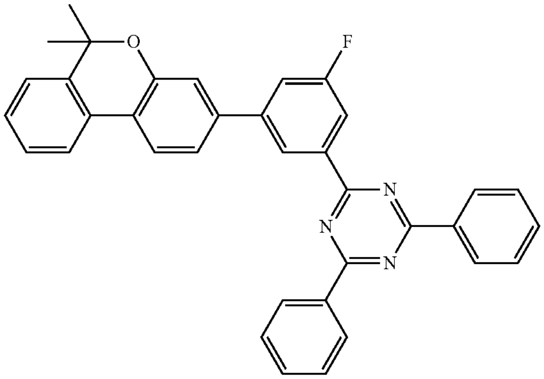
16
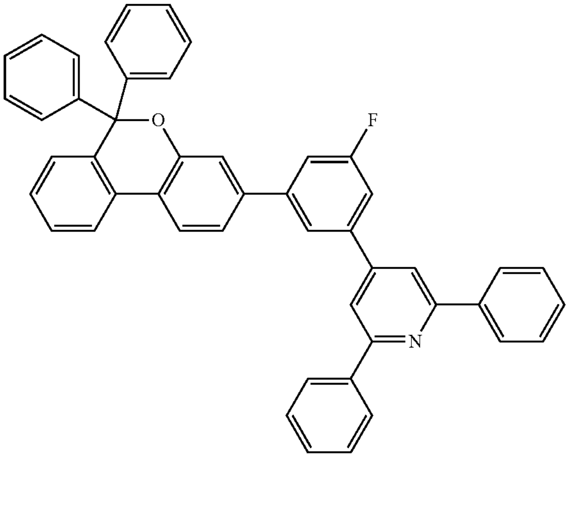

-continued
17
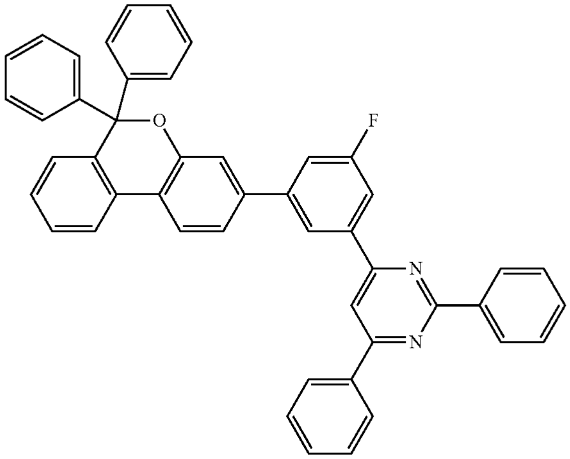
18
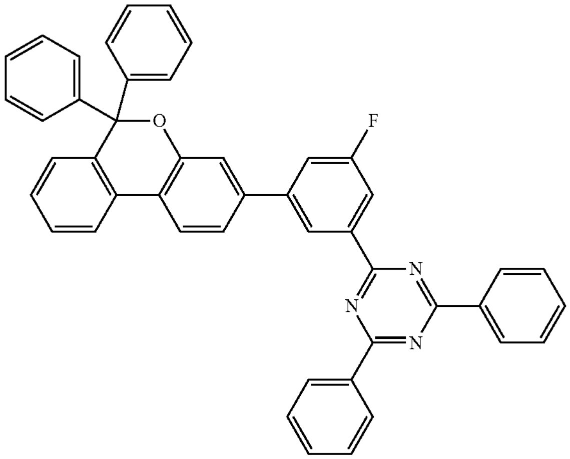
19
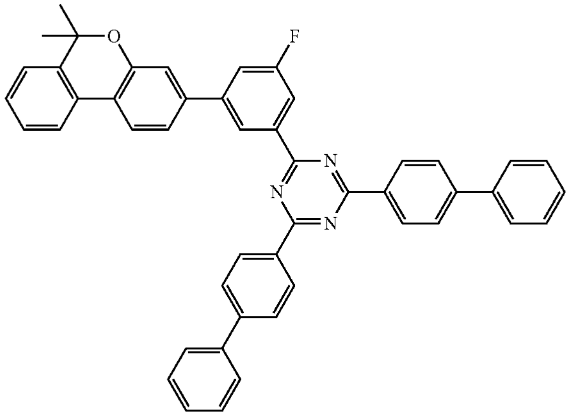
-continued
20
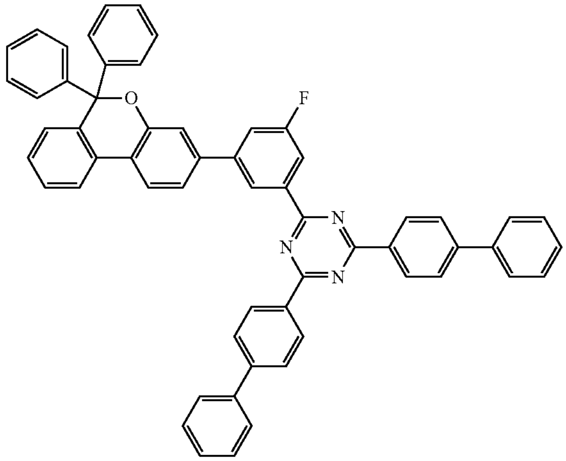
21
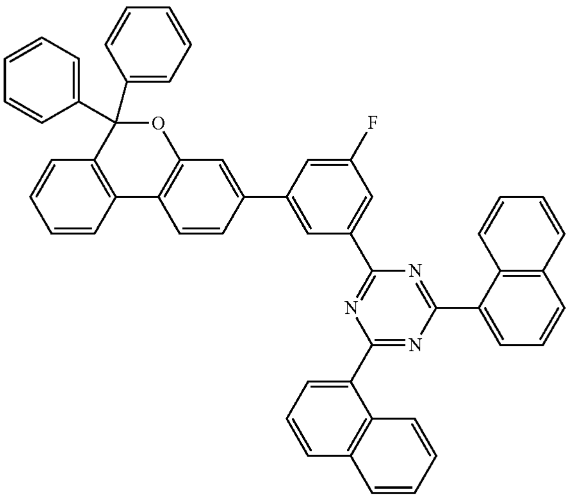
22
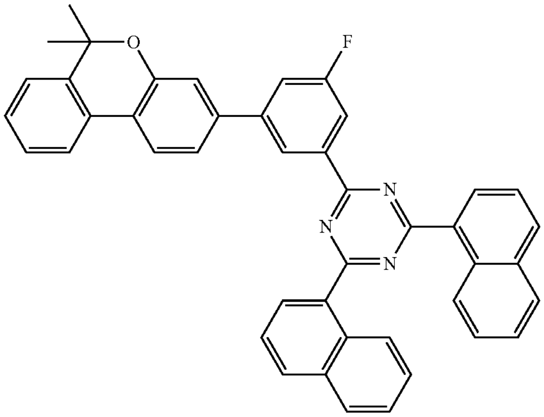

-continued
23
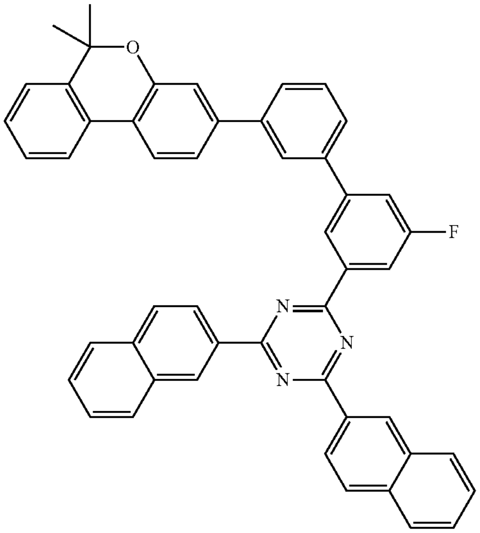
24
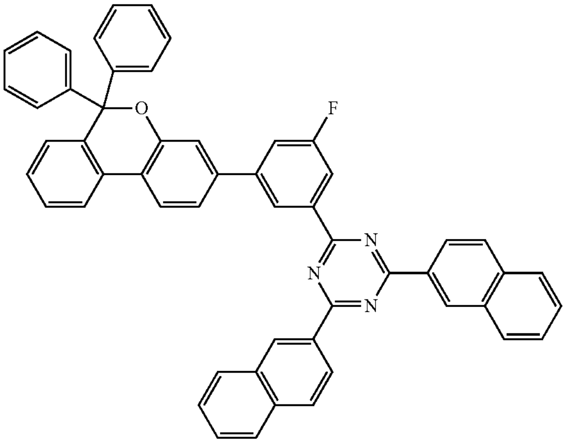
25
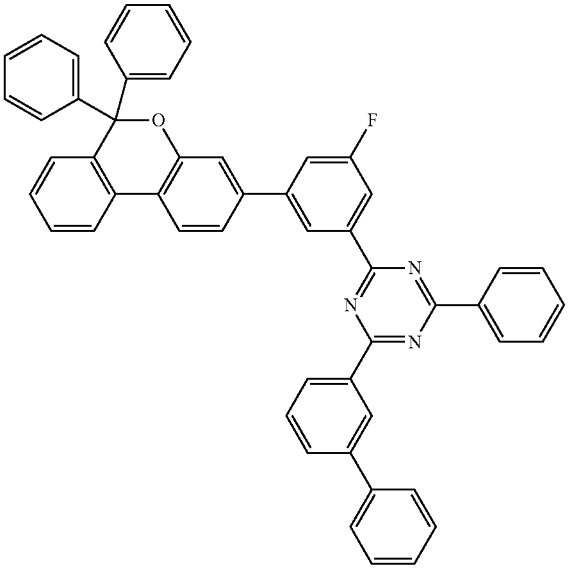
-continued
26
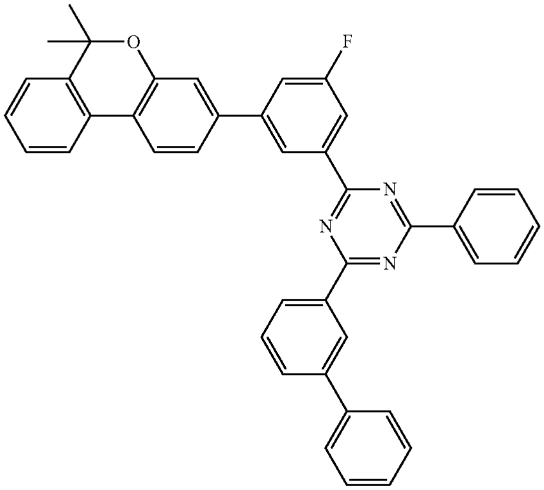
27
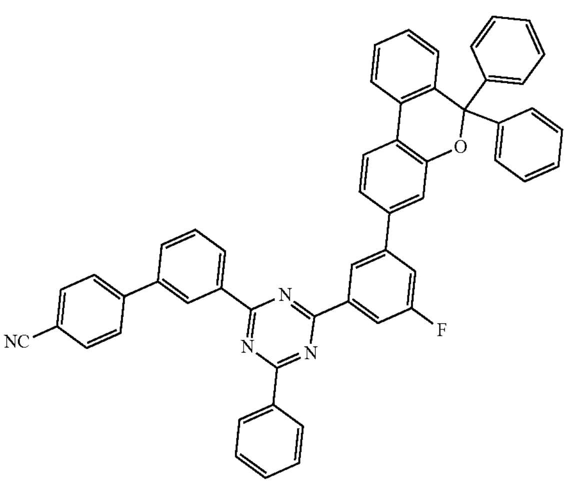
28
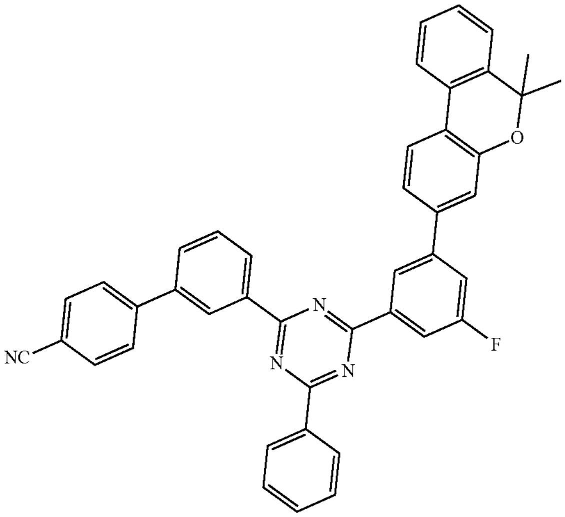

-continued
29
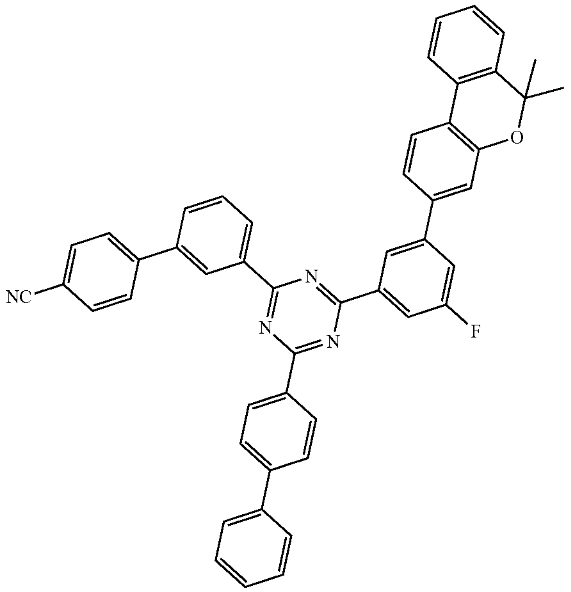
30
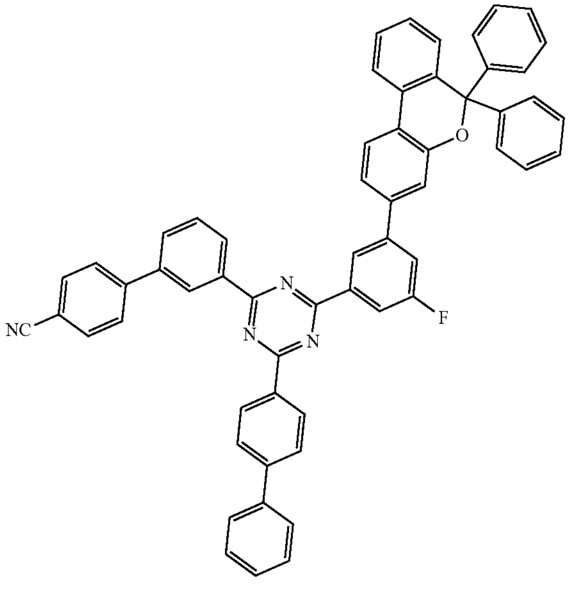
-continued
31
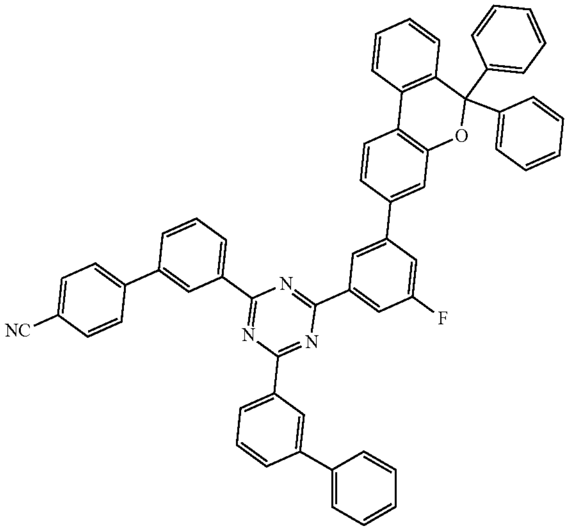
32
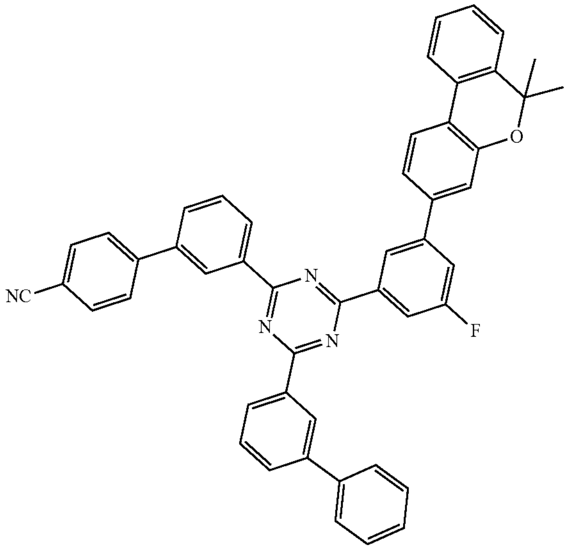
33
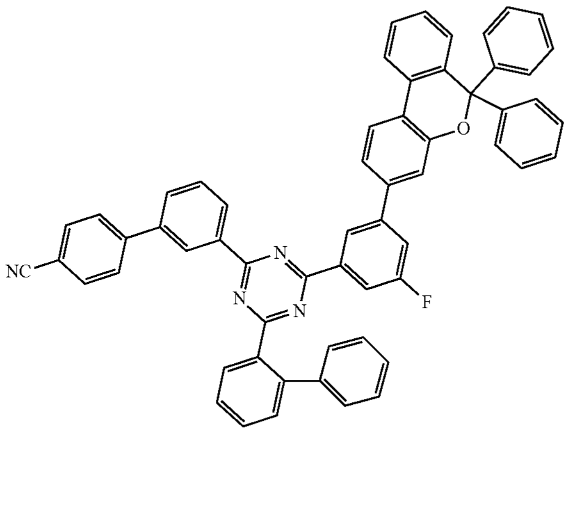

-continued
34
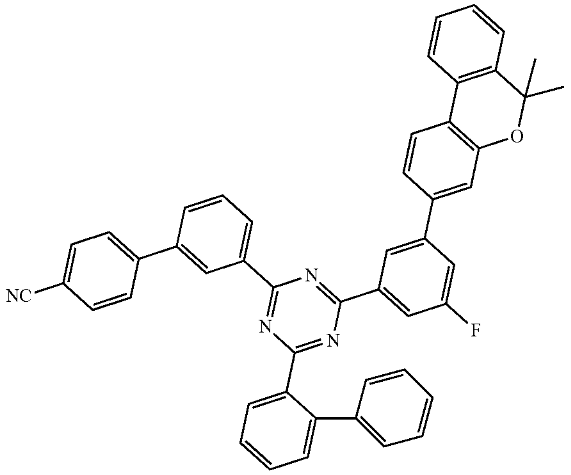
35
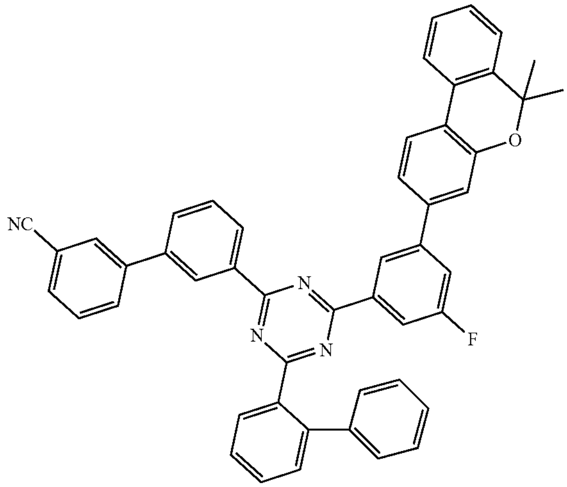
36
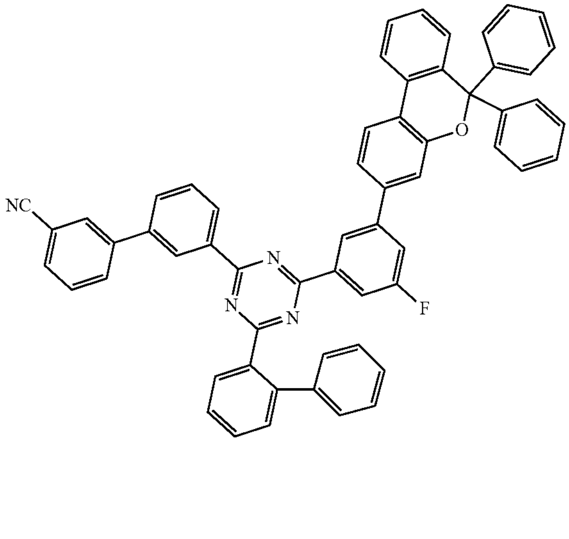
-continued
37
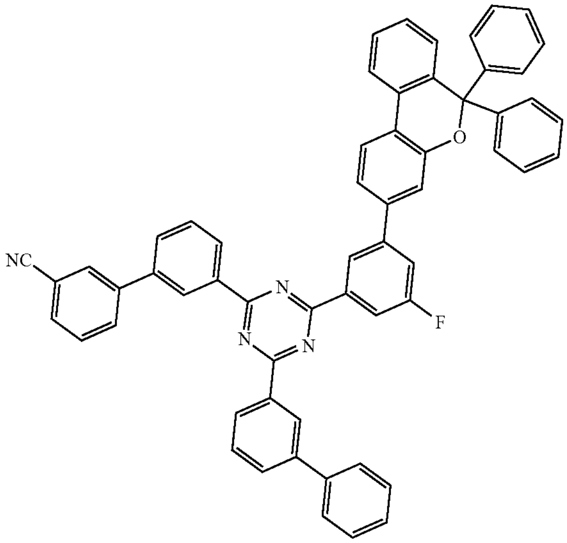
38
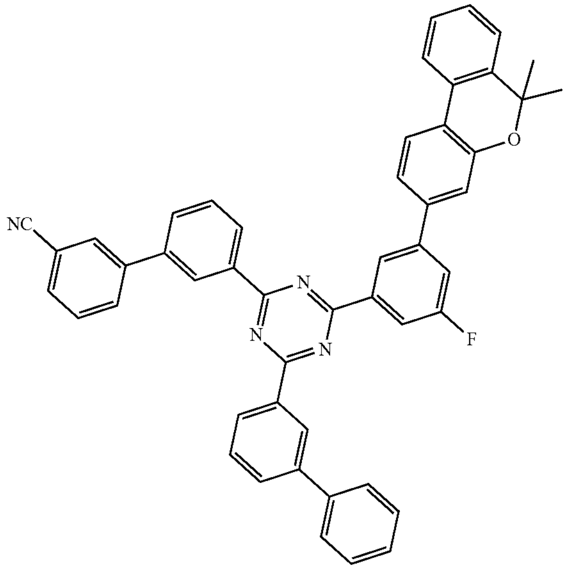

-continued
39
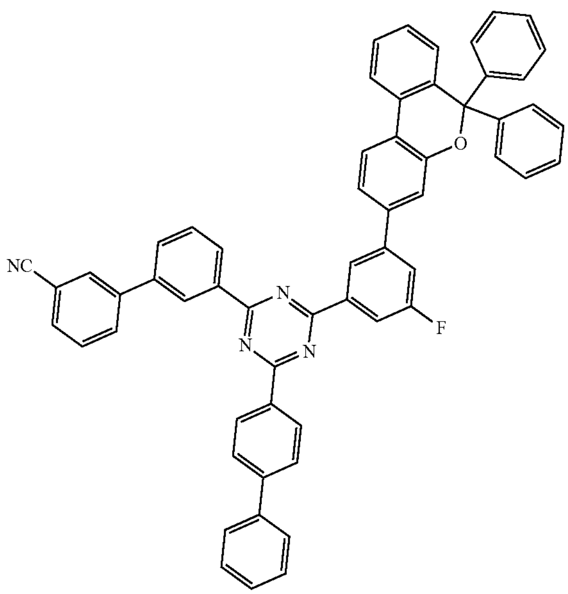
40
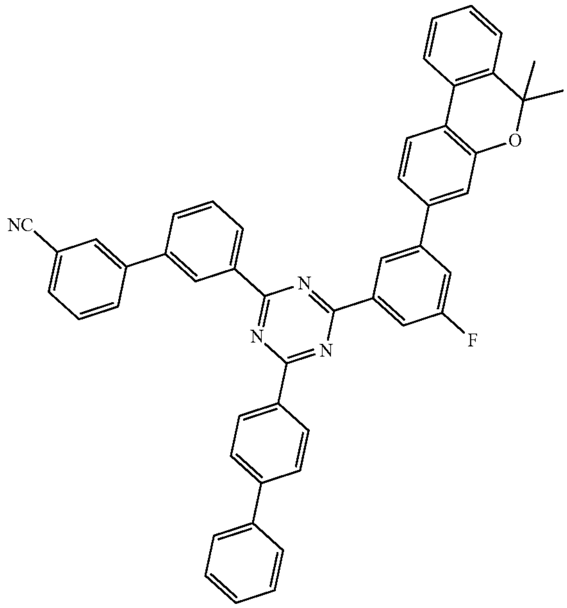
-continued
41
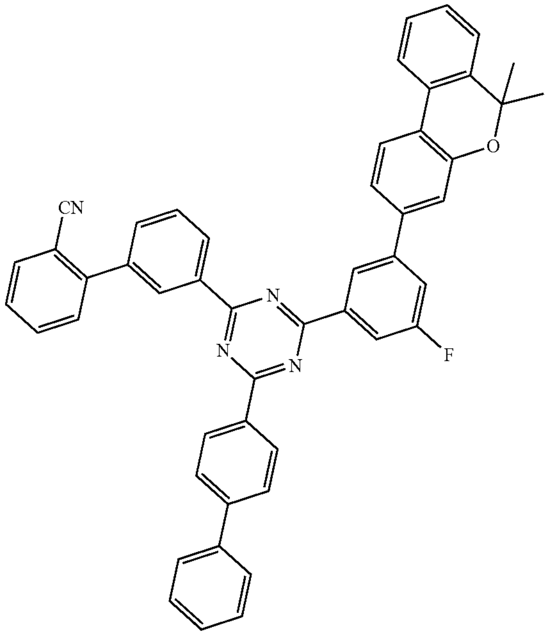
42
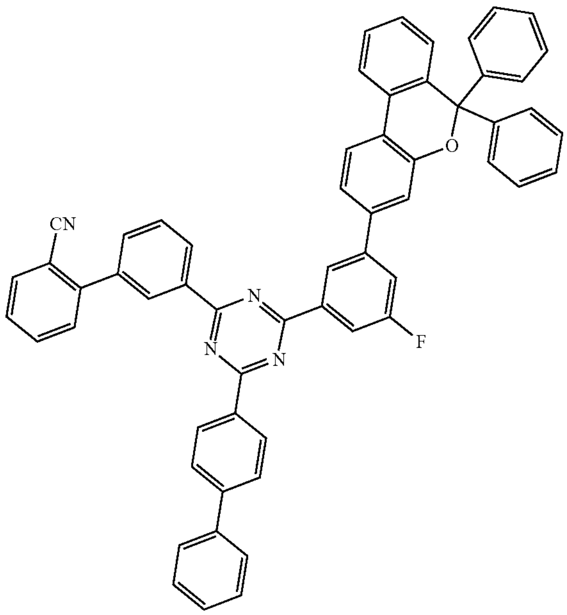

43
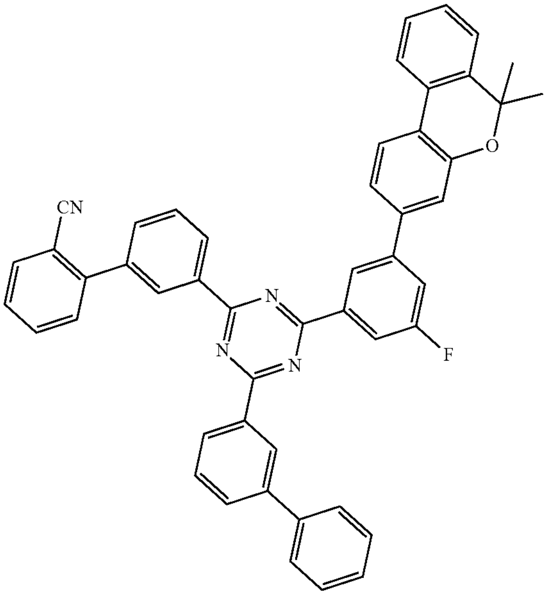
44
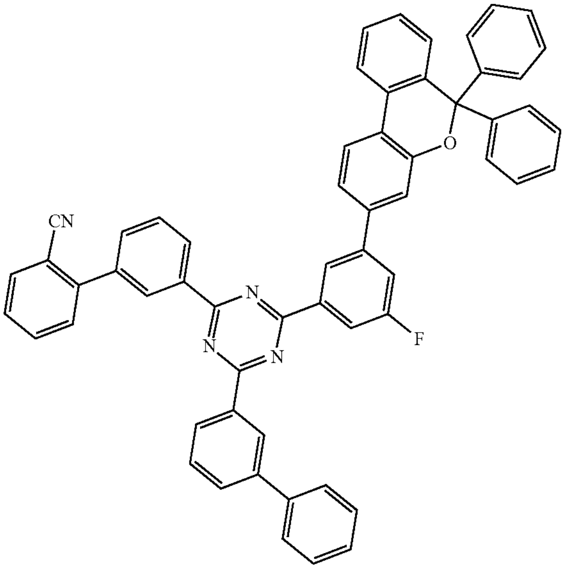
45
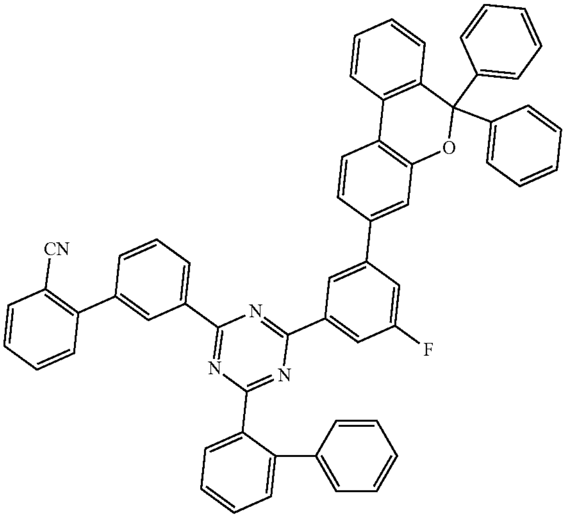
46
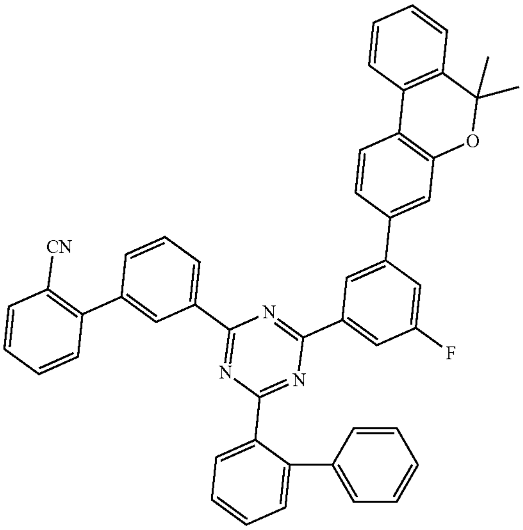
47
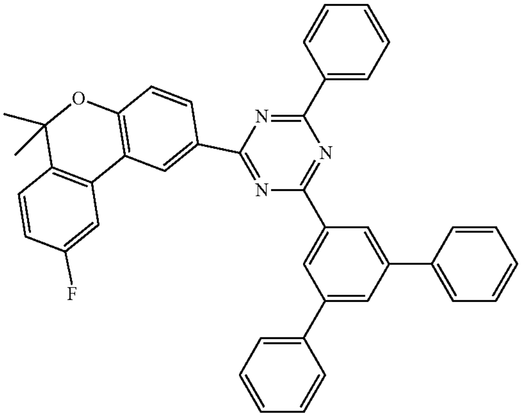

-continued
48
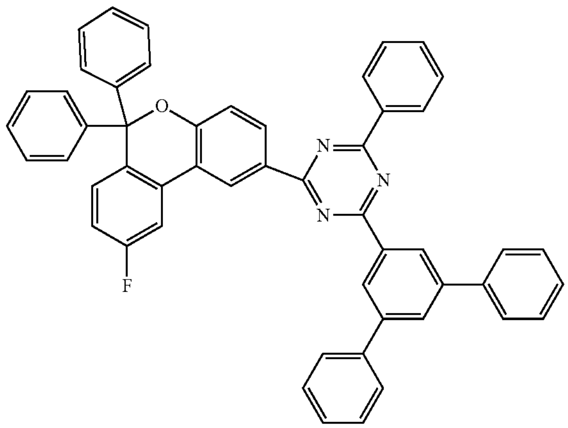
49
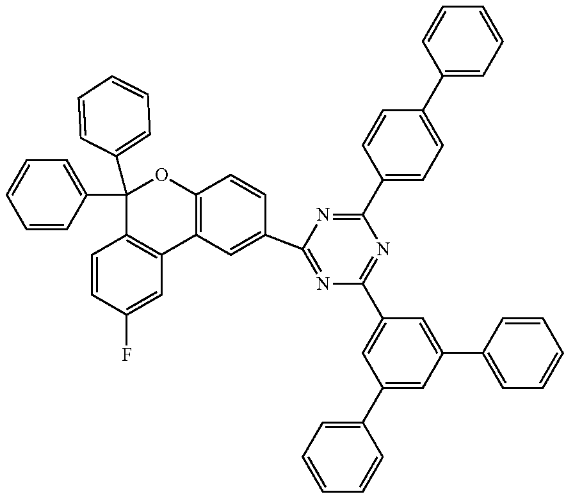
50
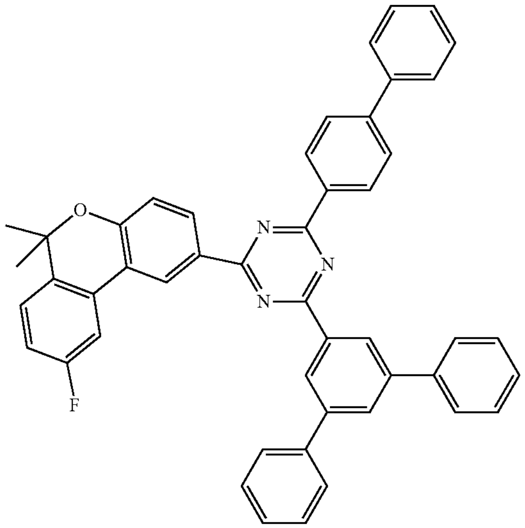
-continued
51
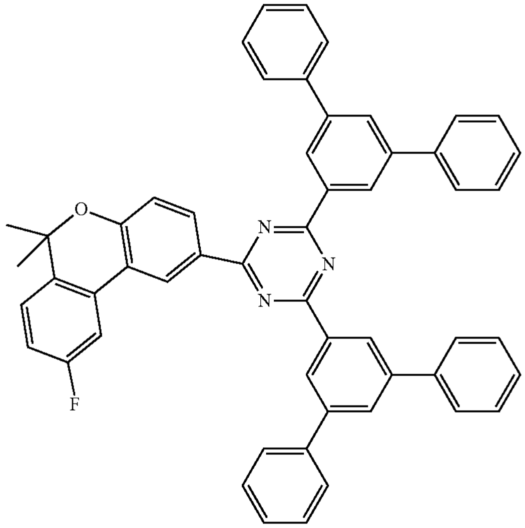
52
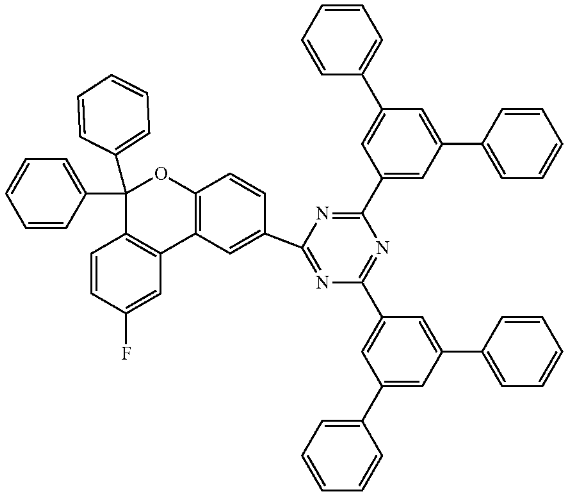
53
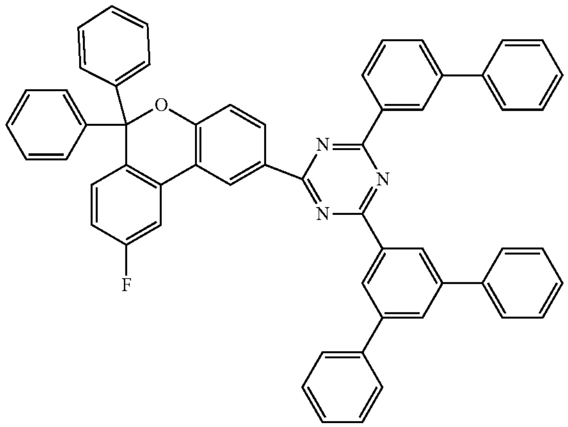

-continued
54
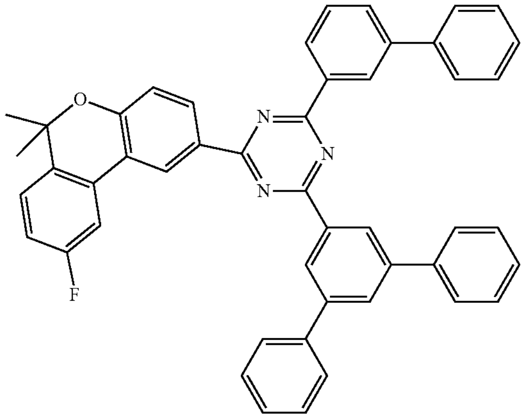
55
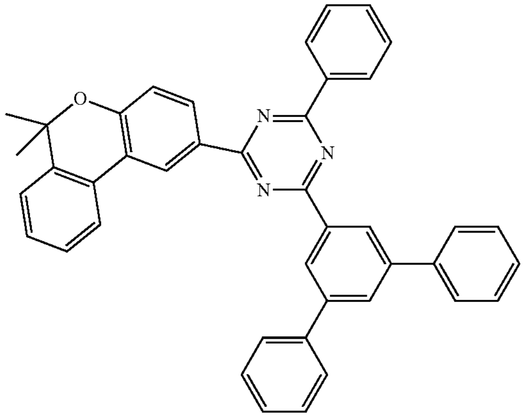
56
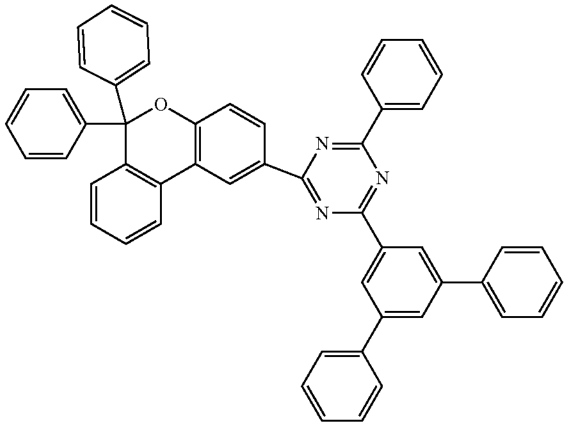
-continued
57
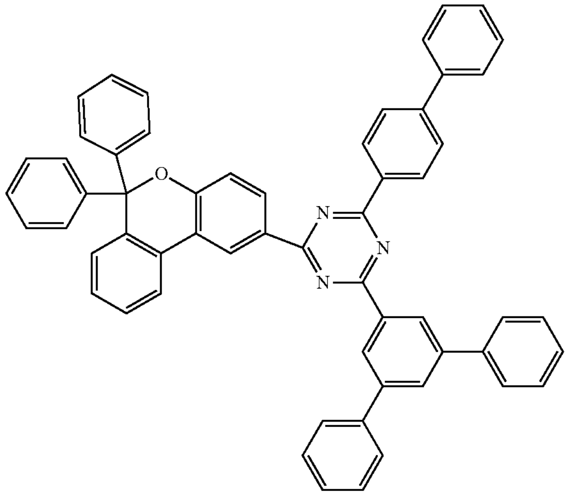
58
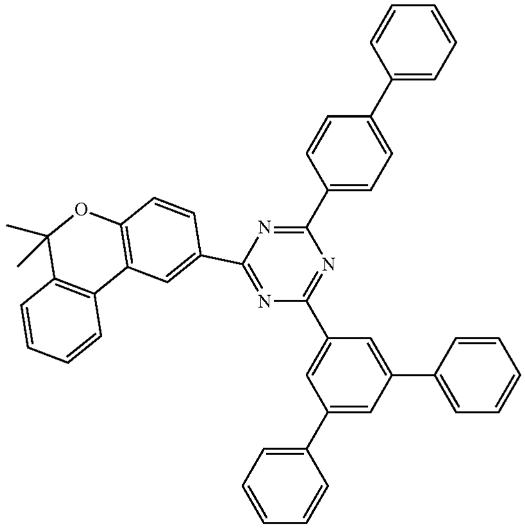
59
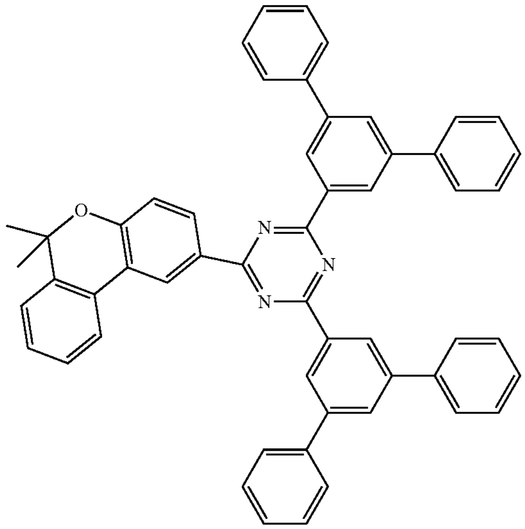

-continued
60
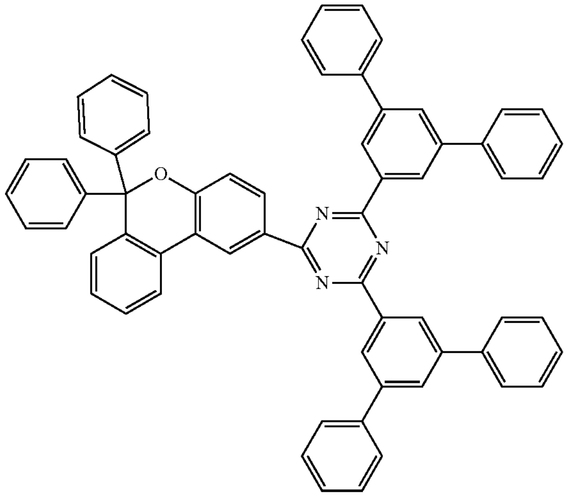
61
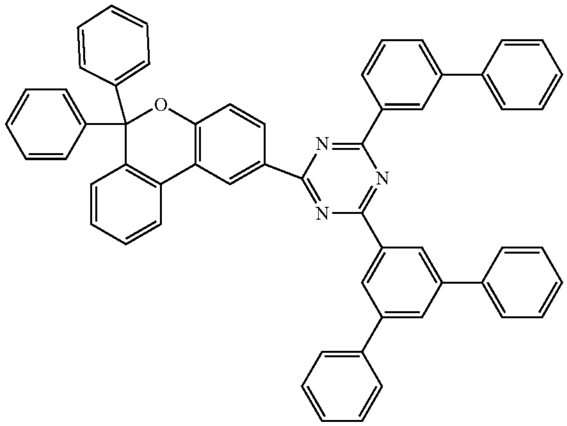
62
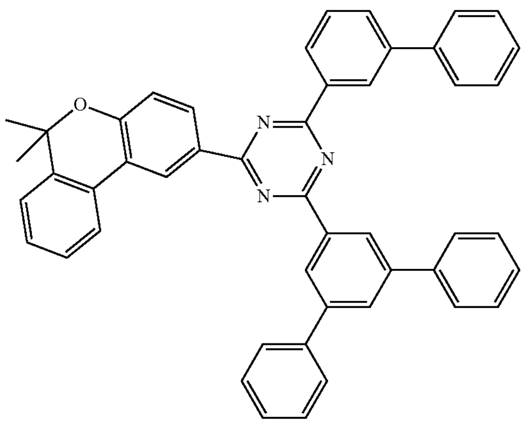
-continued
63
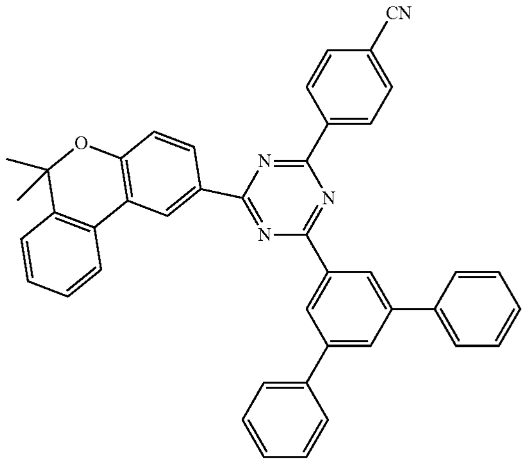
64
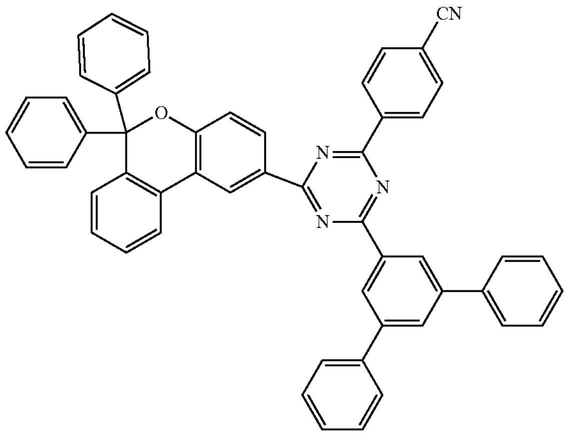
65
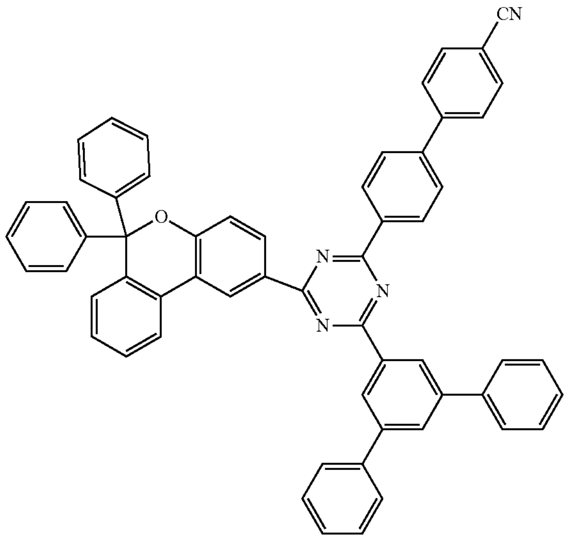

-continued
66
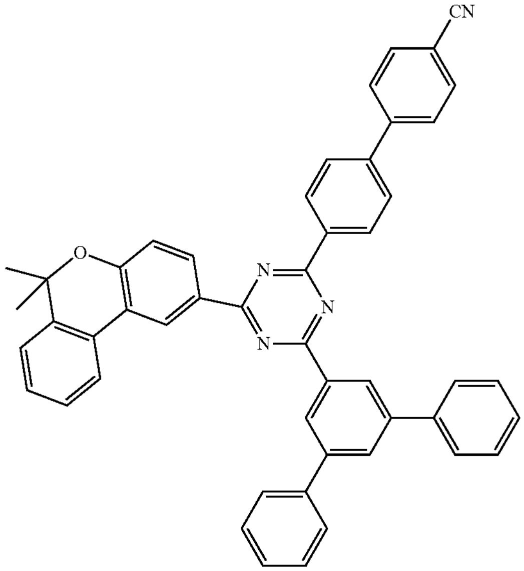
67
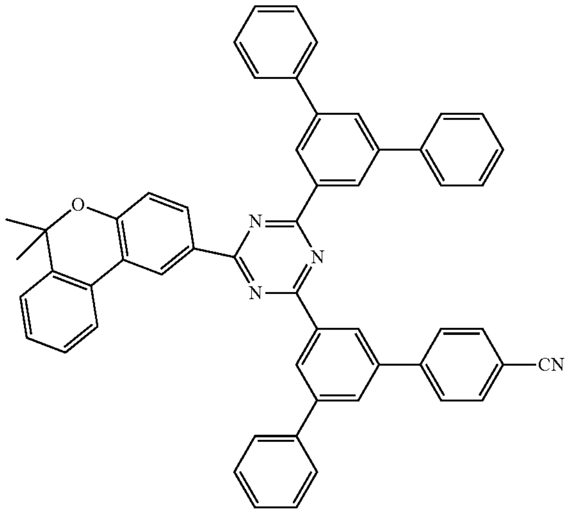
68
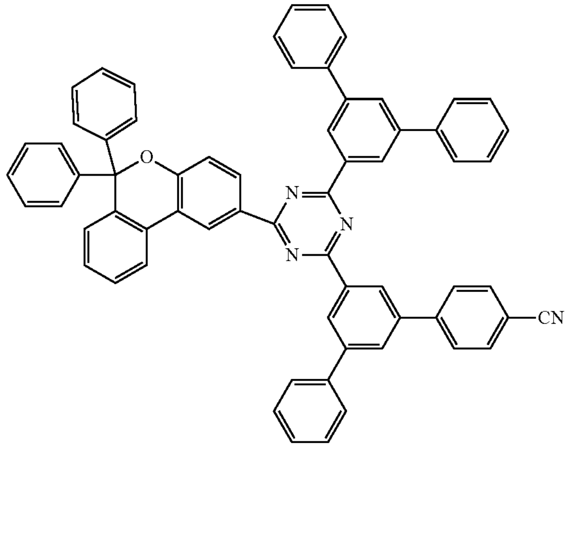
-continued
69
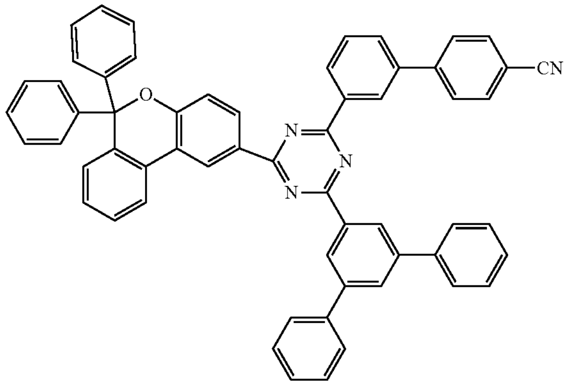
70
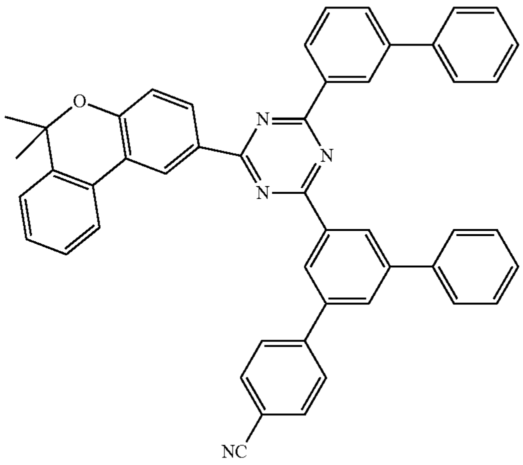
71
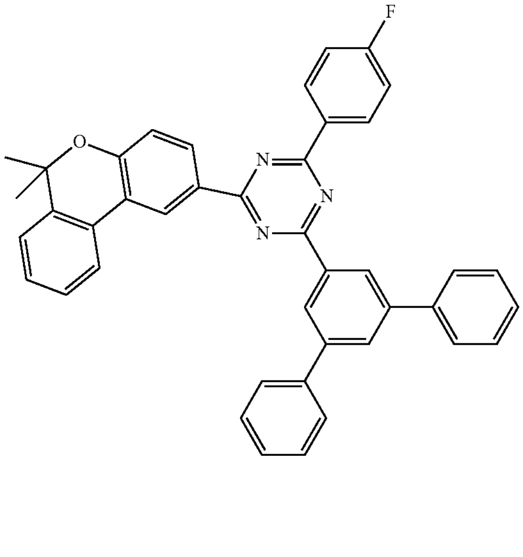

-continued
72
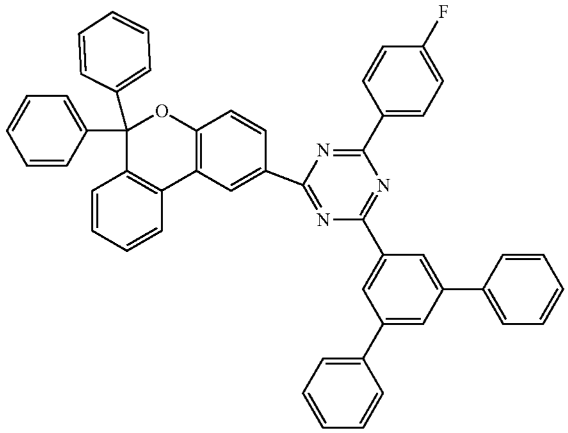
73
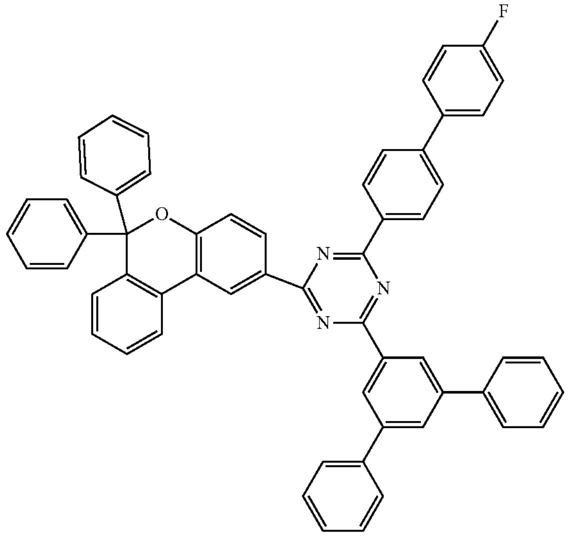
74
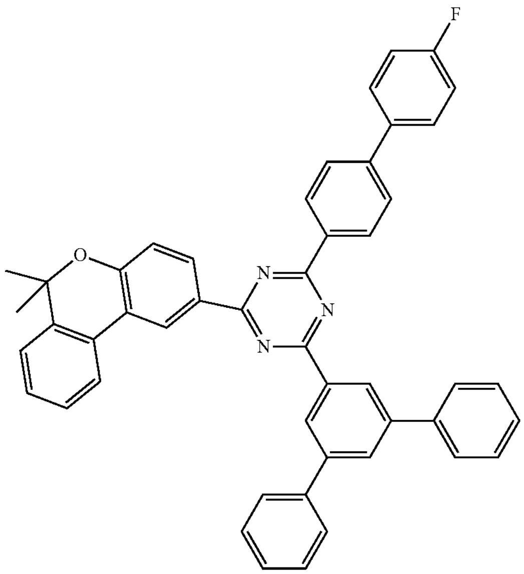
-continued
75
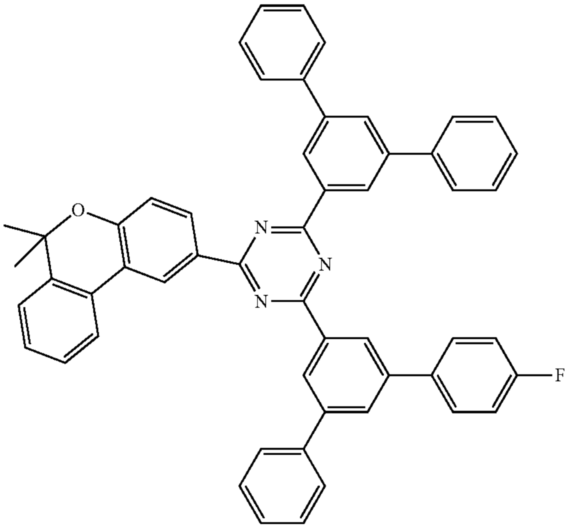
76
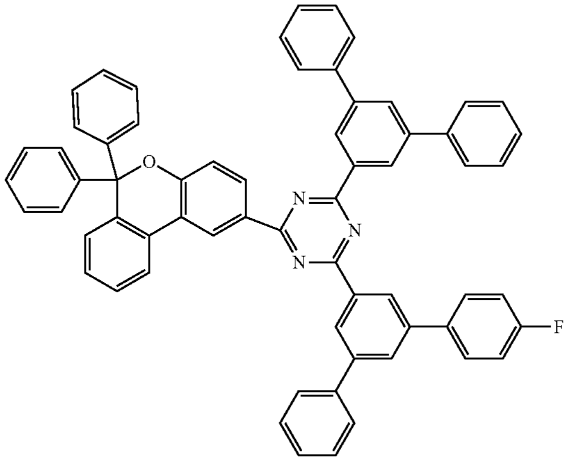
77
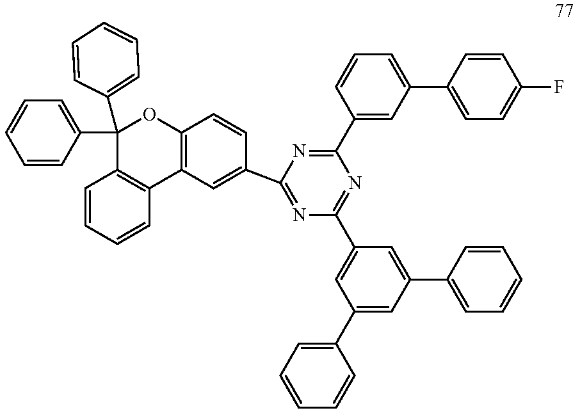

-continued
78
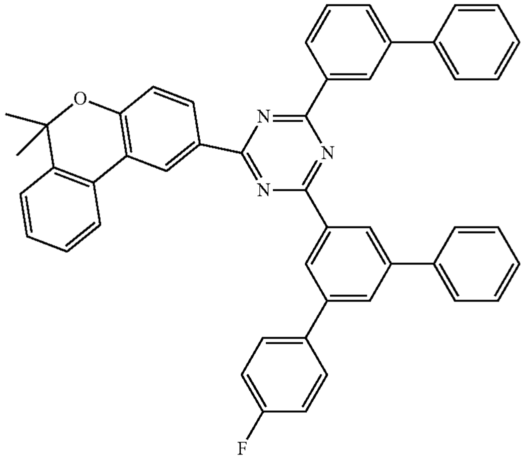
79
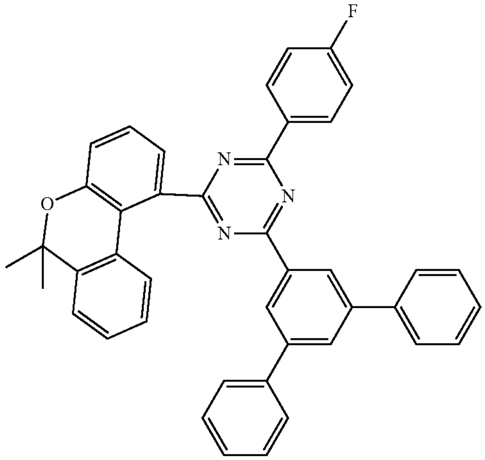
80
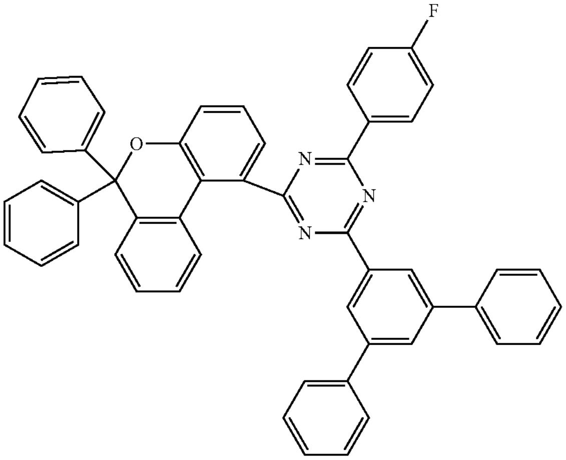
-continued
81
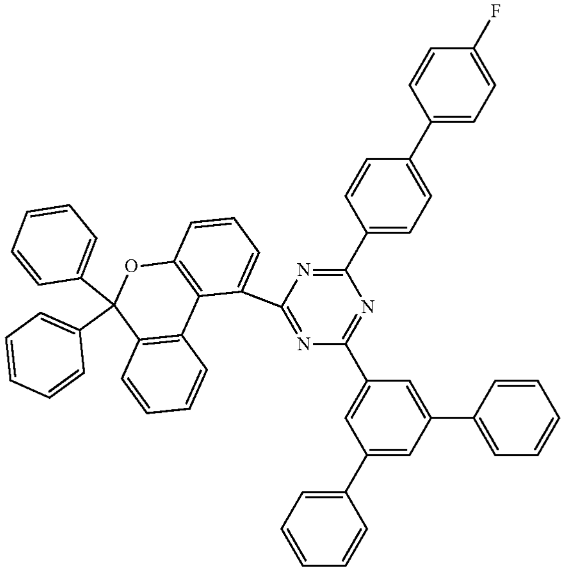
82
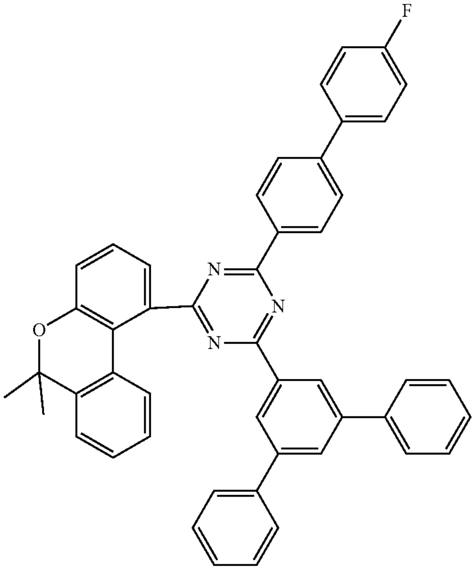

-continued
83
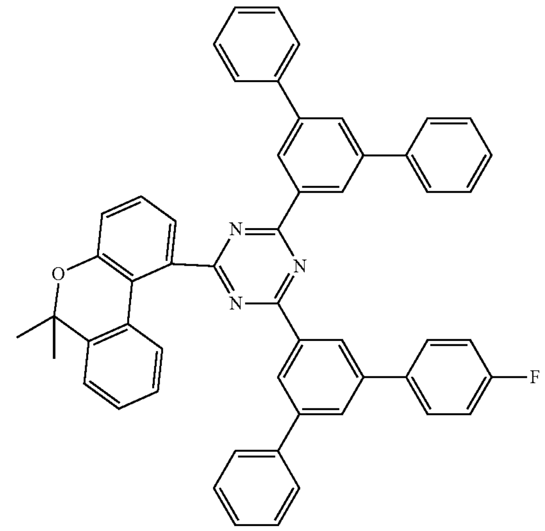
84
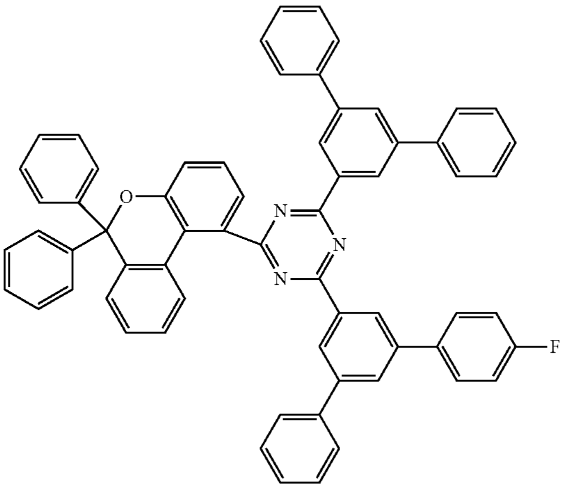
85
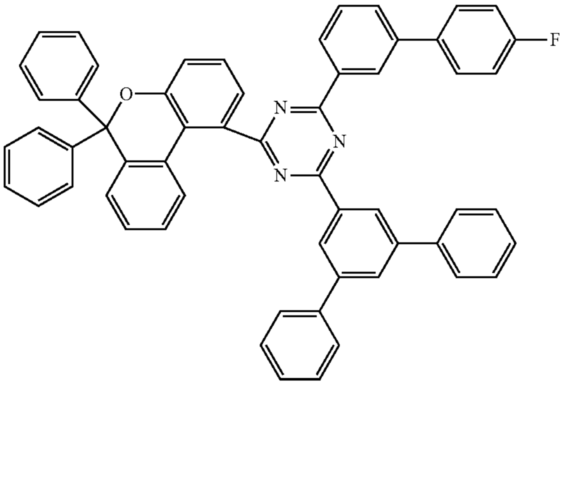
-continued
86
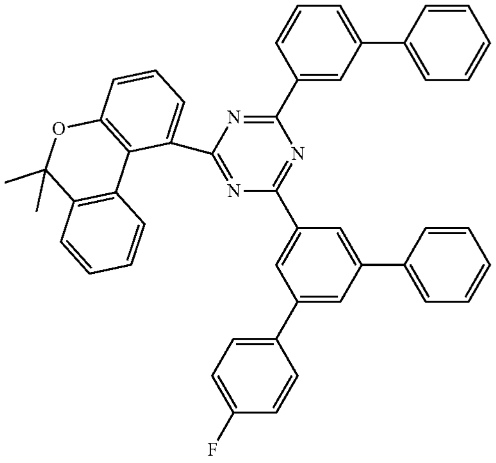
87
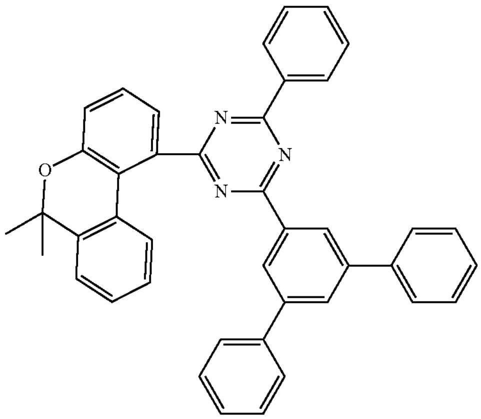
88
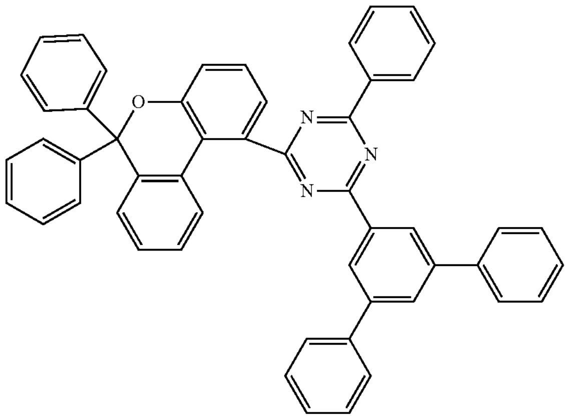

-continued
89
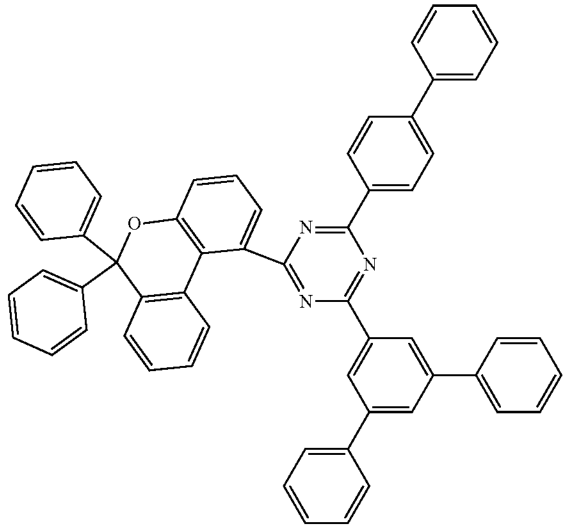
90
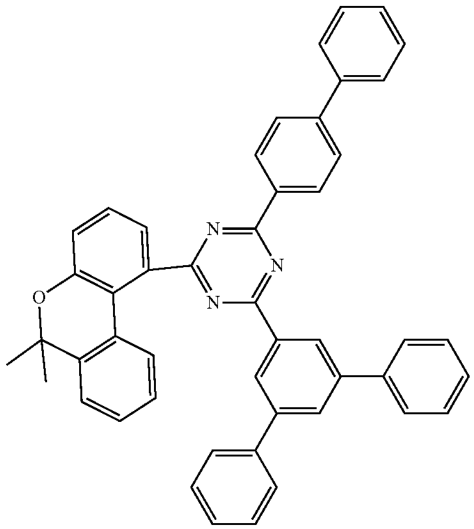
91
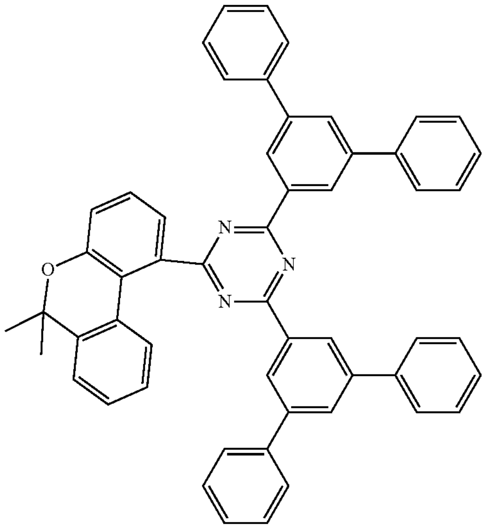
-continued
92
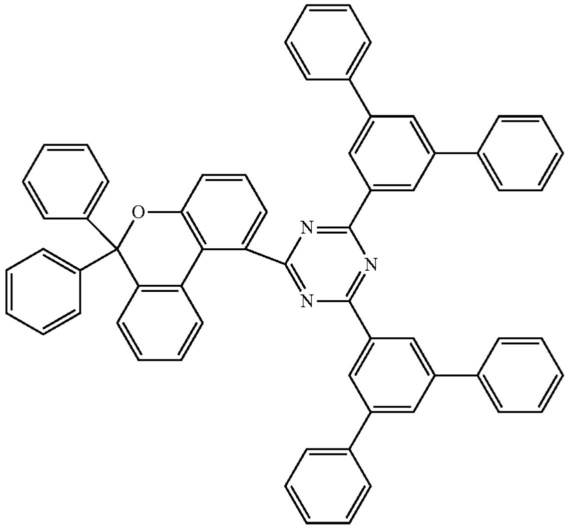
93
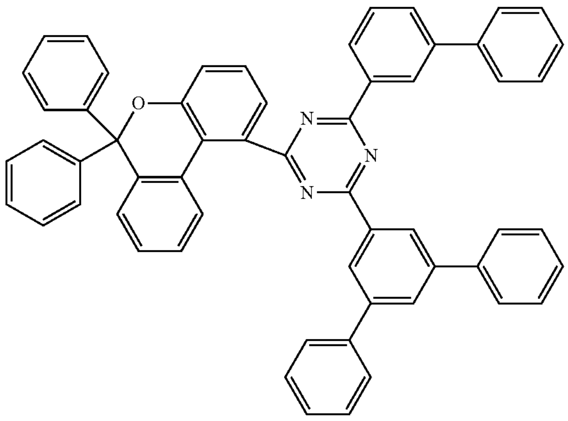
94
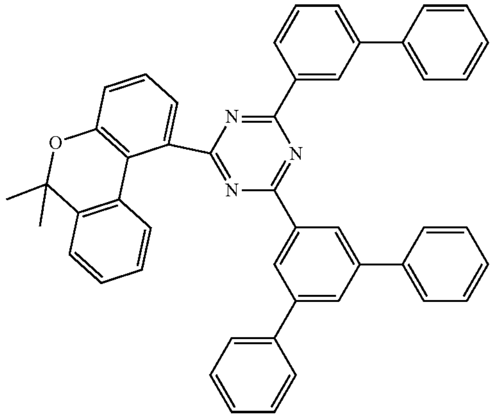

-continued
95
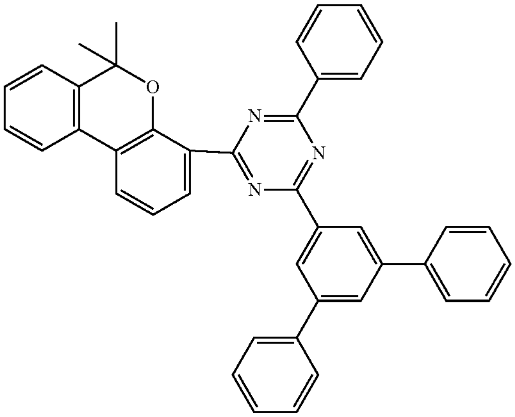
96
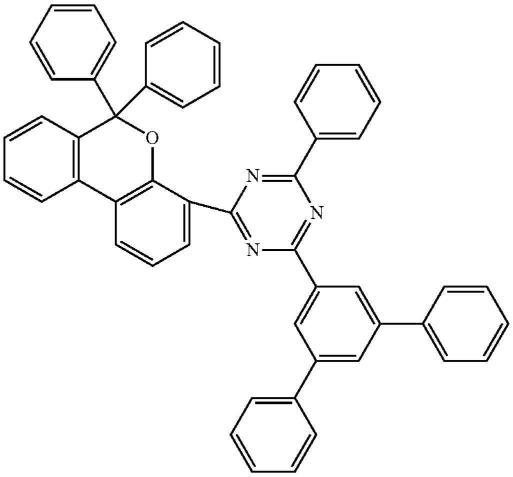
97
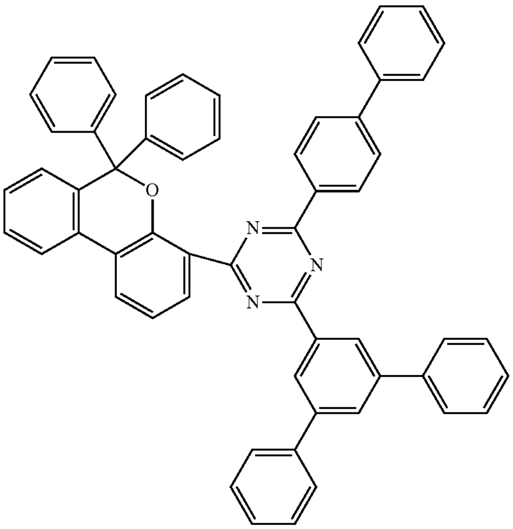
-continued
98
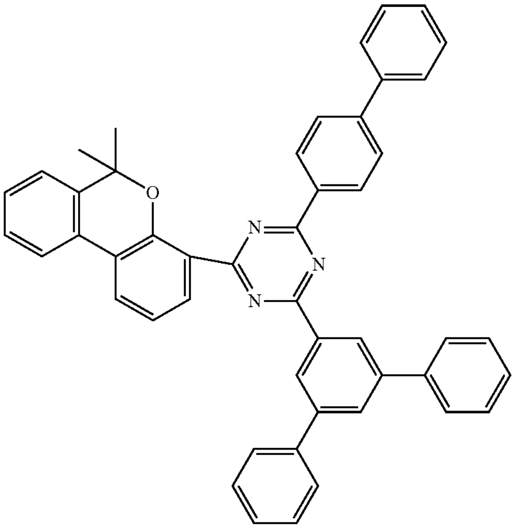
99
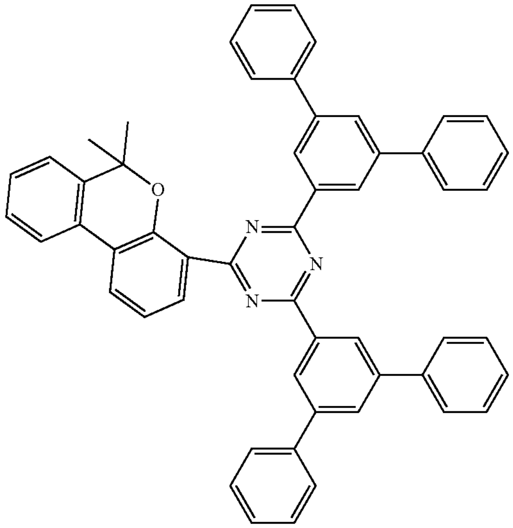
100
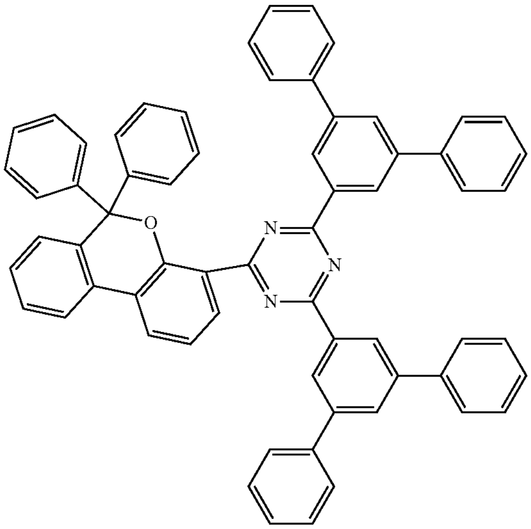

-continued
101
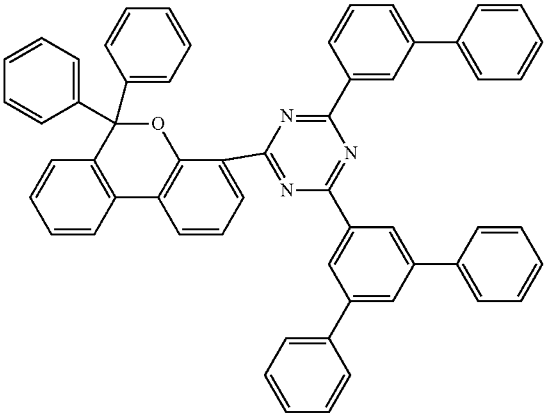
102
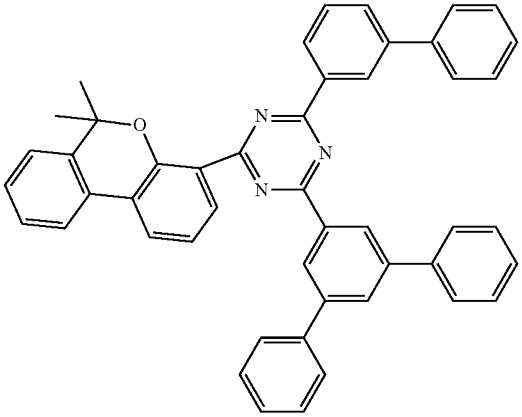
103
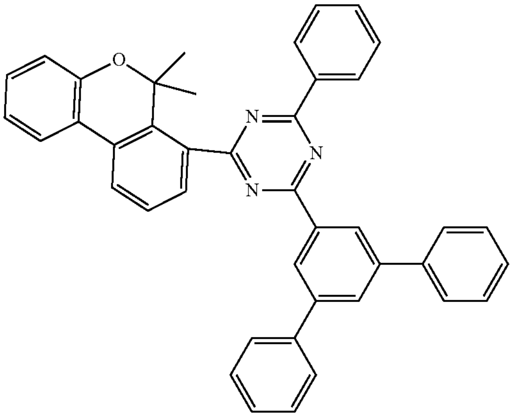
-continued
104
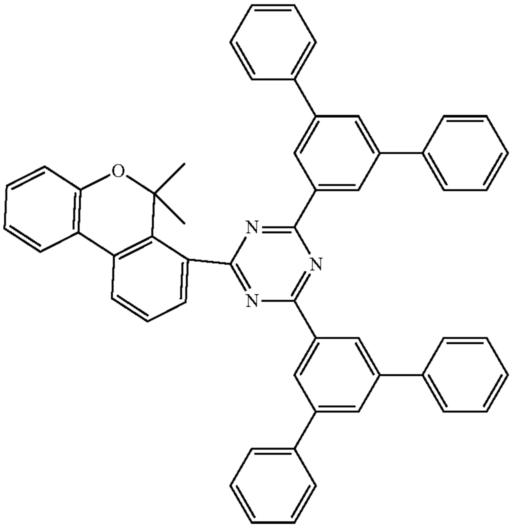
105
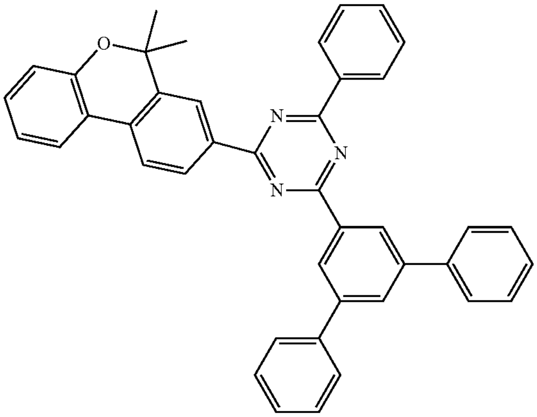
106
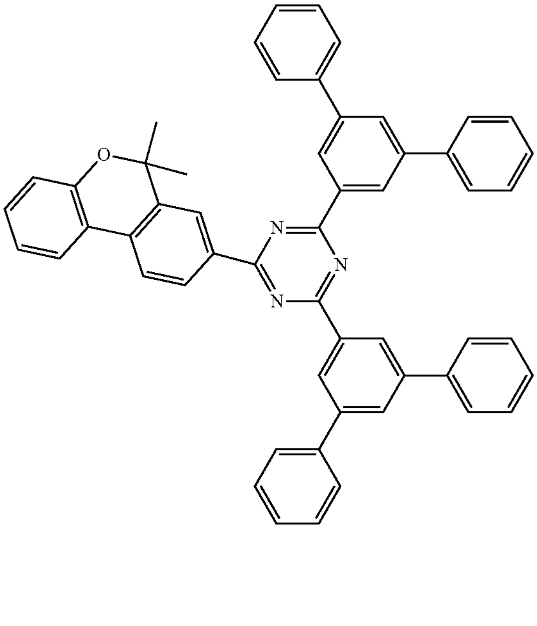

107
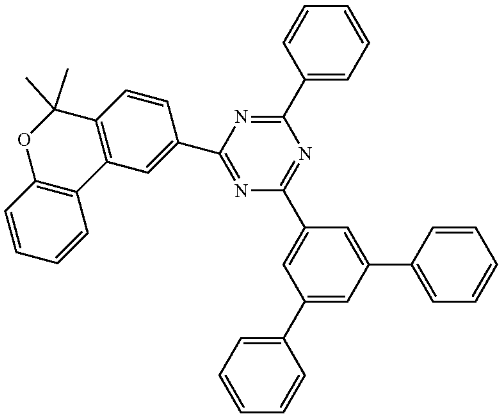
108
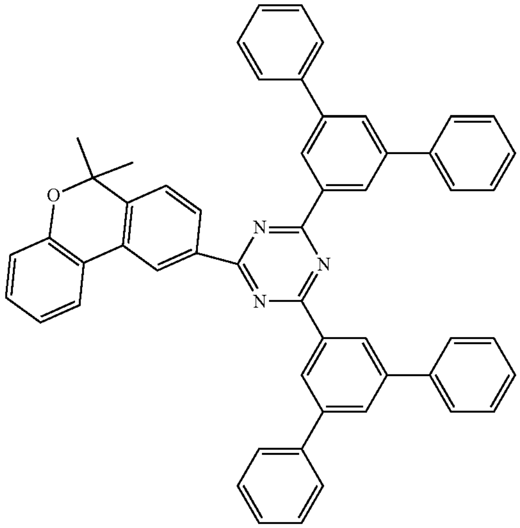
109
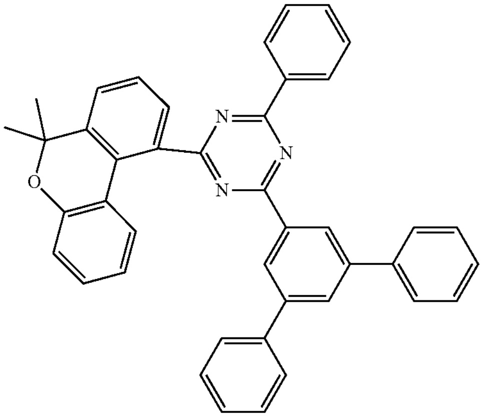
110
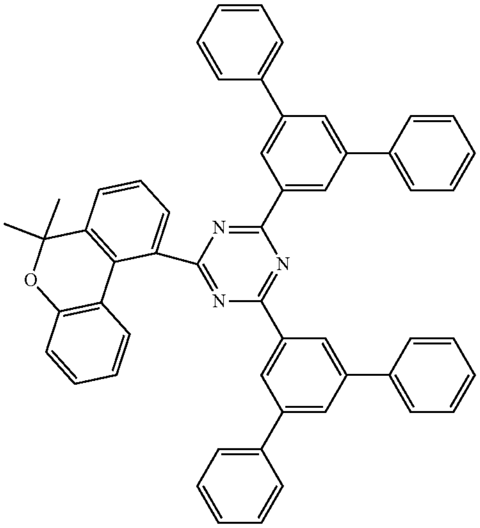
111
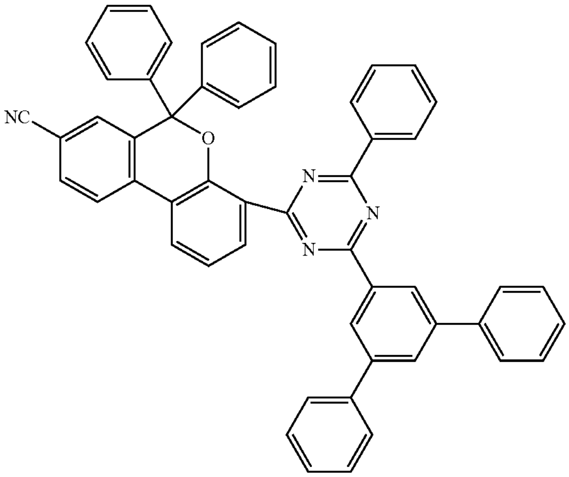
112
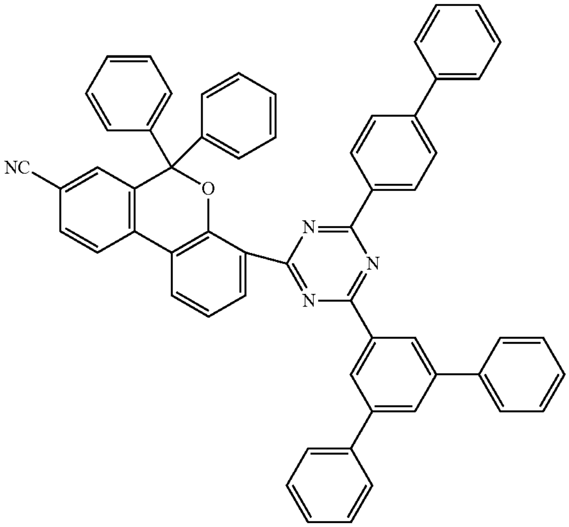

-continued
113
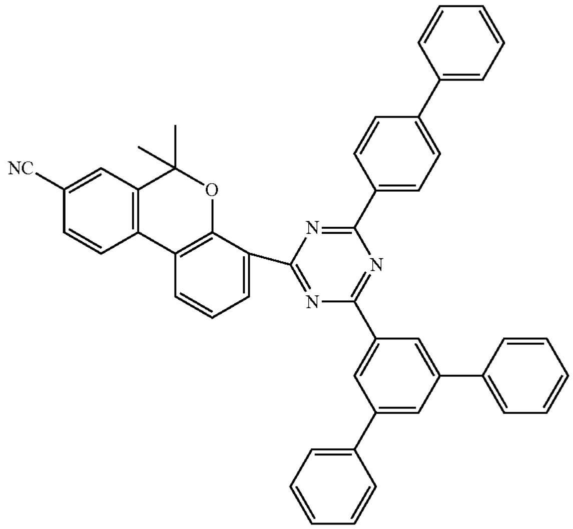
114
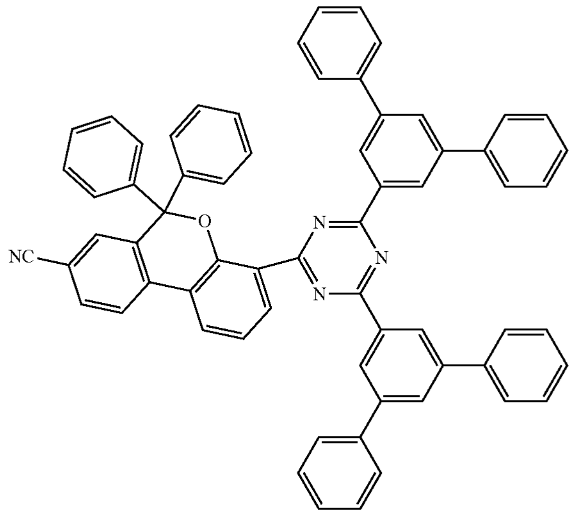
115
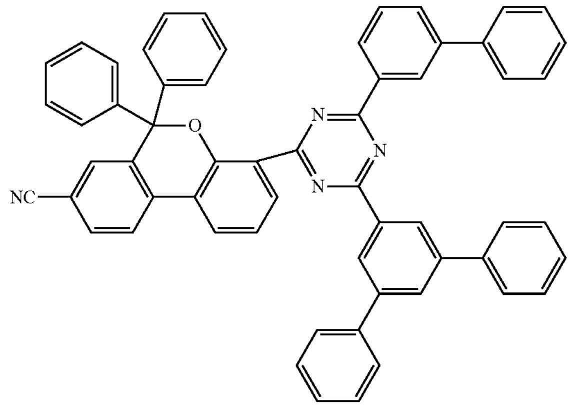
-continued
116
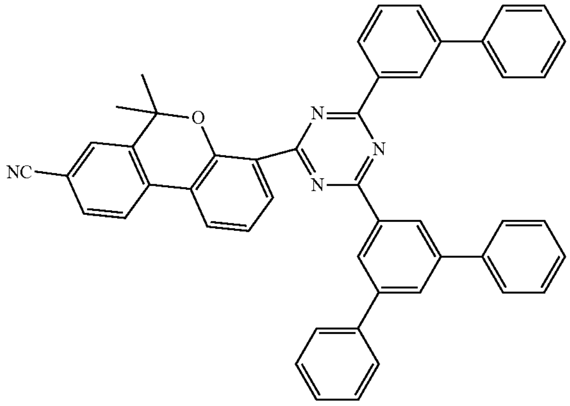
117
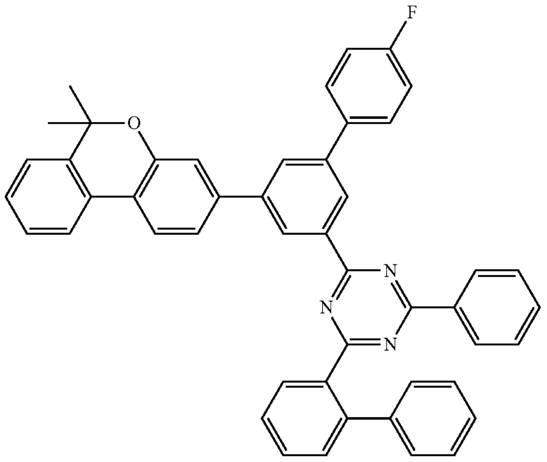
118
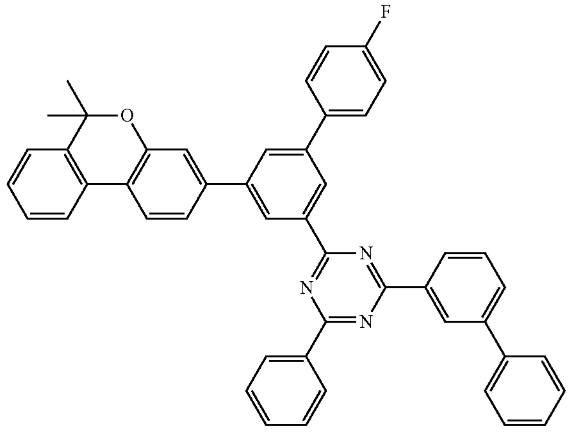

-continued
119
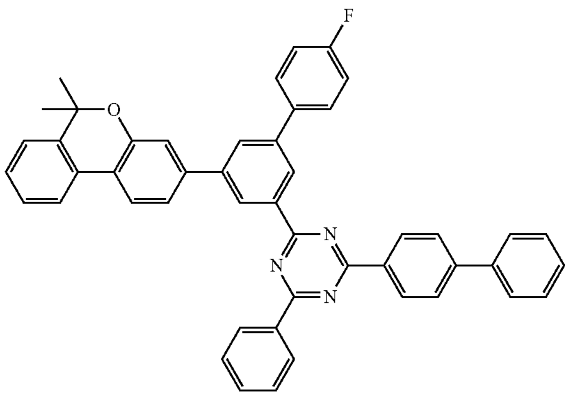
120
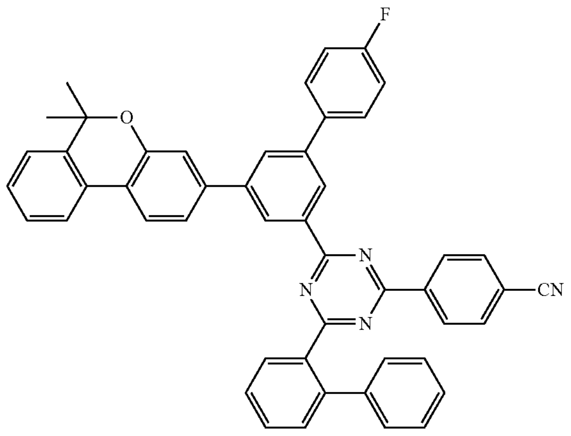
121
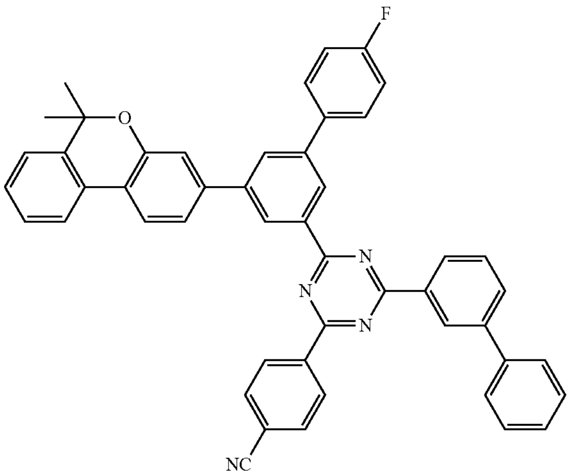
-continued
122
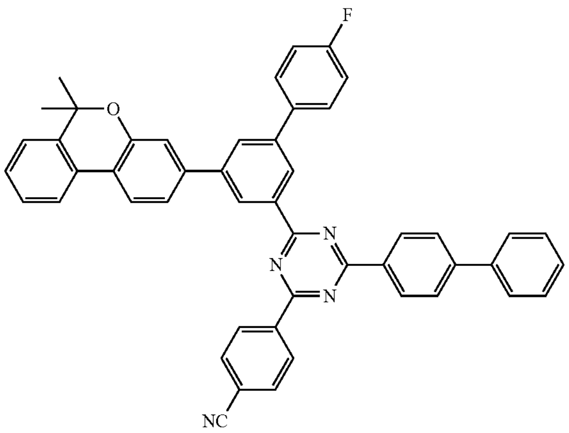
123
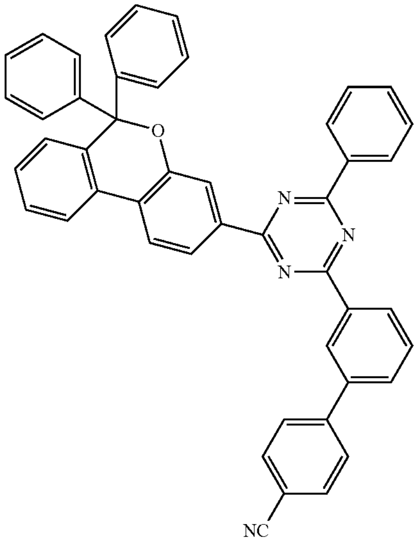
124
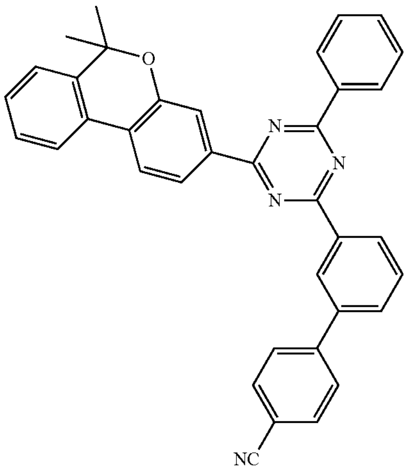

125
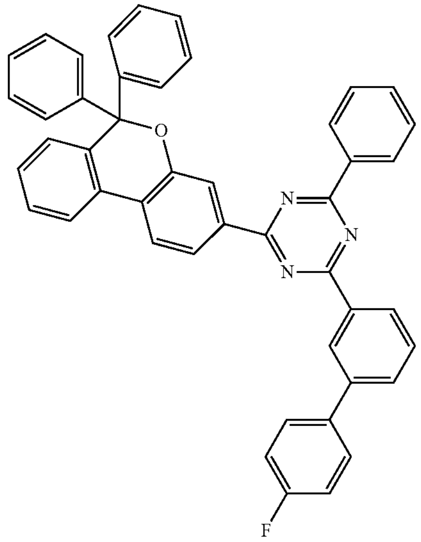
126
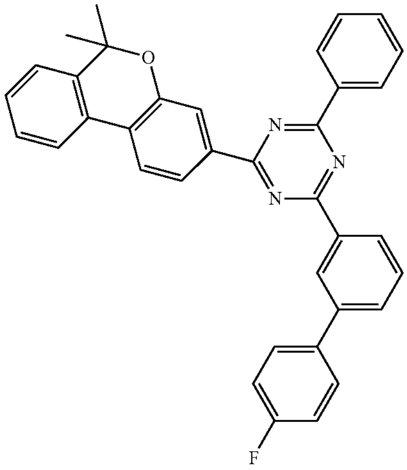
127
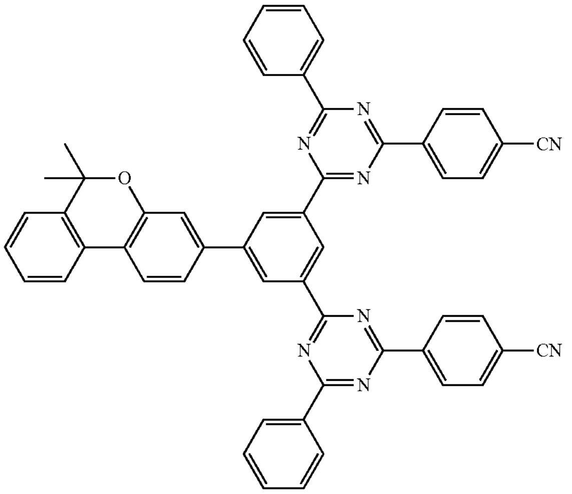
128
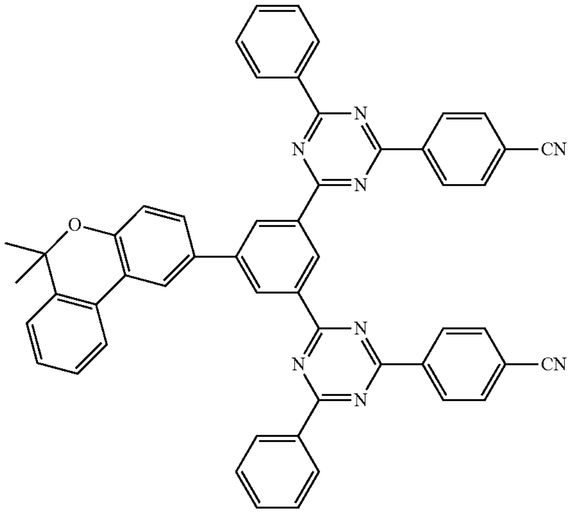
129
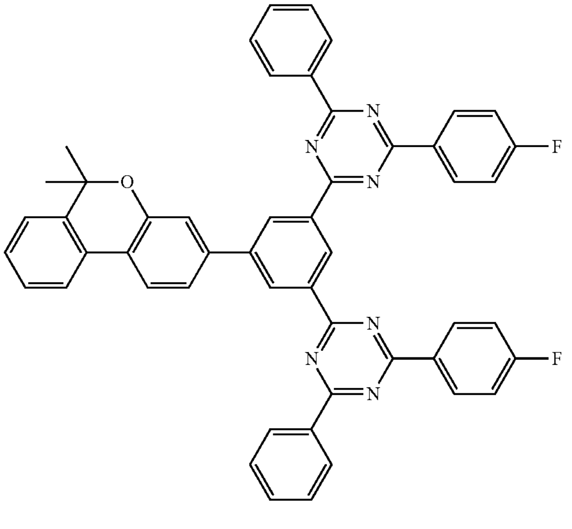
130
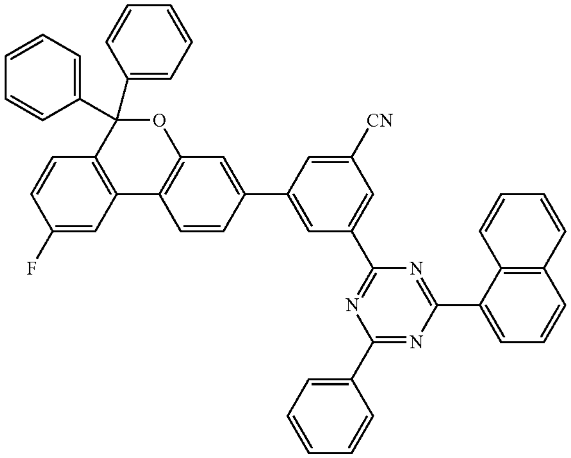

-continued
131
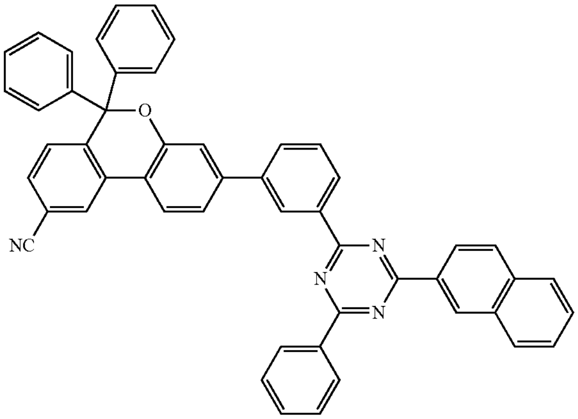
132
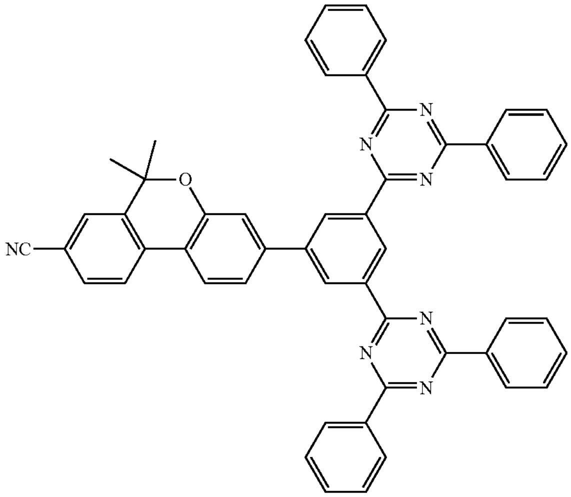
133
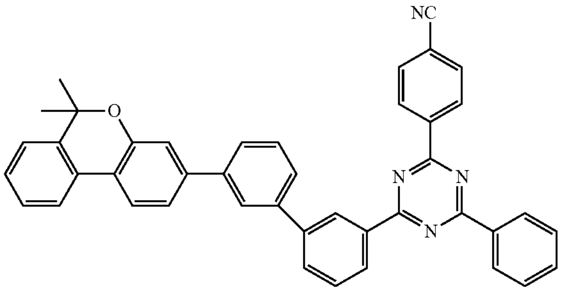
134
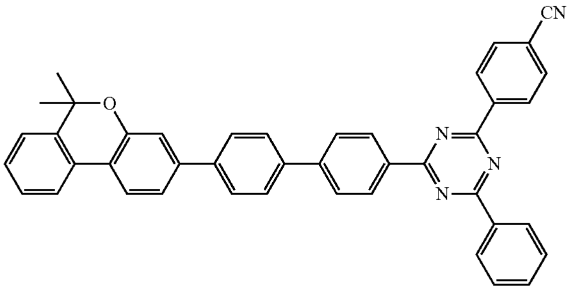
135
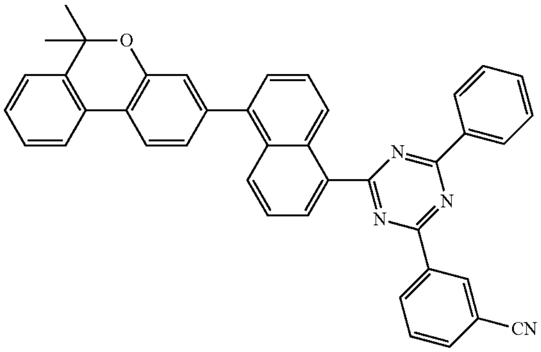
136
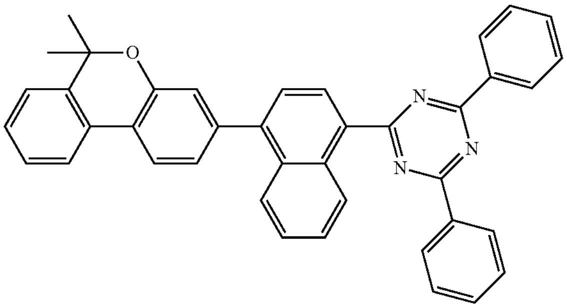

-continued
137
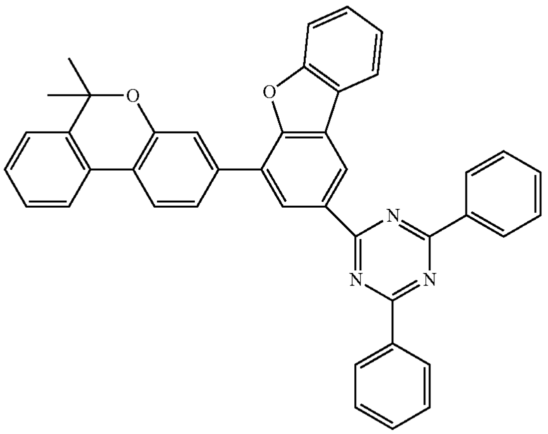
138
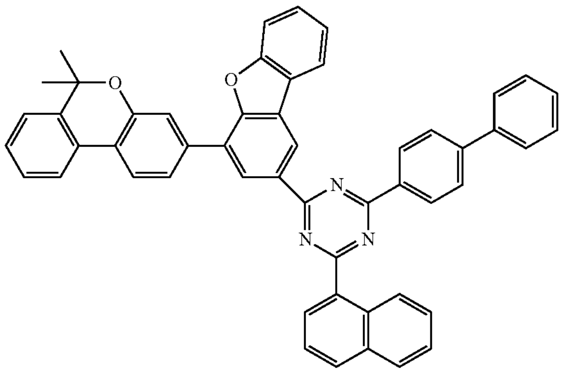
139
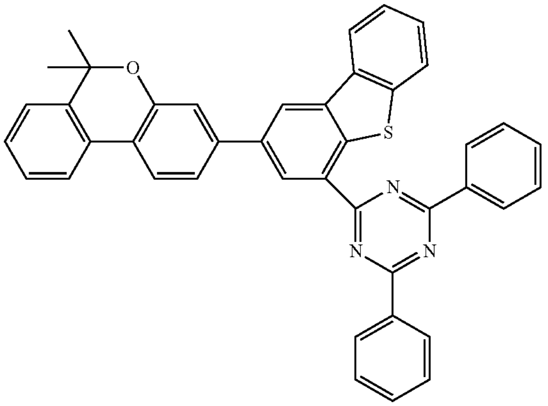
140
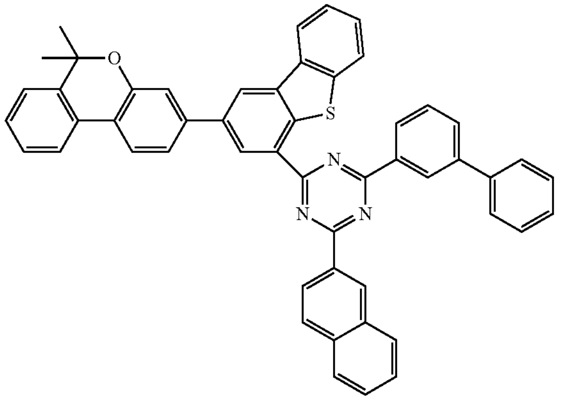
141
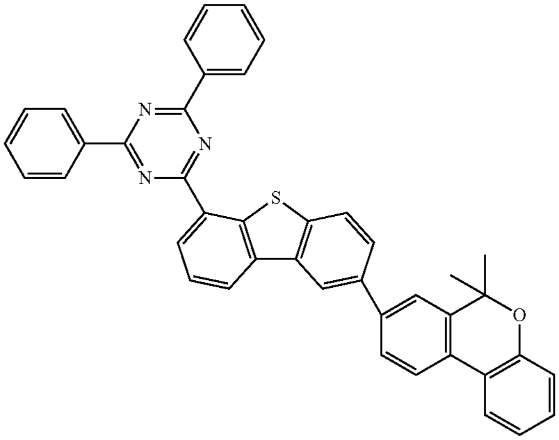
142
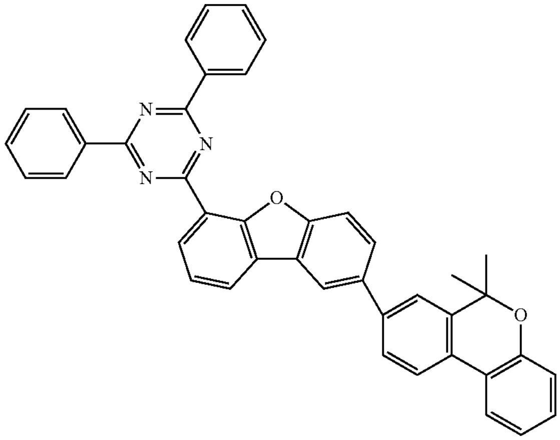

-continued
143
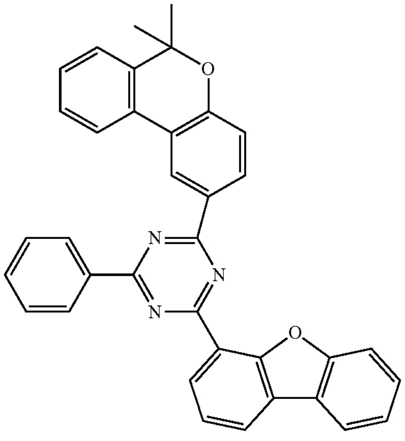
144
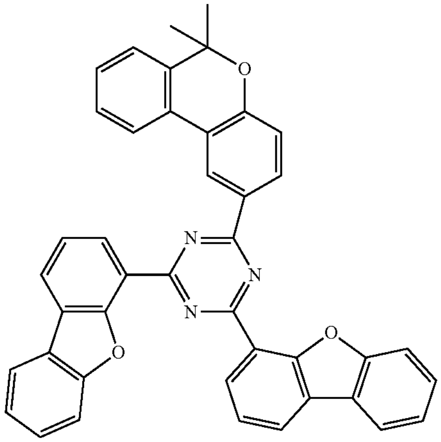
145
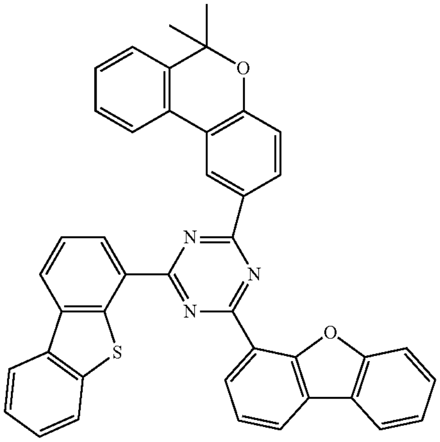
146
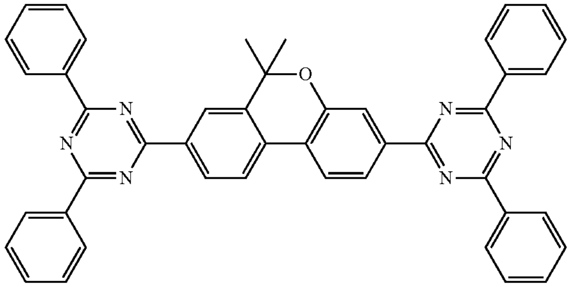
147
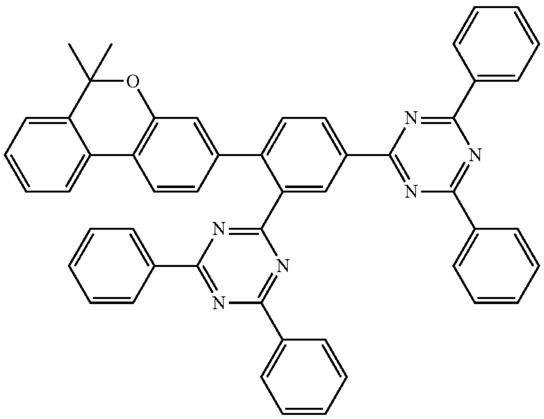
148
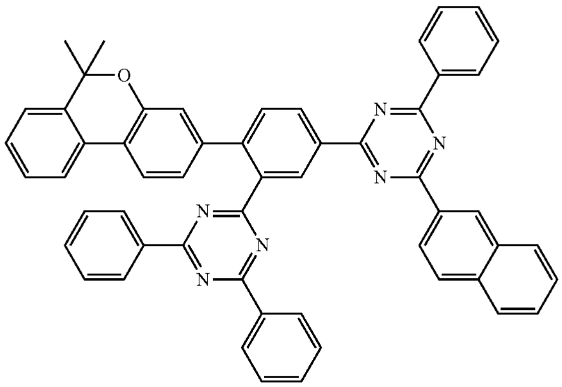

-continued
149
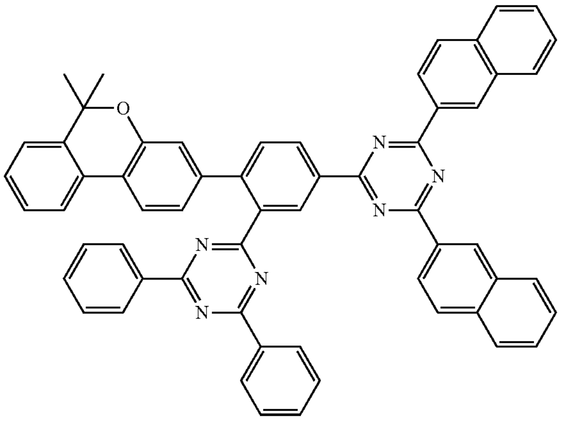
150
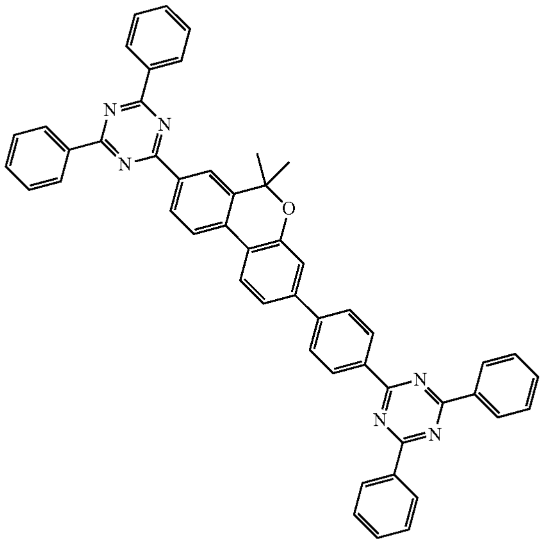
151
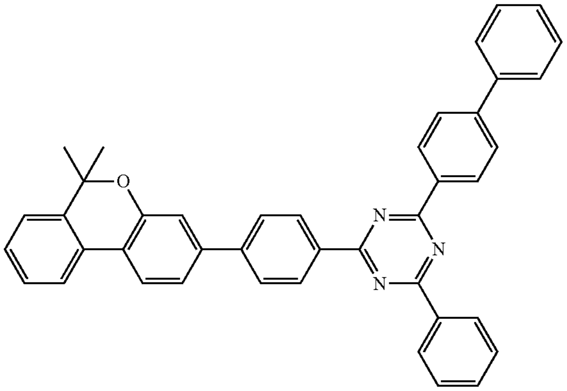
152
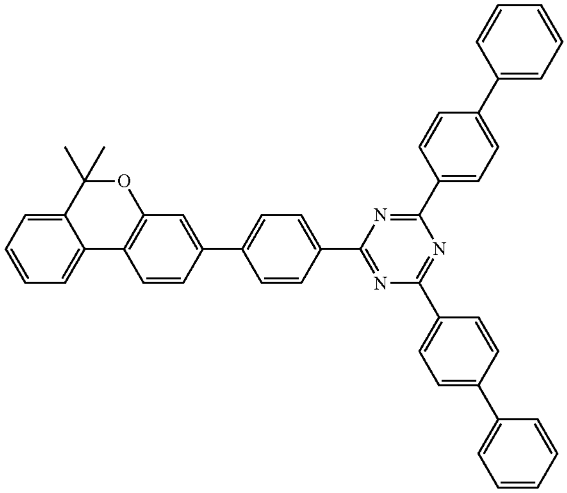
153
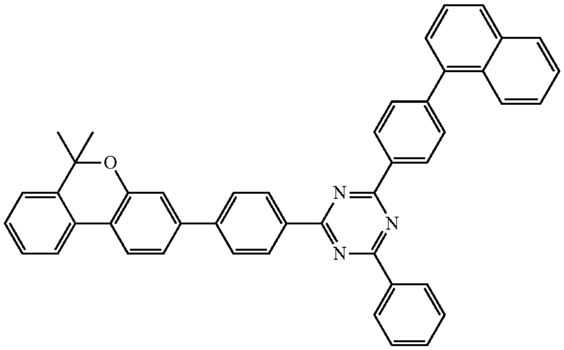
154
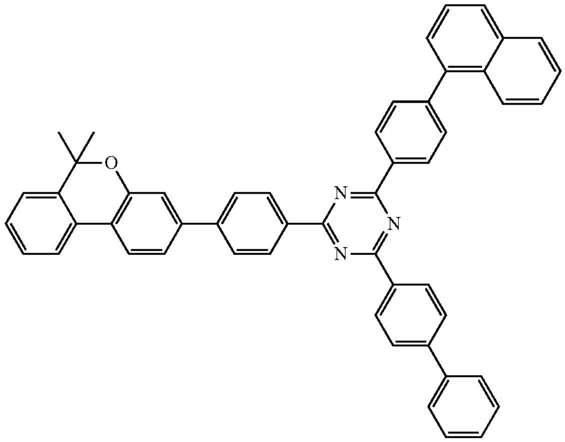

-continued
155
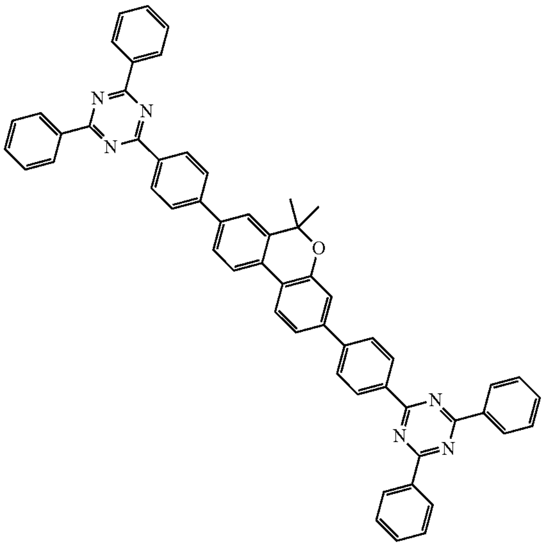
156
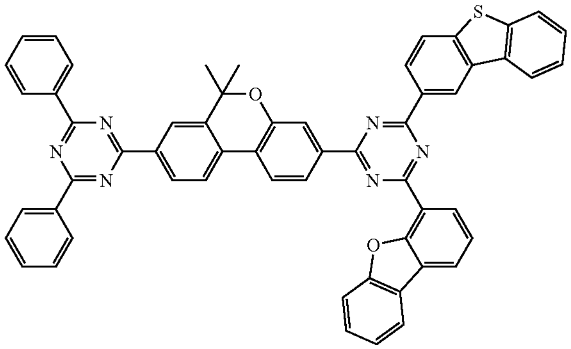
157
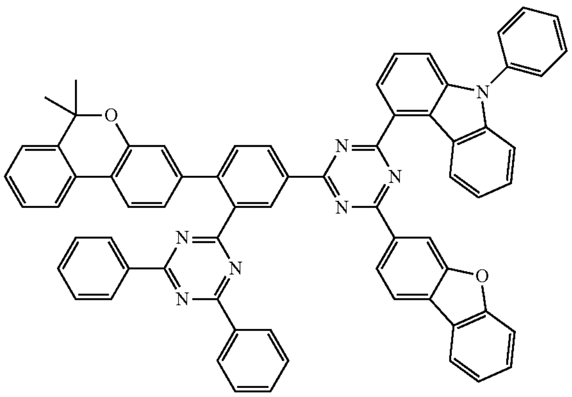
158
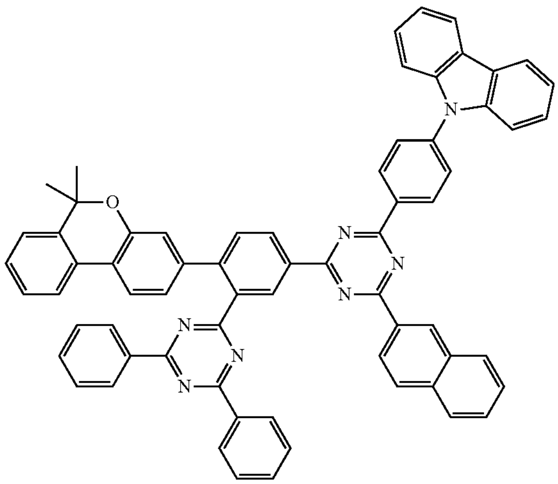
159
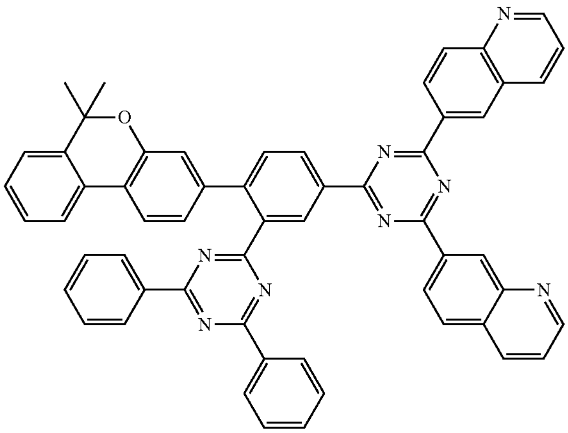
160
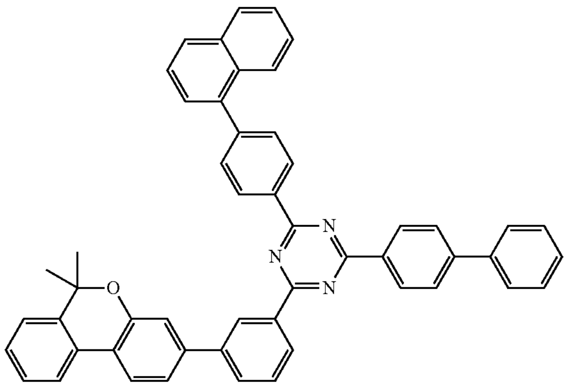

-continued
161
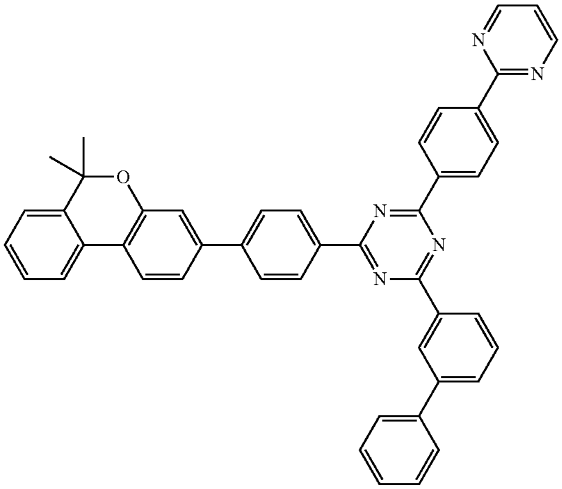
162
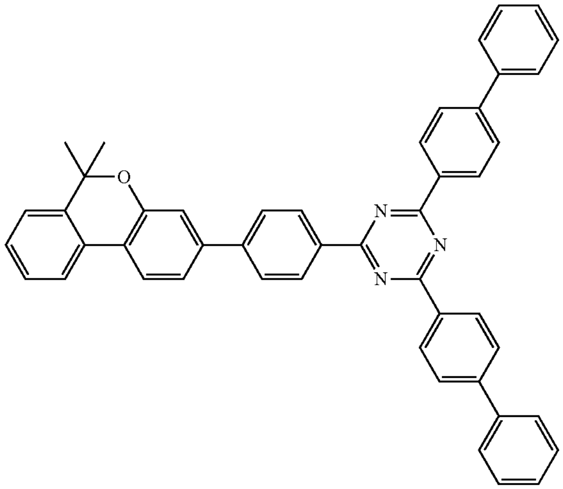
163
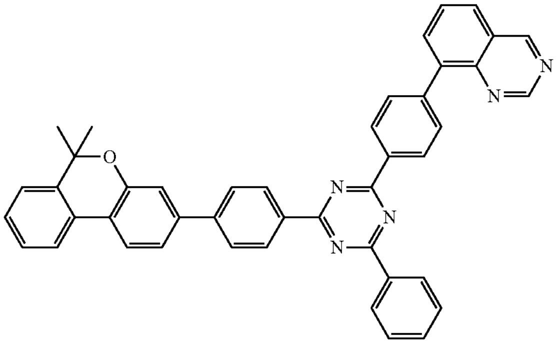
164
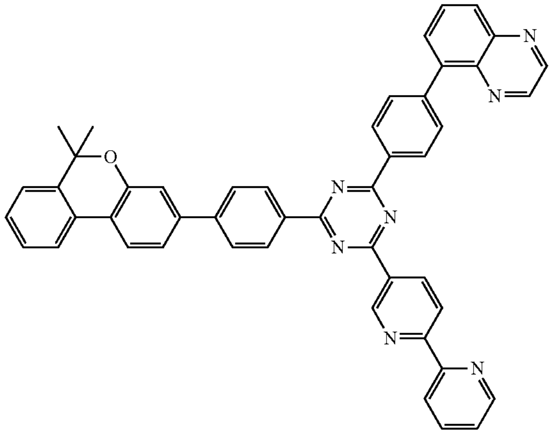
165
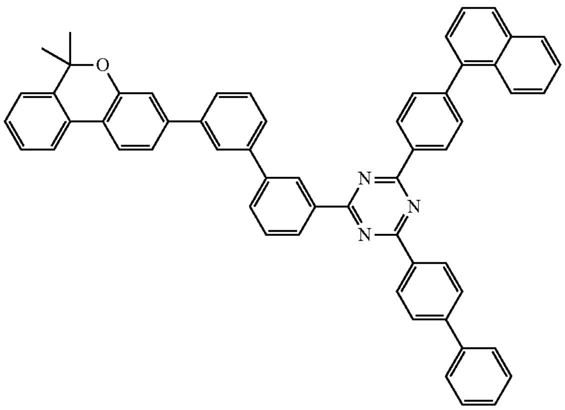
166
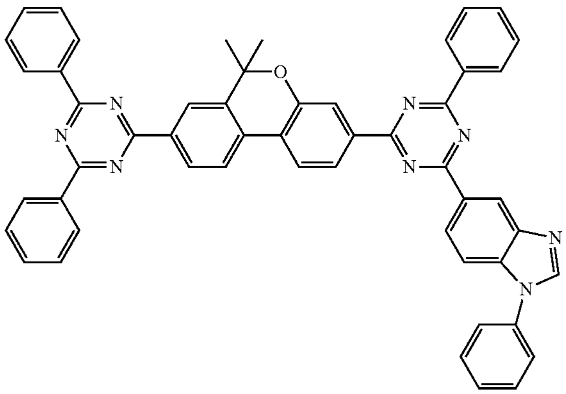

-continued
167
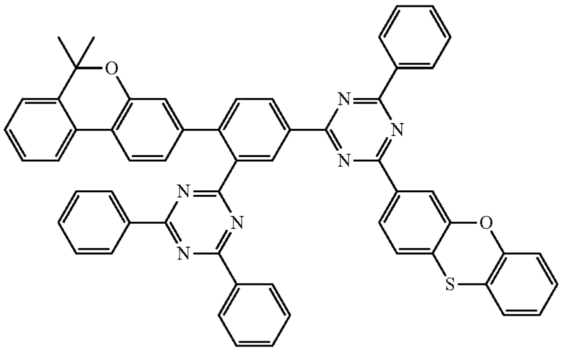
168
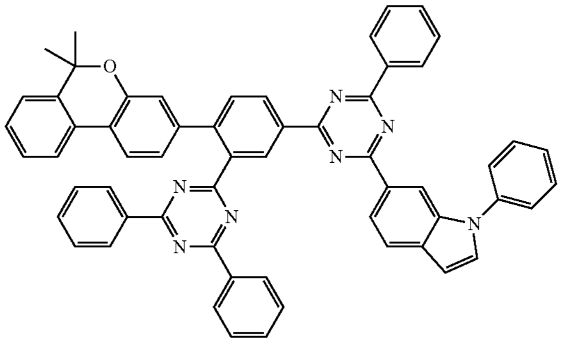
169
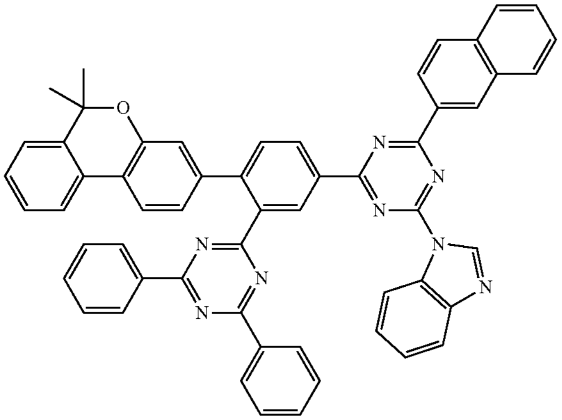
170
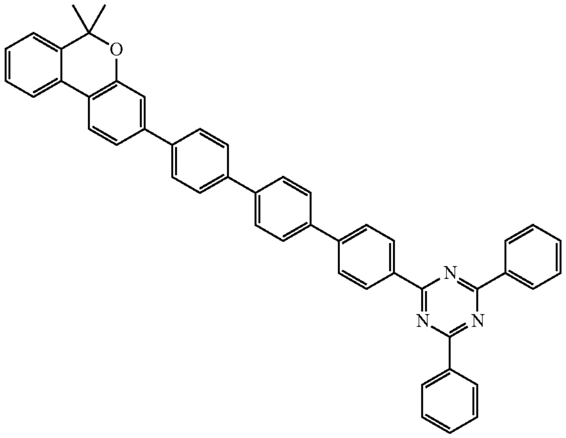
171
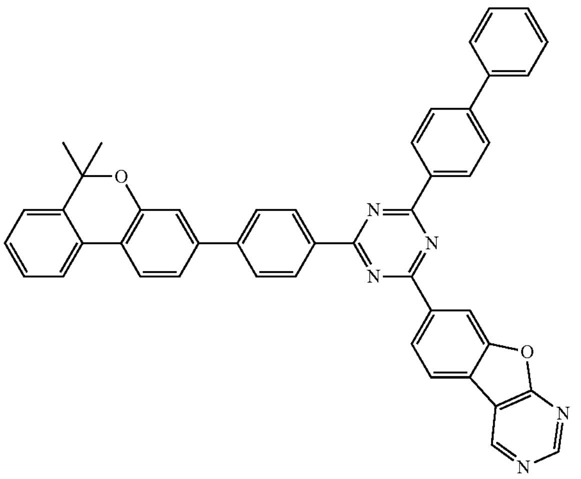
172
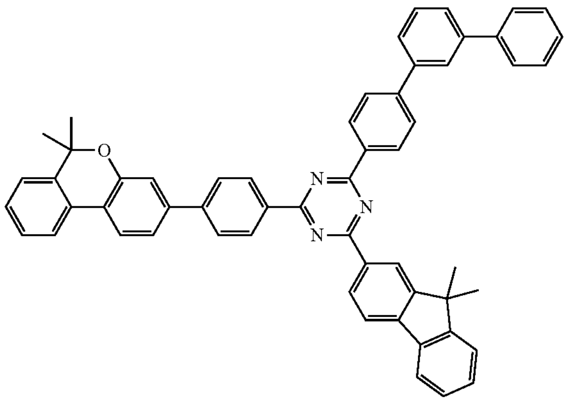

-continued
173
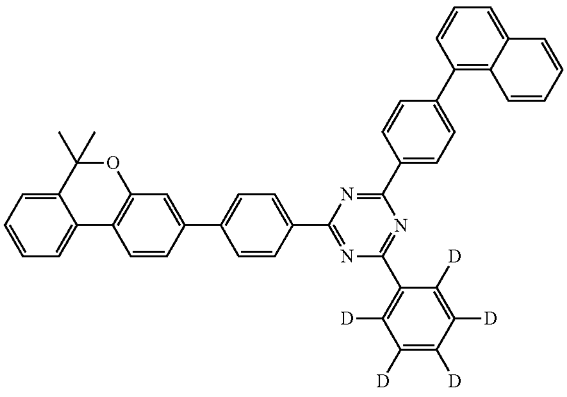
174
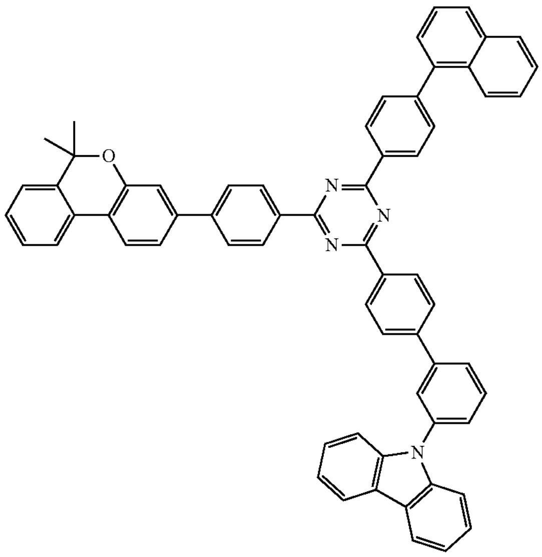
175
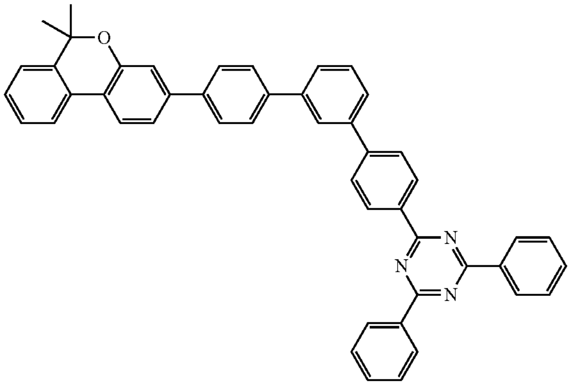
176
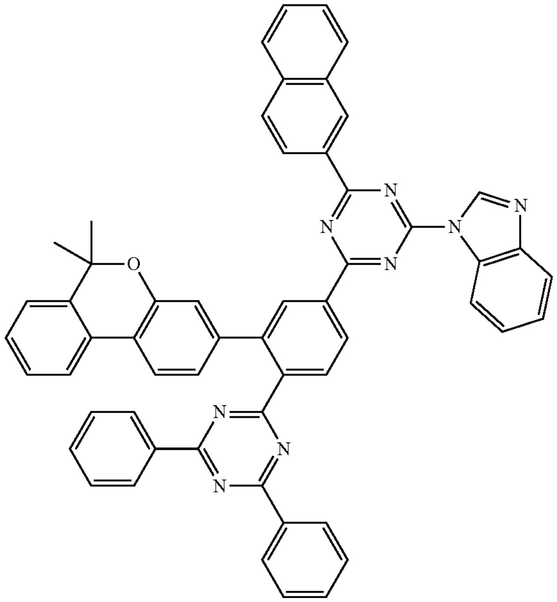

-continued
177
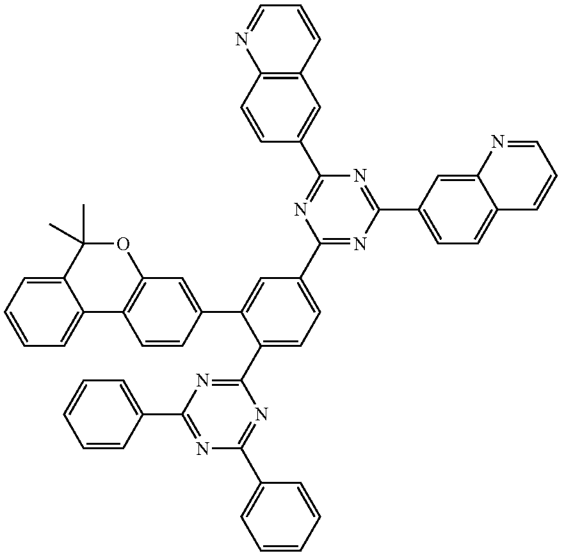
178
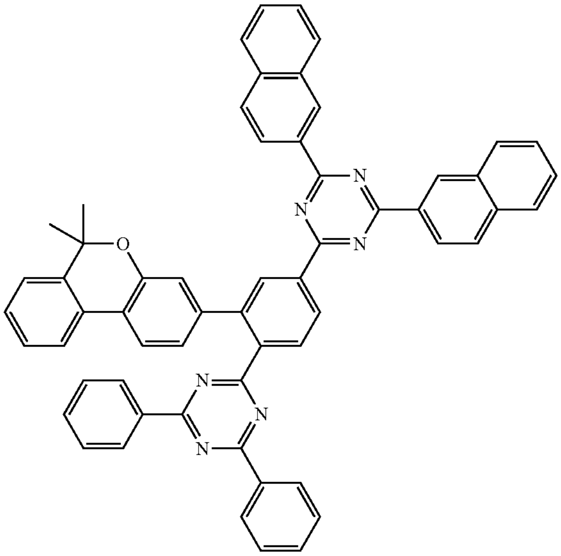
179
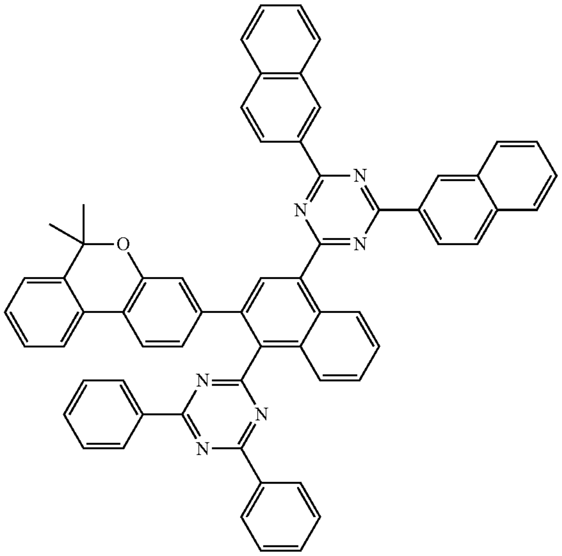
180
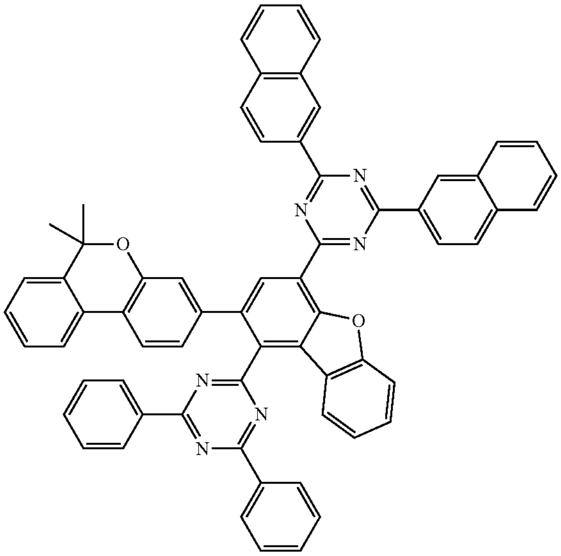
181
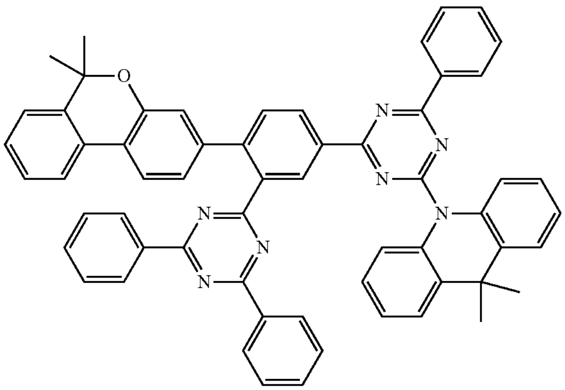
182
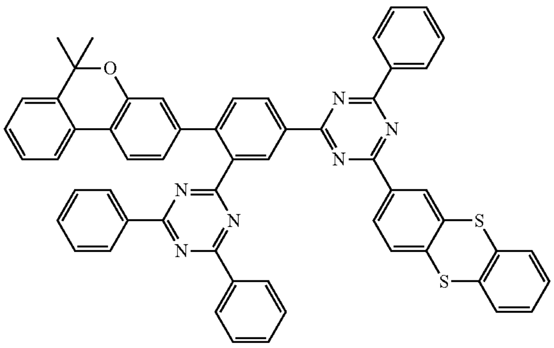

-continued
183
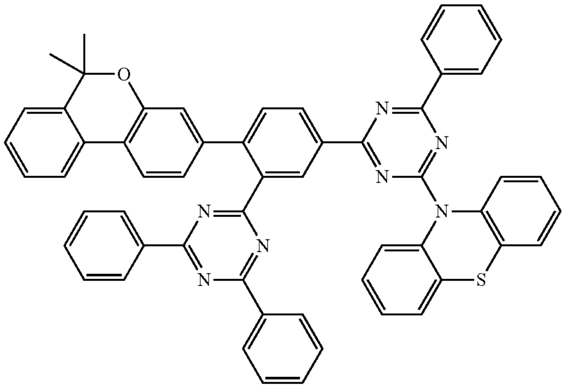
184
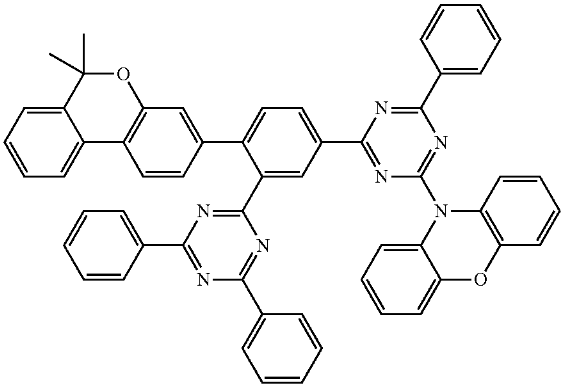
185
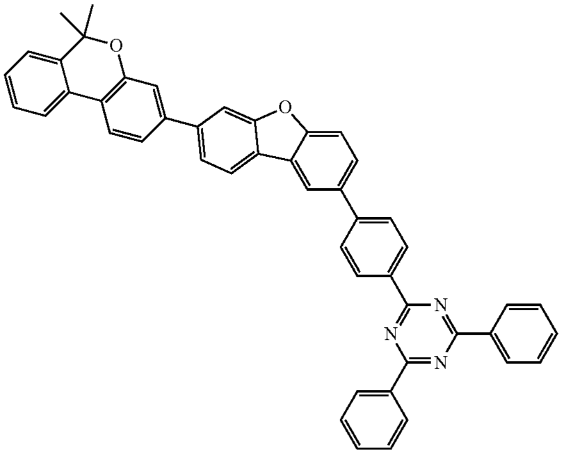
186
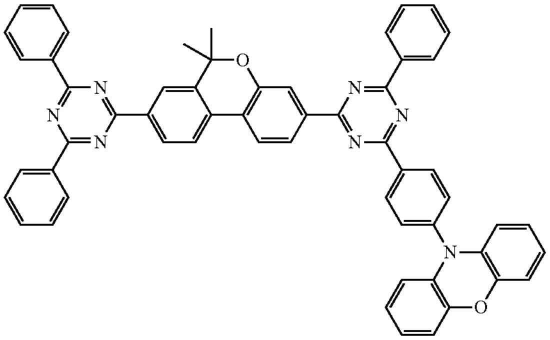
187
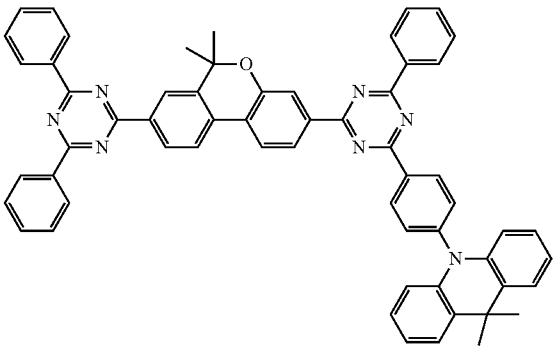
188
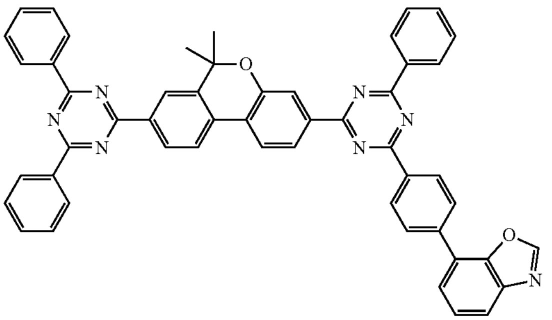

-continued
189
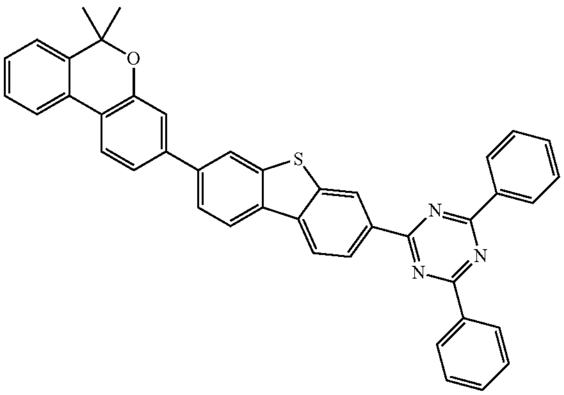
190
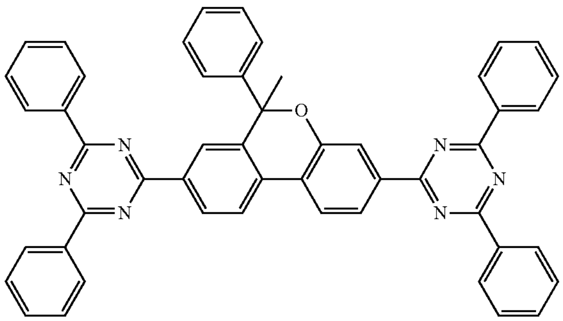
191
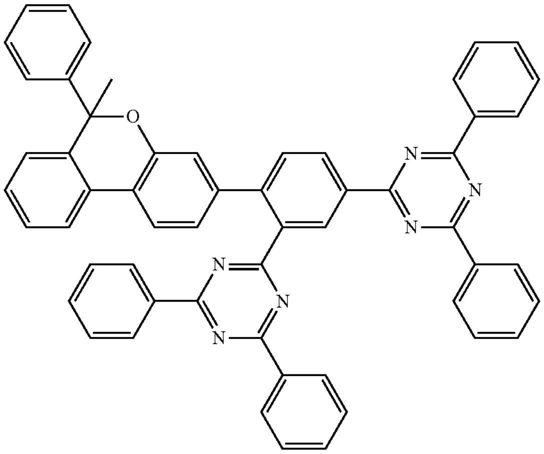
192
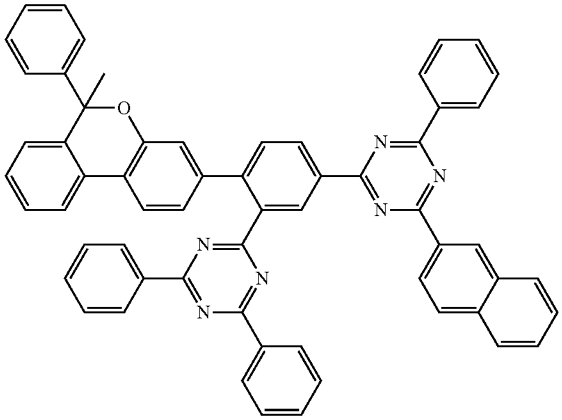
193
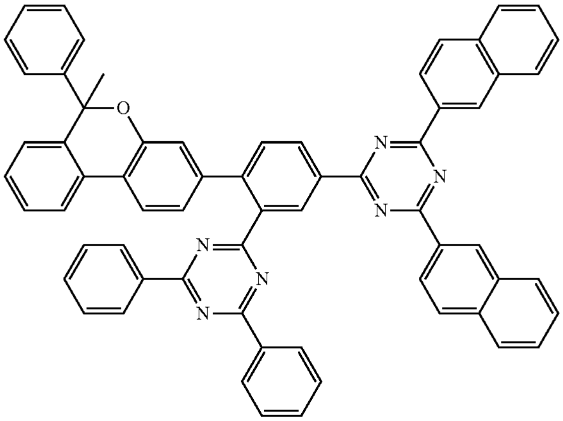
194
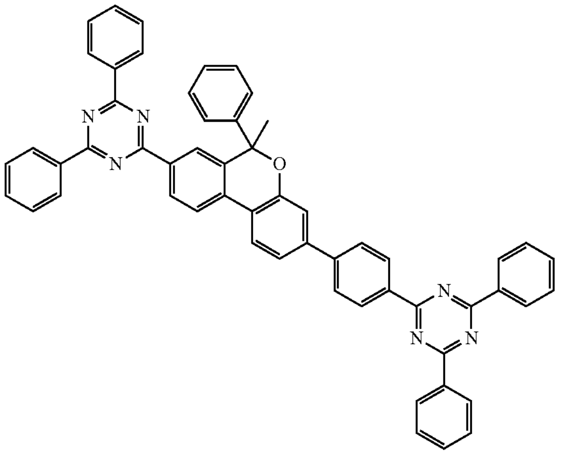

-continued
195
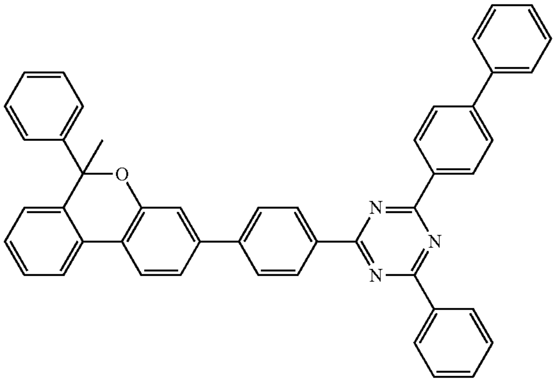
196
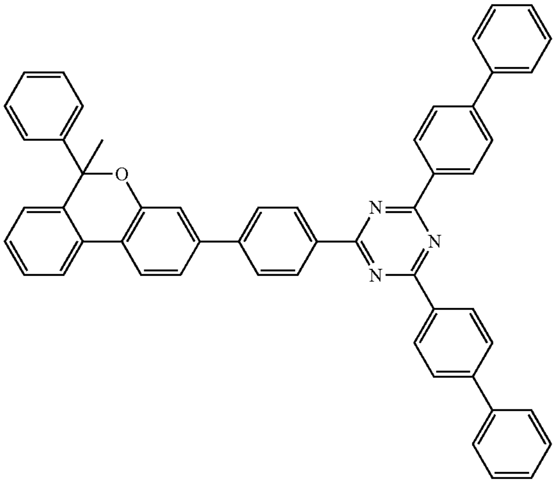
197
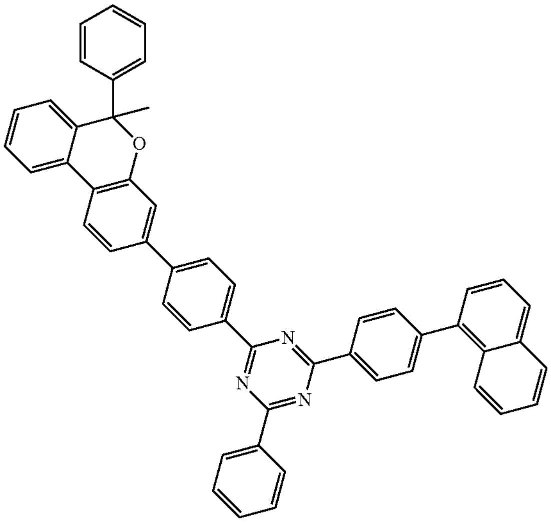
198
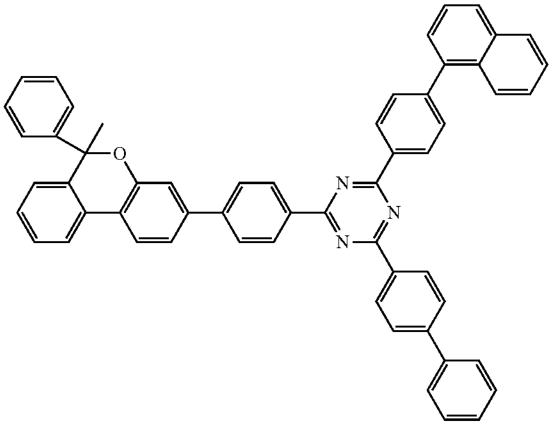
199
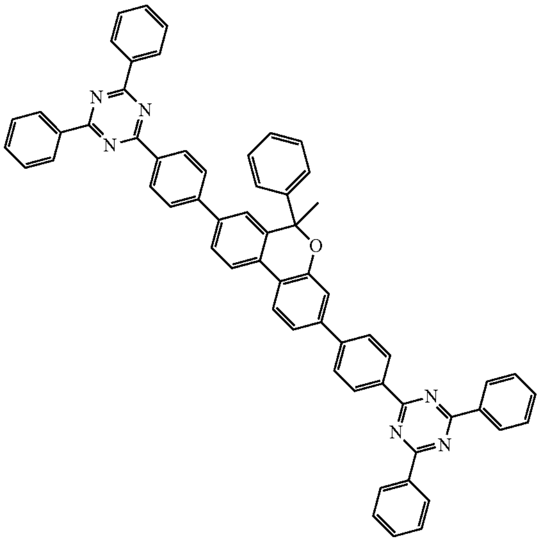
200
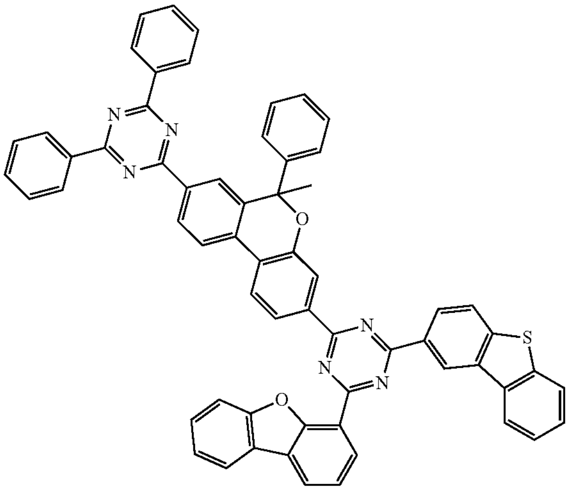

-continued
201
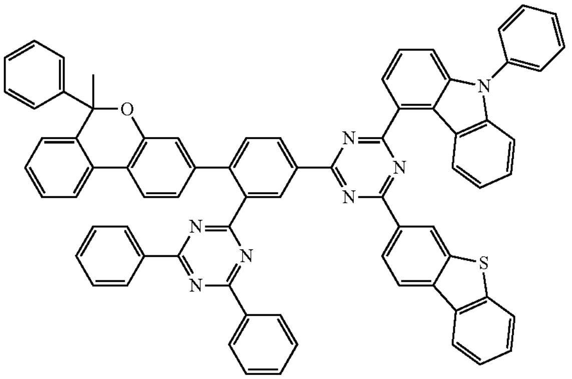
202
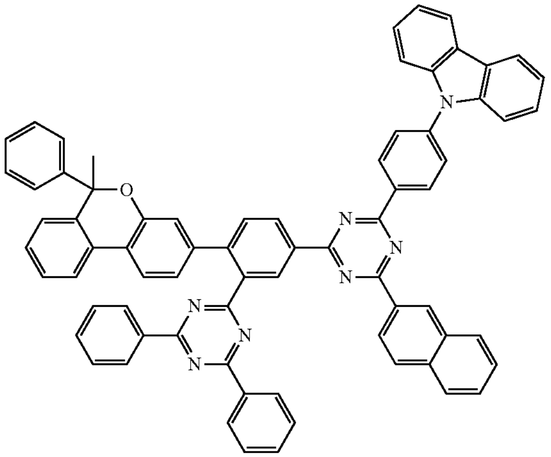
203
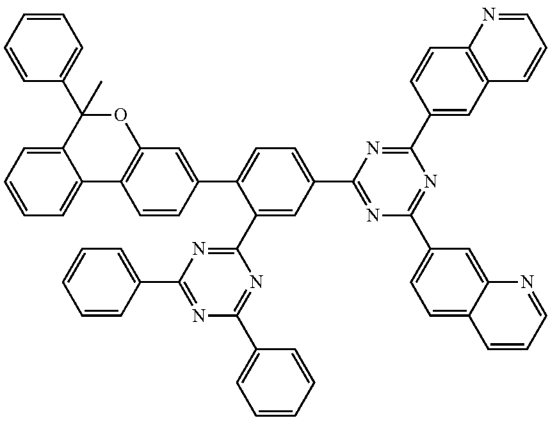
204
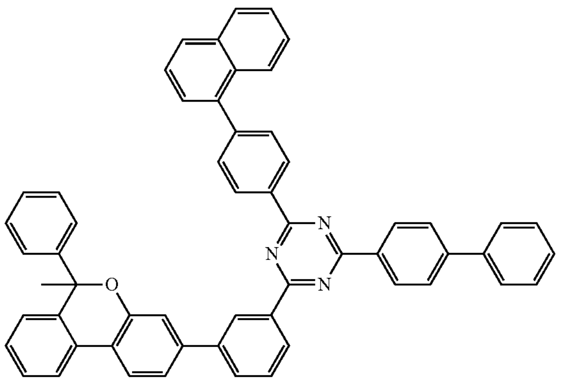
205
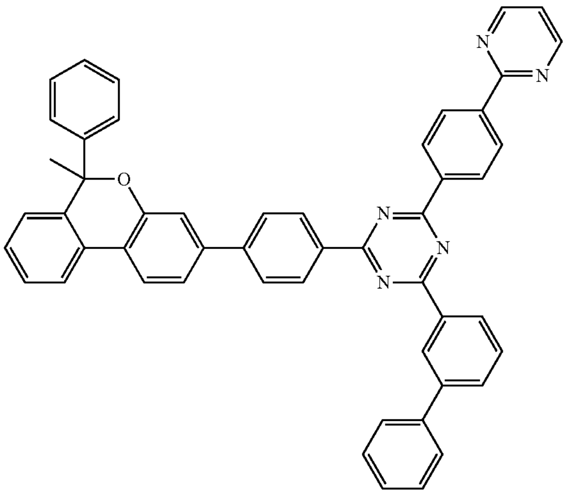
206
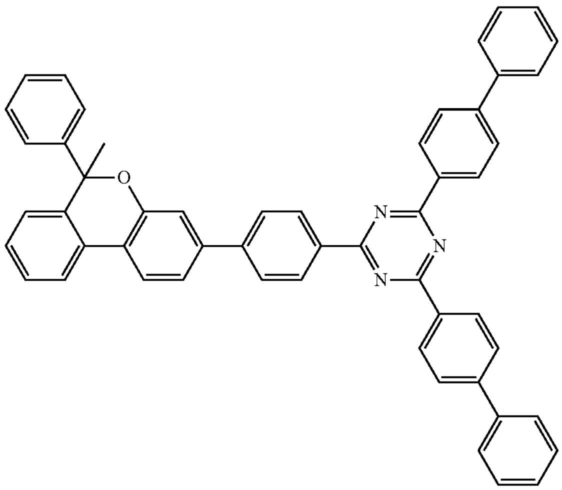

-continued
207
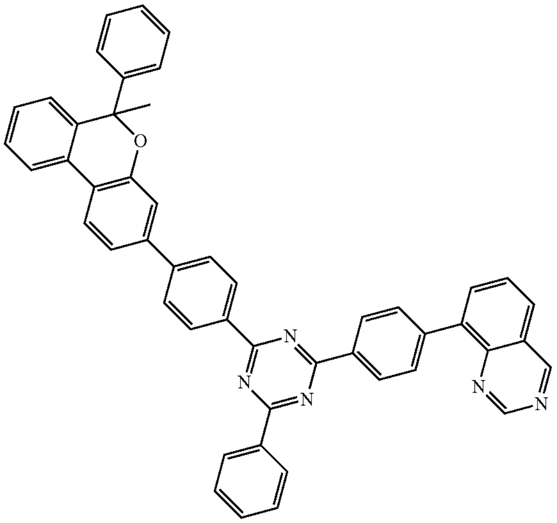
208
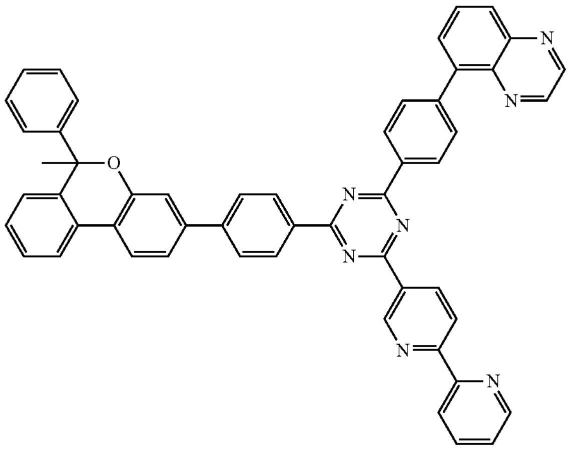
209
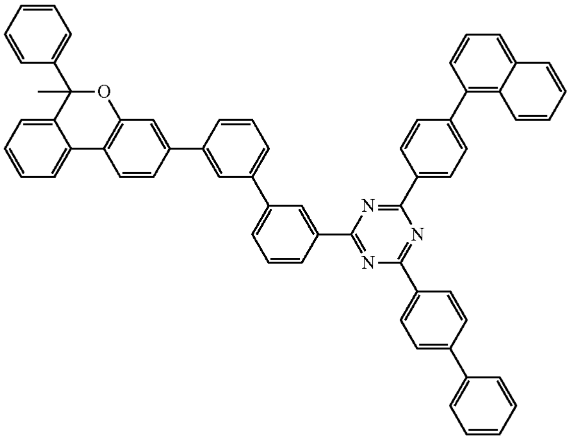
210
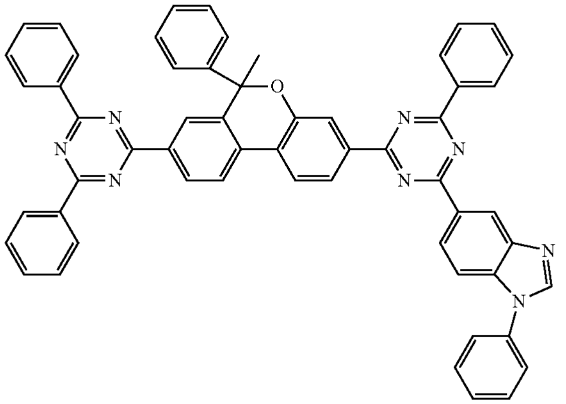
211
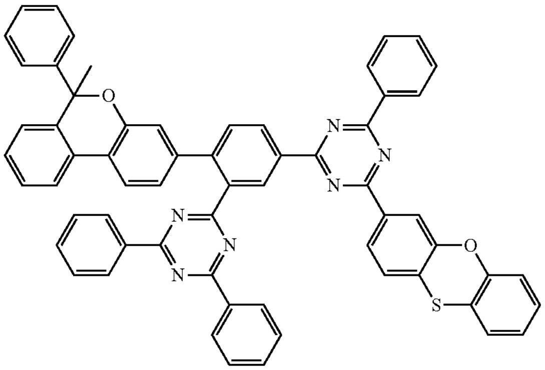
212
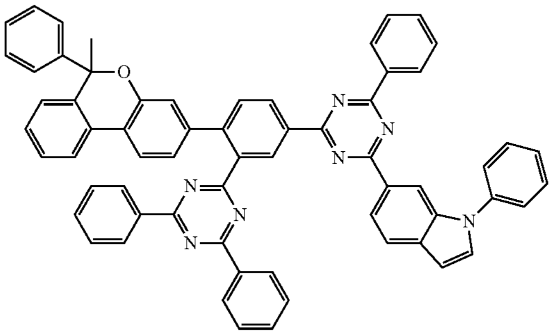

-continued
213
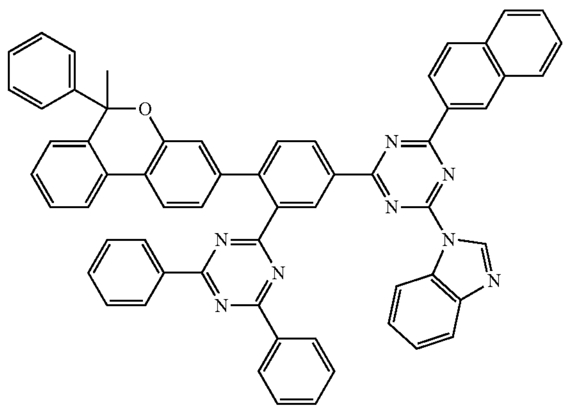
214
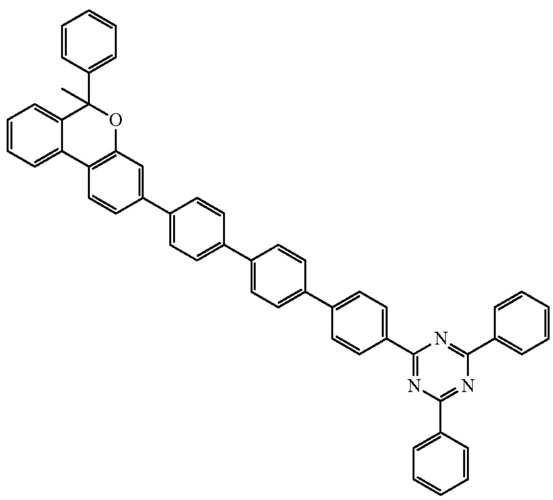
215
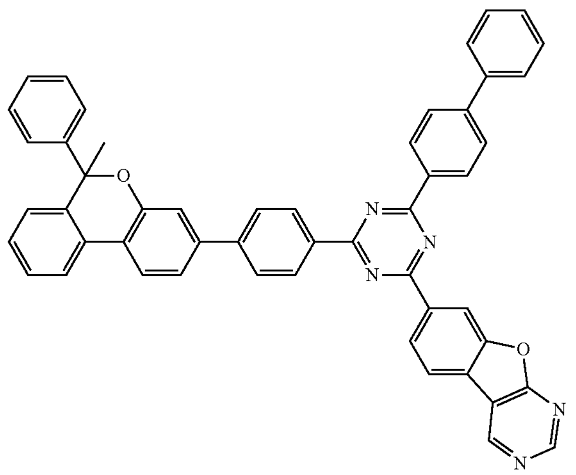
216
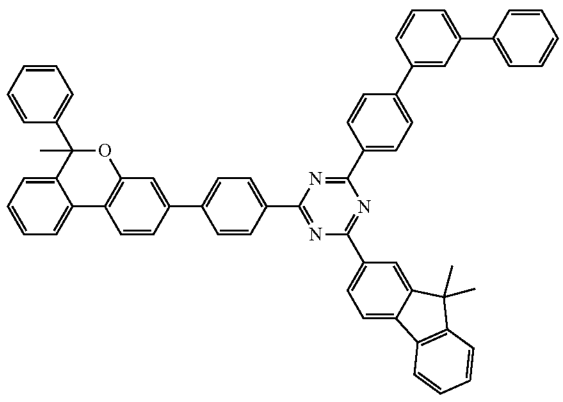
217
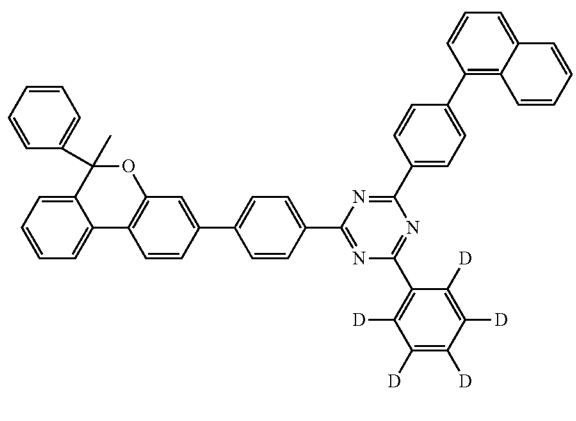
218
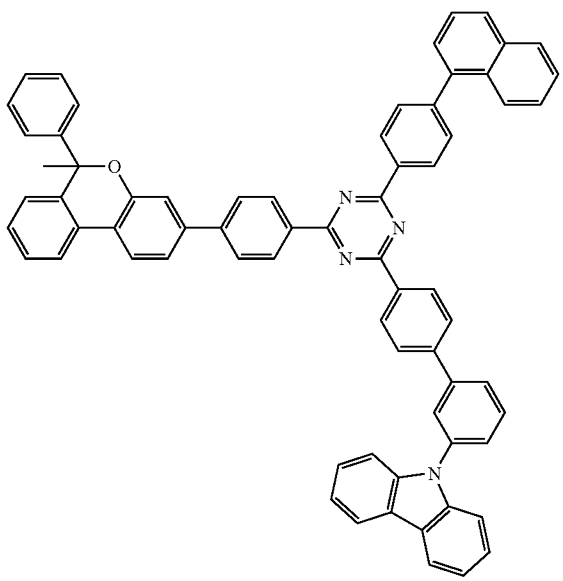

-continued
219
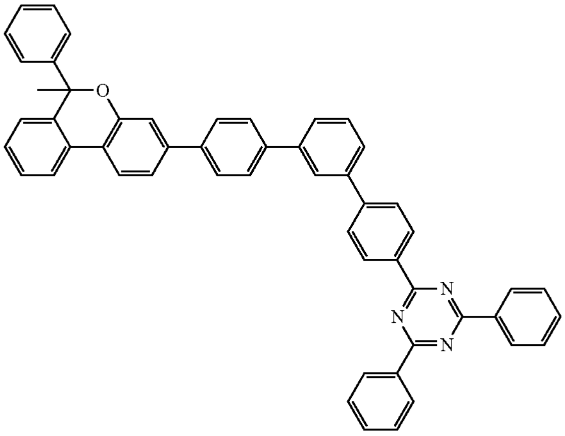
220
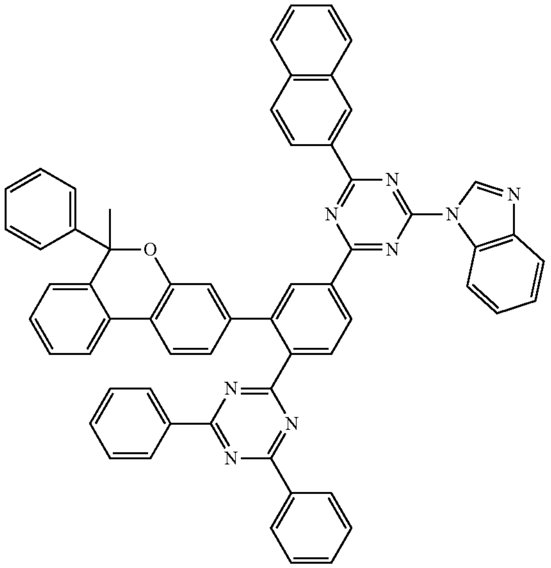
221
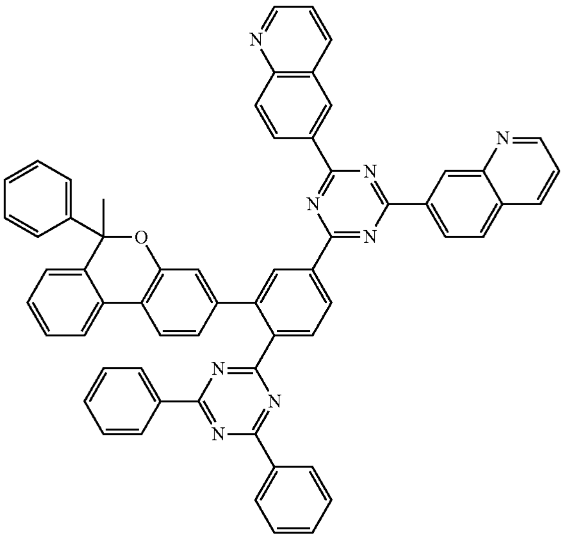
222
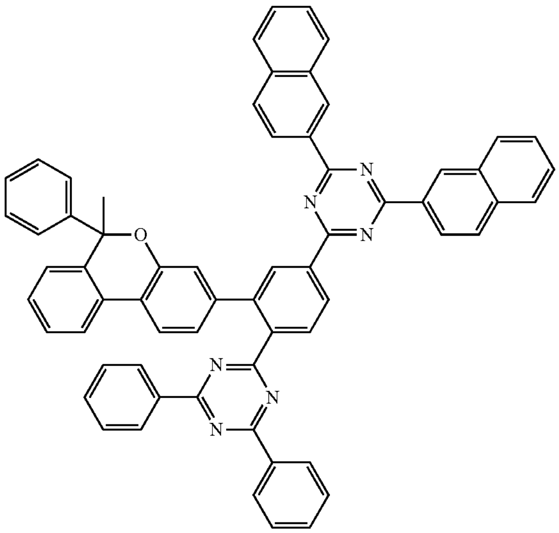

-continued
223
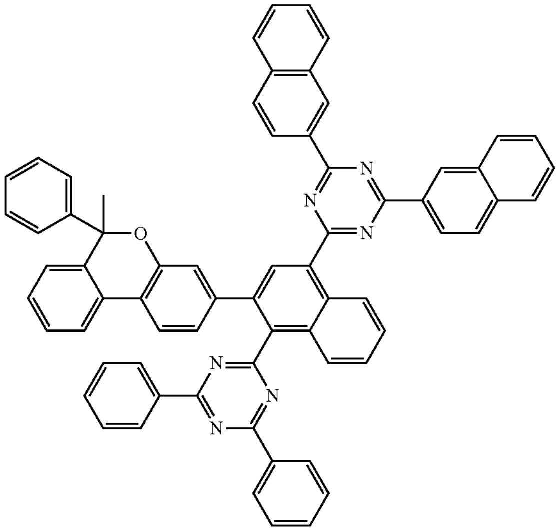
224
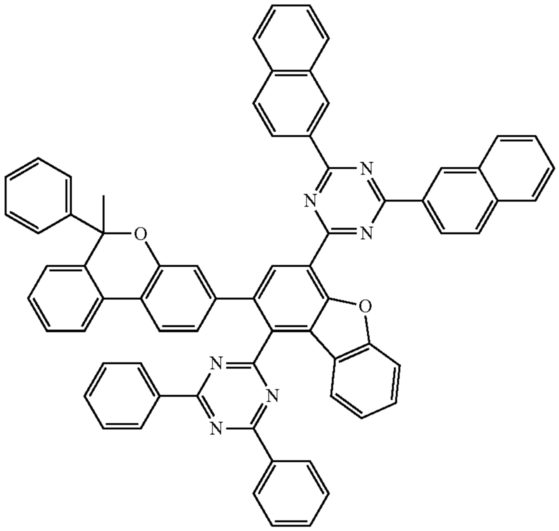
225
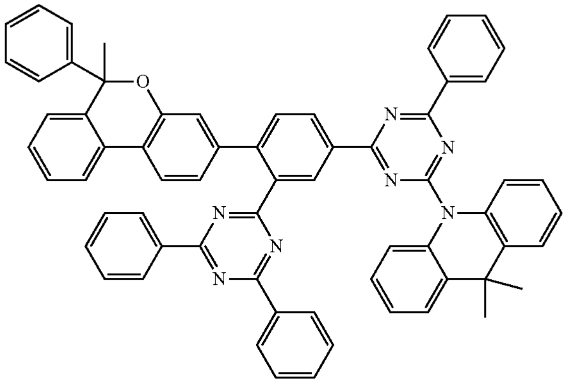
226
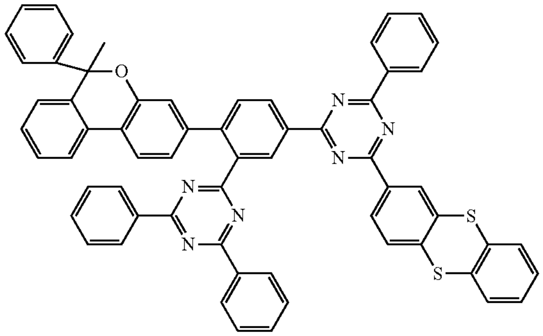
227
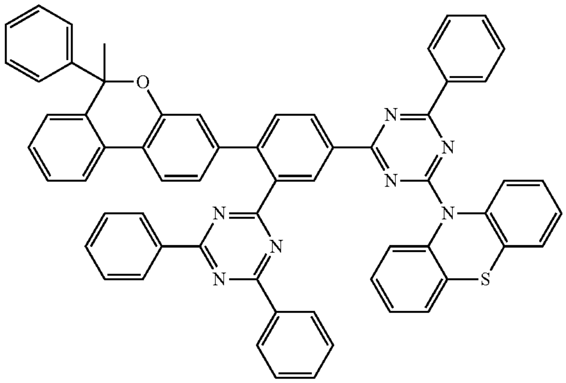
228
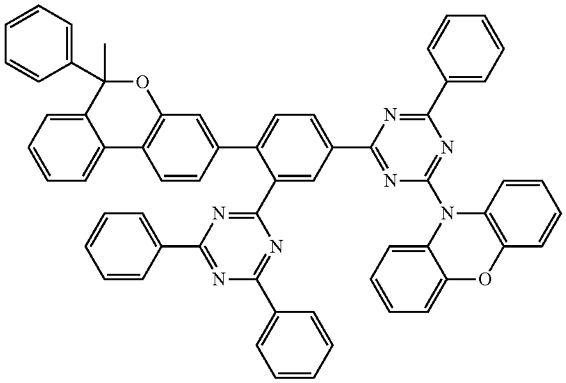

-continued
229
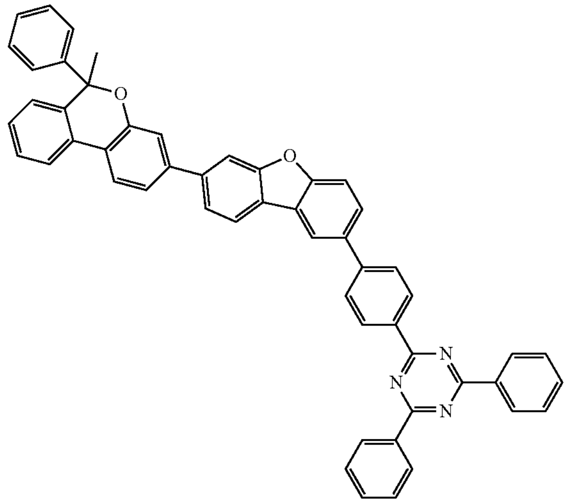
230
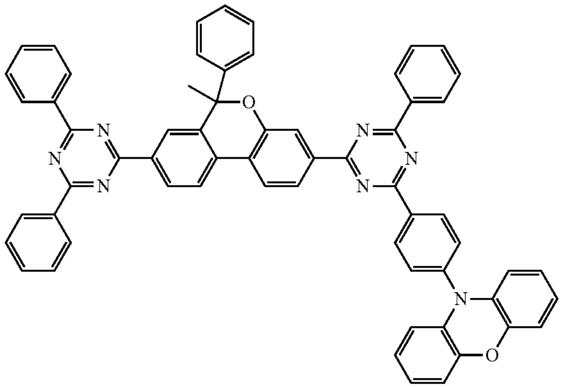
231
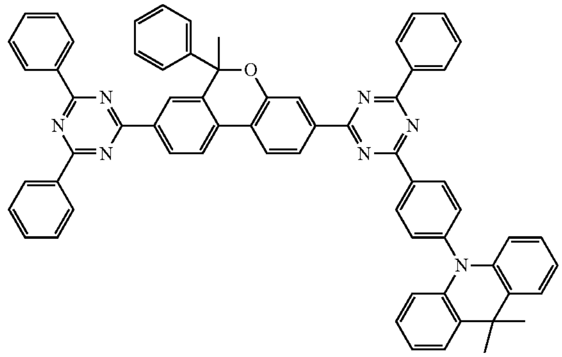
232
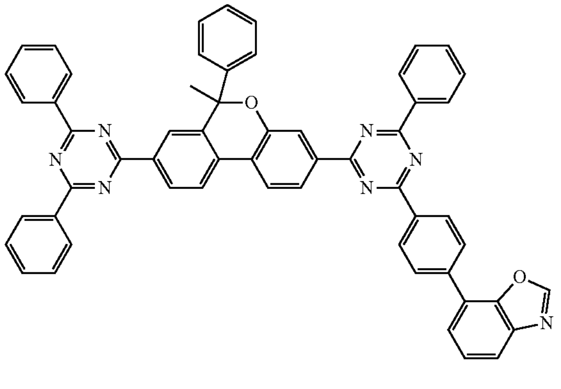
233
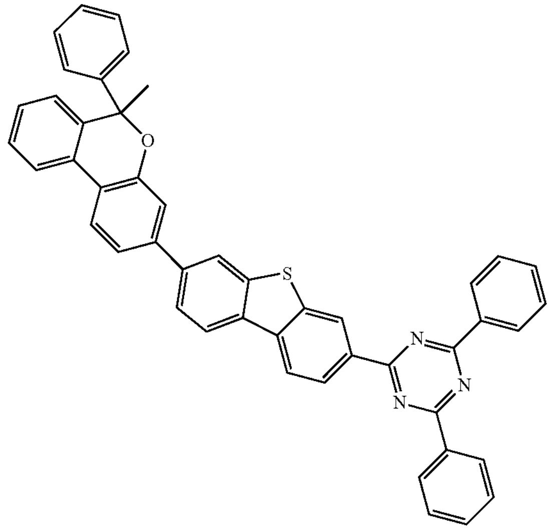
234
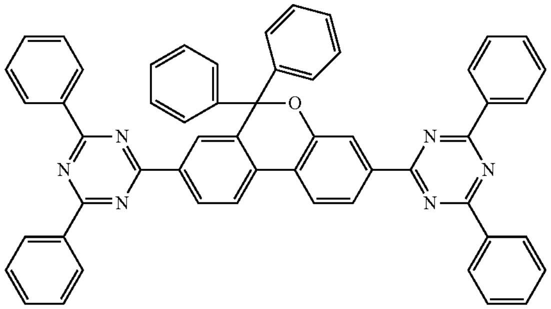

-continued
235
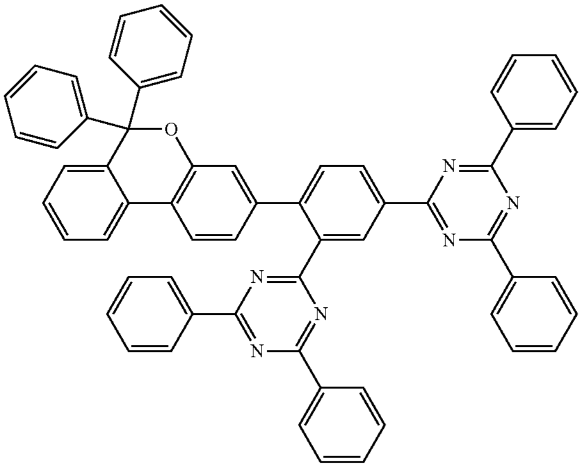
236
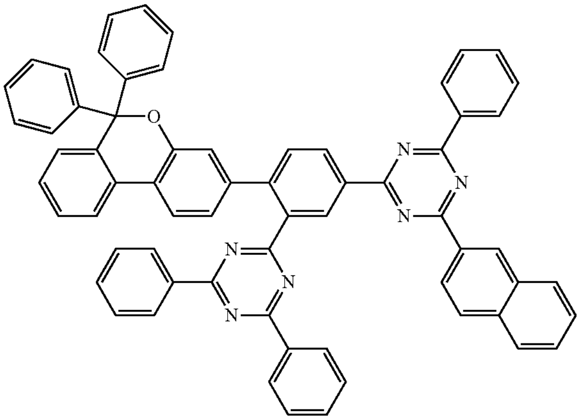
237
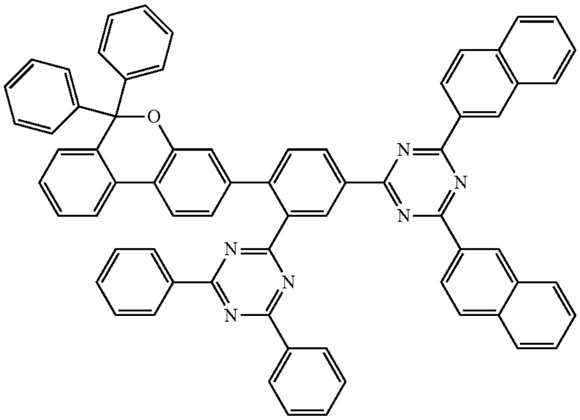
238
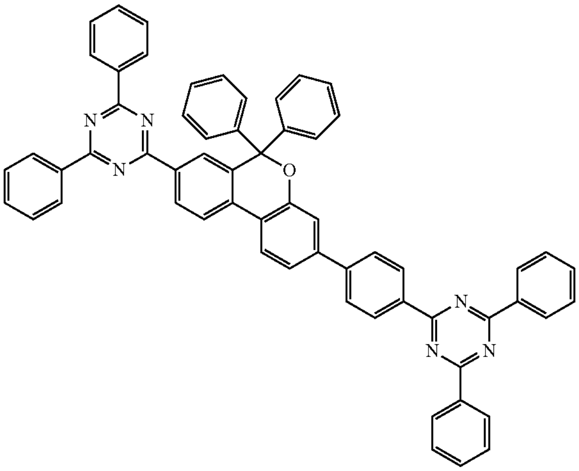
239
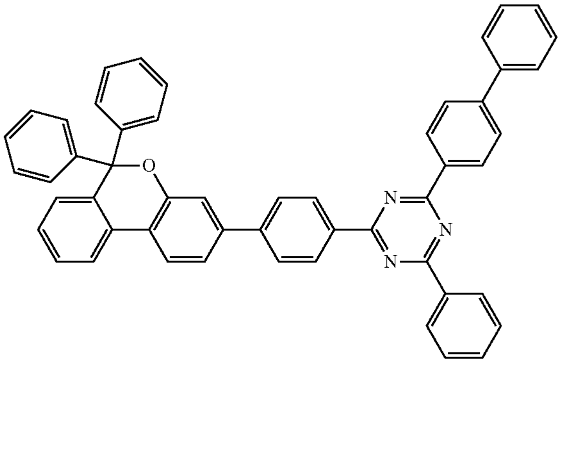
240
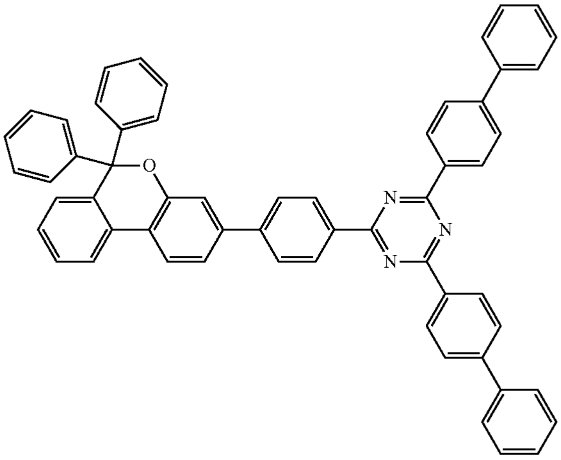

-continued
241
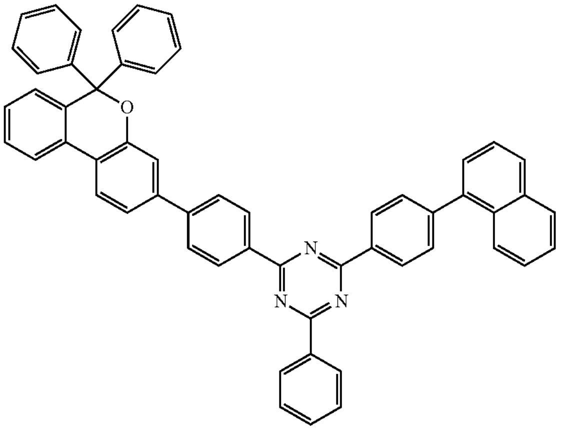
242
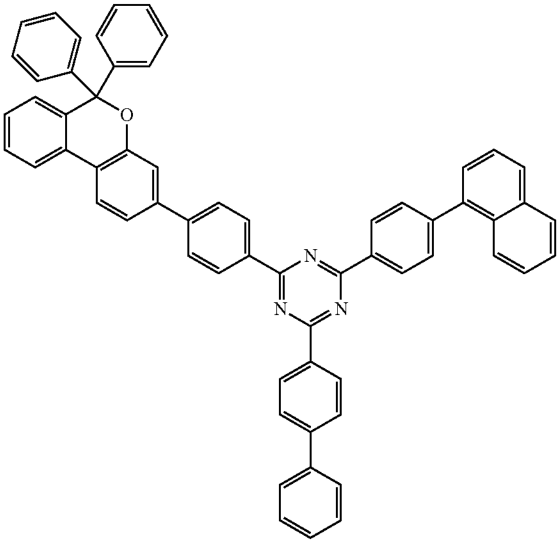
243
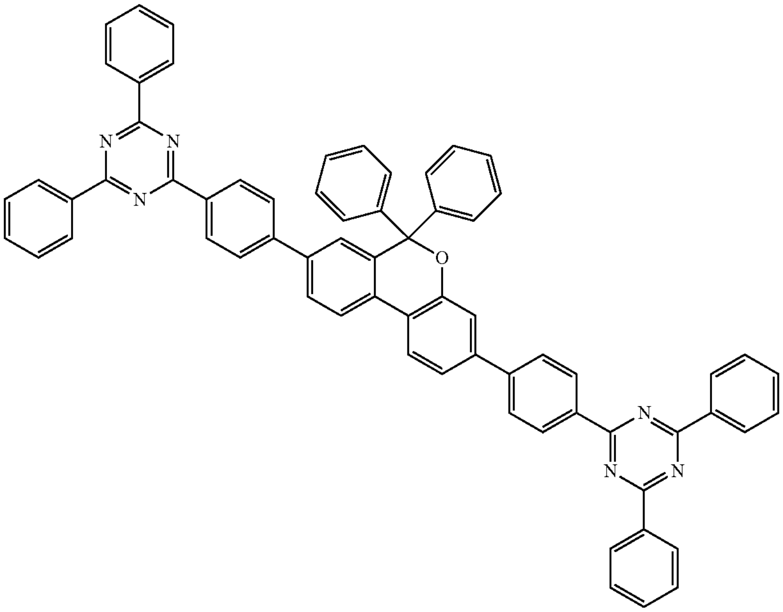
244
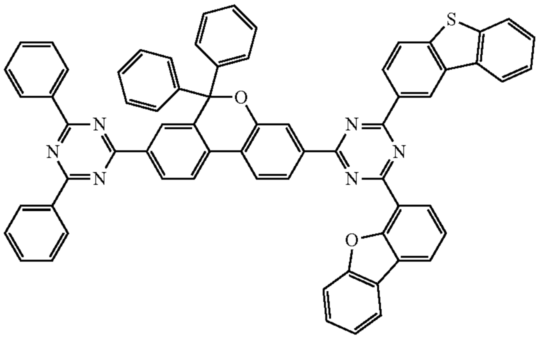
245
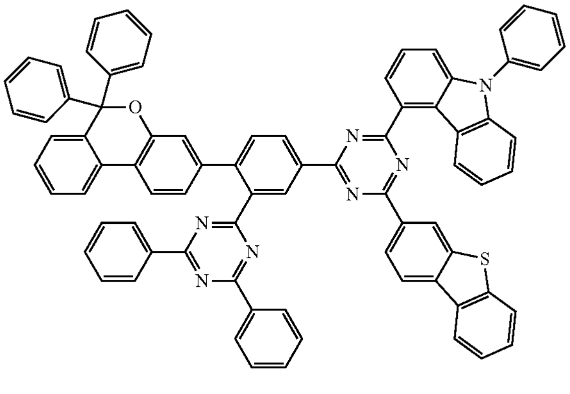

-continued
246
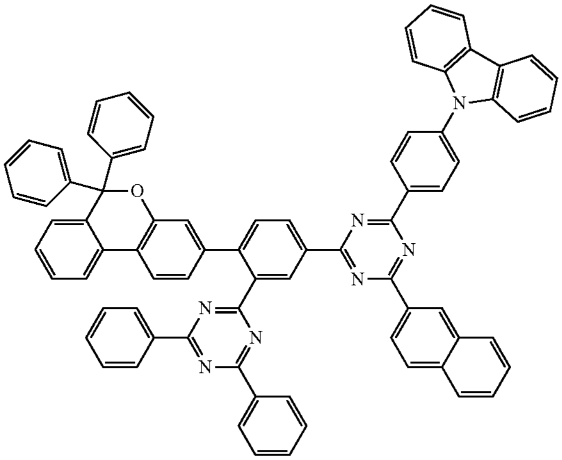
247
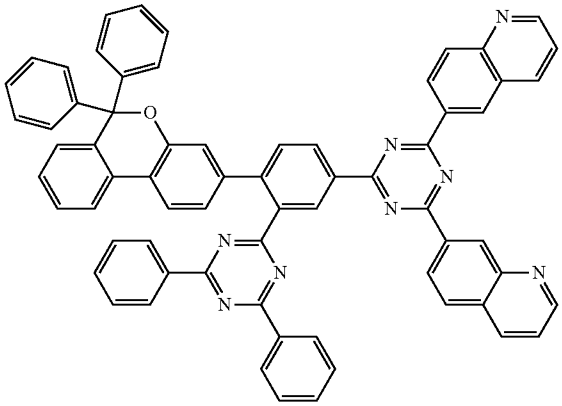
248
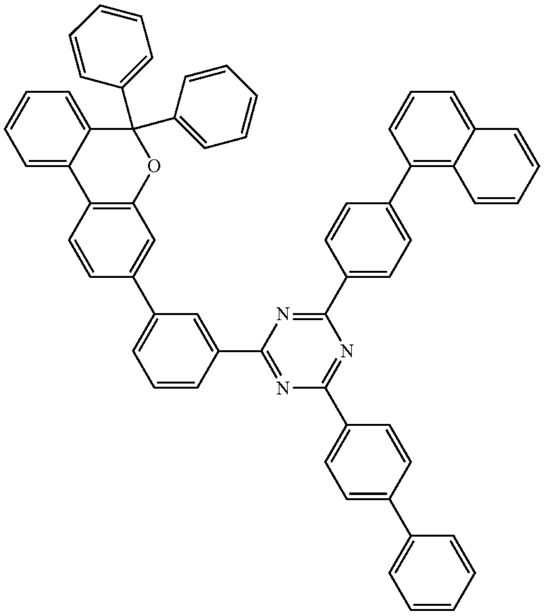
249
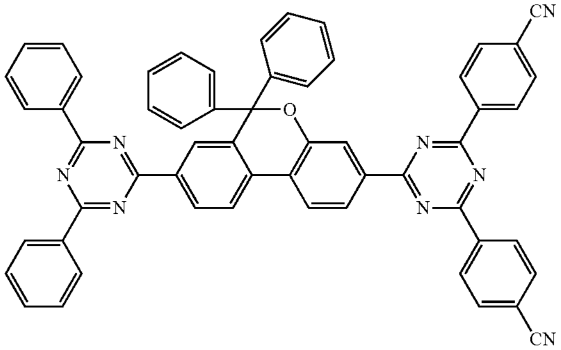
250
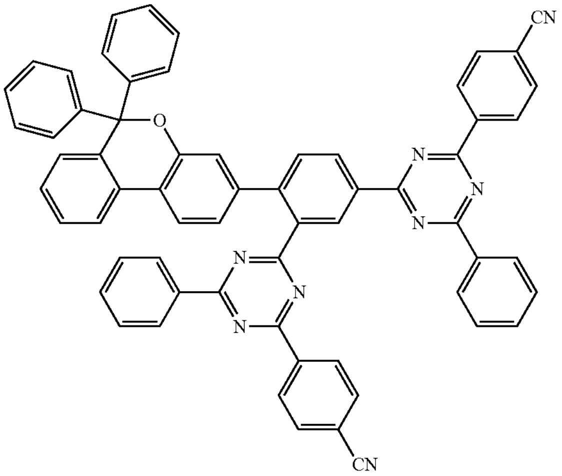
251
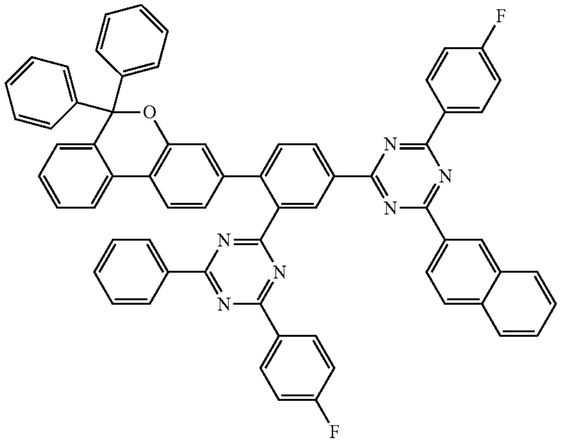

-continued
252
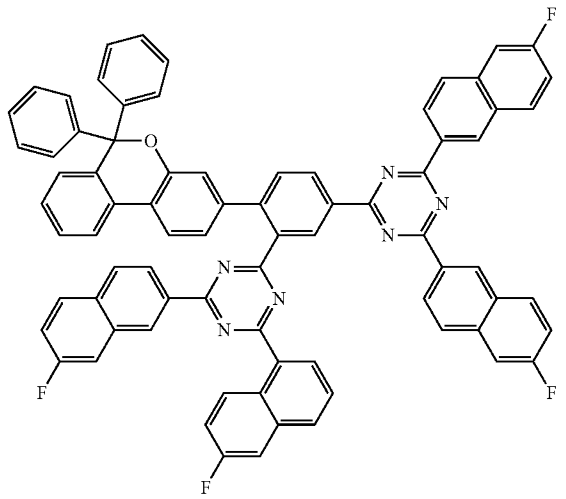
253
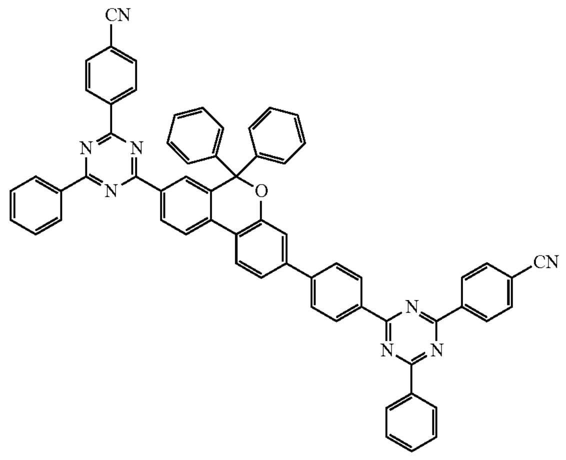
254
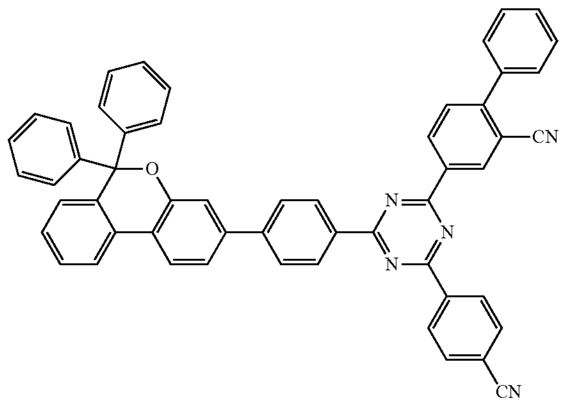
255
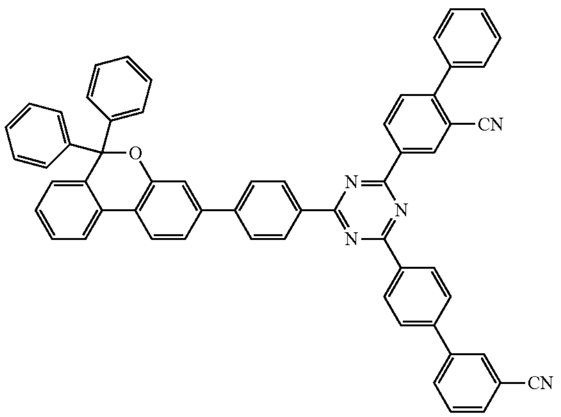
256
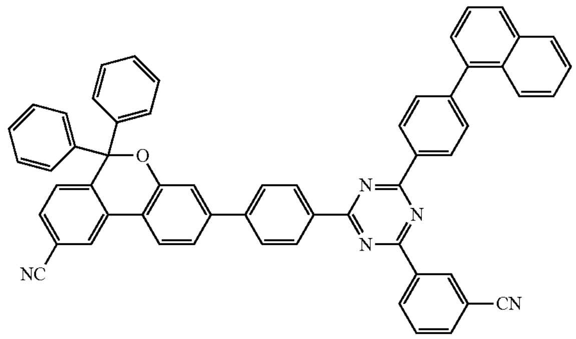
257
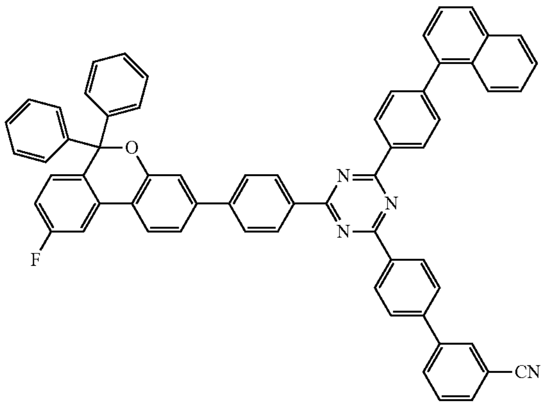

-continued
258
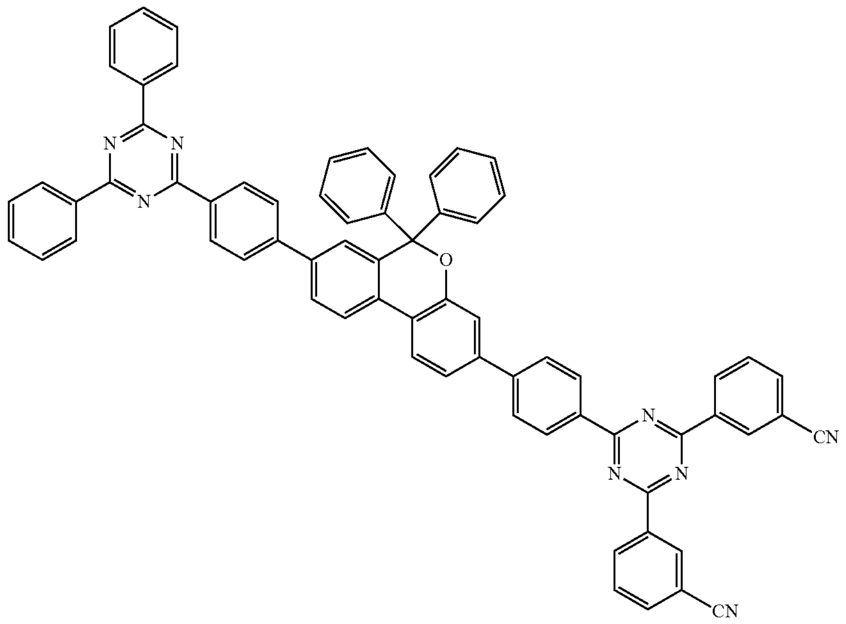
259
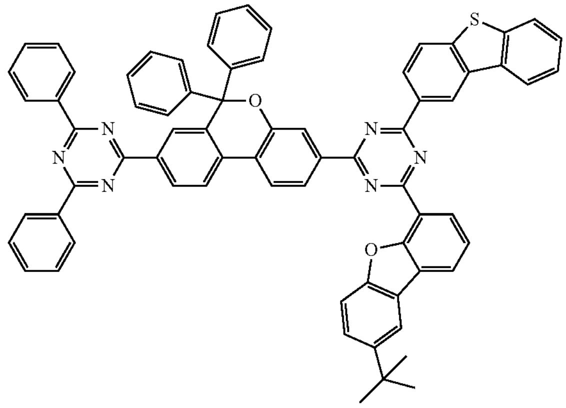
260
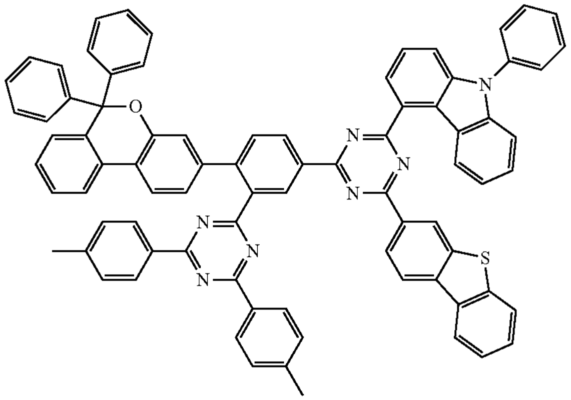
261
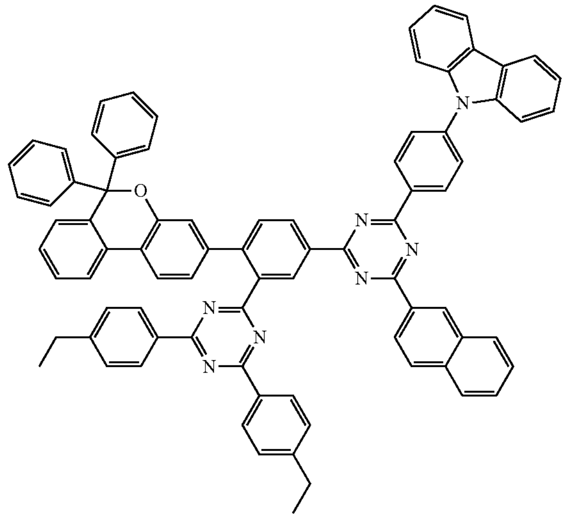
262
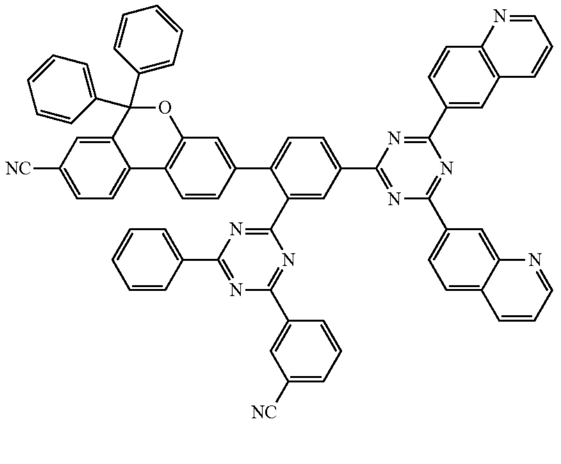

-continued
263
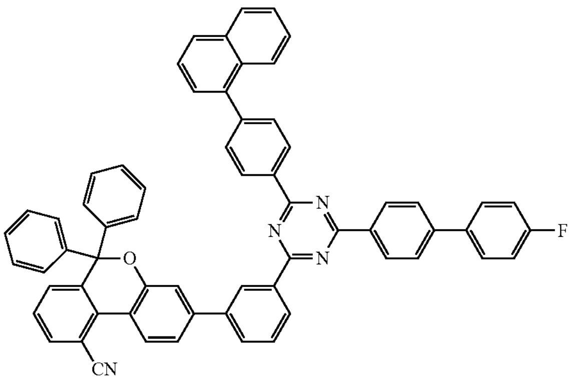
264
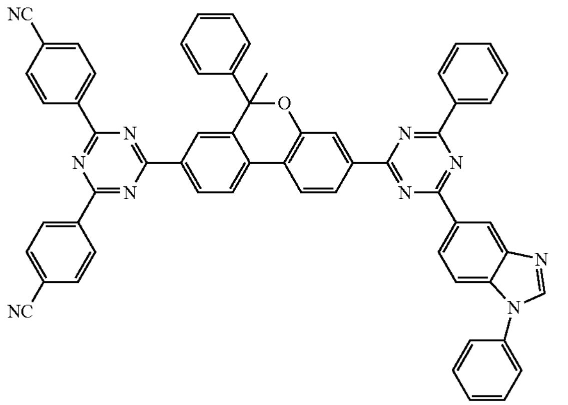
265
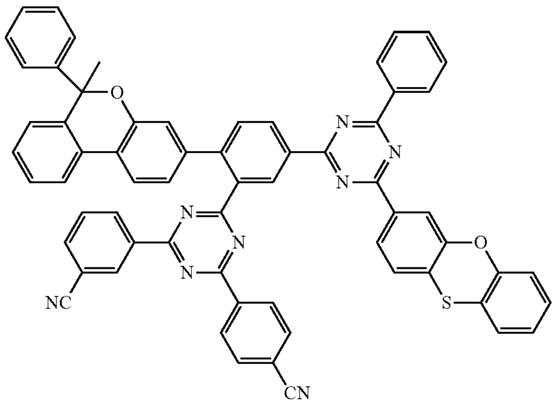
266
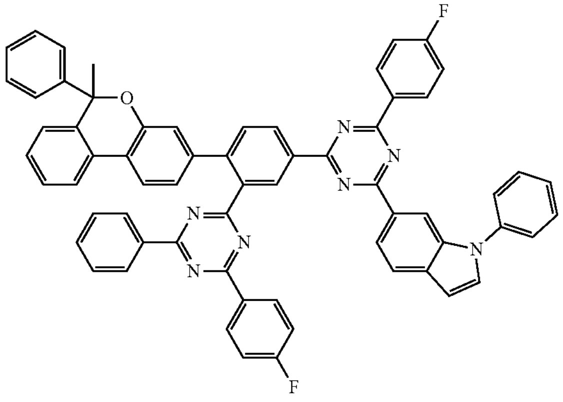
-continued
267
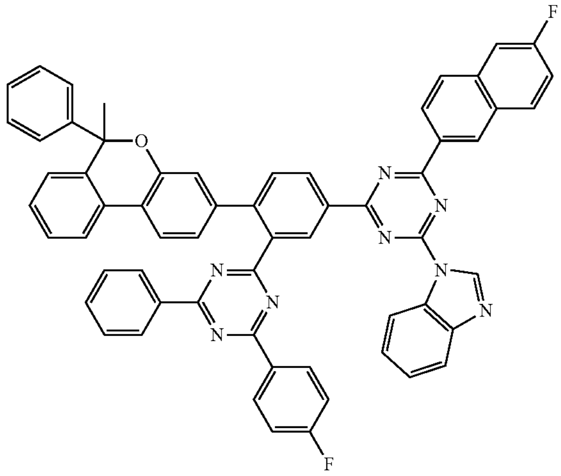
268
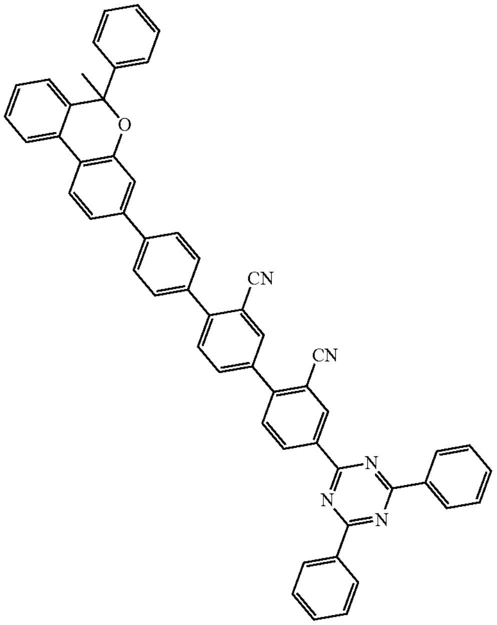

-continued
269
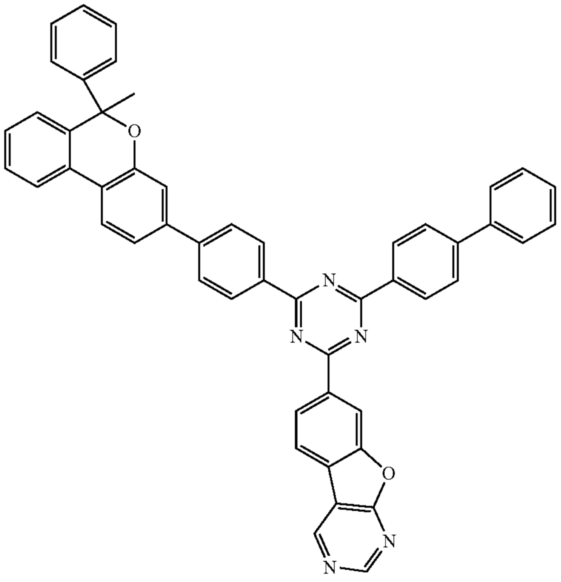
270
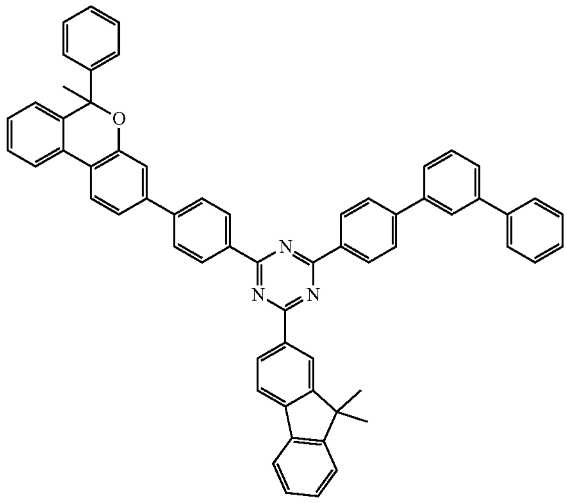
271
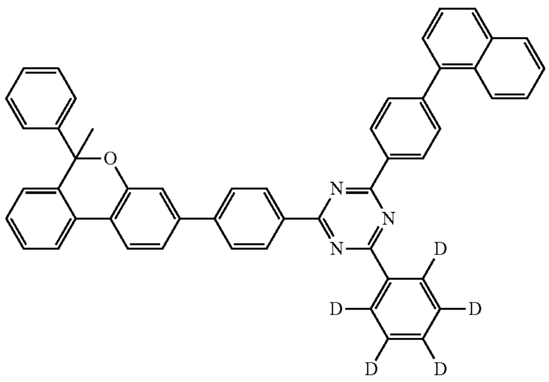
-continued
272
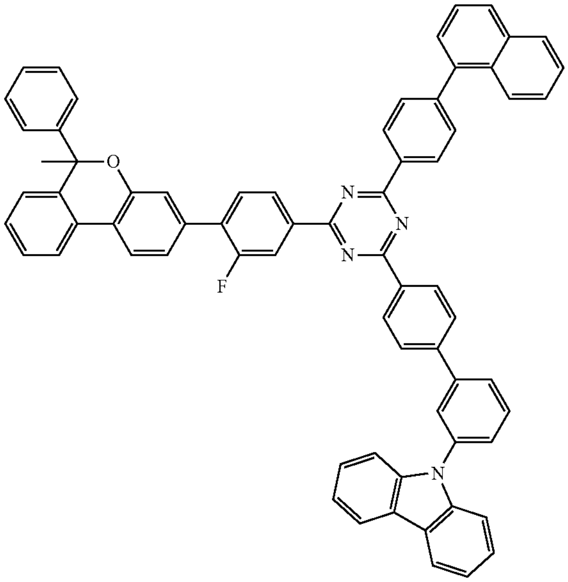
273
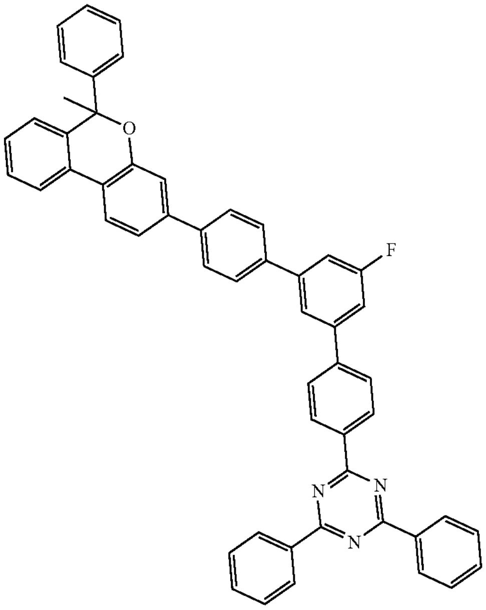

-continued
274
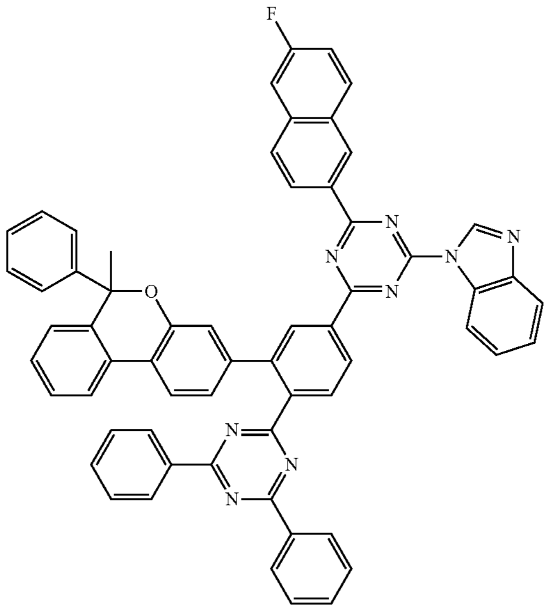
275
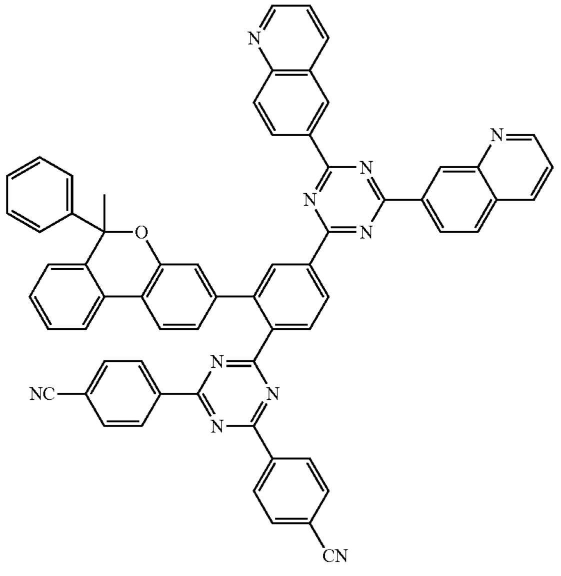
-continued
276
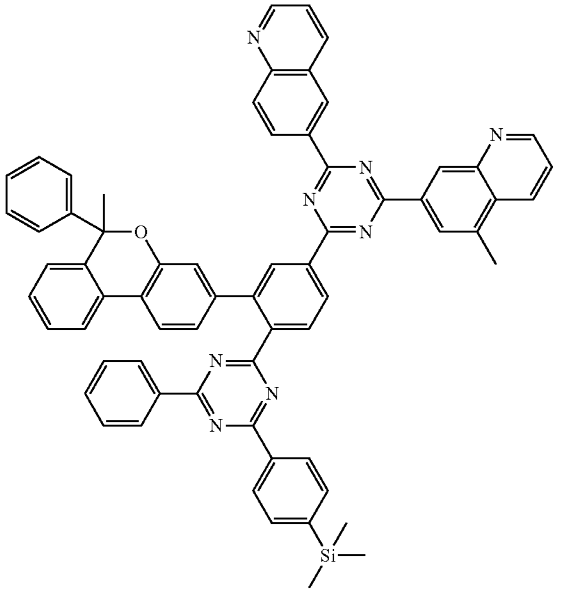
277
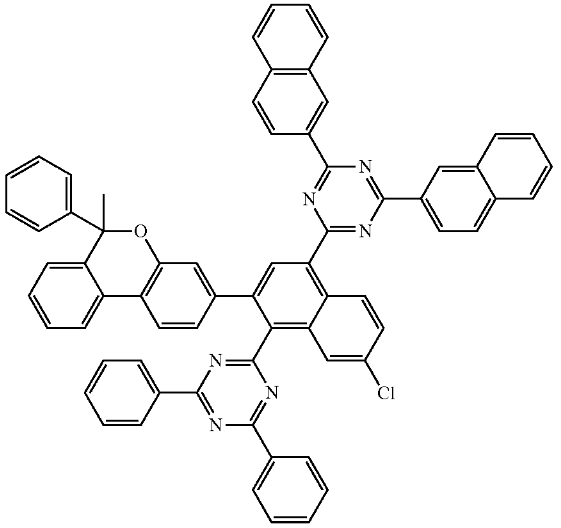

-continued
278
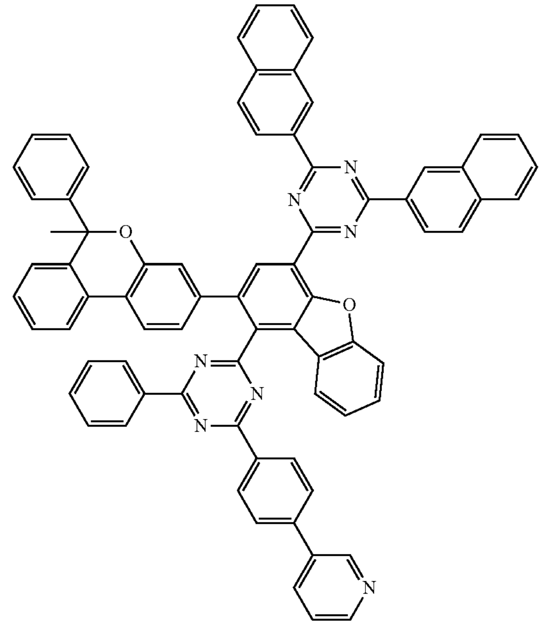
279
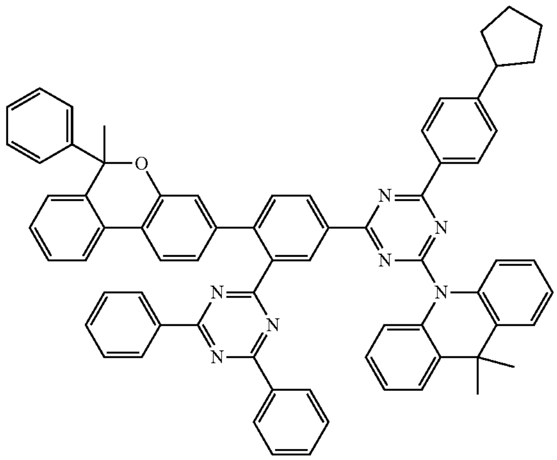
-continued
280
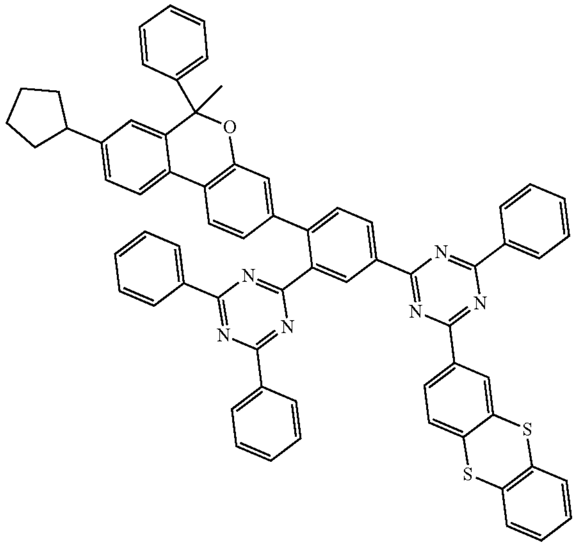
281
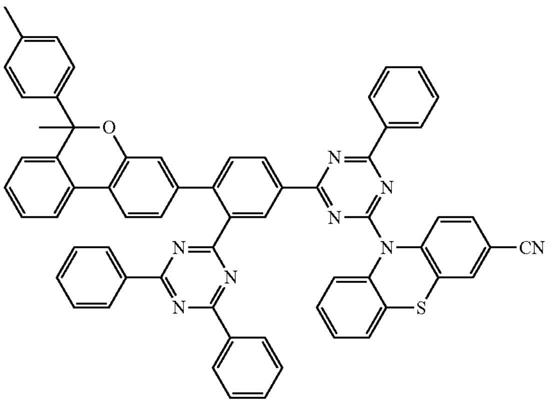
282
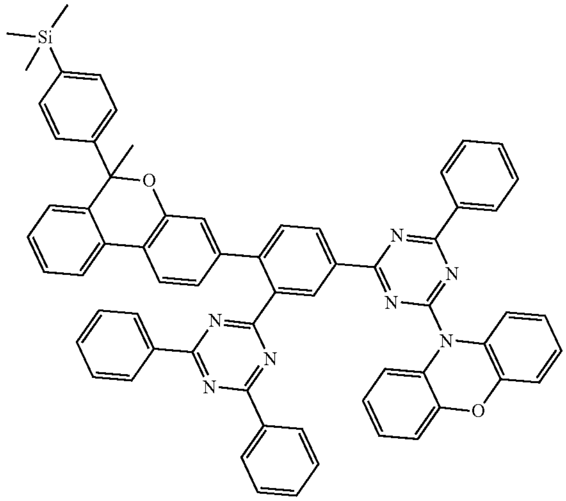

-continued
283
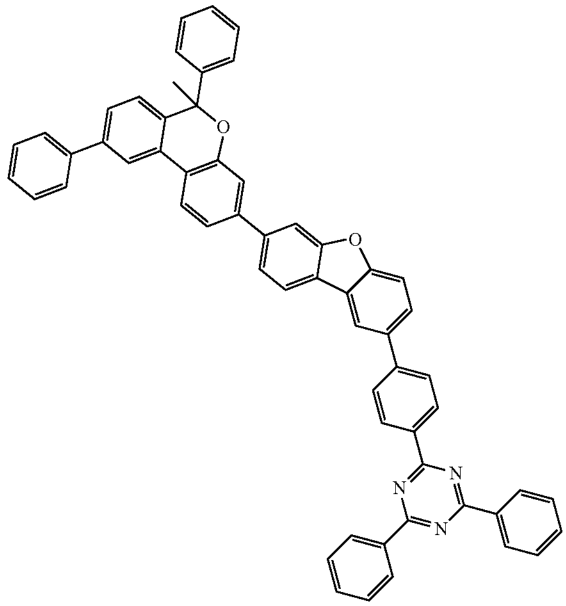
284
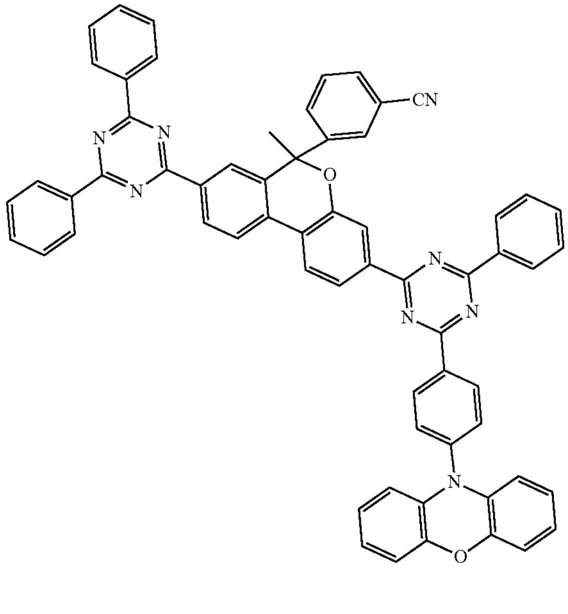
-continued
285
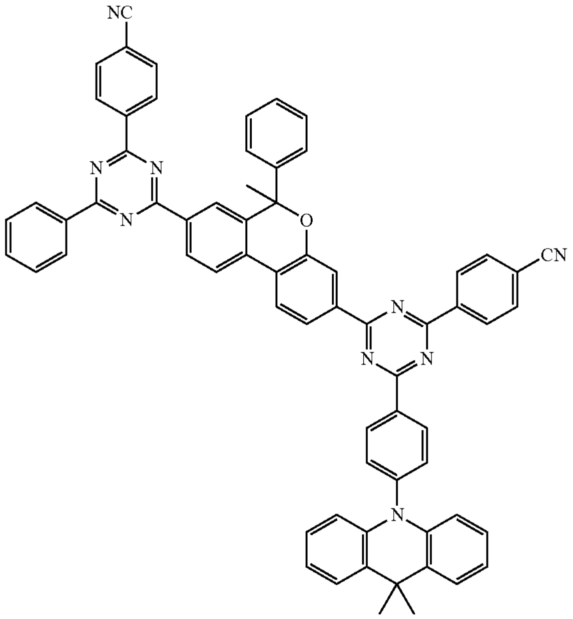
286
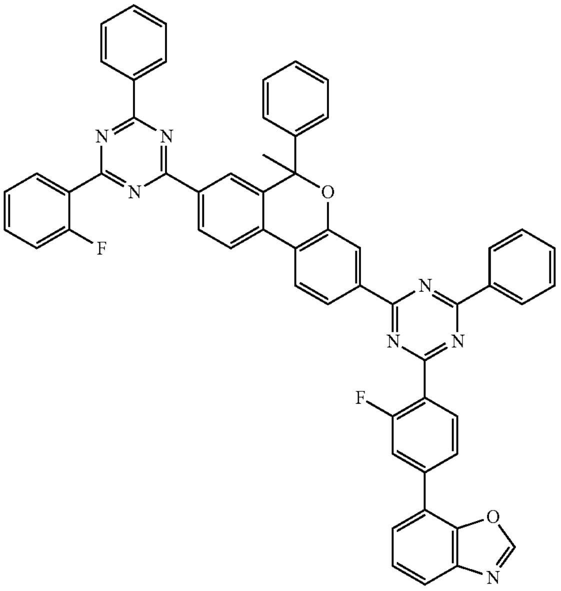

-continued
287
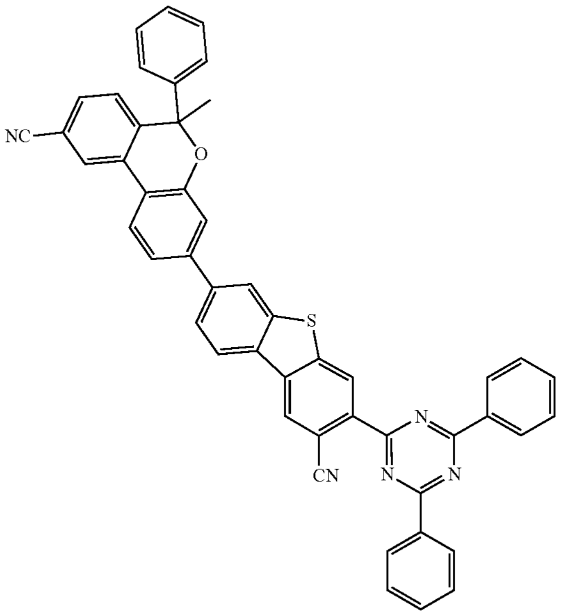
288
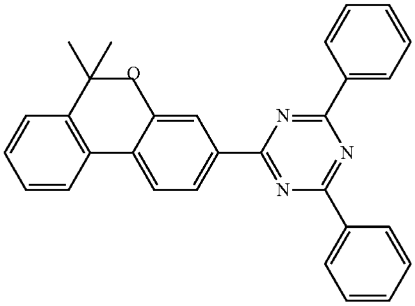
289
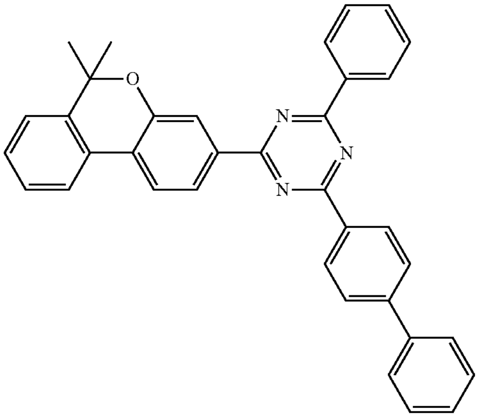
-continued
290
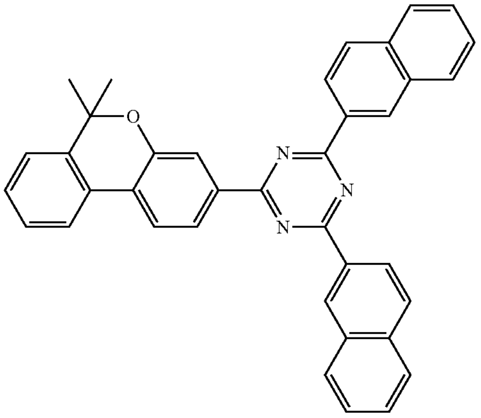
291
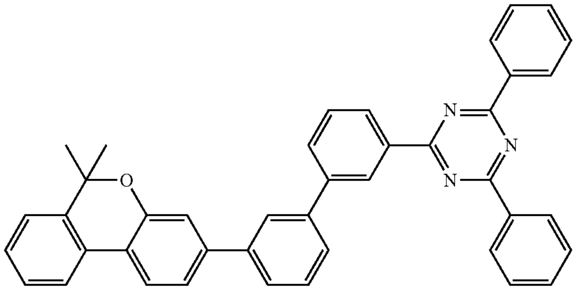
292
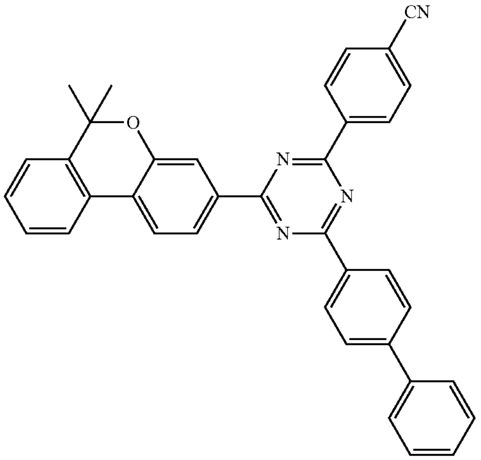
293
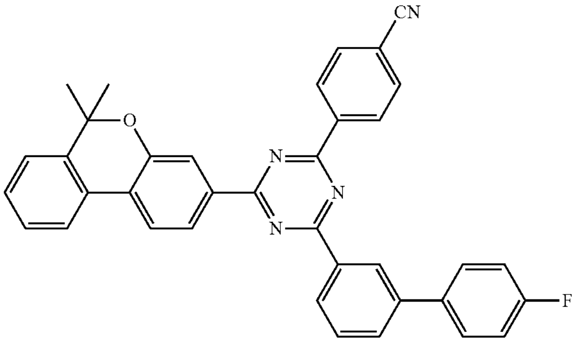

294
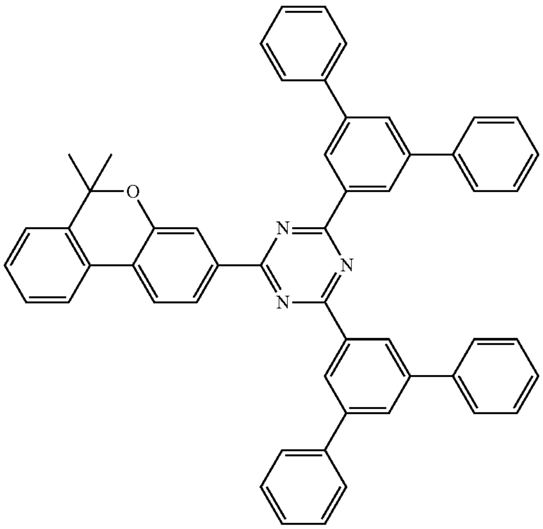
295
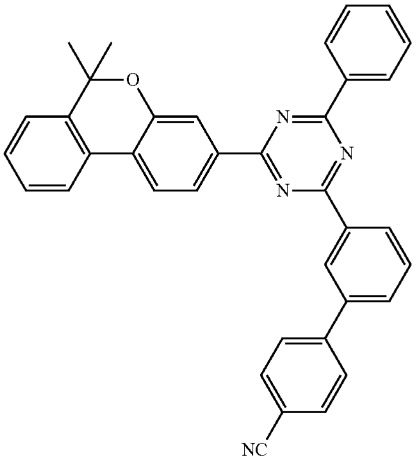
296
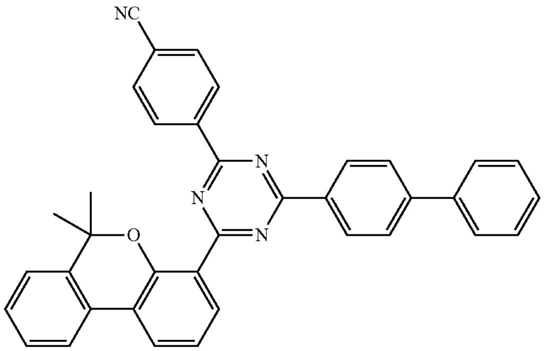
297
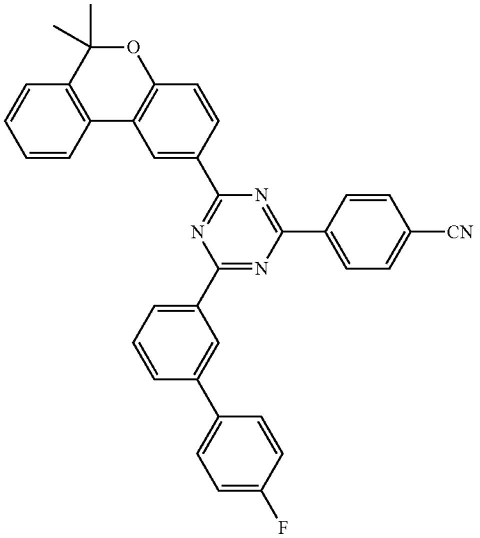
298
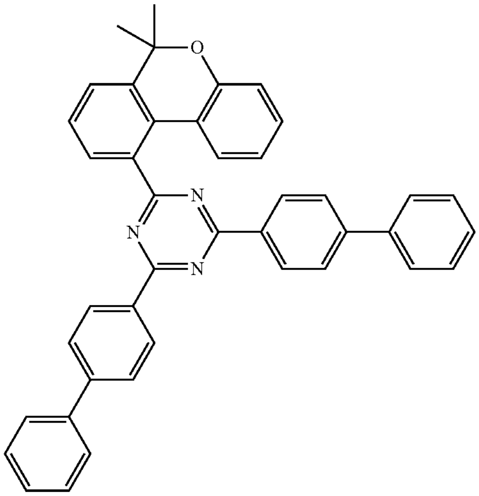
299
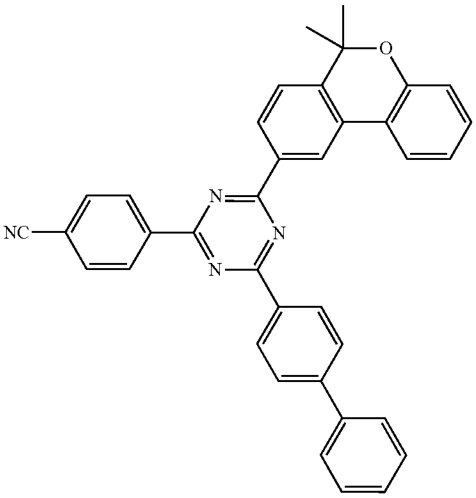

-continued
300
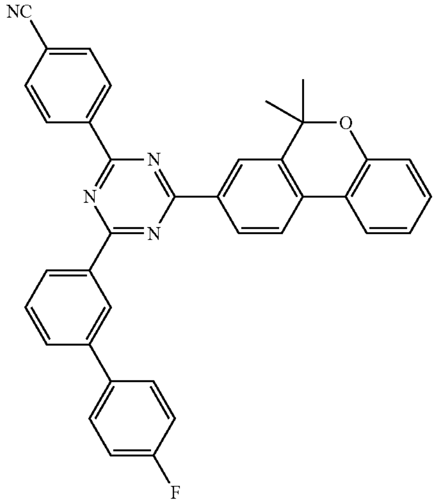
301
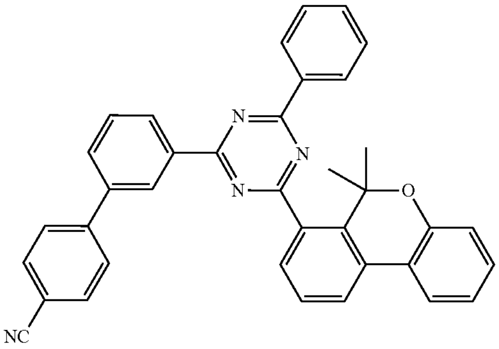
302
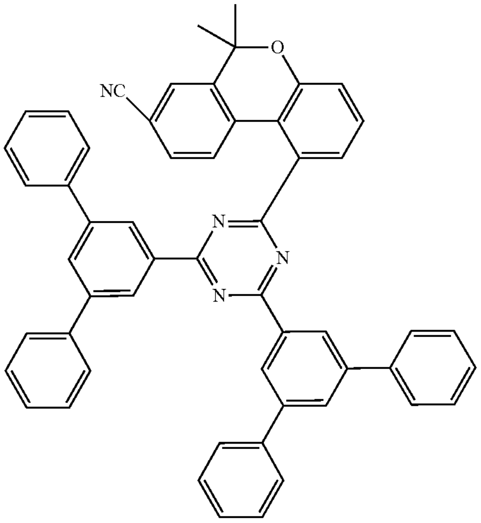
-continued
303
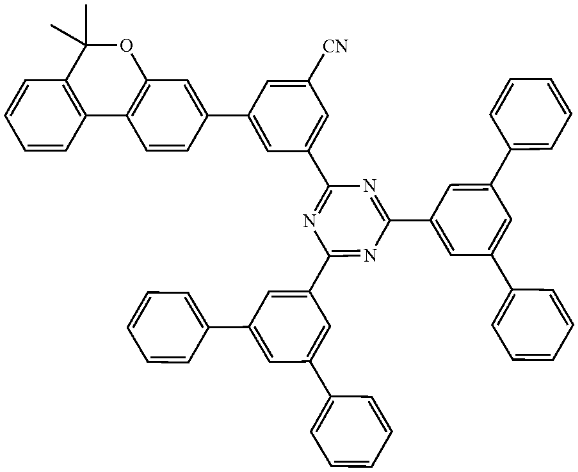
304
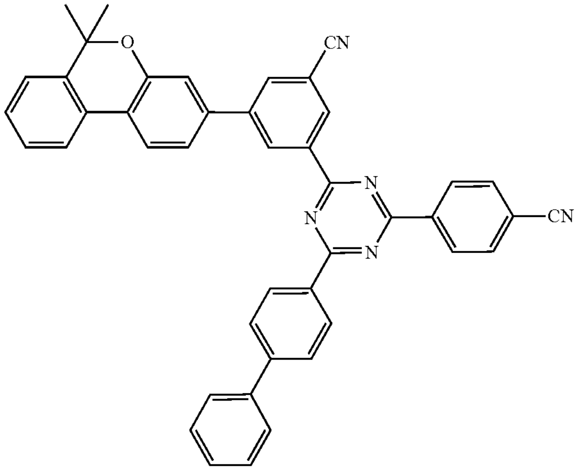
305
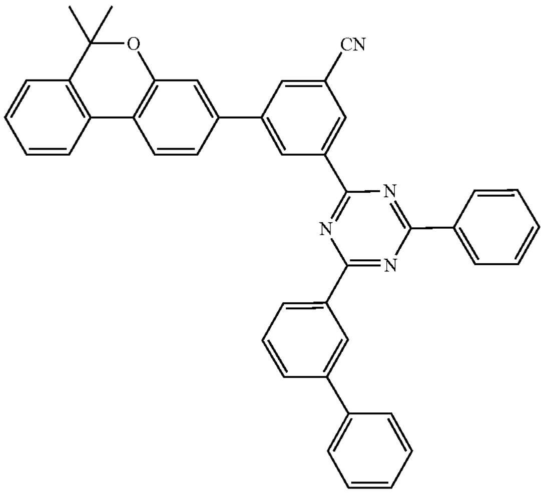

306
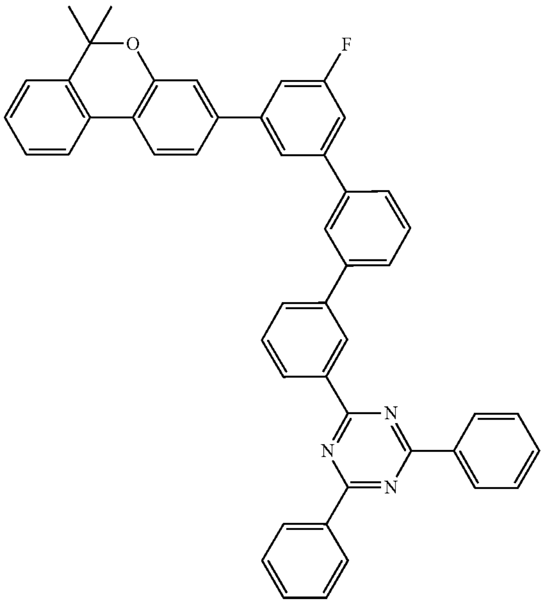
307
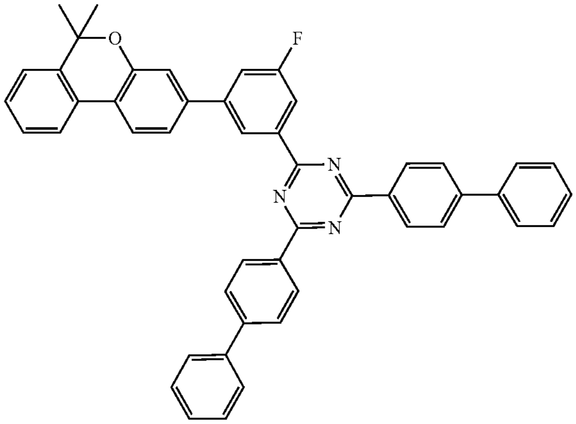
308
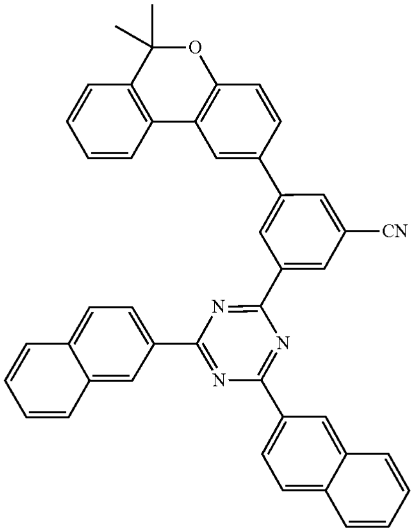
309
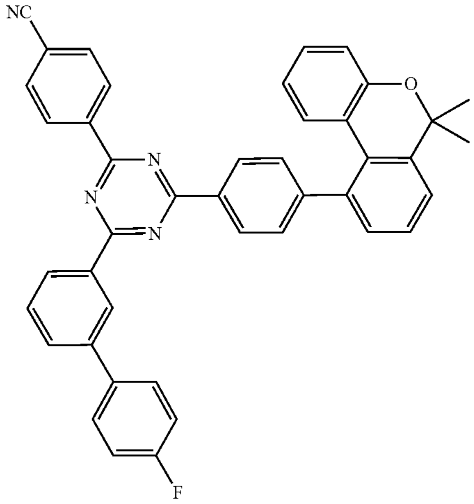
310
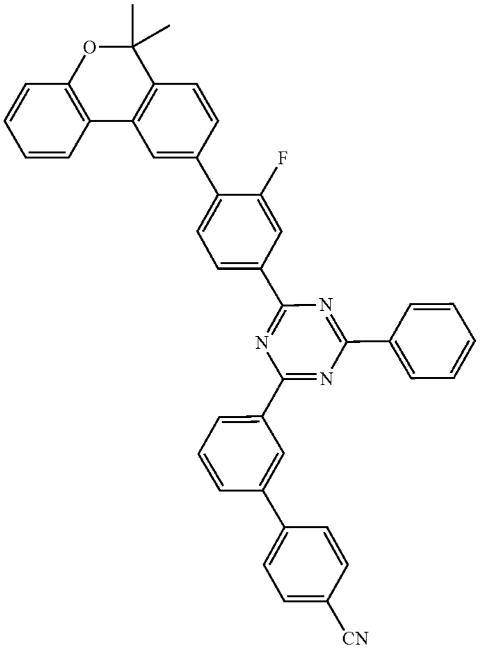
311
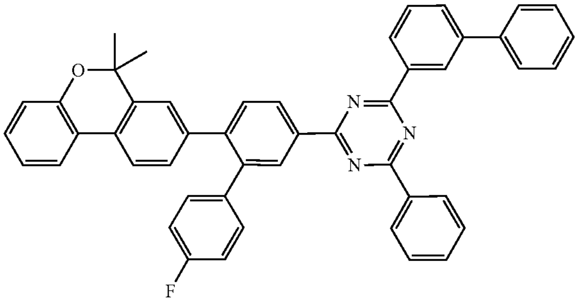

-continued
312
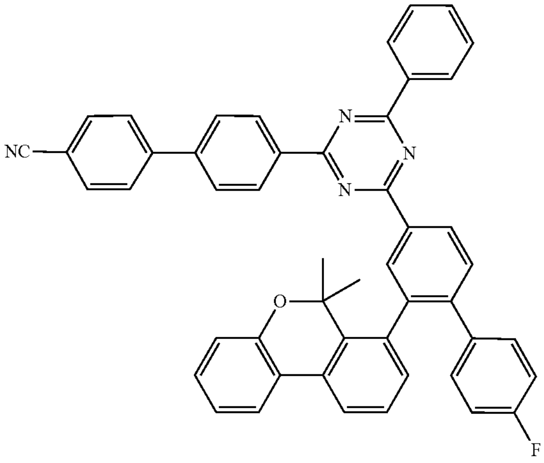
313
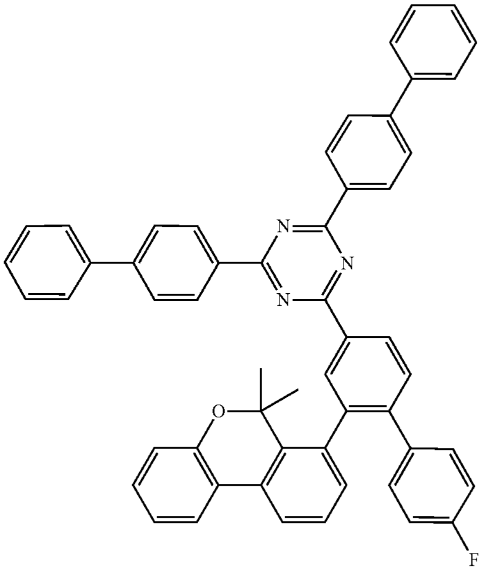
314
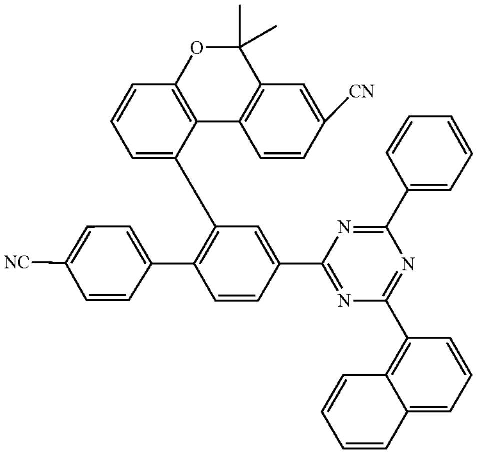
-continued
315
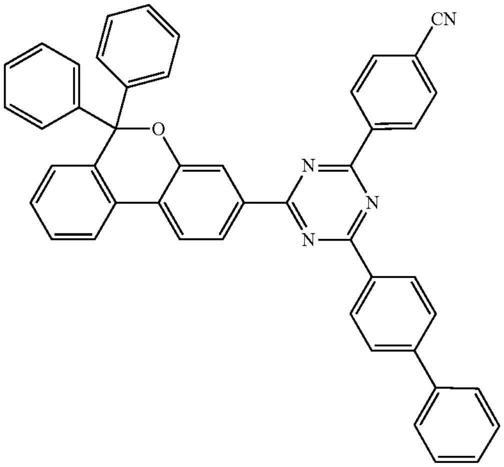
316
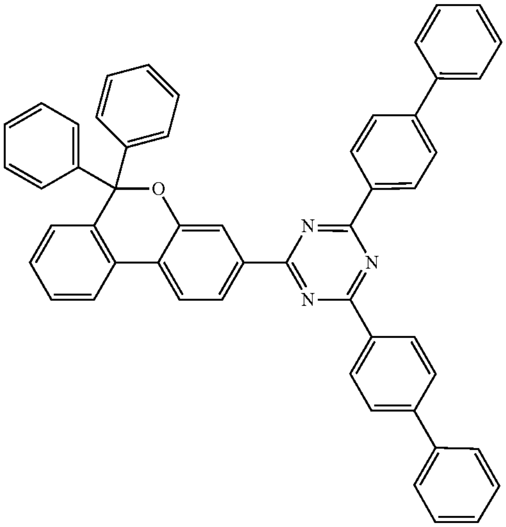
317
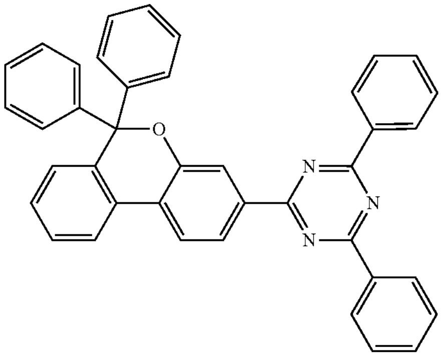

-continued
318
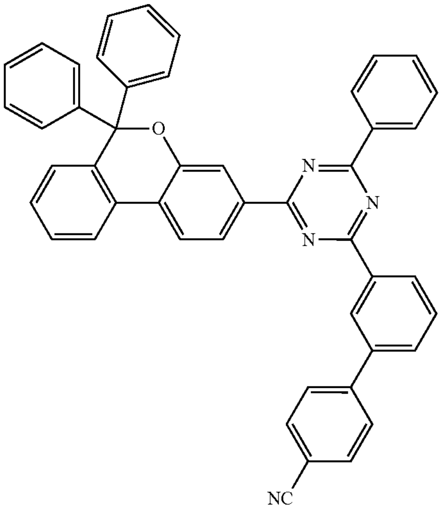
319
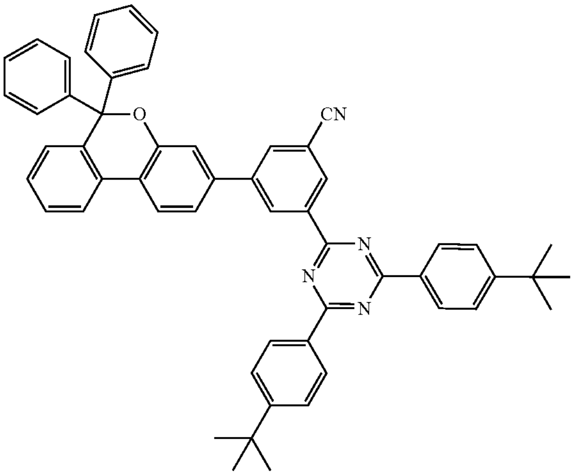
320
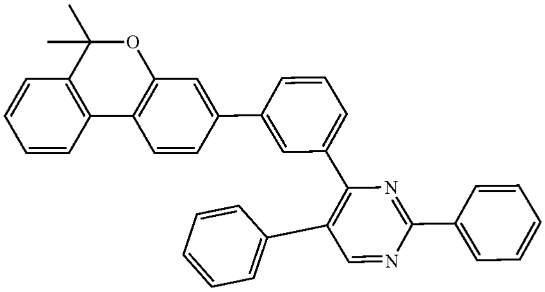
-continued
321
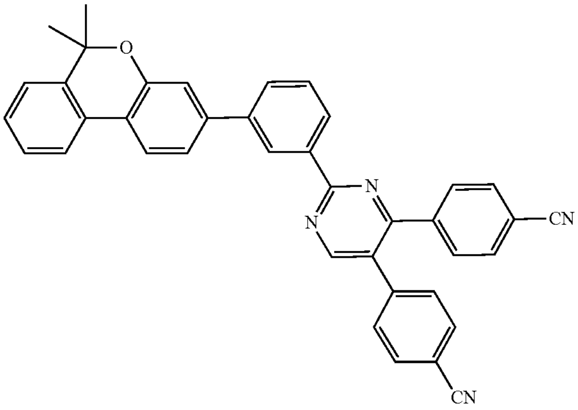
322
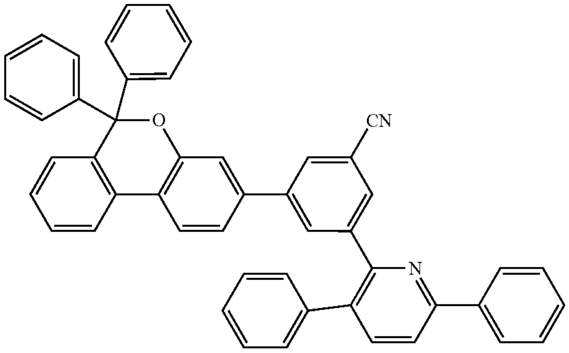
323
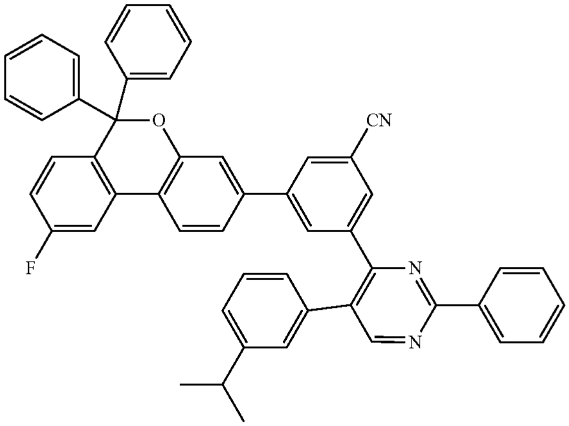

-continued
324
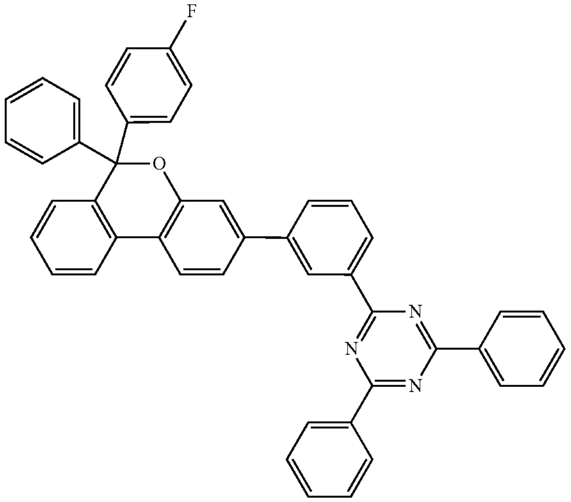
325
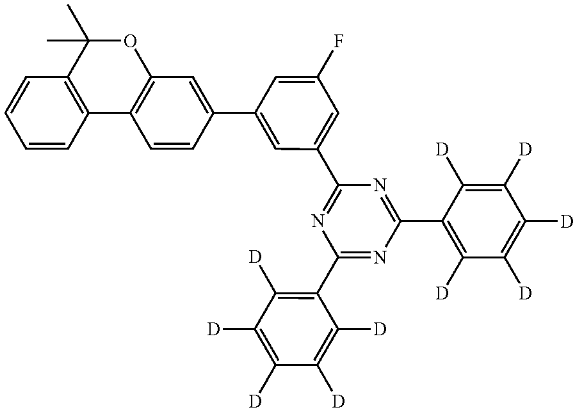
326
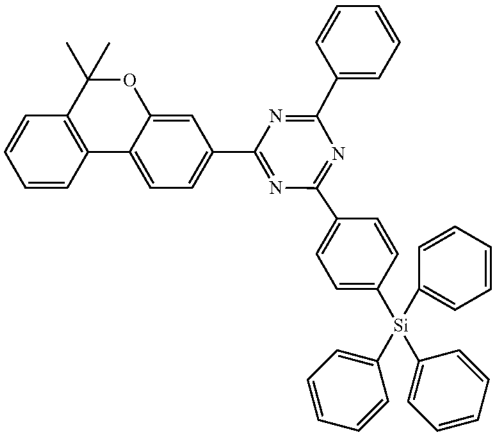
-continued
327
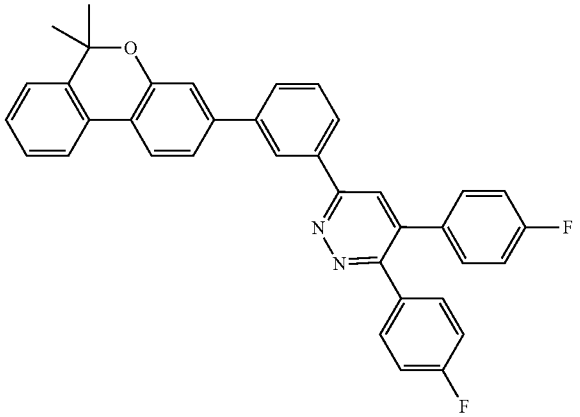
328
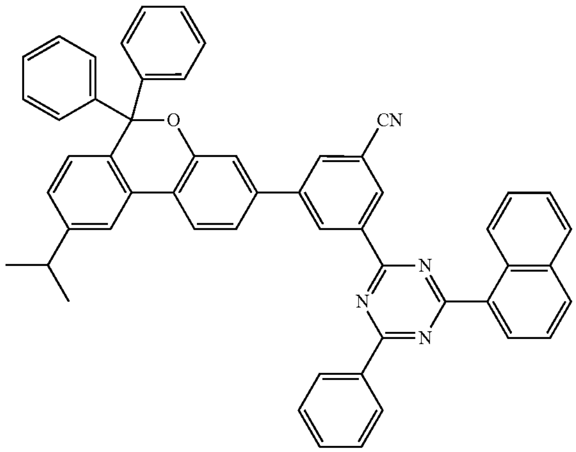
329
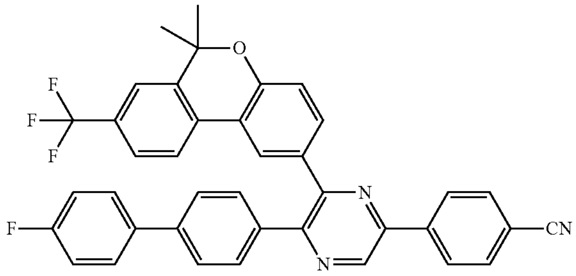

-continued
330
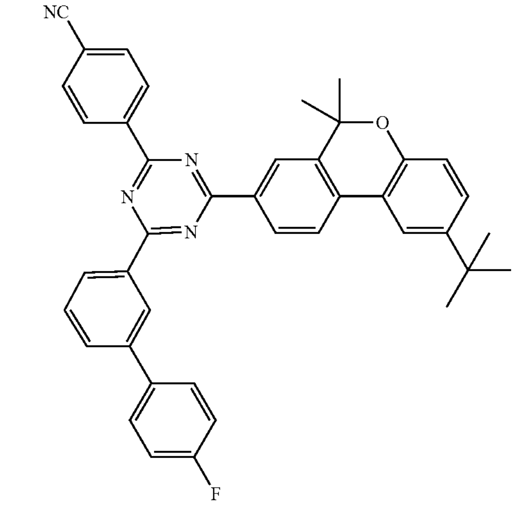
331
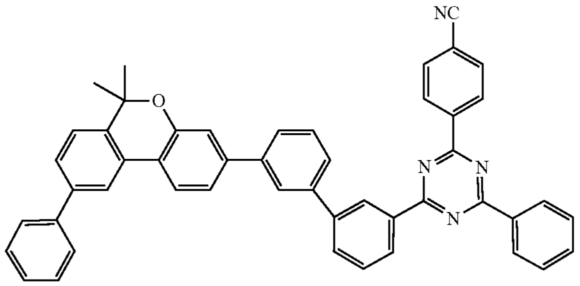
332
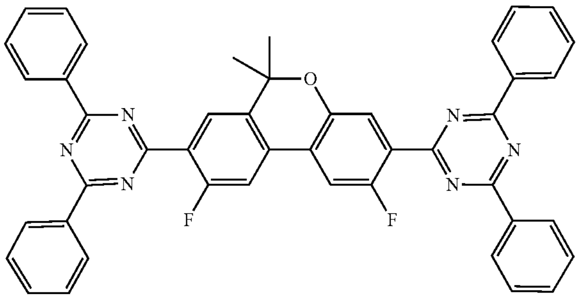
333
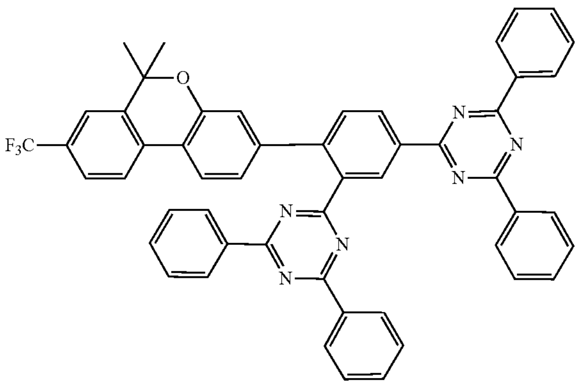
-continued
334
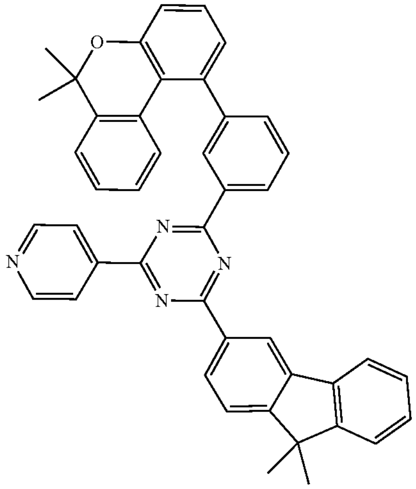
335
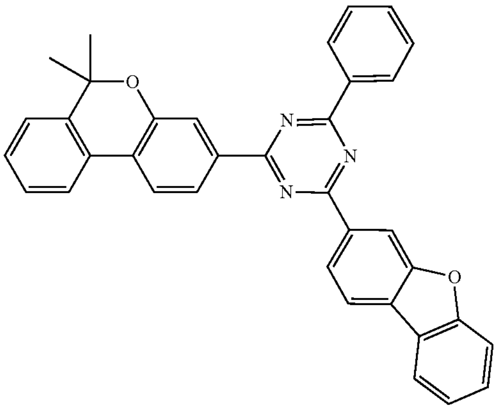
336
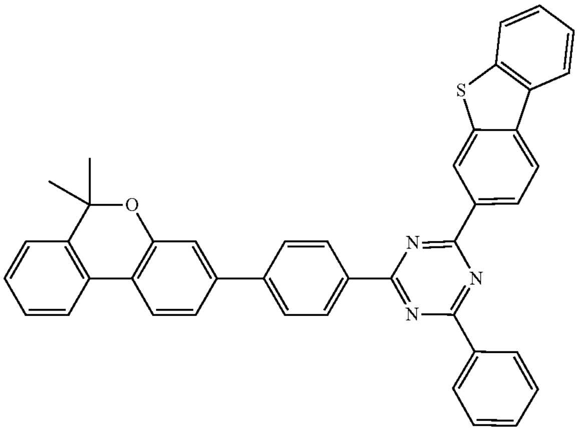

-continued

337

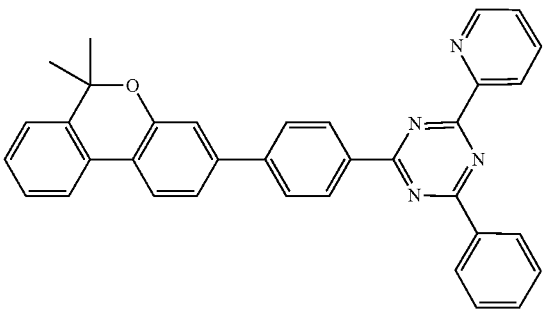

338

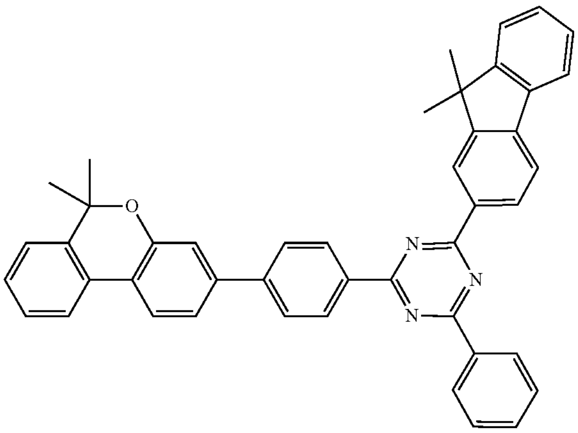

339

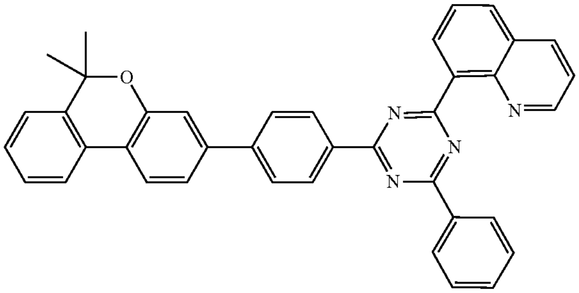

-continued

340

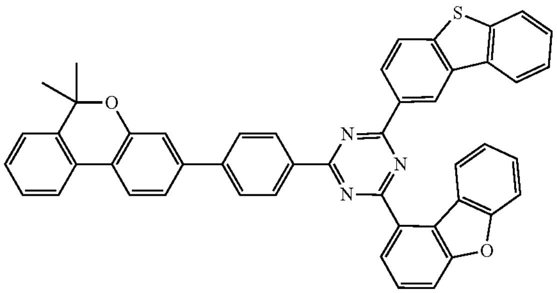

.

16. An electronic element, comprising an anode and a cathode which are disposed oppositely, and a functional layer disposed between the anode and the cathode; and the functional layer comprises the organic compound according to claim 1.

17. The electronic element according to claim 16, wherein the electronic element is an organic electroluminescent device or a photoelectric conversion device.

18. An electronic device, comprising the electronic element according to claim 16.

19. The electronic element according to claim 16, wherein the functional layer comprises an electron transport layer, and the electron transport layer comprises the organic compound.

20. The electronic element according to claim 16, wherein, the functional layer comprises a hole blocking layer, and the hole blocking layer comprises the organic compound.

* * * * *